(12) United States Patent
Gradinaru et al.

(10) Patent No.: US 11,149,256 B2
(45) Date of Patent: Oct. 19, 2021

(54) ADENO-ASSOCIATED VIRUS COMPOSITIONS FOR TARGETED GENE THERAPY

(71) Applicant: California Institute of Technology, Pasadena, CA (US)

(72) Inventors: Viviana Gradinaru, La Canada Flintridge, CA (US); Nicholas C. Flytzanis, San Gabriel, CA (US); Nicholas Goeden, Manhattan Beach, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/582,635

(22) Filed: Sep. 25, 2019

(65) Prior Publication Data

US 2020/0165576 A1      May 28, 2020

Related U.S. Application Data

(60) Provisional application No. 62/736,904, filed on Sep. 26, 2018, provisional application No. 62/832,812, filed on Apr. 11, 2019.

(51) Int. Cl.
*C12N 7/00* (2006.01)

(52) U.S. Cl.
CPC ...... *C12N 7/00* (2013.01); *C12N 2750/14071* (2013.01); *C12N 2750/14121* (2013.01); *C12N 2750/14122* (2013.01)

(58) Field of Classification Search
None
See application file for complete search history.

(56) References Cited

U.S. PATENT DOCUMENTS

| 5,919,676 A | 7/1999 | Graham et al. |
| 6,228,646 B1 | 5/2001 | Hardy |

(Continued)

FOREIGN PATENT DOCUMENTS

| EP | 1290205 A2 | 3/2003 |
| EP | 3561062 A1 | 10/2019 |

(Continued)

OTHER PUBLICATIONS

Venkatakrishnan et al., "Structure and Dynamics of Adeno-Associated Virus Serotype 1 VP1-Unique N-Terminal Domain and Its Role in Capsid Trafficking," Journal of Virology, vol. 87: No. 9: 4974-4984 (Year: 2013).*

(Continued)

*Primary Examiner* — M Franco G Salvoza
(74) *Attorney, Agent, or Firm* — Brown Rudnick LLP

(57) ABSTRACT

Described herein are compositions and kits comprising recombinant adeno-associated viruses (rAAVs) with tropisms showing increased specificity and efficiency of viral transduction in targeted cell-types, for e.g., the brain, and lung. The rAAV compositions described herein also have tropisms showing decreased specificity and decreased efficiency of viral transduction in an off-target cell type, for e.g., the liver. The rAAV compositions described herein encapsidate a transgene, such a therapeutic nucleic acid. Upon systemic delivery to a subject, the rAAV is capable of increased specificity and increased transduction of the transgene in a target cell-type, as compared to a parental or reference AAV.

25 Claims, 211 Drawing Sheets

Specification includes a Sequence Listing.

(56) References Cited

U.S. PATENT DOCUMENTS

| | | | |
|---|---|---|---|
| 6,274,354 | B1 | 8/2001 | Wilson et al. |
| 6,379,943 | B1 | 4/2002 | Graham et al. |
| 6,410,271 | B1 | 6/2002 | Zhu et al. |
| 6,566,118 | B1 | 5/2003 | Atkinson et al. |
| 9,018,138 | B2 | 4/2015 | Lupold et al. |
| 9,585,971 | B2 * | 3/2017 | Deverman ......... A61K 38/1709 |
| 9,957,303 | B2 | 5/2018 | Deverman et al. |
| 10,202,425 | B2 | 2/2019 | Deverman et al. |
| 10,287,607 | B2 | 5/2019 | Tagliatela et al. |
| 10,287,608 | B2 | 5/2019 | Tagliatela et al. |
| 10,301,360 | B2 | 5/2019 | Deverman et al. |
| 10,519,198 | B2 | 12/2019 | Deverman et al. |
| 10,519,465 | B2 | 12/2019 | Tagliatela et al. |
| 2002/0058325 | A1 | 5/2002 | Hardy |
| 2005/0287122 | A1 * | 12/2005 | Bartlett .................... C12N 9/93 424/93.2 |
| 2007/0036760 | A1 | 2/2007 | Wilson et al. |
| 2007/0172460 | A1 | 7/2007 | Kleinschmidt et al. |
| 2007/0243526 | A1 * | 10/2007 | Kay .................... C12N 15/1082 435/5 |
| 2009/0042257 | A1 | 2/2009 | Rodriguez et al. |
| 2009/0093403 | A1 | 4/2009 | Zhang et al. |
| 2009/0202490 | A1 | 8/2009 | Schaffer et al. |
| 2009/0215879 | A1 | 8/2009 | Diprimio et al. |
| 2010/0105123 | A2 | 4/2010 | Hallek et al. |
| 2011/0105998 | A1 | 5/2011 | Zhang et al. |
| 2011/0223635 | A1 | 9/2011 | Deisseroth et al. |
| 2011/0301529 | A1 | 12/2011 | Zhang et al. |
| 2013/0019325 | A1 | 1/2013 | Deisseroth et al. |
| 2013/0059732 | A1 | 3/2013 | Lisowski et al. |
| 2013/0089503 | A1 | 4/2013 | Deisseroth et al. |
| 2013/0090454 | A1 | 4/2013 | Deisseroth et al. |
| 2013/0142764 | A1 | 6/2013 | Davidson et al. |
| 2013/0195801 | A1 | 8/2013 | Gao et al. |
| 2013/0244323 | A1 | 9/2013 | Deisseroth et al. |
| 2014/0024701 | A1 | 1/2014 | Deisseroth et al. |
| 2014/0030192 | A1 | 1/2014 | Deisseroth et al. |
| 2014/0113367 | A1 | 4/2014 | Deisseroth et al. |
| 2014/0358067 | A1 | 12/2014 | Deisseroth et al. |
| 2015/0079038 | A1 | 3/2015 | Deverman et al. |
| 2015/0087001 | A1 | 3/2015 | Gradinaru et al. |
| 2015/0297719 | A1 | 10/2015 | Deisseroth et al. |
| 2015/0315612 | A1 | 11/2015 | Wilson et al. |
| 2016/0038761 | A1 | 2/2016 | Deisseroth et al. |
| 2016/0123854 | A1 | 5/2016 | Gradinaru et al. |
| 2016/0175607 | A1 | 6/2016 | Deisseroth et al. |
| 2016/0287895 | A1 | 10/2016 | Deisseroth et al. |
| 2016/0290899 | A1 | 10/2016 | Deisseroth et al. |
| 2017/0066806 | A1 | 3/2017 | Deisseroth et al. |
| 2017/0067908 | A1 | 3/2017 | Nakai et al. |
| 2017/0143986 | A1 | 5/2017 | Deisseroth et al. |
| 2017/0166926 | A1 | 6/2017 | Deverman et al. |
| 2017/0198017 | A1 | 7/2017 | Deisseroth et al. |
| 2017/0199104 | A1 | 7/2017 | Gradinaru et al. |
| 2017/0204144 | A1 | 7/2017 | Deverman et al. |
| 2017/0240885 | A1 | 8/2017 | Deverman et al. |
| 2018/0044388 | A1 | 2/2018 | Deisseroth et al. |
| 2018/0050219 | A1 | 2/2018 | Deisseroth et al. |
| 2018/0230186 | A1 | 8/2018 | Deverman et al. |
| 2018/0230489 | A1 | 8/2018 | Kotin |
| 2018/0244737 | A1 | 8/2018 | Deisseroth et al. |
| 2018/0311506 | A1 | 11/2018 | Deisseroth et al. |
| 2018/0371496 | A1 * | 12/2018 | Li ........................ C07K 14/005 |
| 2019/0048041 | A1 | 2/2019 | Asokan et al. |
| 2019/0055578 | A1 | 2/2019 | Sah et al. |
| 2019/0071476 | A1 | 3/2019 | Deisseroth et al. |
| 2019/0144509 | A1 | 5/2019 | Deverman et al. |
| 2019/0224493 | A1 | 7/2019 | Deisseroth et al. |
| 2019/0257724 | A1 | 8/2019 | Deisseroth et al. |
| 2019/0292230 | A1 | 9/2019 | Deverman et al. |
| 2019/0336784 | A1 | 11/2019 | Deisseroth et al. |
| 2020/0087353 | A1 | 3/2020 | Deverman et al. |
| 2020/0087358 | A1 | 3/2020 | Gradinaru et al. |
| 2020/0165576 | A1 | 5/2020 | Gradinaru et al. |

FOREIGN PATENT DOCUMENTS

| | | | |
|---|---|---|---|
| JP | 2014/518614 | A | 8/2014 |
| RU | 2457252 | C2 | 7/2012 |
| WO | 98/09657 | A2 | 3/1998 |
| WO | 2001/092551 | A2 | 12/2001 |
| WO | 2005/017101 | A2 | 2/2005 |
| WO | 2008/103993 | A2 | 8/2008 |
| WO | 2009/012176 | A2 | 1/2009 |
| WO | 2012/145601 | A2 | 10/2012 |
| WO | 2014/052789 | A1 | 4/2014 |
| WO | 2014/186579 | A1 | 11/2014 |
| WO | 2015/040002 | A1 | 3/2015 |
| WO | 2015/127128 | A2 | 8/2015 |
| WO | 2015/168666 | A2 | 11/2015 |
| WO | 2016/065001 | A1 | 4/2016 |
| WO | 2016/081811 | A1 | 5/2016 |
| WO | 2016/154344 | A1 | 9/2016 |
| WO | 2017/100671 | A1 | 6/2017 |
| WO | 2017/136202 | A1 | 8/2017 |
| WO | 2017/143100 | A1 | 8/2017 |
| WO | 2017/192750 | A1 | 11/2017 |
| WO | 2017/197355 | A2 | 11/2017 |
| WO | 2017/218842 | A1 | 12/2017 |
| WO | 2018/022905 | A2 | 2/2018 |
| WO | 2018/045347 | A1 | 3/2018 |
| WO | 2018/071831 | A1 | 4/2018 |
| WO | 2018/085688 | A1 | 5/2018 |
| WO | 2018/119330 | A2 | 6/2018 |
| WO | 2018/152333 | A1 | 8/2018 |
| WO | WO-2018204786 | A1 * | 11/2018 ......... A01K 67/0278 |
| WO | 2018/222503 | A1 | 12/2018 |
| WO | 2019/006182 | A1 | 1/2019 |
| WO | 2019/028306 | A2 | 2/2019 |
| WO | 2019/046069 | A1 | 3/2019 |
| WO | 2019/060454 | A2 | 3/2019 |
| WO | 2019/104279 | A1 | 5/2019 |
| WO | 2019/191701 | A1 | 10/2019 |
| WO | 2019/207132 | A1 | 10/2019 |
| WO | 2019/222329 | A1 | 11/2019 |
| WO | 2019/222441 | A1 | 11/2019 |
| WO | 2019/222444 | A2 | 11/2019 |
| WO | 2020/028751 | A2 | 2/2020 |
| WO | 2020/077165 | A1 | 4/2020 |
| WO | 2020/198737 | A1 | 10/2020 |
| WO | 2020/206189 | A1 | 10/2020 |
| WO | 2020/210633 | A1 | 10/2020 |
| WO | 2020/210655 | A1 | 10/2020 |
| WO | 2020/219988 | A2 | 10/2020 |
| WO | 2020/243651 | A1 | 12/2020 |

OTHER PUBLICATIONS

Buning et al., "Capsid Modifications for Targeting and Improving the Efficacy of AAV Vectors", Molecular Therapy: Methods & Clinical Development, vol. 12: 248-265 (Year: 2019).*

DiMattia et al., "Structural Insight into the Unique Properties of Adeno-Associated Virus Serotype-9", Journal of Virology, vol. 86, No. 12: 6947-6958 (Year: 2012).*

Wang et al., "A Rationally Engineered Capsid Variant of AAV9 for Systemic CNS-Directed and Peripheral Tissue-Detargeted Gene Delivery in Neonates," Molecular Therapy: Methods & Clinical Development, vol. 9: 234-246 (Year: 2018).*

Gibson, 2009, Enzymatic assembly of DNA molecules up to several hundred kilobases, Nature Methods, 6(5):343-345.

Gray, 2009, Directed Evolution of a Novel Adena-associated Virus (AAV) Vector That Crosses the Seizure-compromised Blood-Brain Barrier (BBB), Molecular therapy : The Journal of the American Society of Gene Therapy, 18:570-578.

Gray, 2011, Preclinical Differences of Intravascular AAV9 Delivery to Neurons and Glia: A Comparative Study of Adult Mice and Nonhuman Primates, Molecular therapy : The Journal of the American Society of Gene Therapy, 19:1058-1069.

Gray, 2011, Production of recombinant adeno-associated viral vectors and use in in vitro and in vivo administration, Current Protocols in Neuroscience / Editorial Board, Jacqueline N. Crawley . . . [Et Al.], Chapter 4, Unit 4.17, pp. 4.17.1-4.17.30.

(56) References Cited

OTHER PUBLICATIONS

Grieger, 2006, Production and characterization of adeno-associated viral vectors, Nature Protocols, 1(3):1412-1428.
Grimm, 2008, In vitro and in vivo gene therapy vector evolution via multispecies interbreeding and retargeting of adeno-associated viruses, Journal of virology, 82(12):5887-5911.
Groth, 2000, A phage integrase directs efficient site-specific integration in human cells, PNAS, 97(11):5995-6000.
Guenthner, 2013, Permanent genetic access to transiently active neurons via TRAP: targeted recombination in active populations, Neuron, 78:773-784.
Hancock, 1991, A CAAX or a CAAL motif and a second signal are sufficient for plasma membrane targeting of ras proteins, EMBO J., 10:4033-4039.
Handbook of Pharmaceutical Additives, 3rd Edition; Ash and Ash Eds., Gower Publishing Company: 2007.
Handbook of Pharmaceutical Excipients, 5th Edition; Rowe et al., Eds., The Pharmaceutical Press and the American Pharmaceutical Association: 2005.
High, 2014, Current status of haemophilia gene therapy, Haemophilia: the official journal of the World Federation of Hemophilia, 20 Suppl. 4, pp. 43-49.
Hirt, 1967, Selective extraction of polyoma DNA from infected mouse cell cultures, Journal of Molecular Biology, 26(2):365-369.
Huser, 2002, Kinetics and Frequency of Adeno-Associated Virus Site-Specific Integration into Human Chromosome 19 Monitored by Quantitative Real-Time PCR, J. Virol., 76(15):7554-7559.
Hutson, 2012, Corticospinal tract transduction: a comparison of seven adeno-associated viral vector serotypes and a non-integrating lentiviral vector, Gene therapy, 19:49-60.
Inagaki, 2006, Robust systemic transduction with AAV9 vectors in mice: efficient global cardiac gene transfer superior to that of AAV8, Molecular therapy : The Journal of the American Society of Gene Therapy, 14:45-53.
Inagaki, 2008, Frequency and spectrum of genomic integration of recombinant adeno-associated virus serotype 8 vector in neonatal mouse liver, J Virol, 82:9513-9524.
Izpisua Belmonte, 2015, Brains, genes, and primates, Neuron, 86:617-631.
Kaeppel, 2013, A largely random AAV integration profile after LPLD gene therapy, Nat Med, 19:889-891.
Kaplitt, 1994, Long-term gene expression and phenotypic correction using adeno-associated virus vectors in the mammalian brain, Nature, 8:148-154.
Kaplitt, 2007, Safety and tolerability of gene therapy with an adeno-associated virus (AAV) borne GAD gene for Parkinson's disease: an open label, phase I trial, Lancet, 369:2097-2105.
Kawashima, 2013, Functional labeling of neurons and their projections using the synthetic activity-dependent promoter E-SARE, Nat Methods, 10889-895.
Kessler, 1996, Gene delivery to skeletal muscle results in sustained expression and systemic delivery of a therapeutic protein, Proceedings of the National Academy of Sciences USA, 93:14082-14087.
Knipe, 2007, Fields of virology, edition (2006), Section 57, vol. II (Lippincott Williams & Wilkins), pp. 2107-2185.
Koerber, 2008, DNA Shuffling of Adeno-associated Virus Yields Functionally Diverse Viral Progeny, Mol Ther, 16(10):1703-1709.
Koerber, 2009, Molecular Evolution of Adeno-associated Virus for Enhanced Glial Gene Delivery, Mol Ther, 7(12)2088-2095.
Koerber. 2006, Construction of diverse adeno-associated viral libraries for directed evolution of enhanced gene delivery vehicles, Nature protocols, 1:701-706.
Levitt, 1989, Definition of an efficient synthetic poly(A) site, Genes and Development, 3:1019-1025.
Limberis, 2013, Intranasal antibody gene transfer in mice and ferrets elicits broad protection against pandemic influenza, Sci Transl Med, 5(187):187ra72, 10 pages.
Lisowski, 2014, Selection and evaluation of clinically relevant AAV variants in a xenograft liver model, Nature, 506:382-386.
Luo, 2008, Genetic dissection of neural circuits, Neuron, 57:634-660.
Löw, 2013, Direct and retrograde transduction of nigral neurons with AAV6, 8, and 9 and intraneuronal persistence of viral particles, Human gene therapy, 24:613-629.
Maguire, 2008, Safety and efficacy of gene transfer for Leber's congentital amaurosis, N. Engl J Med, 358:2240-2248.
Maguire, 2010, Directed evolution of adeno-associated virus for glioma cell transduction, Journal of neuro-oncology, 96(3):337-347.
Maguire, 2014, Gene therapy for the nervous system: challenges and new strategies, Neurotherapeutics, 11:817-839.
Maheshri, 2006, Directed evolution of adeno-associated virus yields enhanced gene delivery vectors, Nature biotechnology, 24(2):198-204.
Marshel, 2010, Targeting single neuronal networks for gene expression and cell labeling in vivo, Neuron, 67:562-574.
Martino, 2011, The genome of self-complementary adeno-associated viral vectors increases Toll-like receptor 9-dependent innate immune responses in the liver, Blood, 117:6459-6468.
Mcbride, 2011, Preclinical safety of RNAi-mediated HTT suppression in the rhesus macaque as a potential therapy for Huntington 's disease, Molecular Therapy : the Journal of the American Society of Gene Therapy, 19:2152-2162.
McCarty, 2008, Self-complementary AAV vectors; advances and applications, Molecular Therapy: The Journal of the American Society of Gene Therapy, 16:1648-1656.
Mich, 2019, Epignetic landscape and AAV targeting of human neocortical cell classes, bioRxiv.org, 17 pages.
Michelfelder, 2011, Peptime Ligands Incorporated into the Threefold Spike Capsid Domain to Re-Direct Gene Transduction of AAV8 and AAV( In Vivo, PLoS One, 6(8), e23101, 11 pages.
Mittermeyer, 2012, Long-term evaluation of a phase 1 study of AADC gene therapy for Parkinson's disease, Hum Gene Ther, 23:377-381.
Mori, 2004, Two novel adeno-associated viruses from cynomolgus monkey: pseudotyping characterization of capsid protein, Virology, 330(2):375-83.
Muller, 2003, Random peptide libraries displayed on adeno-associated virus to select for targeted gene therapy vectors, Nat Biotechnol, 21:1040-1046.
Nathwani, 2011, Adenovirus-associated virus vector-mediated gene transfer in hemophilia B, The New England Journal of Medicine, 365(25):2357-2365.
Nathwani, 2011, Long-term safety and efficacy following systemic administration of a self-complementary AAV vector encoding human FIX pseudotyped with serotype 5 and 8 capsid proteins, Molecular therapy : The Journal of the American Society of Gene Therapy, 19:876-885.
National Institute of Health. Advisory Committee to the Director, Interim Report: Brain Research Through Advancing Innovation Neurotechnologies (BRAIN) Working Group, Sep. 16, 2013, pp. 1-58.
Nowrouzi, 2012, Integration frequency and intermolecular recombination of rAAV vectors in non-human primate skeletal muscle and liver, Mol Ther, 20:1177-1186.
Ojala, 2015, Adena-associated virus vectors and neurological gene therapy, Neuroscientist, 21:84-98.
Osakada, 2011, New rabies virus variants for monitoring and manipulating activity and gene expression in defined neural circuits, Neuron, 71:617-631.
Pasca, 2015, Functional cortical neurons and astrocytes from human pluripotent stem cells in 3D culture, Nature methods, 12:671-678.
Perdomini, 2014, Prevention and reversal of severe mitochondrial cardiomyopathy by gene therapy in a mouse model of Friedreich's ataxia, Nat. Med., 20:542-547.
Pharmaceutical Preformulation and Formulation, Gibson Ed., CRC Press LLC: Boca Raton, FL, 2004.
Pulicherla, 2011, Engineering Liver-detargeted AAV9 Vectors for Cardiac and Musculoskeletal Gene Transfer, Molecular Therapy: the Journal of the American Society of Gene Therapy, 19:1070-1078.
Qiu, 2002, Characterization of the Transcription Profile of Adena-Associated Virus Type 5 Reveals a Number of Unique Features

(56) References Cited

OTHER PUBLICATIONS

Compared to Previously Characterized Adena-Associated Viruses, Journal of Virology, 76(24):12435-12447.
Remington: The Science and Practice of Pharmacy, 21st Edition; Lippincott Williams & Wilkins: Philadelphia, PA, 2005.
Salegio, 2013, Axonal transport of adeno-associated viral vectors is serotype-dependent, Gene Ther, 20:348-352.
Samaranch, 2011, AAV9 Transduction in the Central Nervous System of Non-Human Primates, Human gene therapy, 22:329-337.
Samaranch, 2012, Adena-associated virus serotype 9 transduction in the central nervous system of nonhuman primates, Hum Gene Ther, 23:382-389.
Sambrook, 1989, Molecular Cloning: A Laboratory Manual, 2nd Ed., Cold Spring Harbor Laboratory Press, Cold Spring Harbor, N.Y., 39 pages.
Savitt, 2005, Bcl-x Is Required for Proper Development of the Mouse Substantia Nigra, The Journal of Neuroscience, 25:6721-6728.
Schaffer, 2008, Molecular Engineering of Viral Gene Delivery Vehicles, Annual Review of Biomedical Engineering, 10:169-194.
Schnepp, 2002, Highly purified recombinant adeno-associated virus vectors. Preparation and quantification, Methods Mol. Med., 69:427-43.
Schuster, 2014, Biodistribution of adeno-associated virus serotype 9 (AAV9) vector after intrathecal and intravenous delivery in mouse, Front Neuroanat, 8(42) 14 pages.
Seo, 2020, Positron emission tomography imaging of novel AAV capsids maps rapid brain accumulation, Nat Commun, 11:2102.
Shaner, 2013, A bright monomeric green fluorescent protein derived from Branchiostoma lanceolatum, Nat Methods, 10(5):407-409.
Simonelli, 2009, Gene Therapy for Leber's Congenital Amaurosis is Safe and Effective Through 1.5 Years After Vector Administration, Molecular Therapy : The Journal of the American Society of Gene Therapy, 18(3):643-650.
Singer, 1998, Genes and Genomes, A changing Perspective, 1, p. 63.
Smith, 1990, The neural network of the basal ganglia as revealed by the study of synaptic connections of identified neurones, Trends Neurosci, 13:259-265.
Sonntag, 2010, A viral assembly factor promotes AAV2 capsid formation in the nucleolus, Proceedings of the National Academy of Sciences of the United States of America, 107:10220-10225.
Southwell, 2009, Intrabody gene therapy ameliorates motor, cognitive, and neuropathological symptoms in multiple mouse models of Huntington's disease, The Journal of Neuroscience : The Official Journal of the Society for Neuroscience, 29(43):13589-13602.
Srivastava, 1983, Nucleotide sequence and organization of the adeno-associated virus 2 genome, J Virol., 45(2):555-64.
Tang, 2008, Role of omithine decarboxylase antizyme inhibitor in vivo, Genes to Cells, 14(1):79-87.
Tomer, 2014, Advanced CLARITY for rapid and high-resolution imaging of intact tissues, Nat Protoc, 9:1682-1697.
Valori, 2010, Systemic delivery of scAAV9 expressing SMN prolongs survival in a model of spinal muscular atrophy, Sci Transl Med, 2(35):35ra42, 9 pages.
Van der Marel, 2011, Neutralizing antibodies against adeno-associated viruses in inflammatory bowel disease patients: Implications for gene therapy, Inflamm Bowel Dis, 17:2436-2442.
Van Duyne, 2001, A Structural View of Cre-loxP Site Specific Recombination, Annu. Rev. Biophys. Biomol. Struct. 30:87-104.
Vandendriessche, 2007, Efficacy and safety of adeno-associated viral vectors based on serotype 8 and 9 vs. lentiviral vectors for hemophilia B gene therapy, Journal of thrombosis and haemostasis : JTH, 5:16-24.
Varadi, 2012, Novel random peptide libraries displayed on AAV serotype 9 for selection of endothelial cell-directed gene transfer vectors, Gene Therapy, 19:800-809.
Wagner, 1998, Efficient and persistent gene transfer of AAV-CFTR in maxillary sinus, Lancet, 351(9117):1702-1703.
Wall, 2010, Monosynaptic circuit tracing in vivo through ere-dependent targeting and complementation of modified rabies virus, Proc Natl Acad Sci USA, 107:21848-21853.
Wall, 2013, Differential innervation of direct- and indirect-pathway striatal projection neurons, Neuron, 79:347-360.
Wang, 2007, Existence of transient functional double-stranded DNA intermediates during recombinant AAV transduction, Proceedings of the National Academy of Sciences of the United States of America, 104(32):13104-13109.
Wang, 2014, Widespread spinal cord transduction by intrathecal injection of rAAV delivers efficacious RNAi therapy for amyotrophic lateral sclerosis, Hum Mol Genet, 23:668-681.
Waterkamp, 2006, Isolation of targeted AAV2 vectors from novel virus display libraries, J Gene Med., 8(11):1307-1319.
Wobus, 2000, Monoclonal antibodies against the adeno-associated virus type 2 (AAV-2) capsid: epitope mapping and identification of capsid domains involved in AAV-2-cell interaction and neutralization of AAV-2 infection, J Virol, 74:9281-9293.
Wu, 2000, Mutational Analysis of the Adeno-Assiciated Virus Type 2 (AAV2) Capsid Gene and Construction of AAV2 Vectors with Altered Tropism, Journal of Virology, 74(18):8635-8647.
Wu, 2006, Adeno-associated virus serotypes: vector toolkit for human gene therapy, Molecular therapy : The Journal of the American Society of Gene Therapy, 14:316-327.
Wu, 2012, Self-complementary AAVs induce more potent transgene product-specific immune responses compared to a single-stranded genome, Mol Ther, 20:572-579.
Xie, 2010, MicroRNA-regulated, Systemically Delivered rAAV9: A step closer to CNS-restricted transgene expression, Molecular therapy, 19:526-535.
Xu, 2008, Adeno-related viral shell modification and tumor targeting therapy, Chinese Science Bulletin, 53(21):2546-2553.
Yang, 2009, A myocardium tropic adeno-associated virus (AAV) evolved by DNA shuffling and in vivo selection, Proceedings of the National Academy of Sciences of the United States of America, 106:3946-3951.
Yang, 2014, Global CNS Transduction of Adult Mice by Intravenously Delivered rAAVrh.8 and rAAVrh.10 and Nonhuman Primates by rAAVrh.10, Molecular Therapy, 22:1299-1309.
Yang, 2014, Single-Cell Phenotyping within Transparent Intact Tissue through Whole-Body Clearing, Cell, 158:945-958.
Ying, 2010, Heart-targeted adeno-associated viral vectors selected by in vivo biopanning of a random viral display peptide library, Gene therapy, 17:980-990.
Zariwala, 2012, A Cre-dependent GCaMP3 reporter mouse for neuronal imaging in vivo, J. Neurosci., 32(9):3131-3141.
Zolotukhin, 1999, Recombinant adeno-associated virus purification using novel methods improves infectious titer and yield, Gene therapy, 6:973-985.
Albert, 1995, Site-Specific integration of DNA into wild-type and mutant lox sites placed in the plant genome, The Plant Journal: for cell and molecular biology, 7(4):649-659.
Araki, 1997, Targeted integration of DNA using mutant lox sites in embryonic stem cells, Nucleic Acids Res, 25:868-872.
Aschauer, 2013, Analyis of transduction efficiency, tropism and axonal transport of AAV serotypes 1, 2, 5, 6, 8, and 9 in the mouse brain, PloS One 8(9), e76310, 16 pages.
Asokan, 2010, Reengineered AAV vectors: old dog, new tricks, Discovery medicine, 9(48):399-403.
Asokan, 2012, The AAV Vector Toolkit: Poised at the Clinical Crossroads, Molecular Therapy: the Journal of the American Society of Gene Therapy, 20(4):699-708.
Ayuso, 2010, High AAV vector purity results in serotype- and tissue-independent enhancement of transduction efficiency, Gene Therapy, 17(4):503-510.
Balazs, 2011, Antibody-based protection against HIV infection by vectored immunoprophylaxis, Nature, 481(7379):81-84.
Balazs, 2013, Broad protection against influenza infection by vectored immunoprophylaxis in mice, Nature Biotechnology, 7:647-52.
Bartel, 2011, Enhancing the Clinical Potential of AAV Vectors by Capsid Engineering to Evade Pre-Existing Immunity, Frontiers in Microbiology, vol. 2, Article 204, 10 pages.

(56) References Cited

OTHER PUBLICATIONS

Bartel, 2012, Directed evolution of novel adeno-associated viruses for therapeutic gene delivery, Gene Therapy, 19:694-700.
Bartlett, 1998, Selective and rapid uptake of adeno-associated virus type 2 in brain, Human Gene Therapy, 9(8)1181-1186.
Bartlett, 1999, Targeted adeno-associated virus vector transduction of nonpermissive cells mediated by a bispecific F(ab'gamma)2 antibody, Nat Biotechnol, 1999, vol. 17, pp. 181-186.
Bedbrook, 2018, Viral Strategies for Targeting the Central and Peripheral Nervous Systems, Annual Review of Neuroscience, 41:323-348.
Betley, 2011, Adeno-associated viral vectors for mapping, monitoring, and manipulating neural circuits, Hum Gene Ther, 2011, vol. 22, pp. 669-677.
Bevan, 2011, Systemic gene delivery in large species for targeting spinal cord, brain, and peripheral tissues for pediatric disorders, Molecular therapy: The Journal of the America Society of Gene Therapy, vol. 19, pp. 1971-1980.
Borel, 2014, Recombinant AAV as a platform for translating the therapeutic potential of RNA interference, Molecular Therapy: The Journal of the American Society of Gene Therapy, vol. 22, pp. 692-701.
Boudreau, 2009, Nonallele-specific silencing of mutant and wild-type huntingtin demonstrates therapeutic efficacy in Huntington's disease mice, Molecular therapy: The Journal of the American Society of Gene Therapy, vol. 17, pp. 1053-1063.
Boutin, 2010, Prevalence of serum IgG and neutralizing factors against adeno-associated virus (AAV) types 1, 2, 5, 6, 8, and 9 in the healthy population: implications for gene therapy using AAV vectors, Hum Gene Ther, 21:704-712.
Calcedo, 2009, Worldwide epidemiology of neutralizing antibodies to adeno-associated viruses, J Infect Dis, 1999:381-390.
Callaway, 2008, Transneuronal circuit tracing with neurotropic viruses, Curr Opin Neurobiol, 18:617-623.
Castle, 2014, Adeno-Associated Virus Serotypes 1, 8 and 9 Share Conserved Mechanisms for Anterograde and Retrograde Axonal Transport, Hum Gene Ther, 25(8):705-720.
Castle, 2014, Long-distance axonal transport of AAV9 is driven by dynein and kinesin-2 and is trafficked in a highly motile Rab7-positive compartment, Molecular Therapy, 22:554-566.
Cearley, 2007, A single injection of an adeno-associated virus vector into neuclei with divergent connections results in widespread vector distribution in the brain and global correction of a neurogenetic disease, The Journal of Neuroscience: The Official Journal of the Society for Neuroscience, 27:9928-9940.
Chakrabarty, 2013, Capsid serotype and timing of injection determines AAV transduction in the neonatal mice brain, PLoS One, 8(6):e67680, 9 pages.
Challis, 2018, Widespread and targeted gene expression by systemic AAV vectors: Production, purification, and administration, bioRxiv. org, 66 pages.
Challis, 2019, Systemic AAV vectors for widespreadand targeted gene delivery in rodents, Nature Protocols, 14:379-414.
Chan, 2017, Engineered AAVs for efficient noninvasive gene delivery to the central and peripheral nervous systems, Nat Neurosci, 20(8):1172-1179.
Chen, 2003, New Insight Into Site-Specific Recombination From FLP Recombinase-DNA Structures, Annu. Rev. Biophys. Biomol. Struct., 32:135-159.
Chiorini, 1999, Cloning and Characterization of adeno-associated virus type, J. Virol., 73:1309-1319.
Chung, 2013, CLARITY for mapping the nervous system, Nat Methods, 10(6):508-513.
Clark, 1999, Highly purified recombinant adeno-associated virus vectors are biologically active and free of detectable helper and wild-type viruses, Hum Gene Ther., 10(6):1031-9.
Coleman, 2018, Visual Biochemistry, 5th edition, Laboratory of Knowledge, Moscow, p. 58.
Dalkara, 2013, In vivo-directed evolution of a new adeno-associated virus for therapeutic outer retinal gene delivery from the vitreous, Science translational medicine, 5(189):189ra176.
De, 2006, High levels of persistent expression of alpha1-antitrypsin rh.10 adeno-associated virus despite preexisting immunity to common human adeno-assiciated viruses, Mol. Ther., 13(1):67-76.
Deverman, 2016, Cre-dependent selection yields AAV variants for widespread gene transfer to the adult brain, Nature Biotechnology, 34-204-209.
Dufour, 2014, Intrajugular vein delivery of AAV9-RNAi prevents neuropathological changes ad weight loss in Huntington's disease mice, Molecular therapy: The Journal of the American Society of Gene Therapy, 22:797-810.
Duque, 2009, Intravenous Administration of Self-complementary AAV9 Enables Transgene Delivery to Adult Motor Neurons, Molecular therapy: The Journal of the American Society of Gene Therapy, 17:1187-1196.
Excoffon, 2009, Directed evolution of adeno-associated virus to an infectious respiratory virus, Proceedings of the National Academy of Sciences of the Untied States of America, 106(10):3865-3870.
Farris, 2008, Improved splicing of adeno-associated viral (AAV) capsid rotein-supplying pre-mRNAs leads to increased recombinant AAV vector prodcution, Human Gene Therapy, 19:1421-1427.
Fenno, 2011, The development and application of optogenetics, Annual review of neuroscience, 34:389-412.
Fenno, 2014, Targeting cells with single vectors using multiple-feature Boolean logic, Nat Methods, 11:763-772.
Flotte, 1998, Adeo-associated virus vectors for gene therapy of cystic fibrosis, Methods Enzymol, 292:717-732.
Flytzanis, 2020, Broad gene expression throughout the mouse and marmoset brain after intravenous delivery of engineered AAV capsids, bioRxiv.org, 21 pages.
Foust, 2009, Intravascular AAV9 preferentially targets neonatal neurons and adult astrocytes, Nature biotechnology, 27:59-65.
Foust, 2010, Rescue of the spinal muscular atrophy phenotype in a mouse model by early postnatal delivery of SMN, Nat Biotechnol, 28:271-274.
Foust, 2013, Therapeutic AAV9-mediated Suppression of Mutant SOD1 Slows Disease Progression and Extends Survival in Models of inherited ALS, Molecular therapy: The Journal of the American Society of Gene Therapy, 21(12):2148-2159.
Gao, 2004, Clades of Adeno-associated viruses are widely disseminated in human tissues, J Virol., 78(12):6381-8.
Garcia, 2004, GFAP-expressing progenitors are the principal source of constitutive neurogenesis in adult mouse forebrain, Nature neuroscience, 7:1233-1241.
Garg, 2013, Systemic Delivery of MeCP2 Rescues Behavioral and Cellular Deficits in Female Mouse Models of Rett Syndrome, The Journal of Neuroscience: The Official Journal of the Society for Neuroscience, 33:13612-13620.
Gaudet, 2010, Review of the clinical development of alipogene tiparvovec gene therapy for lipoprotein lipase deficiency, Atherosclerosis Supplements, 11:55-60.

\* cited by examiner

FIG. 2

| DNA SEQ ID NO | AA SEQ ID NO | Log 10 enrichment in the brain |
|---|---|---|
| 12740 | 11 | 1.912817683 |
| 12741 | 12 | 1.683542214 |
| 12742 | 13 | 1.646549793 |
| 12743 | 14 | 1.624376814 |
| 12744 | 15 | 1.609487799 |
| 12745 | 16 | 1.581298365 |
| 12746 | 17 | 1.560127515 |
| 12747 | 18 | 1.532606441 |
| 12748 | 19 | 1.510809312 |
| 12749 | 20 | 1.497374065 |
| 12750 | 21 | 1.495179943 |
| 12751 | 22 | 1.492959081 |
| 12752 | 23 | 1.465659651 |
| 12753 | 24 | 1.464822053 |
| 12754 | 25 | 1.464030027 |
| 12755 | 26 | 1.458626389 |
| 12756 | 27 | 1.456753138 |
| 12757 | 28 | 1.451684533 |
| 12758 | 29 | 1.44624661 |
| 12759 | 30 | 1.424823398 |
| 12760 | 31 | 1.414846289 |
| 12761 | 32 | 1.414026449 |
| 12762 | 33 | 1.407667705 |
| 12763 | 34 | 1.401327526 |
| 12764 | 35 | 1.397448539 |
| 12765 | 36 | 1.397202271 |
| 12766 | 37 | 1.392230734 |
| 12767 | 38 | 1.381591777 |
| 12768 | 39 | 1.379179167 |
| 12769 | 40 | 1.376188618 |
| 12770 | 41 | 1.367455168 |
| 12771 | 42 | 1.367065364 |
| 12772 | 43 | 1.35551795 |
| 12773 | 44 | 1.352278129 |
| 12774 | 45 | 1.346786579 |
| 12775 | 46 | 1.34383415 |
| 12776 | 47 | 1.341943936 |
| 12777 | 48 | 1.339902445 |
| 12778 | 49 | 1.336311796 |
| 12779 | 50 | 1.329892702 |
| 12780 | 51 | 1.329439904 |
| 12781 | 52 | 1.328486458 |
| 12782 | 53 | 1.327743439 |
| 12783 | 54 | 1.32517543 |
| 12784 | 55 | 1.322496095 |
| 12785 | 56 | 1.320628446 |
| 12786 | 57 | 1.318377088 |
| 12787 | 58 | 1.316220587 |
| 12788 | 59 | 1.315353443 |
| 12789 | 60 | 1.312609696 |
| 12790 | 61 | 1.312160906 |
| 12791 | 62 | 1.310022222 |
| 12792 | 63 | 1.309518619 |
| 12793 | 64 | 1.306381891 |
| 12794 | 65 | 1.301939226 |
| 12795 | 66 | 1.301709563 |
| 12796 | 67 | 1.299175819 |
| 12797 | 68 | 1.290697898 |
| 12798 | 69 | 1.289568392 |
| 12799 | 70 | 1.287980477 |
| 12800 | 71 | 1.286624012 |
| 12801 | 72 | 1.285052291 |
| 12802 | 73 | 1.282728968 |
| 12803 | 74 | 1.278319849 |
| 12804 | 75 | 1.275593274 |
| 12805 | 76 | 1.274661346 |
| 12806 | 77 | 1.273234025 |
| 12807 | 78 | 1.268647757 |
| 12808 | 79 | 1.266338552 |
| 12809 | 80 | 1.263761129 |
| 12810 | 81 | 1.26298491 |
| 12811 | 82 | 1.262610679 |
| 12812 | 83 | 1.262390393 |
| 12813 | 84 | 1.261678178 |
| 12814 | 85 | 1.259605169 |
| 12815 | 86 | 1.257729164 |
| 12816 | 87 | 1.255488603 |
| 12817 | 88 | 1.255155632 |
| 12818 | 89 | 1.254372642 |
| 12819 | 90 | 1.249837762 |
| 12820 | 91 | 1.243541237 |
| 12821 | 92 | 1.239129583 |
| 12822 | 93 | 1.235336594 |
| 12823 | 94 | 1.235150906 |
| 12824 | 95 | 1.234689681 |
| 12825 | 96 | 1.231576445 |
| 12826 | 97 | 1.231576445 |
| 12827 | 98 | 1.231576445 |
| 12828 | 99 | 1.228870552 |
| 12829 | 100 | 1.228347475 |
| 12830 | 101 | 1.227339393 |
| 12831 | 102 | 1.226613026 |
| 12832 | 103 | 1.224627586 |
| 12833 | 104 | 1.224338037 |
| 12834 | 105 | 1.223797829 |
| 12835 | 106 | 1.221816608 |
| 12836 | 107 | 1.221276489 |
| 12837 | 108 | 1.218666529 |
| 12838 | 109 | 1.218414999 |
| 12839 | 110 | 1.218073975 |
| 12840 | 111 | 1.214638024 |
| 12841 | 112 | 1.213424183 |
| 12842 | 113 | 1.212227129 |
| 12843 | 114 | 1.211476697 |
| 12844 | 115 | 1.209857196 |
| 12845 | 116 | 1.209857196 |
| 12846 | 117 | 1.201953979 |
| 12847 | 118 | 1.201928042 |
| 12848 | 119 | 1.201613222 |
| 12849 | 120 | 1.200542212 |
| 12850 | 121 | 1.200167981 |
| 12851 | 122 | 1.199862032 |
| 12852 | 123 | 1.196814339 |
| 12853 | 124 | 1.194084635 |
| 12854 | 125 | 1.193231453 |
| 12855 | 126 | 1.192382724 |
| 12856 | 127 | 1.1866093 |
| 12857 | 128 | 1.186498071 |
| 12858 | 129 | 1.183884455 |
| 12859 | 130 | 1.183884455 |
| 12860 | 131 | 1.182214831 |
| 12861 | 132 | 1.182091082 |
| 12862 | 133 | 1.181831686 |
| 12863 | 134 | 1.180423923 |
| 12864 | 135 | 1.179440243 |
| 12865 | 136 | 1.178498002 |
| 12866 | 137 | 1.176907349 |
| 12867 | 138 | 1.176383945 |
| 12868 | 139 | 1.17146908 |
| 12869 | 140 | 1.171160523 |
| 12870 | 141 | 1.17062002 |
| 12871 | 142 | 1.170381985 |
| 12872 | 143 | 1.167118456 |
| 12873 | 144 | 1.16589767 |
| 12874 | 145 | 1.165446767 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 12875 | 146 | 1.164629656 | 12904 | 175 | 1.126066261 | 12933 | 204 | 1.094993728 | 12962 | 233 | 1.079288101 | 12991 | 262 | 1.066593068 |
| 12876 | 147 | 1.164629656 | 12905 | 176 | 1.125618303 | 12934 | 205 | 1.094738486 | 12963 | 234 | 1.07909396 | 12992 | 263 | 1.066143255 |
| 12877 | 148 | 1.158618564 | 12906 | 177 | 1.125121115 | 12935 | 206 | 1.094403252 | 12964 | 235 | 1.078348069 | 12993 | 264 | 1.064628566 |
| 12878 | 149 | 1.158555508 | 12907 | 178 | 1.121163962 | 12936 | 207 | 1.094342123 | 12965 | 236 | 1.078149171 | 12994 | 265 | 1.063959494 |
| 12879 | 150 | 1.156075683 | 12908 | 179 | 1.121163962 | 12937 | 208 | 1.093830178 | 12966 | 237 | 1.077204436 | 12995 | 266 | 1.063310524 |
| 12880 | 151 | 1.1551881 | 12909 | 180 | 1.120878148 | 12938 | 209 | 1.090813149 | 12967 | 238 | 1.076674485 | 12996 | 267 | 1.062271176 |
| 12881 | 152 | 1.154529329 | 12910 | 181 | 1.120635141 | 12939 | 210 | 1.090813149 | 12968 | 239 | 1.076674485 | 12997 | 268 | 1.061559334 |
| 12882 | 153 | 1.154410491 | 12911 | 182 | 1.120161744 | 12940 | 211 | 1.09046277 | 12969 | 240 | 1.075571748 | 12998 | 269 | 1.060180308 |
| 12883 | 154 | 1.15423934 | 12912 | 183 | 1.119817311 | 12941 | 212 | 1.089343454 | 12970 | 241 | 1.075423516 | 12999 | 270 | 1.060180308 |
| 12884 | 155 | 1.152891253 | 12913 | 184 | 1.119689276 | 12942 | 213 | 1.088908942 | 12971 | 242 | 1.075038723 | 13000 | 271 | 1.058278087 |
| 12885 | 156 | 1.152395199 | 12914 | 185 | 1.119349674 | 12943 | 214 | 1.088683393 | 12972 | 243 | 1.074790342 | 13001 | 272 | 1.058174325 |
| 12886 | 157 | 1.151954067 | 12915 | 186 | 1.118536932 | 12944 | 215 | 1.08797094 | 12973 | 244 | 1.073968592 | 13002 | 273 | 1.058125283 |
| 12887 | 158 | 1.151892834 | 12916 | 187 | 1.118172255 | 12945 | 216 | 1.08766987 | 12974 | 245 | 1.073123935 | 13003 | 274 | 1.057988332 |
| 12888 | 159 | 1.151056849 | 12917 | 188 | 1.118097331 | 12946 | 217 | 1.08674288 | 12975 | 246 | 1.073009531 | 13004 | 275 | 1.057945785 |
| 12889 | 160 | 1.150868679 | 12918 | 189 | 1.116069944 | 12947 | 218 | 1.086361753 | 12976 | 247 | 1.072975919 | 13005 | 276 | 1.057789141 |
| 12890 | 161 | 1.150162318 | 12919 | 190 | 1.112212811 | 12948 | 219 | 1.08544841 | 12977 | 248 | 1.072859282 | 13006 | 277 | 1.055485186 |
| 12891 | 162 | 1.148336343 | 12920 | 191 | 1.109534948 | 12949 | 220 | 1.084523395 | 12978 | 249 | 1.072518526 | 13007 | 278 | 1.055485186 |
| 12892 | 163 | 1.146900889 | 12921 | 192 | 1.109004442 | 12950 | 221 | 1.084130368 | 12979 | 250 | 1.072255397 | 13008 | 279 | 1.053805128 |
| 12893 | 164 | 1.14614625 | 12922 | 193 | 1.106637709 | 12951 | 222 | 1.083973724 | 12980 | 251 | 1.072063324 | 13009 | 280 | 1.05303845 |
| 12894 | 165 | 1.144885598 | 12923 | 194 | 1.105531225 | 12952 | 223 | 1.08351391 | 12981 | 252 | 1.071279454 | 13010 | 281 | 1.050984685 |
| 12895 | 166 | 1.141399815 | 12924 | 195 | 1.104703209 | 12953 | 224 | 1.082637432 | 12982 | 253 | 1.070997353 | 13011 | 282 | 1.049952698 |
| 12896 | 167 | 1.139806072 | 12925 | 196 | 1.101666172 | 12954 | 225 | 1.082407829 | 12983 | 254 | 1.070832878 | 13012 | 283 | 1.047832222 |
| 12897 | 168 | 1.139430222 | 12926 | 197 | 1.101666172 | 12955 | 226 | 1.081928669 | 12984 | 255 | 1.070725153 | 13013 | 284 | 1.047290708 |
| 12898 | 169 | 1.138959329 | 12927 | 198 | 1.100297531 | 12956 | 227 | 1.081814125 | 12985 | 256 | 1.069495901 | 13014 | 285 | 1.046530344 |
| 12899 | 170 | 1.131873532 | 12928 | 199 | 1.100297531 | 12957 | 228 | 1.081526988 | 12986 | 257 | 1.068547659 | 13015 | 286 | 1.045500965 |
| 12900 | 171 | 1.131681579 | 12929 | 200 | 1.097682866 | 12958 | 229 | 1.081190587 | 12987 | 258 | 1.067983732 | 13016 | 287 | 1.043964763 |
| 12901 | 172 | 1.129062555 | 12930 | 201 | 1.096877872 | 12959 | 230 | 1.081039291 | 12988 | 259 | 1.067894444 | 13017 | 288 | 1.04325073 |
| 12902 | 173 | 1.129038347 | 12931 | 202 | 1.096103037 | 12960 | 231 | 1.08030877 | 12989 | 260 | 1.06738441 | 13018 | 289 | 1.042843706 |
| 12903 | 174 | 1.128356959 | 12932 | 203 | 1.095157891 | 12961 | 232 | 1.08030877 | 12990 | 261 | 1.066766197 | 13019 | 290 | 1.042520209 |

FIG. 2 (Cont.)

| DNA SEQ ID NO | AA SEQ ID NO | Log 10 enrichment in the brain |
|---|---|---|
| 13020 | 291 | 1.042223256 |
| 13021 | 292 | 1.040351443 |
| 13022 | 293 | 1.039247988 |
| 13023 | 294 | 1.039038335 |
| 13024 | 295 | 1.037440684 |
| 13025 | 296 | 1.037001781 |
| 13026 | 297 | 1.0352818 |
| 13027 | 298 | 1.035022132 |
| 13028 | 299 | 1.034295887 |
| 13029 | 300 | 1.032470823 |
| 13030 | 301 | 1.031446946 |
| 13031 | 302 | 1.030531904 |
| 13032 | 303 | 1.030531904 |
| 13033 | 304 | 1.029156248 |
| 13034 | 305 | 1.02861304 |
| 13035 | 306 | 1.027941437 |
| 13036 | 307 | 1.027456463 |
| 13037 | 308 | 1.02665886 |
| 13038 | 309 | 1.02619581 |
| 13039 | 310 | 1.026030207 |
| 13040 | 311 | 1.026030207 |
| 13041 | 312 | 1.026030207 |
| 13042 | 313 | 1.025680205 |
| 13043 | 314 | 1.025261204 |
| 13044 | 315 | 1.024861439 |
| 13045 | 316 | 1.024816367 |
| 13046 | 317 | 1.024816367 |
| 13047 | 318 | 1.023770773 |
| 13048 | 319 | 1.021962152 |

| DNA SEQ ID NO | AA SEQ ID NO | Log 10 enrichment in the brain |
|---|---|---|
| 13049 | 320 | 1.021736603 |
| 13050 | 321 | 1.021538657 |
| 13051 | 322 | 1.021271086 |
| 13052 | 323 | 1.02072308 |
| 13053 | 324 | 1.02072308 |
| 13054 | 325 | 1.02072308 |
| 13055 | 326 | 1.02019313 |
| 13056 | 327 | 1.017696626 |
| 13057 | 328 | 1.016855784 |
| 13058 | 329 | 1.015106024 |
| 13059 | 330 | 1.014740219 |
| 13060 | 331 | 1.01428897 |
| 13061 | 332 | 1.013081338 |
| 13062 | 333 | 1.012897743 |
| 13063 | 334 | 1.012632686 |
| 13064 | 335 | 1.010903054 |
| 13065 | 336 | 1.010738859 |
| 13066 | 337 | 1.010563682 |
| 13067 | 338 | 1.010518041 |
| 13068 | 339 | 1.009727696 |
| 13069 | 340 | 1.009727696 |
| 13070 | 341 | 1.009727696 |
| 13071 | 342 | 1.009727696 |
| 13072 | 343 | 1.008488624 |
| 13073 | 344 | 1.006267164 |
| 13074 | 345 | 1.006047212 |
| 13075 | 346 | 1.005797402 |
| 13076 | 347 | 1.005797402 |
| 13077 | 348 | 1.005571736 |

| DNA SEQ ID NO | AA SEQ ID NO | Log 10 enrichment in the brain |
|---|---|---|
| 13078 | 349 | 1.005180068 |
| 13079 | 350 | 1.004706894 |
| 13080 | 351 | 1.004332664 |
| 13081 | 352 | 1.003778363 |
| 13082 | 353 | 1.001127524 |
| 13083 | 354 | 1.001127524 |
| 13084 | 355 | 1.000679567 |
| 13085 | 356 | 0.999729954 |
| 13086 | 357 | 0.99871764 |
| 13087 | 358 | 0.995899496 |
| 13088 | 359 | 0.995813181 |
| 13089 | 360 | 0.995756754 |
| 13090 | 361 | 0.995687439 |
| 13091 | 362 | 0.995118742 |
| 13092 | 363 | 0.995004439 |
| 13093 | 364 | 0.993967148 |
| 13094 | 365 | 0.99373959 |
| 13095 | 366 | 0.993216659 |
| 13096 | 367 | 0.993158594 |
| 13097 | 368 | 0.991998929 |
| 13098 | 369 | 0.99124429 |
| 13099 | 370 | 0.990218455 |
| 13100 | 371 | 0.988538397 |
| 13101 | 372 | 0.988538397 |
| 13102 | 373 | 0.988538397 |
| 13103 | 374 | 0.988538397 |
| 13104 | 375 | 0.987097949 |
| 13105 | 376 | 0.987027806 |
| 13106 | 377 | 0.986541637 |

| DNA SEQ ID NO | AA SEQ ID NO | Log 10 enrichment in the brain |
|---|---|---|
| 13107 | 378 | 0.986063778 |
| 13108 | 379 | 0.98544732 |
| 13109 | 380 | 0.984596211 |
| 13110 | 381 | 0.980713059 |
| 13111 | 382 | 0.980234234 |
| 13112 | 383 | 0.980064089 |
| 13113 | 384 | 0.979764472 |
| 13114 | 385 | 0.979764472 |
| 13115 | 386 | 0.979764472 |
| 13116 | 387 | 0.979238374 |
| 13117 | 388 | 0.979238374 |
| 13118 | 389 | 0.979096841 |
| 13119 | 390 | 0.978645156 |
| 13120 | 391 | 0.978554176 |
| 13121 | 392 | 0.977289853 |
| 13122 | 393 | 0.976768178 |
| 13123 | 394 | 0.975443099 |
| 13124 | 395 | 0.97496559 |
| 13125 | 396 | 0.974180247 |
| 13126 | 397 | 0.973581082 |
| 13127 | 398 | 0.97329843 |
| 13128 | 399 | 0.97329843 |
| 13129 | 400 | 0.973004889 |
| 13130 | 401 | 0.972510951 |
| 13131 | 402 | 0.972510951 |
| 13132 | 403 | 0.972510951 |
| 13133 | 404 | 0.972510951 |
| 13134 | 405 | 0.972301198 |
| 13135 | 406 | 0.972245084 |

| DNA SEQ ID NO | AA SEQ ID NO | Log 10 enrichment in the brain |
|---|---|---|
| 13136 | 407 | 0.971708189 |
| 13137 | 408 | 0.970889691 |
| 13138 | 409 | 0.970663673 |
| 13139 | 410 | 0.970474397 |
| 13140 | 411 | 0.970313577 |
| 13141 | 412 | 0.970054991 |
| 13142 | 413 | 0.969917142 |
| 13143 | 414 | 0.969299039 |
| 13144 | 415 | 0.969299039 |
| 13145 | 416 | 0.969233242 |
| 13146 | 417 | 0.967654831 |
| 13147 | 418 | 0.967063284 |
| 13148 | 419 | 0.966927248 |
| 13149 | 420 | 0.965874412 |
| 13150 | 421 | 0.965620661 |
| 13151 | 422 | 0.965524033 |
| 13152 | 423 | 0.965524033 |
| 13153 | 424 | 0.965057301 |
| 13154 | 425 | 0.964915351 |
| 13155 | 426 | 0.964404717 |
| 13156 | 427 | 0.963714813 |
| 13157 | 428 | 0.963270295 |
| 13158 | 429 | 0.963215567 |
| 13159 | 430 | 0.962731133 |
| 13160 | 431 | 0.962731133 |
| 13161 | 432 | 0.962731133 |
| 13162 | 433 | 0.960808055 |
| 13163 | 434 | 0.960698867 |
| 13164 | 435 | 0.960648182 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13165 | 436 | 0.95940319 | 13194 | 465 | 0.947851308 | 13223 | 494 | 0.933078786 | 13252 | 523 | 0.924206272 | 13281 | 552 | 0.913904778 |
| 13166 | 437 | 0.959318192 | 13195 | 466 | 0.947729572 | 13224 | 495 | 0.932965924 | 13253 | 524 | 0.924080408 | 13282 | 553 | 0.913221866 |
| 13167 | 438 | 0.959191631 | 13196 | 467 | 0.947145712 | 13225 | 496 | 0.932723369 | 13254 | 525 | 0.923670932 | 13283 | 554 | 0.913221866 |
| 13168 | 439 | 0.957698696 | 13197 | 468 | 0.946340717 | 13226 | 497 | 0.931977405 | 13255 | 526 | 0.923247211 | 13284 | 555 | 0.913133648 |
| 13169 | 440 | 0.957054 | 13198 | 469 | 0.946340717 | 13227 | 498 | 0.93054645 | 13256 | 527 | 0.923206087 | 13285 | 556 | 0.912448228 |
| 13170 | 441 | 0.956559882 | 13199 | 470 | 0.946340717 | 13228 | 499 | 0.93054645 | 13257 | 528 | 0.92257752 | 13286 | 557 | 0.91232163 |
| 13171 | 442 | 0.956559882 | 13200 | 471 | 0.94512845 | 13229 | 500 | 0.93054645 | 13258 | 529 | 0.921946278 | 13287 | 558 | 0.91232163 |
| 13172 | 443 | 0.956353713 | 13201 | 472 | 0.944694101 | 13230 | 501 | 0.93054645 | 13259 | 530 | 0.921831218 | 13288 | 559 | 0.912219069 |
| 13173 | 444 | 0.956353713 | 13202 | 473 | 0.94404892 | 13231 | 502 | 0.93054645 | 13260 | 531 | 0.921591607 | 13289 | 560 | 0.910802392 |
| 13174 | 445 | 0.95595103 | 13203 | 474 | 0.943258415 | 13232 | 503 | 0.93054645 | 13261 | 532 | 0.921591607 | 13290 | 561 | 0.910428161 |
| 13175 | 446 | 0.955630793 | 13204 | 475 | 0.943063007 | 13233 | 504 | 0.93054645 | 13262 | 533 | 0.921338448 | 13291 | 562 | 0.910024783 |
| 13176 | 447 | 0.954458607 | 13205 | 476 | 0.942128322 | 13234 | 505 | 0.93054645 | 13263 | 534 | 0.921148675 | 13292 | 563 | 0.909357151 |
| 13177 | 448 | 0.954458607 | 13206 | 477 | 0.941925996 | 13235 | 506 | 0.93054645 | 13264 | 535 | 0.921001132 | 13293 | 564 | 0.909357151 |
| 13178 | 449 | 0.953776291 | 13207 | 478 | 0.941925996 | 13236 | 507 | 0.928422756 | 13265 | 536 | 0.920786613 | 13294 | 565 | 0.908496309 |
| 13179 | 450 | 0.953611754 | 13208 | 479 | 0.941182765 | 13237 | 508 | 0.927969027 | 13266 | 537 | 0.920786613 | 13295 | 566 | 0.908270055 |
| 13180 | 451 | 0.952822845 | 13209 | 480 | 0.940846406 | 13238 | 509 | 0.927969027 | 13267 | 538 | 0.920786613 | 13296 | 567 | 0.908270055 |
| 13181 | 452 | 0.952822845 | 13210 | 481 | 0.940663584 | 13239 | 510 | 0.927906354 | 13268 | 539 | 0.920485124 | 13297 | 568 | 0.908270055 |
| 13182 | 453 | 0.952822845 | 13211 | 482 | 0.938979617 | 13240 | 511 | 0.927906354 | 13269 | 540 | 0.919606464 | 13298 | 569 | 0.907738157 |
| 13183 | 454 | 0.951231049 | 13212 | 483 | 0.938371787 | 13241 | 512 | 0.927698607 | 13270 | 541 | 0.919551065 | 13299 | 570 | 0.907562543 |
| 13184 | 455 | 0.949851605 | 13213 | 484 | 0.938233278 | 13242 | 513 | 0.92726874 | 13271 | 542 | 0.919551065 | 13300 | 571 | 0.906832176 |
| 13185 | 456 | 0.949851605 | 13214 | 485 | 0.938013014 | 13243 | 514 | 0.927058122 | 13272 | 543 | 0.919066632 | 13301 | 572 | 0.906696839 |
| 13186 | 457 | 0.949851605 | 13215 | 486 | 0.937845689 | 13244 | 515 | 0.926818577 | 13273 | 544 | 0.918380543 | 13302 | 573 | 0.906187104 |
| 13187 | 458 | 0.949431794 | 13216 | 487 | 0.937845689 | 13245 | 516 | 0.926137331 | 13274 | 545 | 0.917603843 | 13303 | 574 | 0.905564162 |
| 13188 | 459 | 0.949386273 | 13217 | 488 | 0.937385874 | 13246 | 517 | 0.926045949 | 13275 | 546 | 0.917182488 | 13304 | 575 | 0.905329661 |
| 13189 | 460 | 0.949029855 | 13218 | 489 | 0.93698056 | 13247 | 518 | 0.925950698 | 13276 | 547 | 0.916845172 | 13305 | 576 | 0.905240585 |
| 13190 | 461 | 0.949029855 | 13219 | 490 | 0.935625975 | 13248 | 519 | 0.925950698 | 13277 | 548 | 0.915654894 | 13306 | 577 | 0.904908513 |
| 13191 | 462 | 0.948519821 | 13220 | 491 | 0.934512637 | 13249 | 520 | 0.925525648 | 13278 | 549 | 0.9156061 | 13307 | 578 | 0.904739186 |
| 13192 | 463 | 0.948421174 | 13221 | 492 | 0.93412091 | 13250 | 521 | 0.92540681 | 13279 | 550 | 0.915034284 | 13308 | 579 | 0.904217511 |
| 13193 | 464 | 0.948037182 | 13222 | 493 | 0.933202693 | 13251 | 522 | 0.924869317 | 13280 | 551 | 0.913904778 | 13309 | 580 | 0.904217511 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13310 | 581 | 0.904217511 | 13339 | 610 | 0.895784344 | 13368 | 639 | 0.886342787 | 13397 | 668 | 0.880467585 | 13426 | 697 | 0.872032828 |
| 13311 | 582 | 0.903272365 | 13340 | 611 | 0.895116712 | 13369 | 640 | 0.886342787 | 13398 | 669 | 0.879393927 | 13427 | 698 | 0.871840789 |
| 13312 | 583 | 0.903002701 | 13341 | 612 | 0.89502575 | 13370 | 641 | 0.885964317 | 13399 | 670 | 0.879393927 | 13428 | 699 | 0.871679791 |
| 13313 | 584 | 0.902517726 | 13342 | 613 | 0.894741619 | 13371 | 642 | 0.885624945 | 13400 | 671 | 0.879393927 | 13429 | 700 | 0.871424998 |
| 13314 | 585 | 0.901752257 | 13343 | 614 | 0.894501346 | 13372 | 643 | 0.88531891 | 13401 | 672 | 0.879393927 | 13430 | 701 | 0.871081818 |
| 13315 | 586 | 0.901670322 | 13344 | 615 | 0.894501346 | 13373 | 644 | 0.885041529 | 13402 | 673 | 0.879393927 | 13431 | 702 | 0.87096076 |
| 13316 | 587 | 0.901388221 | 13345 | 616 | 0.894501346 | 13374 | 645 | 0.884558013 | 13403 | 674 | 0.878218569 | 13432 | 703 | 0.870707748 |
| 13317 | 588 | 0.900583226 | 13346 | 617 | 0.893701392 | 13375 | 646 | 0.88424643 | 13404 | 675 | 0.87815838 | 13433 | 704 | 0.869848609 |
| 13318 | 589 | 0.900583226 | 13347 | 618 | 0.893634366 | 13376 | 647 | 0.884014125 | 13405 | 676 | 0.877840099 | 13434 | 705 | 0.869848609 |
| 13319 | 590 | 0.900304922 | 13348 | 619 | 0.893119952 | 13377 | 648 | 0.884014125 | 13406 | 677 | 0.877387945 | 13435 | 706 | 0.869455405 |
| 13320 | 591 | 0.899597313 | 13349 | 620 | 0.892757889 | 13378 | 649 | 0.883970308 | 13407 | 678 | 0.877300938 | 13436 | 707 | 0.869351989 |
| 13321 | 592 | 0.899137986 | 13350 | 621 | 0.892583928 | 13379 | 650 | 0.883803046 | 13408 | 679 | 0.877300938 | 13437 | 708 | 0.869108755 |
| 13322 | 593 | 0.899137986 | 13351 | 622 | 0.8924564 | 13380 | 651 | 0.883803046 | 13409 | 680 | 0.877206041 | 13438 | 709 | 0.868800854 |
| 13323 | 594 | 0.898361766 | 13352 | 623 | 0.892168215 | 13381 | 652 | 0.883433905 | 13410 | 681 | 0.876388417 | 13439 | 710 | 0.868054002 |
| 13324 | 595 | 0.898361766 | 13353 | 624 | 0.891293151 | 13382 | 653 | 0.883324221 | 13411 | 682 | 0.876188787 | 13440 | 711 | 0.86775562 |
| 13325 | 596 | 0.898361766 | 13354 | 625 | 0.890952088 | 13383 | 654 | 0.8831218 | 13412 | 683 | 0.876040285 | 13441 | 712 | 0.867494704 |
| 13326 | 597 | 0.897877333 | 13355 | 626 | 0.89089909 | 13384 | 655 | 0.882622897 | 13413 | 684 | 0.875834117 | 13442 | 713 | 0.86722182 |
| 13327 | 598 | 0.897753936 | 13356 | 627 | 0.890837079 | 13385 | 656 | 0.882622897 | 13414 | 685 | 0.875697782 | 13443 | 714 | 0.867060192 |
| 13328 | 599 | 0.897417031 | 13357 | 628 | 0.890429227 | 13386 | 657 | 0.882622897 | 13415 | 686 | 0.875498883 | 13444 | 715 | 0.866712896 |
| 13329 | 600 | 0.897046828 | 13358 | 629 | 0.889153765 | 13387 | 658 | 0.882622897 | 13416 | 687 | 0.875277361 | 13445 | 716 | 0.866636697 |
| 13330 | 601 | 0.896979102 | 13359 | 630 | 0.889153765 | 13388 | 659 | 0.882420382 | 13417 | 688 | 0.874662268 | 13446 | 717 | 0.86642895 |
| 13331 | 602 | 0.896863337 | 13360 | 631 | 0.889153765 | 13389 | 660 | 0.882358406 | 13418 | 689 | 0.874497658 | 13447 | 718 | 0.86642895 |
| 13332 | 603 | 0.896768023 | 13361 | 632 | 0.888733954 | 13390 | 661 | 0.882358406 | 13419 | 690 | 0.874065094 | 13448 | 719 | 0.865992473 |
| 13333 | 604 | 0.896620329 | 13362 | 633 | 0.887994099 | 13391 | 662 | 0.881813401 | 13420 | 691 | 0.873641598 | 13449 | 720 | 0.865605643 |
| 13334 | 605 | 0.896427267 | 13363 | 634 | 0.887994099 | 13392 | 663 | 0.881697882 | 13421 | 692 | 0.873641598 | 13450 | 721 | 0.864950499 |
| 13335 | 606 | 0.895784344 | 13364 | 635 | 0.887711723 | 13393 | 664 | 0.881697882 | 13422 | 693 | 0.873251046 | 13451 | 722 | 0.864794419 |
| 13336 | 607 | 0.895784344 | 13365 | 636 | 0.887711723 | 13394 | 665 | 0.881497052 | 13423 | 694 | 0.873144978 | 13452 | 723 | 0.864794419 |
| 13337 | 608 | 0.895784344 | 13366 | 637 | 0.887511818 | 13395 | 666 | 0.881328427 | 13424 | 695 | 0.87286306 | 13453 | 724 | 0.864670671 |
| 13338 | 609 | 0.895784344 | 13367 | 638 | 0.887321296 | 13396 | 667 | 0.880632999 | 13425 | 696 | 0.872032828 | 13454 | 725 | 0.864670671 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13455 | 726 | 0.864486881 | 13484 | 755 | 0.855912831 | 13513 | 784 | 0.848054175 | 13542 | 813 | 0.840736777 | 13571 | 842 | 0.833636437 |
| 13456 | 727 | 0.864486881 | 13485 | 756 | 0.855912831 | 13514 | 785 | 0.847955134 | 13543 | 814 | 0.840641338 | 13572 | 843 | 0.833636437 |
| 13457 | 728 | 0.86359966 | 13486 | 757 | 0.855912831 | 13515 | 786 | 0.847955134 | 13544 | 815 | 0.840548431 | 13573 | 844 | 0.833636437 |
| 13458 | 729 | 0.86359966 | 13487 | 758 | 0.855125353 | 13516 | 787 | 0.847955134 | 13545 | 816 | 0.840369819 | 13574 | 845 | 0.831012293 |
| 13459 | 730 | 0.862824826 | 13488 | 759 | 0.855067078 | 13517 | 788 | 0.847876876 | 13546 | 817 | 0.840369819 | 13575 | 846 | 0.830930543 |
| 13460 | 731 | 0.862688234 | 13489 | 760 | 0.854456281 | 13518 | 789 | 0.847209244 | 13547 | 818 | 0.83946598 | 13576 | 847 | 0.83054536 |
| 13461 | 732 | 0.862600133 | 13490 | 761 | 0.854012196 | 13519 | 790 | 0.846864703 | 13548 | 819 | 0.83946598 | 13577 | 848 | 0.830243494 |
| 13462 | 733 | 0.862600133 | 13491 | 762 | 0.853958014 | 13520 | 791 | 0.846864703 | 13549 | 820 | 0.83946598 | 13578 | 849 | 0.830175905 |
| 13463 | 734 | 0.862051372 | 13492 | 763 | 0.85370642 | 13521 | 792 | 0.846864703 | 13550 | 821 | 0.83848894 | 13579 | 850 | 0.830032313 |
| 13464 | 735 | 0.861465531 | 13493 | 764 | 0.853380495 | 13522 | 793 | 0.846491757 | 13551 | 822 | 0.83848894 | 13580 | 851 | 0.829876288 |
| 13465 | 736 | 0.861465531 | 13494 | 765 | 0.853380495 | 13523 | 794 | 0.846457869 | 13552 | 823 | 0.83848894 | 13581 | 852 | 0.829519871 |
| 13466 | 737 | 0.861219958 | 13495 | 766 | 0.853380495 | 13524 | 795 | 0.846225564 | 13553 | 824 | 0.838232188 | 13582 | 853 | 0.829419952 |
| 13467 | 738 | 0.861219958 | 13496 | 767 | 0.853380495 | 13525 | 796 | 0.845970172 | 13554 | 825 | 0.838001242 | 13583 | 854 | 0.829419952 |
| 13468 | 739 | 0.861219958 | 13497 | 768 | 0.853064989 | 13526 | 797 | 0.845928611 | 13555 | 826 | 0.83789426 | 13584 | 855 | 0.829204822 |
| 13469 | 740 | 0.860788683 | 13498 | 769 | 0.852941592 | 13527 | 798 | 0.844360302 | 13556 | 827 | 0.837792397 | 13585 | 856 | 0.829088809 |
| 13470 | 741 | 0.858283872 | 13499 | 770 | 0.852463294 | 13528 | 799 | 0.844186619 | 13557 | 828 | 0.837792397 | 13586 | 857 | 0.828966559 |
| 13471 | 742 | 0.858283872 | 13500 | 771 | 0.852463294 | 13529 | 800 | 0.844186619 | 13558 | 829 | 0.837792397 | 13587 | 858 | 0.828966559 |
| 13472 | 743 | 0.857770117 | 13501 | 772 | 0.852119842 | 13530 | 801 | 0.84397727 | 13559 | 830 | 0.837602624 | 13588 | 859 | 0.828556911 |
| 13473 | 744 | 0.857770117 | 13502 | 773 | 0.851829442 | 13531 | 802 | 0.843181755 | 13560 | 831 | 0.837514092 | 13589 | 860 | 0.82840391 |
| 13474 | 745 | 0.857674678 | 13503 | 774 | 0.851776662 | 13532 | 803 | 0.842716095 | 13561 | 832 | 0.837514092 | 13590 | 861 | 0.82840391 |
| 13475 | 746 | 0.857674678 | 13504 | 775 | 0.851365204 | 13533 | 804 | 0.842069604 | 13562 | 833 | 0.837124765 | 13591 | 862 | 0.828068483 |
| 13476 | 747 | 0.857439351 | 13505 | 776 | 0.851365204 | 13534 | 805 | 0.841988511 | 13563 | 834 | 0.836749672 | 13592 | 863 | 0.828068483 |
| 13477 | 748 | 0.856907779 | 13506 | 777 | 0.851365204 | 13535 | 806 | 0.841605366 | 13564 | 835 | 0.835709445 | 13593 | 864 | 0.828068483 |
| 13478 | 749 | 0.856760236 | 13507 | 778 | 0.851365204 | 13536 | 807 | 0.841605366 | 13565 | 836 | 0.83552879 | 13594 | 865 | 0.828068483 |
| 13479 | 750 | 0.85649932 | 13508 | 779 | 0.850971999 | 13537 | 808 | 0.841605366 | 13566 | 837 | 0.833636437 | 13595 | 866 | 0.827687104 |
| 13480 | 751 | 0.855912831 | 13509 | 780 | 0.850669776 | 13538 | 809 | 0.841461774 | 13567 | 838 | 0.833636437 | 13596 | 867 | 0.827476128 |
| 13481 | 752 | 0.855912831 | 13510 | 781 | 0.85059586 | 13539 | 810 | 0.841368887 | 13568 | 839 | 0.833636437 | 13597 | 868 | 0.827326963 |
| 13482 | 753 | 0.855912831 | 13511 | 782 | 0.850388163 | 13540 | 811 | 0.841146039 | 13569 | 840 | 0.833636437 | 13598 | 869 | 0.827326963 |
| 13483 | 754 | 0.855912831 | 13512 | 783 | 0.848087494 | 13541 | 812 | 0.841146039 | 13570 | 841 | 0.833636437 | 13599 | 870 | 0.827005858 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13600 | 871 | 0.826148415 | 13629 | 900 | 0.817067335 | 13658 | 929 | 0.811232327 | 13687 | 958 | 0.804429166 | 13716 | 987 | 0.797920885 |
| 13601 | 872 | 0.825811099 | 13630 | 901 | 0.816262341 | 13659 | 930 | 0.811232327 | 13688 | 959 | 0.80401397 | 13717 | 988 | 0.797920885 |
| 13602 | 873 | 0.825568815 | 13631 | 902 | 0.816112092 | 13660 | 931 | 0.810773554 | 13689 | 960 | 0.803524762 | 13718 | 989 | 0.797661217 |
| 13603 | 874 | 0.825036265 | 13632 | 903 | 0.815724847 | 13661 | 932 | 0.810155341 | 13690 | 961 | 0.803441651 | 13719 | 990 | 0.797612108 |
| 13604 | 875 | 0.825036265 | 13633 | 904 | 0.815411617 | 13662 | 933 | 0.809869715 | 13691 | 962 | 0.803147115 | 13720 | 991 | 0.797612108 |
| 13605 | 876 | 0.824862512 | 13634 | 905 | 0.815411617 | 13663 | 934 | 0.809757999 | 13692 | 963 | 0.802602203 | 13721 | 992 | 0.797424264 |
| 13606 | 877 | 0.823728148 | 13635 | 906 | 0.815250856 | 13664 | 935 | 0.809502757 | 13693 | 964 | 0.802227973 | 13722 | 993 | 0.797207171 |
| 13607 | 878 | 0.823233676 | 13636 | 907 | 0.815250856 | 13665 | 936 | 0.809502757 | 13694 | 965 | 0.802227973 | 13723 | 994 | 0.797085435 |
| 13608 | 879 | 0.822912571 | 13637 | 908 | 0.815153031 | 13666 | 937 | 0.809013962 | 13695 | 966 | 0.802227973 | 13724 | 995 | 0.797007541 |
| 13609 | 880 | 0.822641052 | 13638 | 909 | 0.815039948 | 13667 | 938 | 0.808930564 | 13696 | 967 | 0.802227973 | 13725 | 996 | 0.797007541 |
| 13610 | 881 | 0.82245227 | 13639 | 910 | 0.814976524 | 13668 | 939 | 0.808812853 | 13697 | 968 | 0.801747292 | 13726 | 997 | 0.796652871 |
| 13611 | 882 | 0.822206975 | 13640 | 911 | 0.814751093 | 13669 | 940 | 0.808552094 | 13698 | 969 | 0.801634268 | 13727 | 998 | 0.796209939 |
| 13612 | 883 | 0.822206975 | 13641 | 912 | 0.814751093 | 13670 | 941 | 0.808504952 | 13699 | 970 | 0.801451753 | 13728 | 999 | 0.796131821 |
| 13613 | 884 | 0.82140198 | 13642 | 913 | 0.814562556 | 13671 | 942 | 0.808330572 | 13700 | 971 | 0.801451753 | 13729 | 1000 | 0.79608143 |
| 13614 | 885 | 0.820955405 | 13643 | 914 | 0.814520146 | 13672 | 943 | 0.80814005 | 13701 | 972 | 0.801251664 | 13730 | 1001 | 0.79608143 |
| 13615 | 886 | 0.820955405 | 13644 | 915 | 0.81445312 | 13673 | 944 | 0.808082332 | 13702 | 973 | 0.801198594 | 13731 | 1002 | 0.795690551 |
| 13616 | 887 | 0.820474991 | 13645 | 916 | 0.81445312 | 13674 | 945 | 0.807700703 | 13703 | 974 | 0.800998024 | 13732 | 1003 | 0.795641118 |
| 13617 | 888 | 0.819774798 | 13646 | 917 | 0.814040881 | 13675 | 946 | 0.807421054 | 13704 | 975 | 0.800700379 | 13733 | 1004 | 0.795291445 |
| 13618 | 889 | 0.819774798 | 13647 | 918 | 0.813576643 | 13676 | 947 | 0.807161541 | 13705 | 976 | 0.800636177 | 13734 | 1005 | 0.79514228 |
| 13619 | 890 | 0.819721922 | 13648 | 919 | 0.813433051 | 13677 | 948 | 0.807038668 | 13706 | 977 | 0.799903465 | 13735 | 1006 | 0.795007034 |
| 13620 | 891 | 0.819395998 | 13649 | 920 | 0.813160851 | 13678 | 949 | 0.806694809 | 13707 | 978 | 0.799829874 | 13736 | 1007 | 0.794883848 |
| 13621 | 892 | 0.818857505 | 13650 | 921 | 0.812951838 | 13679 | 950 | 0.806341939 | 13708 | 979 | 0.799617349 | 13737 | 1008 | 0.794718371 |
| 13622 | 893 | 0.818787316 | 13651 | 922 | 0.812447138 | 13680 | 951 | 0.806239414 | 13709 | 980 | 0.799617349 | 13738 | 1009 | 0.793963732 |
| 13623 | 894 | 0.818787316 | 13652 | 923 | 0.812447138 | 13681 | 952 | 0.805607713 | 13710 | 981 | 0.799388593 | 13739 | 1010 | 0.79389193 |
| 13624 | 895 | 0.818319679 | 13653 | 924 | 0.812447138 | 13682 | 953 | 0.805607713 | 13711 | 982 | 0.799104787 | 13740 | 1011 | 0.793607315 |
| 13625 | 896 | 0.818124271 | 13654 | 925 | 0.811780531 | 13683 | 954 | 0.805607713 | 13712 | 983 | 0.798360676 | 13741 | 1012 | 0.793257275 |
| 13626 | 897 | 0.817648331 | 13655 | 926 | 0.811681861 | 13684 | 955 | 0.805607713 | 13713 | 984 | 0.797920885 | 13742 | 1013 | 0.793162894 |
| 13627 | 898 | 0.817506936 | 13656 | 927 | 0.811360042 | 13685 | 956 | 0.805607713 | 13714 | 985 | 0.797920885 | 13743 | 1014 | 0.792243752 |
| 13628 | 899 | 0.817246021 | 13657 | 928 | 0.811360042 | 13686 | 957 | 0.804946183 | 13715 | 986 | 0.797920885 | 13744 | 1015 | 0.792243752 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13745 | 1016 | 0.792243752 | 13774 | 1045 | 0.784787869 | 13803 | 1074 | 0.77858887 | 13832 | 1103 | 0.773760346 | 13861 | 1132 | 0.767117734 |
| 13746 | 1017 | 0.792243752 | 13775 | 1046 | 0.784010434 | 13804 | 1075 | 0.778528049 | 13833 | 1104 | 0.773548133 | 13862 | 1133 | 0.767044318 |
| 13747 | 1018 | 0.792243752 | 13776 | 1047 | 0.78386482 | 13805 | 1076 | 0.778455467 | 13834 | 1105 | 0.772938596 | 13863 | 1134 | 0.766689647 |
| 13748 | 1019 | 0.791281859 | 13777 | 1048 | 0.783662462 | 13806 | 1077 | 0.778258105 | 13835 | 1106 | 0.772938596 | 13864 | 1135 | 0.766689647 |
| 13749 | 1020 | 0.791232588 | 13778 | 1049 | 0.783662462 | 13807 | 1078 | 0.778258105 | 13836 | 1107 | 0.772938596 | 13865 | 1136 | 0.766689647 |
| 13750 | 1021 | 0.790972025 | 13779 | 1050 | 0.783418887 | 13808 | 1079 | 0.777936287 | 13837 | 1108 | 0.772428562 | 13866 | 1137 | 0.766689647 |
| 13751 | 1022 | 0.790530556 | 13780 | 1051 | 0.783226933 | 13809 | 1080 | 0.777520495 | 13838 | 1109 | 0.771681593 | 13867 | 1138 | 0.766401175 |
| 13752 | 1023 | 0.790170743 | 13781 | 1052 | 0.783100372 | 13810 | 1081 | 0.777318074 | 13839 | 1110 | 0.771681593 | 13868 | 1139 | 0.765563072 |
| 13753 | 1024 | 0.789619608 | 13782 | 1053 | 0.782816835 | 13811 | 1082 | 0.777318074 | 13840 | 1111 | 0.771681593 | 13869 | 1140 | 0.765563072 |
| 13754 | 1025 | 0.789619608 | 13783 | 1054 | 0.782483914 | 13812 | 1083 | 0.777318074 | 13841 | 1112 | 0.77148853 | 13870 | 1141 | 0.765563072 |
| 13755 | 1026 | 0.789432774 | 13784 | 1055 | 0.782483914 | 13813 | 1084 | 0.776962532 | 13842 | 1113 | 0.771225401 | 13871 | 1142 | 0.765450575 |
| 13756 | 1027 | 0.789217297 | 13785 | 1056 | 0.782483914 | 13814 | 1085 | 0.776449484 | 13843 | 1114 | 0.770845607 | 13872 | 1143 | 0.765313118 |
| 13757 | 1028 | 0.788966042 | 13786 | 1057 | 0.782208259 | 13815 | 1086 | 0.776283628 | 13844 | 1115 | 0.770641952 | 13873 | 1144 | 0.764920624 |
| 13758 | 1029 | 0.788669291 | 13787 | 1058 | 0.781840991 | 13816 | 1087 | 0.776097116 | 13845 | 1116 | 0.770641952 | 13874 | 1145 | 0.764920624 |
| 13759 | 1030 | 0.788669291 | 13788 | 1059 | 0.781412904 | 13817 | 1088 | 0.776097116 | 13846 | 1117 | 0.769967357 | 13875 | 1146 | 0.764920624 |
| 13760 | 1031 | 0.78849981 | 13789 | 1060 | 0.780784129 | 13818 | 1089 | 0.775885832 | 13847 | 1118 | 0.76987555 | 13876 | 1147 | 0.764439412 |
| 13761 | 1032 | 0.788439688 | 13790 | 1061 | 0.780557993 | 13819 | 1090 | 0.77564449 | 13848 | 1119 | 0.769802883 | 13877 | 1148 | 0.764439412 |
| 13762 | 1033 | 0.788178563 | 13791 | 1062 | 0.780077845 | 13820 | 1091 | 0.77564449 | 13849 | 1120 | 0.769695157 | 13878 | 1149 | 0.764215028 |
| 13763 | 1034 | 0.788178563 | 13792 | 1063 | 0.780009295 | 13821 | 1092 | 0.77564449 | 13850 | 1121 | 0.769695157 | 13879 | 1150 | 0.764085175 |
| 13764 | 1035 | 0.788107582 | 13793 | 1064 | 0.779902313 | 13822 | 1093 | 0.775439682 | 13851 | 1122 | 0.769178448 | 13880 | 1151 | 0.76359857 |
| 13765 | 1036 | 0.787455451 | 13794 | 1065 | 0.779278774 | 13823 | 1094 | 0.775210412 | 13852 | 1123 | 0.769178448 | 13881 | 1152 | 0.76359857 |
| 13766 | 1037 | 0.787336417 | 13795 | 1066 | 0.779278774 | 13824 | 1095 | 0.775210412 | 13853 | 1124 | 0.769178448 | 13882 | 1153 | 0.763055363 |
| 13767 | 1038 | 0.785712884 | 13796 | 1067 | 0.779278774 | 13825 | 1096 | 0.775041722 | 13854 | 1125 | 0.768762656 | 13883 | 1154 | 0.762954376 |
| 13768 | 1039 | 0.785489424 | 13797 | 1068 | 0.779278774 | 13826 | 1097 | 0.775041722 | 13855 | 1126 | 0.768602842 | 13884 | 1155 | 0.762573081 |
| 13769 | 1040 | 0.785489424 | 13798 | 1069 | 0.779278774 | 13827 | 1098 | 0.774793766 | 13856 | 1127 | 0.768602842 | 13885 | 1156 | 0.761754429 |
| 13770 | 1041 | 0.785124011 | 13799 | 1070 | 0.779278774 | 13828 | 1099 | 0.774658577 | 13857 | 1128 | 0.768602842 | 13886 | 1157 | 0.761754429 |
| 13771 | 1042 | 0.784993258 | 13800 | 1071 | 0.779278774 | 13829 | 1100 | 0.774050747 | 13858 | 1129 | 0.768465905 | 13887 | 1158 | 0.761754429 |
| 13772 | 1043 | 0.784993258 | 13801 | 1072 | 0.779278774 | 13830 | 1101 | 0.773933544 | 13859 | 1130 | 0.767819152 | 13888 | 1159 | 0.760795369 |
| 13773 | 1044 | 0.78483782 | 13802 | 1073 | 0.77858887 | 13831 | 1102 | 0.773933544 | 13860 | 1131 | 0.767819152 | 13889 | 1160 | 0.760529338 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 13890 | 1161 | 0.759952663 | 13919 | 1190 | 0.754455191 | 13948 | 1219 | 0.746768362 | 13977 | 1248 | 0.742555967 | 14006 | 1277 | 0.73755444 |
| 13891 | 1162 | 0.759534716 | 13920 | 1191 | 0.754455191 | 13949 | 1220 | 0.746768362 | 13978 | 1249 | 0.742045933 | 14007 | 1278 | 0.737421851 |
| 13892 | 1163 | 0.759475992 | 13921 | 1192 | 0.754455191 | 13950 | 1221 | 0.746486261 | 13979 | 1250 | 0.741718369 | 14008 | 1279 | 0.737421851 |
| 13893 | 1164 | 0.759307694 | 13922 | 1193 | 0.754455191 | 13951 | 1222 | 0.746182665 | 13980 | 1251 | 0.741490214 | 14009 | 1280 | 0.736726424 |
| 13894 | 1165 | 0.759002818 | 13923 | 1194 | 0.752554555 | 13952 | 1223 | 0.746022023 | 13981 | 1252 | 0.741091229 | 14010 | 1281 | 0.736726424 |
| 13895 | 1166 | 0.75886431 | 13924 | 1195 | 0.75239203 | 13953 | 1224 | 0.746022023 | 13982 | 1253 | 0.740882384 | 14011 | 1282 | 0.736726424 |
| 13896 | 1167 | 0.758733989 | 13925 | 1196 | 0.75219911 | 13954 | 1225 | 0.745855019 | 13983 | 1254 | 0.74081131 | 14012 | 1283 | 0.736726424 |
| 13897 | 1168 | 0.758183063 | 13926 | 1197 | 0.752126528 | 13955 | 1226 | 0.745855019 | 13984 | 1255 | 0.740753913 | 14013 | 1284 | 0.736281222 |
| 13898 | 1169 | 0.758089475 | 13927 | 1198 | 0.752049121 | 13956 | 1227 | 0.745769012 | 13985 | 1256 | 0.740214752 | 14014 | 1285 | 0.736230371 |
| 13899 | 1170 | 0.757481645 | 13928 | 1199 | 0.75196639 | 13957 | 1228 | 0.745500348 | 13986 | 1257 | 0.740214752 | 14015 | 1286 | 0.736083501 |
| 13900 | 1171 | 0.757144329 | 13929 | 1200 | 0.751877768 | 13958 | 1229 | 0.745500348 | 13987 | 1258 | 0.740214752 | 14016 | 1287 | 0.735971785 |
| 13901 | 1172 | 0.757144329 | 13930 | 1201 | 0.751569503 | 13959 | 1230 | 0.745500348 | 13988 | 1259 | 0.740214752 | 14017 | 1288 | 0.735705755 |
| 13902 | 1173 | 0.757095287 | 13931 | 1202 | 0.751319477 | 13960 | 1231 | 0.745214534 | 13989 | 1260 | 0.740214752 | 14018 | 1289 | 0.735392185 |
| 13903 | 1174 | 0.757048001 | 13932 | 1203 | 0.751319477 | 13961 | 1232 | 0.745115164 | 13990 | 1261 | 0.739802903 | 14019 | 1290 | 0.735281183 |
| 13904 | 1175 | 0.757048001 | 13933 | 1204 | 0.751177481 | 13962 | 1233 | 0.745115164 | 13991 | 1262 | 0.739731934 | 14020 | 1291 | 0.734933051 |
| 13905 | 1176 | 0.756874665 | 13934 | 1205 | 0.751022015 | 13963 | 1234 | 0.745115164 | 13992 | 1263 | 0.739731934 | 14021 | 1292 | 0.734933051 |
| 13906 | 1177 | 0.756723052 | 13935 | 1206 | 0.750662202 | 13964 | 1235 | 0.744782308 | 13993 | 1264 | 0.739731934 | 14022 | 1293 | 0.734800503 |
| 13907 | 1178 | 0.756470482 | 13936 | 1207 | 0.750662202 | 13965 | 1236 | 0.74447097 | 13994 | 1265 | 0.739631414 | 14023 | 1294 | 0.734646797 |
| 13908 | 1179 | 0.756364181 | 13937 | 1208 | 0.750560147 | 13966 | 1237 | 0.744236026 | 13995 | 1266 | 0.739631414 | 14024 | 1295 | 0.734251805 |
| 13909 | 1180 | 0.755905257 | 13938 | 1209 | 0.749315551 | 13967 | 1238 | 0.744236026 | 13996 | 1267 | 0.739631414 | 14025 | 1296 | 0.734251805 |
| 13910 | 1181 | 0.754455191 | 13939 | 1210 | 0.749315551 | 13968 | 1239 | 0.744236026 | 13997 | 1268 | 0.739215224 | 14026 | 1297 | 0.733992137 |
| 13911 | 1182 | 0.754455191 | 13940 | 1211 | 0.749026439 | 13969 | 1240 | 0.743939072 | 13998 | 1269 | 0.739215224 | 14027 | 1298 | 0.733933524 |
| 13912 | 1183 | 0.754455191 | 13941 | 1212 | 0.748464827 | 13970 | 1241 | 0.743806456 | 13999 | 1270 | 0.739215224 | 14028 | 1299 | 0.733452244 |
| 13913 | 1184 | 0.754455191 | 13942 | 1213 | 0.748464827 | 13971 | 1242 | 0.743731325 | 14000 | 1271 | 0.739080329 | 14029 | 1300 | 0.733265892 |
| 13914 | 1185 | 0.754455191 | 13943 | 1214 | 0.748115013 | 13972 | 1243 | 0.743459806 | 14001 | 1272 | 0.738660924 | 14030 | 1301 | 0.733265892 |
| 13915 | 1186 | 0.754455191 | 13944 | 1215 | 0.747276606 | 13973 | 1244 | 0.742934768 | 14002 | 1273 | 0.738217992 | 14031 | 1302 | 0.732966275 |
| 13916 | 1187 | 0.754455191 | 13945 | 1216 | 0.747276606 | 13974 | 1245 | 0.742934768 | 14003 | 1274 | 0.738064775 | 14032 | 1303 | 0.732735941 |
| 13917 | 1188 | 0.754455191 | 13946 | 1217 | 0.747094091 | 13975 | 1246 | 0.742873318 | 14004 | 1275 | 0.738064775 | 14033 | 1304 | 0.732553349 |
| 13918 | 1189 | 0.754455191 | 13947 | 1218 | 0.746902053 | 13976 | 1247 | 0.742555967 | 14005 | 1276 | 0.737749497 | 14034 | 1305 | 0.732553349 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14035 | 1306 | 0.732553349 | 14064 | 1335 | 0.726426467 | 14093 | 1364 | 0.72084659 | 14122 | 1393 | 0.716365141 | 14151 | 1422 | 0.711420559 |
| 14036 | 1307 | 0.73240505 | 14065 | 1336 | 0.726002558 | 14094 | 1365 | 0.720596923 | 14123 | 1394 | 0.716365141 | 14152 | 1423 | 0.711117174 |
| 14037 | 1308 | 0.73240505 | 14066 | 1337 | 0.725924102 | 14095 | 1366 | 0.720550527 | 14124 | 1395 | 0.716250838 | 14153 | 1424 | 0.710989497 |
| 14038 | 1309 | 0.732282212 | 14067 | 1338 | 0.725924102 | 14096 | 1367 | 0.719693084 | 14125 | 1396 | 0.715996939 | 14154 | 1425 | 0.710874619 |
| 14039 | 1310 | 0.732178796 | 14068 | 1339 | 0.725810009 | 14097 | 1368 | 0.719693084 | 14126 | 1397 | 0.715996939 | 14155 | 1426 | 0.710676266 |
| 14040 | 1311 | 0.731712064 | 14069 | 1340 | 0.725810009 | 14098 | 1369 | 0.719693084 | 14127 | 1398 | 0.715996939 | 14156 | 1427 | 0.710511041 |
| 14041 | 1312 | 0.731712064 | 14070 | 1341 | 0.725491495 | 14099 | 1370 | 0.719693084 | 14128 | 1399 | 0.715780495 | 14157 | 1428 | 0.710438362 |
| 14042 | 1313 | 0.730974095 | 14071 | 1342 | 0.725296962 | 14100 | 1371 | 0.719693084 | 14129 | 1400 | 0.715702602 | 14158 | 1429 | 0.710251528 |
| 14043 | 1314 | 0.730974095 | 14072 | 1343 | 0.725296962 | 14101 | 1372 | 0.719693084 | 14130 | 1401 | 0.715702602 | 14159 | 1430 | 0.710251528 |
| 14044 | 1315 | 0.730974095 | 14073 | 1344 | 0.725115059 | 14102 | 1373 | 0.719693084 | 14131 | 1402 | 0.715201892 | 14160 | 1431 | 0.709642846 |
| 14045 | 1316 | 0.730974095 | 14074 | 1345 | 0.725000211 | 14103 | 1374 | 0.719693084 | 14132 | 1403 | 0.714660647 | 14161 | 1432 | 0.7086977 |
| 14046 | 1317 | 0.730186616 | 14075 | 1346 | 0.724863318 | 14104 | 1375 | 0.719693084 | 14133 | 1404 | 0.714337968 | 14162 | 1433 | 0.7086977 |
| 14047 | 1318 | 0.730095845 | 14076 | 1347 | 0.72478452 | 14105 | 1376 | 0.718791123 | 14134 | 1405 | 0.714160596 | 14163 | 1434 | 0.7086977 |
| 14048 | 1319 | 0.730095845 | 14077 | 1348 | 0.724491967 | 14106 | 1377 | 0.718739638 | 14135 | 1406 | 0.713971072 | 14164 | 1435 | 0.7086977 |
| 14049 | 1320 | 0.730042132 | 14078 | 1349 | 0.724491967 | 14107 | 1378 | 0.718410087 | 14136 | 1407 | 0.71383734 | 14165 | 1436 | 0.708225897 |
| 14050 | 1321 | 0.729981421 | 14079 | 1350 | 0.724491967 | 14108 | 1379 | 0.718243018 | 14137 | 1408 | 0.71383734 | 14166 | 1437 | 0.707829979 |
| 14051 | 1322 | 0.72934447 | 14080 | 1351 | 0.723889199 | 14109 | 1380 | 0.717938357 | 14138 | 1409 | 0.713550203 | 14167 | 1438 | 0.707556321 |
| 14052 | 1323 | 0.728901086 | 14081 | 1352 | 0.723889199 | 14110 | 1381 | 0.717565924 | 14139 | 1410 | 0.713550203 | 14168 | 1439 | 0.707556321 |
| 14053 | 1324 | 0.728901086 | 14082 | 1353 | 0.723720574 | 14111 | 1382 | 0.717471624 | 14140 | 1411 | 0.713062506 | 14169 | 1440 | 0.707202709 |
| 14054 | 1325 | 0.728574672 | 14083 | 1354 | 0.723420957 | 14112 | 1383 | 0.717471624 | 14141 | 1412 | 0.713062506 | 14170 | 1441 | 0.707202709 |
| 14055 | 1326 | 0.728441758 | 14084 | 1355 | 0.723162832 | 14113 | 1384 | 0.717313383 | 14142 | 1413 | 0.713062506 | 14171 | 1442 | 0.707030541 |
| 14056 | 1327 | 0.728369622 | 14085 | 1356 | 0.723046726 | 14114 | 1385 | 0.716992799 | 14143 | 1414 | 0.712716316 | 14172 | 1443 | 0.707030541 |
| 14057 | 1328 | 0.727471701 | 14086 | 1357 | 0.722740778 | 14115 | 1386 | 0.716839003 | 14144 | 1415 | 0.712490689 | 14173 | 1444 | 0.706813556 |
| 14058 | 1329 | 0.727302945 | 14087 | 1358 | 0.722566046 | 14116 | 1387 | 0.71666663 | 14145 | 1416 | 0.712214274 | 14174 | 1445 | 0.706813556 |
| 14059 | 1330 | 0.727302945 | 14088 | 1359 | 0.722485985 | 14117 | 1388 | 0.71666663 | 14146 | 1417 | 0.712214274 | 14175 | 1446 | 0.706728107 |
| 14060 | 1331 | 0.727016942 | 14089 | 1360 | 0.721366668 | 14118 | 1389 | 0.71666663 | 14147 | 1418 | 0.712051342 | 14176 | 1447 | 0.706531638 |
| 14061 | 1332 | 0.726426467 | 14090 | 1361 | 0.721031435 | 14119 | 1390 | 0.71666663 | 14148 | 1419 | 0.712051342 | 14177 | 1448 | 0.706531638 |
| 14062 | 1333 | 0.726426467 | 14091 | 1362 | 0.720932157 | 14120 | 1391 | 0.716472097 | 14149 | 1420 | 0.711810936 | 14178 | 1449 | 0.70629163 |
| 14063 | 1334 | 0.726426467 | 14092 | 1363 | 0.72084659 | 14121 | 1392 | 0.716365141 | 14150 | 1421 | 0.711642081 | 14179 | 1450 | 0.706150511 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14180 | 1451 | 0.706150511 | 14209 | 1480 | 0.701842854 | 14238 | 1509 | 0.695860475 | 14267 | 1538 | 0.690621637 | 14296 | 1567 | 0.687508401 |
| 14181 | 1452 | 0.705991807 | 14210 | 1481 | 0.701519116 | 14239 | 1510 | 0.695860475 | 14268 | 1539 | 0.690337691 | 14297 | 1568 | 0.687508401 |
| 14182 | 1453 | 0.705606623 | 14211 | 1482 | 0.701209679 | 14240 | 1511 | 0.69567719 | 14269 | 1540 | 0.690337691 | 14298 | 1569 | 0.686190359 |
| 14183 | 1454 | 0.705606623 | 14212 | 1483 | 0.701209679 | 14241 | 1512 | 0.695333739 | 14270 | 1541 | 0.690101212 | 14299 | 1570 | 0.685374272 |
| 14184 | 1455 | 0.705606623 | 14213 | 1484 | 0.700538213 | 14242 | 1513 | 0.695333739 | 14271 | 1542 | 0.690101212 | 14300 | 1571 | 0.685216604 |
| 14185 | 1456 | 0.70531796 | 14214 | 1485 | 0.700387929 | 14243 | 1514 | 0.695018003 | 14272 | 1543 | 0.689901214 | 14301 | 1572 | 0.685216604 |
| 14186 | 1457 | 0.70531796 | 14215 | 1486 | 0.700097528 | 14244 | 1515 | 0.694869501 | 14273 | 1544 | 0.689901214 | 14302 | 1573 | 0.685128699 |
| 14187 | 1458 | 0.705237168 | 14216 | 1487 | 0.700097528 | 14245 | 1516 | 0.694457261 | 14274 | 1545 | 0.689812356 | 14303 | 1574 | 0.685128699 |
| 14188 | 1459 | 0.705093576 | 14217 | 1488 | 0.699742858 | 14246 | 1517 | 0.694457261 | 14275 | 1546 | 0.689729861 | 14304 | 1575 | 0.685033782 |
| 14189 | 1460 | 0.705093576 | 14218 | 1489 | 0.698937863 | 14247 | 1518 | 0.694457261 | 14276 | 1547 | 0.689729861 | 14305 | 1576 | 0.684930978 |
| 14190 | 1461 | 0.704767407 | 14219 | 1490 | 0.698937863 | 14248 | 1519 | 0.694267985 | 14277 | 1548 | 0.68923522 | 14306 | 1577 | 0.684930978 |
| 14191 | 1462 | 0.704767407 | 14220 | 1491 | 0.698597373 | 14249 | 1520 | 0.694088746 | 14278 | 1549 | 0.687508401 | 14307 | 1578 | 0.684697424 |
| 14192 | 1463 | 0.70454174 | 14221 | 1492 | 0.698232266 | 14250 | 1521 | 0.693974443 | 14279 | 1550 | 0.687508401 | 14308 | 1579 | 0.68456402 |
| 14193 | 1464 | 0.704376326 | 14222 | 1493 | 0.697973835 | 14251 | 1522 | 0.693364146 | 14280 | 1551 | 0.687508401 | 14309 | 1580 | 0.68456402 |
| 14194 | 1465 | 0.704150072 | 14223 | 1494 | 0.697973835 | 14252 | 1523 | 0.693185534 | 14281 | 1552 | 0.687508401 | 14310 | 1581 | 0.68456402 |
| 14195 | 1466 | 0.704002579 | 14224 | 1495 | 0.697973835 | 14253 | 1524 | 0.693185534 | 14282 | 1553 | 0.687508401 | 14311 | 1582 | 0.684255244 |
| 14196 | 1467 | 0.704002579 | 14225 | 1496 | 0.697973835 | 14254 | 1525 | 0.693017496 | 14283 | 1554 | 0.687508401 | 14312 | 1583 | 0.684255244 |
| 14197 | 1468 | 0.703898817 | 14226 | 1497 | 0.697550339 | 14255 | 1526 | 0.693017496 | 14284 | 1555 | 0.687508401 | 14313 | 1584 | 0.683874116 |
| 14198 | 1469 | 0.703898817 | 14227 | 1498 | 0.697550339 | 14256 | 1527 | 0.692937153 | 14285 | 1556 | 0.687508401 | 14314 | 1585 | 0.68352402 |
| 14199 | 1470 | 0.703302668 | 14228 | 1499 | 0.69741669 | 14257 | 1528 | 0.692307284 | 14286 | 1557 | 0.687508401 | 14315 | 1586 | 0.683099282 |
| 14200 | 1471 | 0.703302668 | 14229 | 1500 | 0.69741669 | 14258 | 1529 | 0.691962743 | 14287 | 1558 | 0.687508401 | 14316 | 1587 | 0.683099282 |
| 14201 | 1472 | 0.703302668 | 14230 | 1501 | 0.697159787 | 14259 | 1530 | 0.691962743 | 14288 | 1559 | 0.687508401 | 14317 | 1588 | 0.683099282 |
| 14202 | 1473 | 0.702815518 | 14231 | 1502 | 0.697159787 | 14260 | 1531 | 0.69157359 | 14289 | 1560 | 0.687508401 | 14318 | 1589 | 0.682761966 |
| 14203 | 1474 | 0.702748368 | 14232 | 1503 | 0.697159787 | 14261 | 1532 | 0.691173355 | 14290 | 1561 | 0.687508401 | 14319 | 1590 | 0.682637758 |
| 14204 | 1475 | 0.702748368 | 14233 | 1504 | 0.697159787 | 14262 | 1533 | 0.690968933 | 14291 | 1562 | 0.687508401 | 14320 | 1591 | 0.682368761 |
| 14205 | 1476 | 0.702659745 | 14234 | 1505 | 0.696798477 | 14263 | 1534 | 0.690968933 | 14292 | 1563 | 0.687508401 | 14321 | 1592 | 0.682368761 |
| 14206 | 1477 | 0.702357522 | 14235 | 1506 | 0.696463244 | 14264 | 1535 | 0.690968933 | 14293 | 1564 | 0.687508401 | 14322 | 1593 | 0.681639467 |
| 14207 | 1478 | 0.702231658 | 14236 | 1507 | 0.696151363 | 14265 | 1536 | 0.690786111 | 14294 | 1565 | 0.687508401 | 14323 | 1594 | 0.681137219 |
| 14208 | 1479 | 0.701842854 | 14237 | 1508 | 0.696052175 | 14266 | 1537 | 0.690701757 | 14295 | 1566 | 0.687508401 | 14324 | 1595 | 0.681026274 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14325 | 1596 | 0.680668977 | 14354 | 1625 | 0.675273945 | 14383 | 1654 | 0.670134305 | 14412 | 1683 | 0.663374721 | 14441 | 1712 | 0.660185274 |
| 14326 | 1597 | 0.680408061 | 14355 | 1626 | 0.674858153 | 14384 | 1655 | 0.669779634 | 14413 | 1684 | 0.663374721 | 14442 | 1713 | 0.660185274 |
| 14327 | 1598 | 0.680329816 | 14356 | 1627 | 0.674858153 | 14385 | 1656 | 0.669283581 | 14414 | 1685 | 0.66294021 | 14443 | 1714 | 0.659618186 |
| 14328 | 1599 | 0.680269992 | 14357 | 1628 | 0.67477158 | 14386 | 1657 | 0.669283581 | 14415 | 1686 | 0.662841518 | 14444 | 1715 | 0.659618186 |
| 14329 | 1600 | 0.680269992 | 14358 | 1629 | 0.67477158 | 14387 | 1658 | 0.668668578 | 14416 | 1687 | 0.662684817 | 14445 | 1716 | 0.659618186 |
| 14330 | 1601 | 0.680126447 | 14359 | 1630 | 0.673720117 | 14388 | 1659 | 0.668540562 | 14417 | 1688 | 0.662565979 | 14446 | 1717 | 0.659479678 |
| 14331 | 1602 | 0.680126447 | 14360 | 1631 | 0.673631998 | 14389 | 1660 | 0.668540562 | 14418 | 1689 | 0.662565979 | 14447 | 1718 | 0.659479678 |
| 14332 | 1603 | 0.679821572 | 14361 | 1632 | 0.673631998 | 14390 | 1661 | 0.66843452 | 14419 | 1690 | 0.662397681 | 14448 | 1719 | 0.659251642 |
| 14333 | 1604 | 0.679821572 | 14362 | 1633 | 0.673631998 | 14391 | 1662 | 0.66843452 | 14420 | 1691 | 0.662397681 | 14449 | 1720 | 0.659071698 |
| 14334 | 1605 | 0.679490429 | 14363 | 1634 | 0.67342194 | 14392 | 1663 | 0.668345242 | 14421 | 1692 | 0.662140929 | 14450 | 1721 | 0.658926083 |
| 14335 | 1606 | 0.678412896 | 14364 | 1635 | 0.673267962 | 14393 | 1664 | 0.667838874 | 14422 | 1693 | 0.662140929 | 14451 | 1722 | 0.65880583 |
| 14336 | 1607 | 0.678066845 | 14365 | 1636 | 0.673150251 | 14394 | 1665 | 0.667305015 | 14423 | 1694 | 0.661954297 | 14452 | 1723 | 0.65880583 |
| 14337 | 1608 | 0.677920937 | 14366 | 1637 | 0.673150251 | 14395 | 1666 | 0.666319102 | 14424 | 1695 | 0.661701138 | 14453 | 1724 | 0.657545178 |
| 14338 | 1609 | 0.677920937 | 14367 | 1638 | 0.672268435 | 14396 | 1667 | 0.666145349 | 14425 | 1696 | 0.661701138 | 14454 | 1725 | 0.657545178 |
| 14339 | 1610 | 0.677920937 | 14368 | 1639 | 0.672268435 | 14397 | 1668 | 0.666145349 | 14426 | 1697 | 0.661701138 | 14455 | 1726 | 0.657545178 |
| 14340 | 1611 | 0.677693419 | 14369 | 1640 | 0.672268435 | 14398 | 1669 | 0.666145349 | 14427 | 1698 | 0.661475471 | 14456 | 1727 | 0.657545178 |
| 14341 | 1612 | 0.677693419 | 14370 | 1641 | 0.672268435 | 14399 | 1670 | 0.665663068 | 14428 | 1699 | 0.661422833 | 14457 | 1728 | 0.657545178 |
| 14342 | 1613 | 0.677289236 | 14371 | 1642 | 0.671714134 | 14400 | 1671 | 0.665514107 | 14429 | 1700 | 0.661338167 | 14458 | 1729 | 0.657545178 |
| 14343 | 1614 | 0.676941104 | 14372 | 1643 | 0.671617806 | 14401 | 1672 | 0.665514107 | 14430 | 1701 | 0.661179462 | 14459 | 1730 | 0.657545178 |
| 14344 | 1615 | 0.676784536 | 14373 | 1644 | 0.671480956 | 14402 | 1673 | 0.665232006 | 14431 | 1702 | 0.661179462 | 14460 | 1731 | 0.657545178 |
| 14345 | 1616 | 0.676372035 | 14374 | 1645 | 0.671480956 | 14403 | 1674 | 0.665232006 | 14432 | 1703 | 0.661179462 | 14461 | 1732 | 0.657545178 |
| 14346 | 1617 | 0.676227391 | 14375 | 1646 | 0.671271202 | 14404 | 1675 | 0.665232006 | 14433 | 1704 | 0.660774148 | 14462 | 1733 | 0.657545178 |
| 14347 | 1618 | 0.676227391 | 14376 | 1647 | 0.671117985 | 14405 | 1676 | 0.664844416 | 14434 | 1705 | 0.660774148 | 14463 | 1734 | 0.657545178 |
| 14348 | 1619 | 0.676168475 | 14377 | 1648 | 0.670909139 | 14406 | 1677 | 0.664844416 | 14435 | 1706 | 0.660774148 | 14464 | 1735 | 0.6566687 |
| 14349 | 1620 | 0.675926529 | 14378 | 1649 | 0.670909139 | 14407 | 1678 | 0.664494038 | 14436 | 1707 | 0.660774148 | 14465 | 1736 | 0.6566687 |
| 14350 | 1621 | 0.675787599 | 14379 | 1650 | 0.670909139 | 14408 | 1679 | 0.664494038 | 14437 | 1708 | 0.660450168 | 14466 | 1737 | 0.656612214 |
| 14351 | 1622 | 0.675738183 | 14380 | 1651 | 0.670607651 | 14409 | 1680 | 0.663374721 | 14438 | 1709 | 0.660450168 | 14467 | 1738 | 0.656547945 |
| 14352 | 1623 | 0.675738183 | 14381 | 1652 | 0.670134305 | 14410 | 1681 | 0.663374721 | 14439 | 1710 | 0.660450168 | 14468 | 1739 | 0.656388601 |
| 14353 | 1624 | 0.675738183 | 14382 | 1653 | 0.670134305 | 14411 | 1682 | 0.663374721 | 14440 | 1711 | 0.660185274 | 14469 | 1740 | 0.656388601 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14470 | 1741 | 0.656288174 | 14499 | 1770 | 0.652581758 | 14528 | 1799 | 0.646549793 | 14557 | 1828 | 0.641481246 | 14586 | 1857 | 0.638290378 |
| 14471 | 1742 | 0.656288174 | 14500 | 1771 | 0.651792849 | 14529 | 1800 | 0.646361011 | 14558 | 1829 | 0.641481246 | 14587 | 1858 | 0.638290378 |
| 14472 | 1743 | 0.656168649 | 14501 | 1772 | 0.651792849 | 14530 | 1801 | 0.646361011 | 14559 | 1830 | 0.641307979 | 14588 | 1859 | 0.638173774 |
| 14473 | 1744 | 0.655845393 | 14502 | 1773 | 0.651792849 | 14531 | 1802 | 0.645784067 | 14560 | 1831 | 0.641307979 | 14589 | 1860 | 0.638082698 |
| 14474 | 1745 | 0.655845393 | 14503 | 1774 | 0.650914599 | 14532 | 1803 | 0.645784067 | 14561 | 1832 | 0.641098327 | 14590 | 1861 | 0.637634344 |
| 14475 | 1746 | 0.655482017 | 14504 | 1775 | 0.650705753 | 14533 | 1804 | 0.645645954 | 14562 | 1833 | 0.641098327 | 14591 | 1862 | 0.637634344 |
| 14476 | 1747 | 0.655482017 | 14505 | 1776 | 0.650612165 | 14534 | 1805 | 0.645310721 | 14563 | 1834 | 0.641098327 | 14592 | 1863 | 0.637341792 |
| 14477 | 1748 | 0.655323718 | 14506 | 1777 | 0.650524835 | 14535 | 1806 | 0.645310721 | 14564 | 1835 | 0.640976076 | 14593 | 1864 | 0.637341792 |
| 14478 | 1749 | 0.655203962 | 14507 | 1778 | 0.650366593 | 14536 | 1807 | 0.645104553 | 14565 | 1836 | 0.640976076 | 14594 | 1865 | 0.637341792 |
| 14479 | 1750 | 0.654921034 | 14508 | 1779 | 0.650366593 | 14537 | 1808 | 0.644580201 | 14566 | 1837 | 0.640511838 | 14595 | 1866 | 0.636983019 |
| 14480 | 1751 | 0.654752278 | 14509 | 1780 | 0.64971984 | 14538 | 1809 | 0.644580201 | 14567 | 1838 | 0.640511838 | 14596 | 1867 | 0.636655702 |
| 14481 | 1752 | 0.654659489 | 14510 | 1781 | 0.649576248 | 14539 | 1810 | 0.644580201 | 14568 | 1839 | 0.640511838 | 14597 | 1868 | 0.636080224 |
| 14482 | 1753 | 0.654659489 | 14511 | 1782 | 0.649350699 | 14540 | 1811 | 0.644042707 | 14569 | 1840 | 0.640511838 | 14598 | 1869 | 0.636080224 |
| 14483 | 1754 | 0.654152235 | 14512 | 1783 | 0.649219789 | 14541 | 1812 | 0.644042707 | 14570 | 1841 | 0.640511838 | 14599 | 1870 | 0.636080224 |
| 14484 | 1755 | 0.654084646 | 14513 | 1784 | 0.64911201 | 14542 | 1813 | 0.643914275 | 14571 | 1842 | 0.640511838 | 14600 | 1871 | 0.635825928 |
| 14485 | 1756 | 0.654084646 | 14514 | 1785 | 0.648821609 | 14543 | 1814 | 0.643304739 | 14572 | 1843 | 0.640152769 | 14601 | 1872 | 0.635372199 |
| 14486 | 1757 | 0.653785029 | 14515 | 1786 | 0.648651465 | 14544 | 1815 | 0.643304739 | 14573 | 1844 | 0.640083751 | 14602 | 1873 | 0.635268783 |
| 14487 | 1758 | 0.653785029 | 14516 | 1787 | 0.64799986 | 14545 | 1816 | 0.643304739 | 14574 | 1845 | 0.640083751 | 14603 | 1874 | 0.635168957 |
| 14488 | 1759 | 0.653428612 | 14517 | 1788 | 0.64799986 | 14546 | 1817 | 0.643304739 | 14575 | 1846 | 0.640083751 | 14604 | 1875 | 0.63497935 |
| 14489 | 1760 | 0.653428612 | 14518 | 1789 | 0.64799986 | 14547 | 1818 | 0.643304739 | 14576 | 1847 | 0.639981888 | 14605 | 1876 | 0.634802051 |
| 14490 | 1761 | 0.653428612 | 14519 | 1790 | 0.64799986 | 14548 | 1819 | 0.643304739 | 14577 | 1848 | 0.639816411 | 14606 | 1877 | 0.634717648 |
| 14491 | 1762 | 0.653428612 | 14520 | 1791 | 0.647142417 | 14549 | 1820 | 0.642638131 | 14578 | 1849 | 0.63968775 | 14607 | 1878 | 0.634717648 |
| 14492 | 1763 | 0.653428612 | 14521 | 1792 | 0.647007186 | 14550 | 1821 | 0.642638131 | 14579 | 1850 | 0.639500675 | 14608 | 1879 | 0.634635898 |
| 14493 | 1764 | 0.65299755 | 14522 | 1793 | 0.647007186 | 14551 | 1822 | 0.642638131 | 14580 | 1851 | 0.639203722 | 14609 | 1880 | 0.634479874 |
| 14494 | 1765 | 0.65299755 | 14523 | 1794 | 0.647007186 | 14552 | 1823 | 0.64222842 | 14581 | 1852 | 0.639061772 | 14610 | 1881 | 0.634262889 |
| 14495 | 1766 | 0.652900273 | 14524 | 1795 | 0.646821312 | 14553 | 1824 | 0.642033012 | 14582 | 1853 | 0.638659834 | 14611 | 1882 | 0.634064082 |
| 14496 | 1767 | 0.652900273 | 14525 | 1796 | 0.646821312 | 14554 | 1825 | 0.641750911 | 14583 | 1854 | 0.638659834 | 14612 | 1883 | 0.634064082 |
| 14497 | 1768 | 0.652746295 | 14526 | 1797 | 0.646699576 | 14555 | 1826 | 0.641750911 | 14584 | 1855 | 0.638659834 | 14613 | 1884 | 0.634064082 |
| 14498 | 1769 | 0.652581758 | 14527 | 1798 | 0.646549793 | 14556 | 1827 | 0.641557072 | 14585 | 1856 | 0.638659834 | 14614 | 1885 | 0.634064082 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14615 | 1886 | 0.633940545 | 14644 | 1915 | 0.629516454 | 14673 | 1944 | 0.620916282 | 14702 | 1973 | 0.616152493 | 14731 | 2002 | 0.611787687 |
| 14616 | 1887 | 0.633411498 | 14645 | 1916 | 0.629516454 | 14674 | 1945 | 0.620561611 | 14703 | 1974 | 0.616152493 | 14732 | 2003 | 0.611787687 |
| 14617 | 1888 | 0.633411498 | 14646 | 1917 | 0.627968166 | 14675 | 1946 | 0.620561611 | 14704 | 1975 | 0.616152493 | 14733 | 2004 | 0.611787687 |
| 14618 | 1889 | 0.632922703 | 14647 | 1918 | 0.626810561 | 14676 | 1947 | 0.620176428 | 14705 | 1976 | 0.615776643 | 14734 | 2005 | 0.611787687 |
| 14619 | 1890 | 0.632542909 | 14648 | 1919 | 0.626668611 | 14677 | 1948 | 0.620176428 | 14706 | 1977 | 0.615665342 | 14735 | 2006 | 0.611245158 |
| 14620 | 1891 | 0.632542909 | 14649 | 1920 | 0.626510944 | 14678 | 1949 | 0.620176428 | 14707 | 1978 | 0.615665342 | 14736 | 2007 | 0.611189073 |
| 14621 | 1892 | 0.632383095 | 14650 | 1921 | 0.626510944 | 14679 | 1950 | 0.620040562 | 14708 | 1979 | 0.61546039 | 14737 | 2008 | 0.611189073 |
| 14622 | 1893 | 0.632239312 | 14651 | 1922 | 0.626510944 | 14680 | 1951 | 0.619756617 | 14709 | 1980 | 0.61546039 | 14738 | 2009 | 0.610767018 |
| 14623 | 1894 | 0.631693373 | 14652 | 1923 | 0.626334795 | 14681 | 1952 | 0.619756617 | 14710 | 1981 | 0.61546039 | 14739 | 2010 | 0.610548615 |
| 14624 | 1895 | 0.631392459 | 14653 | 1924 | 0.626136713 | 14682 | 1953 | 0.619577932 | 14711 | 1982 | 0.615141329 | 14740 | 2011 | 0.610548615 |
| 14625 | 1896 | 0.631329795 | 14654 | 1925 | 0.625656033 | 14683 | 1954 | 0.619455128 | 14712 | 1983 | 0.614957734 | 14741 | 2012 | 0.610211299 |
| 14626 | 1897 | 0.631329795 | 14655 | 1926 | 0.625656033 | 14684 | 1955 | 0.619297289 | 14713 | 1984 | 0.614957734 | 14742 | 2013 | 0.609962918 |
| 14627 | 1898 | 0.631164633 | 14656 | 1927 | 0.62519508 | 14685 | 1956 | 0.619200186 | 14714 | 1985 | 0.614692678 | 14743 | 2014 | 0.609861766 |
| 14628 | 1899 | 0.629516454 | 14657 | 1928 | 0.624821333 | 14686 | 1957 | 0.618792589 | 14715 | 1986 | 0.614276488 | 14744 | 2015 | 0.609621625 |
| 14629 | 1900 | 0.629516454 | 14658 | 1929 | 0.62460912 | 14687 | 1958 | 0.618792589 | 14716 | 1987 | 0.614276488 | 14745 | 2016 | 0.609313068 |
| 14630 | 1901 | 0.629516454 | 14659 | 1930 | 0.623936577 | 14688 | 1959 | 0.618792589 | 14717 | 1988 | 0.614276488 | 14746 | 2017 | 0.609313068 |
| 14631 | 1902 | 0.629516454 | 14660 | 1931 | 0.62352609 | 14689 | 1960 | 0.618351457 | 14718 | 1989 | 0.614276488 | 14747 | 2018 | 0.609313068 |
| 14632 | 1903 | 0.629516454 | 14661 | 1932 | 0.623176276 | 14690 | 1961 | 0.618235444 | 14719 | 1990 | 0.613964606 | 14748 | 2019 | 0.609123295 |
| 14633 | 1904 | 0.629516454 | 14662 | 1933 | 0.623176276 | 14691 | 1962 | 0.618036636 | 14720 | 1991 | 0.61383625 | 14749 | 2020 | 0.609123295 |
| 14634 | 1905 | 0.629516454 | 14663 | 1934 | 0.622985587 | 14692 | 1963 | 0.618036636 | 14721 | 1992 | 0.613528349 | 14750 | 2021 | 0.608901999 |
| 14635 | 1906 | 0.629516454 | 14664 | 1935 | 0.622783071 | 14693 | 1964 | 0.618036636 | 14722 | 1993 | 0.613528349 | 14751 | 2022 | 0.608776968 |
| 14636 | 1907 | 0.629516454 | 14665 | 1936 | 0.622783071 | 14694 | 1965 | 0.617872473 | 14723 | 1994 | 0.61330091 | 14752 | 2023 | 0.608776968 |
| 14637 | 1908 | 0.629516454 | 14666 | 1937 | 0.622492671 | 14695 | 1966 | 0.617872473 | 14724 | 1995 | 0.61330091 | 14753 | 2024 | 0.608327155 |
| 14638 | 1909 | 0.629516454 | 14667 | 1938 | 0.62233787 | 14696 | 1967 | 0.617617231 | 14725 | 1996 | 0.612702955 | 14754 | 2025 | 0.608327155 |
| 14639 | 1910 | 0.629516454 | 14668 | 1939 | 0.621829625 | 14697 | 1968 | 0.617617231 | 14726 | 1997 | 0.612578032 | 14755 | 2026 | 0.608327155 |
| 14640 | 1911 | 0.629516454 | 14669 | 1940 | 0.621243928 | 14698 | 1969 | 0.617350547 | 14727 | 1998 | 0.612578032 | 14756 | 2027 | 0.608327155 |
| 14641 | 1912 | 0.629516454 | 14670 | 1941 | 0.621243928 | 14699 | 1970 | 0.617350547 | 14728 | 1999 | 0.612578032 | 14757 | 2028 | 0.608327155 |
| 14642 | 1913 | 0.629516454 | 14671 | 1942 | 0.620916282 | 14700 | 1971 | 0.616927327 | 14729 | 2000 | 0.612408551 | 14758 | 2029 | 0.607719325 |
| 14643 | 1914 | 0.629516454 | 14672 | 1943 | 0.620916282 | 14701 | 1972 | 0.616679229 | 14730 | 2001 | 0.611787687 | 14759 | 2030 | 0.607614613 |

FIG. 2 (Cont.)

| DNA SEQ ID NO | AA SEQ ID NO | Log 10 enrichment in the brain |
|---|---|---|
| 14760 | 2031 | 0.607240059 |
| 14761 | 2032 | 0.607135674 |
| 14762 | 2033 | 0.607075585 |
| 14763 | 2034 | 0.606532547 |
| 14764 | 2035 | 0.606532547 |
| 14765 | 2036 | 0.606532547 |
| 14766 | 2037 | 0.606392655 |
| 14767 | 2038 | 0.606392655 |
| 14768 | 2039 | 0.606035358 |
| 14769 | 2040 | 0.606035358 |
| 14770 | 2041 | 0.605516178 |
| 14771 | 2042 | 0.605516178 |
| 14772 | 2043 | 0.605516178 |
| 14773 | 2044 | 0.605516178 |
| 14774 | 2045 | 0.605157108 |
| 14775 | 2046 | 0.605157108 |
| 14776 | 2047 | 0.60469287 |
| 14777 | 2048 | 0.604534166 |
| 14778 | 2049 | 0.604405734 |
| 14779 | 2050 | 0.604134723 |
| 14780 | 2051 | 0.604134723 |
| 14781 | 2052 | 0.603878517 |
| 14782 | 2053 | 0.603187515 |
| 14783 | 2054 | 0.603187515 |
| 14784 | 2055 | 0.603187515 |
| 14785 | 2056 | 0.603187515 |
| 14786 | 2057 | 0.603187515 |
| 14787 | 2058 | 0.603187515 |
| 14788 | 2059 | 0.603187515 |

| DNA SEQ ID NO | AA SEQ ID NO | Log 10 enrichment in the brain |
|---|---|---|
| 14789 | 2060 | 0.603187515 |
| 14790 | 2061 | 0.602242369 |
| 14791 | 2062 | 0.601972705 |
| 14792 | 2063 | 0.601972705 |
| 14793 | 2064 | 0.60168736 |
| 14794 | 2065 | 0.601226815 |
| 14795 | 2066 | 0.601226815 |
| 14796 | 2067 | 0.601063822 |
| 14797 | 2068 | 0.600871273 |
| 14798 | 2069 | 0.600871273 |
| 14799 | 2070 | 0.600871273 |
| 14800 | 2071 | 0.600192369 |
| 14801 | 2072 | 0.600005857 |
| 14802 | 2073 | 0.599553231 |
| 14803 | 2074 | 0.599553231 |
| 14804 | 2075 | 0.599553231 |
| 14805 | 2076 | 0.599274926 |
| 14806 | 2077 | 0.598805092 |
| 14807 | 2078 | 0.598567318 |
| 14808 | 2079 | 0.59810799 |
| 14809 | 2080 | 0.59810799 |
| 14810 | 2081 | 0.59810799 |
| 14811 | 2082 | 0.59810799 |
| 14812 | 2083 | 0.596275521 |
| 14813 | 2084 | 0.596275521 |
| 14814 | 2085 | 0.595949106 |
| 14815 | 2086 | 0.595949106 |
| 14816 | 2087 | 0.595738028 |
| 14817 | 2088 | 0.595738028 |

| DNA SEQ ID NO | AA SEQ ID NO | Log 10 enrichment in the brain |
|---|---|---|
| 14818 | 2089 | 0.594754348 |
| 14819 | 2090 | 0.594754348 |
| 14820 | 2091 | 0.594754348 |
| 14821 | 2092 | 0.594754348 |
| 14822 | 2093 | 0.594754348 |
| 14823 | 2094 | 0.594754348 |
| 14824 | 2095 | 0.594754348 |
| 14825 | 2096 | 0.594754348 |
| 14826 | 2097 | 0.594754348 |
| 14827 | 2098 | 0.594754348 |
| 14828 | 2099 | 0.594754348 |
| 14829 | 2100 | 0.594086716 |
| 14830 | 2101 | 0.594086716 |
| 14831 | 2102 | 0.593995755 |
| 14832 | 2103 | 0.593711624 |
| 14833 | 2104 | 0.593603898 |
| 14834 | 2105 | 0.593304281 |
| 14835 | 2106 | 0.593087189 |
| 14836 | 2107 | 0.593087189 |
| 14837 | 2108 | 0.593087189 |
| 14838 | 2109 | 0.593087189 |
| 14839 | 2110 | 0.592793647 |
| 14840 | 2111 | 0.592793647 |
| 14841 | 2112 | 0.592671397 |
| 14842 | 2113 | 0.592374646 |
| 14843 | 2114 | 0.592089956 |
| 14844 | 2115 | 0.591727893 |
| 14845 | 2116 | 0.591727893 |
| 14846 | 2117 | 0.591727893 |

| DNA SEQ ID NO | AA SEQ ID NO | Log 10 enrichment in the brain |
|---|---|---|
| 14847 | 2118 | 0.591727893 |
| 14848 | 2119 | 0.591553932 |
| 14849 | 2120 | 0.591426405 |
| 14850 | 2121 | 0.591426405 |
| 14851 | 2122 | 0.591251954 |
| 14852 | 2123 | 0.590598388 |
| 14853 | 2124 | 0.590598388 |
| 14854 | 2125 | 0.590598388 |
| 14855 | 2126 | 0.590598388 |
| 14856 | 2127 | 0.590598388 |
| 14857 | 2128 | 0.590007913 |
| 14858 | 2129 | 0.589869094 |
| 14859 | 2130 | 0.589869094 |
| 14860 | 2131 | 0.589771947 |
| 14861 | 2132 | 0.589644942 |
| 14862 | 2133 | 0.589644942 |
| 14863 | 2134 | 0.589644942 |
| 14864 | 2135 | 0.589644942 |
| 14865 | 2136 | 0.589399231 |
| 14866 | 2137 | 0.589221859 |
| 14867 | 2138 | 0.588982908 |
| 14868 | 2139 | 0.588982908 |
| 14869 | 2140 | 0.588643571 |
| 14870 | 2141 | 0.588123769 |
| 14871 | 2142 | 0.588123769 |
| 14872 | 2143 | 0.588123769 |
| 14873 | 2144 | 0.587744307 |
| 14874 | 2145 | 0.587744307 |
| 14875 | 2146 | 0.587654007 |

| DNA SEQ ID NO | AA SEQ ID NO | Log 10 enrichment in the brain |
|---|---|---|
| 14876 | 2147 | 0.587654007 |
| 14877 | 2148 | 0.587507311 |
| 14878 | 2149 | 0.587227392 |
| 14879 | 2150 | 0.587227392 |
| 14880 | 2151 | 0.587227392 |
| 14881 | 2152 | 0.587227392 |
| 14882 | 2153 | 0.587227392 |
| 14883 | 2154 | 0.587227392 |
| 14884 | 2155 | 0.587112606 |
| 14885 | 2156 | 0.586964103 |
| 14886 | 2157 | 0.586964103 |
| 14887 | 2158 | 0.586838239 |
| 14888 | 2159 | 0.586838239 |
| 14889 | 2160 | 0.586838239 |
| 14890 | 2161 | 0.586481822 |
| 14891 | 2162 | 0.586481822 |
| 14892 | 2163 | 0.586481822 |
| 14893 | 2164 | 0.586481822 |
| 14894 | 2165 | 0.586481822 |
| 14895 | 2166 | 0.58605076 |
| 14896 | 2167 | 0.58566317 |
| 14897 | 2168 | 0.585312792 |
| 14898 | 2169 | 0.585312792 |
| 14899 | 2170 | 0.585312792 |
| 14900 | 2171 | 0.584994511 |
| 14901 | 2172 | 0.584846059 |
| 14902 | 2173 | 0.584846059 |
| 14903 | 2174 | 0.58470411 |
| 14904 | 2175 | 0.584438079 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 14905 | 2176 | 0.584438079 | 14934 | 2205 | 0.580467057 | 14963 | 2234 | 0.575534642 | 14992 | 2263 | 0.571185347 | 15021 | 2292 | 0.566464708 |
| 14906 | 2177 | 0.584438079 | 14935 | 2206 | 0.580298431 | 14964 | 2235 | 0.575358422 | 14993 | 2264 | 0.571185347 | 15022 | 2293 | 0.566464708 |
| 14907 | 2178 | 0.584438079 | 14936 | 2207 | 0.580298431 | 14965 | 2236 | 0.575358422 | 14994 | 2265 | 0.571002832 | 15023 | 2294 | 0.566464708 |
| 14908 | 2179 | 0.584438079 | 14937 | 2208 | 0.580223868 | 14966 | 2237 | 0.575158792 | 14995 | 2266 | 0.570810794 | 15024 | 2295 | 0.566464708 |
| 14909 | 2180 | 0.584193475 | 14938 | 2209 | 0.580031091 | 14967 | 2238 | 0.575158792 | 14996 | 2267 | 0.570710967 | 15025 | 2296 | 0.565954674 |
| 14910 | 2181 | 0.584078415 | 14939 | 2210 | 0.578363932 | 14968 | 2239 | 0.574930756 | 14997 | 2268 | 0.570395002 | 15026 | 2297 | 0.565954674 |
| 14911 | 2182 | 0.584078415 | 14940 | 2211 | 0.578363932 | 14969 | 2240 | 0.574667786 | 14998 | 2269 | 0.570395002 | 15027 | 2298 | 0.565847374 |
| 14912 | 2183 | 0.583967809 | 14941 | 2212 | 0.578363932 | 14970 | 2241 | 0.574520593 | 14999 | 2270 | 0.570395002 | 15028 | 2299 | 0.565562747 |
| 14913 | 2184 | 0.583758964 | 14942 | 2213 | 0.578363932 | 14971 | 2242 | 0.574187991 | 15000 | 2271 | 0.570395002 | 15029 | 2300 | 0.565398955 |
| 14914 | 2185 | 0.583473337 | 14943 | 2214 | 0.578363932 | 14972 | 2243 | 0.573792369 | 15001 | 2272 | 0.569930764 | 15030 | 2301 | 0.565398955 |
| 14915 | 2186 | 0.582773051 | 14944 | 2215 | 0.578363932 | 14973 | 2244 | 0.573792369 | 15002 | 2273 | 0.569930764 | 15031 | 2302 | 0.565162475 |
| 14916 | 2187 | 0.582773051 | 14945 | 2216 | 0.578363932 | 14974 | 2245 | 0.573792369 | 15003 | 2274 | 0.569831349 | 15032 | 2303 | 0.565162475 |
| 14917 | 2188 | 0.582403909 | 14946 | 2217 | 0.578363932 | 14975 | 2246 | 0.573719027 | 15004 | 2275 | 0.569677752 | 15033 | 2304 | 0.564791124 |
| 14918 | 2189 | 0.582241587 | 14947 | 2218 | 0.578363932 | 14976 | 2247 | 0.573565049 | 15005 | 2276 | 0.569677752 | 15034 | 2305 | 0.564398276 |
| 14919 | 2190 | 0.581953163 | 14948 | 2219 | 0.578363932 | 14977 | 2248 | 0.573565049 | 15006 | 2277 | 0.569677752 | 15035 | 2306 | 0.564123493 |
| 14920 | 2191 | 0.581824464 | 14949 | 2220 | 0.578363932 | 14978 | 2249 | 0.573565049 | 15007 | 2278 | 0.569409089 | 15036 | 2307 | 0.564123493 |
| 14921 | 2192 | 0.581824464 | 14950 | 2221 | 0.578363932 | 14979 | 2250 | 0.573565049 | 15008 | 2279 | 0.569409089 | 15037 | 2308 | 0.564123493 |
| 14922 | 2193 | 0.581390386 | 14951 | 2222 | 0.578363932 | 14980 | 2251 | 0.573400512 | 15009 | 2280 | 0.569409089 | 15038 | 2309 | 0.563920504 |
| 14923 | 2194 | 0.581390386 | 14952 | 2223 | 0.576810104 | 14981 | 2252 | 0.573400512 | 15010 | 2281 | 0.568818614 | 15039 | 2310 | 0.563920504 |
| 14924 | 2195 | 0.581390386 | 14953 | 2224 | 0.576643951 | 14982 | 2253 | 0.573313939 | 15011 | 2282 | 0.568818614 | 15040 | 2311 | 0.563764423 |
| 14925 | 2196 | 0.581390386 | 14954 | 2225 | 0.576438011 | 14983 | 2254 | 0.573313939 | 15012 | 2283 | 0.568818614 | 15041 | 2312 | 0.563764423 |
| 14926 | 2197 | 0.581211775 | 14955 | 2226 | 0.576357949 | 14984 | 2255 | 0.573035098 | 15013 | 2284 | 0.568818614 | 15042 | 2313 | 0.563640675 |
| 14927 | 2198 | 0.581211775 | 14956 | 2227 | 0.576072135 | 14985 | 2256 | 0.573035098 | 15014 | 2285 | 0.568144767 | 15043 | 2314 | 0.563540155 |
| 14928 | 2199 | 0.58105307 | 14957 | 2228 | 0.576072135 | 14986 | 2257 | 0.572831443 | 15015 | 2286 | 0.567998416 | 15044 | 2315 | 0.563540155 |
| 14929 | 2200 | 0.580911121 | 14958 | 2229 | 0.575957862 | 14987 | 2258 | 0.572723664 | 15016 | 2287 | 0.567368547 | 15045 | 2316 | 0.563386776 |
| 14930 | 2201 | 0.580783406 | 14959 | 2230 | 0.575691342 | 14988 | 2259 | 0.572611603 | 15017 | 2288 | 0.567368547 | 15046 | 2317 | 0.562569664 |
| 14931 | 2202 | 0.580783406 | 14960 | 2231 | 0.575691342 | 14989 | 2260 | 0.572114982 | 15018 | 2289 | 0.56715571 | 15047 | 2318 | 0.562569664 |
| 14932 | 2203 | 0.580562896 | 14961 | 2232 | 0.575691342 | 14990 | 2261 | 0.571833065 | 15019 | 2290 | 0.56693447 | 15048 | 2319 | 0.562569664 |
| 14933 | 2204 | 0.580562896 | 14962 | 2233 | 0.575534642 | 14991 | 2262 | 0.571758565 | 15020 | 2291 | 0.56693447 | 15049 | 2320 | 0.562569664 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 15050 | 2321 | 0.562569664 | 15079 | 2350 | 0.559478588 | 15108 | 2379 | 0.553681467 | 15137 | 2408 | 0.550335208 | 15166 | 2437 | 0.546394726 |
| 15051 | 2322 | 0.562569664 | 15080 | 2351 | 0.559058776 | 15109 | 2380 | 0.553361663 | 15138 | 2409 | 0.550335208 | 15167 | 2438 | 0.546029414 |
| 15052 | 2323 | 0.562569664 | 15081 | 2352 | 0.559058776 | 15110 | 2381 | 0.553128108 | 15139 | 2410 | 0.550335208 | 15168 | 2439 | 0.545571418 |
| 15053 | 2324 | 0.562569664 | 15082 | 2353 | 0.55893538 | 15111 | 2382 | 0.5529822 | 15140 | 2411 | 0.549942003 | 15169 | 2440 | 0.545195568 |
| 15054 | 2325 | 0.562569664 | 15083 | 2354 | 0.55893538 | 15112 | 2383 | 0.552809827 | 15141 | 2412 | 0.549832843 | 15170 | 2441 | 0.544940176 |
| 15055 | 2326 | 0.561973515 | 15084 | 2355 | 0.55893538 | 15113 | 2384 | 0.552809827 | 15142 | 2413 | 0.54963978 | 15171 | 2442 | 0.544086259 |
| 15056 | 2327 | 0.561973515 | 15085 | 2356 | 0.55893538 | 15114 | 2385 | 0.552350499 | 15143 | 2414 | 0.54963978 | 15172 | 2443 | 0.544086259 |
| 15057 | 2328 | 0.561895817 | 15086 | 2357 | 0.55893538 | 15115 | 2386 | 0.552350499 | 15144 | 2415 | 0.549474366 | 15173 | 2444 | 0.543601825 |
| 15058 | 2329 | 0.561895817 | 15087 | 2358 | 0.558709244 | 15116 | 2387 | 0.552350499 | 15145 | 2416 | 0.549205703 | 15174 | 2445 | 0.543601825 |
| 15059 | 2330 | 0.561658238 | 15088 | 2359 | 0.558709244 | 15117 | 2388 | 0.552350499 | 15146 | 2417 | 0.549205703 | 15175 | 2446 | 0.543601825 |
| 15060 | 2331 | 0.561658238 | 15089 | 2360 | 0.558160546 | 15118 | 2389 | 0.552350499 | 15147 | 2418 | 0.548996857 | 15176 | 2447 | 0.543601825 |
| 15061 | 2332 | 0.561658238 | 15090 | 2361 | 0.558160546 | 15119 | 2390 | 0.552034993 | 15148 | 2419 | 0.548908952 | 15177 | 2448 | 0.543601825 |
| 15062 | 2333 | 0.561658238 | 15091 | 2362 | 0.558160546 | 15120 | 2391 | 0.552034993 | 15149 | 2420 | 0.548908952 | 15178 | 2449 | 0.543601825 |
| 15063 | 2334 | 0.561658238 | 15092 | 2363 | 0.558160546 | 15121 | 2392 | 0.552034993 | 15150 | 2421 | 0.548693261 | 15179 | 2450 | 0.543601825 |
| 15064 | 2335 | 0.561570137 | 15093 | 2364 | 0.557749476 | 15122 | 2393 | 0.551911596 | 15151 | 2422 | 0.548400708 | 15180 | 2451 | 0.543071875 |
| 15065 | 2336 | 0.561570137 | 15094 | 2365 | 0.557430025 | 15123 | 2394 | 0.551911596 | 15152 | 2423 | 0.548211514 | 15181 | 2452 | 0.542947274 |
| 15066 | 2337 | 0.561463181 | 15095 | 2366 | 0.556409356 | 15124 | 2395 | 0.551629678 | 15153 | 2424 | 0.548211514 | 15182 | 2453 | 0.542947274 |
| 15067 | 2338 | 0.561161902 | 15096 | 2367 | 0.556409356 | 15125 | 2396 | 0.551629678 | 15154 | 2425 | 0.548079128 | 15183 | 2454 | 0.542746072 |
| 15068 | 2339 | 0.56094004 | 15097 | 2368 | 0.556229486 | 15126 | 2397 | 0.551629678 | 15155 | 2426 | 0.548079128 | 15184 | 2455 | 0.542366278 |
| 15069 | 2340 | 0.56094004 | 15098 | 2369 | 0.555877784 | 15127 | 2398 | 0.551380442 | 15156 | 2427 | 0.547906068 | 15185 | 2456 | 0.542366278 |
| 15070 | 2341 | 0.560435535 | 15099 | 2370 | 0.554882836 | 15128 | 2399 | 0.551380442 | 15157 | 2428 | 0.547329698 | 15186 | 2457 | 0.54201391 |
| 15071 | 2342 | 0.560189963 | 15100 | 2371 | 0.554882836 | 15129 | 2400 | 0.551288654 | 15158 | 2429 | 0.547329698 | 15187 | 2458 | 0.541847098 |
| 15072 | 2343 | 0.560189963 | 15101 | 2372 | 0.554882836 | 15130 | 2401 | 0.550867758 | 15159 | 2430 | 0.547329698 | 15188 | 2459 | 0.541380365 |
| 15073 | 2344 | 0.559992242 | 15102 | 2373 | 0.554882836 | 15131 | 2402 | 0.550867758 | 15160 | 2431 | 0.547329698 | 15189 | 2460 | 0.541380365 |
| 15074 | 2345 | 0.559478588 | 15103 | 2374 | 0.554882836 | 15132 | 2403 | 0.550746667 | 15161 | 2432 | 0.547329698 | 15190 | 2461 | 0.541380365 |
| 15075 | 2346 | 0.559478588 | 15104 | 2375 | 0.554882836 | 15133 | 2404 | 0.550670441 | 15162 | 2433 | 0.546542219 | 15191 | 2462 | 0.541039609 |
| 15076 | 2347 | 0.559478588 | 15105 | 2376 | 0.554882836 | 15134 | 2405 | 0.550335208 | 15163 | 2434 | 0.546542219 | 15192 | 2463 | 0.540958515 |
| 15077 | 2348 | 0.559478588 | 15106 | 2377 | 0.554882836 | 15135 | 2406 | 0.550335208 | 15164 | 2435 | 0.546542219 | 15193 | 2464 | 0.540958515 |
| 15078 | 2349 | 0.559478588 | 15107 | 2378 | 0.553969493 | 15136 | 2407 | 0.550335208 | 15165 | 2436 | 0.546542219 | 15194 | 2465 | 0.540826771 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 15195 | 2466 | 0.540826771 | 15224 | 2495 | 0.538435985 | 15253 | 2524 | 0.532606441 | 15282 | 2553 | 0.529002317 | 15311 | 2582 | 0.525427856 |
| 15196 | 2467 | 0.540826771 | 15225 | 2496 | 0.538435985 | 15254 | 2525 | 0.532606441 | 15283 | 2554 | 0.529002317 | 15312 | 2583 | 0.525009259 |
| 15197 | 2468 | 0.540575371 | 15226 | 2497 | 0.538435985 | 15255 | 2526 | 0.532606441 | 15284 | 2555 | 0.529002317 | 15313 | 2584 | 0.525009259 |
| 15198 | 2469 | 0.540575371 | 15227 | 2498 | 0.538435985 | 15256 | 2527 | 0.532606441 | 15285 | 2556 | 0.528676147 | 15314 | 2585 | 0.525009259 |
| 15199 | 2470 | 0.540338891 | 15228 | 2499 | 0.538435985 | 15257 | 2528 | 0.532606441 | 15286 | 2557 | 0.528676147 | 15315 | 2586 | 0.524781104 |
| 15200 | 2471 | 0.53990568 | 15229 | 2500 | 0.53830842 | 15258 | 2529 | 0.532606441 | 15287 | 2558 | 0.528676147 | 15316 | 2587 | 0.524411963 |
| 15201 | 2472 | 0.53990568 | 15230 | 2501 | 0.538069337 | 15259 | 2530 | 0.532606441 | 15288 | 2559 | 0.528676147 | 15317 | 2588 | 0.524006269 |
| 15202 | 2473 | 0.539706782 | 15231 | 2502 | 0.537646666 | 15260 | 2531 | 0.532606441 | 15289 | 2560 | 0.528489875 | 15318 | 2589 | 0.524006269 |
| 15203 | 2474 | 0.539611343 | 15232 | 2503 | 0.537458944 | 15261 | 2532 | 0.532606441 | 15290 | 2561 | 0.528285067 | 15319 | 2590 | 0.524006269 |
| 15204 | 2475 | 0.539518436 | 15233 | 2504 | 0.537458944 | 15262 | 2533 | 0.532606441 | 15291 | 2562 | 0.528058813 | 15320 | 2591 | 0.523712728 |
| 15205 | 2476 | 0.539518436 | 15234 | 2505 | 0.536572628 | 15263 | 2534 | 0.532606441 | 15292 | 2563 | 0.528058813 | 15321 | 2592 | 0.523398439 |
| 15206 | 2477 | 0.539518436 | 15235 | 2506 | 0.536572628 | 15264 | 2535 | 0.532606441 | 15293 | 2564 | 0.527624041 | 15322 | 2593 | 0.523398439 |
| 15207 | 2478 | 0.539518436 | 15236 | 2507 | 0.536572628 | 15265 | 2536 | 0.532606441 | 15294 | 2565 | 0.527526916 | 15323 | 2594 | 0.523398439 |
| 15208 | 2479 | 0.539339824 | 15237 | 2508 | 0.536094769 | 15266 | 2537 | 0.530939282 | 15295 | 2566 | 0.527211409 | 15324 | 2595 | 0.523398439 |
| 15209 | 2480 | 0.539339824 | 15238 | 2509 | 0.535960083 | 15267 | 2538 | 0.530636848 | 15296 | 2567 | 0.527211409 | 15325 | 2596 | 0.523266415 |
| 15210 | 2481 | 0.539339824 | 15239 | 2510 | 0.535329299 | 15268 | 2539 | 0.530326675 | 15297 | 2568 | 0.527211409 | 15326 | 2597 | 0.523061123 |
| 15211 | 2482 | 0.539170211 | 15240 | 2511 | 0.535329299 | 15269 | 2540 | 0.530200371 | 15298 | 2569 | 0.527211409 | 15327 | 2598 | 0.523061123 |
| 15212 | 2483 | 0.539170211 | 15241 | 2512 | 0.535168658 | 15270 | 2541 | 0.530200371 | 15299 | 2570 | 0.526854112 | 15328 | 2599 | 0.522698152 |
| 15213 | 2484 | 0.539170211 | 15242 | 2513 | 0.535168658 | 15271 | 2542 | 0.530200371 | 15300 | 2571 | 0.526854112 | 15329 | 2600 | 0.522506114 |
| 15214 | 2485 | 0.539170211 | 15243 | 2514 | 0.535025915 | 15272 | 2543 | 0.530059252 | 15301 | 2572 | 0.526446132 | 15330 | 2601 | 0.522506114 |
| 15215 | 2486 | 0.53885539 | 15244 | 2515 | 0.534898238 | 15273 | 2544 | 0.530059252 | 15302 | 2573 | 0.526446132 | 15331 | 2602 | 0.522506114 |
| 15216 | 2487 | 0.53885539 | 15245 | 2516 | 0.534898238 | 15274 | 2545 | 0.530059252 | 15303 | 2574 | 0.526446132 | 15332 | 2603 | 0.522306484 |
| 15217 | 2488 | 0.53885539 | 15246 | 2517 | 0.53467945 | 15275 | 2546 | 0.530059252 | 15304 | 2575 | 0.526446132 | 15333 | 2604 | 0.521882576 |
| 15218 | 2489 | 0.53885539 | 15247 | 2518 | 0.534585007 | 15276 | 2547 | 0.530059252 | 15305 | 2576 | 0.526140399 | 15334 | 2605 | 0.521882576 |
| 15219 | 2490 | 0.53885539 | 15248 | 2519 | 0.534585007 | 15277 | 2548 | 0.529515364 | 15306 | 2577 | 0.526140399 | 15335 | 2606 | 0.521882576 |
| 15220 | 2491 | 0.53885539 | 15249 | 2520 | 0.534498795 | 15278 | 2549 | 0.529515364 | 15307 | 2578 | 0.525975862 | 15336 | 2607 | 0.521422274 |
| 15221 | 2492 | 0.538569388 | 15250 | 2521 | 0.534280025 | 15279 | 2550 | 0.529278498 | 15308 | 2579 | 0.525975862 | 15337 | 2608 | 0.521325431 |
| 15222 | 2493 | 0.538569388 | 15251 | 2522 | 0.534217925 | 15280 | 2551 | 0.529278498 | 15309 | 2580 | 0.525975862 | 15338 | 2609 | 0.521068528 |
| 15223 | 2494 | 0.538435985 | 15252 | 2523 | 0.532606441 | 15281 | 2552 | 0.529278498 | 15310 | 2581 | 0.525975862 | 15339 | 2610 | 0.520707218 |

FIG. 2 (Cont.)

| DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain | DNA SEQ ID NO | AA SEQ ID NO | Log 10 enrichment in the brain |
|---|---|---|---|---|---|---|---|---|---|---|---|---|---|---|
| 15340 | 2611 | 0.520707218 | 15367 | 2638 | 0.516369242 | 15394 | 2665 | 0.511417142 | 15421 | 2692 | 0.508839719 | 15448 | 2719 | 0.504577718 |
| 15341 | 2612 | 0.520707218 | 15368 | 2639 | 0.516216025 | 15395 | 2666 | 0.511417142 | 15422 | 2693 | 0.508472761 | 15449 | 2720 | 0.504577718 |
| 15342 | 2613 | 0.520371985 | 15369 | 2640 | 0.516216025 | 15396 | 2667 | 0.511417142 | 15423 | 2694 | 0.508472761 | 15450 | 2721 | 0.504577718 |
| 15343 | 2614 | 0.520371985 | 15370 | 2641 | 0.516216025 | 15397 | 2668 | 0.511417142 | 15424 | 2695 | 0.508163985 | 15451 | 2722 | 0.504035188 |
| 15344 | 2615 | 0.520371985 | 15371 | 2642 | 0.516216025 | 15398 | 2669 | 0.511417142 | 15425 | 2696 | 0.507983966 | 15452 | 2723 | 0.503864004 |
| 15345 | 2616 | 0.520017314 | 15372 | 2643 | 0.516216025 | 15399 | 2670 | 0.511417142 | 15426 | 2697 | 0.507983966 | 15453 | 2724 | 0.503864004 |
| 15346 | 2617 | 0.519769216 | 15373 | 2644 | 0.51603734 | 15400 | 2671 | 0.511417142 | 15427 | 2698 | 0.507983966 | 15454 | 2725 | 0.503864004 |
| 15347 | 2618 | 0.519769216 | 15374 | 2645 | 0.515871483 | 15401 | 2672 | 0.511417142 | 15428 | 2699 | 0.507983966 | 15455 | 2726 | 0.503864004 |
| 15348 | 2619 | 0.519769216 | 15375 | 2646 | 0.515573102 | 15402 | 2673 | 0.511417142 | 15429 | 2700 | 0.507300576 | 15456 | 2727 | 0.503864004 |
| 15349 | 2620 | 0.519585931 | 15376 | 2647 | 0.515573102 | 15403 | 2674 | 0.511417142 | 15430 | 2701 | 0.507300576 | 15457 | 2728 | 0.503864004 |
| 15350 | 2621 | 0.519444995 | 15377 | 2648 | 0.515573102 | 15404 | 2675 | 0.511417142 | 15431 | 2702 | 0.507300576 | 15458 | 2729 | 0.50339917 |
| 15351 | 2622 | 0.519103971 | 15378 | 2649 | 0.515573102 | 15405 | 2676 | 0.511417142 | 15432 | 2703 | 0.506845579 | 15459 | 2730 | 0.503222663 |
| 15352 | 2623 | 0.518926744 | 15379 | 2650 | 0.515263885 | 15406 | 2677 | 0.511417142 | 15433 | 2704 | 0.506845579 | 15460 | 2731 | 0.503222663 |
| 15353 | 2624 | 0.51886663 | 15380 | 2651 | 0.514877674 | 15407 | 2678 | 0.5107046 | 15434 | 2705 | 0.506670707 | 15461 | 2732 | 0.503222663 |
| 15354 | 2625 | 0.518366002 | 15381 | 2652 | 0.514381621 | 15408 | 2679 | 0.510590701 | 15435 | 2706 | 0.506520873 | 15462 | 2733 | 0.503222663 |
| 15355 | 2626 | 0.518366002 | 15382 | 2653 | 0.514381621 | 15409 | 2680 | 0.510518911 | 15436 | 2707 | 0.506520873 | 15463 | 2734 | 0.503222663 |
| 15356 | 2627 | 0.518366002 | 15383 | 2654 | 0.514381621 | 15410 | 2681 | 0.510330046 | 15437 | 2708 | 0.506277502 | 15464 | 2735 | 0.503222663 |
| 15357 | 2628 | 0.518366002 | 15384 | 2655 | 0.513721097 | 15411 | 2682 | 0.510330046 | 15438 | 2709 | 0.506277502 | 15465 | 2736 | 0.503222663 |
| 15358 | 2629 | 0.518366002 | 15385 | 2656 | 0.513490151 | 15412 | 2683 | 0.510330046 | 15439 | 2710 | 0.506277502 | 15466 | 2737 | 0.503222663 |
| 15359 | 2630 | 0.518366002 | 15386 | 2657 | 0.513490151 | 15413 | 2684 | 0.510202332 | 15440 | 2711 | 0.505548208 | 15467 | 2738 | 0.503222663 |
| 15360 | 2631 | 0.518366002 | 15387 | 2658 | 0.513301286 | 15414 | 2685 | 0.510202332 | 15441 | 2712 | 0.505548208 | 15468 | 2739 | 0.503222663 |
| 15361 | 2632 | 0.518366002 | 15388 | 2659 | 0.513301286 | 15415 | 2686 | 0.510040613 | 15442 | 2713 | 0.505256833 | | | |
| 15362 | 2633 | 0.517542695 | 15389 | 2660 | 0.513010885 | 15416 | 2687 | 0.509829226 | 15443 | 2714 | 0.505168193 | | | |
| 15363 | 2634 | 0.517542695 | 15390 | 2661 | 0.512798048 | 15417 | 2688 | 0.509829226 | 15444 | 2715 | 0.504577718 | | | |
| 15364 | 2635 | 0.517366475 | 15391 | 2662 | 0.51263536 | 15418 | 2689 | 0.509697162 | 15445 | 2716 | 0.504577718 | | | |
| 15365 | 2636 | 0.517366475 | 15392 | 2663 | 0.512506966 | 15419 | 2690 | 0.508942523 | 15446 | 2717 | 0.504577718 | | | |
| 15366 | 2637 | 0.516437943 | 15393 | 2664 | 0.512317235 | 15420 | 2691 | 0.508839719 | 15447 | 2718 | 0.504577718 | | | |

FIG. 3

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 15469 | 2740 | 1.805607713 | 0 | 15495 | 2766 | 1.435696428 | 0 | 15521 | 2792 | 1.339481843 | 0 | 15547 | 2818 | 1.297077994 | 0 |
| 15470 | 2741 | 1.782483914 | 0 | 15496 | 2767 | 1.432491288 | 0 | 15522 | 2793 | 1.338270728 | 0 | 15548 | 2819 | 1.295614353 | -1.155224741 |
| 15471 | 2742 | 1.756796407 | 0 | 15497 | 2768 | 1.429944099 | 0 | 15523 | 2794 | 1.336311796 | 0 | 15549 | 2820 | 1.294022734 | 0 |
| 15472 | 2743 | 1.7086977 | 0 | 15498 | 2769 | 1.417512639 | -0.925181513 | 15524 | 2795 | 1.333449878 | 0 | 15550 | 2821 | 1.29166475 | -0.839051407 |
| 15473 | 2744 | 1.621547524 | 0 | 15499 | 2770 | 1.4131306 | -1.199559314 | 15525 | 2796 | 1.333375379 | 0 | 15551 | 2822 | 1.288127945 | 0 |
| 15474 | 2745 | 1.611787687 | 0 | 15500 | 2771 | 1.411817991 | 0 | 15526 | 2797 | 1.333323519 | -1.222750977 | 15552 | 2823 | 1.281422818 | -0.34186017 |
| 15475 | 2746 | 1.611787687 | 0 | 15501 | 2772 | 1.407667705 | 0 | 15527 | 2798 | 1.332155836 | 0 | 15553 | 2824 | 1.280794468 | 0 |
| 15476 | 2747 | 1.599553231 | 0 | 15502 | 2773 | 1.404438734 | 0 | 15528 | 2799 | 1.329708103 | 0 | 15554 | 2825 | 1.280509778 | 0 |
| 15477 | 2748 | 1.593175811 | 0 | 15503 | 2774 | 1.403779635 | -1.39768257 | 15529 | 2800 | 1.327984093 | -0.761827075 | 15555 | 2826 | 1.277333936 | 0 |
| 15478 | 2749 | 1.559758687 | 0 | 15504 | 2775 | 1.397907867 | 0 | 15530 | 2801 | 1.322187153 | 0 | 15556 | 2827 | 1.276699466 | 0 |
| 15479 | 2750 | 1.534699431 | -1.140781313 | 15505 | 2776 | 1.397404629 | 0 | 15531 | 2802 | 1.317363058 | -0.588238962 | 15557 | 2828 | 1.276082366 | -0.365765777 |
| 15480 | 2751 | 1.532606441 | 0 | 15506 | 2777 | 1.39473782 | 0 | 15532 | 2803 | 1.315218569 | -1.002828148 | 15558 | 2829 | 1.27535537 | 0 |
| 15481 | 2752 | 1.532606441 | 0 | 15507 | 2778 | 1.39394168 | 0 | 15533 | 2804 | 1.314723879 | 0 | 15559 | 2830 | 1.2748016 | 0 |
| 15482 | 2753 | 1.514877674 | 0 | 15508 | 2779 | 1.386478405 | 0 | 15534 | 2805 | 1.312609696 | 0 | 15560 | 2831 | 1.273774125 | 0 |
| 15483 | 2754 | 1.511287094 | -1.321740616 | 15509 | 2780 | 1.38211136 | -1.271968999 | 15535 | 2806 | 1.311982783 | 0 | 15561 | 2832 | 1.273412515 | 0 |
| 15484 | 2755 | 1.497844335 | 0 | 15510 | 2781 | 1.379456849 | 0 | 15536 | 2807 | 1.310757692 | 0 | 15562 | 2833 | 1.272412699 | 0 |
| 15485 | 2756 | 1.496394268 | -1.222750977 | 15511 | 2782 | 1.379378065 | 0 | 15537 | 2808 | 1.310757692 | 0 | 15563 | 2834 | 1.270886179 | -1.103564569 |
| 15486 | 2757 | 1.486848951 | 0 | 15512 | 2783 | 1.374998588 | -0.4875688 | 15538 | 2809 | 1.310757692 | 0 | 15564 | 2835 | 1.269696909 | 0 |
| 15487 | 2758 | 1.480843526 | 0 | 15513 | 2784 | 1.374075258 | 0 | 15539 | 2810 | 1.310757692 | 0 | 15565 | 2836 | 1.269365006 | 0 |
| 15488 | 2759 | 1.457728072 | -1.321740616 | 15514 | 2785 | 1.370525897 | 0 | 15540 | 2811 | 1.3080933 | 0 | 15566 | 2837 | 1.269365006 | 0 |
| 15489 | 2760 | 1.455309339 | 0 | 15515 | 2786 | 1.365741816 | 0 | 15541 | 2812 | 1.305958809 | -0.540814312 | 15567 | 2838 | 1.268005711 | -0.288568261 |
| 15490 | 2761 | 1.445456265 | 0 | 15516 | 2787 | 1.358399326 | -1.4875688 | 15542 | 2813 | 1.302995926 | -0.237691326 | 15568 | 2839 | 1.265117594 | 0 |
| 15491 | 2762 | 1.445456265 | 0 | 15517 | 2788 | 1.345977191 | 0 | 15543 | 2814 | 1.300494616 | 0 | 15569 | 2840 | 1.262245265 | 0 |
| 15492 | 2763 | 1.444470352 | 0 | 15518 | 2789 | 1.345519798 | 0 | 15544 | 2815 | 1.300354931 | 0 | 15570 | 2841 | 1.260221627 | 0 |
| 15493 | 2764 | 1.444085169 | 0 | 15519 | 2790 | 1.340720915 | 0 | 15545 | 2816 | 1.300033826 | 0 | 15571 | 2842 | 1.259605169 | 0 |
| 15494 | 2765 | 1.442429811 | 0 | 15520 | 2791 | 1.340124766 | 0 | 15546 | 2817 | 1.297920467 | 0 | 15572 | 2843 | 1.259605169 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 15573 | 2844 | 1.259605169 | 0 | 15601 | 2872 | 1.231576445 | 0 | 15629 | 2900 | 1.210125444 | 0 | 15657 | 2928 | 1.196814339 | 0 |
| 15574 | 2845 | 1.258899573 | 0 | 15602 | 2873 | 1.229452752 | -1.136564829 | 15630 | 2901 | 1.209731112 | 0 | 15658 | 2929 | 1.196814339 | 0 |
| 15575 | 2846 | 1.258823361 | 0 | 15603 | 2874 | 1.229410384 | -1.429037021 | 15631 | 2902 | 1.20809535 | 0 | 15659 | 2930 | 1.196814339 | 0 |
| 15576 | 2847 | 1.258728692 | 0 | 15604 | 2875 | 1.227750038 | 0 | 15632 | 2903 | 1.20809535 | 0 | 15660 | 2931 | 1.194252122 | -0.418437792 |
| 15577 | 2848 | 1.256882311 | -0.312927607 | 15605 | 2876 | 1.226980694 | 0 | 15633 | 2904 | 1.20809535 | 0 | 15661 | 2932 | 1.194039285 | -0.280347931 |
| 15578 | 2849 | 1.254439328 | -0.995072683 | 15606 | 2877 | 1.225972568 | 0 | 15634 | 2905 | 1.206752862 | 0 | 15662 | 2933 | 1.193787885 | 0 |
| 15579 | 2850 | 1.25385284 | -0.016414393 | 15607 | 2878 | 1.225899313 | 0 | 15635 | 2906 | 1.206392899 | 0 | 15663 | 2934 | 1.193787885 | 0 |
| 15580 | 2851 | 1.253295695 | 0 | 15608 | 2879 | 1.225236267 | 0 | 15636 | 2907 | 1.206392899 | 0 | 15664 | 2935 | 1.192947043 | 0 |
| 15581 | 2852 | 1.25321837 | 0 | 15609 | 2880 | 1.224737021 | -0.454899683 | 15637 | 2908 | 1.206392899 | 0 | 15665 | 2936 | 1.19018376 | 0 |
| 15582 | 2853 | 1.25321837 | -1.262561531 | 15610 | 2881 | 1.224152427 | 0 | 15638 | 2909 | 1.205563013 | 0 | 15666 | 2937 | 1.19018376 | 0 |
| 15583 | 2854 | 1.251779832 | 0 | 15611 | 2882 | 1.221452573 | 0 | 15639 | 2910 | 1.205247507 | 0 | 15667 | 2938 | 1.189567302 | -1.275060076 |
| 15584 | 2855 | 1.249305212 | 0 | 15612 | 2883 | 1.22135728 | 0 | 15640 | 2911 | 1.205247507 | 0 | 15668 | 2939 | 1.188964402 | 0 |
| 15585 | 2856 | 1.248282139 | -1.134441135 | 15613 | 2884 | 1.22119441 | 0 | 15641 | 2912 | 1.204842192 | 0 | 15669 | 2940 | 1.188110752 | -0.874028991 |
| 15586 | 2857 | 1.247181519 | 0 | 15614 | 2885 | 1.22085258 | 0 | 15642 | 2913 | 1.204138197 | -0.992128303 | 15670 | 2941 | 1.187911944 | 0 |
| 15587 | 2858 | 1.244671744 | -1.418097035 | 15615 | 2886 | 1.220636459 | 0 | 15643 | 2914 | 1.204032696 | 0 | 15671 | 2942 | 1.187797521 | 0 |
| 15588 | 2859 | 1.239545375 | 0 | 15616 | 2887 | 1.219410538 | 0 | 15644 | 2915 | 1.203803867 | -1.479949403 | 15672 | 2943 | 1.187372783 | 0 |
| 15589 | 2860 | 1.237566809 | 0 | 15617 | 2888 | 1.217725334 | 0 | 15645 | 2916 | 1.20261275 | 0 | 15673 | 2944 | 1.185818955 | 0 |
| 15590 | 2861 | 1.236655971 | 0 | 15618 | 2889 | 1.217700042 | -1.327238088 | 15646 | 2917 | 1.201905775 | 0 | 15674 | 2945 | 1.184720865 | -0.593202381 |
| 15591 | 2862 | 1.235471489 | 0 | 15619 | 2890 | 1.217640668 | -0.501504578 | 15647 | 2918 | 1.201613222 | 0 | 15675 | 2946 | 1.184151796 | 0 |
| 15592 | 2863 | 1.234023181 | -1.37381423 | 15620 | 2891 | 1.217489984 | -1.399998813 | 15648 | 2919 | 1.201613222 | 0 | 15676 | 2947 | 1.183412885 | 0 |
| 15593 | 2864 | 1.231576445 | 0 | 15621 | 2892 | 1.216336479 | 0 | 15649 | 2920 | 1.201193816 | 0 | 15677 | 2948 | 1.183143371 | 0 |
| 15594 | 2865 | 1.231576445 | 0 | 15622 | 2893 | 1.213249064 | 0 | 15650 | 2921 | 1.20114649 | 0 | 15678 | 2949 | 1.182971112 | 0 |
| 15595 | 2866 | 1.231576445 | 0 | 15623 | 2894 | 1.21309304 | -1.284203456 | 15651 | 2922 | 1.201087123 | 0 | 15679 | 2950 | 1.182918442 | 0 |
| 15596 | 2867 | 1.231576445 | 0 | 15624 | 2895 | 1.21227129 | 0 | 15652 | 2923 | 1.199784611 | 0 | 15680 | 2951 | 1.182727878 | 0 |
| 15597 | 2868 | 1.231576445 | 0 | 15625 | 2896 | 1.211882137 | 0 | 15653 | 2924 | 1.199173359 | -1.310532394 | 15681 | 2952 | 1.182358423 | 0 |
| 15598 | 2869 | 1.231576445 | 0 | 15626 | 2897 | 1.21079284 | 0 | 15654 | 2925 | 1.197893332 | 0 | 15682 | 2953 | 1.18198333 | 0 |
| 15599 | 2870 | 1.231576445 | 0 | 15627 | 2898 | 1.210678521 | 0 | 15655 | 2926 | 1.197671782 | 0 | 15683 | 2954 | 1.181730073 | 0 |
| 15600 | 2871 | 1.231576445 | 0 | 15628 | 2899 | 1.210387146 | 0 | 15656 | 2927 | 1.196814339 | 0 | 15684 | 2955 | 1.181662995 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 15685 | 2956 | 1.18160247 | 0 | 15713 | 2984 | 1.16829461 | -1.498752967 | 15741 | 3012 | 1.152395199 | 0 | 15769 | 3040 | 1.141399815 | 0 |
| 15686 | 2957 | 1.181166942 | 0 | 15714 | 2985 | 1.168090188 | 0 | 15742 | 3013 | 1.151925438 | -0.137740187 | 15770 | 3041 | 1.141399815 | 0 |
| 15687 | 2958 | 1.180966452 | 0 | 15715 | 2986 | 1.167335549 | 0 | 15743 | 3014 | 1.15176073 | 0 | 15771 | 3042 | 1.141399815 | -1.233050933 |
| 15688 | 2959 | 1.180423923 | 0 | 15716 | 2987 | 1.167022469 | 0 | 15744 | 3015 | 1.151699772 | 0 | 15772 | 3043 | 1.141271799 | 0 |
| 15689 | 2960 | 1.180423923 | 0 | 15717 | 2988 | 1.166309714 | 0 | 15745 | 3016 | 1.151170108 | 0 | 15773 | 3044 | 1.140495976 | 0 |
| 15690 | 2961 | 1.180423923 | 0 | 15718 | 2989 | 1.165647932 | 0 | 15746 | 3017 | 1.150753252 | 0 | 15774 | 3045 | 1.140495976 | 0 |
| 15691 | 2962 | 1.179658646 | 0 | 15719 | 2990 | 1.164629656 | 0 | 15747 | 3018 | 1.150041294 | -1.472193938 | 15775 | 3046 | 1.140129328 | 0 |
| 15692 | 2963 | 1.179188376 | -0.225225596 | 15720 | 2991 | 1.164629656 | 0 | 15748 | 3019 | 1.149906399 | 0 | 15776 | 3047 | 1.140061464 | -0.385478274 |
| 15693 | 2964 | 1.178964108 | 0 | 15721 | 2992 | 1.164629656 | 0 | 15749 | 3020 | 1.14870951 | 0 | 15777 | 3048 | 1.139658378 | 0 |
| 15694 | 2965 | 1.178763139 | 0 | 15722 | 2993 | 1.164629656 | 0 | 15750 | 3021 | 1.148089405 | 0 | 15778 | 3049 | 1.138544088 | 0 |
| 15695 | 2966 | 1.178498002 | 0 | 15723 | 2994 | 1.164629656 | 0 | 15751 | 3022 | 1.14725556 | 0 | 15779 | 3050 | 1.137020338 | 0 |
| 15696 | 2967 | 1.178445357 | 0 | 15724 | 2995 | 1.162249954 | 0 | 15752 | 3023 | 1.146862711 | 0 | 15780 | 3051 | 1.136790126 | 0 |
| 15697 | 2968 | 1.177891586 | 0 | 15725 | 2996 | 1.161940517 | 0 | 15753 | 3024 | 1.145324501 | 0 | 15781 | 3052 | 1.135795938 | 0 |
| 15698 | 2969 | 1.177891586 | 0 | 15726 | 2997 | 1.161685275 | 0 | 15754 | 3025 | 1.145324501 | -0.554515589 | 15782 | 3053 | 1.134666432 | 0 |
| 15699 | 2970 | 1.177891586 | 0 | 15727 | 2998 | 1.161538579 | 0 | 15755 | 3026 | 1.145095961 | -1.284203456 | 15783 | 3054 | 1.134666432 | 0 |
| 15700 | 2971 | 1.176059118 | 0 | 15728 | 2999 | 1.160220537 | 0 | 15756 | 3027 | 1.14442627 | 0 | 15784 | 3055 | 1.134666432 | 0 |
| 15701 | 2972 | 1.17509509 | 0 | 15729 | 3000 | 1.159934535 | 0 | 15757 | 3028 | 1.144260414 | -0.191793944 | 15785 | 3056 | 1.134666432 | 0 |
| 15702 | 2973 | 1.17509509 | 0 | 15730 | 3001 | 1.158800112 | 0 | 15758 | 3029 | 1.143154543 | 0 | 15786 | 3057 | 1.134666432 | 0 |
| 15703 | 2974 | 1.174613877 | 0 | 15731 | 3002 | 1.158618564 | 0 | 15759 | 3030 | 1.142938958 | -1.239784316 | 15787 | 3058 | 1.134666432 | -1.186538804 |
| 15704 | 2975 | 1.174433559 | 0 | 15732 | 3003 | 1.157474725 | 0 | 15760 | 3031 | 1.142635362 | 0 | 15788 | 3059 | 1.133289904 | 0 |
| 15705 | 2976 | 1.173584498 | 0 | 15733 | 3004 | 1.156155348 | 0 | 15761 | 3032 | 1.142635362 | 0 | 15789 | 3060 | 1.132500371 | 0 |
| 15706 | 2977 | 1.173584498 | 0 | 15734 | 3005 | 1.155855732 | 0 | 15762 | 3033 | 1.142398883 | 0 | 15790 | 3061 | 1.131062308 | 0 |
| 15707 | 2978 | 1.171677185 | 0 | 15735 | 3006 | 1.155019343 | -0.167233649 | 15763 | 3034 | 1.142353261 | 0 | 15791 | 3062 | 1.130415555 | 0 |
| 15708 | 2979 | 1.171210001 | 0 | 15736 | 3007 | 1.154616659 | 0 | 15764 | 3035 | 1.142353261 | 0 | 15792 | 3063 | 1.12995433 | -1.268855764 |
| 15709 | 2980 | 1.170878605 | 0 | 15737 | 3008 | 1.154561261 | 0 | 15765 | 3036 | 1.142176034 | 0 | 15793 | 3064 | 1.129433906 | 0 |
| 15710 | 2981 | 1.170878605 | -1.441811309 | 15738 | 3009 | 1.153816787 | 0 | 15766 | 3037 | 1.142176034 | 0 | 15794 | 3065 | 1.128506124 | 0 |
| 15711 | 2982 | 1.169621601 | 0 | 15739 | 3010 | 1.153019634 | 0 | 15767 | 3038 | 1.141671334 | 0 | 15795 | 3066 | 1.127284479 | 0 |
| 15712 | 2983 | 1.169215701 | 0 | 15740 | 3011 | 1.152395199 | 0 | 15768 | 3039 | 1.141615292 | 0 | 15796 | 3067 | 1.127069251 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 15797 | 3068 | 1.126841095 | 0 | 15825 | 3096 | 1.117057487 | 0 | 15853 | 3124 | 1.106637709 | 0 | 15881 | 3152 | 1.100512156 | 0 |
| 15798 | 3069 | 1.126634337 | 0 | 15826 | 3097 | 1.116441612 | 0 | 15854 | 3125 | 1.106637709 | 0 | 15882 | 3153 | 1.100512156 | -0.247145416 |
| 15799 | 3070 | 1.126416357 | 0 | 15827 | 3098 | 1.115070876 | 0 | 15855 | 3126 | 1.106637709 | 0 | 15883 | 3154 | 1.100297531 | 0 |
| 15800 | 3071 | 1.126274007 | 0 | 15828 | 3099 | 1.114695352 | 0 | 15856 | 3127 | 1.106637709 | 0 | 15884 | 3155 | 1.099904326 | 0 |
| 15801 | 3072 | 1.126066261 | 0 | 15829 | 3100 | 1.114640527 | 0 | 15857 | 3128 | 1.106637709 | 0 | 15885 | 3156 | 1.099236694 | 0 |
| 15802 | 3073 | 1.125942864 | 0 | 15830 | 3101 | 1.114463046 | 0 | 15858 | 3129 | 1.106637709 | 0 | 15886 | 3157 | 1.099213691 | 0 |
| 15803 | 3074 | 1.125685133 | 0 | 15831 | 3102 | 1.114036431 | 0 | 15859 | 3130 | 1.106637709 | 0 | 15887 | 3158 | 1.09895088 | 0 |
| 15804 | 3075 | 1.123750018 | -0.576090072 | 15832 | 3103 | 1.113899393 | 0 | 15860 | 3131 | 1.106637709 | -0.76929364 | 15888 | 3159 | 1.09895088 | 0 |
| 15805 | 3076 | 1.123236971 | 0 | 15833 | 3104 | 1.113126755 | -0.714112671 | 15861 | 3132 | 1.105748672 | -1.338028568 | 15889 | 3160 | 1.09895088 | -0.154717091 |
| 15806 | 3077 | 1.123236971 | 0 | 15834 | 3105 | 1.112996453 | 0 | 15862 | 3133 | 1.105531225 | 0 | 15890 | 3161 | 1.098609856 | 0 |
| 15807 | 3078 | 1.123236971 | 0 | 15835 | 3106 | 1.112886658 | 0 | 15863 | 3134 | 1.104801366 | 0 | 15891 | 3162 | 1.098609856 | 0 |
| 15808 | 3079 | 1.122431976 | 0 | 15836 | 3107 | 1.112711857 | 0 | 15864 | 3135 | 1.104333754 | 0 | 15892 | 3163 | 1.098237167 | 0 |
| 15809 | 3080 | 1.122431976 | 0 | 15837 | 3108 | 1.112711857 | 0 | 15865 | 3136 | 1.10409052 | 0 | 15893 | 3164 | 1.097546531 | -0.259870878 |
| 15810 | 3081 | 1.122431976 | 0 | 15838 | 3109 | 1.112262323 | 0 | 15866 | 3137 | 1.103789866 | 0 | 15894 | 3165 | 1.096877872 | 0 |
| 15811 | 3082 | 1.122431976 | 0 | 15839 | 3110 | 1.112100605 | 0 | 15867 | 3138 | 1.103408739 | 0 | 15895 | 3166 | 1.096632577 | 0 |
| 15812 | 3083 | 1.122212691 | 0 | 15840 | 3111 | 1.111966542 | 0 | 15868 | 3139 | 1.103092428 | 0 | 15896 | 3167 | 1.096576383 | 0 |
| 15813 | 3084 | 1.120680786 | -1.278129308 | 15841 | 3112 | 1.111889218 | 0 | 15869 | 3140 | 1.103033585 | 0 | 15897 | 3168 | 1.096390174 | 0 |
| 15814 | 3085 | 1.120635141 | -1.363887067 | 15842 | 3113 | 1.111002514 | 0 | 15870 | 3141 | 1.102737668 | 0 | 15898 | 3169 | 1.095913843 | 0 |
| 15815 | 3086 | 1.119943176 | -1.301932223 | 15843 | 3114 | 1.109940344 | -1.243112259 | 15871 | 3142 | 1.101730374 | 0 | 15899 | 3170 | 1.095913843 | -1.215746075 |
| 15816 | 3087 | 1.119704454 | 0 | 15844 | 3115 | 1.109842849 | 0 | 15872 | 3143 | 1.101463075 | 0 | 15900 | 3171 | 1.095472711 | 0 |
| 15817 | 3088 | 1.119602686 | 0 | 15845 | 3116 | 1.109582089 | 0 | 15873 | 3144 | 1.101242677 | 0 | 15901 | 3172 | 1.095356698 | 0 |
| 15818 | 3089 | 1.118872165 | 0 | 15846 | 3117 | 1.108068664 | 0 | 15874 | 3145 | 1.101242677 | 0 | 15902 | 3173 | 1.095356698 | 0 |
| 15819 | 3090 | 1.117633093 | 0 | 15847 | 3118 | 1.108068664 | 0 | 15875 | 3146 | 1.101057831 | -0.19587883 | 15903 | 3174 | 1.095219805 | -1.047527439 |
| 15820 | 3091 | 1.117633093 | 0 | 15848 | 3119 | 1.1079638 | 0 | 15876 | 3147 | 1.100960576 | 0 | 15904 | 3175 | 1.094993728 | 0 |
| 15821 | 3092 | 1.117633093 | 0 | 15849 | 3120 | 1.107514186 | 0 | 15877 | 3148 | 1.100900578 | 0 | 15905 | 3176 | 1.094448046 | 0 |
| 15822 | 3093 | 1.117633093 | 0 | 15850 | 3121 | 1.106637709 | 0 | 15878 | 3149 | 1.100808165 | 0 | 15906 | 3177 | 1.094114589 | 0 |
| 15823 | 3094 | 1.117633093 | 0 | 15851 | 3122 | 1.106637709 | 0 | 15879 | 3150 | 1.100740312 | 0 | 15907 | 3178 | 1.093943438 | 0 |
| 15824 | 3095 | 1.117103143 | 0 | 15852 | 3123 | 1.106637709 | 0 | 15880 | 3151 | 1.100740312 | 0 | 15908 | 3179 | 1.093273747 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 15909 | 3180 | 1.093273747 | -0.76929364 | 15937 | 3208 | 1.086081954 | 0 | 15965 | 3236 | 1.075352431 | 0 | 15993 | 3264 | 1.068373209 | 0 |
| 15910 | 3181 | 1.092809509 | 0 | 15938 | 3209 | 1.086081954 | 0 | 15966 | 3237 | 1.075229245 | -0.58321816 | 15994 | 3265 | 1.068259474 | 0 |
| 15911 | 3182 | 1.092701931 | 0 | 15939 | 3210 | 1.085933384 | 0 | 15967 | 3238 | 1.074790342 | 0 | 15995 | 3266 | 1.067983732 | 0 |
| 15912 | 3183 | 1.092581644 | 0 | 15940 | 3211 | 1.08544841 | 0 | 15968 | 3239 | 1.074578128 | 0 | 15996 | 3267 | 1.067549698 | -1.454220567 |
| 15913 | 3184 | 1.092581644 | 0 | 15941 | 3212 | 1.084448882 | -1.366390212 | 15969 | 3240 | 1.074453025 | 0 | 15997 | 3268 | 1.06738441 | 0 |
| 15914 | 3185 | 1.092529455 | 0 | 15942 | 3213 | 1.084361314 | 0 | 15970 | 3241 | 1.074370531 | 0 | 15998 | 3269 | 1.06722359 | 0 |
| 15915 | 3186 | 1.092468753 | 0 | 15943 | 3214 | 1.083973724 | 0 | 15971 | 3242 | 1.073968592 | 0 | 15999 | 3270 | 1.066593068 | 0 |
| 15916 | 3187 | 1.092262584 | 0 | 15944 | 3215 | 1.083774826 | -1.142874303 | 15972 | 3243 | 1.073968592 | -1.441811309 | 16000 | 3271 | 1.066480571 | 0 |
| 15917 | 3188 | 1.092207993 | 0 | 15945 | 3216 | 1.083289526 | 0 | 15973 | 3244 | 1.073637449 | 0 | 16001 | 3272 | 1.066480571 | 0 |
| 15918 | 3189 | 1.091914452 | 0 | 15946 | 3217 | 1.082637432 | 0 | 15974 | 3245 | 1.073508291 | 0 | 16002 | 3273 | 1.066209052 | 0 |
| 15919 | 3190 | 1.091697359 | 0 | 15947 | 3218 | 1.082637432 | 0 | 15975 | 3246 | 1.073286633 | 0 | 16003 | 3274 | 1.065764826 | 0 |
| 15920 | 3191 | 1.091200739 | 0 | 15948 | 3219 | 1.081691875 | 0 | 15976 | 3247 | 1.073009531 | -0.754229894 | 16004 | 3275 | 1.065704352 | 0 |
| 15921 | 3192 | 1.091125543 | 0 | 15949 | 3220 | 1.081655421 | 0 | 15977 | 3248 | 1.072255397 | 0 | 16005 | 3276 | 1.065245024 | 0 |
| 15922 | 3193 | 1.090422165 | 0 | 15950 | 3221 | 1.081655421 | 0 | 15978 | 3249 | 1.07219088 | 0 | 16006 | 3277 | 1.065245024 | -1.371353631 |
| 15923 | 3194 | 1.089902751 | 0 | 15951 | 3222 | 1.08030877 | 0 | 15979 | 3250 | 1.071875603 | 0 | 16007 | 3278 | 1.065083245 | 0 |
| 15924 | 3195 | 1.089902751 | -0.033431452 | 15952 | 3223 | 1.079715066 | 0 | 15980 | 3251 | 1.071572006 | 0 | 16008 | 3279 | 1.064926743 | 0 |
| 15925 | 3196 | 1.089299495 | 0 | 15953 | 3224 | 1.078808615 | 0 | 15981 | 3252 | 1.071279454 | 0 | 16009 | 3280 | 1.064628566 | 0 |
| 15926 | 3197 | 1.088366413 | -1.376260966 | 15954 | 3225 | 1.078715027 | 0 | 15982 | 3253 | 1.070997353 | -0.343324908 | 16010 | 3281 | 1.064215018 | 0 |
| 15927 | 3198 | 1.088154303 | 0 | 15955 | 3226 | 1.077599501 | 0 | 15983 | 3254 | 1.070208443 | 0 | 16011 | 3282 | 1.064085358 | 0 |
| 15928 | 3199 | 1.08797094 | 0 | 15956 | 3227 | 1.077313624 | 0 | 15984 | 3255 | 1.069997569 | -1.439708184 | 16012 | 3283 | 1.063918354 | 0 |
| 15929 | 3200 | 1.087841223 | 0 | 15957 | 3228 | 1.077024864 | 0 | 15985 | 3256 | 1.069914902 | 0 | 16013 | 3284 | 1.063603077 | 0 |
| 15930 | 3201 | 1.087841223 | 0 | 15958 | 3229 | 1.077024864 | 0 | 15986 | 3257 | 1.069792651 | 0 | 16014 | 3285 | 1.063603077 | 0 |
| 15931 | 3202 | 1.08766987 | 0 | 15959 | 3230 | 1.076674485 | 0 | 15987 | 3258 | 1.069273471 | 0 | 16015 | 3286 | 1.063454116 | 0 |
| 15932 | 3203 | 1.087487355 | 0 | 15960 | 3231 | 1.076674485 | 0 | 15988 | 3259 | 1.069100549 | 0 | 16016 | 3287 | 1.063454116 | 0 |
| 15933 | 3204 | 1.087084172 | 0 | 15961 | 3232 | 1.076240408 | 0 | 15989 | 3260 | 1.06902776 | 0 | 16017 | 3288 | 1.063381667 | 0 |
| 15934 | 3205 | 1.087084172 | 0 | 15962 | 3233 | 1.076169785 | 0 | 15990 | 3261 | 1.068849148 | 0 | 16018 | 3289 | 1.062934674 | 0 |
| 15935 | 3206 | 1.086620595 | 0 | 15963 | 3234 | 1.075878345 | 0 | 15991 | 3262 | 1.068606864 | 0 | 16019 | 3290 | 1.062547041 | 0 |
| 15936 | 3207 | 1.086196549 | 0 | 15964 | 3235 | 1.075380015 | 0 | 15992 | 3263 | 1.068606864 | 0 | 16020 | 3291 | 1.062434046 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16021 | 3292 | 1.062271176 | 0 | 16049 | 3320 | 1.055485186 | 0 | 16077 | 3348 | 1.048185948 | 0 | 16105 | 3376 | 1.042121225 | 0 |
| 16022 | 3293 | 1.061559334 | 0 | 16050 | 3321 | 1.055485186 | 0 | 16078 | 3349 | 1.047516257 | 0 | 16106 | 3377 | 1.042121225 | 0 |
| 16023 | 3294 | 1.061089064 | 0 | 16051 | 3322 | 1.055485186 | 0 | 16079 | 3350 | 1.047290708 | 0 | 16107 | 3378 | 1.041912379 | 0 |
| 16024 | 3295 | 1.060880218 | 0 | 16052 | 3323 | 1.055485186 | 0 | 16080 | 3351 | 1.047052019 | 0 | 16108 | 3379 | 1.041912379 | 0 |
| 16025 | 3296 | 1.060781526 | 0 | 16053 | 3324 | 1.055485186 | 0 | 16081 | 3352 | 1.046885015 | 0 | 16109 | 3380 | 1.041586577 | 0 |
| 16026 | 3297 | 1.060505988 | 0 | 16054 | 3325 | 1.055485186 | 0 | 16082 | 3353 | 1.046850817 | 0 | 16110 | 3381 | 1.041244747 | 0 |
| 16027 | 3298 | 1.060505988 | -0.423517317 | 16055 | 3326 | 1.055485186 | 0 | 16083 | 3354 | 1.046746572 | -1.525514685 | 16111 | 3382 | 1.040699265 | 0 |
| 16028 | 3299 | 1.060032814 | -0.626443314 | 16056 | 3327 | 1.055485186 | 0 | 16084 | 3355 | 1.046530344 | -0.992128303 | 16112 | 3383 | 1.04050803 | 0 |
| 16029 | 3300 | 1.060032814 | -0.92747331 | 16057 | 3328 | 1.055485186 | 0 | 16085 | 3356 | 1.04624453 | 0 | 16113 | 3384 | 1.039903444 | -1.481866821 |
| 16030 | 3301 | 1.059894305 | 0 | 16058 | 3329 | 1.055485186 | 0 | 16086 | 3357 | 1.045939868 | 0 | 16114 | 3385 | 1.039690919 | 0 |
| 16031 | 3302 | 1.059469567 | 0 | 16059 | 3330 | 1.053765206 | -1.528961485 | 16087 | 3358 | 1.045939868 | 0 | 16115 | 3386 | 1.039690919 | 0 |
| 16032 | 3303 | 1.059469567 | 0 | 16060 | 3331 | 1.052812597 | -1.036998572 | 16088 | 3359 | 1.045939868 | 0 | 16116 | 3387 | 1.039690919 | 0 |
| 16033 | 3304 | 1.059362841 | 0 | 16061 | 3332 | 1.052655896 | 0 | 16089 | 3360 | 1.045408296 | 0 | 16117 | 3388 | 1.03933855 | 0 |
| 16034 | 3305 | 1.059030467 | 0 | 16062 | 3333 | 1.052415955 | 0 | 16090 | 3361 | 1.044761321 | 0 | 16118 | 3389 | 1.039017072 | 0 |
| 16035 | 3306 | 1.059030467 | 0 | 16063 | 3334 | 1.052349473 | 0 | 16091 | 3362 | 1.044654339 | 0 | 16119 | 3390 | 1.038970098 | 0 |
| 16036 | 3307 | 1.058787822 | -1.243112259 | 16064 | 3335 | 1.052280047 | 0 | 16092 | 3363 | 1.044489802 | 0 | 16120 | 3391 | 1.038451847 | -1.318965562 |
| 16037 | 3308 | 1.058511641 | 0 | 16065 | 3336 | 1.051590143 | -0.874028991 | 16093 | 3364 | 1.044489802 | -1.20502221 | 16121 | 3392 | 1.03811109 | 0 |
| 16038 | 3309 | 1.057500478 | 0 | 16066 | 3337 | 1.051248133 | 0 | 16094 | 3365 | 1.044055725 | 0 | 16122 | 3393 | 1.037756419 | 0 |
| 16039 | 3310 | 1.055485186 | 0 | 16067 | 3338 | 1.051185206 | 0 | 16095 | 3366 | 1.044055725 | -1.313361685 | 16123 | 3394 | 1.037756419 | 0 |
| 16040 | 3311 | 1.055485186 | 0 | 16068 | 3339 | 1.050984685 | 0 | 16096 | 3367 | 1.043903314 | 0 | 16124 | 3395 | 1.037311217 | 0 |
| 16041 | 3312 | 1.055485186 | 0 | 16069 | 3340 | 1.050984685 | 0 | 16097 | 3368 | 1.043585963 | 0 | 16125 | 3396 | 1.037196401 | 0 |
| 16042 | 3313 | 1.055485186 | 0 | 16070 | 3341 | 1.050156353 | 0 | 16098 | 3369 | 1.043336297 | 0 | 16126 | 3397 | 1.037196401 | 0 |
| 16043 | 3314 | 1.055485186 | 0 | 16071 | 3342 | 1.050056435 | 0 | 16099 | 3370 | 1.04325073 | 0 | 16127 | 3398 | 1.037001781 | 0 |
| 16044 | 3315 | 1.055485186 | 0 | 16072 | 3343 | 1.049616253 | 0 | 16100 | 3371 | 1.043181404 | 0 | 16128 | 3399 | 1.036843076 | 0 |
| 16045 | 3316 | 1.055485186 | 0 | 16073 | 3344 | 1.049616253 | 0 | 16101 | 3372 | 1.043075928 | 0 | 16129 | 3400 | 1.036180031 | 0 |
| 16046 | 3317 | 1.055485186 | 0 | 16074 | 3345 | 1.049236237 | 0 | 16102 | 3373 | 1.042968629 | 0 | 16130 | 3401 | 1.036056635 | -1.329960946 |
| 16047 | 3318 | 1.055485186 | 0 | 16075 | 3346 | 1.049236237 | 0 | 16103 | 3374 | 1.042843706 | 0 | 16131 | 3402 | 1.035830498 | 0 |
| 16048 | 3319 | 1.055485186 | 0 | 16076 | 3347 | 1.049098388 | 0 | 16104 | 3375 | 1.04232374 | 0 | 16132 | 3403 | 1.0352818 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16133 | 3404 | 1.035078336 | 0 | 16161 | 3432 | 1.028211102 | 0 | 16189 | 3460 | 1.0238862 | 0 | 16217 | 3488 | 1.019946861 | 0 |
| 16134 | 3405 | 1.035044026 | -1.065360216 | 16162 | 3433 | 1.028211102 | 0 | 16190 | 3461 | 1.0238862 | 0 | 16218 | 3489 | 1.019946861 | -0.31772649 |
| 16135 | 3406 | 1.035022132 | 0 | 16163 | 3434 | 1.028046938 | 0 | 16191 | 3462 | 1.0238862 | -1.358837074 | 16219 | 3490 | 1.019909032 | -0.707254185 |
| 16136 | 3407 | 1.034995798 | 0 | 16164 | 3435 | 1.027989013 | 0 | 16192 | 3463 | 1.023770773 | 0 | 16220 | 3491 | 1.019135164 | 0 |
| 16137 | 3408 | 1.03470158 | -1.155224741 | 16165 | 3436 | 1.027989013 | 0 | 16193 | 3464 | 1.023770773 | -0.102038049 | 16221 | 3492 | 1.018968353 | 0 |
| 16138 | 3409 | 1.03455128 | 0 | 16166 | 3437 | 1.027791696 | 0 | 16194 | 3465 | 1.02351598 | 0 | 16222 | 3493 | 1.018968353 | 0 |
| 16139 | 3410 | 1.034295887 | 0 | 16167 | 3438 | 1.027456463 | 0 | 16195 | 3466 | 1.02351598 | 0 | 16223 | 3494 | 1.018968353 | 0 |
| 16140 | 3411 | 1.034087042 | -0.188631794 | 16168 | 3439 | 1.027456463 | 0 | 16196 | 3467 | 1.023300503 | 0 | 16224 | 3495 | 1.018762379 | 0 |
| 16141 | 3412 | 1.033765937 | 0 | 16169 | 3440 | 1.027456463 | 0 | 16197 | 3468 | 1.023017298 | 0 | 16225 | 3496 | 1.018682538 | 0 |
| 16142 | 3413 | 1.033765937 | -0.194556776 | 16170 | 3441 | 1.027456463 | 0 | 16198 | 3469 | 1.022955962 | 0 | 16226 | 3497 | 1.018640129 | 0 |
| 16143 | 3414 | 1.033093914 | 0 | 16171 | 3442 | 1.026840005 | -0.320817567 | 16199 | 3470 | 1.022955962 | 0 | 16227 | 3498 | 1.01850162 | 0 |
| 16144 | 3415 | 1.032535988 | 0 | 16172 | 3443 | 1.026761035 | 0 | 16200 | 3471 | 1.022955962 | -1.112612698 | 16228 | 3499 | 1.018022795 | 0 |
| 16145 | 3416 | 1.032398366 | 0 | 16173 | 3444 | 1.026761035 | 0 | 16201 | 3472 | 1.022860711 | 0 | 16229 | 3500 | 1.017901144 | 0 |
| 16146 | 3417 | 1.032004091 | 0 | 16174 | 3445 | 1.026595621 | 0 | 16202 | 3473 | 1.022790169 | 0 | 16230 | 3501 | 1.017901144 | 0 |
| 16147 | 3418 | 1.032004091 | 0 | 16175 | 3446 | 1.026595621 | 0 | 16203 | 3474 | 1.022692673 | 0 | 16231 | 3502 | 1.017696626 | 0 |
| 16148 | 3419 | 1.032004091 | 0 | 16176 | 3447 | 1.02652149 | 0 | 16204 | 3475 | 1.022583017 | 0 | 16232 | 3503 | 1.017696626 | 0 |
| 16149 | 3420 | 1.031616846 | -0.920561315 | 16177 | 3448 | 1.02619581 | 0 | 16205 | 3476 | 1.022484926 | 0 | 16233 | 3504 | 1.017395137 | 0 |
| 16150 | 3421 | 1.031446946 | -0.394686276 | 16178 | 3449 | 1.025521963 | 0 | 16206 | 3477 | 1.022425086 | 0 | 16234 | 3505 | 1.017183578 | 0 |
| 16151 | 3422 | 1.031351507 | -1.171163942 | 16179 | 3450 | 1.025521963 | 0 | 16207 | 3478 | 1.022316823 | -0.958349876 | 16235 | 3506 | 1.016855784 | 0 |
| 16152 | 3423 | 1.031011417 | 0 | 16180 | 3451 | 1.025521963 | 0 | 16208 | 3479 | 1.022178004 | 0 | 16236 | 3507 | 1.016855784 | 0 |
| 16153 | 3424 | 1.031011417 | -1.466285079 | 16181 | 3452 | 1.025399816 | 0 | 16209 | 3480 | 1.021876585 | 0 | 16237 | 3508 | 1.016732597 | 0 |
| 16154 | 3425 | 1.029724324 | 0 | 16182 | 3453 | 1.025102557 | 0 | 16210 | 3481 | 1.021237342 | -0.05218341 | 16238 | 3509 | 1.016732597 | 0 |
| 16155 | 3426 | 1.029156248 | 0 | 16183 | 3454 | 1.024995864 | 0 | 16211 | 3482 | 1.02072308 | 0 | 16239 | 3510 | 1.01656712 | 0 |
| 16156 | 3427 | 1.029156248 | 0 | 16184 | 3455 | 1.024780213 | -1.592708584 | 16212 | 3483 | 1.02072308 | 0 | 16240 | 3511 | 1.01656712 | 0 |
| 16157 | 3428 | 1.028926158 | 0 | 16185 | 3456 | 1.024704852 | -1.103564569 | 16213 | 3484 | 1.02072308 | 0 | 16241 | 3512 | 1.016387326 | 0 |
| 16158 | 3429 | 1.028750933 | 0 | 16186 | 3457 | 1.024450953 | 0 | 16214 | 3485 | 1.02072308 | -0.503025751 | 16242 | 3513 | 1.015976645 | 0 |
| 16159 | 3430 | 1.02865562 | -0.985179443 | 16187 | 3458 | 1.024450953 | 0 | 16215 | 3486 | 1.02072308 | -1.281177001 | 16243 | 3514 | 1.015976645 | 0 |
| 16160 | 3431 | 1.028501697 | 0 | 16188 | 3459 | 1.024450953 | 0 | 16216 | 3487 | 1.02072308 | -1.385912352 | 16244 | 3515 | 1.015976645 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16245 | 3516 | 1.015613674 | 0 | 16273 | 3544 | 1.009727696 | 0 | 16301 | 3572 | 1.005571736 | 0 | 16329 | 3600 | 1.001127524 | 0 |
| 16246 | 3517 | 1.01555724 | 0 | 16274 | 3545 | 1.009727696 | 0 | 16302 | 3573 | 1.005318577 | 0 | 16330 | 3601 | 1.001127524 | 0 |
| 16247 | 3518 | 1.015056529 | 0 | 16275 | 3546 | 1.009727696 | 0 | 16303 | 3574 | 1.005075683 | 0 | 16331 | 3602 | 1.001127524 | 0 |
| 16248 | 3519 | 1.014867335 | -1.351150245 | 16276 | 3547 | 1.009727696 | 0 | 16304 | 3575 | 1.004745295 | 0 | 16332 | 3603 | 1.001127524 | 0 |
| 16249 | 3520 | 1.014691115 | 0 | 16277 | 3548 | 1.009027785 | -1.441811309 | 16305 | 3576 | 1.004706894 | 0 | 16333 | 3604 | 1.001127524 | 0 |
| 16250 | 3521 | 1.014448335 | 0 | 16278 | 3549 | 1.008992227 | -1.42030719 | 16306 | 3577 | 1.004332664 | 0 | 16334 | 3605 | 1.001127524 | -1.259379872 |
| 16251 | 3522 | 1.014092501 | 0 | 16279 | 3550 | 1.008909044 | 0 | 16307 | 3578 | 1.004332664 | -0.858234723 | 16335 | 3606 | 1.000584316 | -0.216017594 |
| 16252 | 3523 | 1.013883656 | 0 | 16280 | 3551 | 1.008859974 | 0 | 16308 | 3579 | 1.003940524 | 0 | 16336 | 3607 | 1.000519694 | 0 |
| 16253 | 3524 | 1.013844262 | -0.414636503 | 16281 | 3552 | 1.008586317 | 0 | 16309 | 3580 | 1.003689741 | 0 | 16337 | 3608 | 1.00043762 | 0 |
| 16254 | 3525 | 1.013786552 | -1.278129308 | 16282 | 3553 | 1.008488624 | 0 | 16310 | 3581 | 1.003689741 | 0 | 16338 | 3609 | 1.000329922 | 0 |
| 16255 | 3526 | 1.013693883 | 0 | 16283 | 3554 | 1.008488624 | 0 | 16311 | 3582 | 1.003689741 | 0 | 16339 | 3610 | 1.000262395 | 0 |
| 16256 | 3527 | 1.013520685 | 0 | 16284 | 3555 | 1.008232705 | 0 | 16312 | 3583 | 1.003567387 | 0 | 16340 | 3611 | 0.999898098 | 0 |
| 16257 | 3528 | 1.01336198 | 0 | 16285 | 3556 | 1.008151308 | 0 | 16313 | 3584 | 1.003456186 | 0 | 16341 | 3612 | 0.999369244 | 0 |
| 16258 | 3529 | 1.013287507 | 0 | 16286 | 3557 | 1.007843552 | 0 | 16314 | 3585 | 1.003456186 | 0 | 16342 | 3613 | 0.999369244 | 0 |
| 16259 | 3530 | 1.013287507 | 0 | 16287 | 3558 | 1.007758103 | 0 | 16315 | 3586 | 1.003387518 | 0 | 16343 | 3614 | 0.999369244 | 0 |
| 16260 | 3531 | 1.013081338 | 0 | 16288 | 3559 | 1.00744793 | 0 | 16316 | 3587 | 1.003387518 | -0.040410768 | 16344 | 3615 | 0.999262262 | -1.271968999 |
| 16261 | 3532 | 1.012733206 | 0 | 16289 | 3560 | 1.00738648 | 0 | 16317 | 3588 | 1.003307175 | 0 | 16345 | 3616 | 0.99900383 | 0 |
| 16262 | 3533 | 1.012450554 | 0 | 16290 | 3561 | 1.007180507 | 0 | 16318 | 3589 | 1.003097117 | -1.468263644 | 16346 | 3617 | 0.998757562 | 0 |
| 16263 | 3534 | 1.012289913 | 0 | 16291 | 3562 | 1.007180507 | 0 | 16319 | 3590 | 1.003097117 | -1.468263644 | 16347 | 3618 | 0.99866227 | 0 |
| 16264 | 3535 | 1.011904615 | 0 | 16292 | 3563 | 1.007063304 | 0 | 16320 | 3591 | 1.002872849 | 0 | 16348 | 3619 | 0.99866227 | 0 |
| 16265 | 3536 | 1.011706262 | 0 | 16293 | 3564 | 1.006934796 | 0 | 16321 | 3592 | 1.002872849 | -1.299027232 | 16349 | 3620 | 0.998446685 | 0 |
| 16266 | 3537 | 1.01162005 | 0 | 16294 | 3565 | 1.006498726 | 0 | 16322 | 3593 | 1.002326681 | 0 | 16350 | 3621 | 0.998189782 | 0 |
| 16267 | 3538 | 1.011468357 | 0 | 16295 | 3566 | 1.006267164 | 0 | 16323 | 3594 | 1.002040867 | 0 | 16351 | 3622 | 0.998107083 | -1.431192333 |
| 16268 | 3539 | 1.011468357 | 0 | 16296 | 3567 | 1.006182415 | 0 | 16324 | 3595 | 1.001902358 | -1.175058986 | 16352 | 3623 | 0.997828473 | 0 |
| 16269 | 3540 | 1.011369643 | 0 | 16297 | 3568 | 1.006123572 | 0 | 16325 | 3596 | 1.001902358 | -1.175058986 | 16353 | 3624 | 0.997759433 | 0 |
| 16270 | 3541 | 1.011006915 | 0 | 16298 | 3569 | 1.005797402 | 0 | 16326 | 3597 | 1.001847747 | -0.808888002 | 16354 | 3625 | 0.997734581 | 0 |
| 16271 | 3542 | 1.010440238 | 0 | 16299 | 3570 | 1.005797402 | 0 | 16327 | 3598 | 1.001722041 | 0 | 16355 | 3626 | 0.997493239 | 0 |
| 16272 | 3543 | 1.010406812 | 0 | 16300 | 3571 | 1.00561113 | 0 | 16328 | 3599 | 1.001609806 | 0 | 16356 | 3627 | 0.997214935 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16357 | 3628 | 0.997138569 | -0.766819021 | 16385 | 3656 | 0.99333728 | 0 | 16413 | 3684 | 0.988538397 | 0 | 16441 | 3712 | 0.983791962 | 0 |
| 16358 | 3629 | 0.996890471 | 0 | 16386 | 3657 | 0.99333728 | 0 | 16414 | 3685 | 0.988538397 | 0 | 16442 | 3713 | 0.983791962 | -0.964690054 |
| 16359 | 3630 | 0.996810923 | 0 | 16387 | 3658 | 0.99333728 | 0 | 16415 | 3686 | 0.987584951 | 0 | 16443 | 3714 | 0.98353687 | 0 |
| 16360 | 3631 | 0.996810923 | 0 | 16388 | 3659 | 0.99333728 | 0 | 16416 | 3687 | 0.987522503 | 0 | 16444 | 3715 | 0.9832528 | 0 |
| 16361 | 3632 | 0.996707186 | 0 | 16389 | 3660 | 0.993101953 | -0.977099312 | 16417 | 3688 | 0.987488107 | 0 | 16445 | 3716 | 0.982934519 | -1.495056821 |
| 16362 | 3633 | 0.99656625 | 0 | 16390 | 3661 | 0.992992738 | 0 | 16418 | 3689 | 0.987411822 | 0 | 16446 | 3717 | 0.982669463 | 0 |
| 16363 | 3634 | 0.996507326 | 0 | 16391 | 3662 | 0.992838377 | 0 | 16419 | 3690 | 0.987274074 | 0 | 16447 | 3718 | 0.98257545 | 0 |
| 16364 | 3635 | 0.996507326 | 0 | 16392 | 3663 | 0.992516695 | 0 | 16420 | 3691 | 0.987220355 | 0 | 16448 | 3719 | 0.981698972 | 0 |
| 16365 | 3636 | 0.995899496 | 0 | 16393 | 3664 | 0.992203351 | 0 | 16421 | 3692 | 0.986908772 | 0 | 16449 | 3720 | 0.981698972 | 0 |
| 16366 | 3637 | 0.995899496 | 0 | 16394 | 3665 | 0.991502876 | 0 | 16422 | 3693 | 0.986864813 | 0 | 16450 | 3721 | 0.981698972 | 0 |
| 16367 | 3638 | 0.995756754 | 0 | 16395 | 3666 | 0.991131207 | 0 | 16423 | 3694 | 0.986769374 | 0 | 16451 | 3722 | 0.981698972 | 0 |
| 16368 | 3639 | 0.995756754 | 0 | 16396 | 3667 | 0.991027197 | 0 | 16424 | 3695 | 0.986662392 | -0.491328949 | 16452 | 3723 | 0.981505134 | 0 |
| 16369 | 3640 | 0.995716981 | 0 | 16397 | 3668 | 0.991027197 | 0 | 16425 | 3696 | 0.986541637 | 0 | 16453 | 3724 | 0.981438056 | 0 |
| 16370 | 3641 | 0.995487257 | 0 | 16398 | 3669 | 0.99093121 | 0 | 16426 | 3697 | 0.986541637 | 0 | 16454 | 3725 | 0.981383466 | -1.009502399 |
| 16371 | 3642 | 0.995487257 | 0 | 16399 | 3670 | 0.990544379 | 0 | 16427 | 3698 | 0.9862466 | 0 | 16455 | 3726 | 0.981299988 | 0 |
| 16372 | 3643 | 0.995487257 | -1.015142666 | 16400 | 3671 | 0.990314655 | 0 | 16428 | 3699 | 0.985849258 | 0 | 16456 | 3727 | 0.981156443 | 0 |
| 16373 | 3644 | 0.995118742 | -1.243112259 | 16401 | 3672 | 0.99005426 | 0 | 16429 | 3700 | 0.985285239 | 0 | 16457 | 3728 | 0.981082514 | -0.718757576 |
| 16374 | 3645 | 0.995004439 | 0 | 16402 | 3673 | 0.989983638 | 0 | 16430 | 3701 | 0.985197654 | 0 | 16458 | 3729 | 0.980985259 | 0 |
| 16375 | 3646 | 0.994584357 | 0 | 16403 | 3674 | 0.989983638 | 0 | 16431 | 3702 | 0.985105221 | 0 | 16459 | 3730 | 0.980851568 | 0 |
| 16376 | 3647 | 0.994584357 | 0 | 16404 | 3675 | 0.989860451 | 0 | 16432 | 3703 | 0.985040704 | 0 | 16460 | 3731 | 0.980420507 | 0 |
| 16377 | 3648 | 0.994487729 | 0 | 16405 | 3676 | 0.989860451 | 0 | 16433 | 3704 | 0.984904112 | 0 | 16461 | 3732 | 0.980234234 | 0 |
| 16378 | 3649 | 0.99421553 | 0 | 16406 | 3677 | 0.988538397 | 0 | 16434 | 3705 | 0.984756418 | 0 | 16462 | 3733 | 0.980105229 | 0 |
| 16379 | 3650 | 0.99421553 | 0 | 16407 | 3678 | 0.988538397 | 0 | 16435 | 3706 | 0.984756418 | -1.363887067 | 16463 | 3734 | 0.979764472 | 0 |
| 16380 | 3651 | 0.993828285 | 0 | 16408 | 3679 | 0.988538397 | 0 | 16436 | 3707 | 0.984677976 | 0 | 16464 | 3735 | 0.979764472 | 0 |
| 16381 | 3652 | 0.993653821 | 0 | 16409 | 3680 | 0.988538397 | 0 | 16437 | 3708 | 0.984421831 | 0 | 16465 | 3736 | 0.979764472 | 0 |
| 16382 | 3653 | 0.993598196 | 0 | 16410 | 3681 | 0.988538397 | 0 | 16438 | 3709 | 0.984231309 | 0 | 16466 | 3737 | 0.979764472 | 0 |
| 16383 | 3654 | 0.993530342 | 0 | 16411 | 3682 | 0.988538397 | 0 | 16439 | 3710 | 0.984129278 | -1.422506154 | 16467 | 3738 | 0.979764472 | -0.669909008 |
| 16384 | 3655 | 0.993490497 | 0 | 16412 | 3683 | 0.988538397 | 0 | 16440 | 3711 | 0.983966834 | 0 | 16468 | 3739 | 0.979479783 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16469 | 3740 | 0.979442892 | -1.411398273 | 16497 | 3768 | 0.97630394 | 0 | 16525 | 3796 | 0.970533975 | 0 | 16553 | 3824 | 0.965710867 | 0 |
| 16470 | 3741 | 0.979330395 | 0 | 16498 | 3769 | 0.975888149 | 0 | 16526 | 3797 | 0.970313577 | 0 | 16554 | 3825 | 0.965710867 | 0 |
| 16471 | 3742 | 0.979330395 | -1.281177001 | 16499 | 3770 | 0.975443099 | 0 | 16527 | 3798 | 0.969856184 | 0 | 16555 | 3826 | 0.965620661 | 0 |
| 16472 | 3743 | 0.979238374 | 0 | 16500 | 3771 | 0.975256185 | 0 | 16528 | 3799 | 0.969631413 | 0 | 16556 | 3827 | 0.965524033 | 0 |
| 16473 | 3744 | 0.979238374 | 0 | 16501 | 3772 | 0.97496559 | 0 | 16529 | 3800 | 0.969570558 | 0 | 16557 | 3828 | 0.965308556 | 0 |
| 16474 | 3745 | 0.979175997 | 0 | 16502 | 3773 | 0.974829255 | 0 | 16530 | 3801 | 0.969375237 | 0 | 16558 | 3829 | 0.965308556 | 0 |
| 16475 | 3746 | 0.979096841 | 0 | 16503 | 3774 | 0.974750112 | 0 | 16531 | 3802 | 0.969375237 | 0 | 16559 | 3830 | 0.965308556 | 0 |
| 16476 | 3747 | 0.978851129 | 0 | 16504 | 3775 | 0.974451935 | 0 | 16532 | 3803 | 0.969175852 | 0 | 16560 | 3831 | 0.965123946 | 0 |
| 16477 | 3748 | 0.978851129 | 0 | 16505 | 3776 | 0.974451935 | 0 | 16533 | 3804 | 0.968335011 | 0 | 16561 | 3832 | 0.965057301 | 0 |
| 16478 | 3749 | 0.978758579 | 0 | 16506 | 3777 | 0.974451935 | -0.673000085 | 16534 | 3805 | 0.968335011 | 0 | 16562 | 3833 | 0.96476055 | 0 |
| 16479 | 3750 | 0.978723414 | 0 | 16507 | 3778 | 0.974012144 | 0 | 16535 | 3806 | 0.968335011 | 0 | 16563 | 3834 | 0.96476055 | 0 |
| 16480 | 3751 | 0.978723414 | 0 | 16508 | 3779 | 0.97381514 | 0 | 16536 | 3807 | 0.968335011 | 0 | 16564 | 3835 | 0.96476055 | 0 |
| 16481 | 3752 | 0.978554176 | 0 | 16509 | 3780 | 0.97329843 | 0 | 16537 | 3808 | 0.968335011 | 0 | 16565 | 3836 | 0.964626239 | 0 |
| 16482 | 3753 | 0.978319232 | 0 | 16510 | 3781 | 0.973044679 | 0 | 16538 | 3809 | 0.968335011 | 0 | 16566 | 3837 | 0.964626239 | -0.94097578 |
| 16483 | 3754 | 0.978163877 | 0 | 16511 | 3782 | 0.973004889 | 0 | 16539 | 3810 | 0.967576418 | 0 | 16567 | 3838 | 0.964404717 | 0 |
| 16484 | 3755 | 0.977880329 | 0 | 16512 | 3783 | 0.97274413 | 0 | 16540 | 3811 | 0.967576418 | 0 | 16568 | 3839 | 0.964404717 | 0 |
| 16485 | 3756 | 0.977880329 | 0 | 16513 | 3784 | 0.972510951 | 0 | 16541 | 3812 | 0.967530016 | 0 | 16569 | 3840 | 0.964038069 | 0 |
| 16486 | 3757 | 0.977402031 | -1.324498051 | 16514 | 3785 | 0.972510951 | 0 | 16542 | 3813 | 0.967349098 | 0 | 16570 | 3841 | 0.963970205 | 0 |
| 16487 | 3758 | 0.977198471 | 0 | 16515 | 3786 | 0.972245084 | 0 | 16543 | 3814 | 0.967269257 | 0 | 16571 | 3842 | 0.963970205 | 0 |
| 16488 | 3759 | 0.977198471 | 0 | 16516 | 3787 | 0.972204029 | 0 | 16544 | 3815 | 0.967269257 | -1.259379872 | 16572 | 3843 | 0.963871513 | 0 |
| 16489 | 3760 | 0.977058579 | 0 | 16517 | 3788 | 0.972111508 | -0.309585187 | 16545 | 3816 | 0.967063284 | 0 | 16573 | 3844 | 0.963827837 | 0 |
| 16490 | 3761 | 0.976878784 | 0 | 16518 | 3789 | 0.971939135 | 0 | 16546 | 3817 | 0.966758622 | 0 | 16574 | 3845 | 0.963714813 | 0 |
| 16491 | 3762 | 0.976878784 | 0 | 16519 | 3790 | 0.971939135 | 0 | 16547 | 3818 | 0.966544103 | 0 | 16575 | 3846 | 0.963714813 | 0 |
| 16492 | 3763 | 0.97630394 | 0 | 16520 | 3791 | 0.971505057 | 0 | 16548 | 3819 | 0.966413351 | 0 | 16576 | 3847 | 0.96354671 | -0.404594565 |
| 16493 | 3764 | 0.97630394 | 0 | 16521 | 3792 | 0.971164301 | 0 | 16549 | 3820 | 0.966262002 | 0 | 16577 | 3848 | 0.963270295 | 0 |
| 16494 | 3765 | 0.97630394 | 0 | 16522 | 3793 | 0.970663673 | 0 | 16550 | 3821 | 0.966084775 | -0.458279424 | 16578 | 3849 | 0.963170925 | 0 |
| 16495 | 3766 | 0.97630394 | 0 | 16523 | 3794 | 0.970663673 | 0 | 16551 | 3822 | 0.966018768 | 0 | 16579 | 3850 | 0.963102484 | 0 |
| 16496 | 3767 | 0.97630394 | 0 | 16524 | 3795 | 0.970663673 | 0 | 16552 | 3823 | 0.965874412 | -0.352624931 | 16580 | 3851 | 0.963102484 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16581 | 3852 | 0.962731133 | 0 | 16609 | 3880 | 0.958575173 | 0 | 16637 | 3908 | 0.953409333 | 0 | 16665 | 3936 | 0.951022036 | 0 |
| 16582 | 3853 | 0.962731133 | 0 | 16610 | 3881 | 0.958067523 | 0 | 16638 | 3909 | 0.953289577 | 0 | 16666 | 3937 | 0.950749836 | 0 |
| 16583 | 3854 | 0.962209458 | 0 | 16611 | 3882 | 0.958029234 | 0 | 16639 | 3910 | 0.953210434 | 0 | 16667 | 3938 | 0.950749836 | 0 |
| 16584 | 3855 | 0.962209458 | 0 | 16612 | 3883 | 0.957984698 | 0 | 16640 | 3911 | 0.953180142 | -0.131235996 | 16668 | 3939 | 0.95048478 | 0 |
| 16585 | 3856 | 0.961994833 | -0.227931489 | 16613 | 3884 | 0.957984698 | 0 | 16641 | 3912 | 0.952822845 | 0 | 16669 | 3940 | 0.949785808 | 0 |
| 16586 | 3857 | 0.961954914 | 0 | 16614 | 3885 | 0.957577941 | 0 | 16642 | 3913 | 0.952822845 | 0 | 16670 | 3941 | 0.949569687 | 0 |
| 16587 | 3858 | 0.961910419 | 0 | 16615 | 3886 | 0.957504163 | 0 | 16643 | 3914 | 0.952822845 | 0 | 16671 | 3942 | 0.949569687 | 0 |
| 16588 | 3859 | 0.961386151 | 0 | 16616 | 3887 | 0.956998785 | 0 | 16644 | 3915 | 0.952822845 | 0 | 16672 | 3943 | 0.949490645 | 0 |
| 16589 | 3860 | 0.960698867 | 0 | 16617 | 3888 | 0.956875389 | 0 | 16645 | 3916 | 0.952822845 | 0 | 16673 | 3944 | 0.949386273 | 0 |
| 16590 | 3861 | 0.960509673 | 0 | 16618 | 3889 | 0.95595103 | 0 | 16646 | 3917 | 0.952822845 | 0 | 16674 | 3945 | 0.949029855 | 0 |
| 16591 | 3862 | 0.960509673 | 0 | 16619 | 3890 | 0.95595103 | 0 | 16647 | 3918 | 0.952822845 | 0 | 16675 | 3946 | 0.949029855 | 0 |
| 16592 | 3863 | 0.96021712 | 0 | 16620 | 3891 | 0.955689485 | 0 | 16648 | 3919 | 0.952822845 | -1.358837074 | 16676 | 3947 | 0.949029855 | 0 |
| 16593 | 3864 | 0.960101693 | 0 | 16621 | 3892 | 0.955630793 | 0 | 16649 | 3920 | 0.952374887 | 0 | 16677 | 3948 | 0.949029855 | 0 |
| 16594 | 3865 | 0.959956079 | 0 | 16622 | 3893 | 0.955114641 | 0 | 16650 | 3921 | 0.952374887 | 0 | 16678 | 3949 | 0.949029855 | 0 |
| 16595 | 3866 | 0.959913524 | 0 | 16623 | 3894 | 0.9550586 | 0 | 16651 | 3922 | 0.952374887 | 0 | 16679 | 3950 | 0.949029855 | -0.913537532 |
| 16596 | 3867 | 0.959835826 | 0 | 16624 | 3895 | 0.954619308 | 0 | 16652 | 3923 | 0.952374887 | -0.635491443 | 16680 | 3951 | 0.948590952 | 0 |
| 16597 | 3868 | 0.959835826 | 0 | 16625 | 3896 | 0.954458607 | 0 | 16653 | 3924 | 0.952326224 | 0 | 16681 | 3952 | 0.948519821 | 0 |
| 16598 | 3869 | 0.95940319 | -1.243112259 | 16626 | 3897 | 0.954458607 | 0 | 16654 | 3925 | 0.952265699 | 0 | 16682 | 3953 | 0.948037182 | 0 |
| 16599 | 3870 | 0.959249021 | 0 | 16627 | 3898 | 0.954458607 | 0 | 16655 | 3926 | 0.952188375 | -1.262561531 | 16683 | 3954 | 0.948037182 | 0 |
| 16600 | 3871 | 0.959249021 | -1.33266684 | 16628 | 3899 | 0.954027546 | 0 | 16656 | 3927 | 0.952086128 | 0 | 16684 | 3955 | 0.948037182 | -0.591223815 |
| 16601 | 3872 | 0.959191631 | 0 | 16629 | 3900 | 0.954027546 | 0 | 16657 | 3928 | 0.951944594 | 0 | 16685 | 3956 | 0.948037182 | -0.989163824 |
| 16602 | 3873 | 0.959066179 | 0 | 16630 | 3901 | 0.954027546 | -1.284203456 | 16658 | 3929 | 0.951735749 | -1.506052205 | 16686 | 3957 | 0.947851308 | 0 |
| 16603 | 3874 | 0.958575173 | 0 | 16631 | 3902 | 0.953887292 | 0 | 16659 | 3930 | 0.951642161 | 0 | 16687 | 3958 | 0.947729572 | 0 |
| 16604 | 3875 | 0.958575173 | 0 | 16632 | 3903 | 0.953776291 | 0 | 16660 | 3931 | 0.951589053 | 0 | 16688 | 3959 | 0.947579789 | 0 |
| 16605 | 3876 | 0.958575173 | 0 | 16633 | 3904 | 0.953611754 | 0 | 16661 | 3932 | 0.951396589 | 0 | 16689 | 3960 | 0.94731666 | 0 |
| 16606 | 3877 | 0.958575173 | 0 | 16634 | 3905 | 0.953449532 | 0 | 16662 | 3933 | 0.951396589 | 0 | 16690 | 3961 | 0.94731666 | 0 |
| 16607 | 3878 | 0.958575173 | 0 | 16635 | 3906 | 0.953409333 | 0 | 16663 | 3934 | 0.951396589 | 0 | 16691 | 3962 | 0.947145712 | 0 |
| 16608 | 3879 | 0.958575173 | 0 | 16636 | 3907 | 0.953409333 | 0 | 16664 | 3935 | 0.951396589 | 0 | 16692 | 3963 | 0.947025724 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16693 | 3964 | 0.946936866 | 0 | 16721 | 3992 | 0.944334734 | 0 | 16749 | 4020 | 0.941182765 | 0 | 16777 | 4048 | 0.937845689 | 0 |
| 16694 | 3965 | 0.946733211 | 0 | 16722 | 3993 | 0.944334734 | 0 | 16750 | 4021 | 0.941113747 | -0.319393649 | 16778 | 4049 | 0.937845689 | 0 |
| 16695 | 3966 | 0.946733211 | 0 | 16723 | 3994 | 0.944334734 | 0 | 16751 | 4022 | 0.941011883 | 0 | 16779 | 4050 | 0.937532571 | 0 |
| 16696 | 3967 | 0.94667595 | -0.790952701 | 16724 | 3995 | 0.944334734 | 0 | 16752 | 4023 | 0.940765615 | 0 | 16780 | 4051 | 0.937532571 | -1.393012692 |
| 16697 | 3968 | 0.94663327 | 0 | 16725 | 3996 | 0.944334734 | 0 | 16753 | 4024 | 0.940765615 | 0 | 16781 | 4052 | 0.937385874 | 0 |
| 16698 | 3969 | 0.946340717 | 0 | 16726 | 3997 | 0.944334734 | 0 | 16754 | 4025 | 0.940530671 | 0 | 16782 | 4053 | 0.937385874 | 0 |
| 16699 | 3970 | 0.946340717 | 0 | 16727 | 3998 | 0.944334734 | -0.520292644 | 16755 | 4026 | 0.940530671 | 0 | 16783 | 4054 | 0.937177029 | 0 |
| 16700 | 3971 | 0.946340717 | 0 | 16728 | 3999 | 0.944089023 | 0 | 16756 | 4027 | 0.940233717 | 0 | 16784 | 4055 | 0.937177029 | 0 |
| 16701 | 3972 | 0.946340717 | 0 | 16729 | 4000 | 0.943910411 | 0 | 16757 | 4028 | 0.940233717 | 0 | 16785 | 4056 | 0.936855924 | 0 |
| 16702 | 3973 | 0.946340717 | 0 | 16730 | 4001 | 0.943910411 | -1.233050933 | 16758 | 4029 | 0.940176434 | 0 | 16786 | 4057 | 0.936795399 | 0 |
| 16703 | 3974 | 0.946058616 | 0 | 16731 | 4002 | 0.943511427 | 0 | 16759 | 4030 | 0.940091768 | -1.080083473 | 16787 | 4058 | 0.936620598 | 0 |
| 16704 | 3975 | 0.946019136 | 0 | 16732 | 4003 | 0.943511427 | 0 | 16760 | 4031 | 0.939953918 | 0 | 16788 | 4059 | 0.936620598 | -0.676069317 |
| 16705 | 3976 | 0.945894142 | 0 | 16733 | 4004 | 0.943258415 | 0 | 16761 | 4032 | 0.939886476 | 0 | 16789 | 4060 | 0.936298779 | 0 |
| 16706 | 3977 | 0.945610196 | 0 | 16734 | 4005 | 0.943063007 | 0 | 16762 | 4033 | 0.939689829 | 0 | 16790 | 4061 | 0.936150327 | -0.271968999 |
| 16707 | 3978 | 0.945610196 | 0 | 16735 | 4006 | 0.942780906 | 0 | 16763 | 4034 | 0.939689829 | 0 | 16791 | 4062 | 0.936009345 | 0 |
| 16708 | 3979 | 0.945610196 | 0 | 16736 | 4007 | 0.942780906 | 0 | 16764 | 4035 | 0.939391857 | 0 | 16792 | 4063 | 0.936009345 | 0 |
| 16709 | 3980 | 0.945523606 | 0 | 16737 | 4008 | 0.942780906 | 0 | 16765 | 4036 | 0.939146622 | 0 | 16793 | 4064 | 0.936009345 | 0 |
| 16710 | 3981 | 0.945269707 | 0 | 16738 | 4009 | 0.942780906 | 0 | 16766 | 4037 | 0.938979617 | 0 | 16794 | 4065 | 0.935875283 | 0 |
| 16711 | 3982 | 0.945159605 | -1.545796712 | 16739 | 4010 | 0.942780906 | 0 | 16767 | 4038 | 0.938979617 | 0 | 16795 | 4066 | 0.935747643 | 0 |
| 16712 | 3983 | 0.945072703 | 0 | 16740 | 4011 | 0.942511242 | 0 | 16768 | 4039 | 0.93866434 | 0 | 16796 | 4067 | 0.935747643 | 0 |
| 16713 | 3984 | 0.94494427 | 0 | 16741 | 4012 | 0.942253209 | 0 | 16769 | 4040 | 0.93866434 | 0 | 16797 | 4068 | 0.935625975 | 0 |
| 16714 | 3985 | 0.944853915 | 0 | 16742 | 4013 | 0.942128322 | 0 | 16770 | 4041 | 0.93866434 | -0.929298079 | 16798 | 4069 | 0.935625975 | -0.754229894 |
| 16715 | 3986 | 0.944694101 | 0 | 16743 | 4014 | 0.941925996 | 0 | 16771 | 4042 | 0.938515379 | 0 | 16799 | 4070 | 0.935509869 | 0 |
| 16716 | 3987 | 0.944632911 | -1.385912352 | 16744 | 4015 | 0.941925996 | 0 | 16772 | 4043 | 0.938371787 | 0 | 16800 | 4071 | 0.935509869 | 0 |
| 16717 | 3988 | 0.944589527 | 0 | 16745 | 4016 | 0.941769154 | 0 | 16773 | 4044 | 0.938371787 | 0 | 16801 | 4072 | 0.935363074 | 0 |
| 16718 | 3989 | 0.944512106 | -1.134441135 | 16746 | 4017 | 0.941182765 | 0 | 16774 | 4045 | 0.938188192 | 0 | 16802 | 4073 | 0.935191355 | 0 |
| 16719 | 3990 | 0.944334734 | 0 | 16747 | 4018 | 0.941182765 | 0 | 16775 | 4046 | 0.938188192 | 0 | 16803 | 4074 | 0.935191355 | 0 |
| 16720 | 3991 | 0.944334734 | 0 | 16748 | 4019 | 0.941182765 | 0 | 16776 | 4047 | 0.938099588 | 0 | 16804 | 4075 | 0.935094078 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16805 | 4076 | 0.934586428 | -1.456254737 | 16833 | 4104 | 0.93054645 | 0 | 16861 | 4132 | 0.928242495 | -1.101272772 | 16889 | 4160 | 0.923367865 | 0 |
| 16806 | 4077 | 0.934441494 | 0 | 16834 | 4105 | 0.93054645 | 0 | 16862 | 4133 | 0.927969027 | 0 | 16890 | 4161 | 0.923367865 | -0.911170799 |
| 16807 | 4078 | 0.934372858 | 0 | 16835 | 4106 | 0.93054645 | 0 | 16863 | 4134 | 0.927969027 | 0 | 16891 | 4162 | 0.923247211 | 0 |
| 16808 | 4079 | 0.934180734 | 0 | 16836 | 4107 | 0.93054645 | 0 | 16864 | 4135 | 0.927906354 | 0 | 16892 | 4163 | 0.923122432 | 0 |
| 16809 | 4080 | 0.93412091 | 0 | 16837 | 4108 | 0.93054645 | 0 | 16865 | 4136 | 0.927771396 | 0 | 16893 | 4164 | 0.923036848 | 0 |
| 16810 | 4081 | 0.933952698 | 0 | 16838 | 4109 | 0.93054645 | 0 | 16866 | 4137 | 0.927698607 | 0 | 16894 | 4165 | 0.922993312 | -1.014207694 |
| 16811 | 4082 | 0.933659685 | 0 | 16839 | 4110 | 0.93054645 | 0 | 16867 | 4138 | 0.92726874 | 0 | 16895 | 4166 | 0.922859621 | -1.483775811 |
| 16812 | 4083 | 0.933572904 | 0 | 16840 | 4111 | 0.93054645 | 0 | 16868 | 4139 | 0.92726874 | 0 | 16896 | 4167 | 0.922273924 | 0 |
| 16813 | 4084 | 0.933572904 | 0 | 16841 | 4112 | 0.93054645 | 0 | 16869 | 4140 | 0.92726874 | 0 | 16897 | 4168 | 0.922273924 | 0 |
| 16814 | 4085 | 0.93349083 | 0 | 16842 | 4113 | 0.93054645 | 0 | 16870 | 4141 | 0.927166709 | 0 | 16898 | 4169 | 0.922145908 | -1.542481471 |
| 16815 | 4086 | 0.93341309 | -1.304817911 | 16843 | 4114 | 0.93054645 | 0 | 16871 | 4142 | 0.926881496 | 0 | 16899 | 4170 | 0.92205834 | 0 |
| 16816 | 4087 | 0.933269308 | 0 | 16844 | 4115 | 0.93054645 | -1.460294715 | 16872 | 4143 | 0.926686029 | 0 | 16900 | 4171 | 0.921591607 | 0 |
| 16817 | 4088 | 0.933269308 | 0 | 16845 | 4116 | 0.93054645 | -1.182745815 | 16873 | 4144 | 0.92639049 | 0 | 16901 | 4172 | 0.921338448 | 0 |
| 16818 | 4089 | 0.933269308 | 0 | 16846 | 4117 | 0.93054645 | 0 | 16874 | 4145 | 0.926225076 | -0.732222329 | 16902 | 4173 | 0.921286089 | 0 |
| 16819 | 4090 | 0.933078786 | 0 | 16847 | 4118 | 0.93054645 | 0 | 16875 | 4146 | 0.926137331 | 0 | 16903 | 4174 | 0.921206424 | 0 |
| 16820 | 4091 | 0.932965924 | -1.077663999 | 16848 | 4119 | 0.93054645 | 0 | 16876 | 4147 | 0.925851329 | 0 | 16904 | 4175 | 0.920786613 | 0 |
| 16821 | 4092 | 0.932862693 | 0 | 16849 | 4120 | 0.93054645 | 0 | 16877 | 4148 | 0.925851329 | 0 | 16905 | 4176 | 0.920786613 | 0 |
| 16822 | 4093 | 0.932814311 | 0 | 16850 | 4121 | 0.93054645 | 0 | 16878 | 4149 | 0.925639115 | 0 | 16906 | 4177 | 0.920607927 | 0 |
| 16823 | 4094 | 0.932814311 | 0 | 16851 | 4122 | 0.93054645 | 0 | 16879 | 4150 | 0.925525648 | 0 | 16907 | 4178 | 0.920422577 | 0 |
| 16824 | 4095 | 0.932639439 | 0 | 16852 | 4123 | 0.93054645 | 0 | 16880 | 4151 | 0.924556086 | 0 | 16908 | 4179 | 0.920327285 | 0 |
| 16825 | 4096 | 0.932078354 | 0 | 16853 | 4124 | 0.93054645 | 0 | 16881 | 4152 | 0.924556086 | 0 | 16909 | 4180 | 0.920258113 | -0.186538804 |
| 16826 | 4097 | 0.93054645 | 0 | 16854 | 4125 | 0.93054645 | -0.028930951 | 16882 | 4153 | 0.924556086 | 0 | 16910 | 4181 | 0.920164414 | 0 |
| 16827 | 4098 | 0.93054645 | 0 | 16855 | 4126 | 0.93054645 | -0.329960946 | 16883 | 4154 | 0.924386141 | 0 | 16911 | 4182 | 0.920116922 | 0 |
| 16828 | 4099 | 0.93054645 | 0 | 16856 | 4127 | 0.928576857 | 0 | 16884 | 4155 | 0.924206272 | 0 | 16912 | 4183 | 0.919822584 | 0 |
| 16829 | 4100 | 0.93054645 | 0 | 16857 | 4128 | 0.928502707 | -0.609122527 | 16885 | 4156 | 0.924206272 | 0 | 16913 | 4184 | 0.919643087 | -1.50965633 |
| 16830 | 4101 | 0.93054645 | 0 | 16858 | 4129 | 0.928290369 | 0 | 16886 | 4157 | 0.924206272 | 0 | 16914 | 4185 | 0.919551065 | 0 |
| 16831 | 4102 | 0.93054645 | 0 | 16859 | 4130 | 0.928290369 | 0 | 16887 | 4158 | 0.924015583 | 0 | 16915 | 4186 | 0.919551065 | 0 |
| 16832 | 4103 | 0.93054645 | 0 | 16860 | 4131 | 0.928242495 | 0 | 16888 | 4159 | 0.923367865 | 0 | 16916 | 4187 | 0.91934855 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 16917 | 4188 | 0.91914699 | 0 | 16945 | 4216 | 0.915823193 | 0 | 16973 | 4244 | 0.912817683 | 0 | 17001 | 4272 | 0.910024783 | 0 |
| 16918 | 4189 | 0.918964577 | 0 | 16946 | 4217 | 0.915722673 | 0 | 16974 | 4245 | 0.912817683 | 0 | 17002 | 4273 | 0.909762844 | 0 |
| 16919 | 4190 | 0.918902469 | 0 | 16947 | 4218 | 0.915722673 | 0 | 16975 | 4246 | 0.912817683 | 0 | 17003 | 4274 | 0.90962935 | 0 |
| 16920 | 4191 | 0.918647226 | 0 | 16948 | 4219 | 0.915722673 | -1.299027232 | 16976 | 4247 | 0.912817683 | 0 | 17004 | 4275 | 0.909357151 | 0 |
| 16921 | 4192 | 0.91850053 | -1.643036862 | 16949 | 4220 | 0.915654894 | 0 | 16977 | 4248 | 0.912550507 | 0 | 17005 | 4276 | 0.909357151 | 0 |
| 16922 | 4193 | 0.918425817 | 0 | 16950 | 4221 | 0.915540541 | 0 | 16978 | 4249 | 0.912394187 | 0 | 17006 | 4277 | 0.909357151 | 0 |
| 16923 | 4194 | 0.918425817 | 0 | 16951 | 4222 | 0.915306483 | 0 | 16979 | 4250 | 0.912394187 | 0 | 17007 | 4278 | 0.909357151 | 0 |
| 16924 | 4195 | 0.918425817 | -0.510054948 | 16952 | 4223 | 0.915306483 | 0 | 16980 | 4251 | 0.912394187 | 0 | 17008 | 4279 | 0.909357151 | 0 |
| 16925 | 4196 | 0.918380543 | 0 | 16953 | 4224 | 0.915306483 | 0 | 16981 | 4252 | 0.91232163 | -0.813072565 | 17009 | 4280 | 0.909357151 | 0 |
| 16926 | 4197 | 0.918311993 | 0 | 16954 | 4225 | 0.915306483 | 0 | 16982 | 4253 | 0.912219069 | 0 | 17010 | 4281 | 0.909357151 | -1.351150245 |
| 16927 | 4198 | 0.918196011 | 0 | 16955 | 4226 | 0.915034284 | 0 | 16983 | 4254 | 0.912150051 | 0 | 17011 | 4282 | 0.909006772 | 0 |
| 16928 | 4199 | 0.918196011 | 0 | 16956 | 4227 | 0.914941376 | 0 | 16984 | 4255 | 0.912063044 | 0 | 17012 | 4283 | 0.9088272 | 0 |
| 16929 | 4200 | 0.918137192 | 0 | 16957 | 4228 | 0.914866246 | 0 | 16985 | 4256 | 0.911797014 | 0 | 17013 | 4284 | 0.908644608 | 0 |
| 16930 | 4201 | 0.918101630 | 0 | 16958 | 4229 | 0.914752183 | -1.175058986 | 16986 | 4257 | 0.911797014 | 0 | 17014 | 4285 | 0.908644608 | -0.73507954 |
| 16931 | 4202 | 0.917957322 | 0 | 16959 | 4230 | 0.914669688 | -1.114845579 | 16987 | 4258 | 0.911661106 | 0 | 17015 | 4286 | 0.908270055 | 0 |
| 16932 | 4203 | 0.917709225 | 0 | 16960 | 4231 | 0.91445963 | 0 | 16988 | 4259 | 0.911661106 | -1.399998813 | 17016 | 4287 | 0.908270055 | -0.329960946 |
| 16933 | 4204 | 0.917581473 | 0 | 16961 | 4232 | 0.914156034 | 0 | 16989 | 4260 | 0.91108397 | 0 | 17017 | 4288 | 0.908105581 | 0 |
| 16934 | 4205 | 0.917503593 | 0 | 16962 | 4233 | 0.913904778 | 0 | 16990 | 4261 | 0.91108397 | 0 | 17018 | 4289 | 0.907882465 | 0 |
| 16935 | 4206 | 0.917182488 | 0 | 16963 | 4234 | 0.913904778 | 0 | 16991 | 4262 | 0.910992913 | 0 | 17019 | 4290 | 0.907882465 | 0 |
| 16936 | 4207 | 0.917182488 | 0 | 16964 | 4235 | 0.913732951 | 0 | 16992 | 4263 | 0.910992913 | 0 | 17020 | 4291 | 0.907738157 | 0 |
| 16937 | 4208 | 0.916902569 | 0 | 16965 | 4236 | 0.913732951 | 0 | 16993 | 4264 | 0.910992913 | -0.850116833 | 17021 | 4292 | 0.907683567 | 0 |
| 16938 | 4209 | 0.916902569 | -1.413642694 | 16966 | 4237 | 0.913608028 | 0 | 16994 | 4265 | 0.910802392 | 0 | 17022 | 4293 | 0.907683567 | -1.318965562 |
| 16939 | 4210 | 0.916845172 | 0 | 16967 | 4238 | 0.913608028 | 0 | 16995 | 4266 | 0.910651621 | 0 | 17023 | 4294 | 0.907562543 | 0 |
| 16940 | 4211 | 0.916758165 | 0 | 16968 | 4239 | 0.913608028 | -1.087262058 | 16996 | 4267 | 0.910651621 | -0.018862556 | 17024 | 4295 | 0.907422651 | 0 |
| 16941 | 4212 | 0.916610672 | 0 | 16969 | 4240 | 0.91351311 | -1.142874303 | 16997 | 4268 | 0.910476467 | 0 | 17025 | 4296 | 0.907422651 | 0 |
| 16942 | 4213 | 0.916438196 | -1.466285079 | 16970 | 4241 | 0.913287444 | 0 | 16998 | 4269 | 0.910343064 | 0 | 17026 | 4297 | 0.907422651 | 0 |
| 16943 | 4214 | 0.916306011 | 0 | 16971 | 4242 | 0.913133648 | -1.18464645 | 16999 | 4270 | 0.910238073 | -1.42030719 | 17027 | 4298 | 0.907344195 | 0 |
| 16944 | 4215 | 0.916306011 | 0 | 16972 | 4243 | 0.912817683 | 0 | 17000 | 4271 | 0.910153291 | 0 | 17028 | 4299 | 0.90729399 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17029 | 4300 | 0.907065354 | 0 | 17057 | 4328 | 0.903002701 | 0 | 17085 | 4356 | 0.900202433 | 0 | 17113 | 4384 | 0.895784344 | 0 |
| 17030 | 4301 | 0.907065354 | 0 | 17058 | 4329 | 0.902875023 | 0 | 17086 | 4357 | 0.900202433 | 0 | 17114 | 4385 | 0.895784344 | 0 |
| 17031 | 4302 | 0.907065354 | -1.182745815 | 17059 | 4330 | 0.902875023 | 0 | 17087 | 4358 | 0.900116494 | 0 | 17115 | 4386 | 0.895784344 | 0 |
| 17032 | 4303 | 0.906696839 | 0 | 17060 | 4331 | 0.902875023 | 0 | 17088 | 4359 | 0.900033834 | 0 | 17116 | 4387 | 0.895784344 | 0 |
| 17033 | 4304 | 0.90641277 | 0 | 17061 | 4332 | 0.902517726 | 0 | 17089 | 4360 | 0.899512216 | 0 | 17117 | 4388 | 0.895784344 | 0 |
| 17034 | 4305 | 0.906046122 | 0 | 17062 | 4333 | 0.902352249 | -0.465789025 | 17090 | 4361 | 0.899137986 | 0 | 17118 | 4389 | 0.895784344 | 0 |
| 17035 | 4306 | 0.905435729 | -1.07523097 | 17063 | 4334 | 0.902315211 | -1.105085742 | 17091 | 4362 | 0.898832037 | 0 | 17119 | 4390 | 0.895784344 | 0 |
| 17036 | 4307 | 0.905042382 | 0 | 17064 | 4335 | 0.901901268 | 0 | 17092 | 4363 | 0.898699083 | 0 | 17120 | 4391 | 0.895784344 | 0 |
| 17037 | 4308 | 0.904992345 | -0.970939004 | 17065 | 4336 | 0.901752257 | 0 | 17093 | 4364 | 0.898699083 | 0 | 17121 | 4392 | 0.895784344 | 0 |
| 17038 | 4309 | 0.90484105 | 0 | 17066 | 4337 | 0.901720124 | 0 | 17094 | 4365 | 0.898699083 | 0 | 17122 | 4393 | 0.895784344 | 0 |
| 17039 | 4310 | 0.904699793 | 0 | 17067 | 4338 | 0.901670322 | 0 | 17095 | 4366 | 0.898699083 | 0 | 17123 | 4394 | 0.895784344 | 0 |
| 17040 | 4311 | 0.904699793 | 0 | 17068 | 4339 | 0.901582754 | 0 | 17096 | 4367 | 0.898577244 | 0 | 17124 | 4395 | 0.895784344 | 0 |
| 17041 | 4312 | 0.904217511 | 0 | 17069 | 4340 | 0.901508242 | 0 | 17097 | 4368 | 0.898520066 | 0 | 17125 | 4396 | 0.895784344 | 0 |
| 17042 | 4313 | 0.904217511 | 0 | 17070 | 4341 | 0.901508242 | 0 | 17098 | 4369 | 0.898361766 | 0 | 17126 | 4397 | 0.895245851 | -0.351473261 |
| 17043 | 4314 | 0.904217511 | 0 | 17071 | 4342 | 0.901162672 | 0 | 17099 | 4370 | 0.898361766 | -1.351150245 | 17127 | 4398 | 0.895218487 | 0 |
| 17044 | 4315 | 0.904217511 | 0 | 17072 | 4343 | 0.901162672 | 0 | 17100 | 4371 | 0.898361766 | 0 | 17128 | 4399 | 0.895188195 | 0 |
| 17045 | 4316 | 0.904217511 | 0 | 17073 | 4344 | 0.901035852 | 0 | 17101 | 4372 | 0.898094426 | 0 | 17129 | 4400 | 0.894970296 | 0 |
| 17046 | 4317 | 0.904217511 | 0 | 17074 | 4345 | 0.901035852 | 0 | 17102 | 4373 | 0.897877333 | 0 | 17130 | 4401 | 0.894970296 | 0 |
| 17047 | 4318 | 0.904217511 | 0 | 17075 | 4346 | 0.901035852 | 0 | 17103 | 4374 | 0.897417031 | -1.37381423 | 17131 | 4402 | 0.894741619 | 0 |
| 17048 | 4319 | 0.904217511 | 0 | 17076 | 4347 | 0.901035852 | 0 | 17104 | 4375 | 0.897305517 | 0 | 17132 | 4403 | 0.894741619 | 0 |
| 17049 | 4320 | 0.904217511 | -0.031778794 | 17077 | 4348 | 0.900954577 | 0 | 17105 | 4376 | 0.897122694 | 0 | 17133 | 4404 | 0.894633894 | 0 |
| 17050 | 4321 | 0.903674303 | 0 | 17078 | 4349 | 0.900954577 | 0 | 17106 | 4377 | 0.897122694 | 0 | 17134 | 4405 | 0.89457123 | 0 |
| 17051 | 4322 | 0.90356296 | 0 | 17079 | 4350 | 0.900583226 | 0 | 17107 | 4378 | 0.896863337 | 0 | 17135 | 4406 | 0.894501346 | -1.178919407 |
| 17052 | 4323 | 0.903488217 | 0 | 17080 | 4351 | 0.900583226 | 0 | 17108 | 4379 | 0.896768023 | 0 | 17136 | 4407 | 0.894422918 | 0 |
| 17053 | 4324 | 0.903394204 | 0 | 17081 | 4352 | 0.900583226 | 0 | 17109 | 4380 | 0.896620329 | 0 | 17137 | 4408 | 0.894422918 | 0 |
| 17054 | 4325 | 0.903394204 | 0 | 17082 | 4353 | 0.900583226 | -1.080083473 | 17110 | 4381 | 0.896392174 | 0 | 17138 | 4409 | 0.894334277 | 0 |
| 17055 | 4326 | 0.903394204 | 0 | 17083 | 4354 | 0.900261646 | 0 | 17111 | 4382 | 0.896360713 | 0 | 17139 | 4410 | 0.894334277 | 0 |
| 17056 | 4327 | 0.903272365 | 0 | 17084 | 4355 | 0.900202433 | 0 | 17112 | 4383 | 0.895784344 | 0 | 17140 | 4411 | 0.894334277 | 0 |

FIG. 3 (Cont.)

| DNA SEQ ID NO | AA SEQ ID NO | Log 10 enrichment in the brain | Log 10 enrichment in the liver |
|---|---|---|---|
| 17141 | 4412 | 0.89423329 | 0 |
| 17142 | 4413 | 0.89423329 | 0 |
| 17143 | 4414 | 0.894117184 | 0 |
| 17144 | 4415 | 0.894117184 | 0 |
| 17145 | 4416 | 0.893823643 | 0 |
| 17146 | 4417 | 0.893823643 | 0 |
| 17147 | 4418 | 0.893222127 | 0 |
| 17148 | 4419 | 0.892950438 | 0 |
| 17149 | 4420 | 0.892950438 | 0 |
| 17150 | 4421 | 0.892913914 | 0 |
| 17151 | 4422 | 0.892757889 | 0 |
| 17152 | 4423 | 0.892757889 | 0 |
| 17153 | 4424 | 0.892757889 | 0 |
| 17154 | 4425 | 0.892757889 | -1.284203456 |
| 17155 | 4426 | 0.8924564 | 0 |
| 17156 | 4427 | 0.8924564 | -1.067021 |
| 17157 | 4428 | 0.892388748 | 0 |
| 17158 | 4429 | 0.892088198 | 0 |
| 17159 | 4430 | 0.892088198 | 0 |
| 17160 | 4431 | 0.891983055 | 0 |
| 17161 | 4432 | 0.891983055 | 0 |
| 17162 | 4433 | 0.891838747 | 0 |
| 17163 | 4434 | 0.891628384 | 0 |
| 17164 | 4435 | 0.891628384 | 0 |
| 17165 | 4436 | 0.891628384 | 0 |
| 17166 | 4437 | 0.891628384 | 0 |
| 17167 | 4438 | 0.891628384 | 0 |
| 17168 | 4439 | 0.891628384 | 0 |
| 17169 | 4440 | 0.891628384 | -1.271968999 |
| 17170 | 4441 | 0.891352729 | 0 |
| 17171 | 4442 | 0.891352729 | -1.42030719 |
| 17172 | 4443 | 0.891293151 | 0 |
| 17173 | 4444 | 0.891200718 | 0 |
| 17174 | 4445 | 0.890952088 | 0 |
| 17175 | 4446 | 0.89089909 | 0 |
| 17176 | 4447 | 0.89089909 | -0.520875982 |
| 17177 | 4448 | 0.890837079 | 0 |
| 17178 | 4449 | 0.890674938 | 0 |
| 17179 | 4450 | 0.890501809 | 0 |
| 17180 | 4451 | 0.890501809 | 0 |
| 17181 | 4452 | 0.890429227 | 0 |
| 17182 | 4453 | 0.890429227 | -0.481228622 |
| 17183 | 4454 | 0.890251855 | 0 |
| 17184 | 4455 | 0.890251855 | 0 |
| 17185 | 4456 | 0.890251855 | 0 |
| 17186 | 4457 | 0.890251855 | 0 |
| 17187 | 4458 | 0.890117793 | -1.381113469 |
| 17188 | 4459 | 0.890012903 | 0 |
| 17189 | 4460 | 0.890012903 | 0 |
| 17190 | 4461 | 0.890012903 | 0 |
| 17191 | 4462 | 0.889928599 | 0 |
| 17192 | 4463 | 0.889752379 | 0 |
| 17193 | 4464 | 0.889752379 | 0 |
| 17194 | 4465 | 0.88952639 | 0 |
| 17195 | 4466 | 0.889494254 | 0 |
| 17196 | 4467 | 0.889153765 | 0 |
| 17197 | 4468 | 0.889153765 | 0 |
| 17198 | 4469 | 0.889153765 | 0 |
| 17199 | 4470 | 0.889153765 | 0 |
| 17200 | 4471 | 0.889153765 | 0 |
| 17201 | 4472 | 0.889153765 | 0 |
| 17202 | 4473 | 0.889153765 | 0 |
| 17203 | 4474 | 0.889153765 | 0 |
| 17204 | 4475 | 0.889153765 | 0 |
| 17205 | 4476 | 0.889153765 | 0 |
| 17206 | 4477 | 0.889153765 | 0 |
| 17207 | 4478 | 0.889153765 | 0 |
| 17208 | 4479 | 0.888620561 | 0 |
| 17209 | 4480 | 0.888537307 | 0 |
| 17210 | 4481 | 0.888537307 | -0.429962036 |
| 17211 | 4482 | 0.888423244 | 0 |
| 17212 | 4483 | 0.888142601 | -1.361369411 |
| 17213 | 4484 | 0.888142601 | -1.361369411 |
| 17214 | 4485 | 0.887994099 | 0 |
| 17215 | 4486 | 0.887868235 | 0 |
| 17216 | 4487 | 0.887794469 | 0 |
| 17217 | 4488 | 0.887794469 | 0 |
| 17218 | 4489 | 0.887794469 | 0 |
| 17219 | 4490 | 0.887511818 | 0 |
| 17220 | 4491 | 0.887321296 | 0 |
| 17221 | 4492 | 0.887321296 | 0 |
| 17222 | 4493 | 0.887247568 | 0 |
| 17223 | 4494 | 0.887247568 | 0 |
| 17224 | 4495 | 0.887080756 | 0 |
| 17225 | 4496 | 0.886965878 | 0 |
| 17226 | 4497 | 0.886640964 | 0 |
| 17227 | 4498 | 0.886342787 | 0 |
| 17228 | 4499 | 0.885964317 | 0 |
| 17229 | 4500 | 0.885964317 | 0 |
| 17230 | 4501 | 0.885734105 | 0 |
| 17231 | 4502 | 0.88531891 | 0 |
| 17232 | 4503 | 0.885223471 | 0 |
| 17233 | 4504 | 0.885108411 | -0.459719871 |
| 17234 | 4505 | 0.885041529 | 0 |
| 17235 | 4506 | 0.884997805 | 0 |
| 17236 | 4507 | 0.884788959 | 0 |
| 17237 | 4508 | 0.884503333 | 0 |
| 17238 | 4509 | 0.884014125 | 0 |
| 17239 | 4510 | 0.884014125 | 0 |
| 17240 | 4511 | 0.883970308 | 0 |
| 17241 | 4512 | 0.883803046 | -1.293158298 |
| 17242 | 4513 | 0.883324221 | 0 |
| 17243 | 4514 | 0.8831218 | 0 |
| 17244 | 4515 | 0.8831218 | 0 |
| 17245 | 4516 | 0.882904815 | 0 |
| 17246 | 4517 | 0.882854459 | -0.523780972 |
| 17247 | 4518 | 0.882622897 | 0 |
| 17248 | 4519 | 0.882420382 | 0 |
| 17249 | 4520 | 0.882420382 | 0 |
| 17250 | 4521 | 0.882420382 | -0.804055746 |
| 17251 | 4522 | 0.88224177 | 0 |
| 17252 | 4523 | 0.88224177 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17253 | 4524 | 0.882133965 | 0 | 17281 | 4552 | 0.879393927 | 0 | 17309 | 4580 | 0.876564637 | 0 | 17337 | 4608 | 0.873144978 | 0 |
| 17254 | 4525 | 0.881328427 | 0 | 17282 | 4553 | 0.879393927 | 0 | 17310 | 4581 | 0.876564637 | 0 | 17338 | 4609 | 0.873144978 | 0 |
| 17255 | 4526 | 0.881061087 | 0 | 17283 | 4554 | 0.879393927 | 0 | 17311 | 4582 | 0.876564637 | 0 | 17339 | 4610 | 0.872921461 | 0 |
| 17256 | 4527 | 0.881061087 | 0 | 17284 | 4555 | 0.879393927 | 0 | 17312 | 4583 | 0.876564637 | 0 | 17340 | 4611 | 0.872921461 | -1.052697673 |
| 17257 | 4528 | 0.880953335 | 0 | 17285 | 4556 | 0.878322917 | 0 | 17313 | 4584 | 0.876388417 | 0 | 17341 | 4612 | 0.872820696 | 0 |
| 17258 | 4529 | 0.880953335 | 0 | 17286 | 4557 | 0.878091694 | 0 | 17314 | 4585 | 0.876388417 | -0.173265614 | 17342 | 4613 | 0.872554503 | 0 |
| 17259 | 4530 | 0.880858666 | -0.818981424 | 17287 | 4558 | 0.877934113 | 0 | 17315 | 4586 | 0.876188787 | 0 | 17343 | 4614 | 0.872554503 | 0 |
| 17260 | 4531 | 0.880774833 | 0 | 17288 | 4559 | 0.877934113 | 0 | 17316 | 4587 | 0.876188787 | -0.289343095 | 17344 | 4615 | 0.872554503 | 0 |
| 17261 | 4532 | 0.880774833 | 0 | 17289 | 4560 | 0.877840099 | 0 | 17317 | 4588 | 0.876188787 | -0.782258617 | 17345 | 4616 | 0.872554503 | 0 |
| 17262 | 4533 | 0.880774833 | 0 | 17290 | 4561 | 0.877840099 | 0 | 17318 | 4589 | 0.876078686 | 0 | 17346 | 4617 | 0.872554503 | 0 |
| 17263 | 4534 | 0.880572475 | 0 | 17291 | 4562 | 0.877733143 | 0 | 17319 | 4590 | 0.875960752 | 0 | 17347 | 4618 | 0.872554503 | 0 |
| 17264 | 4535 | 0.880572475 | 0 | 17292 | 4563 | 0.877610375 | 0 | 17320 | 4591 | 0.875697782 | 0 | 17348 | 4619 | 0.872554503 | -1.108112197 |
| 17265 | 4536 | 0.880572475 | 0 | 17293 | 4564 | 0.877610375 | 0 | 17321 | 4592 | 0.875391185 | 0 | 17349 | 4620 | 0.872215343 | 0 |
| 17266 | 4537 | 0.880467585 | 0 | 17294 | 4565 | 0.877610375 | -1.212200794 | 17322 | 4593 | 0.875217987 | 0 | 17350 | 4621 | 0.872215343 | 0 |
| 17267 | 4538 | 0.879393927 | 0 | 17295 | 4566 | 0.877387945 | 0 | 17323 | 4594 | 0.875029122 | 0 | 17351 | 4622 | 0.872143434 | 0 |
| 17268 | 4539 | 0.879393927 | 0 | 17296 | 4567 | 0.877387945 | -0.763330693 | 17324 | 4595 | 0.875029122 | 0 | 17352 | 4623 | 0.872032828 | 0 |
| 17269 | 4540 | 0.879393927 | 0 | 17297 | 4568 | 0.877300938 | 0 | 17325 | 4596 | 0.874595044 | 0 | 17353 | 4624 | 0.872032828 | 0 |
| 17270 | 4541 | 0.879393927 | 0 | 17298 | 4569 | 0.877300938 | 0 | 17326 | 4597 | 0.874430508 | 0 | 17354 | 4625 | 0.872032828 | 0 |
| 17271 | 4542 | 0.879393927 | 0 | 17299 | 4570 | 0.877300938 | 0 | 17327 | 4598 | 0.874065094 | 0 | 17355 | 4626 | 0.871679791 | 0 |
| 17272 | 4543 | 0.879393927 | 0 | 17300 | 4571 | 0.877300938 | 0 | 17328 | 4599 | 0.874065094 | 0 | 17356 | 4627 | 0.871679791 | 0 |
| 17273 | 4544 | 0.879393927 | 0 | 17301 | 4572 | 0.877206041 | 0 | 17329 | 4600 | 0.87375366 | 0 | 17357 | 4628 | 0.871608671 | 0 |
| 17274 | 4545 | 0.879393927 | 0 | 17302 | 4573 | 0.877206041 | -1.123664044 | 17330 | 4601 | 0.873641598 | 0 | 17358 | 4629 | 0.871424998 | 0 |
| 17275 | 4546 | 0.879393927 | 0 | 17303 | 4574 | 0.877102131 | 0 | 17331 | 4602 | 0.873641598 | 0 | 17359 | 4630 | 0.871424998 | 0 |
| 17276 | 4547 | 0.879393927 | 0 | 17304 | 4575 | 0.877102131 | -0.006654556 | 17332 | 4603 | 0.873641598 | 0 | 17360 | 4631 | 0.871152798 | 0 |
| 17277 | 4548 | 0.879393927 | 0 | 17305 | 4576 | 0.876987858 | 0 | 17333 | 4604 | 0.873403564 | -0.320157043 | 17361 | 4632 | 0.87096076 | 0 |
| 17278 | 4549 | 0.879393927 | 0 | 17306 | 4577 | 0.876987858 | 0 | 17334 | 4605 | 0.873295409 | 0 | 17362 | 4633 | 0.87096076 | 0 |
| 17279 | 4550 | 0.879393927 | 0 | 17307 | 4578 | 0.876861591 | 0 | 17335 | 4606 | 0.873251046 | 0 | 17363 | 4634 | 0.870818017 | 0 |
| 17280 | 4551 | 0.879393927 | 0 | 17308 | 4579 | 0.876861591 | 0 | 17336 | 4607 | 0.873144978 | 0 | 17364 | 4635 | 0.870707748 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17365 | 4636 | 0.870620003 | 0 | 17393 | 4664 | 0.86775562 | 0 | 17421 | 4692 | 0.866192471 | 0 | 17449 | 4720 | 0.86359966 | 0 |
| 17366 | 4637 | 0.870439085 | 0 | 17394 | 4665 | 0.867716226 | 0 | 17422 | 4693 | 0.866192471 | -1.047527439 | 17450 | 4721 | 0.86359966 | 0 |
| 17367 | 4638 | 0.870439085 | 0 | 17395 | 4666 | 0.867687168 | 0 | 17423 | 4694 | 0.866088461 | 0 | 17451 | 4722 | 0.86359966 | 0 |
| 17368 | 4639 | 0.870359244 | 0 | 17396 | 4667 | 0.867494704 | 0 | 17424 | 4695 | 0.866088461 | 0 | 17452 | 4723 | 0.86359966 | 0 |
| 17369 | 4640 | 0.870359244 | 0 | 17397 | 4668 | 0.867494704 | 0 | 17425 | 4696 | 0.866088461 | 0 | 17453 | 4724 | 0.86359966 | 0 |
| 17370 | 4641 | 0.870180005 | 0 | 17398 | 4669 | 0.867494704 | 0 | 17426 | 4697 | 0.865992473 | 0 | 17454 | 4725 | 0.86359966 | 0 |
| 17371 | 4642 | 0.869848609 | 0 | 17399 | 4670 | 0.867494704 | 0 | 17427 | 4698 | 0.865542815 | -1.474145827 | 17455 | 4726 | 0.86359966 | 0 |
| 17372 | 4643 | 0.869848609 | 0 | 17400 | 4671 | 0.867494704 | 0 | 17428 | 4699 | 0.865428271 | 0 | 17456 | 4727 | 0.86359966 | -1.313361685 |
| 17373 | 4644 | 0.869848609 | 0 | 17401 | 4672 | 0.867494704 | 0 | 17429 | 4700 | 0.865428271 | 0 | 17457 | 4728 | 0.86359966 | -0.61439168 |
| 17374 | 4645 | 0.869351989 | 0 | 17402 | 4673 | 0.867494704 | 0 | 17430 | 4701 | 0.865428271 | 0 | 17458 | 4729 | 0.863065144 | 0 |
| 17375 | 4646 | 0.869351989 | 0 | 17403 | 4674 | 0.867494704 | 0 | 17431 | 4702 | 0.865428271 | -0.847376796 | 17459 | 4730 | 0.863036007 | -1.234744091 |
| 17376 | 4647 | 0.869276793 | 0 | 17404 | 4675 | 0.867494704 | -0.818981424 | 17432 | 4703 | 0.865279718 | 0 | 17460 | 4731 | 0.862878839 | 0 |
| 17377 | 4648 | 0.869276793 | 0 | 17405 | 4676 | 0.867159471 | 0 | 17433 | 4704 | 0.865279718 | 0 | 17461 | 4732 | 0.862762062 | 0 |
| 17378 | 4649 | 0.869174762 | 0 | 17406 | 4677 | 0.867159471 | 0 | 17434 | 4705 | 0.865153488 | 0 | 17462 | 4733 | 0.862688234 | 0 |
| 17379 | 4650 | 0.869174762 | 0 | 17407 | 4678 | 0.867159471 | 0 | 17435 | 4706 | 0.865153488 | -0.550255868 | 17463 | 4734 | 0.862688234 | 0 |
| 17380 | 4651 | 0.869174762 | 0 | 17408 | 4679 | 0.867060192 | 0 | 17436 | 4707 | 0.865044901 | 0 | 17464 | 4735 | 0.862600133 | 0 |
| 17381 | 4652 | 0.869028412 | 0 | 17409 | 4680 | 0.86687737 | 0 | 17437 | 4708 | 0.864950499 | 0 | 17465 | 4736 | 0.862360588 | 0 |
| 17382 | 4653 | 0.869028412 | 0 | 17410 | 4681 | 0.86687737 | 0 | 17438 | 4709 | 0.864670671 | 0 | 17466 | 4737 | 0.862360588 | -0.649958781 |
| 17383 | 4654 | 0.868800854 | 0 | 17411 | 4682 | 0.86687737 | 0 | 17439 | 4710 | 0.864570151 | 0 | 17467 | 4738 | 0.862191897 | 0 |
| 17384 | 4655 | 0.868800854 | 0 | 17412 | 4683 | 0.86687737 | -1.070323636 | 17440 | 4711 | 0.864486881 | 0 | 17468 | 4739 | 0.862089069 | 0 |
| 17385 | 4656 | 0.868632097 | 0 | 17413 | 4684 | 0.866776664 | 0 | 17441 | 4712 | 0.86359966 | 0 | 17469 | 4740 | 0.862051372 | 0 |
| 17386 | 4657 | 0.868632097 | 0 | 17414 | 4685 | 0.866712896 | 0 | 17442 | 4713 | 0.86359966 | 0 | 17470 | 4741 | 0.861830637 | 0 |
| 17387 | 4658 | 0.868398543 | 0 | 17415 | 4686 | 0.866712896 | 0 | 17443 | 4714 | 0.86359966 | 0 | 17471 | 4742 | 0.86166516 | 0 |
| 17388 | 4659 | 0.868185706 | 0 | 17416 | 4687 | 0.866712896 | 0 | 17444 | 4715 | 0.86359966 | 0 | 17472 | 4743 | 0.86166516 | 0 |
| 17389 | 4660 | 0.867964466 | 0 | 17417 | 4688 | 0.866712896 | -1.268855764 | 17445 | 4716 | 0.86359966 | 0 | 17473 | 4744 | 0.86166516 | 0 |
| 17390 | 4661 | 0.867964466 | 0 | 17418 | 4689 | 0.86642895 | 0 | 17446 | 4717 | 0.86359966 | 0 | 17474 | 4745 | 0.8615365 | 0 |
| 17391 | 4662 | 0.867812055 | 0 | 17419 | 4690 | 0.86642895 | 0 | 17447 | 4718 | 0.86359966 | 0 | 17475 | 4746 | 0.861465531 | 0 |
| 17392 | 4663 | 0.867812055 | 0 | 17420 | 4691 | 0.86642895 | 0 | 17448 | 4719 | 0.86359966 | 0 | 17476 | 4747 | 0.861219958 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17477 | 4748 | 0.861219958 | 0 | 17505 | 4776 | 0.858853225 | 0 | 17533 | 4804 | 0.857259482 | 0 | 17561 | 4832 | 0.854391658 | 0 |
| 17478 | 4749 | 0.861219958 | 0 | 17506 | 4777 | 0.858853225 | 0 | 17534 | 4805 | 0.857117533 | 0 | 17562 | 4833 | 0.854321036 | 0 |
| 17479 | 4750 | 0.861219958 | -0.242164018 | 17507 | 4778 | 0.858664442 | 0 | 17535 | 4806 | 0.857002655 | 0 | 17563 | 4834 | 0.854321036 | 0 |
| 17480 | 4751 | 0.861219958 | -1.212200794 | 17508 | 4779 | 0.858664442 | 0 | 17536 | 4807 | 0.857002655 | 0 | 17564 | 4835 | 0.854158104 | 0 |
| 17481 | 4752 | 0.861022237 | 0 | 17509 | 4780 | 0.858578859 | 0 | 17537 | 4808 | 0.857002655 | 0 | 17565 | 4836 | 0.854158104 | 0 |
| 17482 | 4753 | 0.860910522 | 0 | 17510 | 4781 | 0.858460021 | 0 | 17538 | 4809 | 0.857002655 | 0 | 17566 | 4837 | 0.853958014 | 0 |
| 17483 | 4754 | 0.860910522 | 0 | 17511 | 4782 | 0.858460021 | 0 | 17539 | 4810 | 0.856907779 | 0 | 17567 | 4838 | 0.853958014 | 0 |
| 17484 | 4755 | 0.860788683 | 0 | 17512 | 4783 | 0.858460021 | 0 | 17540 | 4811 | 0.856760236 | 0 | 17568 | 4839 | 0.853839823 | 0 |
| 17485 | 4756 | 0.860723527 | 0 | 17513 | 4784 | 0.858460021 | -0.013867204 | 17541 | 4812 | 0.856566397 | 0 | 17569 | 4840 | 0.85370642 | 0 |
| 17486 | 4757 | 0.860508583 | 0 | 17514 | 4785 | 0.858351325 | 0 | 17542 | 4813 | 0.856444729 | 0 | 17570 | 4841 | 0.853633065 | 0 |
| 17487 | 4758 | 0.860508583 | 0 | 17515 | 4786 | 0.858283872 | -1.262561531 | 17543 | 4814 | 0.855912831 | 0 | 17571 | 4842 | 0.853633065 | -1.406874331 |
| 17488 | 4759 | 0.860508583 | -1.098968817 | 17516 | 4787 | 0.857995783 | 0 | 17544 | 4815 | 0.855912831 | 0 | 17572 | 4843 | 0.853380495 | 0 |
| 17489 | 4760 | 0.860312025 | 0 | 17517 | 4788 | 0.857995783 | 0 | 17545 | 4816 | 0.855912831 | 0 | 17573 | 4844 | 0.853380495 | 0 |
| 17490 | 4761 | 0.860258917 | 0 | 17518 | 4789 | 0.857995783 | 0 | 17546 | 4817 | 0.855912831 | 0 | 17574 | 4845 | 0.853380495 | 0 |
| 17491 | 4762 | 0.860258917 | 0 | 17519 | 4790 | 0.857995783 | 0 | 17547 | 4818 | 0.855912831 | 0 | 17575 | 4846 | 0.853380495 | 0 |
| 17492 | 4763 | 0.860166484 | 0 | 17520 | 4791 | 0.857995783 | -0.028930951 | 17548 | 4819 | 0.855912831 | 0 | 17576 | 4847 | 0.853380495 | -0.458279424 |
| 17493 | 4764 | 0.860166484 | 0 | 17521 | 4792 | 0.857821821 | 0 | 17549 | 4820 | 0.855912831 | 0 | 17577 | 4848 | 0.853064989 | -1.310532394 |
| 17494 | 4765 | 0.860088772 | -0.26572005 | 17522 | 4793 | 0.857770117 | 0 | 17550 | 4821 | 0.855912831 | 0 | 17578 | 4849 | 0.852941592 | 0 |
| 17495 | 4766 | 0.859965376 | 0 | 17523 | 4794 | 0.857674678 | 0 | 17551 | 4822 | 0.855295497 | 0 | 17579 | 4850 | 0.852941592 | 0 |
| 17496 | 4767 | 0.859832989 | 0 | 17524 | 4795 | 0.857674678 | 0 | 17552 | 4823 | 0.855220729 | 0 | 17580 | 4851 | 0.852941592 | 0 |
| 17497 | 4768 | 0.859832989 | 0 | 17525 | 4796 | 0.857588568 | 0 | 17553 | 4824 | 0.855125353 | 0 | 17581 | 4852 | 0.852659674 | 0 |
| 17498 | 4769 | 0.859615279 | 0 | 17526 | 4797 | 0.857588568 | 0 | 17554 | 4825 | 0.854999488 | 0 | 17582 | 4853 | 0.852659674 | 0 |
| 17499 | 4770 | 0.859537007 | 0 | 17527 | 4798 | 0.857439351 | 0 | 17555 | 4826 | 0.854825736 | 0 | 17583 | 4854 | 0.852659674 | 0 |
| 17500 | 4771 | 0.859483094 | 0 | 17528 | 4799 | 0.857439351 | 0 | 17556 | 4827 | 0.854711463 | 0 | 17584 | 4855 | 0.852659674 | 0 |
| 17501 | 4772 | 0.859190541 | 0 | 17529 | 4800 | 0.857439351 | 0 | 17557 | 4828 | 0.854711463 | 0 | 17585 | 4856 | 0.852463294 | 0 |
| 17502 | 4773 | 0.859190541 | 0 | 17530 | 4801 | 0.857439351 | -0.609122527 | 17558 | 4829 | 0.854711463 | -0.684549534 | 17586 | 4857 | 0.852463294 | 0 |
| 17503 | 4774 | 0.859190541 | 0 | 17531 | 4802 | 0.857314536 | 0 | 17559 | 4830 | 0.854570344 | 0 | 17587 | 4858 | 0.852463294 | 0 |
| 17504 | 4775 | 0.858904539 | 0 | 17532 | 4803 | 0.857314536 | 0 | 17560 | 4831 | 0.854570344 | 0 | 17588 | 4859 | 0.852463294 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17589 | 4860 | 0.852410438 | 0 | 17617 | 4888 | 0.850026853 | 0 | 17645 | 4916 | 0.847424721 | -1.316172662 | 17673 | 4944 | 0.845116254 | 0 |
| 17590 | 4861 | 0.85231865 | 0 | 17618 | 4889 | 0.849938948 | 0 | 17646 | 4917 | 0.847209244 | 0 | 17674 | 4945 | 0.844991188 | 0 |
| 17591 | 4862 | 0.85231865 | 0 | 17619 | 4890 | 0.849723257 | 0 | 17647 | 4918 | 0.847209244 | 0 | 17675 | 4946 | 0.844991188 | -0.02606431 |
| 17592 | 4863 | 0.85231865 | 0 | 17620 | 4891 | 0.849723257 | 0 | 17648 | 4919 | 0.847209244 | 0 | 17676 | 4947 | 0.844868817 | -0.309585187 |
| 17593 | 4864 | 0.852119842 | 0 | 17621 | 4892 | 0.849430704 | 0 | 17649 | 4920 | 0.847209244 | 0 | 17677 | 4948 | 0.844631821 | 0 |
| 17594 | 4865 | 0.852119842 | 0 | 17622 | 4893 | 0.84924151 | 0 | 17650 | 4921 | 0.847000398 | 0 | 17678 | 4949 | 0.844631821 | 0 |
| 17595 | 4866 | 0.852119842 | -0.4875688 | 17623 | 4894 | 0.84924151 | -1.039654816 | 17651 | 4922 | 0.847000398 | 0 | 17679 | 4950 | 0.844631821 | 0 |
| 17596 | 4867 | 0.851989639 | 0 | 17624 | 4895 | 0.84924151 | -1.340684812 | 17652 | 4923 | 0.846949187 | 0 | 17680 | 4951 | 0.844360302 | 0 |
| 17597 | 4868 | 0.851897754 | 0 | 17625 | 4896 | 0.849011298 | 0 | 17653 | 4924 | 0.846864703 | 0 | 17681 | 4952 | 0.844360302 | 0 |
| 17598 | 4869 | 0.851897754 | 0 | 17626 | 4897 | 0.849011298 | 0 | 17654 | 4925 | 0.84669891 | -1.243112259 | 17682 | 4953 | 0.844294505 | 0 |
| 17599 | 4870 | 0.851829442 | 0 | 17627 | 4898 | 0.848787781 | -1.353727668 | 17655 | 4926 | 0.846601414 | 0 | 17683 | 4954 | 0.844294505 | 0 |
| 17600 | 4871 | 0.851776662 | 0 | 17628 | 4899 | 0.848725108 | 0 | 17656 | 4927 | 0.846601414 | 0 | 17684 | 4955 | 0.844294505 | 0 |
| 17601 | 4872 | 0.851365204 | 0 | 17629 | 4900 | 0.848359694 | 0 | 17657 | 4928 | 0.846601414 | 0 | 17685 | 4956 | 0.844294505 | -1.031636844 |
| 17602 | 4873 | 0.851365204 | 0 | 17630 | 4901 | 0.848359694 | 0 | 17658 | 4929 | 0.846537221 | 0 | 17686 | 4957 | 0.844186619 | -1.212200794 |
| 17603 | 4874 | 0.851365204 | 0 | 17631 | 4902 | 0.848359694 | 0 | 17659 | 4930 | 0.846537221 | 0 | 17687 | 4958 | 0.84397727 | 0 |
| 17604 | 4875 | 0.851365204 | 0 | 17632 | 4903 | 0.848359694 | 0 | 17660 | 4931 | 0.846225564 | 0 | 17688 | 4959 | 0.84397727 | 0 |
| 17605 | 4876 | 0.851365204 | 0 | 17633 | 4904 | 0.848359694 | 0 | 17661 | 4932 | 0.846225564 | 0 | 17689 | 4960 | 0.843776068 | 0 |
| 17606 | 4877 | 0.851365204 | -0.20502221 | 17634 | 4905 | 0.848087494 | 0 | 17662 | 4933 | 0.845870893 | 0 | 17690 | 4961 | 0.843776068 | 0 |
| 17607 | 4878 | 0.851365204 | -0.630990942 | 17635 | 4906 | 0.848011562 | 0 | 17663 | 4934 | 0.845645344 | 0 | 17691 | 4962 | 0.843776068 | 0 |
| 17608 | 4879 | 0.850862839 | 0 | 17636 | 4907 | 0.848011562 | -1.443904299 | 17664 | 4935 | 0.84553566 | 0 | 17692 | 4963 | 0.843776068 | 0 |
| 17609 | 4880 | 0.850781867 | 0 | 17637 | 4908 | 0.847919456 | 0 | 17665 | 4936 | 0.84537484 | 0 | 17693 | 4964 | 0.843396274 | 0 |
| 17610 | 4881 | 0.850669776 | 0 | 17638 | 4909 | 0.847876876 | 0 | 17666 | 4937 | 0.84537484 | 0 | 17694 | 4965 | 0.843396274 | 0 |
| 17611 | 4882 | 0.850504362 | 0 | 17639 | 4910 | 0.847876876 | 0 | 17667 | 4938 | 0.84537484 | 0 | 17695 | 4966 | 0.843396274 | 0 |
| 17612 | 4883 | 0.850388163 | 0 | 17640 | 4911 | 0.847876876 | 0 | 17668 | 4939 | 0.84537484 | 0 | 17696 | 4967 | 0.843242078 | 0 |
| 17613 | 4884 | 0.850388163 | 0 | 17641 | 4912 | 0.847761079 | 0 | 17669 | 4940 | 0.84537484 | -1.290193819 | 17697 | 4968 | 0.84312959 | 0 |
| 17614 | 4885 | 0.850104551 | 0 | 17642 | 4913 | 0.847679514 | 0 | 17670 | 4941 | 0.845116254 | 0 | 17698 | 4969 | 0.84312959 | 0 |
| 17615 | 4886 | 0.850104551 | 0 | 17643 | 4914 | 0.847679514 | 0 | 17671 | 4942 | 0.845116254 | 0 | 17699 | 4970 | 0.843043905 | 0 |
| 17616 | 4887 | 0.850026853 | 0 | 17644 | 4915 | 0.847424721 | 0 | 17672 | 4943 | 0.845116254 | 0 | 17700 | 4971 | 0.843043905 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17701 | 4972 | 0.843043905 | 0 | 17729 | 5000 | 0.841255834 | 0 | 17757 | 5028 | 0.839276704 | 0 | 17785 | 5056 | 0.836865407 | -0.022496841 |
| 17702 | 4973 | 0.843043905 | -1.262561531 | 17730 | 5001 | 0.841255834 | 0 | 17758 | 5029 | 0.839276704 | 0 | 17786 | 5057 | 0.836749672 | 0 |
| 17703 | 4974 | 0.842877094 | 0 | 17731 | 5002 | 0.841255834 | 0 | 17759 | 5030 | 0.839276704 | 0 | 17787 | 5058 | 0.836749672 | 0 |
| 17704 | 4975 | 0.842877094 | 0 | 17732 | 5003 | 0.841146039 | -1.361369411 | 17760 | 5031 | 0.839099332 | 0 | 17788 | 5059 | 0.836641947 | 0 |
| 17705 | 4976 | 0.842779816 | 0 | 17733 | 5004 | 0.841092319 | 0 | 17761 | 5032 | 0.838932777 | -1.036998572 | 17789 | 5060 | 0.836641947 | 0 |
| 17706 | 4977 | 0.842716095 | 0 | 17734 | 5005 | 0.840935676 | 0 | 17762 | 5033 | 0.838879492 | 0 | 17790 | 5061 | 0.836541427 | 0 |
| 17707 | 4978 | 0.842716095 | 0 | 17735 | 5006 | 0.840935676 | 0 | 17763 | 5034 | 0.838776076 | 0 | 17791 | 5062 | 0.836198654 | 0 |
| 17708 | 4979 | 0.842637681 | 0 | 17736 | 5007 | 0.840935676 | 0 | 17764 | 5035 | 0.838357075 | 0 | 17792 | 5063 | 0.836198654 | 0 |
| 17709 | 4980 | 0.842637681 | 0 | 17737 | 5008 | 0.840935676 | 0 | 17765 | 5036 | 0.838357075 | 0 | 17793 | 5064 | 0.836055911 | 0 |
| 17710 | 4981 | 0.842591279 | 0 | 17738 | 5009 | 0.840815021 | 0 | 17766 | 5037 | 0.838232188 | 0 | 17794 | 5065 | 0.836055911 | 0 |
| 17711 | 4982 | 0.842591279 | -0.275603284 | 17739 | 5010 | 0.840736777 | 0 | 17767 | 5038 | 0.838001242 | 0 | 17795 | 5066 | 0.835990342 | 0 |
| 17712 | 4983 | 0.842410361 | 0 | 17740 | 5011 | 0.840736777 | 0 | 17768 | 5039 | 0.838001242 | -1.121476158 | 17796 | 5067 | 0.835928234 | 0 |
| 17713 | 4984 | 0.842410361 | 0 | 17741 | 5012 | 0.840736777 | 0 | 17769 | 5040 | 0.837792397 | 0 | 17797 | 5068 | 0.835869318 | 0 |
| 17714 | 4985 | 0.842410361 | 0 | 17742 | 5013 | 0.840736777 | -1.385912352 | 17770 | 5041 | 0.837792397 | 0 | 17798 | 5069 | 0.83576013 | 0 |
| 17715 | 4986 | 0.842410361 | 0 | 17743 | 5014 | 0.840548431 | 0 | 17771 | 5042 | 0.837792397 | 0 | 17799 | 5070 | 0.835661123 | -0.377073491 |
| 17716 | 4987 | 0.842410361 | -0.147030263 | 17744 | 5015 | 0.840369819 | -1.409142192 | 17772 | 5043 | 0.837695293 | 0 | 17800 | 5071 | 0.83552879 | -1.485676446 |
| 17717 | 4988 | 0.84219424 | 0 | 17745 | 5016 | 0.840200206 | 0 | 17773 | 5044 | 0.837695293 | -0.55113058 | 17801 | 5072 | 0.835449778 | 0 |
| 17718 | 4989 | 0.842124547 | 0 | 17746 | 5017 | 0.840200206 | 0 | 17774 | 5045 | 0.837602624 | 0 | 17802 | 5073 | 0.835278384 | 0 |
| 17719 | 4990 | 0.842069604 | 0 | 17747 | 5018 | 0.840200206 | -0.098087895 | 17775 | 5046 | 0.837429426 | 0 | 17803 | 5074 | 0.833636437 | 0 |
| 17720 | 4991 | 0.841856767 | 0 | 17748 | 5019 | 0.840118564 | 0 | 17776 | 5047 | 0.837429426 | 0 | 17804 | 5075 | 0.833636437 | 0 |
| 17721 | 4992 | 0.841856767 | 0 | 17749 | 5020 | 0.840118564 | 0 | 17777 | 5048 | 0.837429426 | -1.182745815 | 17805 | 5076 | 0.833636437 | 0 |
| 17722 | 4993 | 0.841792441 | -1.450123419 | 17750 | 5021 | 0.840038928 | 0 | 17778 | 5049 | 0.837348378 | -1.493196885 | 17806 | 5077 | 0.833636437 | 0 |
| 17723 | 4994 | 0.841605366 | 0 | 17751 | 5022 | 0.839885386 | 0 | 17779 | 5050 | 0.837270721 | 0 | 17807 | 5078 | 0.833636437 | 0 |
| 17724 | 4995 | 0.841605366 | 0 | 17752 | 5023 | 0.839739036 | 0 | 17780 | 5051 | 0.837270721 | 0 | 17808 | 5079 | 0.833636437 | 0 |
| 17725 | 4996 | 0.841461774 | 0 | 17753 | 5024 | 0.839668402 | 0 | 17781 | 5052 | 0.837124765 | 0 | 17809 | 5080 | 0.833636437 | 0 |
| 17726 | 4997 | 0.841255834 | 0 | 17754 | 5025 | 0.839668402 | -1.281177001 | 17782 | 5053 | 0.836990079 | 0 | 17810 | 5081 | 0.833636437 | 0 |
| 17727 | 4998 | 0.841255834 | 0 | 17755 | 5026 | 0.83946598 | 0 | 17783 | 5054 | 0.836926562 | 0 | 17811 | 5082 | 0.833636437 | 0 |
| 17728 | 4999 | 0.841255834 | 0 | 17756 | 5027 | 0.83946598 | 0 | 17784 | 5055 | 0.836865407 | 0 | 17812 | 5083 | 0.833636437 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17813 | 5084 | 0.833636437 | 0 | 17841 | 5112 | 0.833636437 | 0 | 17869 | 5140 | 0.830308493 | 0 | 17897 | 5168 | 0.828068483 | 0 |
| 17814 | 5085 | 0.833636437 | 0 | 17842 | 5113 | 0.833636437 | 0 | 17870 | 5141 | 0.830308493 | 0 | 17898 | 5169 | 0.828008352 | 0 |
| 17815 | 5086 | 0.833636437 | 0 | 17843 | 5114 | 0.833636437 | -0.790952701 | 17871 | 5142 | 0.830175905 | 0 | 17899 | 5170 | 0.827687104 | 0 |
| 17816 | 5087 | 0.833636437 | 0 | 17844 | 5115 | 0.833636437 | -0.620690985 | 17872 | 5143 | 0.830175905 | 0 | 17900 | 5171 | 0.827618403 | 0 |
| 17817 | 5088 | 0.833636437 | 0 | 17845 | 5116 | 0.832141446 | 0 | 17873 | 5144 | 0.830032313 | -0.907596338 | 17901 | 5172 | 0.827476128 | 0 |
| 17818 | 5089 | 0.833636437 | 0 | 17846 | 5117 | 0.831902724 | 0 | 17874 | 5145 | 0.829706143 | 0 | 17902 | 5173 | 0.827476128 | 0 |
| 17819 | 5090 | 0.833636437 | 0 | 17847 | 5118 | 0.831902724 | 0 | 17875 | 5146 | 0.829519871 | 0 | 17903 | 5174 | 0.827476128 | 0 |
| 17820 | 5091 | 0.833636437 | 0 | 17848 | 5119 | 0.831792296 | 0 | 17876 | 5147 | 0.829519871 | -1.151146829 | 17904 | 5175 | 0.827476128 | 0 |
| 17821 | 5092 | 0.833636437 | 0 | 17849 | 5120 | 0.831710516 | -1.479949403 | 17877 | 5148 | 0.829419952 | 0 | 17905 | 5176 | 0.827476128 | -0.852160576 |
| 17822 | 5093 | 0.833636437 | 0 | 17850 | 5121 | 0.831621146 | 0 | 17878 | 5149 | 0.829419952 | -1.441811309 | 17906 | 5177 | 0.827249638 | 0 |
| 17823 | 5094 | 0.833636437 | 0 | 17851 | 5122 | 0.831523077 | 0 | 17879 | 5150 | 0.829315063 | 0 | 17907 | 5178 | 0.827249638 | 0 |
| 17824 | 5095 | 0.833636437 | 0 | 17852 | 5123 | 0.831470375 | 0 | 17880 | 5151 | 0.829315063 | 0 | 17908 | 5179 | 0.827249638 | 0 |
| 17825 | 5096 | 0.833636437 | 0 | 17853 | 5124 | 0.831470375 | 0 | 17881 | 5152 | 0.829088809 | 0 | 17909 | 5180 | 0.827249638 | 0 |
| 17826 | 5097 | 0.833636437 | 0 | 17854 | 5125 | 0.83135667 | 0 | 17882 | 5153 | 0.828837554 | 0 | 17910 | 5181 | 0.827005858 | 0 |
| 17827 | 5098 | 0.833636437 | 0 | 17855 | 5126 | 0.83135667 | -1.406874331 | 17883 | 5154 | 0.828837554 | 0 | 17911 | 5182 | 0.827005858 | 0 |
| 17828 | 5099 | 0.833636437 | 0 | 17856 | 5127 | 0.831230367 | 0 | 17884 | 5155 | 0.828837554 | -1.385912352 | 17912 | 5183 | 0.827005858 | 0 |
| 17829 | 5100 | 0.833636437 | 0 | 17857 | 5128 | 0.831161818 | 0 | 17885 | 5156 | 0.828701219 | 0 | 17913 | 5184 | 0.826832729 | 0 |
| 17830 | 5101 | 0.833636437 | 0 | 17858 | 5129 | 0.831161818 | 0 | 17886 | 5157 | 0.828701219 | 0 | 17914 | 5185 | 0.826742729 | 0 |
| 17831 | 5102 | 0.833636437 | 0 | 17859 | 5130 | 0.831161818 | 0 | 17887 | 5158 | 0.828701219 | 0 | 17915 | 5186 | 0.826742729 | 0 |
| 17832 | 5103 | 0.833636437 | 0 | 17860 | 5131 | 0.831089248 | 0 | 17888 | 5159 | 0.828556911 | 0 | 17916 | 5187 | 0.826650316 | 0 |
| 17833 | 5104 | 0.833636437 | 0 | 17861 | 5132 | 0.831089248 | 0 | 17889 | 5160 | 0.828556911 | 0 | 17917 | 5188 | 0.826457852 | 0 |
| 17834 | 5105 | 0.833636437 | 0 | 17862 | 5133 | 0.831089248 | 0 | 17890 | 5161 | 0.828455924 | 0 | 17918 | 5189 | 0.826457852 | 0 |
| 17835 | 5106 | 0.833636437 | 0 | 17863 | 5134 | 0.830930543 | 0 | 17891 | 5162 | 0.82840391 | 0 | 17919 | 5190 | 0.826457852 | -0.610140803 |
| 17836 | 5107 | 0.833636437 | 0 | 17864 | 5135 | 0.830750749 | 0 | 17892 | 5163 | 0.828241405 | 0 | 17920 | 5191 | 0.825983473 | 0 |
| 17837 | 5108 | 0.833636437 | 0 | 17865 | 5136 | 0.830750749 | -0.158689875 | 17893 | 5164 | 0.828241405 | 0 | 17921 | 5192 | 0.825811099 | 0 |
| 17838 | 5109 | 0.833636437 | 0 | 17866 | 5137 | 0.830651583 | 0 | 17894 | 5165 | 0.828127342 | 0 | 17922 | 5193 | 0.825811099 | 0 |
| 17839 | 5110 | 0.833636437 | 0 | 17867 | 5138 | 0.83054536 | 0 | 17895 | 5166 | 0.828127342 | 0 | 17923 | 5194 | 0.825568815 | 0 |
| 17840 | 5111 | 0.833636437 | 0 | 17868 | 5139 | 0.830431297 | 0 | 17896 | 5167 | 0.828068483 | 0 | 17924 | 5195 | 0.825568815 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 17925 | 5196 | 0.825568815 | 0 | 17953 | 5224 | 0.822912571 | 0 | 17981 | 5252 | 0.82140198 | 0 | 18009 | 5280 | 0.819395998 | 0 |
| 17926 | 5197 | 0.825441958 | 0 | 17954 | 5225 | 0.822571011 | 0 | 17982 | 5253 | 0.82140198 | 0 | 18010 | 5281 | 0.819395998 | 0 |
| 17927 | 5198 | 0.825441958 | 0 | 17955 | 5226 | 0.822571011 | 0 | 17983 | 5254 | 0.82140198 | 0 | 18011 | 5282 | 0.819395998 | 0 |
| 17928 | 5199 | 0.825441958 | 0 | 17956 | 5227 | 0.822571011 | 0 | 17984 | 5255 | 0.82140198 | -1.381113469 | 18012 | 5283 | 0.819395998 | 0 |
| 17929 | 5200 | 0.825311048 | 0 | 17957 | 5228 | 0.822571011 | 0 | 17985 | 5256 | 0.821107843 | 0 | 18013 | 5284 | 0.819395998 | 0 |
| 17930 | 5201 | 0.825244012 | 0 | 17958 | 5229 | 0.82245227 | 0 | 17986 | 5257 | 0.821047309 | 0 | 18014 | 5285 | 0.818995911 | 0 |
| 17931 | 5202 | 0.825244012 | 0 | 17959 | 5230 | 0.82245227 | 0 | 17987 | 5258 | 0.820955405 | 0 | 18015 | 5286 | 0.818995911 | 0 |
| 17932 | 5203 | 0.825203269 | 0 | 17960 | 5231 | 0.82245227 | 0 | 17988 | 5259 | 0.820799212 | 0 | 18016 | 5287 | 0.818995911 | -1.383519539 |
| 17933 | 5204 | 0.825175887 | 0 | 17961 | 5232 | 0.822355426 | 0 | 17989 | 5260 | 0.820799212 | 0 | 18017 | 5288 | 0.81891318 | 0 |
| 17934 | 5205 | 0.825036265 | 0 | 17962 | 5233 | 0.822355426 | 0 | 17990 | 5261 | 0.82067146 | 0 | 18018 | 5289 | 0.81891318 | 0 |
| 17935 | 5206 | 0.825036265 | 0 | 17963 | 5234 | 0.822206975 | 0 | 17991 | 5262 | 0.820474991 | 0 | 18019 | 5290 | 0.818787316 | 0 |
| 17936 | 5207 | 0.825036265 | 0 | 17964 | 5235 | 0.822206975 | 0 | 17992 | 5263 | 0.82033097 | 0 | 18020 | 5291 | 0.818787316 | 0 |
| 17937 | 5208 | 0.824588308 | 0 | 17965 | 5236 | 0.822206975 | 0 | 17993 | 5264 | 0.820133966 | 0 | 18021 | 5292 | 0.818696087 | 0 |
| 17938 | 5209 | 0.824428435 | -1.281177001 | 17966 | 5237 | 0.822206975 | -0.137270425 | 17994 | 5265 | 0.820133966 | 0 | 18022 | 5293 | 0.818696087 | 0 |
| 17939 | 5210 | 0.824091119 | 0 | 17967 | 5238 | 0.821950678 | 0 | 17995 | 5266 | 0.82003326 | 0 | 18023 | 5294 | 0.818696087 | 0 |
| 17940 | 5211 | 0.824091119 | 0 | 17968 | 5239 | 0.821950678 | 0 | 17996 | 5267 | 0.82003326 | 0 | 18024 | 5295 | 0.81857269 | 0 |
| 17941 | 5212 | 0.824091119 | 0 | 17969 | 5240 | 0.821950678 | 0 | 17997 | 5268 | 0.819956739 | 0 | 18025 | 5296 | 0.81857269 | 0 |
| 17942 | 5213 | 0.824091119 | 0 | 17970 | 5241 | 0.821950678 | 0 | 17998 | 5269 | 0.819956739 | 0 | 18026 | 5297 | 0.818319679 | 0 |
| 17943 | 5214 | 0.824091119 | 0 | 17971 | 5242 | 0.821875326 | 0 | 17999 | 5270 | 0.819848152 | 0 | 18027 | 5298 | 0.818124271 | 0 |
| 17944 | 5215 | 0.824091119 | 0 | 17972 | 5243 | 0.821818171 | 0 | 18000 | 5271 | 0.819848152 | 0 | 18028 | 5299 | 0.818124271 | 0 |
| 17945 | 5216 | 0.823728148 | 0 | 17973 | 5244 | 0.821818171 | 0 | 18001 | 5272 | 0.819848152 | 0 | 18029 | 5300 | 0.818124271 | 0 |
| 17946 | 5217 | 0.823728148 | 0 | 17974 | 5245 | 0.821818171 | 0 | 18002 | 5273 | 0.819848152 | 0 | 18030 | 5301 | 0.818124271 | 0 |
| 17947 | 5218 | 0.823728148 | 0 | 17975 | 5246 | 0.821818171 | 0 | 18003 | 5274 | 0.819774798 | 0 | 18031 | 5302 | 0.817923812 | 0 |
| 17948 | 5219 | 0.823728148 | 0 | 17976 | 5247 | 0.821818171 | 0 | 18004 | 5275 | 0.819774798 | 0 | 18032 | 5303 | 0.817923812 | -0.721337185 |
| 17949 | 5220 | 0.823728148 | -1.249692605 | 17977 | 5248 | 0.821737213 | 0 | 18005 | 5276 | 0.819721922 | 0 | 18033 | 5304 | 0.81784217 | 0 |
| 17950 | 5221 | 0.823233676 | 0 | 17978 | 5249 | 0.821737213 | 0 | 18006 | 5277 | 0.819395998 | 0 | 18034 | 5305 | 0.817648331 | 0 |
| 17951 | 5222 | 0.823233676 | 0 | 17979 | 5250 | 0.821643322 | 0 | 18007 | 5278 | 0.819395998 | 0 | 18035 | 5306 | 0.817648331 | 0 |
| 17952 | 5223 | 0.823233676 | 0 | 17980 | 5251 | 0.82140198 | 0 | 18008 | 5279 | 0.819395998 | 0 | 18036 | 5307 | 0.817648331 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18037 | 5308 | 0.817648331 | -0.11550013 | 18065 | 5336 | 0.815153031 | 0 | 18093 | 5364 | 0.813160851 | 0 | 18121 | 5392 | 0.811360042 | 0 |
| 18038 | 5309 | 0.817506936 | 0 | 18066 | 5337 | 0.814935938 | 0 | 18094 | 5365 | 0.813160851 | 0 | 18122 | 5393 | 0.811360042 | 0 |
| 18039 | 5310 | 0.817506936 | 0 | 18067 | 5338 | 0.814751093 | 0 | 18095 | 5366 | 0.813074278 | 0 | 18123 | 5394 | 0.811360042 | 0 |
| 18040 | 5311 | 0.817399238 | 0 | 18068 | 5339 | 0.814751093 | 0 | 18096 | 5367 | 0.812951838 | 0 | 18124 | 5395 | 0.811360042 | 0 |
| 18041 | 5312 | 0.817246021 | 0 | 18069 | 5340 | 0.814751093 | 0 | 18097 | 5368 | 0.812951838 | -0.344336071 | 18125 | 5396 | 0.811232327 | 0 |
| 18042 | 5313 | 0.817246021 | 0 | 18070 | 5341 | 0.814520146 | 0 | 18098 | 5369 | 0.812869398 | 0 | 18126 | 5397 | 0.811070609 | 0 |
| 18043 | 5314 | 0.817142259 | -1.33266684 | 18071 | 5342 | 0.814331282 | 0 | 18099 | 5370 | 0.812447138 | 0 | 18127 | 5398 | 0.810859222 | 0 |
| 18044 | 5315 | 0.817067335 | 0 | 18072 | 5343 | 0.814331282 | 0 | 18100 | 5371 | 0.812447138 | 0 | 18128 | 5399 | 0.810859222 | 0 |
| 18045 | 5316 | 0.816603097 | 0 | 18073 | 5344 | 0.814040881 | 0 | 18101 | 5372 | 0.812447138 | 0 | 18129 | 5400 | 0.810859222 | -0.058441548 |
| 18046 | 5317 | 0.816603097 | 0 | 18074 | 5345 | 0.814040881 | 0 | 18102 | 5373 | 0.812447138 | 0 | 18130 | 5401 | 0.810383977 | 0 |
| 18047 | 5318 | 0.816603097 | 0 | 18075 | 5346 | 0.813828043 | 0 | 18103 | 5374 | 0.812447138 | 0 | 18131 | 5402 | 0.810313008 | 0 |
| 18048 | 5319 | 0.816603097 | 0 | 18076 | 5347 | 0.813828043 | 0 | 18104 | 5375 | 0.812447138 | 0 | 18132 | 5403 | 0.810313008 | 0 |
| 18049 | 5320 | 0.816603097 | 0 | 18077 | 5348 | 0.813665356 | 0 | 18105 | 5376 | 0.812447138 | 0 | 18133 | 5404 | 0.810313008 | 0 |
| 18050 | 5321 | 0.816603097 | 0 | 18078 | 5349 | 0.813665356 | 0 | 18106 | 5377 | 0.812447138 | 0 | 18134 | 5405 | 0.810252618 | 0 |
| 18051 | 5322 | 0.816603097 | -0.841844307 | 18079 | 5350 | 0.813536961 | 0 | 18107 | 5378 | 0.812447138 | 0 | 18135 | 5406 | 0.81004904 | 0 |
| 18052 | 5323 | 0.816223635 | 0 | 18080 | 5351 | 0.813536961 | 0 | 18108 | 5379 | 0.812447138 | 0 | 18136 | 5407 | 0.81004904 | 0 |
| 18053 | 5324 | 0.81617501 | 0 | 18081 | 5352 | 0.813536961 | -0.947572785 | 18109 | 5380 | 0.812447138 | 0 | 18137 | 5408 | 0.809972519 | 0 |
| 18054 | 5325 | 0.816112092 | 0 | 18082 | 5353 | 0.813536961 | -1.42469404 | 18110 | 5381 | 0.812447138 | 0 | 18138 | 5409 | 0.809972519 | 0 |
| 18055 | 5326 | 0.816027492 | 0 | 18083 | 5354 | 0.813433051 | 0 | 18111 | 5382 | 0.812447138 | 0 | 18139 | 5410 | 0.809869715 | 0 |
| 18056 | 5327 | 0.81590767 | 0 | 18084 | 5355 | 0.81334723 | 0 | 18112 | 5383 | 0.812447138 | 0 | 18140 | 5411 | 0.809869715 | 0 |
| 18057 | 5328 | 0.81590767 | 0 | 18085 | 5356 | 0.813275154 | 0 | 18113 | 5384 | 0.812447138 | 0 | 18141 | 5412 | 0.809869715 | 0 |
| 18058 | 5329 | 0.81590767 | 0 | 18086 | 5357 | 0.813275154 | 0 | 18114 | 5385 | 0.812041823 | 0 | 18142 | 5413 | 0.809869715 | 0 |
| 18059 | 5330 | 0.815724847 | 0 | 18087 | 5358 | 0.813275154 | 0 | 18115 | 5386 | 0.811780531 | 0 | 18143 | 5414 | 0.809869715 | 0 |
| 18060 | 5331 | 0.815591934 | 0 | 18088 | 5359 | 0.813275154 | 0 | 18116 | 5387 | 0.811548907 | 0 | 18144 | 5415 | 0.809502757 | 0 |
| 18061 | 5332 | 0.815538215 | 0 | 18089 | 5360 | 0.813275154 | 0 | 18117 | 5388 | 0.811548907 | 0 | 18145 | 5416 | 0.809502757 | 0 |
| 18062 | 5333 | 0.815411617 | -0.591223815 | 18090 | 5361 | 0.813275154 | 0 | 18118 | 5389 | 0.811548907 | 0 | 18146 | 5417 | 0.809502757 | 0 |
| 18063 | 5334 | 0.815153031 | 0 | 18091 | 5362 | 0.813275154 | 0 | 18119 | 5390 | 0.811548907 | 0 | 18147 | 5418 | 0.809502757 | 0 |
| 18064 | 5335 | 0.815153031 | 0 | 18092 | 5363 | 0.813160851 | 0 | 18120 | 5391 | 0.811360042 | 0 | 18148 | 5419 | 0.809502757 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18149 | 5420 | 0.809502757 | 0 | 18177 | 5448 | 0.807700703 | 0 | 18205 | 5476 | 0.805607713 | 0 | 18233 | 5504 | 0.804429166 | 0 |
| 18150 | 5421 | 0.809502757 | -0.017349078 | 18178 | 5449 | 0.807700703 | 0 | 18206 | 5477 | 0.805607713 | 0 | 18234 | 5505 | 0.804429166 | 0 |
| 18151 | 5422 | 0.809502757 | -0.694042688 | 18179 | 5450 | 0.807700703 | 0 | 18207 | 5478 | 0.805607713 | 0 | 18235 | 5506 | 0.804347061 | -0.010447545 |
| 18152 | 5423 | 0.809241998 | 0 | 18180 | 5451 | 0.807700703 | 0 | 18208 | 5479 | 0.805607713 | 0 | 18236 | 5507 | 0.804252659 | 0 |
| 18153 | 5424 | 0.80919398 | 0 | 18181 | 5452 | 0.807700703 | 0 | 18209 | 5480 | 0.805607713 | 0 | 18237 | 5508 | 0.804252659 | -1.155224741 |
| 18154 | 5425 | 0.80919398 | 0 | 18182 | 5453 | 0.807700703 | 0 | 18210 | 5481 | 0.805607713 | 0 | 18238 | 5509 | 0.804102358 | 0 |
| 18155 | 5426 | 0.80919398 | 0 | 18183 | 5454 | 0.807483718 | 0 | 18211 | 5482 | 0.805607713 | 0 | 18239 | 5510 | 0.80401397 | 0 |
| 18156 | 5427 | 0.809124287 | 0 | 18184 | 5455 | 0.807483718 | 0 | 18212 | 5483 | 0.805607713 | 0 | 18240 | 5511 | 0.80401397 | 0 |
| 18157 | 5428 | 0.809124287 | 0 | 18185 | 5456 | 0.807421054 | 0 | 18213 | 5484 | 0.805607713 | 0 | 18241 | 5512 | 0.80401397 | 0 |
| 18158 | 5429 | 0.809124287 | 0 | 18186 | 5457 | 0.807421054 | -1.203208869 | 18214 | 5485 | 0.805607713 | 0 | 18242 | 5513 | 0.803860047 | 0 |
| 18159 | 5430 | 0.809124287 | 0 | 18187 | 5458 | 0.807307498 | 0 | 18215 | 5486 | 0.805607713 | 0 | 18243 | 5514 | 0.803860047 | 0 |
| 18160 | 5431 | 0.809013962 | 0 | 18188 | 5459 | 0.807307498 | 0 | 18216 | 5487 | 0.805607713 | -1.371353631 | 18244 | 5515 | 0.803860047 | 0 |
| 18161 | 5432 | 0.808930564 | -0.985179443 | 18189 | 5460 | 0.807207326 | 0 | 18217 | 5488 | 0.804946183 | 0 | 18245 | 5516 | 0.803673213 | 0 |
| 18162 | 5433 | 0.808812853 | 0 | 18190 | 5461 | 0.807207326 | 0 | 18218 | 5489 | 0.804832879 | 0 | 18246 | 5517 | 0.803673213 | 0 |
| 18163 | 5434 | 0.808812853 | 0 | 18191 | 5462 | 0.807161541 | 0 | 18219 | 5490 | 0.804832879 | 0 | 18247 | 5518 | 0.803673213 | 0 |
| 18164 | 5435 | 0.808733754 | 0 | 18192 | 5463 | 0.807161541 | 0 | 18220 | 5491 | 0.804832879 | -0.61953132 | 18248 | 5519 | 0.803524762 | 0 |
| 18165 | 5436 | 0.808703197 | 0 | 18193 | 5464 | 0.807038668 | 0 | 18221 | 5492 | 0.804760309 | 0 | 18249 | 5520 | 0.803388523 | 0 |
| 18166 | 5437 | 0.808634168 | 0 | 18194 | 5465 | 0.80684326 | 0 | 18222 | 5493 | 0.804760309 | 0 | 18250 | 5521 | 0.803351633 | 0 |
| 18167 | 5438 | 0.808552094 | 0 | 18195 | 5466 | 0.80684326 | 0 | 18223 | 5494 | 0.804760309 | 0 | 18251 | 5522 | 0.803351633 | 0 |
| 18168 | 5439 | 0.808504952 | 0 | 18196 | 5467 | 0.806578204 | 0 | 18224 | 5495 | 0.804760309 | 0 | 18252 | 5523 | 0.803351633 | 0 |
| 18169 | 5440 | 0.808504952 | 0 | 18197 | 5468 | 0.806578204 | 0 | 18225 | 5496 | 0.804672741 | 0 | 18253 | 5524 | 0.803147115 | 0 |
| 18170 | 5441 | 0.808330572 | 0 | 18198 | 5469 | 0.806484191 | 0 | 18226 | 5497 | 0.804672741 | 0 | 18254 | 5525 | 0.80290182 | 0 |
| 18171 | 5442 | 0.80814005 | 0 | 18199 | 5470 | 0.806341939 | 0 | 18227 | 5498 | 0.804672741 | 0 | 18255 | 5526 | 0.80290182 | 0 |
| 18172 | 5443 | 0.807974446 | 0 | 18200 | 5471 | 0.806286829 | 0 | 18228 | 5499 | 0.804672741 | 0 | 18256 | 5527 | 0.802846773 | 0 |
| 18173 | 5444 | 0.807974446 | 0 | 18201 | 5472 | 0.806286829 | 0 | 18229 | 5500 | 0.804564989 | 0 | 18257 | 5528 | 0.80275987 | 0 |
| 18174 | 5445 | 0.807974446 | 0 | 18202 | 5473 | 0.805607713 | 0 | 18230 | 5501 | 0.804564989 | -1.268855764 | 18258 | 5529 | 0.80275987 | 0 |
| 18175 | 5446 | 0.807974446 | 0 | 18203 | 5474 | 0.805607713 | 0 | 18231 | 5502 | 0.80450123 | 0 | 18259 | 5530 | 0.80275987 | 0 |
| 18176 | 5447 | 0.807974446 | 0 | 18204 | 5475 | 0.805607713 | 0 | 18232 | 5503 | 0.80450123 | 0 | 18260 | 5531 | 0.802602203 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18261 | 5532 | 0.802602203 | 0 | 18289 | 5560 | 0.801107212 | 0 | 18317 | 5588 | 0.798522817 | 0 | 18345 | 5616 | 0.796652871 | 0 |
| 18262 | 5533 | 0.802462917 | 0 | 18290 | 5561 | 0.800912592 | 0 | 18318 | 5589 | 0.798360676 | 0 | 18346 | 5617 | 0.796652871 | -1.117067039 |
| 18263 | 5534 | 0.802227973 | 0 | 18291 | 5562 | 0.800787525 | 0 | 18319 | 5590 | 0.798360676 | 0 | 18347 | 5618 | 0.796464334 | 0 |
| 18264 | 5535 | 0.802227973 | 0 | 18292 | 5563 | 0.800700379 | 0 | 18320 | 5591 | 0.79826735 | 0 | 18348 | 5619 | 0.796419692 | 0 |
| 18265 | 5536 | 0.802227973 | -1.236430674 | 18293 | 5564 | 0.800700379 | -0.531162926 | 18321 | 5592 | 0.797920885 | 0 | 18349 | 5620 | 0.796209939 | 0 |
| 18266 | 5537 | 0.802003589 | 0 | 18294 | 5565 | 0.800212681 | 0 | 18322 | 5593 | 0.797920885 | 0 | 18350 | 5621 | 0.796209939 | 0 |
| 18267 | 5538 | 0.801955089 | 0 | 18295 | 5566 | 0.800212681 | 0 | 18323 | 5594 | 0.797920885 | 0 | 18351 | 5622 | 0.796209939 | -1.464297457 |
| 18268 | 5539 | 0.801879841 | 0 | 18296 | 5567 | 0.800212681 | 0 | 18324 | 5595 | 0.797920885 | 0 | 18352 | 5623 | 0.79608143 | 0 |
| 18269 | 5540 | 0.801879841 | 0 | 18297 | 5568 | 0.800212681 | 0 | 18325 | 5596 | 0.797920885 | 0 | 18353 | 5624 | 0.795984468 | 0 |
| 18270 | 5541 | 0.801879841 | 0 | 18298 | 5569 | 0.800212681 | 0 | 18326 | 5597 | 0.797920885 | 0 | 18354 | 5625 | 0.795847876 | 0 |
| 18271 | 5542 | 0.801747292 | 0 | 18299 | 5570 | 0.800212681 | 0 | 18327 | 5598 | 0.797661217 | 0 | 18355 | 5626 | 0.795847876 | 0 |
| 18272 | 5543 | 0.801747292 | 0 | 18300 | 5571 | 0.800212681 | 0 | 18328 | 5599 | 0.797612108 | 0 | 18356 | 5627 | 0.795847876 | 0 |
| 18273 | 5544 | 0.801634268 | 0 | 18301 | 5572 | 0.800212681 | 0 | 18329 | 5600 | 0.797612108 | 0 | 18357 | 5628 | 0.795847876 | 0 |
| 18274 | 5545 | 0.801451753 | 0 | 18302 | 5573 | 0.800212681 | 0 | 18330 | 5601 | 0.797540091 | 0 | 18358 | 5629 | 0.795847876 | 0 |
| 18275 | 5546 | 0.801451753 | 0 | 18303 | 5574 | 0.799829874 | 0 | 18331 | 5602 | 0.797424264 | 0 | 18359 | 5630 | 0.795847876 | -1.381113469 |
| 18276 | 5547 | 0.801451753 | 0 | 18304 | 5575 | 0.799829874 | 0 | 18332 | 5603 | 0.797335187 | 0 | 18360 | 5631 | 0.795641118 | 0 |
| 18277 | 5548 | 0.801451753 | 0 | 18305 | 5576 | 0.799710316 | -1.363887067 | 18333 | 5604 | 0.797335187 | 0 | 18361 | 5632 | 0.795546387 | 0 |
| 18278 | 5549 | 0.801451753 | 0 | 18306 | 5577 | 0.799482161 | 0 | 18334 | 5605 | 0.797119603 | 0 | 18362 | 5633 | 0.795546387 | 0 |
| 18279 | 5550 | 0.801451753 | 0 | 18307 | 5578 | 0.799267535 | 0 | 18335 | 5606 | 0.797085435 | 0 | 18363 | 5634 | 0.795456796 | 0 |
| 18280 | 5551 | 0.801451753 | -0.169306657 | 18308 | 5579 | 0.799267535 | 0 | 18336 | 5607 | 0.797007541 | -1.259379872 | 18364 | 5635 | 0.795291445 | 0 |
| 18281 | 5552 | 0.801310772 | 0 | 18309 | 5580 | 0.799267535 | 0 | 18337 | 5608 | 0.79691363 | 0 | 18365 | 5636 | 0.795073042 | 0 |
| 18282 | 5553 | 0.801251664 | 0 | 18310 | 5581 | 0.799267535 | 0 | 18338 | 5609 | 0.79691363 | 0 | 18366 | 5637 | 0.794883848 | 0 |
| 18283 | 5554 | 0.801251664 | 0 | 18311 | 5582 | 0.799104787 | 0 | 18339 | 5610 | 0.79691363 | 0 | 18367 | 5638 | 0.794883848 | 0 |
| 18284 | 5555 | 0.801251664 | 0 | 18312 | 5583 | 0.799104787 | 0 | 18340 | 5611 | 0.796859039 | 0 | 18368 | 5639 | 0.794718371 | 0 |
| 18285 | 5556 | 0.801251664 | 0 | 18313 | 5584 | 0.799104787 | 0 | 18341 | 5612 | 0.796823349 | 0 | 18369 | 5640 | 0.794718371 | 0 |
| 18286 | 5557 | 0.801174042 | 0 | 18314 | 5585 | 0.798874331 | 0 | 18342 | 5613 | 0.796652871 | 0 | 18370 | 5641 | 0.794572414 | 0 |
| 18287 | 5558 | 0.801107212 | 0 | 18315 | 5586 | 0.798874331 | 0 | 18343 | 5614 | 0.796652871 | 0 | 18371 | 5642 | 0.794484313 | 0 |
| 18288 | 5559 | 0.801107212 | 0 | 18316 | 5587 | 0.798522817 | 0 | 18344 | 5615 | 0.796652871 | 0 | 18372 | 5643 | 0.794442716 | -1.42030719 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18373 | 5644 | 0.794326703 | 0 | 18401 | 5672 | 0.792243752 | 0 | 18429 | 5700 | 0.790884456 | 0 | 18457 | 5728 | 0.788824092 | 0 |
| 18374 | 5645 | 0.794222318 | -1.466285079 | 18402 | 5673 | 0.792243752 | 0 | 18430 | 5701 | 0.790884456 | 0 | 18458 | 5729 | 0.788824092 | 0 |
| 18375 | 5646 | 0.794127896 | 0 | 18403 | 5674 | 0.792243752 | 0 | 18431 | 5702 | 0.790783937 | 0 | 18459 | 5730 | 0.788669291 | 0 |
| 18376 | 5647 | 0.794127896 | 0 | 18404 | 5675 | 0.792243752 | 0 | 18432 | 5703 | 0.790783937 | 0 | 18460 | 5731 | 0.788669291 | 0 |
| 18377 | 5648 | 0.793963732 | 0 | 18405 | 5676 | 0.792243752 | 0 | 18433 | 5704 | 0.790783937 | 0 | 18461 | 5732 | 0.788669291 | 0 |
| 18378 | 5649 | 0.793825883 | 0 | 18406 | 5677 | 0.792243752 | 0 | 18434 | 5705 | 0.790601805 | 0 | 18462 | 5733 | 0.788669291 | 0 |
| 18379 | 5650 | 0.79370849 | 0 | 18407 | 5678 | 0.792243752 | 0 | 18435 | 5706 | 0.790530556 | 0 | 18463 | 5734 | 0.788669291 | 0 |
| 18380 | 5651 | 0.79370849 | -1.296102679 | 18408 | 5679 | 0.792243752 | 0 | 18436 | 5707 | 0.790530556 | 0 | 18464 | 5735 | 0.788669291 | 0 |
| 18381 | 5652 | 0.793519214 | -1.356289885 | 18409 | 5680 | 0.792243752 | 0 | 18437 | 5708 | 0.790530556 | 0 | 18465 | 5736 | 0.788669291 | -0.610140803 |
| 18382 | 5653 | 0.793441806 | -1.082489543 | 18410 | 5681 | 0.792243752 | 0 | 18438 | 5709 | 0.790452844 | 0 | 18466 | 5737 | 0.788439688 | 0 |
| 18383 | 5654 | 0.793373257 | 0 | 18411 | 5682 | 0.792243752 | 0 | 18439 | 5710 | 0.790367747 | 0 | 18467 | 5738 | 0.788439688 | 0 |
| 18384 | 5655 | 0.793373257 | 0 | 18412 | 5683 | 0.792243752 | 0 | 18440 | 5711 | 0.790055865 | 0 | 18468 | 5739 | 0.788439688 | -0.060339415 |
| 18385 | 5656 | 0.793373257 | 0 | 18413 | 5684 | 0.792243752 | 0 | 18441 | 5712 | 0.789927509 | 0 | 18469 | 5740 | 0.788313458 | 0 |
| 18386 | 5657 | 0.793373257 | -1.108112197 | 18414 | 5685 | 0.792243752 | 0 | 18442 | 5713 | 0.789783153 | 0 | 18470 | 5741 | 0.788313458 | -0.129771257 |
| 18387 | 5658 | 0.793312127 | 0 | 18415 | 5686 | 0.792243752 | 0 | 18443 | 5714 | 0.789783153 | 0 | 18471 | 5742 | 0.788178563 | 0 |
| 18388 | 5659 | 0.79320778 | 0 | 18416 | 5687 | 0.792243752 | 0 | 18444 | 5715 | 0.789619608 | 0 | 18472 | 5743 | 0.788178563 | 0 |
| 18389 | 5660 | 0.79320778 | 0 | 18417 | 5688 | 0.792243752 | 0 | 18445 | 5716 | 0.789619608 | 0 | 18473 | 5744 | 0.788107582 | 0 |
| 18390 | 5661 | 0.792913443 | 0 | 18418 | 5689 | 0.792243752 | 0 | 18446 | 5717 | 0.789432774 | 0 | 18474 | 5745 | 0.787878946 | 0 |
| 18391 | 5662 | 0.792243752 | 0 | 18419 | 5690 | 0.792243752 | 0 | 18447 | 5718 | 0.789432774 | 0 | 18475 | 5746 | 0.787878946 | 0 |
| 18392 | 5663 | 0.792243752 | 0 | 18420 | 5691 | 0.792243752 | -1.422506154 | 18448 | 5719 | 0.789217297 | 0 | 18476 | 5747 | 0.787878946 | 0 |
| 18393 | 5664 | 0.792243752 | 0 | 18421 | 5692 | 0.791281859 | 0 | 18449 | 5720 | 0.789054304 | 0 | 18477 | 5748 | 0.787623554 | 0 |
| 18394 | 5665 | 0.792243752 | 0 | 18422 | 5693 | 0.791281859 | 0 | 18450 | 5721 | 0.788966042 | 0 | 18478 | 5749 | 0.787623554 | 0 |
| 18395 | 5666 | 0.792243752 | 0 | 18423 | 5694 | 0.791177998 | 0 | 18451 | 5722 | 0.788966042 | 0 | 18479 | 5750 | 0.78753165 | 0 |
| 18396 | 5667 | 0.792243752 | 0 | 18424 | 5695 | 0.791048993 | 0 | 18452 | 5723 | 0.788966042 | 0 | 18480 | 5751 | 0.78753165 | 0 |
| 18397 | 5668 | 0.792243752 | 0 | 18425 | 5696 | 0.791048993 | 0 | 18453 | 5724 | 0.788966042 | 0 | 18481 | 5752 | 0.78753165 | 0 |
| 18398 | 5669 | 0.792243752 | 0 | 18426 | 5697 | 0.791048993 | 0 | 18454 | 5725 | 0.788872756 | 0 | 18482 | 5753 | 0.787336417 | 0 |
| 18399 | 5670 | 0.792243752 | 0 | 18427 | 5698 | 0.791048993 | -1.385912352 | 18455 | 5726 | 0.788872756 | 0 | 18483 | 5754 | 0.787336417 | 0 |
| 18400 | 5671 | 0.792243752 | 0 | 18428 | 5699 | 0.790972025 | 0 | 18456 | 5727 | 0.788872756 | 0 | 18484 | 5755 | 0.787336417 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18485 | 5756 | 0.787336417 | 0 | 18513 | 5784 | 0.785554816 | -1.485676446 | 18541 | 5812 | 0.784010434 | 0 | 18569 | 5840 | 0.782483914 | 0 |
| 18486 | 5757 | 0.787211314 | 0 | 18514 | 5785 | 0.785489424 | 0 | 18542 | 5813 | 0.783948653 | 0 | 18570 | 5841 | 0.782483914 | -0.478023482 |
| 18487 | 5758 | 0.786893033 | 0 | 18515 | 5786 | 0.785489424 | 0 | 18543 | 5814 | 0.783948653 | 0 | 18571 | 5842 | 0.782483914 | -1.080083473 |
| 18488 | 5759 | 0.786893033 | 0 | 18516 | 5787 | 0.785489424 | 0 | 18544 | 5815 | 0.78386482 | 0 | 18572 | 5843 | 0.782259531 | 0 |
| 18489 | 5760 | 0.786639874 | 0 | 18517 | 5788 | 0.785331757 | 0 | 18545 | 5816 | 0.78386482 | 0 | 18573 | 5844 | 0.782208259 | 0 |
| 18490 | 5761 | 0.786639874 | 0 | 18518 | 5789 | 0.785331757 | 0 | 18546 | 5817 | 0.78386482 | -1.321740616 | 18574 | 5845 | 0.782208259 | 0 |
| 18491 | 5762 | 0.786639874 | 0 | 18519 | 5790 | 0.785124011 | 0 | 18547 | 5818 | 0.783810584 | 0 | 18575 | 5846 | 0.782064509 | -1.539140728 |
| 18492 | 5763 | 0.786639874 | 0 | 18520 | 5791 | 0.785051958 | 0 | 18548 | 5819 | 0.783744567 | 0 | 18576 | 5847 | 0.781976264 | 0 |
| 18493 | 5764 | 0.786639874 | 0 | 18521 | 5792 | 0.785051958 | 0 | 18549 | 5820 | 0.783744567 | 0 | 18577 | 5848 | 0.781976264 | 0 |
| 18494 | 5765 | 0.786639874 | 0 | 18522 | 5793 | 0.784993258 | 0 | 18550 | 5821 | 0.783744567 | 0 | 18578 | 5849 | 0.781840991 | 0 |
| 18495 | 5766 | 0.786639874 | 0 | 18523 | 5794 | 0.784993258 | 0 | 18551 | 5822 | 0.783744567 | 0 | 18579 | 5850 | 0.781840991 | 0 |
| 18496 | 5767 | 0.786302558 | 0 | 18524 | 5795 | 0.784993258 | -1.304817911 | 18552 | 5823 | 0.783662462 | 0 | 18580 | 5851 | 0.781778318 | 0 |
| 18497 | 5768 | 0.786302558 | 0 | 18525 | 5796 | 0.784903388 | 0 | 18553 | 5824 | 0.783557572 | 0 | 18581 | 5852 | 0.781778318 | 0 |
| 18498 | 5769 | 0.786302558 | 0 | 18526 | 5797 | 0.784903388 | -1.077663999 | 18554 | 5825 | 0.783557572 | 0 | 18582 | 5853 | 0.781607437 | 0 |
| 18499 | 5770 | 0.786211787 | 0 | 18527 | 5798 | 0.784903388 | -1.378693995 | 18555 | 5826 | 0.783226933 | 0 | 18583 | 5854 | 0.781607437 | 0 |
| 18500 | 5771 | 0.786211787 | 0 | 18528 | 5799 | 0.78483782 | 0 | 18556 | 5827 | 0.783226933 | 0 | 18584 | 5855 | 0.781607437 | 0 |
| 18501 | 5772 | 0.786054177 | 0 | 18529 | 5800 | 0.784787869 | 0 | 18557 | 5828 | 0.783100372 | 0 | 18585 | 5856 | 0.781607437 | 0 |
| 18502 | 5773 | 0.785922032 | 0 | 18530 | 5801 | 0.784787869 | 0 | 18558 | 5829 | 0.783051991 | 0 | 18586 | 5857 | 0.781607437 | 0 |
| 18503 | 5774 | 0.785922032 | -0.187795808 | 18531 | 5802 | 0.784716796 | -1.589733953 | 18559 | 5830 | 0.782943729 | 0 | 18587 | 5858 | 0.781412904 | 0 |
| 18504 | 5775 | 0.785863655 | 0 | 18532 | 5803 | 0.784418414 | 0 | 18560 | 5831 | 0.782943729 | 0 | 18588 | 5859 | 0.781327337 | 0 |
| 18505 | 5776 | 0.785712884 | 0 | 18533 | 5804 | 0.784418414 | 0 | 18561 | 5832 | 0.782943729 | 0 | 18589 | 5860 | 0.781327337 | -0.371970089 |
| 18506 | 5777 | 0.785712884 | 0 | 18534 | 5805 | 0.784418414 | 0 | 18562 | 5833 | 0.782943729 | 0 | 18590 | 5861 | 0.781107386 | 0 |
| 18507 | 5778 | 0.785712884 | 0 | 18535 | 5806 | 0.784418414 | 0 | 18563 | 5834 | 0.782870126 | 0 | 18591 | 5862 | 0.781107386 | 0 |
| 18508 | 5779 | 0.785712884 | 0 | 18536 | 5807 | 0.784418414 | 0 | 18564 | 5835 | 0.782816835 | 0 | 18592 | 5863 | 0.780985238 | 0 |
| 18509 | 5780 | 0.785712884 | 0 | 18537 | 5808 | 0.784418414 | 0 | 18565 | 5836 | 0.78274483 | 0 | 18593 | 5864 | 0.780930086 | 0 |
| 18510 | 5781 | 0.785712884 | 0 | 18538 | 5809 | 0.784010434 | 0 | 18566 | 5837 | 0.78274483 | 0 | 18594 | 5865 | 0.780930086 | 0 |
| 18511 | 5782 | 0.785712884 | 0 | 18539 | 5810 | 0.784010434 | 0 | 18567 | 5838 | 0.78274483 | 0 | 18595 | 5866 | 0.780784129 | 0 |
| 18512 | 5783 | 0.785554816 | 0 | 18540 | 5811 | 0.784010434 | 0 | 18568 | 5839 | 0.782483914 | 0 | 18596 | 5867 | 0.780784129 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18597 | 5868 | 0.780700362 | 0 | 18625 | 5896 | 0.779278774 | 0 | 18653 | 5924 | 0.777685031 | -1.084882356 | 18681 | 5952 | 0.77564449 | 0 |
| 18598 | 5869 | 0.780661879 | 0 | 18626 | 5897 | 0.779278774 | 0 | 18654 | 5925 | 0.777520495 | 0 | 18682 | 5953 | 0.77564449 | 0 |
| 18599 | 5870 | 0.780557993 | 0 | 18627 | 5898 | 0.779278774 | -0.754229894 | 18655 | 5926 | 0.777457831 | 0 | 18683 | 5954 | 0.77564449 | 0 |
| 18600 | 5871 | 0.780557993 | 0 | 18628 | 5899 | 0.77868507 | 0 | 18656 | 5927 | 0.777457831 | 0 | 18684 | 5955 | 0.77564449 | 0 |
| 18601 | 5872 | 0.780557993 | 0 | 18629 | 5900 | 0.778640575 | 0 | 18657 | 5928 | 0.777318074 | 0 | 18685 | 5956 | 0.77564449 | 0 |
| 18602 | 5873 | 0.780557993 | -1.002828148 | 18630 | 5901 | 0.778640575 | 0 | 18658 | 5929 | 0.777318074 | 0 | 18686 | 5957 | 0.77564449 | 0 |
| 18603 | 5874 | 0.780390925 | 0 | 18631 | 5902 | 0.778528049 | 0 | 18659 | 5930 | 0.777318074 | 0 | 18687 | 5958 | 0.77564449 | 0 |
| 18604 | 5875 | 0.780160591 | 0 | 18632 | 5903 | 0.778528049 | -0.235307014 | 18660 | 5931 | 0.777318074 | 0 | 18688 | 5959 | 0.77564449 | 0 |
| 18605 | 5876 | 0.780160591 | 0 | 18633 | 5904 | 0.778455467 | 0 | 18661 | 5932 | 0.777155081 | 0 | 18689 | 5960 | 0.77564449 | 0 |
| 18606 | 5877 | 0.780077845 | 0 | 18634 | 5905 | 0.778455467 | 0 | 18662 | 5933 | 0.777155081 | 0 | 18690 | 5961 | 0.77564449 | 0 |
| 18607 | 5878 | 0.780077845 | 0 | 18635 | 5906 | 0.778455467 | 0 | 18663 | 5934 | 0.777062981 | 0 | 18691 | 5962 | 0.77564449 | 0 |
| 18608 | 5879 | 0.780077845 | 0 | 18636 | 5907 | 0.778455467 | 0 | 18664 | 5935 | 0.777062981 | 0 | 18692 | 5963 | 0.77564449 | -1.125840964 |
| 18609 | 5880 | 0.780077845 | 0 | 18637 | 5908 | 0.778455467 | 0 | 18665 | 5936 | 0.777062981 | 0 | 18693 | 5964 | 0.77564449 | -1.329960946 |
| 18610 | 5881 | 0.780077845 | -0.781459547 | 18638 | 5909 | 0.778455467 | 0 | 18666 | 5937 | 0.776731585 | 0 | 18694 | 5965 | 0.77564449 | -1.572998995 |
| 18611 | 5882 | 0.780009295 | 0 | 18639 | 5910 | 0.778455467 | 0 | 18667 | 5938 | 0.776731585 | 0 | 18695 | 5966 | 0.77564449 | -1.125840964 |
| 18612 | 5883 | 0.779278774 | 0 | 18640 | 5911 | 0.778367348 | 0 | 18668 | 5939 | 0.776731585 | 0 | 18696 | 5967 | 0.775210412 | 0 |
| 18613 | 5884 | 0.779278774 | 0 | 18641 | 5912 | 0.778367348 | 0 | 18669 | 5940 | 0.776731585 | 0 | 18697 | 5968 | 0.775210412 | 0 |
| 18614 | 5885 | 0.779278774 | 0 | 18642 | 5913 | 0.778258105 | 0 | 18670 | 5941 | 0.776283628 | 0 | 18698 | 5969 | 0.775210412 | 0 |
| 18615 | 5886 | 0.779278774 | 0 | 18643 | 5914 | 0.778119109 | 0 | 18671 | 5942 | 0.776283628 | 0 | 18699 | 5970 | 0.775210412 | 0 |
| 18616 | 5887 | 0.779278774 | 0 | 18644 | 5915 | 0.778034377 | 0 | 18672 | 5943 | 0.776097116 | 0 | 18700 | 5971 | 0.775210412 | 0 |
| 18617 | 5888 | 0.779278774 | 0 | 18645 | 5916 | 0.777936287 | 0 | 18673 | 5944 | 0.776097116 | 0 | 18701 | 5972 | 0.775041722 | 0 |
| 18618 | 5889 | 0.779278774 | 0 | 18646 | 5917 | 0.777936287 | 0 | 18674 | 5945 | 0.776097116 | 0 | 18702 | 5973 | 0.775041722 | 0 |
| 18619 | 5890 | 0.779278774 | 0 | 18647 | 5918 | 0.777936287 | -0.284203456 | 18675 | 5946 | 0.776097116 | 0 | 18703 | 5974 | 0.775041722 | 0 |
| 18620 | 5891 | 0.779278774 | 0 | 18648 | 5919 | 0.777821409 | 0 | 18676 | 5947 | 0.776097116 | 0 | 18704 | 5975 | 0.775041722 | 0 |
| 18621 | 5892 | 0.779278774 | 0 | 18649 | 5920 | 0.777778619 | 0 | 18677 | 5948 | 0.776097116 | -1.262561531 | 18705 | 5976 | 0.774896351 | 0 |
| 18622 | 5893 | 0.779278774 | 0 | 18650 | 5921 | 0.777685031 | 0 | 18678 | 5949 | 0.775994869 | 0 | 18706 | 5977 | 0.77483095 | 0 |
| 18623 | 5894 | 0.779278774 | 0 | 18651 | 5922 | 0.777685031 | 0 | 18679 | 5950 | 0.775930304 | 0 | 18707 | 5978 | 0.774658577 | 0 |
| 18624 | 5895 | 0.779278774 | 0 | 18652 | 5923 | 0.777685031 | 0 | 18680 | 5951 | 0.775930304 | -1.462300698 | 18708 | 5979 | 0.774658577 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18709 | 5980 | 0.774658577 | 0 | 18737 | 6008 | 0.772938596 | 0 | 18765 | 6036 | 0.770845607 | 0 | 18793 | 6064 | 0.768813341 | 0 |
| 18710 | 5981 | 0.774472304 | 0 | 18738 | 6009 | 0.772938596 | 0 | 18766 | 6037 | 0.770845607 | 0 | 18794 | 6065 | 0.768762656 | 0 |
| 18711 | 5982 | 0.774393521 | 0 | 18739 | 6010 | 0.772553413 | 0 | 18767 | 6038 | 0.770845607 | 0 | 18795 | 6066 | 0.768762656 | -0.031013902 |
| 18712 | 5983 | 0.774393521 | -1.299027232 | 18740 | 6011 | 0.77236678 | 0 | 18768 | 6039 | 0.770584691 | 0 | 18796 | 6067 | 0.76869563 | 0 |
| 18713 | 5984 | 0.774199249 | 0 | 18741 | 6012 | 0.77236678 | 0 | 18769 | 6040 | 0.770482636 | 0 | 18797 | 6068 | 0.76869563 | 0 |
| 18714 | 5985 | 0.774199249 | 0 | 18742 | 6013 | 0.77236678 | -1.404594565 | 18770 | 6041 | 0.770394392 | 0 | 18798 | 6069 | 0.768602842 | 0 |
| 18715 | 5986 | 0.774199249 | 0 | 18743 | 6014 | 0.77236678 | -1.404594565 | 18771 | 6042 | 0.770394392 | 0 | 18799 | 6070 | 0.768602842 | 0 |
| 18716 | 5987 | 0.774199249 | 0 | 18744 | 6015 | 0.772287968 | 0 | 18772 | 6043 | 0.770394392 | 0 | 18800 | 6071 | 0.768602842 | 0 |
| 18717 | 5988 | 0.774199249 | 0 | 18745 | 6016 | 0.772183958 | 0 | 18773 | 6044 | 0.770249458 | 0 | 18801 | 6072 | 0.768602842 | 0 |
| 18718 | 5989 | 0.774199249 | 0 | 18746 | 6017 | 0.772183958 | 0 | 18774 | 6045 | 0.770249458 | 0 | 18802 | 6073 | 0.768465905 | -1.51323079 |
| 18719 | 5990 | 0.774050747 | 0 | 18747 | 6018 | 0.772183958 | 0 | 18775 | 6046 | 0.770249458 | 0 | 18803 | 6074 | 0.768243475 | 0 |
| 18720 | 5991 | 0.773933544 | 0 | 18748 | 6019 | 0.772040366 | 0 | 18776 | 6047 | 0.770087014 | 0 | 18804 | 6075 | 0.768243475 | 0 |
| 18721 | 5992 | 0.773760346 | 0 | 18749 | 6020 | 0.772040366 | 0 | 18777 | 6048 | 0.770087014 | 0 | 18805 | 6076 | 0.768070553 | 0 |
| 18722 | 5993 | 0.773760346 | -1.246414895 | 18750 | 6021 | 0.771945923 | 0 | 18778 | 6049 | 0.770087014 | 0 | 18806 | 6077 | 0.768070553 | -0.622770612 |
| 18723 | 5994 | 0.773638507 | 0 | 18751 | 6022 | 0.771829287 | 0 | 18779 | 6050 | 0.770087014 | -1.406874331 | 18807 | 6078 | 0.767997764 | 0 |
| 18724 | 5995 | 0.773638507 | 0 | 18752 | 6023 | 0.771681593 | 0 | 18780 | 6051 | 0.76987555 | 0 | 18808 | 6079 | 0.767997764 | 0 |
| 18725 | 5996 | 0.773638507 | 0 | 18753 | 6024 | 0.77148853 | 0 | 18781 | 6052 | 0.76987555 | 0 | 18809 | 6080 | 0.767819152 | 0 |
| 18726 | 5997 | 0.773548133 | 0 | 18754 | 6025 | 0.77148853 | 0 | 18782 | 6053 | 0.769802883 | 0 | 18810 | 6081 | 0.767819152 | 0 |
| 18727 | 5998 | 0.773478428 | 0 | 18755 | 6026 | 0.771323116 | 0 | 18783 | 6054 | 0.769802883 | 0 | 18811 | 6082 | 0.767819152 | 0 |
| 18728 | 5999 | 0.773478428 | 0 | 18756 | 6027 | 0.771323116 | 0 | 18784 | 6055 | 0.769802883 | 0 | 18812 | 6083 | 0.767645191 | 0 |
| 18729 | 6000 | 0.773377943 | -1.518537917 | 18757 | 6028 | 0.771323116 | 0 | 18785 | 6056 | 0.769695157 | 0 | 18813 | 6084 | 0.767576868 | 0 |
| 18730 | 6001 | 0.773282048 | 0 | 18758 | 6029 | 0.771225401 | 0 | 18786 | 6057 | 0.769178448 | 0 | 18814 | 6085 | 0.767576868 | 0 |
| 18731 | 6002 | 0.772938596 | 0 | 18759 | 6030 | 0.771225401 | 0 | 18787 | 6058 | 0.769178448 | 0 | 18815 | 6086 | 0.767576868 | 0 |
| 18732 | 6003 | 0.772938596 | 0 | 18760 | 6031 | 0.771115104 | 0 | 18788 | 6059 | 0.769178448 | 0 | 18816 | 6087 | 0.767517664 | 0 |
| 18733 | 6004 | 0.772938596 | 0 | 18761 | 6032 | 0.770845607 | 0 | 18789 | 6060 | 0.769178448 | 0 | 18817 | 6088 | 0.767420168 | 0 |
| 18734 | 6005 | 0.772938596 | 0 | 18762 | 6033 | 0.770845607 | 0 | 18790 | 6061 | 0.769178448 | 0 | 18818 | 6089 | 0.767310511 | -1.493196885 |
| 18735 | 6006 | 0.772938596 | 0 | 18763 | 6034 | 0.770845607 | 0 | 18791 | 6062 | 0.769178448 | 0 | 18819 | 6090 | 0.767229479 | 0 |
| 18736 | 6007 | 0.772938596 | 0 | 18764 | 6035 | 0.770845607 | 0 | 18792 | 6063 | 0.769178448 | -1.366390212 | 18820 | 6091 | 0.767117734 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18821 | 6092 | 0.766689647 | 0 | 18849 | 6120 | 0.765450575 | 0 | 18877 | 6148 | 0.764000509 | 0 | 18905 | 6176 | 0.762351672 | 0 |
| 18822 | 6093 | 0.766689647 | 0 | 18850 | 6121 | 0.765450575 | 0 | 18878 | 6149 | 0.764000509 | 0 | 18906 | 6177 | 0.762280528 | 0 |
| 18823 | 6094 | 0.766689647 | 0 | 18851 | 6122 | 0.765450575 | 0 | 18879 | 6150 | 0.763896747 | 0 | 18907 | 6178 | 0.762280528 | 0 |
| 18824 | 6095 | 0.766689647 | 0 | 18852 | 6123 | 0.765450575 | 0 | 18880 | 6151 | 0.763896747 | 0 | 18908 | 6179 | 0.762280528 | 0 |
| 18825 | 6096 | 0.766689647 | 0 | 18853 | 6124 | 0.765371605 | 0 | 18881 | 6152 | 0.763795217 | 0 | 18909 | 6180 | 0.762142019 | 0 |
| 18826 | 6097 | 0.766689647 | 0 | 18854 | 6125 | 0.765313118 | 0 | 18882 | 6153 | 0.76359857 | 0 | 18910 | 6181 | 0.762008329 | 0 |
| 18827 | 6098 | 0.766689647 | 0 | 18855 | 6126 | 0.765232282 | -1.42469404 | 18883 | 6154 | 0.76359857 | 0 | 18911 | 6182 | 0.762008329 | -1.358837074 |
| 18828 | 6099 | 0.766689647 | 0 | 18856 | 6127 | 0.764920624 | 0 | 18884 | 6155 | 0.76359857 | 0 | 18912 | 6183 | 0.761943212 | 0 |
| 18829 | 6100 | 0.766689647 | 0 | 18857 | 6128 | 0.764920624 | 0 | 18885 | 6156 | 0.76359857 | 0 | 18913 | 6184 | 0.761943212 | 0 |
| 18830 | 6101 | 0.766689647 | 0 | 18858 | 6129 | 0.764920624 | 0 | 18886 | 6157 | 0.76359857 | -0.358606128 | 18914 | 6185 | 0.761754429 | 0 |
| 18831 | 6102 | 0.766689647 | 0 | 18859 | 6130 | 0.764920624 | 0 | 18887 | 6158 | 0.763318651 | 0 | 18915 | 6186 | 0.761754429 | 0 |
| 18832 | 6103 | 0.766354414 | -1.460294715 | 18860 | 6131 | 0.764920624 | -0.261503566 | 18888 | 6159 | 0.763318651 | 0 | 18916 | 6187 | 0.761754429 | 0 |
| 18833 | 6104 | 0.76628956 | 0 | 18861 | 6132 | 0.764920624 | -1.215746075 | 18889 | 6160 | 0.763229115 | 0 | 18917 | 6188 | 0.761754429 | 0 |
| 18834 | 6105 | 0.76628956 | 0 | 18862 | 6133 | 0.764920624 | -1.340684812 | 18890 | 6161 | 0.763229115 | 0 | 18918 | 6189 | 0.761754429 | 0 |
| 18835 | 6106 | 0.76628956 | 0 | 18863 | 6134 | 0.764555518 | 0 | 18891 | 6162 | 0.763229115 | 0 | 18919 | 6190 | 0.761754429 | 0 |
| 18836 | 6107 | 0.766193594 | 0 | 18864 | 6135 | 0.764555518 | 0 | 18892 | 6163 | 0.763055363 | 0 | 18920 | 6191 | 0.761754429 | -0.176533672 |
| 18837 | 6108 | 0.766193594 | 0 | 18865 | 6136 | 0.764555518 | 0 | 18893 | 6164 | 0.763055363 | 0 | 18921 | 6192 | 0.761754429 | -0.498752967 |
| 18838 | 6109 | 0.766193594 | 0 | 18866 | 6137 | 0.764439412 | 0 | 18894 | 6165 | 0.762888358 | 0 | 18922 | 6193 | 0.761754429 | -0.720601716 |
| 18839 | 6110 | 0.766193594 | -0.33595131 | 18867 | 6138 | 0.764439412 | 0 | 18895 | 6166 | 0.762573081 | 0 | 18923 | 6194 | 0.761517045 | 0 |
| 18840 | 6111 | 0.766037063 | 0 | 18868 | 6139 | 0.764348431 | 0 | 18896 | 6167 | 0.762573081 | 0 | 18924 | 6195 | 0.761517045 | 0 |
| 18841 | 6112 | 0.766037063 | 0 | 18869 | 6140 | 0.764348431 | 0 | 18897 | 6168 | 0.762573081 | 0 | 18925 | 6196 | 0.761404051 | 0 |
| 18842 | 6113 | 0.765914813 | 0 | 18870 | 6141 | 0.764348431 | 0 | 18898 | 6169 | 0.762573081 | 0 | 18926 | 6197 | 0.761404051 | 0 |
| 18843 | 6114 | 0.765914813 | 0 | 18871 | 6142 | 0.764348431 | 0 | 18899 | 6170 | 0.762573081 | 0 | 18927 | 6198 | 0.761294615 | 0 |
| 18844 | 6115 | 0.765736201 | 0 | 18872 | 6143 | 0.764348431 | 0 | 18900 | 6171 | 0.762573081 | 0 | 18928 | 6199 | 0.761294615 | 0 |
| 18845 | 6116 | 0.765736201 | 0 | 18873 | 6144 | 0.764215028 | 0 | 18901 | 6172 | 0.762573081 | -1.151146829 | 18929 | 6200 | 0.761294615 | 0 |
| 18846 | 6117 | 0.765736201 | 0 | 18874 | 6145 | 0.764215028 | 0 | 18902 | 6173 | 0.762573081 | -1.327238088 | 18930 | 6201 | 0.761294615 | 0 |
| 18847 | 6118 | 0.765736201 | -1.006654556 | 18875 | 6146 | 0.764215028 | -1.371353631 | 18903 | 6174 | 0.76242412 | 0 | 18931 | 6202 | 0.76108577 | 0 |
| 18848 | 6119 | 0.765611993 | 0 | 18876 | 6147 | 0.764085175 | 0 | 18904 | 6175 | 0.762351672 | 0 | 18932 | 6203 | 0.76108577 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 18933 | 6204 | 0.76108577 | 0 | 18961 | 6232 | 0.759307694 | 0 | 18989 | 6260 | 0.757684161 | 0 | 19017 | 6288 | 0.756654155 | -1.42030719 |
| 18934 | 6205 | 0.760937318 | 0 | 18962 | 6233 | 0.759307694 | 0 | 18990 | 6261 | 0.75761371 | 0 | 19018 | 6289 | 0.75658932 | 0 |
| 18935 | 6206 | 0.760937318 | 0 | 18963 | 6234 | 0.759150312 | 0 | 18991 | 6262 | 0.75761371 | 0 | 19019 | 6290 | 0.756528199 | 0 |
| 18936 | 6207 | 0.760795369 | 0 | 18964 | 6235 | 0.759002818 | 0 | 18992 | 6263 | 0.75761371 | 0 | 19020 | 6291 | 0.756470482 | 0 |
| 18937 | 6208 | 0.760795369 | 0 | 18965 | 6236 | 0.759002818 | -1.103564569 | 18993 | 6264 | 0.757360181 | 0 | 19021 | 6292 | 0.756470482 | -1.458279424 |
| 18938 | 6209 | 0.760795369 | 0 | 18966 | 6237 | 0.75886431 | 0 | 18994 | 6265 | 0.757360181 | 0 | 19022 | 6293 | 0.756415892 | 0 |
| 18939 | 6210 | 0.760795369 | 0 | 18967 | 6238 | 0.758733989 | 0 | 18995 | 6266 | 0.757360181 | 0 | 19023 | 6294 | 0.756415892 | 0 |
| 18940 | 6211 | 0.760795369 | 0 | 18968 | 6239 | 0.758733989 | 0 | 18996 | 6267 | 0.757360181 | 0 | 19024 | 6295 | 0.756364181 | 0 |
| 18941 | 6212 | 0.760529338 | 0 | 18969 | 6240 | 0.758733989 | 0 | 18997 | 6268 | 0.757360181 | 0 | 19025 | 6296 | 0.756141773 | 0 |
| 18942 | 6213 | 0.760529338 | 0 | 18970 | 6241 | 0.758733989 | 0 | 18998 | 6269 | 0.757360181 | 0 | 19026 | 6297 | 0.756141773 | 0 |
| 18943 | 6214 | 0.760529338 | 0 | 18971 | 6242 | 0.758733989 | 0 | 18999 | 6270 | 0.757360181 | -1.299027232 | 19027 | 6298 | 0.756031579 | 0 |
| 18944 | 6215 | 0.760529338 | 0 | 18972 | 6243 | 0.758733989 | 0 | 19000 | 6271 | 0.757248091 | 0 | 19028 | 6299 | 0.755965782 | 0 |
| 18945 | 6216 | 0.760284734 | 0 | 18973 | 6244 | 0.758495169 | 0 | 19001 | 6272 | 0.757144329 | 0 | 19029 | 6300 | 0.755965782 | 0 |
| 18946 | 6217 | 0.760284734 | 0 | 18974 | 6245 | 0.758495169 | 0 | 19002 | 6273 | 0.757144329 | 0 | 19030 | 6301 | 0.754455191 | 0 |
| 18947 | 6218 | 0.760284734 | 0 | 18975 | 6246 | 0.758281599 | 0 | 19003 | 6274 | 0.757144329 | 0 | 19031 | 6302 | 0.754455191 | 0 |
| 18948 | 6219 | 0.760059068 | 0 | 18976 | 6247 | 0.758281599 | 0 | 19004 | 6275 | 0.757144329 | 0 | 19032 | 6303 | 0.754455191 | 0 |
| 18949 | 6220 | 0.760059068 | -0.887392952 | 18977 | 6248 | 0.758281599 | 0 | 19005 | 6276 | 0.757048001 | 0 | 19033 | 6304 | 0.754455191 | 0 |
| 18950 | 6221 | 0.760059068 | -1.012331689 | 18978 | 6249 | 0.758281599 | -1.479949403 | 19006 | 6277 | 0.757048001 | 0 | 19034 | 6305 | 0.754455191 | 0 |
| 18951 | 6222 | 0.759918086 | 0 | 18979 | 6250 | 0.758089475 | 0 | 19007 | 6278 | 0.756958336 | 0 | 19035 | 6306 | 0.754455191 | 0 |
| 18952 | 6223 | 0.759918086 | 0 | 18980 | 6251 | 0.758089475 | 0 | 19008 | 6279 | 0.756958336 | 0 | 19036 | 6307 | 0.754455191 | 0 |
| 18953 | 6224 | 0.759918086 | 0 | 18981 | 6252 | 0.758089475 | 0 | 19009 | 6280 | 0.756874665 | 0 | 19037 | 6308 | 0.754455191 | 0 |
| 18954 | 6225 | 0.759850223 | 0 | 18982 | 6253 | 0.758000472 | 0 | 19010 | 6281 | 0.756874665 | -0.533595955 | 19038 | 6309 | 0.754455191 | 0 |
| 18955 | 6226 | 0.759784024 | 0 | 18983 | 6254 | 0.757915723 | 0 | 19011 | 6282 | 0.756796407 | 0 | 19039 | 6310 | 0.754455191 | 0 |
| 18956 | 6227 | 0.759656384 | 0 | 18984 | 6255 | 0.757915723 | 0 | 19012 | 6283 | 0.756796407 | 0 | 19040 | 6311 | 0.754455191 | 0 |
| 18957 | 6228 | 0.759656384 | 0 | 18985 | 6256 | 0.757915723 | 0 | 19013 | 6284 | 0.756796407 | 0 | 19041 | 6312 | 0.754455191 | 0 |
| 18958 | 6229 | 0.759475992 | 0 | 18986 | 6257 | 0.757915723 | 0 | 19014 | 6285 | 0.756723052 | 0 | 19042 | 6313 | 0.754455191 | 0 |
| 18959 | 6230 | 0.759475992 | 0 | 18987 | 6258 | 0.757834931 | 0 | 19015 | 6286 | 0.756723052 | -1.406874331 | 19043 | 6314 | 0.754455191 | 0 |
| 18960 | 6231 | 0.759307694 | 0 | 18988 | 6259 | 0.757757826 | 0 | 19016 | 6287 | 0.756654155 | 0 | 19044 | 6315 | 0.754455191 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19045 | 6316 | 0.754455191 | 0 | 19073 | 6344 | 0.754455191 | 0 | 19101 | 6372 | 0.752449208 | 0 | 19129 | 6400 | 0.751449681 | 0 |
| 19046 | 6317 | 0.754455191 | 0 | 19074 | 6345 | 0.754455191 | 0 | 19102 | 6373 | 0.75239203 | -1.450123419 | 19130 | 6401 | 0.751449681 | 0 |
| 19047 | 6318 | 0.754455191 | 0 | 19075 | 6346 | 0.754455191 | 0 | 19103 | 6374 | 0.752267305 | 0 | 19131 | 6402 | 0.751449681 | 0 |
| 19048 | 6319 | 0.754455191 | 0 | 19076 | 6347 | 0.754455191 | 0 | 19104 | 6375 | 0.752267305 | 0 | 19132 | 6403 | 0.751449681 | 0 |
| 19049 | 6320 | 0.754455191 | 0 | 19077 | 6348 | 0.754455191 | 0 | 19105 | 6376 | 0.75219911 | 0 | 19133 | 6404 | 0.751449681 | -1.287208966 |
| 19050 | 6321 | 0.754455191 | 0 | 19078 | 6349 | 0.754455191 | 0 | 19106 | 6377 | 0.75219911 | 0 | 19134 | 6405 | 0.751319477 | 0 |
| 19051 | 6322 | 0.754455191 | 0 | 19079 | 6350 | 0.754455191 | 0 | 19107 | 6378 | 0.75219911 | 0 | 19135 | 6406 | 0.751319477 | 0 |
| 19052 | 6323 | 0.754455191 | 0 | 19080 | 6351 | 0.754455191 | 0 | 19108 | 6379 | 0.75219911 | 0 | 19136 | 6407 | 0.751319477 | 0 |
| 19053 | 6324 | 0.754455191 | 0 | 19081 | 6352 | 0.754455191 | 0 | 19109 | 6380 | 0.752126528 | 0 | 19137 | 6408 | 0.751319477 | 0 |
| 19054 | 6325 | 0.754455191 | 0 | 19082 | 6353 | 0.754455191 | 0 | 19110 | 6381 | 0.752126528 | 0 | 19138 | 6409 | 0.751319477 | 0 |
| 19055 | 6326 | 0.754455191 | 0 | 19083 | 6354 | 0.754455191 | -1.381113469 | 19111 | 6382 | 0.752049121 | 0 | 19139 | 6410 | 0.751250051 | 0 |
| 19056 | 6327 | 0.754455191 | 0 | 19084 | 6355 | 0.754455191 | 0 | 19112 | 6383 | 0.752049121 | 0 | 19140 | 6411 | 0.751177481 | 0 |
| 19057 | 6328 | 0.754455191 | 0 | 19085 | 6356 | 0.754455191 | 0 | 19113 | 6384 | 0.752049121 | 0 | 19141 | 6412 | 0.751177481 | 0 |
| 19058 | 6329 | 0.754455191 | 0 | 19086 | 6357 | 0.754455191 | 0 | 19114 | 6385 | 0.75196639 | 0 | 19142 | 6413 | 0.751022015 | 0 |
| 19059 | 6330 | 0.754455191 | 0 | 19087 | 6358 | 0.754455191 | 0 | 19115 | 6386 | 0.75196639 | 0 | 19143 | 6414 | 0.751022015 | 0 |
| 19060 | 6331 | 0.754455191 | 0 | 19088 | 6359 | 0.754455191 | 0 | 19116 | 6387 | 0.751877768 | 0 | 19144 | 6415 | 0.750851066 | 0 |
| 19061 | 6332 | 0.754455191 | 0 | 19089 | 6360 | 0.754455191 | 0 | 19117 | 6388 | 0.751877768 | 0 | 19145 | 6416 | 0.750662202 | 0 |
| 19062 | 6333 | 0.754455191 | 0 | 19090 | 6361 | 0.754455191 | 0 | 19118 | 6389 | 0.751782601 | 0 | 19146 | 6417 | 0.750662202 | 0 |
| 19063 | 6334 | 0.754455191 | 0 | 19091 | 6362 | 0.754455191 | 0 | 19119 | 6390 | 0.751782601 | 0 | 19147 | 6418 | 0.750662202 | 0 |
| 19064 | 6335 | 0.754455191 | 0 | 19092 | 6363 | 0.754455191 | 0 | 19120 | 6391 | 0.751782601 | 0 | 19148 | 6419 | 0.750662202 | 0 |
| 19065 | 6336 | 0.754455191 | 0 | 19093 | 6364 | 0.754455191 | 0 | 19121 | 6392 | 0.751782601 | -0.860907313 | 19149 | 6420 | 0.750338625 | -0.02081306 |
| 19066 | 6337 | 0.754455191 | 0 | 19094 | 6365 | 0.754455191 | -1.159264719 | 19122 | 6393 | 0.751680137 | 0 | 19150 | 6421 | 0.750218138 | 0 |
| 19067 | 6338 | 0.754455191 | 0 | 19095 | 6366 | 0.75273521 | 0 | 19123 | 6394 | 0.751680137 | 0 | 19151 | 6422 | 0.750218138 | 0 |
| 19068 | 6339 | 0.754455191 | 0 | 19096 | 6367 | 0.752693345 | 0 | 19124 | 6395 | 0.751569503 | 0 | 19152 | 6423 | 0.750090385 | 0 |
| 19069 | 6340 | 0.754455191 | 0 | 19097 | 6368 | 0.75264939 | 0 | 19125 | 6396 | 0.751569503 | 0 | 19153 | 6424 | 0.750090385 | 0 |
| 19070 | 6341 | 0.754455191 | 0 | 19098 | 6369 | 0.752603186 | 0 | 19126 | 6397 | 0.751569503 | 0 | 19154 | 6425 | 0.74995469 | 0 |
| 19071 | 6342 | 0.754455191 | 0 | 19099 | 6370 | 0.752554555 | 0 | 19127 | 6398 | 0.751569503 | 0 | 19155 | 6426 | 0.74995469 | 0 |
| 19072 | 6343 | 0.754455191 | 0 | 19100 | 6371 | 0.752449208 | 0 | 19128 | 6399 | 0.751449681 | 0 | 19156 | 6427 | 0.74995469 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19157 | 6428 | 0.749656308 | 0 | 19185 | 6456 | 0.747924324 | 0 | 19213 | 6484 | 0.746486261 | 0 | 19241 | 6512 | 0.745115164 | 0 |
| 19158 | 6429 | 0.749656308 | 0 | 19186 | 6457 | 0.747924324 | 0 | 19214 | 6485 | 0.746486261 | 0 | 19242 | 6513 | 0.745115164 | 0 |
| 19159 | 6430 | 0.749656308 | 0 | 19187 | 6458 | 0.747924324 | 0 | 19215 | 6486 | 0.746486261 | 0 | 19243 | 6514 | 0.744909873 | 0 |
| 19160 | 6431 | 0.749491771 | 0 | 19188 | 6459 | 0.747924324 | 0 | 19216 | 6487 | 0.746486261 | 0 | 19244 | 6515 | 0.744909873 | 0 |
| 19161 | 6432 | 0.749491771 | 0 | 19189 | 6460 | 0.747924324 | 0 | 19217 | 6488 | 0.746486261 | 0 | 19245 | 6516 | 0.744909873 | 0 |
| 19162 | 6433 | 0.749315551 | 0 | 19190 | 6461 | 0.747721808 | 0 | 19218 | 6489 | 0.746486261 | 0 | 19246 | 6517 | 0.744909873 | 0 |
| 19163 | 6434 | 0.749315551 | 0 | 19191 | 6462 | 0.747615766 | 0 | 19219 | 6490 | 0.746486261 | 0 | 19247 | 6518 | 0.744909873 | 0 |
| 19164 | 6435 | 0.749315551 | 0 | 19192 | 6463 | 0.747615766 | 0 | 19220 | 6491 | 0.746486261 | 0 | 19248 | 6519 | 0.744782308 | 0 |
| 19165 | 6436 | 0.749315551 | 0 | 19193 | 6464 | 0.747615766 | 0 | 19221 | 6492 | 0.746486261 | 0 | 19249 | 6520 | 0.744695353 | 0 |
| 19166 | 6437 | 0.749126357 | 0 | 19194 | 6465 | 0.747615766 | 0 | 19222 | 6493 | 0.746486261 | 0 | 19250 | 6521 | 0.744695353 | 0 |
| 19167 | 6438 | 0.748922702 | 0 | 19195 | 6466 | 0.747615766 | 0 | 19223 | 6494 | 0.746486261 | 0 | 19251 | 6522 | 0.744695353 | 0 |
| 19168 | 6439 | 0.748922702 | 0 | 19196 | 6467 | 0.747615766 | 0 | 19224 | 6495 | 0.746260712 | 0 | 19252 | 6523 | 0.744695353 | 0 |
| 19169 | 6440 | 0.748922702 | 0 | 19197 | 6468 | 0.747450289 | 0 | 19225 | 6496 | 0.746260712 | 0 | 19253 | 6524 | 0.744584437 | 0 |
| 19170 | 6441 | 0.748814923 | 0 | 19198 | 6469 | 0.747450289 | 0 | 19226 | 6497 | 0.746182665 | 0 | 19254 | 6525 | 0.744516668 | 0 |
| 19171 | 6442 | 0.748778058 | 0 | 19199 | 6470 | 0.747276606 | 0 | 19227 | 6498 | 0.746182665 | 0 | 19255 | 6526 | 0.744516668 | 0 |
| 19172 | 6443 | 0.748702862 | -0.052412047 | 19200 | 6471 | 0.747276606 | 0 | 19228 | 6499 | 0.746022023 | 0 | 19256 | 6527 | 0.744516668 | 0 |
| 19173 | 6444 | 0.748464827 | 0 | 19201 | 6472 | 0.747276606 | 0 | 19229 | 6500 | 0.746022023 | 0 | 19257 | 6528 | 0.744516668 | 0 |
| 19174 | 6445 | 0.748464827 | 0 | 19202 | 6473 | 0.747276606 | 0 | 19230 | 6501 | 0.746022023 | 0 | 19258 | 6529 | 0.74447097 | 0 |
| 19175 | 6446 | 0.748464827 | 0 | 19203 | 6474 | 0.747276606 | 0 | 19231 | 6502 | 0.745855019 | 0 | 19259 | 6530 | 0.744236026 | 0 |
| 19176 | 6447 | 0.748464827 | 0 | 19204 | 6475 | 0.747094091 | 0 | 19232 | 6503 | 0.745855019 | 0 | 19260 | 6531 | 0.744236026 | 0 |
| 19177 | 6448 | 0.748464827 | -0.290193819 | 19205 | 6476 | 0.747031173 | 0 | 19233 | 6504 | 0.745855019 | -1.310532394 | 19261 | 6532 | 0.744236026 | 0 |
| 19178 | 6449 | 0.748294882 | 0 | 19206 | 6477 | 0.747031173 | 0 | 19234 | 6505 | 0.745716576 | 0 | 19262 | 6533 | 0.744236026 | 0 |
| 19179 | 6450 | 0.748294882 | 0 | 19207 | 6478 | 0.747031173 | 0 | 19235 | 6506 | 0.745716576 | 0 | 19263 | 6534 | 0.744236026 | 0 |
| 19180 | 6451 | 0.748206241 | 0 | 19208 | 6479 | 0.746902053 | -1.190298953 | 19236 | 6507 | 0.745681266 | 0 | 19264 | 6535 | 0.744236026 | 0 |
| 19181 | 6452 | 0.748206241 | 0 | 19209 | 6480 | 0.746822402 | 0 | 19237 | 6508 | 0.74565587 | 0 | 19265 | 6536 | 0.744236026 | 0 |
| 19182 | 6453 | 0.748206241 | 0 | 19210 | 6481 | 0.746768362 | 0 | 19238 | 6509 | 0.745500348 | 0 | 19266 | 6537 | 0.744236026 | 0 |
| 19183 | 6454 | 0.748206241 | 0 | 19211 | 6482 | 0.746768362 | -1.358837074 | 19239 | 6510 | 0.745500348 | 0 | 19267 | 6538 | 0.743939072 | 0 |
| 19184 | 6455 | 0.748115013 | 0 | 19212 | 6483 | 0.746486261 | 0 | 19240 | 6511 | 0.745500348 | -0.515007048 | 19268 | 6539 | 0.743624343 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19269 | 6540 | 0.743624343 | 0 | 19297 | 6568 | 0.742045933 | 0 | 19325 | 6596 | 0.740753913 | 0 | 19353 | 6624 | 0.739802903 | 0 |
| 19270 | 6541 | 0.743459806 | 0 | 19298 | 6569 | 0.742045933 | 0 | 19326 | 6597 | 0.740753913 | 0 | 19354 | 6625 | 0.739802903 | 0 |
| 19271 | 6542 | 0.743459806 | 0 | 19299 | 6570 | 0.742045933 | 0 | 19327 | 6598 | 0.740753913 | 0 | 19355 | 6626 | 0.739802903 | 0 |
| 19272 | 6543 | 0.743459806 | 0 | 19300 | 6571 | 0.742045933 | -1.278129308 | 19328 | 6599 | 0.740753913 | -1.031636844 | 19356 | 6627 | 0.739802903 | 0 |
| 19273 | 6544 | 0.743459806 | 0 | 19301 | 6572 | 0.741866063 | 0 | 19329 | 6600 | 0.740753913 | -1.33266684 | 19357 | 6628 | 0.739731934 | 0 |
| 19274 | 6545 | 0.743366219 | 0 | 19302 | 6573 | 0.741866063 | 0 | 19330 | 6601 | 0.740666906 | 0 | 19358 | 6629 | 0.739731934 | -1.381113469 |
| 19275 | 6546 | 0.743290193 | 0 | 19303 | 6574 | 0.741866063 | 0 | 19331 | 6602 | 0.740666906 | 0 | 19359 | 6630 | 0.739631414 | 0 |
| 19276 | 6547 | 0.743290193 | 0 | 19304 | 6575 | 0.741866063 | -0.669909008 | 19332 | 6603 | 0.740666906 | -0.086922898 | 19360 | 6631 | 0.739631414 | 0 |
| 19277 | 6548 | 0.74317418 | 0 | 19305 | 6576 | 0.741718369 | 0 | 19333 | 6604 | 0.740604079 | 0 | 19361 | 6632 | 0.739631414 | 0 |
| 19278 | 6549 | 0.74317418 | 0 | 19306 | 6577 | 0.741718369 | 0 | 19334 | 6605 | 0.740604079 | 0 | 19362 | 6633 | 0.739631414 | -0.18508388 |
| 19279 | 6550 | 0.74317418 | 0 | 19307 | 6578 | 0.741718369 | 0 | 19335 | 6606 | 0.740519413 | 0 | 19363 | 6634 | 0.739478035 | 0 |
| 19280 | 6551 | 0.743089827 | 0 | 19308 | 6579 | 0.741490214 | 0 | 19336 | 6607 | 0.740214752 | 0 | 19364 | 6635 | 0.739478035 | 0 |
| 19281 | 6552 | 0.743025729 | 0 | 19309 | 6580 | 0.741490214 | 0 | 19337 | 6608 | 0.740214752 | 0 | 19365 | 6636 | 0.739478035 | 0 |
| 19282 | 6553 | 0.743025729 | 0 | 19310 | 6581 | 0.741490214 | 0 | 19338 | 6609 | 0.740214752 | 0 | 19366 | 6637 | 0.73936652 | 0 |
| 19283 | 6554 | 0.743025729 | -1.012331689 | 19311 | 6582 | 0.741490214 | 0 | 19339 | 6610 | 0.740214752 | 0 | 19367 | 6638 | 0.739215224 | 0 |
| 19284 | 6555 | 0.742873318 | 0 | 19312 | 6583 | 0.741490214 | 0 | 19340 | 6611 | 0.740214752 | 0 | 19368 | 6639 | 0.739215224 | 0 |
| 19285 | 6556 | 0.742829023 | 0 | 19313 | 6584 | 0.741490214 | 0 | 19341 | 6612 | 0.740214752 | 0 | 19369 | 6640 | 0.739215224 | 0 |
| 19286 | 6557 | 0.742795578 | 0 | 19314 | 6585 | 0.741253734 | 0 | 19342 | 6613 | 0.740214752 | 0 | 19370 | 6641 | 0.739215224 | 0 |
| 19287 | 6558 | 0.742795578 | 0 | 19315 | 6586 | 0.741253734 | 0 | 19343 | 6614 | 0.740214752 | 0 | 19371 | 6642 | 0.739080329 | 0 |
| 19288 | 6559 | 0.742555967 | 0 | 19316 | 6587 | 0.741253734 | 0 | 19344 | 6615 | 0.740214752 | 0 | 19372 | 6643 | 0.739080329 | 0 |
| 19289 | 6560 | 0.742555967 | 0 | 19317 | 6588 | 0.741253734 | -0.09328493 | 19345 | 6616 | 0.740214752 | 0 | 19373 | 6644 | 0.73899824 | 0 |
| 19290 | 6561 | 0.742555967 | 0 | 19318 | 6589 | 0.741253734 | -0.64958743 | 19346 | 6617 | 0.740214752 | 0 | 19374 | 6645 | 0.738850117 | 0 |
| 19291 | 6562 | 0.742555967 | 0 | 19319 | 6590 | 0.741091229 | 0 | 19347 | 6618 | 0.740214752 | 0 | 19375 | 6646 | 0.738660924 | 0 |
| 19292 | 6563 | 0.742555967 | 0 | 19320 | 6591 | 0.741091229 | 0 | 19348 | 6619 | 0.740214752 | 0 | 19376 | 6647 | 0.738660924 | 0 |
| 19293 | 6564 | 0.742555967 | 0 | 19321 | 6592 | 0.740882384 | 0 | 19349 | 6620 | 0.740214752 | -0.08572374 | 19377 | 6648 | 0.738660924 | 0 |
| 19294 | 6565 | 0.742555967 | 0 | 19322 | 6593 | 0.740882384 | 0 | 19350 | 6621 | 0.740214752 | -1.219262649 | 19378 | 6649 | 0.738660924 | 0 |
| 19295 | 6566 | 0.742555967 | 0 | 19323 | 6594 | 0.740882384 | 0 | 19351 | 6622 | 0.739928938 | 0 | 19379 | 6650 | 0.738660924 | 0 |
| 19296 | 6567 | 0.742151408 | -0.533595955 | 19324 | 6595 | 0.740882384 | -1.239784316 | 19352 | 6623 | 0.739855682 | -1.208626334 | 19380 | 6651 | 0.738660924 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19381 | 6652 | 0.738410826 | 0 | 19409 | 6680 | 0.736726424 | 0 | 19437 | 6708 | 0.735392185 | -1.338028568 | 19465 | 6736 | 0.733671585 | 0 |
| 19382 | 6653 | 0.738308555 | 0 | 19410 | 6681 | 0.736726424 | 0 | 19438 | 6709 | 0.73532018 | 0 | 19466 | 6737 | 0.733671585 | 0 |
| 19383 | 6654 | 0.738308555 | 0 | 19411 | 6682 | 0.736726424 | 0 | 19439 | 6710 | 0.735150036 | 0 | 19467 | 6738 | 0.733671585 | 0 |
| 19384 | 6655 | 0.738308555 | 0 | 19412 | 6683 | 0.736726424 | 0 | 19440 | 6711 | 0.735150036 | 0 | 19468 | 6739 | 0.733521284 | 0 |
| 19385 | 6656 | 0.738308555 | 0 | 19413 | 6684 | 0.736726424 | 0 | 19441 | 6712 | 0.735150036 | 0 | 19469 | 6740 | 0.733521284 | 0 |
| 19386 | 6657 | 0.738308555 | 0 | 19414 | 6685 | 0.736726424 | 0 | 19442 | 6713 | 0.734992711 | 0 | 19470 | 6741 | 0.733265892 | 0 |
| 19387 | 6658 | 0.738217992 | 0 | 19415 | 6686 | 0.736726424 | 0 | 19443 | 6714 | 0.734933051 | 0 | 19471 | 6742 | 0.733265892 | 0 |
| 19388 | 6659 | 0.738064775 | 0 | 19416 | 6687 | 0.736726424 | 0 | 19444 | 6715 | 0.734933051 | 0 | 19472 | 6743 | 0.733265892 | 0 |
| 19389 | 6660 | 0.738064775 | 0 | 19417 | 6688 | 0.736726424 | 0 | 19445 | 6716 | 0.734933051 | -0.084882356 | 19473 | 6744 | 0.733265892 | 0 |
| 19390 | 6661 | 0.738064775 | 0 | 19418 | 6689 | 0.736726424 | 0 | 19446 | 6717 | 0.734800503 | 0 | 19474 | 6745 | 0.733265892 | 0 |
| 19391 | 6662 | 0.738064775 | 0 | 19419 | 6690 | 0.736726424 | -0.280742924 | 19447 | 6718 | 0.734800503 | 0 | 19475 | 6746 | 0.733265892 | 0 |
| 19392 | 6663 | 0.738064775 | 0 | 19420 | 6691 | 0.736726424 | -1.125840964 | 19448 | 6719 | 0.734800503 | 0 | 19476 | 6747 | 0.733265892 | 0 |
| 19393 | 6664 | 0.738064775 | 0 | 19421 | 6692 | 0.736726424 | -1.368879012 | 19449 | 6720 | 0.734800503 | 0 | 19477 | 6748 | 0.733265892 | 0 |
| 19394 | 6665 | 0.737940103 | 0 | 19422 | 6693 | 0.736281222 | 0 | 19450 | 6721 | 0.734251805 | 0 | 19478 | 6749 | 0.733265892 | 0 |
| 19395 | 6666 | 0.737749497 | 0 | 19423 | 6694 | 0.735971785 | 0 | 19451 | 6722 | 0.734251805 | 0 | 19479 | 6750 | 0.733265892 | 0 |
| 19396 | 6667 | 0.737749497 | 0 | 19424 | 6695 | 0.735971785 | 0 | 19452 | 6723 | 0.734251805 | 0 | 19480 | 6751 | 0.733265892 | 0 |
| 19397 | 6668 | 0.737641692 | 0 | 19425 | 6696 | 0.735813081 | 0 | 19453 | 6724 | 0.734251805 | 0 | 19481 | 6752 | 0.733265892 | 0 |
| 19398 | 6669 | 0.737641692 | 0 | 19426 | 6697 | 0.735813081 | 0 | 19454 | 6725 | 0.734251805 | 0 | 19482 | 6753 | 0.733265892 | 0 |
| 19399 | 6670 | 0.73755444 | 0 | 19427 | 6698 | 0.735705755 | 0 | 19455 | 6726 | 0.734251805 | -0.593202381 | 19483 | 6754 | 0.733057046 | 0 |
| 19400 | 6671 | 0.737421851 | 0 | 19428 | 6699 | 0.735569847 | 0 | 19456 | 6727 | 0.734251805 | -1.468263644 | 19484 | 6755 | 0.733057046 | 0 |
| 19401 | 6672 | 0.737421851 | 0 | 19429 | 6700 | 0.735569847 | 0 | 19457 | 6728 | 0.733992137 | -1.504238865 | 19485 | 6756 | 0.733057046 | 0 |
| 19402 | 6673 | 0.737421851 | -0.063693057 | 19430 | 6701 | 0.735569847 | 0 | 19458 | 6729 | 0.733933524 | 0 | 19486 | 6757 | 0.733057046 | 0 |
| 19403 | 6674 | 0.737325864 | 0 | 19431 | 6702 | 0.735569847 | 0 | 19459 | 6730 | 0.733840736 | 0 | 19487 | 6758 | 0.732966275 | 0 |
| 19404 | 6675 | 0.737325864 | -1.383519539 | 19432 | 6703 | 0.735569847 | 0 | 19460 | 6731 | 0.733840736 | 0 | 19488 | 6759 | 0.732966275 | 0 |
| 19405 | 6676 | 0.737253161 | 0 | 19433 | 6704 | 0.735392185 | 0 | 19461 | 6732 | 0.733840736 | 0 | 19489 | 6760 | 0.732966275 | 0 |
| 19406 | 6677 | 0.737112635 | -0.671457297 | 19434 | 6705 | 0.735392185 | 0 | 19462 | 6733 | 0.733840736 | -1.003787915 | 19490 | 6761 | 0.732966275 | 0 |
| 19407 | 6678 | 0.737081095 | -0.465434354 | 19435 | 6706 | 0.735392185 | 0 | 19463 | 6734 | 0.733671585 | 0 | 19491 | 6762 | 0.732966275 | 0 |
| 19408 | 6679 | 0.736726424 | 0 | 19436 | 6707 | 0.735392185 | 0 | 19464 | 6735 | 0.733671585 | 0 | 19492 | 6763 | 0.732966275 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19493 | 6764 | 0.732883085 | 0 | 19521 | 6792 | 0.731712064 | 0 | 19549 | 6820 | 0.730095845 | 0 | 19577 | 6848 | 0.728901086 | 0 |
| 19494 | 6765 | 0.732883085 | -1.481866821 | 19522 | 6793 | 0.731712064 | -0.139343434 | 19550 | 6821 | 0.730095845 | 0 | 19578 | 6849 | 0.728901086 | 0 |
| 19495 | 6766 | 0.732735941 | 0 | 19523 | 6794 | 0.731646898 | 0 | 19551 | 6822 | 0.730042132 | 0 | 19579 | 6850 | 0.728901086 | 0 |
| 19496 | 6767 | 0.732735941 | 0 | 19524 | 6795 | 0.731646898 | 0 | 19552 | 6823 | 0.729981421 | 0 | 19580 | 6851 | 0.728901086 | 0 |
| 19497 | 6768 | 0.732735941 | 0 | 19525 | 6796 | 0.731592308 | -1.495056821 | 19553 | 6824 | 0.72991225 | 0 | 19581 | 6852 | 0.728901086 | 0 |
| 19498 | 6769 | 0.732735941 | 0 | 19526 | 6797 | 0.730974095 | 0 | 19554 | 6825 | 0.729832716 | 0 | 19582 | 6853 | 0.728694329 | 0 |
| 19499 | 6770 | 0.732735941 | 0 | 19527 | 6798 | 0.730974095 | 0 | 19555 | 6826 | 0.729832716 | 0 | 19583 | 6854 | 0.728574672 | 0 |
| 19500 | 6771 | 0.732553349 | 0 | 19528 | 6799 | 0.730974095 | 0 | 19556 | 6827 | 0.729832716 | 0 | 19584 | 6855 | 0.728441758 | 0 |
| 19501 | 6772 | 0.73240505 | 0 | 19529 | 6800 | 0.730974095 | 0 | 19557 | 6828 | 0.729832716 | -0.150463439 | 19585 | 6856 | 0.728441758 | 0 |
| 19502 | 6773 | 0.73240505 | 0 | 19530 | 6801 | 0.730974095 | 0 | 19558 | 6829 | 0.729740303 | 0 | 19586 | 6857 | 0.728441758 | 0 |
| 19503 | 6774 | 0.73240505 | 0 | 19531 | 6802 | 0.730974095 | 0 | 19559 | 6830 | 0.729740303 | 0 | 19587 | 6858 | 0.728441758 | 0 |
| 19504 | 6775 | 0.73240505 | 0 | 19532 | 6803 | 0.730974095 | 0 | 19560 | 6831 | 0.729631607 | 0 | 19588 | 6859 | 0.728369622 | 0 |
| 19505 | 6776 | 0.73240505 | 0 | 19533 | 6804 | 0.730974095 | 0 | 19561 | 6832 | 0.729631607 | 0 | 19589 | 6860 | 0.728126252 | 0 |
| 19506 | 6777 | 0.732282212 | 0 | 19534 | 6805 | 0.730974095 | 0 | 19562 | 6833 | 0.729631607 | 0 | 19590 | 6861 | 0.728126252 | 0 |
| 19507 | 6778 | 0.732178796 | 0 | 19535 | 6806 | 0.730974095 | 0 | 19563 | 6834 | 0.729631607 | 0 | 19591 | 6862 | 0.728126252 | 0 |
| 19508 | 6779 | 0.732178796 | 0 | 19536 | 6807 | 0.730974095 | 0 | 19564 | 6835 | 0.729631607 | 0 | 19592 | 6863 | 0.728126252 | -1.435471131 |
| 19509 | 6780 | 0.732178796 | 0 | 19537 | 6808 | 0.730974095 | 0 | 19565 | 6836 | 0.729501909 | 0 | 19593 | 6864 | 0.727896162 | 0 |
| 19510 | 6781 | 0.732178796 | 0 | 19538 | 6809 | 0.730974095 | 0 | 19566 | 6837 | 0.729501909 | 0 | 19594 | 6865 | 0.727832711 | 0 |
| 19511 | 6782 | 0.732178796 | 0 | 19539 | 6810 | 0.730974095 | 0 | 19567 | 6838 | 0.72934447 | 0 | 19595 | 6866 | 0.727720937 | 0 |
| 19512 | 6783 | 0.732178796 | 0 | 19540 | 6811 | 0.730974095 | 0 | 19568 | 6839 | 0.72934447 | 0 | 19596 | 6867 | 0.727720937 | 0 |
| 19513 | 6784 | 0.732014322 | 0 | 19541 | 6812 | 0.730974095 | 0 | 19569 | 6840 | 0.72934447 | 0 | 19597 | 6868 | 0.727720937 | 0 |
| 19514 | 6785 | 0.732014322 | 0 | 19542 | 6813 | 0.730974095 | 0 | 19570 | 6841 | 0.72934447 | 0 | 19598 | 6869 | 0.727720937 | 0 |
| 19515 | 6786 | 0.731889363 | 0 | 19543 | 6814 | 0.730974095 | -1.44598725 | 19571 | 6842 | 0.729219367 | 0 | 19599 | 6870 | 0.727720937 | 0 |
| 19516 | 6787 | 0.731889363 | 0 | 19544 | 6815 | 0.730454914 | 0 | 19572 | 6843 | 0.729219367 | 0 | 19600 | 6871 | 0.727471701 | 0 |
| 19517 | 6788 | 0.731889363 | 0 | 19545 | 6816 | 0.730372995 | 0 | 19573 | 6844 | 0.729219367 | 0 | 19601 | 6872 | 0.727471701 | 0 |
| 19518 | 6789 | 0.731791206 | 0 | 19546 | 6817 | 0.730260382 | 0 | 19574 | 6845 | 0.729149325 | 0 | 19602 | 6873 | 0.727471701 | 0 |
| 19519 | 6790 | 0.731791206 | 0 | 19547 | 6818 | 0.730260382 | 0 | 19575 | 6846 | 0.729149325 | 0 | 19603 | 6874 | 0.727471701 | 0 |
| 19520 | 6791 | 0.731791206 | 0 | 19548 | 6819 | 0.730095845 | 0 | 19576 | 6847 | 0.729149325 | 0 | 19604 | 6875 | 0.727471701 | -1.044919056 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19605 | 6876 | 0.727302945 | 0 | 19633 | 6904 | 0.725731039 | 0 | 19661 | 6932 | 0.724170387 | 0 | 19689 | 6960 | 0.722740778 | 0 |
| 19606 | 6877 | 0.727302945 | 0 | 19634 | 6905 | 0.725628865 | 0 | 19662 | 6933 | 0.724072562 | 0 | 19690 | 6961 | 0.722740778 | 0 |
| 19607 | 6878 | 0.727181106 | 0 | 19635 | 6906 | 0.725628865 | 0 | 19663 | 6934 | 0.724072562 | 0 | 19691 | 6962 | 0.722566046 | 0 |
| 19608 | 6879 | 0.727181106 | 0 | 19636 | 6907 | 0.725628865 | 0 | 19664 | 6935 | 0.723997327 | 0 | 19692 | 6963 | 0.722270507 | 0 |
| 19609 | 6880 | 0.727181106 | 0 | 19637 | 6908 | 0.725491495 | 0 | 19665 | 6936 | 0.723889199 | 0 | 19693 | 6964 | 0.722270507 | 0 |
| 19610 | 6881 | 0.727181106 | 0 | 19638 | 6909 | 0.725296962 | 0 | 19666 | 6937 | 0.723889199 | 0 | 19694 | 6965 | 0.722270507 | 0 |
| 19611 | 6882 | 0.727181106 | 0 | 19639 | 6910 | 0.725296962 | 0 | 19667 | 6938 | 0.723889199 | 0 | 19695 | 6966 | 0.722270507 | 0 |
| 19612 | 6883 | 0.727181106 | -0.4875688 | 19640 | 6911 | 0.725296962 | 0 | 19668 | 6939 | 0.723889199 | 0 | 19696 | 6967 | 0.722085898 | 0 |
| 19613 | 6884 | 0.727016942 | 0 | 19641 | 6912 | 0.725296962 | 0 | 19669 | 6940 | 0.723889199 | 0 | 19697 | 6968 | 0.721925966 | 0 |
| 19614 | 6885 | 0.727016942 | 0 | 19642 | 6913 | 0.725296962 | 0 | 19670 | 6941 | 0.723720574 | 0 | 19698 | 6969 | 0.721925966 | 0 |
| 19615 | 6886 | 0.727016942 | -1.293158298 | 19643 | 6914 | 0.725115059 | 0 | 19671 | 6942 | 0.723720574 | 0 | 19699 | 6970 | 0.721925966 | 0 |
| 19616 | 6887 | 0.726911441 | 0 | 19644 | 6915 | 0.725115059 | 0 | 19672 | 6943 | 0.723641243 | 0 | 19700 | 6971 | 0.721786074 | 0 |
| 19617 | 6888 | 0.726911441 | 0 | 19645 | 6916 | 0.725115059 | 0 | 19673 | 6944 | 0.723420957 | 0 | 19701 | 6972 | 0.721662677 | 0 |
| 19618 | 6889 | 0.726911441 | -1.378693995 | 19646 | 6917 | 0.725000211 | 0 | 19674 | 6945 | 0.723420957 | 0 | 19702 | 6973 | 0.721662677 | 0 |
| 19619 | 6890 | 0.726837926 | 0 | 19647 | 6918 | 0.724863318 | 0 | 19675 | 6946 | 0.723420957 | 0 | 19703 | 6974 | 0.721662677 | -1.468263644 |
| 19620 | 6891 | 0.726837926 | 0 | 19648 | 6919 | 0.72478452 | 0 | 19676 | 6947 | 0.723420957 | 0 | 19704 | 6975 | 0.721454931 | 0 |
| 19621 | 6892 | 0.726426467 | 0 | 19649 | 6920 | 0.72478452 | 0 | 19677 | 6948 | 0.723420957 | 0 | 19705 | 6976 | 0.721454931 | 0 |
| 19622 | 6893 | 0.726426467 | 0 | 19650 | 6921 | 0.72478452 | 0 | 19678 | 6949 | 0.723420957 | 0 | 19706 | 6977 | 0.721366668 | 0 |
| 19623 | 6894 | 0.726426467 | 0 | 19651 | 6922 | 0.72478452 | 0 | 19679 | 6950 | 0.723420957 | -0.588238962 | 19707 | 6978 | 0.721286827 | 0 |
| 19624 | 6895 | 0.726426467 | 0 | 19652 | 6923 | 0.724491967 | 0 | 19680 | 6951 | 0.723162832 | 0 | 19708 | 6979 | 0.721148009 | 0 |
| 19625 | 6896 | 0.726426467 | 0 | 19653 | 6924 | 0.724491967 | 0 | 19681 | 6952 | 0.723046726 | 0 | 19709 | 6980 | 0.721031435 | 0 |
| 19626 | 6897 | 0.726426467 | -0.506052205 | 19654 | 6925 | 0.724491967 | 0 | 19682 | 6953 | 0.723046726 | -1.236430674 | 19710 | 6981 | 0.721031435 | 0 |
| 19627 | 6898 | 0.726426467 | -1.476088982 | 19655 | 6926 | 0.724491967 | 0 | 19683 | 6954 | 0.722938139 | 0 | 19711 | 6982 | 0.720932157 | 0 |
| 19628 | 6899 | 0.726103452 | 0 | 19656 | 6927 | 0.724491967 | 0 | 19684 | 6955 | 0.722886441 | -1.558810255 | 19712 | 6983 | 0.720932157 | 0 |
| 19629 | 6900 | 0.726059819 | 0 | 19657 | 6928 | 0.724491967 | 0 | 19685 | 6956 | 0.722740778 | 0 | 19713 | 6984 | 0.720932157 | 0 |
| 19630 | 6901 | 0.726002558 | -1.136564829 | 19658 | 6929 | 0.724231208 | 0 | 19686 | 6957 | 0.722740778 | 0 | 19714 | 6985 | 0.720932157 | 0 |
| 19631 | 6902 | 0.725810009 | 0 | 19659 | 6930 | 0.724170387 | 0 | 19687 | 6958 | 0.722740778 | 0 | 19715 | 6986 | 0.72084659 | 0 |
| 19632 | 6903 | 0.725810009 | -0.974030081 | 19660 | 6931 | 0.724170387 | 0 | 19688 | 6959 | 0.722740778 | 0 | 19716 | 6987 | 0.72084659 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19717 | 6988 | 0.72084659 | 0 | 19745 | 7016 | 0.719693084 | 0 | 19773 | 7044 | 0.717732384 | 0 | 19801 | 7072 | 0.716472097 | 0 |
| 19718 | 6989 | 0.720772078 | 0 | 19746 | 7017 | 0.719693084 | -0.93875432 | 19774 | 7045 | 0.717732384 | 0 | 19802 | 7073 | 0.716472097 | 0 |
| 19719 | 6990 | 0.720772078 | 0 | 19747 | 7018 | 0.719693084 | -1.169203242 | 19775 | 7046 | 0.717610133 | 0 | 19803 | 7074 | 0.716472097 | 0 |
| 19720 | 6991 | 0.720706608 | 0 | 19748 | 7019 | 0.718879036 | 0 | 19776 | 7047 | 0.717471624 | 0 | 19804 | 7075 | 0.716365141 | 0 |
| 19721 | 6992 | 0.719693084 | 0 | 19749 | 7020 | 0.718879036 | 0 | 19777 | 7048 | 0.717471624 | 0 | 19805 | 7076 | 0.716365141 | 0 |
| 19722 | 6993 | 0.719693084 | 0 | 19750 | 7021 | 0.718879036 | 0 | 19778 | 7049 | 0.717313383 | 0 | 19806 | 7077 | 0.716250838 | 0 |
| 19723 | 6994 | 0.719693084 | 0 | 19751 | 7022 | 0.718837332 | 0 | 19779 | 7050 | 0.717313383 | 0 | 19807 | 7078 | 0.716250838 | 0 |
| 19724 | 6995 | 0.719693084 | 0 | 19752 | 7023 | 0.718837332 | 0 | 19780 | 7051 | 0.717130868 | 0 | 19808 | 7079 | 0.716250838 | -1.404594565 |
| 19725 | 6996 | 0.719693084 | 0 | 19753 | 7024 | 0.718837332 | 0 | 19781 | 7052 | 0.717130868 | 0 | 19809 | 7080 | 0.716250838 | -1.404594565 |
| 19726 | 6997 | 0.719693084 | 0 | 19754 | 7025 | 0.718791123 | 0 | 19782 | 7053 | 0.717130868 | 0 | 19810 | 7081 | 0.716153583 | 0 |
| 19727 | 6998 | 0.719693084 | 0 | 19755 | 7026 | 0.718739638 | 0 | 19783 | 7054 | 0.717130868 | 0 | 19811 | 7082 | 0.715996939 | 0 |
| 19728 | 6999 | 0.719693084 | 0 | 19756 | 7027 | 0.718542635 | 0 | 19784 | 7055 | 0.717130868 | 0 | 19812 | 7083 | 0.715996939 | 0 |
| 19729 | 7000 | 0.719693084 | 0 | 19757 | 7028 | 0.718457537 | 0 | 19785 | 7056 | 0.717130868 | 0 | 19813 | 7084 | 0.715996939 | -0.674844226 |
| 19730 | 7001 | 0.719693084 | 0 | 19758 | 7029 | 0.718457537 | 0 | 19786 | 7057 | 0.716992799 | 0 | 19814 | 7085 | 0.715996939 | -1.37381423 |
| 19731 | 7002 | 0.719693084 | 0 | 19759 | 7030 | 0.718457537 | 0 | 19787 | 7058 | 0.716992799 | 0 | 19815 | 7086 | 0.715702602 | 0 |
| 19732 | 7003 | 0.719693084 | 0 | 19760 | 7031 | 0.718358845 | 0 | 19788 | 7059 | 0.71691803 | 0 | 19816 | 7087 | 0.715537125 | 0 |
| 19733 | 7004 | 0.719693084 | 0 | 19761 | 7032 | 0.718358845 | 0 | 19789 | 7060 | 0.71691803 | 0 | 19817 | 7088 | 0.715537125 | 0 |
| 19734 | 7005 | 0.719693084 | 0 | 19762 | 7033 | 0.718358845 | 0 | 19790 | 7061 | 0.71691803 | 0 | 19818 | 7089 | 0.715537125 | 0 |
| 19735 | 7006 | 0.719693084 | 0 | 19763 | 7034 | 0.718243018 | 0 | 19791 | 7062 | 0.71691803 | 0 | 19819 | 7090 | 0.715537125 | 0 |
| 19736 | 7007 | 0.719693084 | 0 | 19764 | 7035 | 0.718243018 | 0 | 19792 | 7063 | 0.71666663 | 0 | 19820 | 7091 | 0.715537125 | -1.147030263 |
| 19737 | 7008 | 0.719693084 | 0 | 19765 | 7036 | 0.718105169 | 0 | 19793 | 7064 | 0.71666663 | 0 | 19821 | 7092 | 0.715537125 | -1.147030263 |
| 19738 | 7009 | 0.719693084 | 0 | 19766 | 7037 | 0.718105169 | 0 | 19794 | 7065 | 0.71666663 | 0 | 19822 | 7093 | 0.71535733 | 0 |
| 19739 | 7010 | 0.719693084 | 0 | 19767 | 7038 | 0.718105169 | 0 | 19795 | 7066 | 0.71666663 | 0 | 19823 | 7094 | 0.71535733 | 0 |
| 19740 | 7011 | 0.719693084 | 0 | 19768 | 7039 | 0.718025925 | 0 | 19796 | 7067 | 0.71666663 | 0 | 19824 | 7095 | 0.71526147 | 0 |
| 19741 | 7012 | 0.719693084 | 0 | 19769 | 7040 | 0.71784108 | 0 | 19797 | 7068 | 0.71666663 | 0 | 19825 | 7096 | 0.71526147 | 0 |
| 19742 | 7013 | 0.719693084 | 0 | 19770 | 7041 | 0.71784108 | 0 | 19798 | 7069 | 0.716523038 | 0 | 19826 | 7097 | 0.71526147 | 0 |
| 19743 | 7014 | 0.719693084 | 0 | 19771 | 7042 | 0.717732384 | 0 | 19799 | 7070 | 0.716523038 | 0 | 19827 | 7098 | 0.71526147 | -1.42030719 |
| 19744 | 7015 | 0.719693084 | 0 | 19772 | 7043 | 0.717732384 | 0 | 19800 | 7071 | 0.716472097 | 0 | 19828 | 7099 | 0.715161275 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19829 | 7100 | 0.714946649 | 0 | 19857 | 7128 | 0.71366112 | 0 | 19885 | 7156 | 0.712051342 | 0 | 19913 | 7184 | 0.710676266 | 0 |
| 19830 | 7101 | 0.714946649 | 0 | 19858 | 7129 | 0.713550203 | 0 | 19886 | 7157 | 0.712051342 | -0.423517317 | 19914 | 7185 | 0.710676266 | 0 |
| 19831 | 7102 | 0.714946649 | 0 | 19859 | 7130 | 0.713550203 | 0 | 19887 | 7158 | 0.712051342 | -1.361369411 | 19915 | 7186 | 0.710676266 | 0 |
| 19832 | 7103 | 0.714946649 | 0 | 19860 | 7131 | 0.713473964 | 0 | 19888 | 7159 | 0.71190284 | 0 | 19916 | 7187 | 0.710438362 | 0 |
| 19833 | 7104 | 0.714946649 | 0 | 19861 | 7132 | 0.713418339 | 0 | 19889 | 7160 | 0.71190284 | 0 | 19917 | 7188 | 0.710438362 | 0 |
| 19834 | 7105 | 0.714946649 | 0 | 19862 | 7133 | 0.713418339 | 0 | 19890 | 7161 | 0.711810936 | 0 | 19918 | 7189 | 0.710438362 | 0 |
| 19835 | 7106 | 0.714946649 | 0 | 19863 | 7134 | 0.713062506 | 0 | 19891 | 7162 | 0.711810936 | 0 | 19919 | 7190 | 0.710251528 | 0 |
| 19836 | 7107 | 0.714946649 | -0.964690054 | 19864 | 7135 | 0.713062506 | 0 | 19892 | 7163 | 0.711810936 | 0 | 19920 | 7191 | 0.710251528 | 0 |
| 19837 | 7108 | 0.71474582 | -1.615799443 | 19865 | 7136 | 0.713062506 | 0 | 19893 | 7164 | 0.711810936 | 0 | 19921 | 7192 | 0.710251528 | 0 |
| 19838 | 7109 | 0.714660647 | 0 | 19866 | 7137 | 0.713062506 | 0 | 19894 | 7165 | 0.711420559 | 0 | 19922 | 7193 | 0.710251528 | 0 |
| 19839 | 7110 | 0.714660647 | 0 | 19867 | 7138 | 0.713062506 | 0 | 19895 | 7166 | 0.711420559 | 0 | 19923 | 7194 | 0.710100915 | 0 |
| 19840 | 7111 | 0.714583679 | 0 | 19868 | 7139 | 0.713062506 | 0 | 19896 | 7167 | 0.711420559 | 0 | 19924 | 7195 | 0.710100915 | 0 |
| 19841 | 7112 | 0.714450029 | 0 | 19869 | 7140 | 0.713062506 | 0 | 19897 | 7168 | 0.711420559 | -1.248056842 | 19925 | 7196 | 0.709976919 | 0 |
| 19842 | 7113 | 0.714288461 | 0 | 19870 | 7141 | 0.712663887 | 0 | 19898 | 7169 | 0.711186501 | 0 | 19926 | 7197 | 0.709976919 | 0 |
| 19843 | 7114 | 0.714160596 | 0 | 19871 | 7142 | 0.712663887 | 0 | 19899 | 7170 | 0.711186501 | 0 | 19927 | 7198 | 0.709976919 | 0 |
| 19844 | 7115 | 0.714160596 | 0 | 19872 | 7143 | 0.712592744 | 0 | 19900 | 7171 | 0.711186501 | 0 | 19928 | 7199 | 0.709976919 | 0 |
| 19845 | 7116 | 0.714160596 | 0 | 19873 | 7144 | 0.712592744 | 0 | 19901 | 7172 | 0.711186501 | 0 | 19929 | 7200 | 0.709976919 | 0 |
| 19846 | 7117 | 0.714026534 | 0 | 19874 | 7145 | 0.712592744 | 0 | 19902 | 7173 | 0.711117174 | 0 | 19930 | 7201 | 0.709976919 | 0 |
| 19847 | 7118 | 0.713921644 | -0.908313588 | 19875 | 7146 | 0.712592744 | 0 | 19903 | 7174 | 0.711117174 | 0 | 19931 | 7202 | 0.709976919 | 0 |
| 19848 | 7119 | 0.71383734 | 0 | 19876 | 7147 | 0.712592744 | 0 | 19904 | 7175 | 0.710989497 | 0 | 19932 | 7203 | 0.709976919 | 0 |
| 19849 | 7120 | 0.71383734 | 0 | 19877 | 7148 | 0.712592744 | -1.393012692 | 19905 | 7176 | 0.710989497 | 0 | 19933 | 7204 | 0.709873058 | 0 |
| 19850 | 7121 | 0.71383734 | 0 | 19878 | 7149 | 0.712592744 | -1.694042688 | 19906 | 7177 | 0.710989497 | 0 | 19934 | 7205 | 0.709784796 | 0 |
| 19851 | 7122 | 0.71383734 | 0 | 19879 | 7150 | 0.712490689 | 0 | 19907 | 7178 | 0.710874619 | 0 | 19935 | 7206 | 0.709784796 | 0 |
| 19852 | 7123 | 0.71383734 | 0 | 19880 | 7151 | 0.712331985 | 0 | 19908 | 7179 | 0.710874619 | 0 | 19936 | 7207 | 0.709784796 | 0 |
| 19853 | 7124 | 0.71383734 | 0 | 19881 | 7152 | 0.712331985 | 0 | 19909 | 7180 | 0.710821394 | 0 | 19937 | 7208 | 0.709784796 | 0 |
| 19854 | 7125 | 0.71383734 | -0.697937732 | 19882 | 7153 | 0.712051342 | 0 | 19910 | 7181 | 0.710676266 | 0 | 19938 | 7209 | 0.709642846 | 0 |
| 19855 | 7126 | 0.71366112 | 0 | 19883 | 7154 | 0.712051342 | 0 | 19911 | 7182 | 0.710676266 | 0 | 19939 | 7210 | 0.709642846 | 0 |
| 19856 | 7127 | 0.71366112 | 0 | 19884 | 7155 | 0.712051342 | 0 | 19912 | 7183 | 0.710676266 | 0 | 19940 | 7211 | 0.709533686 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 19941 | 7212 | 0.709533686 | 0 | 19969 | 7240 | 0.7086977 | 0 | 19997 | 7268 | 0.707030541 | 0 | 20025 | 7296 | 0.705606623 | 0 |
| 19942 | 7213 | 0.709533686 | -1.363887067 | 19970 | 7241 | 0.7086977 | 0 | 19998 | 7269 | 0.707030541 | 0 | 20026 | 7297 | 0.705606623 | 0 |
| 19943 | 7214 | 0.70944713 | 0 | 19971 | 7242 | 0.7086977 | 0 | 19999 | 7270 | 0.706891899 | 0 | 20027 | 7298 | 0.705606623 | 0 |
| 19944 | 7215 | 0.70944713 | 0 | 19972 | 7243 | 0.7086977 | 0 | 20000 | 7271 | 0.706891899 | 0 | 20028 | 7299 | 0.705606623 | 0 |
| 19945 | 7216 | 0.709376816 | 0 | 19973 | 7244 | 0.7086977 | 0 | 20001 | 7272 | 0.706891899 | 0 | 20029 | 7300 | 0.705606623 | 0 |
| 19946 | 7217 | 0.709376816 | 0 | 19974 | 7245 | 0.7086977 | 0 | 20002 | 7273 | 0.706813556 | 0 | 20030 | 7301 | 0.70531796 | -0.981158169 |
| 19947 | 7218 | 0.709376816 | 0 | 19975 | 7246 | 0.7086977 | -0.852839692 | 20003 | 7274 | 0.706813556 | 0 | 20031 | 7302 | 0.70531796 | -1.157249428 |
| 19948 | 7219 | 0.709376816 | -0.454220567 | 19976 | 7247 | 0.708111212 | 0 | 20004 | 7275 | 0.706813556 | 0 | 20032 | 7303 | 0.705093576 | 0 |
| 19949 | 7220 | 0.709318564 | 0 | 19977 | 7248 | 0.707922866 | 0 | 20005 | 7276 | 0.706813556 | 0 | 20033 | 7304 | 0.704969828 | 0 |
| 19950 | 7221 | 0.709269517 | 0 | 19978 | 7249 | 0.707829979 | 0 | 20006 | 7277 | 0.706728107 | 0 | 20034 | 7305 | 0.704767407 | 0 |
| 19951 | 7222 | 0.7086977 | 0 | 19979 | 7250 | 0.707829979 | 0 | 20007 | 7278 | 0.706531638 | 0 | 20035 | 7306 | 0.704767407 | 0 |
| 19952 | 7223 | 0.7086977 | 0 | 19980 | 7251 | 0.707711787 | 0 | 20008 | 7279 | 0.706531638 | 0 | 20036 | 7307 | 0.704767407 | 0 |
| 19953 | 7224 | 0.7086977 | 0 | 19981 | 7252 | 0.707711787 | 0 | 20009 | 7280 | 0.706531638 | 0 | 20037 | 7308 | 0.704767407 | 0 |
| 19954 | 7225 | 0.7086977 | 0 | 19982 | 7253 | 0.707711787 | 0 | 20010 | 7281 | 0.706531638 | 0 | 20038 | 7309 | 0.704767407 | 0 |
| 19955 | 7226 | 0.7086977 | 0 | 19983 | 7254 | 0.707711787 | 0 | 20011 | 7282 | 0.70629163 | 0 | 20039 | 7310 | 0.704767407 | 0 |
| 19956 | 7227 | 0.7086977 | 0 | 19984 | 7255 | 0.707711787 | 0 | 20012 | 7283 | 0.70629163 | 0 | 20040 | 7311 | 0.704767407 | 0 |
| 19957 | 7228 | 0.7086977 | 0 | 19985 | 7256 | 0.707711787 | -1.293158298 | 20013 | 7284 | 0.706237102 | 0 | 20041 | 7312 | 0.704608818 | 0 |
| 19958 | 7229 | 0.7086977 | 0 | 19986 | 7257 | 0.707556321 | 0 | 20014 | 7285 | 0.706150511 | 0 | 20042 | 7313 | 0.70454174 | 0 |
| 19959 | 7230 | 0.7086977 | 0 | 19987 | 7258 | 0.707342646 | 0 | 20015 | 7286 | 0.706150511 | 0 | 20043 | 7314 | 0.70454174 | 0 |
| 19960 | 7231 | 0.7086977 | 0 | 19988 | 7259 | 0.707342646 | 0 | 20016 | 7287 | 0.706150511 | 0 | 20044 | 7315 | 0.704376326 | 0 |
| 19961 | 7232 | 0.7086977 | 0 | 19989 | 7260 | 0.707342646 | 0 | 20017 | 7288 | 0.706150511 | -0.253326889 | 20045 | 7316 | 0.704376326 | 0 |
| 19962 | 7233 | 0.7086977 | 0 | 19990 | 7261 | 0.707342646 | 0 | 20018 | 7289 | 0.706150511 | -0.70562456 | 20046 | 7317 | 0.704376326 | 0 |
| 19963 | 7234 | 0.7086977 | 0 | 19991 | 7262 | 0.707342646 | -0.678103487 | 20019 | 7290 | 0.705991807 | 0 | 20047 | 7318 | 0.704376326 | 0 |
| 19964 | 7235 | 0.7086977 | 0 | 19992 | 7263 | 0.707202709 | 0 | 20020 | 7291 | 0.705991807 | 0 | 20048 | 7319 | 0.704376326 | 0 |
| 19965 | 7236 | 0.7086977 | 0 | 19993 | 7264 | 0.707030541 | 0 | 20021 | 7292 | 0.7059048 | 0 | 20049 | 7320 | 0.704249876 | 0 |
| 19966 | 7237 | 0.7086977 | 0 | 19994 | 7265 | 0.707030541 | 0 | 20022 | 7293 | 0.7059048 | 0 | 20050 | 7321 | 0.704249876 | -0.054312682 |
| 19967 | 7238 | 0.7086977 | 0 | 19995 | 7266 | 0.707030541 | 0 | 20023 | 7294 | 0.7059048 | -0.966783044 | 20051 | 7322 | 0.704150072 | 0 |
| 19968 | 7239 | 0.7086977 | 0 | 19996 | 7267 | 0.707030541 | 0 | 20024 | 7295 | 0.705606623 | 0 | 20052 | 7323 | 0.704150072 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20053 | 7324 | 0.704150072 | 0 | 20081 | 7352 | 0.702910529 | 0 | 20109 | 7380 | 0.701926139 | -0.801619305 | 20137 | 7408 | 0.700097528 | 0 |
| 20054 | 7325 | 0.704002579 | 0 | 20082 | 7353 | 0.702815518 | 0 | 20110 | 7381 | 0.701842854 | 0 | 20138 | 7409 | 0.700097528 | 0 |
| 20055 | 7326 | 0.704002579 | 0 | 20083 | 7354 | 0.702748368 | 0 | 20111 | 7382 | 0.701842854 | 0 | 20139 | 7410 | 0.699742858 | 0 |
| 20056 | 7327 | 0.704002579 | 0 | 20084 | 7355 | 0.702748368 | 0 | 20112 | 7383 | 0.701842854 | 0 | 20140 | 7411 | 0.69968568 | 0 |
| 20057 | 7328 | 0.704002579 | -1.316172662 | 20085 | 7356 | 0.702748368 | 0 | 20113 | 7384 | 0.701842854 | 0 | 20141 | 7412 | 0.69968568 | 0 |
| 20058 | 7329 | 0.703898817 | 0 | 20086 | 7357 | 0.702748368 | -0.304153683 | 20114 | 7385 | 0.701697142 | 0 | 20142 | 7413 | 0.699606523 | 0 |
| 20059 | 7330 | 0.703898817 | 0 | 20087 | 7358 | 0.702659745 | 0 | 20115 | 7386 | 0.701519116 | 0 | 20143 | 7414 | 0.699606523 | 0 |
| 20060 | 7331 | 0.703898817 | 0 | 20088 | 7359 | 0.702659745 | 0 | 20116 | 7387 | 0.701519116 | -0.066072759 | 20144 | 7415 | 0.699606523 | 0 |
| 20061 | 7332 | 0.703898817 | 0 | 20089 | 7360 | 0.702659745 | 0 | 20117 | 7388 | 0.701134444 | 0 | 20145 | 7416 | 0.699606523 | -1.37381423 |
| 20062 | 7333 | 0.703898817 | 0 | 20090 | 7361 | 0.702537391 | 0 | 20118 | 7389 | 0.701010872 | 0 | 20146 | 7417 | 0.699152382 | 0 |
| 20063 | 7334 | 0.703898817 | 0 | 20091 | 7362 | 0.702537391 | 0 | 20119 | 7390 | 0.701010872 | 0 | 20147 | 7418 | 0.699152382 | 0 |
| 20064 | 7335 | 0.703898817 | 0 | 20092 | 7363 | 0.702537391 | -1.278129308 | 20120 | 7391 | 0.701010872 | 0 | 20148 | 7419 | 0.699152382 | 0 |
| 20065 | 7336 | 0.703821849 | 0 | 20093 | 7364 | 0.702456914 | 0 | 20121 | 7392 | 0.701010872 | 0 | 20149 | 7420 | 0.699152382 | 0 |
| 20066 | 7337 | 0.703821849 | 0 | 20094 | 7365 | 0.702357522 | 0 | 20122 | 7393 | 0.701010872 | 0 | 20150 | 7421 | 0.699090274 | 0 |
| 20067 | 7338 | 0.703821849 | -1.144957254 | 20095 | 7366 | 0.702357522 | 0 | 20123 | 7394 | 0.700872363 | 0 | 20151 | 7422 | 0.698937863 | 0 |
| 20068 | 7339 | 0.7037153 | -1.545796712 | 20096 | 7367 | 0.702357522 | 0 | 20124 | 7395 | 0.700770332 | 0 | 20152 | 7423 | 0.698937863 | 0 |
| 20069 | 7340 | 0.703302668 | 0 | 20097 | 7368 | 0.702357522 | 0 | 20125 | 7396 | 0.700770332 | 0 | 20153 | 7424 | 0.698937863 | 0 |
| 20070 | 7341 | 0.703302668 | 0 | 20098 | 7369 | 0.702231658 | 0 | 20126 | 7397 | 0.700770332 | 0 | 20154 | 7425 | 0.698937863 | 0 |
| 20071 | 7342 | 0.703302668 | 0 | 20099 | 7370 | 0.702231658 | 0 | 20127 | 7398 | 0.700770332 | 0 | 20155 | 7426 | 0.698789412 | 0 |
| 20072 | 7343 | 0.703302668 | 0 | 20100 | 7371 | 0.702231658 | 0 | 20128 | 7399 | 0.700770332 | 0 | 20156 | 7427 | 0.698731105 | 0 |
| 20073 | 7344 | 0.703302668 | 0 | 20101 | 7372 | 0.702067121 | 0 | 20129 | 7400 | 0.700770332 | 0 | 20157 | 7428 | 0.698731105 | 0 |
| 20074 | 7345 | 0.703302668 | 0 | 20102 | 7373 | 0.702067121 | 0 | 20130 | 7401 | 0.700538213 | 0 | 20158 | 7429 | 0.698731105 | 0 |
| 20075 | 7346 | 0.703302668 | 0 | 20103 | 7374 | 0.702067121 | 0 | 20131 | 7402 | 0.700097528 | 0 | 20159 | 7430 | 0.698597373 | 0 |
| 20076 | 7347 | 0.703302668 | 0 | 20104 | 7375 | 0.702067121 | 0 | 20132 | 7403 | 0.700097528 | 0 | 20160 | 7431 | 0.698597373 | 0 |
| 20077 | 7348 | 0.703302668 | 0 | 20105 | 7376 | 0.702067121 | 0 | 20133 | 7404 | 0.700097528 | 0 | 20161 | 7432 | 0.698597373 | 0 |
| 20078 | 7349 | 0.703302668 | 0 | 20106 | 7377 | 0.702067121 | 0 | 20134 | 7405 | 0.700097528 | 0 | 20162 | 7433 | 0.698597373 | 0 |
| 20079 | 7350 | 0.703302668 | 0 | 20107 | 7378 | 0.702067121 | 0 | 20135 | 7406 | 0.700097528 | 0 | 20163 | 7434 | 0.698597373 | 0 |
| 20080 | 7351 | 0.703302668 | -0.381113469 | 20108 | 7379 | 0.702067121 | 0 | 20136 | 7407 | 0.700097528 | 0 | 20164 | 7435 | 0.698503785 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20165 | 7436 | 0.698434625 | 0 | 20193 | 7464 | 0.697312305 | 0 | 20221 | 7492 | 0.696052175 | 0 | 20249 | 7520 | 0.694457261 | 0 |
| 20166 | 7437 | 0.698339249 | 0 | 20194 | 7465 | 0.697159787 | 0 | 20222 | 7493 | 0.695974449 | 0 | 20250 | 7521 | 0.694457261 | -1.395353908 |
| 20167 | 7438 | 0.698339249 | 0 | 20195 | 7466 | 0.697159787 | 0 | 20223 | 7494 | 0.695860475 | 0 | 20251 | 7522 | 0.694207163 | 0 |
| 20168 | 7439 | 0.698339249 | 0 | 20196 | 7467 | 0.697159787 | 0 | 20224 | 7495 | 0.695860475 | 0 | 20252 | 7523 | 0.694088746 | 0 |
| 20169 | 7440 | 0.698339249 | -0.121476158 | 20197 | 7468 | 0.697159787 | 0 | 20225 | 7496 | 0.695860475 | 0 | 20253 | 7524 | 0.694088746 | 0 |
| 20170 | 7441 | 0.698276585 | 0 | 20198 | 7469 | 0.697159787 | 0 | 20226 | 7497 | 0.695860475 | 0 | 20254 | 7525 | 0.694088746 | 0 |
| 20171 | 7442 | 0.697973835 | 0 | 20199 | 7470 | 0.697011942 | 0 | 20227 | 7498 | 0.695860475 | 0 | 20255 | 7526 | 0.694088746 | 0 |
| 20172 | 7443 | 0.697973835 | 0 | 20200 | 7471 | 0.697011942 | 0 | 20228 | 7499 | 0.69567719 | 0 | 20256 | 7527 | 0.693974443 | 0 |
| 20173 | 7444 | 0.697973835 | 0 | 20201 | 7472 | 0.69691587 | 0 | 20229 | 7500 | 0.69567719 | 0 | 20257 | 7528 | 0.693918768 | 0 |
| 20174 | 7445 | 0.697973835 | 0 | 20202 | 7473 | 0.69691587 | 0 | 20230 | 7501 | 0.69567719 | 0 | 20258 | 7529 | 0.69375735 | 0 |
| 20175 | 7446 | 0.697973835 | 0 | 20203 | 7474 | 0.696848427 | 0 | 20231 | 7502 | 0.69567719 | 0 | 20259 | 7530 | 0.69375735 | 0 |
| 20176 | 7447 | 0.697973835 | 0 | 20204 | 7475 | 0.696798477 | 0 | 20232 | 7503 | 0.69567719 | 0 | 20260 | 7531 | 0.69375735 | 0 |
| 20177 | 7448 | 0.697973835 | 0 | 20205 | 7476 | 0.696798477 | 0 | 20233 | 7504 | 0.695588532 | -0.55113058 | 20261 | 7532 | 0.69375735 | 0 |
| 20178 | 7449 | 0.697973835 | 0 | 20206 | 7477 | 0.696798477 | -0.915891437 | 20234 | 7505 | 0.695333739 | 0 | 20262 | 7533 | 0.69375735 | 0 |
| 20179 | 7450 | 0.697973835 | 0 | 20207 | 7478 | 0.696729437 | 0 | 20235 | 7506 | 0.695333739 | 0 | 20263 | 7534 | 0.69375735 | 0 |
| 20180 | 7451 | 0.697973835 | 0 | 20208 | 7479 | 0.696683978 | 0 | 20236 | 7507 | 0.695333739 | 0 | 20264 | 7535 | 0.69375735 | -1.26572005 |
| 20181 | 7452 | 0.697973835 | -0.437594825 | 20209 | 7480 | 0.696463244 | 0 | 20237 | 7508 | 0.695333739 | 0 | 20265 | 7536 | 0.693554362 | -0.757284733 |
| 20182 | 7453 | 0.697757714 | -0.474794512 | 20210 | 7481 | 0.696463244 | 0 | 20238 | 7509 | 0.695333739 | 0 | 20266 | 7537 | 0.693457734 | 0 |
| 20183 | 7454 | 0.697687644 | 0 | 20211 | 7482 | 0.696463244 | 0 | 20239 | 7510 | 0.695333739 | 0 | 20267 | 7538 | 0.693457734 | 0 |
| 20184 | 7455 | 0.697632274 | 0 | 20212 | 7483 | 0.696463244 | 0 | 20240 | 7511 | 0.695333739 | -1.167233649 | 20268 | 7539 | 0.693185534 | 0 |
| 20185 | 7456 | 0.697632274 | 0 | 20213 | 7484 | 0.696463244 | 0 | 20241 | 7512 | 0.69514119 | 0 | 20269 | 7540 | 0.693185534 | 0 |
| 20186 | 7457 | 0.697550339 | -0.513739034 | 20214 | 7485 | 0.696211989 | 0 | 20242 | 7513 | 0.695018003 | 0 | 20270 | 7541 | 0.693185534 | 0 |
| 20187 | 7458 | 0.697550339 | -1.358837074 | 20215 | 7486 | 0.696151363 | 0 | 20243 | 7514 | 0.695018003 | 0 | 20271 | 7542 | 0.693185534 | 0 |
| 20188 | 7459 | 0.69741669 | 0 | 20216 | 7487 | 0.696151363 | -0.248602781 | 20244 | 7515 | 0.694869501 | 0 | 20272 | 7543 | 0.693185534 | 0 |
| 20189 | 7460 | 0.69741669 | 0 | 20217 | 7488 | 0.696151363 | -1.42469404 | 20245 | 7516 | 0.694869501 | 0 | 20273 | 7544 | 0.693185534 | 0 |
| 20190 | 7461 | 0.69741669 | 0 | 20218 | 7489 | 0.696052175 | 0 | 20246 | 7517 | 0.694726758 | -1.378693995 | 20274 | 7545 | 0.693185534 | 0 |
| 20191 | 7462 | 0.697312305 | 0 | 20219 | 7490 | 0.696052175 | 0 | 20247 | 7518 | 0.694457261 | 0 | 20275 | 7546 | 0.693185534 | 0 |
| 20192 | 7463 | 0.697312305 | 0 | 20220 | 7491 | 0.696052175 | 0 | 20248 | 7519 | 0.694457261 | 0 | 20276 | 7547 | 0.693017496 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20277 | 7548 | 0.692937153 | 0 | 20305 | 7576 | 0.691664361 | 0 | 20333 | 7604 | 0.690214294 | 0 | 20361 | 7632 | 0.689284659 | 0 |
| 20278 | 7549 | 0.692709595 | 0 | 20306 | 7577 | 0.691664361 | 0 | 20334 | 7605 | 0.690101212 | 0 | 20362 | 7633 | 0.68923522 | -0.747363435 |
| 20279 | 7550 | 0.692709595 | 0 | 20307 | 7578 | 0.691664361 | 0 | 20335 | 7606 | 0.690101212 | 0 | 20363 | 7634 | 0.689144164 | 0 |
| 20280 | 7551 | 0.692709595 | 0 | 20308 | 7579 | 0.691529675 | 0 | 20336 | 7607 | 0.690101212 | -0.87143618 | 20364 | 7635 | 0.689102144 | 0 |
| 20281 | 7552 | 0.692709595 | 0 | 20309 | 7580 | 0.691529675 | 0 | 20337 | 7608 | 0.689997202 | 0 | 20365 | 7636 | 0.689062229 | 0 |
| 20282 | 7553 | 0.692709595 | 0 | 20310 | 7581 | 0.691403445 | 0 | 20338 | 7609 | 0.689997202 | 0 | 20366 | 7637 | 0.689024265 | 0 |
| 20283 | 7554 | 0.692709595 | 0 | 20311 | 7582 | 0.691403445 | -0.694042688 | 20339 | 7610 | 0.689997202 | 0 | 20367 | 7638 | 0.689024265 | 0 |
| 20284 | 7555 | 0.692500347 | 0 | 20312 | 7583 | 0.691403445 | -1.472193938 | 20340 | 7611 | 0.689997202 | 0 | 20368 | 7639 | 0.688920742 | 0 |
| 20285 | 7556 | 0.692500347 | -1.363887067 | 20313 | 7584 | 0.691284899 | -1.485676446 | 20341 | 7612 | 0.689901214 | 0 | 20369 | 7640 | 0.688776415 | -1.65986707 |
| 20286 | 7557 | 0.692434289 | 0 | 20314 | 7585 | 0.691173355 | 0 | 20342 | 7613 | 0.689901214 | 0 | 20370 | 7641 | 0.687508401 | 0 |
| 20287 | 7558 | 0.692307284 | 0 | 20315 | 7586 | 0.691173355 | 0 | 20343 | 7614 | 0.689901214 | 0 | 20371 | 7642 | 0.687508401 | 0 |
| 20288 | 7559 | 0.692307284 | 0 | 20316 | 7587 | 0.691173355 | 0 | 20344 | 7615 | 0.689901214 | 0 | 20372 | 7643 | 0.687508401 | 0 |
| 20289 | 7560 | 0.692307284 | 0 | 20317 | 7588 | 0.690968933 | 0 | 20345 | 7616 | 0.689812356 | 0 | 20373 | 7644 | 0.687508401 | 0 |
| 20290 | 7561 | 0.692307284 | 0 | 20318 | 7589 | 0.690968933 | 0 | 20346 | 7617 | 0.689812356 | 0 | 20374 | 7645 | 0.687508401 | 0 |
| 20291 | 7562 | 0.692307284 | 0 | 20319 | 7590 | 0.690968933 | 0 | 20347 | 7618 | 0.689812356 | -1.098968817 | 20375 | 7646 | 0.687508401 | 0 |
| 20292 | 7563 | 0.692128599 | 0 | 20320 | 7591 | 0.690968933 | 0 | 20348 | 7619 | 0.689729861 | 0 | 20376 | 7647 | 0.687508401 | 0 |
| 20293 | 7564 | 0.692128599 | 0 | 20321 | 7592 | 0.690968933 | 0 | 20349 | 7620 | 0.689729861 | 0 | 20377 | 7648 | 0.687508401 | 0 |
| 20294 | 7565 | 0.692128599 | 0 | 20322 | 7593 | 0.690875042 | -0.933714096 | 20350 | 7621 | 0.689729861 | 0 | 20378 | 7649 | 0.687508401 | 0 |
| 20295 | 7566 | 0.691962743 | 0 | 20323 | 7594 | 0.690786111 | 0 | 20351 | 7622 | 0.68965307 | -0.653041083 | 20379 | 7650 | 0.687508401 | 0 |
| 20296 | 7567 | 0.691962743 | 0 | 20324 | 7595 | 0.690621637 | 0 | 20352 | 7623 | 0.68965307 | -1.431192333 | 20380 | 7651 | 0.687508401 | 0 |
| 20297 | 7568 | 0.691962743 | 0 | 20325 | 7596 | 0.690621637 | 0 | 20353 | 7624 | 0.68958141 | 0 | 20381 | 7652 | 0.687508401 | 0 |
| 20298 | 7569 | 0.691858633 | -0.043754727 | 20326 | 7597 | 0.69047288 | 0 | 20354 | 7625 | 0.68958141 | 0 | 20382 | 7653 | 0.687508401 | 0 |
| 20299 | 7570 | 0.691808382 | 0 | 20327 | 7598 | 0.690337691 | 0 | 20355 | 7626 | 0.68958141 | 0 | 20383 | 7654 | 0.687508401 | 0 |
| 20300 | 7571 | 0.691808382 | 0 | 20328 | 7599 | 0.690337691 | 0 | 20356 | 7627 | 0.68958141 | 0 | 20384 | 7655 | 0.687508401 | 0 |
| 20301 | 7572 | 0.691808382 | 0 | 20329 | 7600 | 0.690337691 | 0 | 20357 | 7628 | 0.689451556 | 0 | 20385 | 7656 | 0.687508401 | 0 |
| 20302 | 7573 | 0.691808382 | 0 | 20330 | 7601 | 0.690214294 | 0 | 20358 | 7629 | 0.689451556 | 0 | 20386 | 7657 | 0.687508401 | 0 |
| 20303 | 7574 | 0.691664361 | 0 | 20331 | 7602 | 0.690214294 | 0 | 20359 | 7630 | 0.689337012 | 0 | 20387 | 7658 | 0.687508401 | 0 |
| 20304 | 7575 | 0.691664361 | 0 | 20332 | 7603 | 0.690214294 | 0 | 20360 | 7631 | 0.689337012 | 0 | 20388 | 7659 | 0.687508401 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20389 | 7660 | 0.687508401 | 0 | 20417 | 7688 | 0.687508401 | 0 | 20445 | 7716 | 0.685573901 | 0 | 20473 | 7744 | 0.684255244 | 0 |
| 20390 | 7661 | 0.687508401 | 0 | 20418 | 7689 | 0.687508401 | 0 | 20446 | 7717 | 0.685511641 | 0 | 20474 | 7745 | 0.684255244 | 0 |
| 20391 | 7662 | 0.687508401 | 0 | 20419 | 7690 | 0.687508401 | 0 | 20447 | 7718 | 0.685445241 | 0 | 20475 | 7746 | 0.684167658 | 0 |
| 20392 | 7663 | 0.687508401 | 0 | 20420 | 7691 | 0.687508401 | 0 | 20448 | 7719 | 0.685445241 | 0 | 20476 | 7747 | 0.684075225 | 0 |
| 20393 | 7664 | 0.687508401 | 0 | 20421 | 7692 | 0.687508401 | 0 | 20449 | 7720 | 0.685374272 | 0 | 20477 | 7748 | 0.684075225 | 0 |
| 20394 | 7665 | 0.687508401 | 0 | 20422 | 7693 | 0.687508401 | 0 | 20450 | 7721 | 0.685374272 | 0 | 20478 | 7749 | 0.684075225 | 0 |
| 20395 | 7666 | 0.687508401 | 0 | 20423 | 7694 | 0.687508401 | 0 | 20451 | 7722 | 0.685298246 | 0 | 20479 | 7750 | 0.683977532 | 0 |
| 20396 | 7667 | 0.687508401 | 0 | 20424 | 7695 | 0.687508401 | 0 | 20452 | 7723 | 0.685298246 | 0 | 20480 | 7751 | 0.683977532 | 0 |
| 20397 | 7668 | 0.687508401 | 0 | 20425 | 7696 | 0.687508401 | 0 | 20453 | 7724 | 0.685216604 | 0 | 20481 | 7752 | 0.683874116 | 0 |
| 20398 | 7669 | 0.687508401 | 0 | 20426 | 7697 | 0.687508401 | 0 | 20454 | 7725 | 0.685128699 | 0 | 20482 | 7753 | 0.683874116 | 0 |
| 20399 | 7670 | 0.687508401 | 0 | 20427 | 7698 | 0.687508401 | 0 | 20455 | 7726 | 0.685128699 | 0 | 20483 | 7754 | 0.683874116 | 0 |
| 20400 | 7671 | 0.687508401 | 0 | 20428 | 7699 | 0.687508401 | 0 | 20456 | 7727 | 0.685033782 | 0 | 20484 | 7755 | 0.68376446 | 0 |
| 20401 | 7672 | 0.687508401 | 0 | 20429 | 7700 | 0.687508401 | 0 | 20457 | 7728 | 0.685033782 | 0 | 20485 | 7756 | 0.68376446 | 0 |
| 20402 | 7673 | 0.687508401 | 0 | 20430 | 7701 | 0.687508401 | 0 | 20458 | 7729 | 0.685033782 | 0 | 20486 | 7757 | 0.68364798 | 0 |
| 20403 | 7674 | 0.687508401 | 0 | 20431 | 7702 | 0.687508401 | 0 | 20459 | 7730 | 0.685033782 | 0 | 20487 | 7758 | 0.68364798 | 0 |
| 20404 | 7675 | 0.687508401 | 0 | 20432 | 7703 | 0.687508401 | 0 | 20460 | 7731 | 0.685033782 | 0 | 20488 | 7759 | 0.68364798 | 0 |
| 20405 | 7676 | 0.687508401 | 0 | 20433 | 7704 | 0.687508401 | 0 | 20461 | 7732 | 0.684930978 | 0 | 20489 | 7760 | 0.68364798 | 0 |
| 20406 | 7677 | 0.687508401 | 0 | 20434 | 7705 | 0.687508401 | 0 | 20462 | 7733 | 0.684930978 | 0 | 20490 | 7761 | 0.68364798 | 0 |
| 20407 | 7678 | 0.687508401 | 0 | 20435 | 7706 | 0.687508401 | -0.515007048 | 20463 | 7734 | 0.684697424 | 0 | 20491 | 7762 | 0.68352402 | 0 |
| 20408 | 7679 | 0.687508401 | 0 | 20436 | 7707 | 0.687508401 | -1.147030263 | 20464 | 7735 | 0.68456402 | 0 | 20492 | 7763 | 0.68352402 | 0 |
| 20409 | 7680 | 0.687508401 | 0 | 20437 | 7708 | 0.687508401 | -1.271968999 | 20465 | 7736 | 0.68456402 | 0 | 20493 | 7764 | 0.68352402 | 0 |
| 20410 | 7681 | 0.687508401 | 0 | 20438 | 7709 | 0.687508401 | -1.5507226 | 20466 | 7737 | 0.68456402 | 0 | 20494 | 7765 | 0.683391835 | 0 |
| 20411 | 7682 | 0.687508401 | 0 | 20439 | 7710 | 0.687508401 | -0.985179443 | 20467 | 7738 | 0.684417324 | 0 | 20495 | 7766 | 0.683391835 | 0 |
| 20412 | 7683 | 0.687508401 | 0 | 20440 | 7711 | 0.685960113 | 0 | 20468 | 7739 | 0.684417324 | 0 | 20496 | 7767 | 0.683391835 | -1.452176825 |
| 20413 | 7684 | 0.687508401 | 0 | 20441 | 7712 | 0.685960113 | -1.574547284 | 20469 | 7740 | 0.684417324 | 0 | 20497 | 7768 | 0.683250578 | 0 |
| 20414 | 7685 | 0.687508401 | 0 | 20442 | 7713 | 0.685687457 | 0 | 20470 | 7741 | 0.684417324 | 0 | 20498 | 7769 | 0.683099282 | 0 |
| 20415 | 7686 | 0.687508401 | 0 | 20443 | 7714 | 0.685573901 | 0 | 20471 | 7742 | 0.684417324 | 0 | 20499 | 7770 | 0.683099282 | 0 |
| 20416 | 7687 | 0.687508401 | 0 | 20444 | 7715 | 0.685573901 | 0 | 20472 | 7743 | 0.684255244 | 0 | 20500 | 7771 | 0.682936838 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20501 | 7772 | 0.682936838 | 0 | 20529 | 7800 | 0.681904524 | 0 | 20557 | 7828 | 0.679821572 | 0 | 20585 | 7856 | 0.678522677 | 0 |
| 20502 | 7773 | 0.682936838 | 0 | 20530 | 7801 | 0.681904524 | 0 | 20558 | 7829 | 0.679821572 | 0 | 20586 | 7857 | 0.678412896 | 0 |
| 20503 | 7774 | 0.682936838 | 0 | 20531 | 7802 | 0.681775057 | 0 | 20559 | 7830 | 0.679821572 | 0 | 20587 | 7858 | 0.678412896 | 0 |
| 20504 | 7775 | 0.682936838 | 0 | 20532 | 7803 | 0.681730562 | -1.180836825 | 20560 | 7831 | 0.679821572 | 0 | 20588 | 7859 | 0.678412896 | 0 |
| 20505 | 7776 | 0.682936838 | -1.105844335 | 20533 | 7804 | 0.681639467 | 0 | 20561 | 7832 | 0.679821572 | -0.802534573 | 20589 | 7860 | 0.678412896 | 0 |
| 20506 | 7777 | 0.682761966 | 0 | 20534 | 7805 | 0.681545454 | -0.354320292 | 20562 | 7833 | 0.679821572 | -1.006654556 | 20590 | 7861 | 0.678300399 | 0 |
| 20507 | 7778 | 0.682761966 | 0 | 20535 | 7806 | 0.681348092 | 0 | 20563 | 7834 | 0.679575861 | 0 | 20591 | 7862 | 0.678300399 | 0 |
| 20508 | 7779 | 0.682761966 | 0 | 20536 | 7807 | 0.681348092 | 0 | 20564 | 7835 | 0.679575861 | 0 | 20592 | 7863 | 0.678300399 | 0 |
| 20509 | 7780 | 0.682761966 | 0 | 20537 | 7808 | 0.681348092 | 0 | 20565 | 7836 | 0.679575861 | 0 | 20593 | 7864 | 0.678300399 | 0 |
| 20510 | 7781 | 0.682761966 | 0 | 20538 | 7809 | 0.681348092 | 0 | 20566 | 7837 | 0.679490429 | 0 | 20594 | 7865 | 0.678300399 | 0 |
| 20511 | 7782 | 0.682761966 | 0 | 20539 | 7810 | 0.681348092 | 0 | 20567 | 7838 | 0.679490429 | 0 | 20595 | 7866 | 0.678300399 | 0 |
| 20512 | 7783 | 0.682761966 | -0.390658787 | 20540 | 7811 | 0.681348092 | -1.278129308 | 20568 | 7839 | 0.679490429 | -0.061931211 | 20596 | 7867 | 0.678300399 | 0 |
| 20513 | 7784 | 0.682573183 | 0 | 20541 | 7812 | 0.681026274 | 0 | 20569 | 7840 | 0.679490429 | -1.340684812 | 20597 | 7868 | 0.678066845 | 0 |
| 20514 | 7785 | 0.682368761 | 0 | 20542 | 7813 | 0.681026274 | 0 | 20570 | 7841 | 0.679313922 | 0 | 20598 | 7869 | 0.678066845 | 0 |
| 20515 | 7786 | 0.682146673 | 0 | 20543 | 7814 | 0.681026274 | 0 | 20571 | 7842 | 0.67912947 | 0 | 20599 | 7870 | 0.678066845 | 0 |
| 20516 | 7787 | 0.682146673 | 0 | 20544 | 7815 | 0.680668977 | 0 | 20572 | 7843 | 0.67912947 | 0 | 20600 | 7871 | 0.678066845 | 0 |
| 20517 | 7788 | 0.682146673 | 0 | 20545 | 7816 | 0.680668977 | 0 | 20573 | 7844 | 0.67912947 | 0 | 20601 | 7872 | 0.678066845 | 0 |
| 20518 | 7789 | 0.682146673 | 0 | 20546 | 7817 | 0.680668977 | 0 | 20574 | 7845 | 0.678734477 | 0 | 20602 | 7873 | 0.678066845 | 0 |
| 20519 | 7790 | 0.682146673 | 0 | 20547 | 7818 | 0.680269992 | 0 | 20575 | 7846 | 0.678734477 | 0 | 20603 | 7874 | 0.678066845 | -1.094323912 |
| 20520 | 7791 | 0.682146673 | 0 | 20548 | 7819 | 0.680269992 | 0 | 20576 | 7847 | 0.678734477 | 0 | 20604 | 7875 | 0.677821134 | 0 |
| 20521 | 7792 | 0.682146673 | 0 | 20549 | 7820 | 0.680126447 | 0 | 20577 | 7848 | 0.678734477 | 0 | 20605 | 7876 | 0.677821134 | 0 |
| 20522 | 7793 | 0.682068316 | 0 | 20550 | 7821 | 0.680126447 | -1.07523097 | 20578 | 7849 | 0.678734477 | 0 | 20606 | 7877 | 0.677821134 | 0 |
| 20523 | 7794 | 0.682068316 | 0 | 20551 | 7822 | 0.680052519 | 0 | 20579 | 7850 | 0.678734477 | 0 | 20607 | 7878 | 0.677821134 | 0 |
| 20524 | 7795 | 0.681904524 | 0 | 20552 | 7823 | 0.679821572 | 0 | 20580 | 7851 | 0.678734477 | 0 | 20608 | 7879 | 0.677821134 | 0 |
| 20525 | 7796 | 0.681904524 | 0 | 20553 | 7824 | 0.679821572 | 0 | 20581 | 7852 | 0.678734477 | 0 | 20609 | 7880 | 0.677821134 | 0 |
| 20526 | 7797 | 0.681904524 | 0 | 20554 | 7825 | 0.679821572 | 0 | 20582 | 7853 | 0.678734477 | 0 | 20610 | 7881 | 0.677821134 | 0 |
| 20527 | 7798 | 0.681904524 | 0 | 20555 | 7826 | 0.679821572 | 0 | 20583 | 7854 | 0.678734477 | 0 | 20611 | 7882 | 0.677821134 | -1.560409868 |
| 20528 | 7799 | 0.681904524 | 0 | 20556 | 7827 | 0.679821572 | 0 | 20584 | 7855 | 0.678734477 | -1.000902227 | 20612 | 7883 | 0.677693419 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20613 | 7884 | 0.677693419 | -1.077663999 | 20641 | 7912 | 0.676568415 | 0 | 20669 | 7940 | 0.675273945 | 0 | 20697 | 7968 | 0.673935594 | 0 |
| 20614 | 7885 | 0.677615161 | 0 | 20642 | 7913 | 0.676568415 | -0.82697703 | 20670 | 7941 | 0.675273945 | 0 | 20698 | 7969 | 0.673935594 | 0 |
| 20615 | 7886 | 0.677289236 | 0 | 20643 | 7914 | 0.676372035 | 0 | 20671 | 7942 | 0.675273945 | 0 | 20699 | 7970 | 0.673935594 | 0 |
| 20616 | 7887 | 0.677289236 | 0 | 20644 | 7915 | 0.676372035 | 0 | 20672 | 7943 | 0.675273945 | 0 | 20700 | 7971 | 0.673631998 | 0 |
| 20617 | 7888 | 0.677289236 | 0 | 20645 | 7916 | 0.676372035 | 0 | 20673 | 7944 | 0.675273945 | 0 | 20701 | 7972 | 0.673631998 | 0 |
| 20618 | 7889 | 0.677289236 | 0 | 20646 | 7917 | 0.676372035 | 0 | 20674 | 7945 | 0.675273945 | 0 | 20702 | 7973 | 0.673631998 | 0 |
| 20619 | 7890 | 0.677289236 | 0 | 20647 | 7918 | 0.676372035 | 0 | 20675 | 7946 | 0.674964728 | 0 | 20703 | 7974 | 0.673631998 | 0 |
| 20620 | 7891 | 0.677289236 | 0 | 20648 | 7919 | 0.676227391 | 0 | 20676 | 7947 | 0.674919274 | -1.515007048 | 20704 | 7975 | 0.673631998 | 0 |
| 20621 | 7892 | 0.677289236 | 0 | 20649 | 7920 | 0.676168475 | 0 | 20677 | 7948 | 0.674858153 | 0 | 20705 | 7976 | 0.67342194 | 0 |
| 20622 | 7893 | 0.677289236 | 0 | 20650 | 7921 | 0.676168475 | -1.112612698 | 20678 | 7949 | 0.674858153 | 0 | 20706 | 7977 | 0.67342194 | 0 |
| 20623 | 7894 | 0.677289236 | 0 | 20651 | 7922 | 0.676116417 | 0 | 20679 | 7950 | 0.674858153 | -1.44598725 | 20707 | 7978 | 0.67342194 | 0 |
| 20624 | 7895 | 0.677289236 | 0 | 20652 | 7923 | 0.676028583 | 0 | 20680 | 7951 | 0.67477158 | 0 | 20708 | 7979 | 0.67342194 | 0 |
| 20625 | 7896 | 0.677289236 | 0 | 20653 | 7924 | 0.676028583 | 0 | 20681 | 7952 | 0.67477158 | 0 | 20709 | 7980 | 0.67342194 | 0 |
| 20626 | 7897 | 0.677042967 | 0 | 20654 | 7925 | 0.676028583 | 0 | 20682 | 7953 | 0.67477158 | 0 | 20710 | 7981 | 0.67342194 | 0 |
| 20627 | 7898 | 0.677000764 | 0 | 20655 | 7926 | 0.676028583 | 0 | 20683 | 7954 | 0.674639475 | 0 | 20711 | 7982 | 0.673150251 | 0 |
| 20628 | 7899 | 0.676941104 | -1.142874303 | 20656 | 7927 | 0.675926529 | 0 | 20684 | 7955 | 0.674639475 | 0 | 20712 | 7983 | 0.673150251 | 0 |
| 20629 | 7900 | 0.676850333 | 0 | 20657 | 7928 | 0.675926529 | -1.5507226 | 20685 | 7956 | 0.674639475 | 0 | 20713 | 7984 | 0.672982148 | 0 |
| 20630 | 7901 | 0.676850333 | 0 | 20658 | 7929 | 0.675848789 | 0 | 20686 | 7957 | 0.674639475 | 0 | 20714 | 7985 | 0.672982148 | 0 |
| 20631 | 7902 | 0.676850333 | 0 | 20659 | 7930 | 0.675848789 | 0 | 20687 | 7958 | 0.674639475 | 0 | 20715 | 7986 | 0.672982148 | 0 |
| 20632 | 7903 | 0.676850333 | 0 | 20660 | 7931 | 0.675848789 | 0 | 20688 | 7959 | 0.674639475 | 0 | 20716 | 7987 | 0.672982148 | 0 |
| 20633 | 7904 | 0.676850333 | 0 | 20661 | 7932 | 0.675848789 | 0 | 20689 | 7960 | 0.674543424 | 0 | 20717 | 7988 | 0.672867875 | 0 |
| 20634 | 7905 | 0.676850333 | 0 | 20662 | 7933 | 0.675738183 | 0 | 20690 | 7961 | 0.674413103 | 0 | 20718 | 7989 | 0.672867875 | 0 |
| 20635 | 7906 | 0.676850333 | 0 | 20663 | 7934 | 0.675738183 | 0 | 20691 | 7962 | 0.674413103 | 0 | 20719 | 7990 | 0.672867875 | 0 |
| 20636 | 7907 | 0.676695532 | 0 | 20664 | 7935 | 0.675738183 | 0 | 20692 | 7963 | 0.674226189 | 0 | 20720 | 7991 | 0.672785144 | 0 |
| 20637 | 7908 | 0.676695532 | 0 | 20665 | 7936 | 0.675609178 | 0 | 20693 | 7964 | 0.674226189 | -1.345949052 | 20721 | 7992 | 0.672785144 | 0 |
| 20638 | 7909 | 0.676695532 | 0 | 20666 | 7937 | 0.675273945 | 0 | 20694 | 7965 | 0.67414444 | 0 | 20722 | 7993 | 0.672785144 | 0 |
| 20639 | 7910 | 0.676568415 | 0 | 20667 | 7938 | 0.675273945 | 0 | 20695 | 7966 | 0.67414444 | 0 | 20723 | 7994 | 0.672785144 | 0 |
| 20640 | 7911 | 0.676568415 | 0 | 20668 | 7939 | 0.675273945 | 0 | 20696 | 7967 | 0.673935594 | 0 | 20724 | 7995 | 0.672268435 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20725 | 7996 | 0.672268435 | 0 | 20753 | 8024 | 0.671388405 | 0 | 20781 | 8052 | 0.670400498 | 0 | 20809 | 8080 | 0.668826188 | 0 |
| 20726 | 7997 | 0.672268435 | 0 | 20754 | 8025 | 0.671388405 | 0 | 20782 | 8053 | 0.670400498 | -0.590106898 | 20810 | 8081 | 0.668826188 | 0 |
| 20727 | 7998 | 0.672268435 | 0 | 20755 | 8026 | 0.671271202 | 0 | 20783 | 8054 | 0.670134305 | 0 | 20811 | 8082 | 0.668826188 | 0 |
| 20728 | 7999 | 0.672268435 | 0 | 20756 | 8027 | 0.671271202 | 0 | 20784 | 8055 | 0.670134305 | 0 | 20812 | 8083 | 0.668826188 | 0 |
| 20729 | 8000 | 0.672268435 | 0 | 20757 | 8028 | 0.671271202 | 0 | 20785 | 8056 | 0.670134305 | 0 | 20813 | 8084 | 0.668826188 | 0 |
| 20730 | 8001 | 0.672268435 | 0 | 20758 | 8029 | 0.671271202 | 0 | 20786 | 8057 | 0.670134305 | 0 | 20814 | 8085 | 0.668826188 | -0.92747331 |
| 20731 | 8002 | 0.672268435 | 0 | 20759 | 8030 | 0.671271202 | 0 | 20787 | 8058 | 0.670134305 | -0.106412412 | 20815 | 8086 | 0.668668578 | 0 |
| 20732 | 8003 | 0.672268435 | 0 | 20760 | 8031 | 0.671271202 | 0 | 20788 | 8059 | 0.669910269 | 0 | 20816 | 8087 | 0.668540562 | 0 |
| 20733 | 8004 | 0.672268435 | 0 | 20761 | 8032 | 0.671117985 | 0 | 20789 | 8060 | 0.669779634 | 0 | 20817 | 8088 | 0.668540562 | 0 |
| 20734 | 8005 | 0.672268435 | 0 | 20762 | 8033 | 0.671117985 | 0 | 20790 | 8061 | 0.669779634 | 0 | 20818 | 8089 | 0.668540562 | -0.591966834 |
| 20735 | 8006 | 0.672268435 | 0 | 20763 | 8034 | 0.670909139 | 0 | 20791 | 8062 | 0.669633677 | 0 | 20819 | 8090 | 0.66843452 | 0 |
| 20736 | 8007 | 0.672268435 | 0 | 20764 | 8035 | 0.670909139 | 0 | 20792 | 8063 | 0.669633677 | 0 | 20820 | 8091 | 0.668345242 | 0 |
| 20737 | 8008 | 0.672268435 | 0 | 20765 | 8036 | 0.670909139 | 0 | 20793 | 8064 | 0.669633677 | 0 | 20821 | 8092 | 0.668345242 | 0 |
| 20738 | 8009 | 0.672268435 | 0 | 20766 | 8037 | 0.670909139 | 0 | 20794 | 8065 | 0.669633677 | 0 | 20822 | 8093 | 0.668345242 | 0 |
| 20739 | 8010 | 0.672268435 | 0 | 20767 | 8038 | 0.670909139 | 0 | 20795 | 8066 | 0.669633677 | 0 | 20823 | 8094 | 0.668345242 | 0 |
| 20740 | 8011 | 0.672268435 | -1.190298953 | 20768 | 8039 | 0.670909139 | -0.216017594 | 20796 | 8067 | 0.669633677 | 0 | 20824 | 8095 | 0.668345242 | 0 |
| 20741 | 8012 | 0.671920303 | 0 | 20769 | 8040 | 0.670721984 | 0 | 20797 | 8068 | 0.669503979 | 0 | 20825 | 8096 | 0.668345242 | -0.038406843 |
| 20742 | 8013 | 0.671785617 | -0.331895446 | 20770 | 8041 | 0.670721984 | 0 | 20798 | 8069 | 0.669503979 | 0 | 20826 | 8097 | 0.668203246 | 0 |
| 20743 | 8014 | 0.671714134 | 0 | 20771 | 8042 | 0.670721984 | 0 | 20799 | 8070 | 0.669503979 | 0 | 20827 | 8098 | 0.668203246 | 0 |
| 20744 | 8015 | 0.671714134 | 0 | 20772 | 8043 | 0.670721984 | 0 | 20800 | 8071 | 0.669283581 | 0 | 20828 | 8099 | 0.668203246 | 0 |
| 20745 | 8016 | 0.671617806 | 0 | 20773 | 8044 | 0.670721984 | 0 | 20801 | 8072 | 0.669283581 | 0 | 20829 | 8100 | 0.668203246 | 0 |
| 20746 | 8017 | 0.671617806 | 0 | 20774 | 8045 | 0.670721984 | 0 | 20802 | 8073 | 0.669283581 | 0 | 20830 | 8101 | 0.668203246 | -0.554515589 |
| 20747 | 8018 | 0.671480956 | 0 | 20775 | 8046 | 0.670607651 | 0 | 20803 | 8074 | 0.669283581 | 0 | 20831 | 8102 | 0.66809536 | 0 |
| 20748 | 8019 | 0.671480956 | 0 | 20776 | 8047 | 0.670607651 | 0 | 20804 | 8075 | 0.669283581 | -1.466285079 | 20832 | 8103 | 0.66809536 | 0 |
| 20749 | 8020 | 0.671480956 | 0 | 20777 | 8048 | 0.670607651 | 0 | 20805 | 8076 | 0.669024995 | 0 | 20833 | 8104 | 0.66809536 | 0 |
| 20750 | 8021 | 0.671480956 | 0 | 20778 | 8049 | 0.670475062 | 0 | 20806 | 8077 | 0.669024995 | 0 | 20834 | 8105 | 0.66809536 | -0.485202066 |
| 20751 | 8022 | 0.671480956 | 0 | 20779 | 8050 | 0.670475062 | 0 | 20807 | 8078 | 0.669024995 | 0 | 20835 | 8106 | 0.66809536 | -1.388292053 |
| 20752 | 8023 | 0.671480956 | 0 | 20780 | 8051 | 0.670475062 | 0 | 20808 | 8079 | 0.669024995 | 0 | 20836 | 8107 | 0.668010611 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20837 | 8108 | 0.668010611 | 0 | 20865 | 8136 | 0.666688557 | 0 | 20893 | 8164 | 0.665514107 | -0.490257938 | 20921 | 8192 | 0.664027305 | 0 |
| 20838 | 8109 | 0.668010611 | 0 | 20866 | 8137 | 0.666624836 | 0 | 20894 | 8165 | 0.665232006 | 0 | 20922 | 8193 | 0.664027305 | 0 |
| 20839 | 8110 | 0.668010611 | 0 | 20867 | 8138 | 0.666624836 | -0.755250563 | 20895 | 8166 | 0.665232006 | 0 | 20923 | 8194 | 0.664027305 | 0 |
| 20840 | 8111 | 0.667942278 | 0 | 20868 | 8139 | 0.666546422 | 0 | 20896 | 8167 | 0.665232006 | 0 | 20924 | 8195 | 0.664027305 | 0 |
| 20841 | 8112 | 0.667305015 | 0 | 20869 | 8140 | 0.666447573 | 0 | 20897 | 8168 | 0.665232006 | 0 | 20925 | 8196 | 0.663885356 | 0 |
| 20842 | 8113 | 0.667305015 | 0 | 20870 | 8141 | 0.666447573 | 0 | 20898 | 8169 | 0.665232006 | 0 | 20926 | 8197 | 0.663885356 | 0 |
| 20843 | 8114 | 0.667305015 | 0 | 20871 | 8142 | 0.666447573 | 0 | 20899 | 8170 | 0.665117129 | 0 | 20927 | 8198 | 0.663885356 | 0 |
| 20844 | 8115 | 0.667305015 | 0 | 20872 | 8143 | 0.666447573 | 0 | 20900 | 8171 | 0.664844416 | 0 | 20928 | 8199 | 0.663730555 | 0 |
| 20845 | 8116 | 0.667305015 | 0 | 20873 | 8144 | 0.666447573 | 0 | 20901 | 8172 | 0.664844416 | 0 | 20929 | 8200 | 0.663730555 | 0 |
| 20846 | 8117 | 0.667305015 | 0 | 20874 | 8145 | 0.666447573 | 0 | 20902 | 8173 | 0.664844416 | 0 | 20930 | 8201 | 0.663730555 | 0 |
| 20847 | 8118 | 0.667305015 | 0 | 20875 | 8146 | 0.666145349 | 0 | 20903 | 8174 | 0.664844416 | 0 | 20931 | 8202 | 0.663374721 | 0 |
| 20848 | 8119 | 0.667305015 | 0 | 20876 | 8147 | 0.666145349 | 0 | 20904 | 8175 | 0.664844416 | 0 | 20932 | 8203 | 0.663374721 | 0 |
| 20849 | 8120 | 0.667305015 | 0 | 20877 | 8148 | 0.666145349 | 0 | 20905 | 8176 | 0.664844416 | 0 | 20933 | 8204 | 0.663374721 | 0 |
| 20850 | 8121 | 0.667305015 | 0 | 20878 | 8149 | 0.666145349 | -0.444599726 | 20906 | 8177 | 0.664844416 | 0 | 20934 | 8205 | 0.663374721 | 0 |
| 20851 | 8122 | 0.667305015 | 0 | 20879 | 8150 | 0.666033288 | 0 | 20907 | 8178 | 0.664590666 | 0 | 20935 | 8206 | 0.663374721 | 0 |
| 20852 | 8123 | 0.667305015 | 0 | 20880 | 8151 | 0.665897252 | 0 | 20908 | 8179 | 0.664590666 | 0 | 20936 | 8207 | 0.663374721 | 0 |
| 20853 | 8124 | 0.667305015 | 0 | 20881 | 8152 | 0.665897252 | 0 | 20909 | 8180 | 0.664590666 | -0.678103487 | 20937 | 8208 | 0.663374721 | 0 |
| 20854 | 8125 | 0.667305015 | 0 | 20882 | 8153 | 0.665897252 | 0 | 20910 | 8181 | 0.664494038 | 0 | 20938 | 8209 | 0.663374721 | 0 |
| 20855 | 8126 | 0.667305015 | 0 | 20883 | 8154 | 0.665789151 | -1.282692865 | 20911 | 8182 | 0.664494038 | 0 | 20939 | 8210 | 0.663374721 | 0 |
| 20856 | 8127 | 0.667305015 | 0 | 20884 | 8155 | 0.665728627 | 0 | 20912 | 8183 | 0.664374824 | -0.967200434 | 20940 | 8211 | 0.663374721 | 0 |
| 20857 | 8128 | 0.667305015 | -0.417111122 | 20885 | 8156 | 0.665728627 | 0 | 20913 | 8184 | 0.66427856 | 0 | 20941 | 8212 | 0.663374721 | -1.171163942 |
| 20858 | 8129 | 0.667305015 | -1.121476158 | 20886 | 8157 | 0.665728627 | 0 | 20914 | 8185 | 0.66427856 | 0 | 20942 | 8213 | 0.663374721 | -1.472193938 |
| 20859 | 8130 | 0.667305015 | -1.246414895 | 20887 | 8158 | 0.665728627 | -0.691688782 | 20915 | 8186 | 0.66427856 | 0 | 20943 | 8214 | 0.663008073 | 0 |
| 20860 | 8131 | 0.667305015 | -1.371353631 | 20888 | 8159 | 0.665663068 | -1.248056842 | 20916 | 8187 | 0.66427856 | 0 | 20944 | 8215 | 0.66294021 | 0 |
| 20861 | 8132 | 0.666823802 | 0 | 20889 | 8160 | 0.665514107 | 0 | 20917 | 8188 | 0.664132653 | 0 | 20945 | 8216 | 0.66294021 | -1.125840964 |
| 20862 | 8133 | 0.666785834 | 0 | 20890 | 8161 | 0.665514107 | 0 | 20918 | 8189 | 0.664132653 | -0.023278448 | 20946 | 8217 | 0.662841518 | 0 |
| 20863 | 8134 | 0.666688557 | 0 | 20891 | 8162 | 0.665514107 | 0 | 20919 | 8190 | 0.664132653 | -0.206922845 | 20947 | 8218 | 0.662684817 | 0 |
| 20864 | 8135 | 0.666688557 | 0 | 20892 | 8163 | 0.665514107 | -0.131235996 | 20920 | 8191 | 0.664132653 | -1.008555191 | 20948 | 8219 | 0.662684817 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 20949 | 8220 | 0.662565979 | 0 | 20977 | 8248 | 0.661701138 | 0 | 21005 | 8276 | 0.660356155 | 0 | 21033 | 8304 | 0.659251642 | 0 |
| 20950 | 8221 | 0.662397681 | 0 | 20978 | 8249 | 0.661701138 | 0 | 21006 | 8277 | 0.660356155 | 0 | 21034 | 8305 | 0.659251642 | 0 |
| 20951 | 8222 | 0.662397681 | 0 | 20979 | 8250 | 0.661338167 | 0 | 21007 | 8278 | 0.660185274 | 0 | 21035 | 8306 | 0.659251642 | 0 |
| 20952 | 8223 | 0.662397681 | 0 | 20980 | 8251 | 0.661338167 | 0 | 21008 | 8279 | 0.660185274 | 0 | 21036 | 8307 | 0.659071698 | 0 |
| 20953 | 8224 | 0.662397681 | 0 | 20981 | 8252 | 0.661338167 | 0 | 21009 | 8280 | 0.660185274 | 0 | 21037 | 8308 | 0.659071698 | 0 |
| 20954 | 8225 | 0.662397681 | 0 | 20982 | 8253 | 0.661179462 | 0 | 21010 | 8281 | 0.660185274 | 0 | 21038 | 8309 | 0.658926083 | -1.321740616 |
| 20955 | 8226 | 0.662397681 | 0 | 20983 | 8254 | 0.661179462 | 0 | 21011 | 8282 | 0.660185274 | 0 | 21039 | 8310 | 0.65880583 | 0 |
| 20956 | 8227 | 0.662397681 | 0 | 20984 | 8255 | 0.661033506 | 0 | 21012 | 8283 | 0.660185274 | 0 | 21040 | 8311 | 0.65880583 | 0 |
| 20957 | 8228 | 0.662397681 | -0.598109716 | 20985 | 8256 | 0.661033506 | 0 | 21013 | 8284 | 0.660185274 | 0 | 21041 | 8312 | 0.65880583 | -1.361369411 |
| 20958 | 8229 | 0.662240299 | 0 | 20986 | 8257 | 0.661033506 | 0 | 21014 | 8285 | 0.660185274 | 0 | 21042 | 8313 | 0.658704843 | 0 |
| 20959 | 8230 | 0.662140929 | 0 | 20987 | 8258 | 0.660964837 | 0 | 21015 | 8286 | 0.659964652 | 0 | 21043 | 8314 | 0.658544705 | 0 |
| 20960 | 8231 | 0.662140929 | 0 | 20988 | 8259 | 0.660964837 | -0.227931489 | 21016 | 8287 | 0.659964652 | 0 | 21044 | 8315 | 0.658219025 | 0 |
| 20961 | 8232 | 0.662140929 | 0 | 20989 | 8260 | 0.660774148 | 0 | 21017 | 8288 | 0.659964652 | 0 | 21045 | 8316 | 0.657545178 | 0 |
| 20962 | 8233 | 0.662140929 | 0 | 20990 | 8261 | 0.660774148 | 0 | 21018 | 8289 | 0.659964652 | 0 | 21046 | 8317 | 0.657545178 | 0 |
| 20963 | 8234 | 0.662140929 | 0 | 20991 | 8262 | 0.660774148 | 0 | 21019 | 8290 | 0.659778059 | 0 | 21047 | 8318 | 0.657545178 | 0 |
| 20964 | 8235 | 0.662140929 | -0.320817567 | 20992 | 8263 | 0.660774148 | 0 | 21020 | 8291 | 0.659778059 | 0 | 21048 | 8319 | 0.657545178 | 0 |
| 20965 | 8236 | 0.66202248 | 0 | 20993 | 8264 | 0.660774148 | 0 | 21021 | 8292 | 0.659778059 | 0 | 21049 | 8320 | 0.657545178 | 0 |
| 20966 | 8237 | 0.66202248 | -0.068975592 | 20994 | 8265 | 0.660774148 | 0 | 21022 | 8293 | 0.659778059 | 0 | 21050 | 8321 | 0.657545178 | 0 |
| 20967 | 8238 | 0.661701138 | 0 | 20995 | 8266 | 0.660774148 | 0 | 21023 | 8294 | 0.659778059 | 0 | 21051 | 8322 | 0.657545178 | 0 |
| 20968 | 8239 | 0.661701138 | 0 | 20996 | 8267 | 0.660550688 | 0 | 21024 | 8295 | 0.659778059 | -0.635491443 | 21052 | 8323 | 0.657545178 | 0 |
| 20969 | 8240 | 0.661701138 | 0 | 20997 | 8268 | 0.660550688 | 0 | 21025 | 8296 | 0.659618186 | 0 | 21053 | 8324 | 0.657545178 | 0 |
| 20970 | 8241 | 0.661701138 | 0 | 20998 | 8269 | 0.660450168 | 0 | 21026 | 8297 | 0.659618186 | 0 | 21054 | 8325 | 0.657545178 | 0 |
| 20971 | 8242 | 0.661701138 | 0 | 20999 | 8270 | 0.660450168 | 0 | 21027 | 8298 | 0.659618186 | 0 | 21055 | 8326 | 0.657545178 | 0 |
| 20972 | 8243 | 0.661701138 | 0 | 21000 | 8271 | 0.660450168 | 0 | 21028 | 8299 | 0.659479678 | 0 | 21056 | 8327 | 0.657545178 | 0 |
| 20973 | 8244 | 0.661701138 | 0 | 21001 | 8272 | 0.660450168 | 0 | 21029 | 8300 | 0.659479678 | 0 | 21057 | 8328 | 0.657545178 | 0 |
| 20974 | 8245 | 0.661701138 | 0 | 21002 | 8273 | 0.660450168 | 0 | 21030 | 8301 | 0.659479678 | 0 | 21058 | 8329 | 0.657545178 | 0 |
| 20975 | 8246 | 0.661701138 | 0 | 21003 | 8274 | 0.660450168 | 0 | 21031 | 8302 | 0.659358518 | 0 | 21059 | 8330 | 0.657545178 | 0 |
| 20976 | 8247 | 0.661701138 | 0 | 21004 | 8275 | 0.660450168 | 0 | 21032 | 8303 | 0.659358518 | 0 | 21060 | 8331 | 0.657545178 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21061 | 8332 | 0.657545178 | 0 | 21089 | 8360 | 0.656168649 | 0 | 21117 | 8388 | 0.654921034 | 0 | 21145 | 8416 | 0.653941053 | 0 |
| 21062 | 8333 | 0.657545178 | 0 | 21090 | 8361 | 0.656099937 | 0 | 21118 | 8389 | 0.654921034 | 0 | 21146 | 8417 | 0.653785029 | 0 |
| 21063 | 8334 | 0.657545178 | 0 | 21091 | 8362 | 0.656024005 | 0 | 21119 | 8390 | 0.654659489 | 0 | 21147 | 8418 | 0.653785029 | 0 |
| 21064 | 8335 | 0.657545178 | 0 | 21092 | 8363 | 0.656024005 | 0 | 21120 | 8391 | 0.654659489 | 0 | 21148 | 8419 | 0.653785029 | 0 |
| 21065 | 8336 | 0.657545178 | 0 | 21093 | 8364 | 0.655845393 | 0 | 21121 | 8392 | 0.654659489 | 0 | 21149 | 8420 | 0.653785029 | 0 |
| 21066 | 8337 | 0.657545178 | 0 | 21094 | 8365 | 0.655845393 | 0 | 21122 | 8393 | 0.654659489 | 0 | 21150 | 8421 | 0.653701839 | 0 |
| 21067 | 8338 | 0.657545178 | 0 | 21095 | 8366 | 0.655845393 | 0 | 21123 | 8394 | 0.654659489 | 0 | 21151 | 8422 | 0.653650134 | 0 |
| 21068 | 8339 | 0.657545178 | 0 | 21096 | 8367 | 0.655739377 | 0 | 21124 | 8395 | 0.654659489 | 0 | 21152 | 8423 | 0.653428612 | 0 |
| 21069 | 8340 | 0.657545178 | 0 | 21097 | 8368 | 0.655739377 | 0 | 21125 | 8396 | 0.654560324 | 0 | 21153 | 8424 | 0.653428612 | 0 |
| 21070 | 8341 | 0.657545178 | 0 | 21098 | 8369 | 0.655619257 | 0 | 21126 | 8397 | 0.654560324 | 0 | 21154 | 8425 | 0.653428612 | 0 |
| 21071 | 8342 | 0.657545178 | 0 | 21099 | 8370 | 0.655619257 | 0 | 21127 | 8398 | 0.654340038 | 0 | 21155 | 8426 | 0.653428612 | 0 |
| 21072 | 8343 | 0.657545178 | 0 | 21100 | 8371 | 0.655619257 | 0 | 21128 | 8399 | 0.654340038 | 0 | 21156 | 8427 | 0.653428612 | 0 |
| 21073 | 8344 | 0.657545178 | 0 | 21101 | 8372 | 0.655619257 | 0 | 21129 | 8400 | 0.654340038 | 0 | 21157 | 8428 | 0.653428612 | 0 |
| 21074 | 8345 | 0.657545178 | 0 | 21102 | 8373 | 0.655619257 | 0 | 21130 | 8401 | 0.654340038 | 0 | 21158 | 8429 | 0.653428612 | 0 |
| 21075 | 8346 | 0.657545178 | 0 | 21103 | 8374 | 0.655482017 | 0 | 21131 | 8402 | 0.654340038 | 0 | 21159 | 8430 | 0.653428612 | 0 |
| 21076 | 8347 | 0.657545178 | -1.256174732 | 21104 | 8375 | 0.655482017 | 0 | 21132 | 8403 | 0.654340038 | 0 | 21160 | 8431 | 0.653428612 | 0 |
| 21077 | 8348 | 0.657545178 | -1.343324908 | 21105 | 8376 | 0.655323718 | 0 | 21133 | 8404 | 0.654340038 | 0 | 21161 | 8432 | 0.653428612 | 0 |
| 21078 | 8349 | 0.657545178 | -1.176993486 | 21106 | 8377 | 0.655323718 | 0 | 21134 | 8405 | 0.654340038 | 0 | 21162 | 8433 | 0.653180372 | 0 |
| 21079 | 8350 | 0.6566687 | 0 | 21107 | 8378 | 0.655323718 | 0 | 21135 | 8406 | 0.654340038 | 0 | 21163 | 8434 | 0.653113563 | 0 |
| 21080 | 8351 | 0.656612214 | 0 | 21108 | 8379 | 0.655323718 | 0 | 21136 | 8407 | 0.654152235 | 0 | 21164 | 8435 | 0.653113563 | 0 |
| 21081 | 8352 | 0.656547945 | 0 | 21109 | 8380 | 0.655139108 | 0 | 21137 | 8408 | 0.654084646 | 0 | 21165 | 8436 | 0.653113563 | 0 |
| 21082 | 8353 | 0.656547945 | -1.464297457 | 21110 | 8381 | 0.655139108 | 0 | 21138 | 8409 | 0.654084646 | 0 | 21166 | 8437 | 0.653113563 | 0 |
| 21083 | 8354 | 0.656474167 | 0 | 21111 | 8382 | 0.655070559 | 0 | 21139 | 8410 | 0.654084646 | 0 | 21167 | 8438 | 0.65299755 | 0 |
| 21084 | 8355 | 0.656474167 | 0 | 21112 | 8383 | 0.654921034 | 0 | 21140 | 8411 | 0.654084646 | 0 | 21168 | 8439 | 0.65299755 | 0 |
| 21085 | 8356 | 0.656388601 | 0 | 21113 | 8384 | 0.654921034 | 0 | 21141 | 8412 | 0.654084646 | -0.360910083 | 21169 | 8440 | 0.65299755 | 0 |
| 21086 | 8357 | 0.656288174 | 0 | 21114 | 8385 | 0.654921034 | 0 | 21142 | 8413 | 0.653941053 | 0 | 21170 | 8441 | 0.65299755 | 0 |
| 21087 | 8358 | 0.656168649 | 0 | 21115 | 8386 | 0.654921034 | 0 | 21143 | 8414 | 0.653941053 | 0 | 21171 | 8442 | 0.652900273 | 0 |
| 21088 | 8359 | 0.656168649 | 0 | 21116 | 8387 | 0.654921034 | 0 | 21144 | 8415 | 0.653941053 | 0 | 21172 | 8443 | 0.652746295 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21173 | 8444 | 0.652746295 | 0 | 21201 | 8472 | 0.651792849 | 0 | 21229 | 8500 | 0.650914599 | 0 | 21257 | 8528 | 0.649513083 | 0 |
| 21174 | 8445 | 0.652746295 | 0 | 21202 | 8473 | 0.651792849 | 0 | 21230 | 8501 | 0.650914599 | 0 | 21258 | 8529 | 0.649350699 | 0 |
| 21175 | 8446 | 0.652746295 | 0 | 21203 | 8474 | 0.651792849 | 0 | 21231 | 8502 | 0.650785594 | 0 | 21259 | 8530 | 0.649350699 | 0 |
| 21176 | 8447 | 0.652746295 | 0 | 21204 | 8475 | 0.651792849 | 0 | 21232 | 8503 | 0.650705753 | 0 | 21260 | 8531 | 0.649350699 | 0 |
| 21177 | 8448 | 0.652746295 | 0 | 21205 | 8476 | 0.651792849 | -0.70562456 | 21233 | 8504 | 0.650705753 | 0 | 21261 | 8532 | 0.649350699 | 0 |
| 21178 | 8449 | 0.652581758 | 0 | 21206 | 8477 | 0.651792849 | -1.404594565 | 21234 | 8505 | 0.650705753 | 0 | 21262 | 8533 | 0.649219789 | 0 |
| 21179 | 8450 | 0.652465652 | 0 | 21207 | 8478 | 0.651384869 | 0 | 21235 | 8506 | 0.650705753 | 0 | 21263 | 8534 | 0.64911201 | 0 |
| 21180 | 8451 | 0.652465652 | 0 | 21208 | 8479 | 0.651384869 | -1.153190571 | 21236 | 8507 | 0.650705753 | 0 | 21264 | 8535 | 0.64911201 | 0 |
| 21181 | 8452 | 0.652465652 | 0 | 21209 | 8480 | 0.651296228 | 0 | 21237 | 8508 | 0.650366593 | 0 | 21265 | 8536 | 0.64911201 | 0 |
| 21182 | 8453 | 0.652465652 | 0 | 21210 | 8481 | 0.651296228 | 0 | 21238 | 8509 | 0.650366593 | 0 | 21266 | 8537 | 0.64911201 | 0 |
| 21183 | 8454 | 0.652465652 | 0 | 21211 | 8482 | 0.651296228 | 0 | 21239 | 8510 | 0.650366593 | 0 | 21267 | 8538 | 0.64911201 | 0 |
| 21184 | 8455 | 0.652312651 | 0 | 21212 | 8483 | 0.651158379 | 0 | 21240 | 8511 | 0.650366593 | 0 | 21268 | 8539 | 0.64911201 | 0 |
| 21185 | 8456 | 0.652312651 | 0 | 21213 | 8484 | 0.651158379 | 0 | 21241 | 8512 | 0.650366593 | 0 | 21269 | 8540 | 0.648945006 | 0 |
| 21186 | 8457 | 0.652312651 | 0 | 21214 | 8485 | 0.651158379 | 0 | 21242 | 8513 | 0.650163224 | 0 | 21270 | 8541 | 0.648945006 | 0 |
| 21187 | 8458 | 0.652216344 | 0 | 21215 | 8486 | 0.651158379 | 0 | 21243 | 8514 | 0.650102985 | 0 | 21271 | 8542 | 0.648945006 | 0 |
| 21188 | 8459 | 0.652216344 | 0 | 21216 | 8487 | 0.651158379 | 0 | 21244 | 8515 | 0.650102985 | 0 | 21272 | 8543 | 0.648945006 | 0 |
| 21189 | 8460 | 0.652216344 | 0 | 21217 | 8488 | 0.651158379 | 0 | 21245 | 8516 | 0.650102985 | 0 | 21273 | 8544 | 0.648945006 | 0 |
| 21190 | 8461 | 0.651792849 | 0 | 21218 | 8489 | 0.651158379 | 0 | 21246 | 8517 | 0.650102985 | 0 | 21274 | 8545 | 0.648821609 | 0 |
| 21191 | 8462 | 0.651792849 | 0 | 21219 | 8490 | 0.651158379 | 0 | 21247 | 8518 | 0.64999204 | 0 | 21275 | 8546 | 0.648821609 | 0 |
| 21192 | 8463 | 0.651792849 | 0 | 21220 | 8491 | 0.651056132 | 0 | 21248 | 8519 | 0.649892214 | 0 | 21276 | 8547 | 0.648821609 | 0 |
| 21193 | 8464 | 0.651792849 | 0 | 21221 | 8492 | 0.651056132 | 0 | 21249 | 8520 | 0.649892214 | 0 | 21277 | 8548 | 0.648821609 | -1.371353631 |
| 21194 | 8465 | 0.651792849 | 0 | 21222 | 8493 | 0.651056132 | 0 | 21250 | 8521 | 0.64971984 | 0 | 21278 | 8549 | 0.648726713 | 0 |
| 21195 | 8466 | 0.651792849 | 0 | 21223 | 8494 | 0.651056132 | 0 | 21251 | 8522 | 0.64971984 | 0 | 21279 | 8550 | 0.648726713 | -0.009720692 |
| 21196 | 8467 | 0.651792849 | 0 | 21224 | 8495 | 0.651056132 | 0 | 21252 | 8523 | 0.64971984 | 0 | 21280 | 8551 | 0.648651465 | 0 |
| 21197 | 8468 | 0.651792849 | 0 | 21225 | 8496 | 0.650914599 | 0 | 21253 | 8524 | 0.64971984 | 0 | 21281 | 8552 | 0.648590335 | 0 |
| 21198 | 8469 | 0.651792849 | 0 | 21226 | 8497 | 0.650914599 | 0 | 21254 | 8525 | 0.64971984 | 0 | 21282 | 8553 | 0.648539691 | 0 |
| 21199 | 8470 | 0.651792849 | 0 | 21227 | 8498 | 0.650914599 | 0 | 21255 | 8526 | 0.649513083 | 0 | 21283 | 8554 | 0.64799986 | 0 |
| 21200 | 8471 | 0.651792849 | 0 | 21228 | 8499 | 0.650914599 | 0 | 21256 | 8527 | 0.649513083 | 0 | 21284 | 8555 | 0.64799986 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21285 | 8556 | 0.64799986 | 0 | 21313 | 8584 | 0.646821312 | 0 | 21341 | 8612 | 0.645645954 | 0 | 21369 | 8640 | 0.644580201 | 0 |
| 21286 | 8557 | 0.64799986 | 0 | 21314 | 8585 | 0.646821312 | 0 | 21342 | 8613 | 0.645645954 | -1.393012692 | 21370 | 8641 | 0.644383732 | 0 |
| 21287 | 8558 | 0.64799986 | 0 | 21315 | 8586 | 0.646699576 | 0 | 21343 | 8614 | 0.645310721 | 0 | 21371 | 8642 | 0.644383732 | 0 |
| 21288 | 8559 | 0.64799986 | 0 | 21316 | 8587 | 0.646549793 | 0 | 21344 | 8615 | 0.645310721 | 0 | 21372 | 8643 | 0.644383732 | 0 |
| 21289 | 8560 | 0.64799986 | 0 | 21317 | 8588 | 0.646549793 | 0 | 21345 | 8616 | 0.645310721 | 0 | 21373 | 8644 | 0.644383732 | 0 |
| 21290 | 8561 | 0.64799986 | 0 | 21318 | 8589 | 0.646549793 | 0 | 21346 | 8617 | 0.645310721 | 0 | 21374 | 8645 | 0.644239711 | 0 |
| 21291 | 8562 | 0.64799986 | 0 | 21319 | 8590 | 0.646549793 | 0 | 21347 | 8618 | 0.645310721 | 0 | 21375 | 8646 | 0.644239711 | 0 |
| 21292 | 8563 | 0.64799986 | 0 | 21320 | 8591 | 0.646361011 | 0 | 21348 | 8619 | 0.645310721 | 0 | 21376 | 8647 | 0.644239711 | 0 |
| 21293 | 8564 | 0.64799986 | 0 | 21321 | 8592 | 0.646361011 | 0 | 21349 | 8620 | 0.645310721 | -1.335355978 | 21377 | 8648 | 0.644239711 | 0 |
| 21294 | 8565 | 0.64799986 | -0.186538804 | 21322 | 8593 | 0.646115716 | 0 | 21350 | 8621 | 0.644989141 | 0 | 21378 | 8649 | 0.644239711 | 0 |
| 21295 | 8566 | 0.64799986 | -0.446176115 | 21323 | 8594 | 0.646115716 | 0 | 21351 | 8622 | 0.644989141 | 0 | 21379 | 8650 | 0.644239711 | 0 |
| 21296 | 8567 | 0.64799986 | -1.4875688 | 21324 | 8595 | 0.646115716 | 0 | 21352 | 8623 | 0.644989141 | 0 | 21380 | 8651 | 0.64412961 | 0 |
| 21297 | 8568 | 0.647444851 | 0 | 21325 | 8596 | 0.646115716 | 0 | 21353 | 8624 | 0.644989141 | 0 | 21381 | 8652 | 0.64412961 | 0 |
| 21298 | 8569 | 0.647326013 | 0 | 21326 | 8597 | 0.646115716 | 0 | 21354 | 8625 | 0.644989141 | 0 | 21382 | 8653 | 0.644042707 | 0 |
| 21299 | 8570 | 0.647245221 | 0 | 21327 | 8598 | 0.646115716 | -1.313361685 | 21355 | 8626 | 0.644989141 | 0 | 21383 | 8654 | 0.644042707 | 0 |
| 21300 | 8571 | 0.647245221 | 0 | 21328 | 8599 | 0.64590687 | 0 | 21356 | 8627 | 0.644989141 | -0.235307014 | 21384 | 8655 | 0.644042707 | 0 |
| 21301 | 8572 | 0.647245221 | 0 | 21329 | 8600 | 0.64590687 | 0 | 21357 | 8628 | 0.644864146 | 0 | 21385 | 8656 | 0.644042707 | 0 |
| 21302 | 8573 | 0.647142417 | 0 | 21330 | 8601 | 0.64590687 | 0 | 21358 | 8629 | 0.644864146 | 0 | 21386 | 8657 | 0.643914275 | 0 |
| 21303 | 8574 | 0.647142417 | 0 | 21331 | 8602 | 0.64590687 | -1.443904299 | 21359 | 8630 | 0.644864146 | 0 | 21387 | 8658 | 0.643914275 | 0 |
| 21304 | 8575 | 0.647142417 | 0 | 21332 | 8603 | 0.645784067 | 0 | 21360 | 8631 | 0.644864146 | 0 | 21388 | 8659 | 0.643914275 | 0 |
| 21305 | 8576 | 0.647142417 | 0 | 21333 | 8604 | 0.645784067 | 0 | 21361 | 8632 | 0.644864146 | 0 | 21389 | 8660 | 0.643823919 | 0 |
| 21306 | 8577 | 0.647142417 | -0.876606414 | 21334 | 8605 | 0.645784067 | 0 | 21362 | 8633 | 0.644864146 | 0 | 21390 | 8661 | 0.643823919 | 0 |
| 21307 | 8578 | 0.647007186 | 0 | 21335 | 8606 | 0.645784067 | 0 | 21363 | 8634 | 0.644864146 | 0 | 21391 | 8662 | 0.643756893 | 0 |
| 21308 | 8579 | 0.647007186 | 0 | 21336 | 8607 | 0.645784067 | 0 | 21364 | 8635 | 0.644756421 | 0 | 21392 | 8663 | 0.643756893 | 0 |
| 21309 | 8580 | 0.646922205 | 0 | 21337 | 8608 | 0.645784067 | 0 | 21365 | 8636 | 0.644580201 | 0 | 21393 | 8664 | 0.643304739 | 0 |
| 21310 | 8581 | 0.646821312 | 0 | 21338 | 8609 | 0.645784067 | 0 | 21366 | 8637 | 0.644580201 | 0 | 21394 | 8665 | 0.643304739 | 0 |
| 21311 | 8582 | 0.646821312 | 0 | 21339 | 8610 | 0.645645954 | 0 | 21367 | 8638 | 0.644580201 | 0 | 21395 | 8666 | 0.643304739 | 0 |
| 21312 | 8583 | 0.646821312 | 0 | 21340 | 8611 | 0.645645954 | 0 | 21368 | 8639 | 0.644580201 | 0 | 21396 | 8667 | 0.643304739 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21397 | 8668 | 0.643304739 | 0 | 21425 | 8696 | 0.64222842 | 0 | 21453 | 8724 | 0.640511838 | 0 | 21481 | 8752 | 0.639816411 | 0 |
| 21398 | 8669 | 0.643304739 | 0 | 21426 | 8697 | 0.642105581 | 0 | 21454 | 8725 | 0.640511838 | 0 | 21482 | 8753 | 0.63968775 | 0 |
| 21399 | 8670 | 0.643304739 | 0 | 21427 | 8698 | 0.642033012 | 0 | 21455 | 8726 | 0.640511838 | 0 | 21483 | 8754 | 0.639500675 | 0 |
| 21400 | 8671 | 0.643304739 | 0 | 21428 | 8699 | 0.642033012 | 0 | 21456 | 8727 | 0.640511838 | 0 | 21484 | 8755 | 0.639500675 | 0 |
| 21401 | 8672 | 0.643304739 | 0 | 21429 | 8700 | 0.641750911 | 0 | 21457 | 8728 | 0.640511838 | 0 | 21485 | 8756 | 0.639500675 | 0 |
| 21402 | 8673 | 0.643304739 | 0 | 21430 | 8701 | 0.641750911 | 0 | 21458 | 8729 | 0.640511838 | 0 | 21486 | 8757 | 0.639500675 | 0 |
| 21403 | 8674 | 0.643304739 | 0 | 21431 | 8702 | 0.641750911 | 0 | 21459 | 8730 | 0.640511838 | 0 | 21487 | 8758 | 0.639500675 | 0 |
| 21404 | 8675 | 0.643304739 | 0 | 21432 | 8703 | 0.641750911 | 0 | 21460 | 8731 | 0.640511838 | 0 | 21488 | 8759 | 0.639500675 | 0 |
| 21405 | 8676 | 0.643304739 | 0 | 21433 | 8704 | 0.641750911 | 0 | 21461 | 8732 | 0.640511838 | 0 | 21489 | 8760 | 0.639500675 | 0 |
| 21406 | 8677 | 0.643304739 | 0 | 21434 | 8705 | 0.641557072 | 0 | 21462 | 8733 | 0.640511838 | 0 | 21490 | 8761 | 0.639500675 | 0 |
| 21407 | 8678 | 0.643304739 | 0 | 21435 | 8706 | 0.641481246 | 0 | 21463 | 8734 | 0.640511838 | 0 | 21491 | 8762 | 0.639500675 | -1.060339415 |
| 21408 | 8679 | 0.643304739 | 0 | 21436 | 8707 | 0.641481246 | 0 | 21464 | 8735 | 0.640511838 | 0 | 21492 | 8763 | 0.639320358 | 0 |
| 21409 | 8680 | 0.643304739 | 0 | 21437 | 8708 | 0.641481246 | -1.378693995 | 21465 | 8736 | 0.640511838 | -1.318965562 | 21493 | 8764 | 0.639203722 | 0 |
| 21410 | 8681 | 0.643304739 | 0 | 21438 | 8709 | 0.641307979 | 0 | 21466 | 8737 | 0.640511838 | -1.415875575 | 21494 | 8765 | 0.639203722 | 0 |
| 21411 | 8682 | 0.643304739 | -1.395353908 | 21439 | 8710 | 0.641187258 | 0 | 21467 | 8738 | 0.640152769 | 0 | 21495 | 8766 | 0.639203722 | 0 |
| 21412 | 8683 | 0.642821921 | 0 | 21440 | 8711 | 0.641187258 | 0 | 21468 | 8739 | 0.640152769 | 0 | 21496 | 8767 | 0.639203722 | 0 |
| 21413 | 8684 | 0.64274472 | 0 | 21441 | 8712 | 0.641098327 | 0 | 21469 | 8740 | 0.640083751 | 0 | 21497 | 8768 | 0.639203722 | 0 |
| 21414 | 8685 | 0.64274472 | 0 | 21442 | 8713 | 0.641098327 | 0 | 21470 | 8741 | 0.640083751 | 0 | 21498 | 8769 | 0.639203722 | 0 |
| 21415 | 8686 | 0.642638131 | 0 | 21443 | 8714 | 0.641098327 | 0 | 21471 | 8742 | 0.640083751 | 0 | 21499 | 8770 | 0.639061772 | 0 |
| 21416 | 8687 | 0.642638131 | 0 | 21444 | 8715 | 0.641098327 | 0 | 21472 | 8743 | 0.640083751 | 0 | 21500 | 8771 | 0.639061772 | 0 |
| 21417 | 8688 | 0.642638131 | 0 | 21445 | 8716 | 0.641098327 | 0 | 21473 | 8744 | 0.640083751 | 0 | 21501 | 8772 | 0.639061772 | 0 |
| 21418 | 8689 | 0.642638131 | 0 | 21446 | 8717 | 0.641098327 | 0 | 21474 | 8745 | 0.639981888 | 0 | 21502 | 8773 | 0.639061772 | 0 |
| 21419 | 8690 | 0.642481431 | 0 | 21447 | 8718 | 0.641098327 | -0.995072683 | 21475 | 8746 | 0.639981888 | 0 | 21503 | 8774 | 0.639061772 | 0 |
| 21420 | 8691 | 0.642481431 | 0 | 21448 | 8719 | 0.640976076 | 0 | 21476 | 8747 | 0.639981888 | 0 | 21504 | 8775 | 0.639061772 | 0 |
| 21421 | 8692 | 0.642481431 | -1.246414895 | 21449 | 8720 | 0.640976076 | 0 | 21477 | 8748 | 0.639981888 | -0.437594825 | 21505 | 8776 | 0.639061772 | -0.779053477 |
| 21422 | 8693 | 0.642371775 | 0 | 21450 | 8721 | 0.640839484 | 0 | 21478 | 8749 | 0.639816411 | 0 | 21506 | 8777 | 0.639061772 | -0.536015429 |
| 21423 | 8694 | 0.64222842 | 0 | 21451 | 8722 | 0.640797465 | 0 | 21479 | 8750 | 0.639816411 | 0 | 21507 | 8778 | 0.638978582 | 0 |
| 21424 | 8695 | 0.64222842 | 0 | 21452 | 8723 | 0.640511838 | 0 | 21480 | 8751 | 0.639816411 | 0 | 21508 | 8779 | 0.638978582 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21509 | 8780 | 0.638659834 | 0 | 21537 | 8808 | 0.638173774 | -0.821905977 | 21565 | 8836 | 0.637069592 | -1.182745815 | 21593 | 8864 | 0.635950564 | 0 |
| 21510 | 8781 | 0.638659834 | 0 | 21538 | 8809 | 0.637949622 | 0 | 21566 | 8837 | 0.636983019 | 0 | 21594 | 8865 | 0.635950564 | 0 |
| 21511 | 8782 | 0.638659834 | 0 | 21539 | 8810 | 0.637949622 | 0 | 21567 | 8838 | 0.636983019 | 0 | 21595 | 8866 | 0.635950564 | 0 |
| 21512 | 8783 | 0.638659834 | 0 | 21540 | 8811 | 0.637949622 | 0 | 21568 | 8839 | 0.636815693 | 0 | 21596 | 8867 | 0.635950564 | 0 |
| 21513 | 8784 | 0.638659834 | 0 | 21541 | 8812 | 0.637949622 | 0 | 21569 | 8840 | 0.636815693 | 0 | 21597 | 8868 | 0.635825928 | 0 |
| 21514 | 8785 | 0.638659834 | 0 | 21542 | 8813 | 0.637949622 | 0 | 21570 | 8841 | 0.636815693 | 0 | 21598 | 8869 | 0.635825928 | 0 |
| 21515 | 8786 | 0.638659834 | 0 | 21543 | 8814 | 0.637820617 | 0 | 21571 | 8842 | 0.636815693 | 0 | 21599 | 8870 | 0.635825928 | 0 |
| 21516 | 8787 | 0.638659834 | 0 | 21544 | 8815 | 0.637736784 | 0 | 21572 | 8843 | 0.636655702 | 0 | 21600 | 8871 | 0.635825928 | 0 |
| 21517 | 8788 | 0.638659834 | 0 | 21545 | 8816 | 0.637736784 | 0 | 21573 | 8844 | 0.636655702 | 0 | 21601 | 8872 | 0.635825928 | 0 |
| 21518 | 8789 | 0.638659834 | 0 | 21546 | 8817 | 0.637736784 | 0 | 21574 | 8845 | 0.636655702 | 0 | 21602 | 8873 | 0.635825928 | 0 |
| 21519 | 8790 | 0.638659834 | 0 | 21547 | 8818 | 0.637736784 | 0 | 21575 | 8846 | 0.636655702 | 0 | 21603 | 8874 | 0.635590602 | 0 |
| 21520 | 8791 | 0.638659834 | 0 | 21548 | 8819 | 0.637736784 | 0 | 21576 | 8847 | 0.636655702 | 0 | 21604 | 8875 | 0.635590602 | 0 |
| 21521 | 8792 | 0.638659834 | 0 | 21549 | 8820 | 0.637634344 | 0 | 21577 | 8848 | 0.636655702 | -1.383519539 | 21605 | 8876 | 0.635590602 | 0 |
| 21522 | 8793 | 0.638659834 | 0 | 21550 | 8821 | 0.637634344 | 0 | 21578 | 8849 | 0.636578309 | 0 | 21606 | 8877 | 0.635590602 | 0 |
| 21523 | 8794 | 0.638659834 | -0.496908826 | 21551 | 8822 | 0.637574097 | 0 | 21579 | 8850 | 0.636355879 | 0 | 21607 | 8878 | 0.635590602 | 0 |
| 21524 | 8795 | 0.638361861 | 0 | 21552 | 8823 | 0.637341792 | 0 | 21580 | 8851 | 0.636355879 | 0 | 21608 | 8879 | 0.635590602 | 0 |
| 21525 | 8796 | 0.638361861 | 0 | 21553 | 8824 | 0.637341792 | 0 | 21581 | 8852 | 0.636355879 | 0 | 21609 | 8880 | 0.635590602 | 0 |
| 21526 | 8797 | 0.638290378 | 0 | 21554 | 8825 | 0.637341792 | 0 | 21582 | 8853 | 0.636355879 | 0 | 21610 | 8881 | 0.635372199 | 0 |
| 21527 | 8798 | 0.638290378 | 0 | 21555 | 8826 | 0.637341792 | 0 | 21583 | 8854 | 0.636355879 | 0 | 21611 | 8882 | 0.635372199 | 0 |
| 21528 | 8799 | 0.638290378 | 0 | 21556 | 8827 | 0.637341792 | 0 | 21584 | 8855 | 0.636355879 | 0 | 21612 | 8883 | 0.635268783 | 0 |
| 21529 | 8800 | 0.638290378 | -0.572998995 | 21557 | 8828 | 0.637341792 | 0 | 21585 | 8856 | 0.636355879 | 0 | 21613 | 8884 | 0.635268783 | 0 |
| 21530 | 8801 | 0.638173774 | 0 | 21558 | 8829 | 0.637341792 | 0 | 21586 | 8857 | 0.636355879 | -0.288359416 | 21614 | 8885 | 0.635268783 | 0 |
| 21531 | 8802 | 0.638173774 | 0 | 21559 | 8830 | 0.637341792 | 0 | 21587 | 8858 | 0.636147033 | 0 | 21615 | 8886 | 0.635168957 | 0 |
| 21532 | 8803 | 0.638173774 | 0 | 21560 | 8831 | 0.637341792 | 0 | 21588 | 8859 | 0.636080224 | 0 | 21616 | 8887 | 0.63497935 | 0 |
| 21533 | 8804 | 0.638173774 | 0 | 21561 | 8832 | 0.637341792 | 0 | 21589 | 8860 | 0.636080224 | 0 | 21617 | 8888 | 0.63497935 | 0 |
| 21534 | 8805 | 0.638173774 | 0 | 21562 | 8833 | 0.637341792 | 0 | 21590 | 8861 | 0.636080224 | 0 | 21618 | 8889 | 0.63497935 | 0 |
| 21535 | 8806 | 0.638173774 | 0 | 21563 | 8834 | 0.637341792 | 0 | 21591 | 8862 | 0.636080224 | 0 | 21619 | 8890 | 0.63497935 | 0 |
| 21536 | 8807 | 0.638173774 | 0 | 21564 | 8835 | 0.637122506 | 0 | 21592 | 8863 | 0.635950564 | 0 | 21620 | 8891 | 0.63497935 | -0.210554698 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21621 | 8892 | 0.63497935 | -1.023468055 | 21649 | 8920 | 0.633150739 | 0 | 21677 | 8948 | 0.632109265 | 0 | 21705 | 8976 | 0.631329795 | 0 |
| 21622 | 8893 | 0.634717648 | 0 | 21650 | 8921 | 0.633150739 | 0 | 21678 | 8949 | 0.632109265 | 0 | 21706 | 8977 | 0.631329795 | 0 |
| 21623 | 8894 | 0.634717648 | 0 | 21651 | 8922 | 0.633150739 | 0 | 21679 | 8950 | 0.632109265 | 0 | 21707 | 8978 | 0.631216239 | 0 |
| 21624 | 8895 | 0.634717648 | -0.141829069 | 21652 | 8923 | 0.633150739 | 0 | 21680 | 8951 | 0.631991073 | 0 | 21708 | 8979 | 0.631116067 | 0 |
| 21625 | 8896 | 0.634479874 | 0 | 21653 | 8924 | 0.633150739 | -1.201387925 | 21681 | 8952 | 0.631991073 | 0 | 21709 | 8980 | 0.630875749 | 0 |
| 21626 | 8897 | 0.634479874 | 0 | 21654 | 8925 | 0.633150739 | -1.502417921 | 21682 | 8953 | 0.631991073 | 0 | 21710 | 8981 | 0.629516454 | 0 |
| 21627 | 8898 | 0.634479874 | 0 | 21655 | 8926 | 0.633033028 | 0 | 21683 | 8954 | 0.631991073 | 0 | 21711 | 8982 | 0.629516454 | 0 |
| 21628 | 8899 | 0.634479874 | 0 | 21656 | 8927 | 0.632922703 | 0 | 21684 | 8955 | 0.631991073 | 0 | 21712 | 8983 | 0.629516454 | 0 |
| 21629 | 8900 | 0.634262889 | 0 | 21657 | 8928 | 0.632922703 | 0 | 21685 | 8956 | 0.631991073 | 0 | 21713 | 8984 | 0.629516454 | 0 |
| 21630 | 8901 | 0.634262889 | 0 | 21658 | 8929 | 0.632922703 | 0 | 21686 | 8957 | 0.631991073 | 0 | 21714 | 8985 | 0.629516454 | 0 |
| 21631 | 8902 | 0.634262889 | -0.043489671 | 21659 | 8930 | 0.632922703 | 0 | 21687 | 8958 | 0.631991073 | 0 | 21715 | 8986 | 0.629516454 | 0 |
| 21632 | 8903 | 0.634064082 | 0 | 21660 | 8931 | 0.632922703 | 0 | 21688 | 8959 | 0.631991073 | 0 | 21716 | 8987 | 0.629516454 | 0 |
| 21633 | 8904 | 0.634064082 | 0 | 21661 | 8932 | 0.632922703 | 0 | 21689 | 8960 | 0.631883187 | 0 | 21717 | 8988 | 0.629516454 | 0 |
| 21634 | 8905 | 0.634064082 | 0 | 21662 | 8933 | 0.632922703 | 0 | 21690 | 8961 | 0.631883187 | 0 | 21718 | 8989 | 0.629516454 | 0 |
| 21635 | 8906 | 0.63388126 | 0 | 21663 | 8934 | 0.63281909 | 0 | 21691 | 8962 | 0.631784316 | 0 | 21719 | 8990 | 0.629516454 | 0 |
| 21636 | 8907 | 0.633712569 | 0 | 21664 | 8935 | 0.632721594 | -1.256174732 | 21692 | 8963 | 0.631693373 | 0 | 21720 | 8991 | 0.629516454 | 0 |
| 21637 | 8908 | 0.633712569 | 0 | 21665 | 8936 | 0.632542909 | 0 | 21693 | 8964 | 0.631693373 | 0 | 21721 | 8992 | 0.629516454 | 0 |
| 21638 | 8909 | 0.633712569 | -0.184435679 | 21666 | 8937 | 0.632542909 | 0 | 21694 | 8965 | 0.631693373 | 0 | 21722 | 8993 | 0.629516454 | 0 |
| 21639 | 8910 | 0.633712569 | -1.138678188 | 21667 | 8938 | 0.632383095 | 0 | 21695 | 8966 | 0.631693373 | 0 | 21723 | 8994 | 0.629516454 | 0 |
| 21640 | 8911 | 0.633556432 | 0 | 21668 | 8939 | 0.632383095 | 0 | 21696 | 8967 | 0.631693373 | -1.123664044 | 21724 | 8995 | 0.629516454 | 0 |
| 21641 | 8912 | 0.633556432 | 0 | 21669 | 8940 | 0.632383095 | 0 | 21697 | 8968 | 0.631609444 | 0 | 21725 | 8996 | 0.629516454 | 0 |
| 21642 | 8913 | 0.633411498 | 0 | 21670 | 8941 | 0.632383095 | 0 | 21698 | 8969 | 0.631609444 | 0 | 21726 | 8997 | 0.629516454 | 0 |
| 21643 | 8914 | 0.633411498 | 0 | 21671 | 8942 | 0.632383095 | 0 | 21699 | 8970 | 0.631609444 | 0 | 21727 | 8998 | 0.629516454 | 0 |
| 21644 | 8915 | 0.633411498 | 0 | 21672 | 8943 | 0.632383095 | 0 | 21700 | 8971 | 0.631609444 | -0.839751318 | 21728 | 8999 | 0.629516454 | 0 |
| 21645 | 8916 | 0.633276603 | 0 | 21673 | 8944 | 0.632239312 | 0 | 21701 | 8972 | 0.631531745 | 0 | 21729 | 9000 | 0.629516454 | 0 |
| 21646 | 8917 | 0.633276603 | -0.64247076 | 21674 | 8945 | 0.632239312 | 0 | 21702 | 8973 | 0.631531745 | 0 | 21730 | 9001 | 0.629516454 | 0 |
| 21647 | 8918 | 0.633150739 | 0 | 21675 | 8946 | 0.632239312 | 0 | 21703 | 8974 | 0.631392459 | 0 | 21731 | 9002 | 0.629516454 | 0 |
| 21648 | 8919 | 0.633150739 | 0 | 21676 | 8947 | 0.632239312 | 0 | 21704 | 8975 | 0.631392459 | -1.489452944 | 21732 | 9003 | 0.629516454 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21733 | 9004 | 0.629516454 | 0 | 21761 | 9032 | 0.629516454 | 0 | 21789 | 9060 | 0.627581954 | 0 | 21817 | 9088 | 0.626668611 | 0 |
| 21734 | 9005 | 0.629516454 | 0 | 21762 | 9033 | 0.629516454 | 0 | 21790 | 9061 | 0.627510471 | 0 | 21818 | 9089 | 0.626668611 | 0 |
| 21735 | 9006 | 0.629516454 | 0 | 21763 | 9034 | 0.629516454 | 0 | 21791 | 9062 | 0.627433503 | 0 | 21819 | 9090 | 0.626668611 | 0 |
| 21736 | 9007 | 0.629516454 | 0 | 21764 | 9035 | 0.629516454 | 0 | 21792 | 9063 | 0.627433503 | -1.44598725 | 21820 | 9091 | 0.626668611 | -0.009502399 |
| 21737 | 9008 | 0.629516454 | 0 | 21765 | 9036 | 0.629516454 | 0 | 21793 | 9064 | 0.627350392 | 0 | 21821 | 9092 | 0.626510944 | 0 |
| 21738 | 9009 | 0.629516454 | 0 | 21766 | 9037 | 0.629516454 | 0 | 21794 | 9065 | 0.627350392 | 0 | 21822 | 9093 | 0.626510944 | 0 |
| 21739 | 9010 | 0.629516454 | 0 | 21767 | 9038 | 0.629516454 | 0 | 21795 | 9066 | 0.627350392 | 0 | 21823 | 9094 | 0.626510944 | 0 |
| 21740 | 9011 | 0.629516454 | 0 | 21768 | 9039 | 0.629516454 | 0 | 21796 | 9067 | 0.627350392 | 0 | 21824 | 9095 | 0.626510944 | 0 |
| 21741 | 9012 | 0.629516454 | 0 | 21769 | 9040 | 0.629516454 | 0 | 21797 | 9068 | 0.627350392 | -1.128007025 | 21825 | 9096 | 0.626510944 | 0 |
| 21742 | 9013 | 0.629516454 | 0 | 21770 | 9041 | 0.629516454 | 0 | 21798 | 9069 | 0.627260374 | 0 | 21826 | 9097 | 0.626510944 | 0 |
| 21743 | 9014 | 0.629516454 | 0 | 21771 | 9042 | 0.629516454 | 0 | 21799 | 9070 | 0.627260374 | 0 | 21827 | 9098 | 0.626510944 | -0.98617897 |
| 21744 | 9015 | 0.629516454 | 0 | 21772 | 9043 | 0.629516454 | 0 | 21800 | 9071 | 0.627260374 | 0 | 21828 | 9099 | 0.626334795 | 0 |
| 21745 | 9016 | 0.629516454 | 0 | 21773 | 9044 | 0.629516454 | 0 | 21801 | 9072 | 0.627260374 | 0 | 21829 | 9100 | 0.626334795 | -0.032112609 |
| 21746 | 9017 | 0.629516454 | 0 | 21774 | 9045 | 0.629516454 | 0 | 21802 | 9073 | 0.627260374 | 0 | 21830 | 9101 | 0.626334795 | -0.961531535 |
| 21747 | 9018 | 0.629516454 | 0 | 21775 | 9046 | 0.629516454 | 0 | 21803 | 9074 | 0.627162549 | 0 | 21831 | 9102 | 0.626238744 | 0 |
| 21748 | 9019 | 0.629516454 | 0 | 21776 | 9047 | 0.629516454 | 0 | 21804 | 9075 | 0.627055856 | 0 | 21832 | 9103 | 0.626136713 | 0 |
| 21749 | 9020 | 0.629516454 | 0 | 21777 | 9048 | 0.629516454 | -0.028930951 | 21805 | 9076 | 0.627055856 | 0 | 21833 | 9104 | 0.626136713 | 0 |
| 21750 | 9021 | 0.629516454 | 0 | 21778 | 9049 | 0.629516454 | -0.545560747 | 21806 | 9077 | 0.627055856 | 0 | 21834 | 9105 | 0.626136713 | 0 |
| 21751 | 9022 | 0.629516454 | 0 | 21779 | 9050 | 0.629516454 | -1.20502221 | 21807 | 9078 | 0.627055856 | 0 | 21835 | 9106 | 0.626136713 | 0 |
| 21752 | 9023 | 0.629516454 | 0 | 21780 | 9051 | 0.629516454 | -1.460294715 | 21808 | 9079 | 0.626939031 | 0 | 21836 | 9107 | 0.626136713 | 0 |
| 21753 | 9024 | 0.629516454 | 0 | 21781 | 9052 | 0.629516454 | -1.476088982 | 21809 | 9080 | 0.626939031 | 0 | 21837 | 9108 | 0.62591233 | 0 |
| 21754 | 9025 | 0.629516454 | 0 | 21782 | 9053 | 0.629516454 | -1.560409868 | 21810 | 9081 | 0.626939031 | 0 | 21838 | 9109 | 0.62591233 | 0 |
| 21755 | 9026 | 0.629516454 | 0 | 21783 | 9054 | 0.627968166 | 0 | 21811 | 9082 | 0.626939031 | 0 | 21839 | 9110 | 0.62591233 | 0 |
| 21756 | 9027 | 0.629516454 | 0 | 21784 | 9055 | 0.627823296 | -0.836804083 | 21812 | 9083 | 0.626939031 | 0 | 21840 | 9111 | 0.62591233 | 0 |
| 21757 | 9028 | 0.629516454 | 0 | 21785 | 9056 | 0.627710653 | 0 | 21813 | 9084 | 0.626939031 | -0.052697673 | 21841 | 9112 | 0.625656033 | 0 |
| 21758 | 9029 | 0.629516454 | 0 | 21786 | 9057 | 0.627648518 | 0 | 21814 | 9085 | 0.626939031 | -0.353727668 | 21842 | 9113 | 0.625656033 | 0 |
| 21759 | 9030 | 0.629516454 | 0 | 21787 | 9058 | 0.627648518 | 0 | 21815 | 9086 | 0.626810561 | 0 | 21843 | 9114 | 0.625656033 | 0 |
| 21760 | 9031 | 0.629516454 | 0 | 21788 | 9059 | 0.627648518 | 0 | 21816 | 9087 | 0.626810561 | 0 | 21844 | 9115 | 0.625656033 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21845 | 9116 | 0.625656033 | 0 | 21873 | 9144 | 0.62460912 | 0 | 21901 | 9172 | 0.62352609 | 0 | 21929 | 9200 | 0.62233787 | 0 |
| 21846 | 9117 | 0.625656033 | 0 | 21874 | 9145 | 0.624456655 | 0 | 21902 | 9173 | 0.62352609 | 0 | 21930 | 9201 | 0.62233787 | 0 |
| 21847 | 9118 | 0.625656033 | 0 | 21875 | 9146 | 0.624376814 | 0 | 21903 | 9174 | 0.62352609 | 0 | 21931 | 9202 | 0.62233787 | 0 |
| 21848 | 9119 | 0.625656033 | 0 | 21876 | 9147 | 0.624376814 | 0 | 21904 | 9175 | 0.62352609 | 0 | 21932 | 9203 | 0.62233787 | 0 |
| 21849 | 9120 | 0.625513712 | 0 | 21877 | 9148 | 0.624376814 | 0 | 21905 | 9176 | 0.623297334 | 0 | 21933 | 9204 | 0.62233787 | 0 |
| 21850 | 9121 | 0.625513712 | 0 | 21878 | 9149 | 0.624376814 | 0 | 21906 | 9177 | 0.623297334 | 0 | 21934 | 9205 | 0.622176091 | 0 |
| 21851 | 9122 | 0.625360494 | 0 | 21879 | 9150 | 0.624376814 | 0 | 21907 | 9178 | 0.623297334 | 0 | 21935 | 9206 | 0.622176091 | 0 |
| 21852 | 9123 | 0.625360494 | 0 | 21880 | 9151 | 0.624294413 | 0 | 21908 | 9179 | 0.623176276 | 0 | 21936 | 9207 | 0.622176091 | 0 |
| 21853 | 9124 | 0.625360494 | 0 | 21881 | 9152 | 0.624121422 | 0 | 21909 | 9180 | 0.623176276 | 0 | 21937 | 9208 | 0.622176091 | -1.378693995 |
| 21854 | 9125 | 0.625360494 | 0 | 21882 | 9153 | 0.624121422 | 0 | 21910 | 9181 | 0.623050412 | 0 | 21938 | 9209 | 0.622092436 | 0 |
| 21855 | 9126 | 0.62519508 | 0 | 21883 | 9154 | 0.624121422 | 0 | 21911 | 9182 | 0.623050412 | 0 | 21939 | 9210 | 0.622092436 | 0 |
| 21856 | 9127 | 0.62519508 | -1.431192333 | 21884 | 9155 | 0.624121422 | 0 | 21912 | 9183 | 0.623050412 | 0 | 21940 | 9211 | 0.621829625 | 0 |
| 21857 | 9128 | 0.62519508 | -1.431192333 | 21885 | 9156 | 0.624121422 | 0 | 21913 | 9184 | 0.622783071 | 0 | 21941 | 9212 | 0.621829625 | 0 |
| 21858 | 9129 | 0.625015953 | 0 | 21886 | 9157 | 0.624121422 | 0 | 21914 | 9185 | 0.622783071 | 0 | 21942 | 9213 | 0.621829625 | 0 |
| 21859 | 9130 | 0.625015953 | 0 | 21887 | 9158 | 0.624121422 | 0 | 21915 | 9186 | 0.622783071 | 0 | 21943 | 9214 | 0.621829625 | 0 |
| 21860 | 9131 | 0.625015953 | 0 | 21888 | 9159 | 0.624121422 | 0 | 21916 | 9187 | 0.622783071 | 0 | 21944 | 9215 | 0.621829625 | 0 |
| 21861 | 9132 | 0.625015953 | 0 | 21889 | 9160 | 0.624121422 | 0 | 21917 | 9188 | 0.622783071 | 0 | 21945 | 9216 | 0.621829625 | 0 |
| 21862 | 9133 | 0.625015953 | 0 | 21890 | 9161 | 0.623936577 | 0 | 21918 | 9189 | 0.622783071 | -1.540814312 | 21946 | 9217 | 0.621829625 | 0 |
| 21863 | 9134 | 0.625015953 | 0 | 21891 | 9162 | 0.623936577 | 0 | 21919 | 9190 | 0.622611786 | 0 | 21947 | 9218 | 0.621829625 | 0 |
| 21864 | 9135 | 0.62488805 | 0 | 21892 | 9163 | 0.623839321 | 0 | 21920 | 9191 | 0.622492671 | 0 | 21948 | 9219 | 0.621829625 | 0 |
| 21865 | 9136 | 0.624821333 | 0 | 21893 | 9164 | 0.623839321 | 0 | 21921 | 9192 | 0.622492671 | 0 | 21949 | 9220 | 0.621829625 | 0 |
| 21866 | 9137 | 0.624821333 | 0 | 21894 | 9165 | 0.623839321 | 0 | 21922 | 9193 | 0.622492671 | 0 | 21950 | 9221 | 0.621829625 | 0 |
| 21867 | 9138 | 0.624821333 | 0 | 21895 | 9166 | 0.623839321 | 0 | 21923 | 9194 | 0.622492671 | 0 | 21951 | 9222 | 0.621829625 | -1.483775811 |
| 21868 | 9139 | 0.624821333 | 0 | 21896 | 9167 | 0.623839321 | 0 | 21924 | 9195 | 0.622492671 | 0 | 21952 | 9223 | 0.621547524 | 0 |
| 21869 | 9140 | 0.624752664 | 0 | 21897 | 9168 | 0.623839321 | 0 | 21925 | 9196 | 0.622492671 | 0 | 21953 | 9224 | 0.621547524 | 0 |
| 21870 | 9141 | 0.62460912 | 0 | 21898 | 9169 | 0.623738615 | 0 | 21926 | 9197 | 0.622492671 | 0 | 21954 | 9225 | 0.621547524 | 0 |
| 21871 | 9142 | 0.62460912 | 0 | 21899 | 9170 | 0.62352609 | 0 | 21927 | 9198 | 0.622492671 | 0 | 21955 | 9226 | 0.621448832 | 0 |
| 21872 | 9143 | 0.62460912 | 0 | 21900 | 9171 | 0.62352609 | 0 | 21928 | 9199 | 0.62233787 | 0 | 21956 | 9227 | 0.621448832 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 21957 | 9228 | 0.621448832 | 0 | 21985 | 9256 | 0.620561611 | 0 | 22013 | 9284 | 0.619297289 | 0 | 22041 | 9312 | 0.618351457 | 0 |
| 21958 | 9229 | 0.621243928 | 0 | 21986 | 9257 | 0.620561611 | 0 | 22014 | 9285 | 0.619297289 | 0 | 22042 | 9313 | 0.618351457 | 0 |
| 21959 | 9230 | 0.621243928 | 0 | 21987 | 9258 | 0.620561611 | -1.418097035 | 22015 | 9286 | 0.619297289 | 0 | 22043 | 9314 | 0.618351457 | 0 |
| 21960 | 9231 | 0.621243928 | 0 | 21988 | 9259 | 0.620256093 | 0 | 22016 | 9287 | 0.619297289 | 0 | 22044 | 9315 | 0.618351457 | 0 |
| 21961 | 9232 | 0.621243928 | 0 | 21989 | 9260 | 0.620176428 | 0 | 22017 | 9288 | 0.619200186 | 0 | 22045 | 9316 | 0.618351457 | 0 |
| 21962 | 9233 | 0.621243928 | 0 | 21990 | 9261 | 0.620040562 | 0 | 22018 | 9289 | 0.619200186 | 0 | 22046 | 9317 | 0.618351457 | 0 |
| 21963 | 9234 | 0.621243928 | 0 | 21991 | 9262 | 0.620040562 | 0 | 22019 | 9290 | 0.619134418 | 0 | 22047 | 9318 | 0.618351457 | 0 |
| 21964 | 9235 | 0.621243928 | 0 | 21992 | 9263 | 0.620040562 | 0 | 22020 | 9291 | 0.618792589 | 0 | 22048 | 9319 | 0.618235444 | 0 |
| 21965 | 9236 | 0.621243928 | 0 | 21993 | 9264 | 0.620040562 | 0 | 22021 | 9292 | 0.618792589 | 0 | 22049 | 9320 | 0.618235444 | 0 |
| 21966 | 9237 | 0.621243928 | 0 | 21994 | 9265 | 0.620040562 | 0 | 22022 | 9293 | 0.618792589 | 0 | 22050 | 9321 | 0.618235444 | 0 |
| 21967 | 9238 | 0.621028344 | 0 | 21995 | 9266 | 0.620040562 | -1.268855764 | 22023 | 9294 | 0.618792589 | 0 | 22051 | 9322 | 0.618235444 | 0 |
| 21968 | 9239 | 0.621028344 | 0 | 21996 | 9267 | 0.61992899 | 0 | 22024 | 9295 | 0.618792589 | 0 | 22052 | 9323 | 0.618235444 | 0 |
| 21969 | 9240 | 0.621028344 | 0 | 21997 | 9268 | 0.61992899 | 0 | 22025 | 9296 | 0.618792589 | 0 | 22053 | 9324 | 0.618235444 | 0 |
| 21970 | 9241 | 0.621028344 | 0 | 21998 | 9269 | 0.61992899 | 0 | 22026 | 9297 | 0.618792589 | 0 | 22054 | 9325 | 0.618235444 | 0 |
| 21971 | 9242 | 0.621028344 | 0 | 21999 | 9270 | 0.619756617 | 0 | 22027 | 9298 | 0.618792589 | 0 | 22055 | 9326 | 0.618235444 | 0 |
| 21972 | 9243 | 0.621028344 | -1.316172662 | 22000 | 9271 | 0.619756617 | 0 | 22028 | 9299 | 0.618792589 | 0 | 22056 | 9327 | 0.618235444 | 0 |
| 21973 | 9244 | 0.620916282 | 0 | 22001 | 9272 | 0.619756617 | 0 | 22029 | 9300 | 0.618792589 | 0 | 22057 | 9328 | 0.618235444 | -1.318965562 |
| 21974 | 9245 | 0.620916282 | 0 | 22002 | 9273 | 0.619756617 | 0 | 22030 | 9301 | 0.618792589 | 0 | 22058 | 9329 | 0.61815109 | 0 |
| 21975 | 9246 | 0.620847614 | 0 | 22003 | 9274 | 0.619756617 | 0 | 22031 | 9302 | 0.618792589 | 0 | 22059 | 9330 | 0.618036636 | 0 |
| 21976 | 9247 | 0.620561611 | 0 | 22004 | 9275 | 0.619756617 | -0.955144736 | 22032 | 9303 | 0.618792589 | 0 | 22060 | 9331 | 0.618036636 | 0 |
| 21977 | 9248 | 0.620561611 | 0 | 22005 | 9276 | 0.619577932 | 0 | 22033 | 9304 | 0.618792589 | 0 | 22061 | 9332 | 0.618036636 | 0 |
| 21978 | 9249 | 0.620561611 | 0 | 22006 | 9277 | 0.619577932 | 0 | 22034 | 9305 | 0.618792589 | 0 | 22062 | 9333 | 0.618036636 | 0 |
| 21979 | 9250 | 0.620561611 | 0 | 22007 | 9278 | 0.619577932 | 0 | 22035 | 9306 | 0.618792589 | 0 | 22063 | 9334 | 0.617872473 | 0 |
| 21980 | 9251 | 0.620561611 | 0 | 22008 | 9279 | 0.619577932 | 0 | 22036 | 9307 | 0.618792589 | 0 | 22064 | 9335 | 0.617872473 | 0 |
| 21981 | 9252 | 0.620561611 | 0 | 22009 | 9280 | 0.619455128 | 0 | 22037 | 9308 | 0.618792589 | 0 | 22065 | 9336 | 0.617872473 | -1.402302768 |
| 21982 | 9253 | 0.620561611 | 0 | 22010 | 9281 | 0.619455128 | 0 | 22038 | 9309 | 0.618792589 | -1.039654816 | 22066 | 9337 | 0.617617231 | 0 |
| 21983 | 9254 | 0.620561611 | 0 | 22011 | 9282 | 0.619455128 | 0 | 22039 | 9310 | 0.618481155 | 0 | 22067 | 9338 | 0.617617231 | 0 |
| 21984 | 9255 | 0.620561611 | 0 | 22012 | 9283 | 0.619297289 | 0 | 22040 | 9311 | 0.618427482 | 0 | 22068 | 9339 | 0.617427955 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22069 | 9340 | 0.617350547 | 0 | 22097 | 9368 | 0.616152493 | 0 | 22125 | 9396 | 0.614957734 | 0 | 22153 | 9424 | 0.613528349 | 0 |
| 22070 | 9341 | 0.617350547 | 0 | 22098 | 9369 | 0.616152493 | 0 | 22126 | 9397 | 0.614957734 | 0 | 22154 | 9425 | 0.613528349 | 0 |
| 22071 | 9342 | 0.617350547 | 0 | 22099 | 9370 | 0.616152493 | 0 | 22127 | 9398 | 0.614957734 | 0 | 22155 | 9426 | 0.613528349 | 0 |
| 22072 | 9343 | 0.617350547 | 0 | 22100 | 9371 | 0.616152493 | 0 | 22128 | 9399 | 0.614793197 | 0 | 22156 | 9427 | 0.613528349 | 0 |
| 22073 | 9344 | 0.617166016 | 0 | 22101 | 9372 | 0.616152493 | 0 | 22129 | 9400 | 0.614793197 | -1.506052205 | 22157 | 9428 | 0.613528349 | 0 |
| 22074 | 9345 | 0.617166016 | 0 | 22102 | 9373 | 0.616152493 | 0 | 22130 | 9401 | 0.614692678 | 0 | 22158 | 9429 | 0.613528349 | 0 |
| 22075 | 9346 | 0.617166016 | 0 | 22103 | 9374 | 0.616152493 | 0 | 22131 | 9402 | 0.614692678 | 0 | 22159 | 9430 | 0.613528349 | 0 |
| 22076 | 9347 | 0.616927327 | 0 | 22104 | 9375 | 0.616152493 | 0 | 22132 | 9403 | 0.614692678 | 0 | 22160 | 9431 | 0.613528349 | 0 |
| 22077 | 9348 | 0.616927327 | 0 | 22105 | 9376 | 0.616152493 | 0 | 22133 | 9404 | 0.614692678 | 0 | 22161 | 9432 | 0.613528349 | 0 |
| 22078 | 9349 | 0.616927327 | 0 | 22106 | 9377 | 0.616152493 | 0 | 22134 | 9405 | 0.614692678 | 0 | 22162 | 9433 | 0.613528349 | 0 |
| 22079 | 9350 | 0.616927327 | 0 | 22107 | 9378 | 0.616152493 | 0 | 22135 | 9406 | 0.614576104 | 0 | 22163 | 9434 | 0.61330091 | 0 |
| 22080 | 9351 | 0.616779633 | 0 | 22108 | 9379 | 0.616152493 | 0 | 22136 | 9407 | 0.614576104 | 0 | 22164 | 9435 | 0.61330091 | 0 |
| 22081 | 9352 | 0.616779633 | 0 | 22109 | 9380 | 0.616152493 | 0 | 22137 | 9408 | 0.614576104 | 0 | 22165 | 9436 | 0.613237754 | 0 |
| 22082 | 9353 | 0.616779633 | -1.062857071 | 22110 | 9381 | 0.616152493 | 0 | 22138 | 9409 | 0.614576104 | -0.839751318 | 22166 | 9437 | 0.613126038 | 0 |
| 22083 | 9354 | 0.616679229 | 0 | 22111 | 9382 | 0.616152493 | -0.820446163 | 22139 | 9410 | 0.614510546 | 0 | 22167 | 9438 | 0.613126038 | 0 |
| 22084 | 9355 | 0.616679229 | 0 | 22112 | 9383 | 0.61572817 | 0 | 22140 | 9411 | 0.614468526 | 0 | 22168 | 9439 | 0.613126038 | 0 |
| 22085 | 9356 | 0.616606538 | 0 | 22113 | 9384 | 0.61572817 | 0 | 22141 | 9412 | 0.614276488 | 0 | 22169 | 9440 | 0.613126038 | 0 |
| 22086 | 9357 | 0.616606538 | 0 | 22114 | 9385 | 0.615665342 | 0 | 22142 | 9413 | 0.614276488 | 0 | 22170 | 9441 | 0.613126038 | 0 |
| 22087 | 9358 | 0.616606538 | 0 | 22115 | 9386 | 0.615580676 | 0 | 22143 | 9414 | 0.614276488 | 0 | 22171 | 9442 | 0.613126038 | 0 |
| 22088 | 9359 | 0.616551477 | 0 | 22116 | 9387 | 0.615580676 | 0 | 22144 | 9415 | 0.614276488 | 0 | 22172 | 9443 | 0.613126038 | 0 |
| 22089 | 9360 | 0.616152493 | 0 | 22117 | 9388 | 0.61546039 | 0 | 22145 | 9416 | 0.614276488 | 0 | 22173 | 9444 | 0.612874783 | 0 |
| 22090 | 9361 | 0.616152493 | 0 | 22118 | 9389 | 0.61546039 | 0 | 22146 | 9417 | 0.614276488 | 0 | 22174 | 9445 | 0.612874783 | 0 |
| 22091 | 9362 | 0.616152493 | 0 | 22119 | 9390 | 0.61546039 | 0 | 22147 | 9418 | 0.614276488 | 0 | 22175 | 9446 | 0.612874783 | 0 |
| 22092 | 9363 | 0.616152493 | 0 | 22120 | 9391 | 0.615276015 | 0 | 22148 | 9419 | 0.614276488 | -0.449936263 | 22176 | 9447 | 0.612874783 | 0 |
| 22093 | 9364 | 0.616152493 | 0 | 22121 | 9392 | 0.615276015 | 0 | 22149 | 9420 | 0.613964606 | 0 | 22177 | 9448 | 0.612874783 | 0 |
| 22094 | 9365 | 0.616152493 | 0 | 22122 | 9393 | 0.615276015 | 0 | 22150 | 9421 | 0.613964606 | 0 | 22178 | 9449 | 0.612874783 | 0 |
| 22095 | 9366 | 0.616152493 | 0 | 22123 | 9394 | 0.615141329 | 0 | 22151 | 9422 | 0.61383625 | 0 | 22179 | 9450 | 0.612874783 | -0.103564569 |
| 22096 | 9367 | 0.616152493 | 0 | 22124 | 9395 | 0.614957734 | 0 | 22152 | 9423 | 0.613722187 | 0 | 22180 | 9451 | 0.612702955 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22181 | 9452 | 0.612702955 | 0 | 22209 | 9480 | 0.611787687 | 0 | 22237 | 9508 | 0.610400164 | 0 | 22265 | 9536 | 0.609621625 | 0 |
| 22182 | 9453 | 0.612702955 | 0 | 22210 | 9481 | 0.611787687 | 0 | 22238 | 9509 | 0.610400164 | 0 | 22266 | 9537 | 0.609621625 | 0 |
| 22183 | 9454 | 0.612702955 | 0 | 22211 | 9482 | 0.611787687 | 0 | 22239 | 9510 | 0.610211299 | 0 | 22267 | 9538 | 0.609621625 | 0 |
| 22184 | 9455 | 0.612702955 | 0 | 22212 | 9483 | 0.611787687 | 0 | 22240 | 9511 | 0.610211299 | 0 | 22268 | 9539 | 0.609621625 | 0 |
| 22185 | 9456 | 0.612578032 | 0 | 22213 | 9484 | 0.611787687 | 0 | 22241 | 9512 | 0.610211299 | 0 | 22269 | 9540 | 0.609621625 | 0 |
| 22186 | 9457 | 0.612578032 | 0 | 22214 | 9485 | 0.611189073 | 0 | 22242 | 9513 | 0.610211299 | 0 | 22270 | 9541 | 0.609398165 | 0 |
| 22187 | 9458 | 0.612578032 | 0 | 22215 | 9486 | 0.611189073 | 0 | 22243 | 9514 | 0.610211299 | 0 | 22271 | 9542 | 0.609313068 | 0 |
| 22188 | 9459 | 0.612408551 | 0 | 22216 | 9487 | 0.611189073 | 0 | 22244 | 9515 | 0.610211299 | 0 | 22272 | 9543 | 0.609313068 | 0 |
| 22189 | 9460 | 0.612408551 | 0 | 22217 | 9488 | 0.611120055 | 0 | 22245 | 9516 | 0.610211299 | 0 | 22273 | 9544 | 0.609313068 | 0 |
| 22190 | 9461 | 0.612348429 | 0 | 22218 | 9489 | 0.611120055 | 0 | 22246 | 9517 | 0.610211299 | 0 | 22274 | 9545 | 0.609123295 | 0 |
| 22191 | 9462 | 0.611787687 | 0 | 22219 | 9490 | 0.611120055 | 0 | 22247 | 9518 | 0.610211299 | 0 | 22275 | 9546 | 0.609123295 | 0 |
| 22192 | 9463 | 0.611787687 | 0 | 22220 | 9491 | 0.611120055 | 0 | 22248 | 9519 | 0.610211299 | 0 | 22276 | 9547 | 0.609123295 | 0 |
| 22193 | 9464 | 0.611787687 | 0 | 22221 | 9492 | 0.611033048 | 0 | 22249 | 9520 | 0.610211299 | 0 | 22277 | 9548 | 0.609123295 | 0 |
| 22194 | 9465 | 0.611787687 | 0 | 22222 | 9493 | 0.611033048 | 0 | 22250 | 9521 | 0.610211299 | 0 | 22278 | 9549 | 0.609123295 | 0 |
| 22195 | 9466 | 0.611787687 | 0 | 22223 | 9494 | 0.611033048 | 0 | 22251 | 9522 | 0.610211299 | 0 | 22279 | 9550 | 0.609123295 | 0 |
| 22196 | 9467 | 0.611787687 | 0 | 22224 | 9495 | 0.610919966 | 0 | 22252 | 9523 | 0.610211299 | -1.089628791 | 22280 | 9551 | 0.609123295 | 0 |
| 22197 | 9468 | 0.611787687 | 0 | 22225 | 9496 | 0.610919966 | 0 | 22253 | 9524 | 0.610053974 | 0 | 22281 | 9552 | 0.609123295 | -0.464297457 |
| 22198 | 9469 | 0.611787687 | 0 | 22226 | 9497 | 0.610919966 | -1.348557435 | 22254 | 9525 | 0.610053974 | 0 | 22282 | 9553 | 0.608901999 | 0 |
| 22199 | 9470 | 0.611787687 | 0 | 22227 | 9498 | 0.610767018 | 0 | 22255 | 9526 | 0.610053974 | 0 | 22283 | 9554 | 0.608901999 | 0 |
| 22200 | 9471 | 0.611787687 | 0 | 22228 | 9499 | 0.610767018 | 0 | 22256 | 9527 | 0.609962918 | 0 | 22284 | 9555 | 0.608901999 | 0 |
| 22201 | 9472 | 0.611787687 | 0 | 22229 | 9500 | 0.610767018 | 0 | 22257 | 9528 | 0.609962918 | 0 | 22285 | 9556 | 0.608901999 | 0 |
| 22202 | 9473 | 0.611787687 | 0 | 22230 | 9501 | 0.610767018 | 0 | 22258 | 9529 | 0.609962918 | 0 | 22286 | 9557 | 0.608901999 | 0 |
| 22203 | 9474 | 0.611787687 | 0 | 22231 | 9502 | 0.610767018 | -0.164185956 | 22259 | 9530 | 0.609962918 | 0 | 22287 | 9558 | 0.608901999 | -1.304817911 |
| 22204 | 9475 | 0.611787687 | 0 | 22232 | 9503 | 0.610548615 | 0 | 22260 | 9531 | 0.609962918 | 0 | 22288 | 9559 | 0.608901999 | -0.70275792 |
| 22205 | 9476 | 0.611787687 | 0 | 22233 | 9504 | 0.610548615 | 0 | 22261 | 9532 | 0.609962918 | 0 | 22289 | 9560 | 0.608776968 | 0 |
| 22206 | 9477 | 0.611787687 | 0 | 22234 | 9505 | 0.610548615 | 0 | 22262 | 9533 | 0.609962918 | 0 | 22290 | 9561 | 0.608776968 | 0 |
| 22207 | 9478 | 0.611787687 | 0 | 22235 | 9506 | 0.610548615 | 0 | 22263 | 9534 | 0.609962918 | 0 | 22291 | 9562 | 0.608776968 | 0 |
| 22208 | 9479 | 0.611787687 | 0 | 22236 | 9507 | 0.610400164 | 0 | 22264 | 9535 | 0.609861766 | 0 | 22292 | 9563 | 0.608776968 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22293 | 9564 | 0.608776968 | 0 | 22321 | 9592 | 0.607719325 | 0 | 22349 | 9620 | 0.606532547 | 0 | 22377 | 9648 | 0.605516178 | 0 |
| 22294 | 9565 | 0.608776968 | 0 | 22322 | 9593 | 0.607466313 | 0 | 22350 | 9621 | 0.606392655 | 0 | 22378 | 9649 | 0.605516178 | 0 |
| 22295 | 9566 | 0.60869661 | 0 | 22323 | 9594 | 0.607466313 | 0 | 22351 | 9622 | 0.606392655 | 0 | 22379 | 9650 | 0.605321645 | 0 |
| 22296 | 9567 | 0.608327155 | 0 | 22324 | 9595 | 0.607466313 | 0 | 22352 | 9623 | 0.606392655 | 0 | 22380 | 9651 | 0.605157108 | 0 |
| 22297 | 9568 | 0.608327155 | 0 | 22325 | 9596 | 0.607466313 | 0 | 22353 | 9624 | 0.606392655 | 0 | 22381 | 9652 | 0.605157108 | 0 |
| 22298 | 9569 | 0.608327155 | 0 | 22326 | 9597 | 0.607466313 | 0 | 22354 | 9625 | 0.606263994 | 0 | 22382 | 9653 | 0.605157108 | 0 |
| 22299 | 9570 | 0.608327155 | 0 | 22327 | 9598 | 0.607466313 | 0 | 22355 | 9626 | 0.606263994 | 0 | 22383 | 9654 | 0.605157108 | 0 |
| 22300 | 9571 | 0.608327155 | 0 | 22328 | 9599 | 0.607466313 | 0 | 22356 | 9627 | 0.606263994 | 0 | 22384 | 9655 | 0.605016126 | 0 |
| 22301 | 9572 | 0.608327155 | 0 | 22329 | 9600 | 0.607466313 | 0 | 22357 | 9628 | 0.606263994 | -1.149093423 | 22385 | 9656 | 0.605016126 | 0 |
| 22302 | 9573 | 0.608327155 | 0 | 22330 | 9601 | 0.607466313 | 0 | 22358 | 9629 | 0.606203461 | 0 | 22386 | 9657 | 0.604893979 | 0 |
| 22303 | 9574 | 0.608327155 | 0 | 22331 | 9602 | 0.607240059 | 0 | 22359 | 9630 | 0.606203461 | 0 | 22387 | 9658 | 0.604893979 | 0 |
| 22304 | 9575 | 0.608327155 | 0 | 22332 | 9603 | 0.607240059 | 0 | 22360 | 9631 | 0.606035358 | 0 | 22388 | 9659 | 0.604893979 | 0 |
| 22305 | 9576 | 0.608327155 | 0 | 22333 | 9604 | 0.607135674 | -1.165255083 | 22361 | 9632 | 0.606035358 | 0 | 22389 | 9660 | 0.604893979 | 0 |
| 22306 | 9577 | 0.608327155 | 0 | 22334 | 9605 | 0.606852469 | 0 | 22362 | 9633 | 0.606035358 | 0 | 22390 | 9661 | 0.604893979 | 0 |
| 22307 | 9578 | 0.608327155 | 0 | 22335 | 9606 | 0.606852469 | 0 | 22363 | 9634 | 0.606035358 | 0 | 22391 | 9662 | 0.604787129 | 0 |
| 22308 | 9579 | 0.608327155 | 0 | 22336 | 9607 | 0.606852469 | 0 | 22364 | 9635 | 0.606035358 | 0 | 22392 | 9663 | 0.60469287 | 0 |
| 22309 | 9580 | 0.608327155 | 0 | 22337 | 9608 | 0.606852469 | 0 | 22365 | 9636 | 0.606035358 | 0 | 22393 | 9664 | 0.60469287 | 0 |
| 22310 | 9581 | 0.608327155 | 0 | 22338 | 9609 | 0.606852469 | 0 | 22366 | 9637 | 0.606035358 | 0 | 22394 | 9665 | 0.60469287 | 0 |
| 22311 | 9582 | 0.608327155 | 0 | 22339 | 9610 | 0.606852469 | 0 | 22367 | 9638 | 0.606035358 | 0 | 22395 | 9666 | 0.60469287 | 0 |
| 22312 | 9583 | 0.608327155 | 0 | 22340 | 9611 | 0.606852469 | 0 | 22368 | 9639 | 0.606035358 | 0 | 22396 | 9667 | 0.60469287 | 0 |
| 22313 | 9584 | 0.608327155 | -0.226211509 | 22341 | 9612 | 0.606852469 | 0 | 22369 | 9640 | 0.606035358 | -0.228503306 | 22397 | 9668 | 0.60469287 | 0 |
| 22314 | 9585 | 0.608327155 | -1.226211509 | 22342 | 9613 | 0.606852469 | 0 | 22370 | 9641 | 0.605749732 | 0 | 22398 | 9669 | 0.60469287 | 0 |
| 22315 | 9586 | 0.607944348 | 0 | 22343 | 9614 | 0.606852469 | 0 | 22371 | 9642 | 0.605749732 | 0 | 22399 | 9670 | 0.604534166 | 0 |
| 22316 | 9587 | 0.607857394 | -1.393012692 | 22344 | 9615 | 0.606852469 | 0 | 22372 | 9643 | 0.605749732 | 0 | 22400 | 9671 | 0.604534166 | 0 |
| 22317 | 9588 | 0.607719325 | 0 | 22345 | 9616 | 0.606852469 | 0 | 22373 | 9644 | 0.605749732 | 0 | 22401 | 9672 | 0.604534166 | 0 |
| 22318 | 9589 | 0.607719325 | 0 | 22346 | 9617 | 0.606852469 | -0.197722971 | 22374 | 9645 | 0.605749732 | 0 | 22402 | 9673 | 0.604534166 | 0 |
| 22319 | 9590 | 0.607719325 | 0 | 22347 | 9618 | 0.606852469 | -0.37381423 | 22375 | 9646 | 0.605749732 | -0.353727668 | 22403 | 9674 | 0.604534166 | 0 |
| 22320 | 9591 | 0.607719325 | 0 | 22348 | 9619 | 0.606653571 | 0 | 22376 | 9647 | 0.605516178 | 0 | 22404 | 9675 | 0.604534166 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22405 | 9676 | 0.604534166 | 0 | 22433 | 9704 | 0.603187515 | 0 | 22461 | 9732 | 0.602414061 | 0 | 22489 | 9760 | 0.60168736 | 0 |
| 22406 | 9677 | 0.604534166 | 0 | 22434 | 9705 | 0.603187515 | 0 | 22462 | 9733 | 0.602364208 | 0 | 22490 | 9761 | 0.60168736 | 0 |
| 22407 | 9678 | 0.604534166 | 0 | 22435 | 9706 | 0.603187515 | 0 | 22463 | 9734 | 0.602307486 | 0 | 22491 | 9762 | 0.60168736 | 0 |
| 22408 | 9679 | 0.604405734 | 0 | 22436 | 9707 | 0.603187515 | 0 | 22464 | 9735 | 0.602307486 | 0 | 22492 | 9763 | 0.60168736 | 0 |
| 22409 | 9680 | 0.604405734 | 0 | 22437 | 9708 | 0.603187515 | 0 | 22465 | 9736 | 0.602242369 | 0 | 22493 | 9764 | 0.601487731 | 0 |
| 22410 | 9681 | 0.604405734 | 0 | 22438 | 9709 | 0.603187515 | 0 | 22466 | 9737 | 0.602242369 | 0 | 22494 | 9765 | 0.601487731 | 0 |
| 22411 | 9682 | 0.604405734 | 0 | 22439 | 9710 | 0.603187515 | 0 | 22467 | 9738 | 0.602166846 | 0 | 22495 | 9766 | 0.601487731 | 0 |
| 22412 | 9683 | 0.604299666 | 0 | 22440 | 9711 | 0.603187515 | 0 | 22468 | 9739 | 0.602166846 | 0 | 22496 | 9767 | 0.601487731 | 0 |
| 22413 | 9684 | 0.604299666 | 0 | 22441 | 9712 | 0.603187515 | 0 | 22469 | 9740 | 0.602166846 | 0 | 22497 | 9768 | 0.601487731 | 0 |
| 22414 | 9685 | 0.604210589 | 0 | 22442 | 9713 | 0.603187515 | 0 | 22470 | 9741 | 0.602166846 | -0.223771646 | 22498 | 9769 | 0.601487731 | 0 |
| 22415 | 9686 | 0.604210589 | 0 | 22443 | 9714 | 0.603187515 | 0 | 22471 | 9742 | 0.602078206 | 0 | 22499 | 9770 | 0.601487731 | 0 |
| 22416 | 9687 | 0.604134723 | 0 | 22444 | 9715 | 0.603187515 | 0 | 22472 | 9743 | 0.602078206 | 0 | 22500 | 9771 | 0.601366572 | 0 |
| 22417 | 9688 | 0.604069332 | 0 | 22445 | 9716 | 0.603187515 | 0 | 22473 | 9744 | 0.601972705 | 0 | 22501 | 9772 | 0.601366572 | 0 |
| 22418 | 9689 | 0.604069332 | -1.516776071 | 22446 | 9717 | 0.603187515 | 0 | 22474 | 9745 | 0.601972705 | 0 | 22502 | 9773 | 0.601366572 | 0 |
| 22419 | 9690 | 0.604012386 | 0 | 22447 | 9718 | 0.603187515 | 0 | 22475 | 9746 | 0.601972705 | 0 | 22503 | 9774 | 0.601226815 | 0 |
| 22420 | 9691 | 0.60396235 | 0 | 22448 | 9719 | 0.603187515 | 0 | 22476 | 9747 | 0.601972705 | 0 | 22504 | 9775 | 0.601226815 | 0 |
| 22421 | 9692 | 0.603878517 | 0 | 22449 | 9720 | 0.603187515 | 0 | 22477 | 9748 | 0.601972705 | 0 | 22505 | 9776 | 0.601226815 | 0 |
| 22422 | 9693 | 0.603187515 | 0 | 22450 | 9721 | 0.603187515 | 0 | 22478 | 9749 | 0.601972705 | 0 | 22506 | 9777 | 0.601226815 | 0 |
| 22423 | 9694 | 0.603187515 | 0 | 22451 | 9722 | 0.603187515 | 0 | 22479 | 9750 | 0.601972705 | 0 | 22507 | 9778 | 0.601226815 | 0 |
| 22424 | 9695 | 0.603187515 | 0 | 22452 | 9723 | 0.603187515 | 0 | 22480 | 9751 | 0.601972705 | 0 | 22508 | 9779 | 0.601226815 | 0 |
| 22425 | 9696 | 0.603187515 | 0 | 22453 | 9724 | 0.603187515 | 0 | 22481 | 9752 | 0.601972705 | 0 | 22509 | 9780 | 0.601226815 | 0 |
| 22426 | 9697 | 0.603187515 | 0 | 22454 | 9725 | 0.603187515 | 0 | 22482 | 9753 | 0.601972705 | -0.264750642 | 22510 | 9781 | 0.601226815 | 0 |
| 22427 | 9698 | 0.603187515 | 0 | 22455 | 9726 | 0.603187515 | 0 | 22483 | 9754 | 0.601845028 | 0 | 22511 | 9782 | 0.601226815 | 0 |
| 22428 | 9699 | 0.603187515 | 0 | 22456 | 9727 | 0.603187515 | 0 | 22484 | 9755 | 0.601845028 | 0 | 22512 | 9783 | 0.601226815 | 0 |
| 22429 | 9700 | 0.603187515 | 0 | 22457 | 9728 | 0.603187515 | 0 | 22485 | 9756 | 0.601845028 | 0 | 22513 | 9784 | 0.601063822 | -1.437594825 |
| 22430 | 9701 | 0.603187515 | 0 | 22458 | 9729 | 0.603187515 | 0 | 22486 | 9757 | 0.601845028 | 0 | 22514 | 9785 | 0.600871273 | 0 |
| 22431 | 9702 | 0.603187515 | 0 | 22459 | 9730 | 0.603187515 | 0 | 22487 | 9758 | 0.601845028 | 0 | 22515 | 9786 | 0.600871273 | 0 |
| 22432 | 9703 | 0.603187515 | 0 | 22460 | 9731 | 0.603187515 | -0.771263233 | 22488 | 9759 | 0.601845028 | 0 | 22516 | 9787 | 0.600871273 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22517 | 9788 | 0.600871273 | 0 | 22545 | 9816 | 0.599553231 | 0 | 22573 | 9844 | 0.598702507 | 0 | 22601 | 9872 | 0.597547248 | 0 |
| 22518 | 9789 | 0.600871273 | 0 | 22546 | 9817 | 0.599553231 | 0 | 22574 | 9845 | 0.598702507 | 0 | 22602 | 9873 | 0.597547248 | 0 |
| 22519 | 9790 | 0.600871273 | -0.320817567 | 22547 | 9818 | 0.599553231 | 0 | 22575 | 9846 | 0.598567318 | 0 | 22603 | 9874 | 0.597547248 | -1.015142666 |
| 22520 | 9791 | 0.600640326 | 0 | 22548 | 9819 | 0.599553231 | 0 | 22576 | 9847 | 0.598567318 | 0 | 22604 | 9875 | 0.597547248 | -1.617202658 |
| 22521 | 9792 | 0.600640326 | 0 | 22549 | 9820 | 0.599553231 | 0 | 22577 | 9848 | 0.598567318 | 0 | 22605 | 9876 | 0.597331771 | 0 |
| 22522 | 9793 | 0.600640326 | 0 | 22550 | 9821 | 0.599553231 | 0 | 22578 | 9849 | 0.598567318 | 0 | 22606 | 9877 | 0.597331771 | 0 |
| 22523 | 9794 | 0.600640326 | 0 | 22551 | 9822 | 0.599553231 | 0 | 22579 | 9850 | 0.598567318 | 0 | 22607 | 9878 | 0.597331771 | 0 |
| 22524 | 9795 | 0.600640326 | 0 | 22552 | 9823 | 0.599333945 | 0 | 22580 | 9851 | 0.598567318 | 0 | 22608 | 9879 | 0.597331771 | 0 |
| 22525 | 9796 | 0.600640326 | -1.358837074 | 22553 | 9824 | 0.599172438 | 0 | 22581 | 9852 | 0.598567318 | -1.402302768 | 22609 | 9880 | 0.597331771 | 0 |
| 22526 | 9797 | 0.600552758 | -0.057894647 | 22554 | 9825 | 0.599172438 | 0 | 22582 | 9853 | 0.598567318 | -1.402302768 | 22610 | 9881 | 0.597331771 | -0.572998995 |
| 22527 | 9798 | 0.600358225 | 0 | 22555 | 9826 | 0.599172438 | 0 | 22583 | 9854 | 0.59848222 | 0 | 22611 | 9882 | 0.597147161 | 0 |
| 22528 | 9799 | 0.600358225 | 0 | 22556 | 9827 | 0.599172438 | 0 | 22584 | 9855 | 0.59848222 | 0 | 22612 | 9883 | 0.597147161 | 0 |
| 22529 | 9800 | 0.600358225 | 0 | 22557 | 9828 | 0.599172438 | 0 | 22585 | 9856 | 0.598423726 | -0.963113666 | 22613 | 9884 | 0.597147161 | 0 |
| 22530 | 9801 | 0.600358225 | 0 | 22558 | 9829 | 0.599172438 | 0 | 22586 | 9857 | 0.598381045 | 0 | 22614 | 9885 | 0.597147161 | 0 |
| 22531 | 9802 | 0.600358225 | 0 | 22559 | 9830 | 0.598950462 | 0 | 22587 | 9858 | 0.59810799 | 0 | 22615 | 9886 | 0.597147161 | -0.304338292 |
| 22532 | 9803 | 0.600358225 | -0.271968999 | 22560 | 9831 | 0.598950462 | 0 | 22588 | 9859 | 0.59810799 | 0 | 22616 | 9887 | 0.59706443 | 0 |
| 22533 | 9804 | 0.600192369 | -1.589733953 | 22561 | 9832 | 0.598950462 | 0 | 22589 | 9860 | 0.59810799 | 0 | 22617 | 9888 | 0.596847337 | 0 |
| 22534 | 9805 | 0.600132676 | -0.155224741 | 22562 | 9833 | 0.598950462 | 0 | 22590 | 9861 | 0.59810799 | 0 | 22618 | 9889 | 0.596847337 | 0 |
| 22535 | 9806 | 0.600005857 | 0 | 22563 | 9834 | 0.598950462 | 0 | 22591 | 9862 | 0.59810799 | 0 | 22619 | 9890 | 0.596847337 | 0 |
| 22536 | 9807 | 0.600005857 | 0 | 22564 | 9835 | 0.598950462 | 0 | 22592 | 9863 | 0.59810799 | 0 | 22620 | 9891 | 0.596847337 | 0 |
| 22537 | 9808 | 0.600005857 | 0 | 22565 | 9836 | 0.598950462 | -0.837648193 | 22593 | 9864 | 0.59810799 | 0 | 22621 | 9892 | 0.596847337 | 0 |
| 22538 | 9809 | 0.600005857 | 0 | 22566 | 9837 | 0.598805092 | 0 | 22594 | 9865 | 0.59810799 | 0 | 22622 | 9893 | 0.596847337 | 0 |
| 22539 | 9810 | 0.600005857 | 0 | 22567 | 9838 | 0.598702507 | 0 | 22595 | 9866 | 0.59810799 | -1.060339415 | 22623 | 9894 | 0.596847337 | 0 |
| 22540 | 9811 | 0.599868051 | 0 | 22568 | 9839 | 0.598702507 | 0 | 22596 | 9867 | 0.59810799 | -1.361369411 | 22624 | 9895 | 0.596847337 | 0 |
| 22541 | 9812 | 0.599868051 | 0 | 22569 | 9840 | 0.598702507 | 0 | 22597 | 9868 | 0.59774743 | 0 | 22625 | 9896 | 0.596847337 | 0 |
| 22542 | 9813 | 0.599868051 | 0 | 22570 | 9841 | 0.598702507 | 0 | 22598 | 9869 | 0.59774743 | -1.507858006 | 22626 | 9897 | 0.596847337 | 0 |
| 22543 | 9814 | 0.599553231 | 0 | 22571 | 9842 | 0.598702507 | 0 | 22599 | 9870 | 0.597547248 | 0 | 22627 | 9898 | 0.596847337 | 0 |
| 22544 | 9815 | 0.599553231 | 0 | 22572 | 9843 | 0.598702507 | 0 | 22600 | 9871 | 0.597547248 | 0 | 22628 | 9899 | 0.596516194 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22629 | 9900 | 0.596516194 | 0 | 22657 | 9928 | 0.595397271 | 0 | 22685 | 9956 | 0.594754348 | 0 | 22713 | 9984 | 0.593711624 | 0 |
| 22630 | 9901 | 0.596516194 | 0 | 22658 | 9929 | 0.595397271 | 0 | 22686 | 9957 | 0.594754348 | 0 | 22714 | 9985 | 0.59347135 | 0 |
| 22631 | 9902 | 0.596516194 | 0 | 22659 | 9930 | 0.595397271 | 0 | 22687 | 9958 | 0.594754348 | 0 | 22715 | 9986 | 0.59347135 | 0 |
| 22632 | 9903 | 0.596516194 | 0 | 22660 | 9931 | 0.595330718 | 0 | 22688 | 9959 | 0.594754348 | 0 | 22716 | 9987 | 0.59347135 | 0 |
| 22633 | 9904 | 0.596387036 | 0 | 22661 | 9932 | 0.595330718 | -1.525514685 | 22689 | 9960 | 0.594754348 | 0 | 22717 | 9988 | 0.59347135 | 0 |
| 22634 | 9905 | 0.596275521 | 0 | 22662 | 9933 | 0.594754348 | 0 | 22690 | 9961 | 0.594754348 | 0 | 22718 | 9989 | 0.59347135 | 0 |
| 22635 | 9906 | 0.596275521 | -0.501504578 | 22663 | 9934 | 0.594754348 | 0 | 22691 | 9962 | 0.594754348 | 0 | 22719 | 9990 | 0.59347135 | 0 |
| 22636 | 9907 | 0.596275521 | -0.70562456 | 22664 | 9935 | 0.594754348 | 0 | 22692 | 9963 | 0.594754348 | 0 | 22720 | 9991 | 0.593304281 | 0 |
| 22637 | 9908 | 0.596275521 | -0.08237527 | 22665 | 9936 | 0.594754348 | 0 | 22693 | 9964 | 0.594754348 | 0 | 22721 | 9992 | 0.593304281 | 0 |
| 22638 | 9909 | 0.596275521 | -1.103564569 | 22666 | 9937 | 0.594754348 | 0 | 22694 | 9965 | 0.594754348 | 0 | 22722 | 9993 | 0.593304281 | 0 |
| 22639 | 9910 | 0.596092699 | 0 | 22667 | 9938 | 0.594754348 | 0 | 22695 | 9966 | 0.594754348 | 0 | 22723 | 9994 | 0.593087189 | 0 |
| 22640 | 9911 | 0.595949106 | 0 | 22668 | 9939 | 0.594754348 | 0 | 22696 | 9967 | 0.594336958 | 0 | 22724 | 9995 | 0.593087189 | 0 |
| 22641 | 9912 | 0.595949106 | 0 | 22669 | 9940 | 0.594754348 | 0 | 22697 | 9968 | 0.594086716 | 0 | 22725 | 9996 | 0.592793647 | 0 |
| 22642 | 9913 | 0.595949106 | 0 | 22670 | 9941 | 0.594754348 | 0 | 22698 | 9969 | 0.593995755 | 0 | 22726 | 9997 | 0.592793647 | 0 |
| 22643 | 9914 | 0.595949106 | 0 | 22671 | 9942 | 0.594754348 | 0 | 22699 | 9970 | 0.593995755 | 0 | 22727 | 9998 | 0.592793647 | 0 |
| 22644 | 9915 | 0.595949106 | -1.50965633 | 22672 | 9943 | 0.594754348 | 0 | 22700 | 9971 | 0.593995755 | 0 | 22728 | 9999 | 0.592793647 | 0 |
| 22645 | 9916 | 0.595738028 | 0 | 22673 | 9944 | 0.594754348 | 0 | 22701 | 9972 | 0.593995755 | 0 | 22729 | 10000 | 0.592793647 | 0 |
| 22646 | 9917 | 0.595738028 | 0 | 22674 | 9945 | 0.594754348 | 0 | 22702 | 9973 | 0.593995755 | 0 | 22730 | 10001 | 0.592671397 | 0 |
| 22647 | 9918 | 0.595738028 | 0 | 22675 | 9946 | 0.594754348 | 0 | 22703 | 9974 | 0.593876098 | 0 | 22731 | 10002 | 0.592671397 | 0 |
| 22648 | 9919 | 0.595738028 | 0 | 22676 | 9947 | 0.594754348 | 0 | 22704 | 9975 | 0.593876098 | 0 | 22732 | 10003 | 0.592671397 | 0 |
| 22649 | 9920 | 0.595590334 | 0 | 22677 | 9948 | 0.594754348 | 0 | 22705 | 9976 | 0.593876098 | 0 | 22733 | 10004 | 0.592671397 | -0.843927258 |
| 22650 | 9921 | 0.595590334 | 0 | 22678 | 9949 | 0.594754348 | 0 | 22706 | 9977 | 0.593876098 | -0.229381556 | 22734 | 10005 | 0.592604371 | 0 |
| 22651 | 9922 | 0.595590334 | 0 | 22679 | 9950 | 0.594754348 | 0 | 22707 | 9978 | 0.593711624 | 0 | 22735 | 10006 | 0.592374646 | 0 |
| 22652 | 9923 | 0.595590334 | 0 | 22680 | 9951 | 0.594754348 | 0 | 22708 | 9979 | 0.593711624 | 0 | 22736 | 10007 | 0.592374646 | 0 |
| 22653 | 9924 | 0.595590334 | 0 | 22681 | 9952 | 0.594754348 | 0 | 22709 | 9980 | 0.593711624 | 0 | 22737 | 10008 | 0.592374646 | 0 |
| 22654 | 9925 | 0.595481201 | 0 | 22682 | 9953 | 0.594754348 | 0 | 22710 | 9981 | 0.593711624 | 0 | 22738 | 10009 | 0.592374646 | 0 |
| 22655 | 9926 | 0.595481201 | 0 | 22683 | 9954 | 0.594754348 | 0 | 22711 | 9982 | 0.593711624 | 0 | 22739 | 10010 | 0.592374646 | 0 |
| 22656 | 9927 | 0.595481201 | 0 | 22684 | 9955 | 0.594754348 | 0 | 22712 | 9983 | 0.593711624 | 0 | 22740 | 10011 | 0.592374646 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22741 | 10012 | 0.592374646 | 0 | 22769 | 10040 | 0.591727893 | 0 | 22797 | 10068 | 0.590598388 | 0 | 22825 | 10096 | 0.589869094 | 0 |
| 22742 | 10013 | 0.592374646 | 0 | 22770 | 10041 | 0.591553932 | 0 | 22798 | 10069 | 0.590598388 | 0 | 22826 | 10097 | 0.589869094 | 0 |
| 22743 | 10014 | 0.592374646 | 0 | 22771 | 10042 | 0.591553932 | 0 | 22799 | 10070 | 0.590598388 | 0 | 22827 | 10098 | 0.589771947 | 0 |
| 22744 | 10015 | 0.592374646 | 0 | 22772 | 10043 | 0.591426405 | 0 | 22800 | 10071 | 0.590598388 | 0 | 22828 | 10099 | 0.589771947 | 0 |
| 22745 | 10016 | 0.592374646 | 0 | 22773 | 10044 | 0.591426405 | 0 | 22801 | 10072 | 0.590598388 | 0 | 22829 | 10100 | 0.589644942 | 0 |
| 22746 | 10017 | 0.592374646 | 0 | 22774 | 10045 | 0.591426405 | 0 | 22802 | 10073 | 0.590598388 | 0 | 22830 | 10101 | 0.589644942 | 0 |
| 22747 | 10018 | 0.592374646 | 0 | 22775 | 10046 | 0.591426405 | 0 | 22803 | 10074 | 0.590598388 | 0 | 22831 | 10102 | 0.589644942 | 0 |
| 22748 | 10019 | 0.592374646 | -1.212200794 | 22776 | 10047 | 0.591426405 | 0 | 22804 | 10075 | 0.590598388 | 0 | 22832 | 10103 | 0.589644942 | 0 |
| 22749 | 10020 | 0.592374646 | -1.212200794 | 22777 | 10048 | 0.591426405 | -0.942082264 | 22805 | 10076 | 0.590598388 | 0 | 22833 | 10104 | 0.589644942 | 0 |
| 22750 | 10021 | 0.592089956 | 0 | 22778 | 10049 | 0.591251954 | 0 | 22806 | 10077 | 0.590598388 | -0.125840964 | 22834 | 10105 | 0.589644942 | 0 |
| 22751 | 10022 | 0.592089956 | 0 | 22779 | 10050 | 0.591251954 | 0 | 22807 | 10078 | 0.590598388 | -0.544970271 | 22835 | 10106 | 0.589471813 | 0 |
| 22752 | 10023 | 0.591979294 | 0 | 22780 | 10051 | 0.59113822 | 0 | 22808 | 10079 | 0.590222538 | 0 | 22836 | 10107 | 0.589221859 | 0 |
| 22753 | 10024 | 0.591979294 | 0 | 22781 | 10052 | 0.59113822 | 0 | 22809 | 10080 | 0.590222538 | 0 | 22837 | 10108 | 0.589221859 | 0 |
| 22754 | 10025 | 0.591979294 | 0 | 22782 | 10053 | 0.59113822 | 0 | 22810 | 10081 | 0.590102335 | 0 | 22838 | 10109 | 0.589221859 | 0 |
| 22755 | 10026 | 0.591979294 | 0 | 22783 | 10054 | 0.59113822 | 0 | 22811 | 10082 | 0.590102335 | 0 | 22839 | 10110 | 0.589221859 | 0 |
| 22756 | 10027 | 0.591979294 | 0 | 22784 | 10055 | 0.59113822 | 0 | 22812 | 10083 | 0.590102335 | 0 | 22840 | 10111 | 0.589221859 | 0 |
| 22757 | 10028 | 0.591979294 | 0 | 22785 | 10056 | 0.59113822 | 0 | 22813 | 10084 | 0.590007913 | 0 | 22841 | 10112 | 0.589221859 | 0 |
| 22758 | 10029 | 0.591979294 | 0 | 22786 | 10057 | 0.590998844 | 0 | 22814 | 10085 | 0.590007913 | 0 | 22842 | 10113 | 0.589221859 | 0 |
| 22759 | 10030 | 0.591979294 | 0 | 22787 | 10058 | 0.590998844 | 0 | 22815 | 10086 | 0.590007913 | 0 | 22843 | 10114 | 0.589221859 | 0 |
| 22760 | 10031 | 0.591979294 | 0 | 22788 | 10059 | 0.590953059 | -1.61156239 | 22816 | 10087 | 0.590007913 | 0 | 22844 | 10115 | 0.589221859 | 0 |
| 22761 | 10032 | 0.591883918 | 0 | 22789 | 10060 | 0.590598388 | 0 | 22817 | 10088 | 0.590007913 | 0 | 22845 | 10116 | 0.589221859 | 0 |
| 22762 | 10033 | 0.591727893 | 0 | 22790 | 10061 | 0.590598388 | 0 | 22818 | 10089 | 0.590007913 | 0 | 22846 | 10117 | 0.589221859 | 0 |
| 22763 | 10034 | 0.591727893 | 0 | 22791 | 10062 | 0.590598388 | 0 | 22819 | 10090 | 0.590007913 | 0 | 22847 | 10118 | 0.589221859 | -1.324498051 |
| 22764 | 10035 | 0.591727893 | 0 | 22792 | 10063 | 0.590598388 | 0 | 22820 | 10091 | 0.589869094 | 0 | 22848 | 10119 | 0.589221859 | -1.324498051 |
| 22765 | 10036 | 0.591727893 | 0 | 22793 | 10064 | 0.590598388 | 0 | 22821 | 10092 | 0.589869094 | 0 | 22849 | 10120 | 0.5890501 | 0 |
| 22766 | 10037 | 0.591727893 | 0 | 22794 | 10065 | 0.590598388 | 0 | 22822 | 10093 | 0.589869094 | 0 | 22850 | 10121 | 0.588982908 | 0 |
| 22767 | 10038 | 0.591727893 | 0 | 22795 | 10066 | 0.590598388 | 0 | 22823 | 10094 | 0.589869094 | 0 | 22851 | 10122 | 0.588982908 | 0 |
| 22768 | 10039 | 0.591727893 | 0 | 22796 | 10067 | 0.590598388 | 0 | 22824 | 10095 | 0.589869094 | 0 | 22852 | 10123 | 0.588982908 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22853 | 10124 | 0.588982908 | 0 | 22881 | 10152 | 0.588123769 | 0 | 22909 | 10180 | 0.587227392 | 0 | 22937 | 10208 | 0.586481822 | 0 |
| 22854 | 10125 | 0.588829365 | 0 | 22882 | 10153 | 0.588123769 | 0 | 22910 | 10181 | 0.587227392 | 0 | 22938 | 10209 | 0.586481822 | 0 |
| 22855 | 10126 | 0.588829365 | 0 | 22883 | 10154 | 0.588123769 | 0 | 22911 | 10182 | 0.587227392 | 0 | 22939 | 10210 | 0.586481822 | 0 |
| 22856 | 10127 | 0.588829365 | 0 | 22884 | 10155 | 0.588123769 | 0 | 22912 | 10183 | 0.587227392 | 0 | 22940 | 10211 | 0.586481822 | 0 |
| 22857 | 10128 | 0.588829365 | 0 | 22885 | 10156 | 0.587654007 | 0 | 22913 | 10184 | 0.587227392 | 0 | 22941 | 10212 | 0.586481822 | 0 |
| 22858 | 10129 | 0.588829365 | 0 | 22886 | 10157 | 0.587654007 | 0 | 22914 | 10185 | 0.587227392 | 0 | 22942 | 10213 | 0.586481822 | -1.151146829 |
| 22859 | 10130 | 0.588829365 | 0 | 22887 | 10158 | 0.587654007 | 0 | 22915 | 10186 | 0.587227392 | 0 | 22943 | 10214 | 0.586481822 | -1.151146829 |
| 22860 | 10131 | 0.588643571 | 0 | 22888 | 10159 | 0.587654007 | 0 | 22916 | 10187 | 0.587227392 | 0 | 22944 | 10215 | 0.586481822 | -1.327238088 |
| 22861 | 10132 | 0.588643571 | 0 | 22889 | 10160 | 0.587654007 | 0 | 22917 | 10188 | 0.587227392 | 0 | 22945 | 10216 | 0.586154176 | 0 |
| 22862 | 10133 | 0.588643571 | 0 | 22890 | 10161 | 0.587654007 | 0 | 22918 | 10189 | 0.587227392 | -0.158370188 | 22946 | 10217 | 0.586154176 | 0 |
| 22863 | 10134 | 0.588643571 | 0 | 22891 | 10162 | 0.587654007 | 0 | 22919 | 10190 | 0.587067519 | 0 | 22947 | 10218 | 0.586154176 | 0 |
| 22864 | 10135 | 0.588643571 | 0 | 22892 | 10163 | 0.587507311 | 0 | 22920 | 10191 | 0.586964103 | 0 | 22948 | 10219 | 0.586154176 | 0 |
| 22865 | 10136 | 0.588643571 | 0 | 22893 | 10164 | 0.587507311 | 0 | 22921 | 10192 | 0.586964103 | 0 | 22949 | 10220 | 0.58605076 | 0 |
| 22866 | 10137 | 0.588643571 | -1.348557435 | 22894 | 10165 | 0.587507311 | 0 | 22922 | 10193 | 0.586964103 | 0 | 22950 | 10221 | 0.58605076 | -0.874028991 |
| 22867 | 10138 | 0.588535228 | 0 | 22895 | 10166 | 0.587507311 | 0 | 22923 | 10194 | 0.586964103 | -1.301932223 | 22951 | 10222 | 0.585851953 | 0 |
| 22868 | 10139 | 0.588535228 | 0 | 22896 | 10167 | 0.587507311 | 0 | 22924 | 10195 | 0.586838239 | 0 | 22952 | 10223 | 0.585851953 | 0 |
| 22869 | 10140 | 0.588535228 | 0 | 22897 | 10168 | 0.587507311 | 0 | 22925 | 10196 | 0.586838239 | 0 | 22953 | 10224 | 0.585851953 | 0 |
| 22870 | 10141 | 0.588535228 | -1.149093423 | 22898 | 10169 | 0.587507311 | 0 | 22926 | 10197 | 0.586838239 | 0 | 22954 | 10225 | 0.585851953 | 0 |
| 22871 | 10142 | 0.588123769 | 0 | 22899 | 10170 | 0.587507311 | 0 | 22927 | 10198 | 0.586838239 | 0 | 22955 | 10226 | 0.585851953 | 0 |
| 22872 | 10143 | 0.588123769 | 0 | 22900 | 10171 | 0.587393248 | 0 | 22928 | 10199 | 0.586764474 | 0 | 22956 | 10227 | 0.585851953 | 0 |
| 22873 | 10144 | 0.588123769 | 0 | 22901 | 10172 | 0.587393248 | 0 | 22929 | 10200 | 0.586764474 | 0 | 22957 | 10228 | 0.585851953 | -0.145146119 |
| 22874 | 10145 | 0.588123769 | 0 | 22902 | 10173 | 0.587393248 | 0 | 22930 | 10201 | 0.586481822 | 0 | 22958 | 10229 | 0.585851953 | -1.186538804 |
| 22875 | 10146 | 0.588123769 | 0 | 22903 | 10174 | 0.587227392 | 0 | 22931 | 10202 | 0.586481822 | 0 | 22959 | 10230 | 0.58573753 | 0 |
| 22876 | 10147 | 0.588123769 | 0 | 22904 | 10175 | 0.587227392 | 0 | 22932 | 10203 | 0.586481822 | 0 | 22960 | 10231 | 0.58566317 | 0 |
| 22877 | 10148 | 0.588123769 | 0 | 22905 | 10176 | 0.587227392 | 0 | 22933 | 10204 | 0.586481822 | 0 | 22961 | 10232 | 0.58566317 | 0 |
| 22878 | 10149 | 0.588123769 | 0 | 22906 | 10177 | 0.587227392 | 0 | 22934 | 10205 | 0.586481822 | 0 | 22962 | 10233 | 0.585572304 | 0 |
| 22879 | 10150 | 0.588123769 | 0 | 22907 | 10178 | 0.587227392 | 0 | 22935 | 10206 | 0.586481822 | 0 | 22963 | 10234 | 0.585312792 | 0 |
| 22880 | 10151 | 0.588123769 | 0 | 22908 | 10179 | 0.587227392 | 0 | 22936 | 10207 | 0.586481822 | 0 | 22964 | 10235 | 0.585312792 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 22965 | 10236 | 0.585312792 | 0 | 22993 | 10264 | 0.584438079 | 0 | 23021 | 10292 | 0.583565125 | 0 | 23049 | 10320 | 0.582403909 | 0 |
| 22966 | 10237 | 0.585312792 | 0 | 22994 | 10265 | 0.584438079 | 0 | 23022 | 10293 | 0.583473337 | 0 | 23050 | 10321 | 0.582403909 | -1.155224741 |
| 22967 | 10238 | 0.585312792 | 0 | 22995 | 10266 | 0.584438079 | 0 | 23023 | 10294 | 0.583473337 | 0 | 23051 | 10322 | 0.582241587 | 0 |
| 22968 | 10239 | 0.585312792 | 0 | 22996 | 10267 | 0.584438079 | 0 | 23024 | 10295 | 0.583473337 | 0 | 23052 | 10323 | 0.582091804 | 0 |
| 22969 | 10240 | 0.585312792 | 0 | 22997 | 10268 | 0.584078415 | 0 | 23025 | 10296 | 0.583473337 | 0 | 23053 | 10324 | 0.582091804 | 0 |
| 22970 | 10241 | 0.585312792 | 0 | 22998 | 10269 | 0.584078415 | 0 | 23026 | 10297 | 0.583384733 | -1.53746067 | 23054 | 10325 | 0.582091804 | 0 |
| 22971 | 10242 | 0.585312792 | 0 | 22999 | 10270 | 0.584078415 | 0 | 23027 | 10298 | 0.583216434 | 0 | 23055 | 10326 | 0.582091804 | 0 |
| 22972 | 10243 | 0.585312792 | 0 | 23000 | 10271 | 0.584078415 | 0 | 23028 | 10299 | 0.583216434 | 0 | 23056 | 10327 | 0.581953163 | 0 |
| 22973 | 10244 | 0.585312792 | 0 | 23001 | 10272 | 0.584078415 | 0 | 23029 | 10300 | 0.583216434 | 0 | 23057 | 10328 | 0.581953163 | 0 |
| 22974 | 10245 | 0.585312792 | 0 | 23002 | 10273 | 0.584078415 | 0 | 23030 | 10301 | 0.583216434 | 0 | 23058 | 10329 | 0.581953163 | 0 |
| 22975 | 10246 | 0.585312792 | 0 | 23003 | 10274 | 0.584078415 | -1.304817911 | 23031 | 10302 | 0.583216434 | 0 | 23059 | 10330 | 0.581824464 | 0 |
| 22976 | 10247 | 0.584994511 | 0 | 23004 | 10275 | 0.583967809 | 0 | 23032 | 10303 | 0.582984129 | 0 | 23060 | 10331 | 0.581824464 | 0 |
| 22977 | 10248 | 0.584994511 | 0 | 23005 | 10276 | 0.583967809 | 0 | 23033 | 10304 | 0.582984129 | 0 | 23061 | 10332 | 0.581824464 | 0 |
| 22978 | 10249 | 0.584994511 | 0 | 23006 | 10277 | 0.583967809 | 0 | 23034 | 10305 | 0.582984129 | 0 | 23062 | 10333 | 0.581824464 | 0 |
| 22979 | 10250 | 0.584994511 | 0 | 23007 | 10278 | 0.583967809 | 0 | 23035 | 10306 | 0.582984129 | 0 | 23063 | 10334 | 0.581824464 | -1.523780972 |
| 22980 | 10251 | 0.584846059 | 0 | 23008 | 10279 | 0.583758964 | 0 | 23036 | 10307 | 0.582984129 | 0 | 23064 | 10335 | 0.581592902 | 0 |
| 22981 | 10252 | 0.584846059 | 0 | 23009 | 10280 | 0.583758964 | 0 | 23037 | 10308 | 0.582773051 | 0 | 23065 | 10336 | 0.581592902 | 0 |
| 22982 | 10253 | 0.584846059 | 0 | 23010 | 10281 | 0.583758964 | 0 | 23038 | 10309 | 0.582773051 | 0 | 23066 | 10337 | 0.581592902 | 0 |
| 22983 | 10254 | 0.584846059 | 0 | 23011 | 10282 | 0.583758964 | 0 | 23039 | 10310 | 0.582773051 | 0 | 23067 | 10338 | 0.581592902 | 0 |
| 22984 | 10255 | 0.584846059 | 0 | 23012 | 10283 | 0.583758964 | 0 | 23040 | 10311 | 0.582773051 | 0 | 23068 | 10339 | 0.581488366 | 0 |
| 22985 | 10256 | 0.584846059 | 0 | 23013 | 10284 | 0.583758964 | 0 | 23041 | 10312 | 0.582773051 | 0 | 23069 | 10340 | 0.581488366 | -0.225898052 |
| 22986 | 10257 | 0.584846059 | -1.249692605 | 23014 | 10285 | 0.583758964 | 0 | 23042 | 10313 | 0.582773051 | 0 | 23070 | 10341 | 0.581390386 | 0 |
| 22987 | 10258 | 0.58470411 | 0 | 23015 | 10286 | 0.583758964 | 0 | 23043 | 10314 | 0.582580416 | 0 | 23071 | 10342 | 0.581390386 | 0 |
| 22988 | 10259 | 0.58470411 | 0 | 23016 | 10287 | 0.583758964 | 0 | 23044 | 10315 | 0.582580416 | 0 | 23072 | 10343 | 0.581390386 | 0 |
| 22989 | 10260 | 0.58470411 | 0 | 23017 | 10288 | 0.583758964 | 0 | 23045 | 10316 | 0.582580416 | 0 | 23073 | 10344 | 0.581390386 | 0 |
| 22990 | 10261 | 0.58470411 | 0 | 23018 | 10289 | 0.583758964 | 0 | 23046 | 10317 | 0.582403909 | 0 | 23074 | 10345 | 0.581390386 | 0 |
| 22991 | 10262 | 0.58470411 | -0.736501127 | 23019 | 10290 | 0.583758964 | 0 | 23047 | 10318 | 0.582403909 | 0 | 23075 | 10346 | 0.581211775 | 0 |
| 22992 | 10263 | 0.584438079 | 0 | 23020 | 10291 | 0.583758964 | -0.727900955 | 23048 | 10319 | 0.582403909 | 0 | 23076 | 10347 | 0.581211775 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23077 | 10348 | 0.581211775 | 0 | 23105 | 10376 | 0.578363932 | 0 | 23133 | 10404 | 0.578363932 | 0 | 23161 | 10432 | 0.578363932 | 0 |
| 23078 | 10349 | 0.58105307 | 0 | 23106 | 10377 | 0.578363932 | 0 | 23134 | 10405 | 0.578363932 | 0 | 23162 | 10433 | 0.578363932 | 0 |
| 23079 | 10350 | 0.58105307 | 0 | 23107 | 10378 | 0.578363932 | 0 | 23135 | 10406 | 0.578363932 | 0 | 23163 | 10434 | 0.578363932 | 0 |
| 23080 | 10351 | 0.58105307 | 0 | 23108 | 10379 | 0.578363932 | 0 | 23136 | 10407 | 0.578363932 | 0 | 23164 | 10435 | 0.578363932 | 0 |
| 23081 | 10352 | 0.580911121 | 0 | 23109 | 10380 | 0.578363932 | 0 | 23137 | 10408 | 0.578363932 | 0 | 23165 | 10436 | 0.578363932 | 0 |
| 23082 | 10353 | 0.580911121 | 0 | 23110 | 10381 | 0.578363932 | 0 | 23138 | 10409 | 0.578363932 | 0 | 23166 | 10437 | 0.578363932 | 0 |
| 23083 | 10354 | 0.580783406 | 0 | 23111 | 10382 | 0.578363932 | 0 | 23139 | 10410 | 0.578363932 | 0 | 23167 | 10438 | 0.578363932 | 0 |
| 23084 | 10355 | 0.580783406 | 0 | 23112 | 10383 | 0.578363932 | 0 | 23140 | 10411 | 0.578363932 | 0 | 23168 | 10439 | 0.578363932 | 0 |
| 23085 | 10356 | 0.580783406 | 0 | 23113 | 10384 | 0.578363932 | 0 | 23141 | 10412 | 0.578363932 | 0 | 23169 | 10440 | 0.578363932 | 0 |
| 23086 | 10357 | 0.580783406 | 0 | 23114 | 10385 | 0.578363932 | 0 | 23142 | 10413 | 0.578363932 | 0 | 23170 | 10441 | 0.578363932 | 0 |
| 23087 | 10358 | 0.580783406 | 0 | 23115 | 10386 | 0.578363932 | 0 | 23143 | 10414 | 0.578363932 | 0 | 23171 | 10442 | 0.578363932 | 0 |
| 23088 | 10359 | 0.580783406 | 0 | 23116 | 10387 | 0.578363932 | 0 | 23144 | 10415 | 0.578363932 | 0 | 23172 | 10443 | 0.578363932 | 0 |
| 23089 | 10360 | 0.580667887 | 0 | 23117 | 10388 | 0.578363932 | 0 | 23145 | 10416 | 0.578363932 | 0 | 23173 | 10444 | 0.578363932 | 0 |
| 23090 | 10361 | 0.580562896 | -1.42030719 | 23118 | 10389 | 0.578363932 | 0 | 23146 | 10417 | 0.578363932 | 0 | 23174 | 10445 | 0.578363932 | 0 |
| 23091 | 10362 | 0.580467057 | 0 | 23119 | 10390 | 0.578363932 | 0 | 23147 | 10418 | 0.578363932 | 0 | 23175 | 10446 | 0.578363932 | 0 |
| 23092 | 10363 | 0.580467057 | 0 | 23120 | 10391 | 0.578363932 | 0 | 23148 | 10419 | 0.578363932 | 0 | 23176 | 10447 | 0.578363932 | 0 |
| 23093 | 10364 | 0.580298431 | 0 | 23121 | 10392 | 0.578363932 | 0 | 23149 | 10420 | 0.578363932 | 0 | 23177 | 10448 | 0.578363932 | 0 |
| 23094 | 10365 | 0.580298431 | 0 | 23122 | 10393 | 0.578363932 | 0 | 23150 | 10421 | 0.578363932 | 0 | 23178 | 10449 | 0.578363932 | -0.314166679 |
| 23095 | 10366 | 0.580298431 | 0 | 23123 | 10394 | 0.578363932 | 0 | 23151 | 10422 | 0.578363932 | 0 | 23179 | 10450 | 0.578363932 | -0.343324908 |
| 23096 | 10367 | 0.580298431 | 0 | 23124 | 10395 | 0.578363932 | 0 | 23152 | 10423 | 0.578363932 | 0 | 23180 | 10451 | 0.578363932 | -0.858234723 |
| 23097 | 10368 | 0.580223868 | 0 | 23125 | 10396 | 0.578363932 | 0 | 23153 | 10424 | 0.578363932 | 0 | 23181 | 10452 | 0.578363932 | -0.955144736 |
| 23098 | 10369 | 0.580154839 | 0 | 23126 | 10397 | 0.578363932 | 0 | 23154 | 10425 | 0.578363932 | 0 | 23182 | 10453 | 0.578363932 | -1.034325983 |
| 23099 | 10370 | 0.580090751 | 0 | 23127 | 10398 | 0.578363932 | 0 | 23155 | 10426 | 0.578363932 | 0 | 23183 | 10454 | 0.578363932 | -1.478023482 |
| 23100 | 10371 | 0.580031091 | 0 | 23128 | 10399 | 0.578363932 | 0 | 23156 | 10427 | 0.578363932 | 0 | 23184 | 10455 | 0.578363932 | -0.495056821 |
| 23101 | 10372 | 0.579975416 | 0 | 23129 | 10400 | 0.578363932 | 0 | 23157 | 10428 | 0.578363932 | 0 | 23185 | 10456 | 0.578363932 | -1.460294715 |
| 23102 | 10373 | 0.579975416 | 0 | 23130 | 10401 | 0.578363932 | 0 | 23158 | 10429 | 0.578363932 | 0 | 23186 | 10457 | 0.576703148 | 0 |
| 23103 | 10374 | 0.579923339 | 0 | 23131 | 10402 | 0.578363932 | 0 | 23159 | 10430 | 0.578363932 | 0 | 23187 | 10458 | 0.576580379 | 0 |
| 23104 | 10375 | 0.579923339 | -1.268855764 | 23132 | 10403 | 0.578363932 | 0 | 23160 | 10431 | 0.578363932 | 0 | 23188 | 10459 | 0.576511927 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23189 | 10460 | 0.576438011 | 0 | 23217 | 10488 | 0.575534642 | 0 | 23245 | 10516 | 0.574361189 | 0 | 23273 | 10544 | 0.573792369 | 0 |
| 23190 | 10461 | 0.576438011 | 0 | 23218 | 10489 | 0.575449193 | 0 | 23246 | 10517 | 0.574361189 | 0 | 23274 | 10545 | 0.573792369 | 0 |
| 23191 | 10462 | 0.576438011 | 0 | 23219 | 10490 | 0.575358422 | 0 | 23247 | 10518 | 0.574361189 | 0 | 23275 | 10546 | 0.573792369 | 0 |
| 23192 | 10463 | 0.576270942 | 0 | 23220 | 10491 | 0.575358422 | 0 | 23248 | 10519 | 0.574361189 | 0 | 23276 | 10547 | 0.573565049 | 0 |
| 23193 | 10464 | 0.576270942 | 0 | 23221 | 10492 | 0.575358422 | 0 | 23249 | 10520 | 0.574361189 | 0 | 23277 | 10548 | 0.573565049 | 0 |
| 23194 | 10465 | 0.576176046 | 0 | 23222 | 10493 | 0.575358422 | -0.083088983 | 23250 | 10521 | 0.574361189 | 0 | 23278 | 10549 | 0.573565049 | 0 |
| 23195 | 10466 | 0.576176046 | 0 | 23223 | 10494 | 0.575158792 | 0 | 23251 | 10522 | 0.574361189 | 0 | 23279 | 10550 | 0.573565049 | 0 |
| 23196 | 10467 | 0.576176046 | 0 | 23224 | 10495 | 0.575158792 | 0 | 23252 | 10523 | 0.574361189 | 0 | 23280 | 10551 | 0.573565049 | 0 |
| 23197 | 10468 | 0.576176046 | 0 | 23225 | 10496 | 0.575158792 | 0 | 23253 | 10524 | 0.574361189 | 0 | 23281 | 10552 | 0.573565049 | 0 |
| 23198 | 10469 | 0.576176046 | 0 | 23226 | 10497 | 0.575158792 | 0 | 23254 | 10525 | 0.574361189 | 0 | 23282 | 10553 | 0.573565049 | 0 |
| 23199 | 10470 | 0.576072135 | 0 | 23227 | 10498 | 0.575158792 | 0 | 23255 | 10526 | 0.574361189 | 0 | 23283 | 10554 | 0.573565049 | 0 |
| 23200 | 10471 | 0.576072135 | 0 | 23228 | 10499 | 0.575048691 | 0 | 23256 | 10527 | 0.574361189 | 0 | 23284 | 10555 | 0.573565049 | 0 |
| 23201 | 10472 | 0.576072135 | -1.103564569 | 23229 | 10500 | 0.574930756 | 0 | 23257 | 10528 | 0.574361189 | 0 | 23285 | 10556 | 0.573565049 | 0 |
| 23202 | 10473 | 0.575957862 | 0 | 23230 | 10501 | 0.574930756 | 0 | 23258 | 10529 | 0.574361189 | 0 | 23286 | 10557 | 0.573565049 | 0 |
| 23203 | 10474 | 0.575957862 | 0 | 23231 | 10502 | 0.574930756 | 0 | 23259 | 10530 | 0.574361189 | 0 | 23287 | 10558 | 0.573565049 | 0 |
| 23204 | 10475 | 0.575957862 | 0 | 23232 | 10503 | 0.574930756 | 0 | 23260 | 10531 | 0.574247365 | 0 | 23288 | 10559 | 0.573565049 | -1.084882356 |
| 23205 | 10476 | 0.575957862 | 0 | 23233 | 10504 | 0.574930756 | 0 | 23261 | 10532 | 0.574187991 | 0 | 23289 | 10560 | 0.573400512 | 0 |
| 23206 | 10477 | 0.575957862 | -1.383519539 | 23234 | 10505 | 0.574930756 | 0 | 23262 | 10533 | 0.574187991 | 0 | 23290 | 10561 | 0.573400512 | 0 |
| 23207 | 10478 | 0.575831595 | 0 | 23235 | 10506 | 0.574930756 | 0 | 23263 | 10534 | 0.573999126 | 0 | 23291 | 10562 | 0.573313939 | 0 |
| 23208 | 10479 | 0.575831595 | 0 | 23236 | 10507 | 0.574804121 | 0 | 23264 | 10535 | 0.573999126 | 0 | 23292 | 10563 | 0.573313939 | -1.363887067 |
| 23209 | 10480 | 0.575831595 | -1.361369411 | 23237 | 10508 | 0.574804121 | 0 | 23265 | 10536 | 0.573999126 | 0 | 23293 | 10564 | 0.573224292 | 0 |
| 23210 | 10481 | 0.575691342 | 0 | 23238 | 10509 | 0.574667786 | 0 | 23266 | 10537 | 0.573999126 | 0 | 23294 | 10565 | 0.573035098 | 0 |
| 23211 | 10482 | 0.575691342 | 0 | 23239 | 10510 | 0.574667786 | 0 | 23267 | 10538 | 0.573999126 | 0 | 23295 | 10566 | 0.573035098 | 0 |
| 23212 | 10483 | 0.575691342 | 0 | 23240 | 10511 | 0.574667786 | 0 | 23268 | 10539 | 0.573999126 | 0 | 23296 | 10567 | 0.573035098 | 0 |
| 23213 | 10484 | 0.575691342 | 0 | 23241 | 10512 | 0.574667786 | 0 | 23269 | 10540 | 0.573999126 | 0 | 23297 | 10568 | 0.573035098 | 0 |
| 23214 | 10485 | 0.575691342 | 0 | 23242 | 10513 | 0.574667786 | 0 | 23270 | 10541 | 0.573999126 | 0 | 23298 | 10569 | 0.573035098 | 0 |
| 23215 | 10486 | 0.575534642 | 0 | 23243 | 10514 | 0.574520593 | 0 | 23271 | 10542 | 0.573999126 | 0 | 23299 | 10570 | 0.573035098 | 0 |
| 23216 | 10487 | 0.575534642 | 0 | 23244 | 10515 | 0.574520593 | -0.335738785 | 23272 | 10543 | 0.573792369 | 0 | 23300 | 10571 | 0.573035098 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23301 | 10572 | 0.573035098 | -0.671678031 | 23329 | 10600 | 0.571833065 | 0 | 23357 | 10628 | 0.571002832 | 0 | 23385 | 10656 | 0.569930764 | 0 |
| 23302 | 10573 | 0.573035098 | -0.340684812 | 23330 | 10601 | 0.571833065 | -1.429037021 | 23358 | 10629 | 0.571002832 | 0 | 23386 | 10657 | 0.569930764 | 0 |
| 23303 | 10574 | 0.572723664 | 0 | 23331 | 10602 | 0.571524507 | 0 | 23359 | 10630 | 0.570810794 | 0 | 23387 | 10658 | 0.569930764 | 0 |
| 23304 | 10575 | 0.572723664 | -0.236991416 | 23332 | 10603 | 0.571524507 | 0 | 23360 | 10631 | 0.570810794 | 0 | 23388 | 10659 | 0.569930764 | 0 |
| 23305 | 10576 | 0.572611603 | 0 | 23333 | 10604 | 0.571524507 | 0 | 23361 | 10632 | 0.570810794 | 0 | 23389 | 10660 | 0.569930764 | 0 |
| 23306 | 10577 | 0.572611603 | 0 | 23334 | 10605 | 0.571524507 | 0 | 23362 | 10633 | 0.570810794 | 0 | 23390 | 10661 | 0.569930764 | 0 |
| 23307 | 10578 | 0.572611603 | 0 | 23335 | 10606 | 0.571524507 | 0 | 23363 | 10634 | 0.570710967 | 0 | 23391 | 10662 | 0.569930764 | 0 |
| 23308 | 10579 | 0.572373568 | 0 | 23336 | 10607 | 0.571524507 | 0 | 23364 | 10635 | 0.570710967 | 0 | 23392 | 10663 | 0.569831349 | 0 |
| 23309 | 10580 | 0.572373568 | 0 | 23337 | 10608 | 0.571524507 | 0 | 23365 | 10636 | 0.570395002 | 0 | 23393 | 10664 | 0.569677752 | 0 |
| 23310 | 10581 | 0.572373568 | 0 | 23338 | 10609 | 0.571524507 | 0 | 23366 | 10637 | 0.570395002 | 0 | 23394 | 10665 | 0.569677752 | 0 |
| 23311 | 10582 | 0.572373568 | 0 | 23339 | 10610 | 0.571524507 | 0 | 23367 | 10638 | 0.570395002 | 0 | 23395 | 10666 | 0.569677752 | 0 |
| 23312 | 10583 | 0.572373568 | 0 | 23340 | 10611 | 0.571524507 | 0 | 23368 | 10639 | 0.570395002 | 0 | 23396 | 10667 | 0.569677752 | 0 |
| 23313 | 10584 | 0.572373568 | 0 | 23341 | 10612 | 0.571524507 | 0 | 23369 | 10640 | 0.570395002 | 0 | 23397 | 10668 | 0.569677752 | 0 |
| 23314 | 10585 | 0.572373568 | 0 | 23342 | 10613 | 0.571524507 | 0 | 23370 | 10641 | 0.570395002 | 0 | 23398 | 10669 | 0.569677752 | 0 |
| 23315 | 10586 | 0.572373568 | 0 | 23343 | 10614 | 0.571524507 | 0 | 23371 | 10642 | 0.570395002 | 0 | 23399 | 10670 | 0.569677752 | 0 |
| 23316 | 10587 | 0.572373568 | 0 | 23344 | 10615 | 0.571524507 | 0 | 23372 | 10643 | 0.570395002 | 0 | 23400 | 10671 | 0.569677752 | 0 |
| 23317 | 10588 | 0.572373568 | 0 | 23345 | 10616 | 0.571273252 | 0 | 23373 | 10644 | 0.570395002 | 0 | 23401 | 10672 | 0.569677752 | 0 |
| 23318 | 10589 | 0.572114982 | 0 | 23346 | 10617 | 0.571273252 | 0 | 23374 | 10645 | 0.570395002 | 0 | 23402 | 10673 | 0.569677752 | 0 |
| 23319 | 10590 | 0.571977133 | 0 | 23347 | 10618 | 0.571185347 | 0 | 23375 | 10646 | 0.570395002 | 0 | 23403 | 10674 | 0.569677752 | 0 |
| 23320 | 10591 | 0.571977133 | 0 | 23348 | 10619 | 0.571185347 | 0 | 23376 | 10647 | 0.570395002 | 0 | 23404 | 10675 | 0.569677752 | -1.130162337 |
| 23321 | 10592 | 0.571977133 | 0 | 23349 | 10620 | 0.571185347 | 0 | 23377 | 10648 | 0.570395002 | 0 | 23405 | 10676 | 0.569518524 | 0 |
| 23322 | 10593 | 0.571977133 | 0 | 23350 | 10621 | 0.571185347 | 0 | 23378 | 10649 | 0.570395002 | 0 | 23406 | 10677 | 0.569409089 | 0 |
| 23323 | 10594 | 0.571977133 | 0 | 23351 | 10622 | 0.571185347 | 0 | 23379 | 10650 | 0.570395002 | 0 | 23407 | 10678 | 0.569409089 | 0 |
| 23324 | 10595 | 0.571977133 | 0 | 23352 | 10623 | 0.571185347 | 0 | 23380 | 10651 | 0.570395002 | 0 | 23408 | 10679 | 0.569409089 | 0 |
| 23325 | 10596 | 0.571977133 | 0 | 23353 | 10624 | 0.571113438 | 0 | 23381 | 10652 | 0.570395002 | -0.042294912 | 23409 | 10680 | 0.569409089 | 0 |
| 23326 | 10597 | 0.571977133 | 0 | 23354 | 10625 | 0.571002832 | 0 | 23382 | 10653 | 0.570051822 | 0 | 23410 | 10681 | 0.569409089 | 0 |
| 23327 | 10598 | 0.571891465 | 0 | 23355 | 10626 | 0.571002832 | 0 | 23383 | 10654 | 0.570051822 | 0 | 23411 | 10682 | 0.569409089 | 0 |
| 23328 | 10599 | 0.571833065 | 0 | 23356 | 10627 | 0.571002832 | 0 | 23384 | 10655 | 0.570051822 | -1.450123419 | 23412 | 10683 | 0.569409089 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23413 | 10684 | 0.569409089 | 0 | 23441 | 10712 | 0.568321993 | 0 | 23469 | 10740 | 0.567368547 | 0 | 23497 | 10768 | 0.566464708 | 0 |
| 23414 | 10685 | 0.569409089 | -0.251765613 | 23442 | 10713 | 0.568321993 | 0 | 23470 | 10741 | 0.567368547 | 0 | 23498 | 10769 | 0.566464708 | 0 |
| 23415 | 10686 | 0.569409089 | -0.816037044 | 23443 | 10714 | 0.568321993 | 0 | 23471 | 10742 | 0.567368547 | 0 | 23499 | 10770 | 0.566464708 | 0 |
| 23416 | 10687 | 0.569268427 | 0 | 23444 | 10715 | 0.568246797 | 0 | 23472 | 10743 | 0.567368547 | -1.20502221 | 23500 | 10771 | 0.566464708 | 0 |
| 23417 | 10688 | 0.569268427 | 0 | 23445 | 10716 | 0.568246797 | 0 | 23473 | 10744 | 0.56715571 | 0 | 23501 | 10772 | 0.566464708 | 0 |
| 23418 | 10689 | 0.569268427 | 0 | 23446 | 10717 | 0.568144767 | 0 | 23474 | 10745 | 0.56715571 | 0 | 23502 | 10773 | 0.566464708 | -0.393012692 |
| 23419 | 10690 | 0.569268427 | -1.110368277 | 23447 | 10718 | 0.568144767 | 0 | 23475 | 10746 | 0.56715571 | 0 | 23503 | 10774 | 0.565954674 | 0 |
| 23420 | 10691 | 0.569181888 | 0 | 23448 | 10719 | 0.568144767 | 0 | 23476 | 10747 | 0.56715571 | 0 | 23504 | 10775 | 0.565847374 | 0 |
| 23421 | 10692 | 0.568818614 | 0 | 23449 | 10720 | 0.568144767 | 0 | 23477 | 10748 | 0.56715571 | -1.02071062 | 23505 | 10776 | 0.565847374 | 0 |
| 23422 | 10693 | 0.568818614 | 0 | 23450 | 10721 | 0.568144767 | 0 | 23478 | 10749 | 0.567024006 | 0 | 23506 | 10777 | 0.565847374 | 0 |
| 23423 | 10694 | 0.568818614 | 0 | 23451 | 10722 | 0.568144767 | 0 | 23479 | 10750 | 0.56693447 | 0 | 23507 | 10778 | 0.565847374 | 0 |
| 23424 | 10695 | 0.568818614 | 0 | 23452 | 10723 | 0.568144767 | -0.810461942 | 23480 | 10751 | 0.56693447 | 0 | 23508 | 10779 | 0.565847374 | 0 |
| 23425 | 10696 | 0.568818614 | 0 | 23453 | 10724 | 0.567998416 | 0 | 23481 | 10752 | 0.56693447 | 0 | 23509 | 10780 | 0.565847374 | 0 |
| 23426 | 10697 | 0.568818614 | 0 | 23454 | 10725 | 0.567998416 | 0 | 23482 | 10753 | 0.566464708 | 0 | 23510 | 10781 | 0.565847374 | 0 |
| 23427 | 10698 | 0.568818614 | 0 | 23455 | 10726 | 0.567770858 | 0 | 23483 | 10754 | 0.566464708 | 0 | 23511 | 10782 | 0.565847374 | -1.371353631 |
| 23428 | 10699 | 0.568818614 | 0 | 23456 | 10727 | 0.567770858 | 0 | 23484 | 10755 | 0.566464708 | 0 | 23512 | 10783 | 0.5656829 | 0 |
| 23429 | 10700 | 0.568818614 | 0 | 23457 | 10728 | 0.567770858 | 0 | 23485 | 10756 | 0.566464708 | 0 | 23513 | 10784 | 0.5656829 | 0 |
| 23430 | 10701 | 0.568818614 | 0 | 23458 | 10729 | 0.567770858 | 0 | 23486 | 10757 | 0.566464708 | 0 | 23514 | 10785 | 0.5656829 | 0 |
| 23431 | 10702 | 0.568818614 | 0 | 23459 | 10730 | 0.567770858 | 0 | 23487 | 10758 | 0.566464708 | 0 | 23515 | 10786 | 0.5656829 | 0 |
| 23432 | 10703 | 0.568818614 | 0 | 23460 | 10731 | 0.567770858 | 0 | 23488 | 10759 | 0.566464708 | 0 | 23516 | 10787 | 0.5656829 | 0 |
| 23433 | 10704 | 0.568818614 | 0 | 23461 | 10732 | 0.567770858 | 0 | 23489 | 10760 | 0.566464708 | 0 | 23517 | 10788 | 0.565562747 | 0 |
| 23434 | 10705 | 0.568818614 | 0 | 23462 | 10733 | 0.567770858 | 0 | 23490 | 10761 | 0.566464708 | 0 | 23518 | 10789 | 0.565562747 | 0 |
| 23435 | 10706 | 0.568818614 | 0 | 23463 | 10734 | 0.567770858 | 0 | 23491 | 10762 | 0.566464708 | 0 | 23519 | 10790 | 0.565514045 | 0 |
| 23436 | 10707 | 0.568818614 | 0 | 23464 | 10735 | 0.567770858 | 0 | 23492 | 10763 | 0.566464708 | 0 | 23520 | 10791 | 0.565398955 | 0 |
| 23437 | 10708 | 0.568493178 | 0 | 23465 | 10736 | 0.567770858 | 0 | 23493 | 10764 | 0.566464708 | 0 | 23521 | 10792 | 0.565398955 | 0 |
| 23438 | 10709 | 0.568425409 | 0 | 23466 | 10737 | 0.567770858 | 0 | 23494 | 10765 | 0.566464708 | 0 | 23522 | 10793 | 0.565398955 | 0 |
| 23439 | 10710 | 0.568425409 | 0 | 23467 | 10738 | 0.567770858 | -1.522040311 | 23495 | 10766 | 0.566464708 | 0 | 23523 | 10794 | 0.565398955 | 0 |
| 23440 | 10711 | 0.568321993 | 0 | 23468 | 10739 | 0.567533084 | 0 | 23496 | 10767 | 0.566464708 | 0 | 23524 | 10795 | 0.565398955 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23525 | 10796 | 0.564791124 | 0 | 23553 | 10824 | 0.563920504 | 0 | 23581 | 10852 | 0.562569664 | 0 | 23609 | 10880 | 0.561895817 | 0 |
| 23526 | 10797 | 0.564791124 | 0 | 23554 | 10825 | 0.563764423 | 0 | 23582 | 10853 | 0.562569664 | 0 | 23610 | 10881 | 0.561895817 | 0 |
| 23527 | 10798 | 0.564791124 | 0 | 23555 | 10826 | 0.563764423 | 0 | 23583 | 10854 | 0.562569664 | 0 | 23611 | 10882 | 0.561895817 | 0 |
| 23528 | 10799 | 0.564791124 | 0 | 23556 | 10827 | 0.563764423 | 0 | 23584 | 10855 | 0.562569664 | 0 | 23612 | 10883 | 0.561895817 | 0 |
| 23529 | 10800 | 0.564791124 | 0 | 23557 | 10828 | 0.563764423 | 0 | 23585 | 10856 | 0.562569664 | 0 | 23613 | 10884 | 0.56179483 | 0 |
| 23530 | 10801 | 0.564791124 | 0 | 23558 | 10829 | 0.563764423 | 0 | 23586 | 10857 | 0.562569664 | 0 | 23614 | 10885 | 0.56179483 | 0 |
| 23531 | 10802 | 0.564791124 | 0 | 23559 | 10830 | 0.563764423 | 0 | 23587 | 10858 | 0.562569664 | 0 | 23615 | 10886 | 0.56179483 | 0 |
| 23532 | 10803 | 0.564791124 | 0 | 23560 | 10831 | 0.563764423 | -0.731505079 | 23588 | 10859 | 0.562569664 | 0 | 23616 | 10887 | 0.56179483 | 0 |
| 23533 | 10804 | 0.564791124 | 0 | 23561 | 10832 | 0.563540155 | 0 | 23589 | 10860 | 0.562569664 | 0 | 23617 | 10888 | 0.56179483 | 0 |
| 23534 | 10805 | 0.564791124 | -1.415875575 | 23562 | 10833 | 0.563540155 | 0 | 23590 | 10861 | 0.562569664 | 0 | 23618 | 10889 | 0.561658238 | 0 |
| 23535 | 10806 | 0.56451282 | 0 | 23563 | 10834 | 0.563540155 | 0 | 23591 | 10862 | 0.562569664 | 0 | 23619 | 10890 | 0.561658238 | 0 |
| 23536 | 10807 | 0.564398276 | 0 | 23564 | 10835 | 0.563540155 | 0 | 23592 | 10863 | 0.562569664 | 0 | 23620 | 10891 | 0.561658238 | 0 |
| 23537 | 10808 | 0.564398276 | 0 | 23565 | 10836 | 0.563540155 | 0 | 23593 | 10864 | 0.562569664 | 0 | 23621 | 10892 | 0.561658238 | 0 |
| 23538 | 10809 | 0.564398276 | 0 | 23566 | 10837 | 0.563540155 | 0 | 23594 | 10865 | 0.562569664 | 0 | 23622 | 10893 | 0.561658238 | 0 |
| 23539 | 10810 | 0.564398276 | -1.324498051 | 23567 | 10838 | 0.563540155 | 0 | 23595 | 10866 | 0.562569664 | 0 | 23623 | 10894 | 0.561463181 | 0 |
| 23540 | 10811 | 0.564123493 | 0 | 23568 | 10839 | 0.563540155 | 0 | 23596 | 10867 | 0.562569664 | 0 | 23624 | 10895 | 0.561463181 | 0 |
| 23541 | 10812 | 0.564123493 | 0 | 23569 | 10840 | 0.563386776 | 0 | 23597 | 10868 | 0.562569664 | 0 | 23625 | 10896 | 0.561463181 | 0 |
| 23542 | 10813 | 0.564123493 | 0 | 23570 | 10841 | 0.563386776 | 0 | 23598 | 10869 | 0.562569664 | 0 | 23626 | 10897 | 0.561463181 | 0 |
| 23543 | 10814 | 0.564123493 | 0 | 23571 | 10842 | 0.563386776 | 0 | 23599 | 10870 | 0.562569664 | 0 | 23627 | 10898 | 0.561463181 | 0 |
| 23544 | 10815 | 0.564123493 | 0 | 23572 | 10843 | 0.563386776 | 0 | 23600 | 10871 | 0.562569664 | 0 | 23628 | 10899 | 0.561463181 | 0 |
| 23545 | 10816 | 0.564123493 | 0 | 23573 | 10844 | 0.563386776 | 0 | 23601 | 10872 | 0.562569664 | 0 | 23629 | 10900 | 0.561463181 | 0 |
| 23546 | 10817 | 0.564123493 | 0 | 23574 | 10845 | 0.563386776 | 0 | 23602 | 10873 | 0.562569664 | 0 | 23630 | 10901 | 0.561463181 | 0 |
| 23547 | 10818 | 0.564123493 | 0 | 23575 | 10846 | 0.563386776 | 0 | 23603 | 10874 | 0.562569664 | 0 | 23631 | 10902 | 0.561463181 | 0 |
| 23548 | 10819 | 0.564123493 | 0 | 23576 | 10847 | 0.563386776 | 0 | 23604 | 10875 | 0.562569664 | 0 | 23632 | 10903 | 0.561463181 | 0 |
| 23549 | 10820 | 0.563982006 | -1.612979339 | 23577 | 10848 | 0.563386776 | 0 | 23605 | 10876 | 0.562569664 | 0 | 23633 | 10904 | 0.561463181 | 0 |
| 23550 | 10821 | 0.563920504 | 0 | 23578 | 10849 | 0.563190529 | 0 | 23606 | 10877 | 0.562569664 | -0.426870959 | 23634 | 10905 | 0.561463181 | -0.243112259 |
| 23551 | 10822 | 0.563920504 | 0 | 23579 | 10850 | 0.563123965 | 0 | 23607 | 10878 | 0.562569664 | -0.874028991 | 23635 | 10906 | 0.561330592 | 0 |
| 23552 | 10823 | 0.563920504 | 0 | 23580 | 10851 | 0.562569664 | 0 | 23608 | 10879 | 0.562569664 | -1.175058986 | 23636 | 10907 | 0.561330592 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23637 | 10908 | 0.561330592 | 0 | 23665 | 10936 | 0.560635165 | -1.301932223 | 23693 | 10964 | 0.559478588 | 0 | 23721 | 10992 | 0.55893538 | 0 |
| 23638 | 10909 | 0.561161902 | 0 | 23666 | 10937 | 0.56035951 | 0 | 23694 | 10965 | 0.559478588 | 0 | 23722 | 10993 | 0.55893538 | 0 |
| 23639 | 10910 | 0.561161902 | 0 | 23667 | 10938 | 0.56035951 | 0 | 23695 | 10966 | 0.559478588 | 0 | 23723 | 10994 | 0.558841792 | -1.562003611 |
| 23640 | 10911 | 0.561161902 | 0 | 23668 | 10939 | 0.56035951 | 0 | 23696 | 10967 | 0.559478588 | 0 | 23724 | 10995 | 0.558709244 | 0 |
| 23641 | 10912 | 0.561161902 | 0 | 23669 | 10940 | 0.56035951 | 0 | 23697 | 10968 | 0.559478588 | 0 | 23725 | 10996 | 0.558709244 | 0 |
| 23642 | 10913 | 0.561161902 | 0 | 23670 | 10941 | 0.56035951 | 0 | 23698 | 10969 | 0.559478588 | 0 | 23726 | 10997 | 0.558709244 | 0 |
| 23643 | 10914 | 0.561161902 | 0 | 23671 | 10942 | 0.56035951 | 0 | 23699 | 10970 | 0.559478588 | 0 | 23727 | 10998 | 0.558709244 | 0 |
| 23644 | 10915 | 0.561161902 | -1.439708184 | 23672 | 10943 | 0.560189963 | 0 | 23700 | 10971 | 0.559478588 | 0 | 23728 | 10999 | 0.558709244 | 0 |
| 23645 | 10916 | 0.56094004 | 0 | 23673 | 10944 | 0.560189963 | 0 | 23701 | 10972 | 0.559478588 | 0 | 23729 | 11000 | 0.558709244 | 0 |
| 23646 | 10917 | 0.56094004 | 0 | 23674 | 10945 | 0.560189963 | 0 | 23702 | 10973 | 0.559478588 | 0 | 23730 | 11001 | 0.558709244 | 0 |
| 23647 | 10918 | 0.56094004 | 0 | 23675 | 10946 | 0.560189963 | 0 | 23703 | 10974 | 0.559478588 | 0 | 23731 | 11002 | 0.558709244 | 0 |
| 23648 | 10919 | 0.56094004 | 0 | 23676 | 10947 | 0.560189963 | 0 | 23704 | 10975 | 0.559478588 | 0 | 23732 | 11003 | 0.558709244 | -1.479949403 |
| 23649 | 10920 | 0.56094004 | 0 | 23677 | 10948 | 0.560189963 | 0 | 23705 | 10976 | 0.559478588 | 0 | 23733 | 11004 | 0.558507011 | 0 |
| 23650 | 10921 | 0.56094004 | -1.376260966 | 23678 | 10949 | 0.560189963 | 0 | 23706 | 10977 | 0.559478588 | 0 | 23734 | 11005 | 0.558507011 | 0 |
| 23651 | 10922 | 0.56094004 | -1.376260966 | 23679 | 10950 | 0.560189963 | 0 | 23707 | 10978 | 0.559478588 | 0 | 23735 | 11006 | 0.558507011 | 0 |
| 23652 | 10923 | 0.56094004 | -1.376260966 | 23680 | 10951 | 0.560189963 | 0 | 23708 | 10979 | 0.559478588 | 0 | 23736 | 11007 | 0.558507011 | 0 |
| 23653 | 10924 | 0.560849684 | 0 | 23681 | 10952 | 0.560189963 | 0 | 23709 | 10980 | 0.559478588 | -1.399998813 | 23737 | 11008 | 0.558507011 | 0 |
| 23654 | 10925 | 0.560800642 | 0 | 23682 | 10953 | 0.560189963 | -1.212200794 | 23710 | 10981 | 0.559136489 | 0 | 23738 | 11009 | 0.558507011 | -1.077663999 |
| 23655 | 10926 | 0.560635165 | 0 | 23683 | 10954 | 0.559992242 | 0 | 23711 | 10982 | 0.559058776 | 0 | 23739 | 11010 | 0.558507011 | -0.600542744 |
| 23656 | 10927 | 0.560635165 | 0 | 23684 | 10955 | 0.559992242 | 0 | 23712 | 10983 | 0.559058776 | 0 | 23740 | 11011 | 0.558413705 | 0 |
| 23657 | 10928 | 0.560635165 | 0 | 23685 | 10956 | 0.559880526 | 0 | 23713 | 10984 | 0.559058776 | 0 | 23741 | 11012 | 0.558160546 | 0 |
| 23658 | 10929 | 0.560635165 | 0 | 23686 | 10957 | 0.559880526 | 0 | 23714 | 10985 | 0.559058776 | 0 | 23742 | 11013 | 0.558160546 | 0 |
| 23659 | 10930 | 0.560635165 | 0 | 23687 | 10958 | 0.559880526 | 0 | 23715 | 10986 | 0.559058776 | 0 | 23743 | 11014 | 0.558160546 | 0 |
| 23660 | 10931 | 0.560635165 | 0 | 23688 | 10959 | 0.559880526 | 0 | 23716 | 10987 | 0.559058776 | 0 | 23744 | 11015 | 0.558160546 | 0 |
| 23661 | 10932 | 0.560635165 | 0 | 23689 | 10960 | 0.559880526 | 0 | 23717 | 10988 | 0.559058776 | 0 | 23745 | 11016 | 0.558160546 | 0 |
| 23662 | 10933 | 0.560635165 | 0 | 23690 | 10961 | 0.559880526 | 0 | 23718 | 10989 | 0.55893538 | 0 | 23746 | 11017 | 0.558160546 | 0 |
| 23663 | 10934 | 0.560635165 | 0 | 23691 | 10962 | 0.559880526 | -1.159264719 | 23719 | 10990 | 0.55893538 | 0 | 23747 | 11018 | 0.558160546 | 0 |
| 23664 | 10935 | 0.560635165 | -0.824810968 | 23692 | 10963 | 0.559758687 | -1.617202658 | 23720 | 10991 | 0.55893538 | 0 | 23748 | 11019 | 0.558160546 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23749 | 11020 | 0.558160546 | 0 | 23777 | 11048 | 0.556965787 | 0 | 23805 | 11076 | 0.556087537 | 0 | 23833 | 11104 | 0.554882836 | 0 |
| 23750 | 11021 | 0.558160546 | -0.468263644 | 23778 | 11049 | 0.556965787 | 0 | 23806 | 11077 | 0.556087537 | -0.779053477 | 23834 | 11105 | 0.554882836 | 0 |
| 23751 | 11022 | 0.558160546 | -1.070323636 | 23779 | 11050 | 0.556965787 | 0 | 23807 | 11078 | 0.555972659 | 0 | 23835 | 11106 | 0.554882836 | 0 |
| 23752 | 11023 | 0.557874543 | 0 | 23780 | 11051 | 0.556965787 | 0 | 23808 | 11079 | 0.555972659 | 0 | 23836 | 11107 | 0.554882836 | 0 |
| 23753 | 11024 | 0.557874543 | 0 | 23781 | 11052 | 0.556965787 | -1.443904299 | 23809 | 11080 | 0.555972659 | 0 | 23837 | 11108 | 0.554882836 | 0 |
| 23754 | 11025 | 0.557749476 | 0 | 23782 | 11053 | 0.556791826 | 0 | 23810 | 11081 | 0.555972659 | 0 | 23838 | 11109 | 0.554882836 | 0 |
| 23755 | 11026 | 0.557749476 | 0 | 23783 | 11054 | 0.556791826 | 0 | 23811 | 11082 | 0.555972659 | 0 | 23839 | 11110 | 0.554882836 | 0 |
| 23756 | 11027 | 0.557749476 | 0 | 23784 | 11055 | 0.556644682 | 0 | 23812 | 11083 | 0.555877784 | 0 | 23840 | 11111 | 0.554882836 | 0 |
| 23757 | 11028 | 0.557749476 | 0 | 23785 | 11056 | 0.556644682 | 0 | 23813 | 11084 | 0.55573024 | 0 | 23841 | 11112 | 0.554882836 | 0 |
| 23758 | 11029 | 0.557749476 | -0.526666661 | 23786 | 11057 | 0.556644682 | 0 | 23814 | 11085 | 0.554882836 | 0 | 23842 | 11113 | 0.554882836 | 0 |
| 23759 | 11030 | 0.557634447 | 0 | 23787 | 11058 | 0.556644682 | 0 | 23815 | 11086 | 0.554882836 | 0 | 23843 | 11114 | 0.554882836 | 0 |
| 23760 | 11031 | 0.557430025 | 0 | 23788 | 11059 | 0.556644682 | 0 | 23816 | 11087 | 0.554882836 | 0 | 23844 | 11115 | 0.554882836 | 0 |
| 23761 | 11032 | 0.557430025 | 0 | 23789 | 11060 | 0.556644682 | 0 | 23817 | 11088 | 0.554882836 | 0 | 23845 | 11116 | 0.554882836 | 0 |
| 23762 | 11033 | 0.557430025 | 0 | 23790 | 11061 | 0.556644682 | -1.039654816 | 23818 | 11089 | 0.554882836 | 0 | 23846 | 11117 | 0.554882836 | 0 |
| 23763 | 11034 | 0.557430025 | 0 | 23791 | 11062 | 0.556409356 | 0 | 23819 | 11090 | 0.554882836 | 0 | 23847 | 11118 | 0.554882836 | 0 |
| 23764 | 11035 | 0.557430025 | 0 | 23792 | 11063 | 0.556409356 | 0 | 23820 | 11091 | 0.554882836 | 0 | 23848 | 11119 | 0.554882836 | 0 |
| 23765 | 11036 | 0.557430025 | 0 | 23793 | 11064 | 0.556409356 | -1.579159304 | 23821 | 11092 | 0.554882836 | 0 | 23849 | 11120 | 0.554882836 | 0 |
| 23766 | 11037 | 0.557430025 | 0 | 23794 | 11065 | 0.556229486 | 0 | 23822 | 11093 | 0.554882836 | 0 | 23850 | 11121 | 0.554882836 | 0 |
| 23767 | 11038 | 0.557430025 | 0 | 23795 | 11066 | 0.556229486 | 0 | 23823 | 11094 | 0.554882836 | 0 | 23851 | 11122 | 0.554882836 | -0.667835999 |
| 23768 | 11039 | 0.557430025 | -0.3148972 | 23796 | 11067 | 0.556229486 | 0 | 23824 | 11095 | 0.554882836 | 0 | 23852 | 11123 | 0.554882836 | -1.006654556 |
| 23769 | 11040 | 0.557174633 | 0 | 23797 | 11068 | 0.556229486 | 0 | 23825 | 11096 | 0.554882836 | 0 | 23853 | 11124 | 0.554882836 | -1.307684552 |
| 23770 | 11041 | 0.557174633 | 0 | 23798 | 11069 | 0.556229486 | 0 | 23826 | 11097 | 0.554882836 | 0 | 23854 | 11125 | 0.554882836 | -1.404594565 |
| 23771 | 11042 | 0.557174633 | 0 | 23799 | 11070 | 0.556229486 | 0 | 23827 | 11098 | 0.554882836 | 0 | 23855 | 11126 | 0.554190733 | 0 |
| 23772 | 11043 | 0.557174633 | 0 | 23800 | 11071 | 0.556229486 | 0 | 23828 | 11099 | 0.554882836 | 0 | 23856 | 11127 | 0.554037082 | 0 |
| 23773 | 11044 | 0.557174633 | 0 | 23801 | 11072 | 0.556087537 | 0 | 23829 | 11100 | 0.554882836 | 0 | 23857 | 11128 | 0.553969493 | 0 |
| 23774 | 11045 | 0.557174633 | 0 | 23802 | 11073 | 0.556087537 | 0 | 23830 | 11101 | 0.554882836 | 0 | 23858 | 11129 | 0.553969493 | 0 |
| 23775 | 11046 | 0.557174633 | 0 | 23803 | 11074 | 0.556087537 | 0 | 23831 | 11102 | 0.554882836 | 0 | 23859 | 11130 | 0.553890162 | 0 |
| 23776 | 11047 | 0.556965787 | 0 | 23804 | 11075 | 0.556087537 | 0 | 23832 | 11103 | 0.554882836 | 0 | 23860 | 11131 | 0.553890162 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23861 | 11132 | 0.553890162 | 0 | 23889 | 11160 | 0.553128108 | 0 | 23917 | 11188 | 0.552034993 | 0 | 23945 | 11216 | 0.551211686 | 0 |
| 23862 | 11133 | 0.55379574 | 0 | 23890 | 11161 | 0.5529822 | 0 | 23918 | 11189 | 0.552034993 | 0 | 23946 | 11217 | 0.551089847 | 0 |
| 23863 | 11134 | 0.55379574 | 0 | 23891 | 11162 | 0.5529822 | 0 | 23919 | 11190 | 0.552034993 | 0 | 23947 | 11218 | 0.551089847 | 0 |
| 23864 | 11135 | 0.55379574 | 0 | 23892 | 11163 | 0.5529822 | 0 | 23920 | 11191 | 0.551911596 | 0 | 23948 | 11219 | 0.551089847 | 0 |
| 23865 | 11136 | 0.55379574 | 0 | 23893 | 11164 | 0.5529822 | 0 | 23921 | 11192 | 0.551911596 | 0 | 23949 | 11220 | 0.551089847 | 0 |
| 23866 | 11137 | 0.553681467 | 0 | 23894 | 11165 | 0.552809827 | 0 | 23922 | 11193 | 0.551911596 | -0.623165604 | 23950 | 11221 | 0.551089847 | 0 |
| 23867 | 11138 | 0.553681467 | 0 | 23895 | 11166 | 0.552809827 | 0 | 23923 | 11194 | 0.551629678 | 0 | 23951 | 11222 | 0.550959643 | 0 |
| 23868 | 11139 | 0.553681467 | 0 | 23896 | 11167 | 0.552809827 | 0 | 23924 | 11195 | 0.551629678 | 0 | 23952 | 11223 | 0.550867758 | 0 |
| 23869 | 11140 | 0.553681467 | 0 | 23897 | 11168 | 0.552809827 | 0 | 23925 | 11196 | 0.551629678 | 0 | 23953 | 11224 | 0.550867758 | 0 |
| 23870 | 11141 | 0.553681467 | 0 | 23898 | 11169 | 0.552809827 | 0 | 23926 | 11197 | 0.551629678 | 0 | 23954 | 11225 | 0.550867758 | 0 |
| 23871 | 11142 | 0.553681467 | 0 | 23899 | 11170 | 0.552809827 | 0 | 23927 | 11198 | 0.551629678 | 0 | 23955 | 11226 | 0.550867758 | 0 |
| 23872 | 11143 | 0.553681467 | 0 | 23900 | 11171 | 0.552809827 | -1.448060258 | 23928 | 11199 | 0.551629678 | 0 | 23956 | 11227 | 0.550867758 | 0 |
| 23873 | 11144 | 0.553681467 | -0.021791703 | 23901 | 11172 | 0.552676424 | 0 | 23929 | 11200 | 0.551629678 | 0 | 23957 | 11228 | 0.550867758 | 0 |
| 23874 | 11145 | 0.553614822 | 0 | 23902 | 11173 | 0.55260307 | 0 | 23930 | 11201 | 0.551629678 | 0 | 23958 | 11229 | 0.550867758 | 0 |
| 23875 | 11146 | 0.553540348 | 0 | 23903 | 11174 | 0.55260307 | 0 | 23931 | 11202 | 0.551629678 | 0 | 23959 | 11230 | 0.550867758 | 0 |
| 23876 | 11147 | 0.553540348 | 0 | 23904 | 11175 | 0.55260307 | 0 | 23932 | 11203 | 0.551629678 | 0 | 23960 | 11231 | 0.550867758 | -0.296635883 |
| 23877 | 11148 | 0.553540348 | 0 | 23905 | 11176 | 0.55260307 | 0 | 23933 | 11204 | 0.551629678 | 0 | 23961 | 11232 | 0.550867758 | -1.338028568 |
| 23878 | 11149 | 0.553540348 | 0 | 23906 | 11177 | 0.55260307 | -0.707904327 | 23934 | 11205 | 0.551629678 | 0 | 23962 | 11233 | 0.550746667 | 0 |
| 23879 | 11150 | 0.553540348 | 0 | 23907 | 11178 | 0.552350499 | 0 | 23935 | 11206 | 0.551629678 | 0 | 23963 | 11234 | 0.550746667 | 0 |
| 23880 | 11151 | 0.553540348 | 0 | 23908 | 11179 | 0.552350499 | 0 | 23936 | 11207 | 0.551380442 | 0 | 23964 | 11235 | 0.550746667 | 0 |
| 23881 | 11152 | 0.553361663 | 0 | 23909 | 11180 | 0.552350499 | 0 | 23937 | 11208 | 0.551380442 | 0 | 23965 | 11236 | 0.550746667 | 0 |
| 23882 | 11153 | 0.553361663 | 0 | 23910 | 11181 | 0.552350499 | 0 | 23938 | 11209 | 0.551380442 | 0 | 23966 | 11237 | 0.550746667 | 0 |
| 23883 | 11154 | 0.553361663 | 0 | 23911 | 11182 | 0.552350499 | 0 | 23939 | 11210 | 0.551288654 | 0 | 23967 | 11238 | 0.550746667 | 0 |
| 23884 | 11155 | 0.553253211 | 0 | 23912 | 11183 | 0.552350499 | 0 | 23940 | 11211 | 0.551288654 | 0 | 23968 | 11239 | 0.550335208 | 0 |
| 23885 | 11156 | 0.553128108 | 0 | 23913 | 11184 | 0.552350499 | -0.458279424 | 23941 | 11212 | 0.551288654 | 0 | 23969 | 11240 | 0.550335208 | 0 |
| 23886 | 11157 | 0.553128108 | 0 | 23914 | 11185 | 0.552148549 | 0 | 23942 | 11213 | 0.551288654 | 0 | 23970 | 11241 | 0.550335208 | 0 |
| 23887 | 11158 | 0.553128108 | 0 | 23915 | 11186 | 0.552034993 | 0 | 23943 | 11214 | 0.551288654 | 0 | 23971 | 11242 | 0.550335208 | 0 |
| 23888 | 11159 | 0.553128108 | 0 | 23916 | 11187 | 0.552034993 | 0 | 23944 | 11215 | 0.551288654 | -0.431669842 | 23972 | 11243 | 0.550335208 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 23973 | 11244 | 0.550335208 | 0 | 24001 | 11272 | 0.54963978 | 0 | 24029 | 11300 | 0.548529407 | 0 | 24057 | 11328 | 0.547329698 | 0 |
| 23974 | 11245 | 0.550335208 | 0 | 24002 | 11273 | 0.54963978 | -0.181358292 | 24030 | 11301 | 0.548400708 | 0 | 24058 | 11329 | 0.547329698 | 0 |
| 23975 | 11246 | 0.550335208 | 0 | 24003 | 11274 | 0.54963978 | -1.222750977 | 24031 | 11302 | 0.548400708 | 0 | 24059 | 11330 | 0.547329698 | 0 |
| 23976 | 11247 | 0.550335208 | 0 | 24004 | 11275 | 0.549474366 | 0 | 24032 | 11303 | 0.548400708 | 0 | 24060 | 11331 | 0.547329698 | 0 |
| 23977 | 11248 | 0.550335208 | 0 | 24005 | 11276 | 0.549474366 | 0 | 24033 | 11304 | 0.548400708 | 0 | 24061 | 11332 | 0.547329698 | 0 |
| 23978 | 11249 | 0.550335208 | 0 | 24006 | 11277 | 0.549474366 | 0 | 24034 | 11305 | 0.548400708 | 0 | 24062 | 11333 | 0.547329698 | 0 |
| 23979 | 11250 | 0.550335208 | 0 | 24007 | 11278 | 0.549474366 | 0 | 24035 | 11306 | 0.548400708 | 0 | 24063 | 11334 | 0.547329698 | 0 |
| 23980 | 11251 | 0.550335208 | 0 | 24008 | 11279 | 0.549205703 | 0 | 24036 | 11307 | 0.548400708 | 0 | 24064 | 11335 | 0.547329698 | 0 |
| 23981 | 11252 | 0.550335208 | 0 | 24009 | 11280 | 0.549205703 | 0 | 24037 | 11308 | 0.548296947 | -0.601512152 | 24065 | 11336 | 0.547329698 | 0 |
| 23982 | 11253 | 0.550335208 | 0 | 24010 | 11281 | 0.549205703 | 0 | 24038 | 11309 | 0.548211514 | 0 | 24066 | 11337 | 0.547329698 | 0 |
| 23983 | 11254 | 0.550335208 | 0 | 24011 | 11282 | 0.549205703 | 0 | 24039 | 11310 | 0.548211514 | 0 | 24067 | 11338 | 0.547329698 | 0 |
| 23984 | 11255 | 0.550335208 | -0.2507797 | 24012 | 11283 | 0.549205703 | 0 | 24040 | 11311 | 0.548211514 | 0 | 24068 | 11339 | 0.547329698 | 0 |
| 23985 | 11256 | 0.549942003 | 0 | 24013 | 11284 | 0.549205703 | 0 | 24041 | 11312 | 0.548211514 | 0 | 24069 | 11340 | 0.547329698 | 0 |
| 23986 | 11257 | 0.549942003 | 0 | 24014 | 11285 | 0.549205703 | 0 | 24042 | 11313 | 0.548211514 | 0 | 24070 | 11341 | 0.547329698 | 0 |
| 23987 | 11258 | 0.549942003 | 0 | 24015 | 11286 | 0.549205703 | 0 | 24043 | 11314 | 0.548211514 | 0 | 24071 | 11342 | 0.547329698 | 0 |
| 23988 | 11259 | 0.549942003 | 0 | 24016 | 11287 | 0.549205703 | 0 | 24044 | 11315 | 0.548211514 | 0 | 24072 | 11343 | 0.547329698 | 0 |
| 23989 | 11260 | 0.549942003 | 0 | 24017 | 11288 | 0.549205703 | -1.313361685 | 24045 | 11316 | 0.548211514 | -1.039654816 | 24073 | 11344 | 0.547329698 | 0 |
| 23990 | 11261 | 0.549942003 | 0 | 24018 | 11289 | 0.548908952 | 0 | 24046 | 11317 | 0.548079128 | 0 | 24074 | 11345 | 0.547329698 | 0 |
| 23991 | 11262 | 0.549832843 | 0 | 24019 | 11290 | 0.548829853 | 0 | 24047 | 11318 | 0.548079128 | 0 | 24075 | 11346 | 0.547329698 | 0 |
| 23992 | 11263 | 0.549832843 | 0 | 24020 | 11291 | 0.548693261 | 0 | 24048 | 11319 | 0.548079128 | 0 | 24076 | 11347 | 0.547329698 | 0 |
| 23993 | 11264 | 0.549751871 | 0 | 24021 | 11292 | 0.548693261 | 0 | 24049 | 11320 | 0.548079128 | 0 | 24077 | 11348 | 0.547329698 | 0 |
| 23994 | 11265 | 0.54963978 | 0 | 24022 | 11293 | 0.548693261 | 0 | 24050 | 11321 | 0.548079128 | -1.411398273 | 24078 | 11349 | 0.547329698 | 0 |
| 23995 | 11266 | 0.54963978 | 0 | 24023 | 11294 | 0.548693261 | 0 | 24051 | 11322 | 0.548079128 | -1.411398273 | 24079 | 11350 | 0.547329698 | 0 |
| 23996 | 11267 | 0.54963978 | 0 | 24024 | 11295 | 0.548693261 | 0 | 24052 | 11323 | 0.547981303 | 0 | 24080 | 11351 | 0.547329698 | 0 |
| 23997 | 11268 | 0.54963978 | 0 | 24025 | 11296 | 0.548693261 | 0 | 24053 | 11324 | 0.547906068 | 0 | 24081 | 11352 | 0.547329698 | 0 |
| 23998 | 11269 | 0.54963978 | 0 | 24026 | 11297 | 0.548693261 | 0 | 24054 | 11325 | 0.547906068 | 0 | 24082 | 11353 | 0.547329698 | 0 |
| 23999 | 11270 | 0.54963978 | 0 | 24027 | 11298 | 0.548529407 | 0 | 24055 | 11326 | 0.547846408 | 0 | 24083 | 11354 | 0.547329698 | 0 |
| 24000 | 11271 | 0.54963978 | 0 | 24028 | 11299 | 0.548529407 | 0 | 24056 | 11327 | 0.547329698 | 0 | 24084 | 11355 | 0.547329698 | -0.889268957 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24085 | 11356 | 0.546795182 | 0 | 24113 | 11384 | 0.546029414 | 0 | 24141 | 11412 | 0.545195568 | 0 | 24169 | 11440 | 0.544344844 | 0 |
| 24086 | 11357 | 0.546731084 | 0 | 24114 | 11385 | 0.546029414 | 0 | 24142 | 11413 | 0.545195568 | 0 | 24170 | 11441 | 0.544344844 | 0 |
| 24087 | 11358 | 0.546649519 | 0 | 24115 | 11386 | 0.546029414 | -1.474145827 | 24143 | 11414 | 0.545195568 | 0 | 24171 | 11442 | 0.544344844 | 0 |
| 24088 | 11359 | 0.546649519 | 0 | 24116 | 11387 | 0.545834707 | 0 | 24144 | 11415 | 0.545195568 | 0 | 24172 | 11443 | 0.544188314 | 0 |
| 24089 | 11360 | 0.546649519 | 0 | 24117 | 11388 | 0.545834707 | 0 | 24145 | 11416 | 0.544940176 | 0 | 24173 | 11444 | 0.544188314 | 0 |
| 24090 | 11361 | 0.546649519 | 0 | 24118 | 11389 | 0.545834707 | 0 | 24146 | 11417 | 0.544940176 | 0 | 24174 | 11445 | 0.544188314 | 0 |
| 24091 | 11362 | 0.546649519 | 0 | 24119 | 11390 | 0.545834707 | -0.568544654 | 24147 | 11418 | 0.544840898 | 0 | 24175 | 11446 | 0.544086259 | 0 |
| 24092 | 11363 | 0.546649519 | -0.175466966 | 24120 | 11391 | 0.545668914 | 0 | 24148 | 11419 | 0.544840898 | 0 | 24176 | 11447 | 0.544086259 | 0 |
| 24093 | 11364 | 0.546542219 | 0 | 24121 | 11392 | 0.545668914 | 0 | 24149 | 11420 | 0.544840898 | 0 | 24177 | 11448 | 0.544086259 | 0 |
| 24094 | 11365 | 0.546542219 | 0 | 24122 | 11393 | 0.545668914 | 0 | 24150 | 11421 | 0.544840898 | 0 | 24178 | 11449 | 0.544086259 | 0 |
| 24095 | 11366 | 0.546542219 | 0 | 24123 | 11394 | 0.545571418 | 0 | 24151 | 11422 | 0.544840898 | 0 | 24179 | 11450 | 0.544086259 | 0 |
| 24096 | 11367 | 0.546542219 | 0 | 24124 | 11395 | 0.545571418 | 0 | 24152 | 11423 | 0.544840898 | 0 | 24180 | 11451 | 0.543601825 | 0 |
| 24097 | 11368 | 0.546542219 | 0 | 24125 | 11396 | 0.545571418 | 0 | 24153 | 11424 | 0.544840898 | 0 | 24181 | 11452 | 0.543601825 | 0 |
| 24098 | 11369 | 0.546542219 | -0.135386282 | 24126 | 11397 | 0.545571418 | 0 | 24154 | 11425 | 0.544615349 | 0 | 24182 | 11453 | 0.543601825 | 0 |
| 24099 | 11370 | 0.546394726 | 0 | 24127 | 11398 | 0.545571418 | 0 | 24155 | 11426 | 0.544615349 | 0 | 24183 | 11454 | 0.543601825 | 0 |
| 24100 | 11371 | 0.546394726 | 0 | 24128 | 11399 | 0.545571418 | 0 | 24156 | 11427 | 0.544615349 | 0 | 24184 | 11455 | 0.543601825 | 0 |
| 24101 | 11372 | 0.546394726 | 0 | 24129 | 11400 | 0.545571418 | 0 | 24157 | 11428 | 0.544615349 | 0 | 24185 | 11456 | 0.543601825 | 0 |
| 24102 | 11373 | 0.546394726 | 0 | 24130 | 11401 | 0.545571418 | 0 | 24158 | 11429 | 0.544615349 | 0 | 24186 | 11457 | 0.543601825 | 0 |
| 24103 | 11374 | 0.546394726 | 0 | 24131 | 11402 | 0.545571418 | 0 | 24159 | 11430 | 0.544615349 | -1.155224741 | 24187 | 11458 | 0.543601825 | 0 |
| 24104 | 11375 | 0.546394726 | 0 | 24132 | 11403 | 0.545571418 | 0 | 24160 | 11431 | 0.544459268 | 0 | 24188 | 11459 | 0.543601825 | 0 |
| 24105 | 11376 | 0.546298119 | -1.097426029 | 24133 | 11404 | 0.545571418 | 0 | 24161 | 11432 | 0.544344844 | 0 | 24189 | 11460 | 0.543601825 | 0 |
| 24106 | 11377 | 0.546179248 | 0 | 24134 | 11405 | 0.545195568 | 0 | 24162 | 11433 | 0.544344844 | 0 | 24190 | 11461 | 0.543601825 | 0 |
| 24107 | 11378 | 0.546179248 | 0 | 24135 | 11406 | 0.545195568 | 0 | 24163 | 11434 | 0.544344844 | 0 | 24191 | 11462 | 0.543601825 | 0 |
| 24108 | 11379 | 0.546179248 | 0 | 24136 | 11407 | 0.545195568 | 0 | 24164 | 11435 | 0.544344844 | 0 | 24192 | 11463 | 0.543601825 | 0 |
| 24109 | 11380 | 0.546179248 | 0 | 24137 | 11408 | 0.545195568 | 0 | 24165 | 11436 | 0.544344844 | 0 | 24193 | 11464 | 0.543601825 | 0 |
| 24110 | 11381 | 0.546179248 | 0 | 24138 | 11409 | 0.545195568 | 0 | 24166 | 11437 | 0.544344844 | 0 | 24194 | 11465 | 0.543601825 | 0 |
| 24111 | 11382 | 0.546179248 | -1.527241504 | 24139 | 11410 | 0.545195568 | 0 | 24167 | 11438 | 0.544344844 | 0 | 24195 | 11466 | 0.543601825 | 0 |
| 24112 | 11383 | 0.546029414 | 0 | 24140 | 11411 | 0.545195568 | 0 | 24168 | 11439 | 0.544344844 | 0 | 24196 | 11467 | 0.543601825 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24197 | 11468 | 0.543601825 | 0 | 24225 | 11496 | 0.542366278 | 0 | 24253 | 11524 | 0.541380365 | 0 | 24281 | 11552 | 0.540958515 | 0 |
| 24198 | 11469 | 0.543601825 | 0 | 24226 | 11497 | 0.542366278 | 0 | 24254 | 11525 | 0.541380365 | 0 | 24282 | 11553 | 0.540958515 | 0 |
| 24199 | 11470 | 0.543601825 | 0 | 24227 | 11498 | 0.542366278 | 0 | 24255 | 11526 | 0.541380365 | 0 | 24283 | 11554 | 0.540958515 | 0 |
| 24200 | 11471 | 0.543601825 | 0 | 24228 | 11499 | 0.542366278 | 0 | 24256 | 11527 | 0.541380365 | 0 | 24284 | 11555 | 0.540958515 | 0 |
| 24201 | 11472 | 0.543601825 | 0 | 24229 | 11500 | 0.542366278 | 0 | 24257 | 11528 | 0.541380365 | 0 | 24285 | 11556 | 0.540826771 | 0 |
| 24202 | 11473 | 0.543601825 | 0 | 24230 | 11501 | 0.542366278 | 0 | 24258 | 11529 | 0.541380365 | 0 | 24286 | 11557 | 0.540826771 | 0 |
| 24203 | 11474 | 0.543601825 | -0.591966834 | 24231 | 11502 | 0.542366278 | 0 | 24259 | 11530 | 0.541380365 | 0 | 24287 | 11558 | 0.540826771 | 0 |
| 24204 | 11475 | 0.543601825 | -1.495056821 | 24232 | 11503 | 0.542366278 | 0 | 24260 | 11531 | 0.541380365 | 0 | 24288 | 11559 | 0.540826771 | 0 |
| 24205 | 11476 | 0.543156623 | 0 | 24233 | 11504 | 0.542366278 | 0 | 24261 | 11532 | 0.541380365 | 0 | 24289 | 11560 | 0.540826771 | 0 |
| 24206 | 11477 | 0.543071875 | 0 | 24234 | 11505 | 0.542151759 | 0 | 24262 | 11533 | 0.541380365 | 0 | 24290 | 11561 | 0.540826771 | 0 |
| 24207 | 11478 | 0.543071875 | 0 | 24235 | 11506 | 0.542151759 | 0 | 24263 | 11534 | 0.541380365 | 0 | 24291 | 11562 | 0.540826771 | 0 |
| 24208 | 11479 | 0.543071875 | 0 | 24236 | 11507 | 0.54201391 | 0 | 24264 | 11535 | 0.541380365 | 0 | 24292 | 11563 | 0.540575371 | 0 |
| 24209 | 11480 | 0.543071875 | 0 | 24237 | 11508 | 0.54201391 | 0 | 24265 | 11536 | 0.541380365 | 0 | 24293 | 11564 | 0.540575371 | 0 |
| 24210 | 11481 | 0.542947274 | 0 | 24238 | 11509 | 0.54201391 | 0 | 24266 | 11537 | 0.541380365 | 0 | 24294 | 11565 | 0.540575371 | 0 |
| 24211 | 11482 | 0.542947274 | 0 | 24239 | 11510 | 0.54201391 | 0 | 24267 | 11538 | 0.541380365 | 0 | 24295 | 11566 | 0.540575371 | 0 |
| 24212 | 11483 | 0.542947274 | 0 | 24240 | 11511 | 0.54201391 | 0 | 24268 | 11539 | 0.541380365 | 0 | 24296 | 11567 | 0.540575371 | 0 |
| 24213 | 11484 | 0.542860075 | 0 | 24241 | 11512 | 0.54201391 | 0 | 24269 | 11540 | 0.541380365 | 0 | 24297 | 11568 | 0.540575371 | 0 |
| 24214 | 11485 | 0.542746072 | 0 | 24242 | 11513 | 0.54201391 | 0 | 24270 | 11541 | 0.541380365 | 0 | 24298 | 11569 | 0.540575371 | 0 |
| 24215 | 11486 | 0.542746072 | 0 | 24243 | 11514 | 0.541847098 | 0 | 24271 | 11542 | 0.541380365 | 0 | 24299 | 11570 | 0.540575371 | 0 |
| 24216 | 11487 | 0.542746072 | 0 | 24244 | 11515 | 0.541847098 | 0 | 24272 | 11543 | 0.541380365 | 0 | 24300 | 11571 | 0.540575371 | -1.460294715 |
| 24217 | 11488 | 0.542746072 | 0 | 24245 | 11516 | 0.541847098 | 0 | 24273 | 11544 | 0.541380365 | 0 | 24301 | 11572 | 0.540575371 | -0.381113469 |
| 24218 | 11489 | 0.542746072 | 0 | 24246 | 11517 | 0.541847098 | 0 | 24274 | 11545 | 0.541380365 | -1.515007048 | 24302 | 11573 | 0.540338891 | 0 |
| 24219 | 11490 | 0.542590662 | 0 | 24247 | 11518 | 0.541847098 | 0 | 24275 | 11546 | 0.541094551 | 0 | 24303 | 11574 | 0.540338891 | 0 |
| 24220 | 11491 | 0.542590662 | 0 | 24248 | 11519 | 0.541847098 | 0 | 24276 | 11547 | 0.541039609 | 0 | 24304 | 11575 | 0.540338891 | 0 |
| 24221 | 11492 | 0.542590662 | 0 | 24249 | 11520 | 0.541847098 | 0 | 24277 | 11548 | 0.541039609 | 0 | 24305 | 11576 | 0.540338891 | 0 |
| 24222 | 11493 | 0.542366278 | 0 | 24250 | 11521 | 0.541749821 | 0 | 24278 | 11549 | 0.540958515 | 0 | 24306 | 11577 | 0.540338891 | 0 |
| 24223 | 11494 | 0.542366278 | 0 | 24251 | 11522 | 0.541749821 | 0 | 24279 | 11550 | 0.540958515 | 0 | 24307 | 11578 | 0.540225838 | 0 |
| 24224 | 11495 | 0.542366278 | 0 | 24252 | 11523 | 0.541686099 | 0 | 24280 | 11551 | 0.540958515 | 0 | 24308 | 11579 | 0.540225838 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24309 | 11580 | 0.540225838 | 0 | 24337 | 11608 | 0.539339824 | 0 | 24365 | 11636 | 0.538435985 | 0 | 24393 | 11664 | 0.537202193 | 0 |
| 24310 | 11581 | 0.53990568 | 0 | 24338 | 11609 | 0.539339824 | 0 | 24366 | 11637 | 0.538435985 | -0.216921433 | 24394 | 11665 | 0.536971247 | 0 |
| 24311 | 11582 | 0.53990568 | 0 | 24339 | 11610 | 0.539339824 | 0 | 24367 | 11638 | 0.538435985 | -1.296102679 | 24395 | 11666 | 0.536971247 | 0 |
| 24312 | 11583 | 0.53990568 | 0 | 24340 | 11611 | 0.539339824 | 0 | 24368 | 11639 | 0.53830842 | 0 | 24396 | 11667 | 0.536971247 | 0 |
| 24313 | 11584 | 0.53990568 | 0 | 24341 | 11612 | 0.539170211 | 0 | 24369 | 11640 | 0.538069337 | 0 | 24397 | 11668 | 0.536971247 | 0 |
| 24314 | 11585 | 0.53990568 | 0 | 24342 | 11613 | 0.539170211 | 0 | 24370 | 11641 | 0.538069337 | 0 | 24398 | 11669 | 0.536971247 | 0 |
| 24315 | 11586 | 0.53990568 | 0 | 24343 | 11614 | 0.539170211 | 0 | 24371 | 11642 | 0.538069337 | 0 | 24399 | 11670 | 0.536971247 | 0 |
| 24316 | 11587 | 0.53990568 | 0 | 24344 | 11615 | 0.539170211 | 0 | 24372 | 11643 | 0.538069337 | 0 | 24400 | 11671 | 0.536971247 | 0 |
| 24317 | 11588 | 0.53990568 | 0 | 24345 | 11616 | 0.53885539 | 0 | 24373 | 11644 | 0.538069337 | 0 | 24401 | 11672 | 0.536829759 | 0 |
| 24318 | 11589 | 0.53990568 | 0 | 24346 | 11617 | 0.53885539 | 0 | 24374 | 11645 | 0.538069337 | -0.370255541 | 24402 | 11673 | 0.536762401 | 0 |
| 24319 | 11590 | 0.53990568 | 0 | 24347 | 11618 | 0.53885539 | 0 | 24375 | 11646 | 0.538069337 | -0.722438059 | 24403 | 11674 | 0.536762401 | 0 |
| 24320 | 11591 | 0.53990568 | 0 | 24348 | 11619 | 0.53885539 | 0 | 24376 | 11647 | 0.537746081 | 0 | 24404 | 11675 | 0.536762401 | 0 |
| 24321 | 11592 | 0.53990568 | 0 | 24349 | 11620 | 0.53885539 | 0 | 24377 | 11648 | 0.537746081 | 0 | 24405 | 11676 | 0.536572628 | 0 |
| 24322 | 11593 | 0.53990568 | 0 | 24350 | 11621 | 0.53885539 | 0 | 24378 | 11649 | 0.537746081 | 0 | 24406 | 11677 | 0.536572628 | 0 |
| 24323 | 11594 | 0.539668296 | 0 | 24351 | 11622 | 0.53885539 | 0 | 24379 | 11650 | 0.537746081 | 0 | 24407 | 11678 | 0.536572628 | 0 |
| 24324 | 11595 | 0.539518436 | 0 | 24352 | 11623 | 0.53885539 | 0 | 24380 | 11651 | 0.537646666 | 0 | 24408 | 11679 | 0.536572628 | 0 |
| 24325 | 11596 | 0.539518436 | 0 | 24353 | 11624 | 0.53885539 | 0 | 24381 | 11652 | 0.537646666 | 0 | 24409 | 11680 | 0.536572628 | 0 |
| 24326 | 11597 | 0.539518436 | 0 | 24354 | 11625 | 0.53885539 | 0 | 24382 | 11653 | 0.537458944 | 0 | 24410 | 11681 | 0.536572628 | 0 |
| 24327 | 11598 | 0.539518436 | 0 | 24355 | 11626 | 0.53885539 | 0 | 24383 | 11654 | 0.537458944 | 0 | 24411 | 11682 | 0.536572628 | -1.163267462 |
| 24328 | 11599 | 0.539518436 | 0 | 24356 | 11627 | 0.538638406 | 0 | 24384 | 11655 | 0.537458944 | 0 | 24412 | 11683 | 0.53639943 | 0 |
| 24329 | 11600 | 0.539339824 | 0 | 24357 | 11628 | 0.538569388 | 0 | 24385 | 11656 | 0.537458944 | 0 | 24413 | 11684 | 0.53639943 | 0 |
| 24330 | 11601 | 0.539339824 | 0 | 24358 | 11629 | 0.538569388 | 0 | 24386 | 11657 | 0.537458944 | 0 | 24414 | 11685 | 0.53639943 | 0 |
| 24331 | 11602 | 0.539339824 | 0 | 24359 | 11630 | 0.538435985 | 0 | 24387 | 11658 | 0.537458944 | 0 | 24415 | 11686 | 0.536240726 | 0 |
| 24332 | 11603 | 0.539339824 | 0 | 24360 | 11631 | 0.538435985 | 0 | 24388 | 11659 | 0.537458944 | 0 | 24416 | 11687 | 0.536240726 | 0 |
| 24333 | 11604 | 0.539339824 | 0 | 24361 | 11632 | 0.538435985 | 0 | 24389 | 11660 | 0.537458944 | 0 | 24417 | 11688 | 0.536240726 | 0 |
| 24334 | 11605 | 0.539339824 | 0 | 24362 | 11633 | 0.538435985 | 0 | 24390 | 11661 | 0.537458944 | 0 | 24418 | 11689 | 0.536094769 | 0 |
| 24335 | 11606 | 0.539339824 | 0 | 24363 | 11634 | 0.538435985 | 0 | 24391 | 11662 | 0.537458944 | -0.262317614 | 24419 | 11690 | 0.536094769 | 0 |
| 24336 | 11607 | 0.539339824 | 0 | 24364 | 11635 | 0.538435985 | 0 | 24392 | 11663 | 0.537202193 | 0 | 24420 | 11691 | 0.536094769 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24421 | 11692 | 0.535960083 | 0 | 24449 | 11720 | 0.535329299 | 0 | 24477 | 11748 | 0.53467945 | 0 | 24505 | 11776 | 0.532606441 | 0 |
| 24422 | 11693 | 0.535960083 | 0 | 24450 | 11721 | 0.535168658 | 0 | 24478 | 11749 | 0.53467945 | 0 | 24506 | 11777 | 0.532606441 | 0 |
| 24423 | 11694 | 0.535960083 | 0 | 24451 | 11722 | 0.535168658 | 0 | 24479 | 11750 | 0.534585007 | 0 | 24507 | 11778 | 0.532606441 | 0 |
| 24424 | 11695 | 0.535960083 | 0 | 24452 | 11723 | 0.535168658 | 0 | 24480 | 11751 | 0.534585007 | 0 | 24508 | 11779 | 0.532606441 | 0 |
| 24425 | 11696 | 0.535960083 | 0 | 24453 | 11724 | 0.535168658 | 0 | 24481 | 11752 | 0.534585007 | 0 | 24509 | 11780 | 0.532606441 | 0 |
| 24426 | 11697 | 0.535960083 | 0 | 24454 | 11725 | 0.535168658 | 0 | 24482 | 11753 | 0.534585007 | -1.466285079 | 24510 | 11781 | 0.532606441 | 0 |
| 24427 | 11698 | 0.535960083 | 0 | 24455 | 11726 | 0.535168658 | 0 | 24483 | 11754 | 0.534498795 | 0 | 24511 | 11782 | 0.532606441 | 0 |
| 24428 | 11699 | 0.535835411 | -0.349855775 | 24456 | 11727 | 0.535025915 | 0 | 24484 | 11755 | 0.534498795 | 0 | 24512 | 11783 | 0.532606441 | 0 |
| 24429 | 11700 | 0.535835411 | -0.035461818 | 24457 | 11728 | 0.535025915 | 0 | 24485 | 11756 | 0.534498795 | 0 | 24513 | 11784 | 0.532606441 | 0 |
| 24430 | 11701 | 0.535719677 | 0 | 24458 | 11729 | 0.535025915 | 0 | 24486 | 11757 | 0.534498795 | 0 | 24514 | 11785 | 0.532606441 | 0 |
| 24431 | 11702 | 0.535719677 | 0 | 24459 | 11730 | 0.535025915 | 0 | 24487 | 11758 | 0.534498795 | -0.786706442 | 24515 | 11786 | 0.532606441 | 0 |
| 24432 | 11703 | 0.535719677 | 0 | 24460 | 11731 | 0.535025915 | 0 | 24488 | 11759 | 0.534419782 | 0 | 24516 | 11787 | 0.532606441 | 0 |
| 24433 | 11704 | 0.535719677 | 0 | 24461 | 11732 | 0.535025915 | 0 | 24489 | 11760 | 0.534419782 | 0 | 24517 | 11788 | 0.532606441 | 0 |
| 24434 | 11705 | 0.535719677 | 0 | 24462 | 11733 | 0.535025915 | 0 | 24490 | 11761 | 0.534419782 | 0 | 24518 | 11789 | 0.532606441 | 0 |
| 24435 | 11706 | 0.535611951 | 0 | 24463 | 11734 | 0.535025915 | 0 | 24491 | 11762 | 0.534347103 | 0 | 24519 | 11790 | 0.532606441 | 0 |
| 24436 | 11707 | 0.535611951 | 0 | 24464 | 11735 | 0.535025915 | 0 | 24492 | 11763 | 0.534280025 | 0 | 24520 | 11791 | 0.532606441 | 0 |
| 24437 | 11708 | 0.535611951 | 0 | 24465 | 11736 | 0.535025915 | 0 | 24493 | 11764 | 0.534280025 | 0 | 24521 | 11792 | 0.532606441 | 0 |
| 24438 | 11709 | 0.535511432 | 0 | 24466 | 11737 | 0.534898238 | 0 | 24494 | 11765 | 0.533924483 | 0 | 24522 | 11793 | 0.532606441 | 0 |
| 24439 | 11710 | 0.535511432 | 0 | 24467 | 11738 | 0.534898238 | 0 | 24495 | 11766 | 0.532606441 | 0 | 24523 | 11794 | 0.532606441 | 0 |
| 24440 | 11711 | 0.535511432 | 0 | 24468 | 11739 | 0.534898238 | 0 | 24496 | 11767 | 0.532606441 | 0 | 24524 | 11795 | 0.532606441 | 0 |
| 24441 | 11712 | 0.535329299 | 0 | 24469 | 11740 | 0.534898238 | 0 | 24497 | 11768 | 0.532606441 | 0 | 24525 | 11796 | 0.532606441 | 0 |
| 24442 | 11713 | 0.535329299 | 0 | 24470 | 11741 | 0.534898238 | 0 | 24498 | 11769 | 0.532606441 | 0 | 24526 | 11797 | 0.532606441 | 0 |
| 24443 | 11714 | 0.535329299 | 0 | 24471 | 11742 | 0.534898238 | 0 | 24499 | 11770 | 0.532606441 | 0 | 24527 | 11798 | 0.532606441 | 0 |
| 24444 | 11715 | 0.535329299 | 0 | 24472 | 11743 | 0.53478336 | 0 | 24500 | 11771 | 0.532606441 | 0 | 24528 | 11799 | 0.532606441 | 0 |
| 24445 | 11716 | 0.535329299 | 0 | 24473 | 11744 | 0.53478336 | 0 | 24501 | 11772 | 0.532606441 | 0 | 24529 | 11800 | 0.532606441 | 0 |
| 24446 | 11717 | 0.535329299 | 0 | 24474 | 11745 | 0.53478336 | 0 | 24502 | 11773 | 0.532606441 | 0 | 24530 | 11801 | 0.532606441 | 0 |
| 24447 | 11718 | 0.535329299 | 0 | 24475 | 11746 | 0.53467945 | 0 | 24503 | 11774 | 0.532606441 | 0 | 24531 | 11802 | 0.532606441 | 0 |
| 24448 | 11719 | 0.535329299 | 0 | 24476 | 11747 | 0.53467945 | 0 | 24504 | 11775 | 0.532606441 | 0 | 24532 | 11803 | 0.532606441 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24533 | 11804 | 0.532606441 | 0 | 24561 | 11832 | 0.532606441 | 0 | 24589 | 11860 | 0.530326675 | 0 | 24617 | 11888 | 0.529515364 | 0 |
| 24534 | 11805 | 0.532606441 | 0 | 24562 | 11833 | 0.532606441 | 0 | 24590 | 11861 | 0.530326675 | 0 | 24618 | 11889 | 0.529515364 | 0 |
| 24535 | 11806 | 0.532606441 | 0 | 24563 | 11834 | 0.532606441 | 0 | 24591 | 11862 | 0.530326675 | 0 | 24619 | 11890 | 0.529401301 | 0 |
| 24536 | 11807 | 0.532606441 | 0 | 24564 | 11835 | 0.532606441 | 0 | 24592 | 11863 | 0.530326675 | -0.12812073 | 24620 | 11891 | 0.529401301 | 0 |
| 24537 | 11808 | 0.532606441 | 0 | 24565 | 11836 | 0.532606441 | 0 | 24593 | 11864 | 0.530200371 | 0 | 24621 | 11892 | 0.529278498 | 0 |
| 24538 | 11809 | 0.532606441 | 0 | 24566 | 11837 | 0.532606441 | 0 | 24594 | 11865 | 0.530200371 | 0 | 24622 | 11893 | 0.529278498 | 0 |
| 24539 | 11810 | 0.532606441 | 0 | 24567 | 11838 | 0.532606441 | -0.2507797 | 24595 | 11866 | 0.530059252 | 0 | 24623 | 11894 | 0.529278498 | 0 |
| 24540 | 11811 | 0.532606441 | 0 | 24568 | 11839 | 0.532606441 | -0.329960946 | 24596 | 11867 | 0.530059252 | 0 | 24624 | 11895 | 0.529278498 | 0 |
| 24541 | 11812 | 0.532606441 | 0 | 24569 | 11840 | 0.532606441 | -0.807082201 | 24597 | 11868 | 0.530059252 | 0 | 24625 | 11896 | 0.529278498 | 0 |
| 24542 | 11813 | 0.532606441 | 0 | 24570 | 11841 | 0.532606441 | -0.93875432 | 24598 | 11869 | 0.530059252 | 0 | 24626 | 11897 | 0.529145909 | 0 |
| 24543 | 11814 | 0.532606441 | 0 | 24571 | 11842 | 0.532606441 | -1.271968999 | 24599 | 11870 | 0.530059252 | -0.756777083 | 24627 | 11898 | 0.529002317 | 0 |
| 24544 | 11815 | 0.532606441 | 0 | 24572 | 11843 | 0.531207746 | 0 | 24600 | 11871 | 0.529900548 | 0 | 24628 | 11899 | 0.529002317 | 0 |
| 24545 | 11816 | 0.532606441 | 0 | 24573 | 11844 | 0.531000914 | 0 | 24601 | 11872 | 0.529900548 | 0 | 24629 | 11900 | 0.529002317 | 0 |
| 24546 | 11817 | 0.532606441 | 0 | 24574 | 11845 | 0.530872728 | 0 | 24602 | 11873 | 0.529900548 | 0 | 24630 | 11901 | 0.529002317 | 0 |
| 24547 | 11818 | 0.532606441 | 0 | 24575 | 11846 | 0.530872728 | 0 | 24603 | 11874 | 0.529900548 | 0 | 24631 | 11902 | 0.529002317 | 0 |
| 24548 | 11819 | 0.532606441 | 0 | 24576 | 11847 | 0.53080064 | 0 | 24604 | 11875 | 0.529900548 | 0 | 24632 | 11903 | 0.529002317 | 0 |
| 24549 | 11820 | 0.532606441 | 0 | 24577 | 11848 | 0.53080064 | 0 | 24605 | 11876 | 0.529900548 | 0 | 24633 | 11904 | 0.529002317 | 0 |
| 24550 | 11821 | 0.532606441 | 0 | 24578 | 11849 | 0.530636848 | 0 | 24606 | 11877 | 0.529900548 | 0 | 24634 | 11905 | 0.528846292 | 0 |
| 24551 | 11822 | 0.532606441 | 0 | 24579 | 11850 | 0.530636848 | 0 | 24607 | 11878 | 0.529900548 | 0 | 24635 | 11906 | 0.528846292 | -1.491328949 |
| 24552 | 11823 | 0.532606441 | 0 | 24580 | 11851 | 0.530636848 | 0 | 24608 | 11879 | 0.529900548 | 0 | 24636 | 11907 | 0.528676147 | 0 |
| 24553 | 11824 | 0.532606441 | 0 | 24581 | 11852 | 0.530543281 | 0 | 24609 | 11880 | 0.529900548 | 0 | 24637 | 11908 | 0.528676147 | 0 |
| 24554 | 11825 | 0.532606441 | 0 | 24582 | 11853 | 0.530440379 | 0 | 24610 | 11881 | 0.529720753 | 0 | 24638 | 11909 | 0.528676147 | 0 |
| 24555 | 11826 | 0.532606441 | 0 | 24583 | 11854 | 0.530440379 | 0 | 24611 | 11882 | 0.529720753 | 0 | 24639 | 11910 | 0.528676147 | 0 |
| 24556 | 11827 | 0.532606441 | 0 | 24584 | 11855 | 0.530326675 | 0 | 24612 | 11883 | 0.529720753 | 0 | 24640 | 11911 | 0.528676147 | 0 |
| 24557 | 11828 | 0.532606441 | 0 | 24585 | 11856 | 0.530326675 | 0 | 24613 | 11884 | 0.529720753 | 0 | 24641 | 11912 | 0.528676147 | 0 |
| 24558 | 11829 | 0.532606441 | 0 | 24586 | 11857 | 0.530326675 | 0 | 24614 | 11885 | 0.529720753 | 0 | 24642 | 11913 | 0.528489875 | 0 |
| 24559 | 11830 | 0.532606441 | 0 | 24587 | 11858 | 0.530326675 | 0 | 24615 | 11886 | 0.529621588 | 0 | 24643 | 11914 | 0.528489875 | 0 |
| 24560 | 11831 | 0.532606441 | 0 | 24588 | 11859 | 0.530326675 | 0 | 24616 | 11887 | 0.529515364 | 0 | 24644 | 11915 | 0.528489875 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24645 | 11916 | 0.528489875 | 0 | 24673 | 11944 | 0.527807558 | 0 | 24701 | 11972 | 0.526854112 | 0 | 24729 | 12000 | 0.525975862 | 0 |
| 24646 | 11917 | 0.528489875 | 0 | 24674 | 11945 | 0.527807558 | 0 | 24702 | 11973 | 0.526854112 | 0 | 24730 | 12001 | 0.525975862 | 0 |
| 24647 | 11918 | 0.528489875 | 0 | 24675 | 11946 | 0.527807558 | -0.863033606 | 24703 | 11974 | 0.526854112 | 0 | 24731 | 12002 | 0.525975862 | 0 |
| 24648 | 11919 | 0.528489875 | -0.850116833 | 24676 | 11947 | 0.527807558 | -1.084882356 | 24704 | 11975 | 0.526854112 | 0 | 24732 | 12003 | 0.525975862 | 0 |
| 24649 | 11920 | 0.528285067 | 0 | 24677 | 11948 | 0.527526916 | 0 | 24705 | 11976 | 0.526854112 | 0 | 24733 | 12004 | 0.525975862 | 0 |
| 24650 | 11921 | 0.528285067 | 0 | 24678 | 11949 | 0.527526916 | 0 | 24706 | 11977 | 0.526854112 | 0 | 24734 | 12005 | 0.525975862 | 0 |
| 24651 | 11922 | 0.528285067 | 0 | 24679 | 11950 | 0.527526916 | 0 | 24707 | 11978 | 0.526854112 | 0 | 24735 | 12006 | 0.525802733 | 0 |
| 24652 | 11923 | 0.528285067 | 0 | 24680 | 11951 | 0.527526916 | 0 | 24708 | 11979 | 0.526854112 | 0 | 24736 | 12007 | 0.525802733 | 0 |
| 24653 | 11924 | 0.528285067 | 0 | 24681 | 11952 | 0.527526916 | 0 | 24709 | 11980 | 0.526854112 | 0 | 24737 | 12008 | 0.525802733 | 0 |
| 24654 | 11925 | 0.528285067 | 0 | 24682 | 11953 | 0.527526916 | 0 | 24710 | 11981 | 0.526854112 | 0 | 24738 | 12009 | 0.525802733 | 0 |
| 24655 | 11926 | 0.528285067 | 0 | 24683 | 11954 | 0.527526916 | 0 | 24711 | 11982 | 0.526446132 | 0 | 24739 | 12010 | 0.525802733 | 0 |
| 24656 | 11927 | 0.528285067 | 0 | 24684 | 11955 | 0.527526916 | 0 | 24712 | 11983 | 0.526446132 | 0 | 24740 | 12011 | 0.525802733 | 0 |
| 24657 | 11928 | 0.528285067 | 0 | 24685 | 11956 | 0.527526916 | 0 | 24713 | 11984 | 0.526446132 | 0 | 24741 | 12012 | 0.525802733 | -1.411398273 |
| 24658 | 11929 | 0.528285067 | -0.732222329 | 24686 | 11957 | 0.527526916 | 0 | 24714 | 11985 | 0.526446132 | 0 | 24742 | 12013 | 0.525712733 | 0 |
| 24659 | 11930 | 0.528285067 | -1.431192333 | 24687 | 11958 | 0.527526916 | 0 | 24715 | 11986 | 0.526446132 | 0 | 24743 | 12014 | 0.525712733 | 0 |
| 24660 | 11931 | 0.528058813 | 0 | 24688 | 11959 | 0.527526916 | 0 | 24716 | 11987 | 0.526446132 | 0 | 24744 | 12015 | 0.525712733 | 0 |
| 24661 | 11932 | 0.528058813 | 0 | 24689 | 11960 | 0.527425929 | 0 | 24717 | 11988 | 0.526446132 | 0 | 24745 | 12016 | 0.525427856 | 0 |
| 24662 | 11933 | 0.528058813 | 0 | 24690 | 11961 | 0.527425929 | 0 | 24718 | 11989 | 0.526446132 | 0 | 24746 | 12017 | 0.525427856 | 0 |
| 24663 | 11934 | 0.528058813 | 0 | 24691 | 11962 | 0.527425929 | 0 | 24719 | 11990 | 0.526446132 | 0 | 24747 | 12018 | 0.525427856 | 0 |
| 24664 | 11935 | 0.528058813 | -1.409142192 | 24692 | 11963 | 0.527211409 | 0 | 24720 | 11991 | 0.526446132 | 0 | 24748 | 12019 | 0.525427856 | 0 |
| 24665 | 11936 | 0.528058813 | -1.409142192 | 24693 | 11964 | 0.527211409 | 0 | 24721 | 11992 | 0.526446132 | -1.454220567 | 24749 | 12020 | 0.525427856 | 0 |
| 24666 | 11937 | 0.527978037 | 0 | 24694 | 11965 | 0.527211409 | 0 | 24722 | 11993 | 0.526219642 | 0 | 24750 | 12021 | 0.525427856 | 0 |
| 24667 | 11938 | 0.527807558 | 0 | 24695 | 11966 | 0.527211409 | 0 | 24723 | 11994 | 0.526140399 | 0 | 24751 | 12022 | 0.525427856 | 0 |
| 24668 | 11939 | 0.527807558 | 0 | 24696 | 11967 | 0.527211409 | 0 | 24724 | 11995 | 0.526140399 | 0 | 24752 | 12023 | 0.525427856 | 0 |
| 24669 | 11940 | 0.527807558 | 0 | 24697 | 11968 | 0.527211409 | 0 | 24725 | 11996 | 0.526140399 | 0 | 24753 | 12024 | 0.525427856 | 0 |
| 24670 | 11941 | 0.527807558 | 0 | 24698 | 11969 | 0.527211409 | -1.335355978 | 24726 | 11997 | 0.526140399 | 0 | 24754 | 12025 | 0.525427856 | 0 |
| 24671 | 11942 | 0.527807558 | 0 | 24699 | 11970 | 0.526978356 | 0 | 24727 | 11998 | 0.525975862 | 0 | 24755 | 12026 | 0.525427856 | 0 |
| 24672 | 11943 | 0.527807558 | 0 | 24700 | 11971 | 0.526854112 | 0 | 24728 | 11999 | 0.525975862 | 0 | 24756 | 12027 | 0.525427856 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24757 | 12028 | 0.52511842 | 0 | 24785 | 12056 | 0.524006269 | 0 | 24813 | 12084 | 0.523061123 | -0.545560747 | 24841 | 12112 | 0.521882576 | 0 |
| 24758 | 12029 | 0.52511842 | -1.495056821 | 24786 | 12057 | 0.524006269 | 0 | 24814 | 12085 | 0.522846604 | 0 | 24842 | 12113 | 0.521882576 | 0 |
| 24759 | 12030 | 0.525009259 | 0 | 24787 | 12058 | 0.524006269 | 0 | 24815 | 12086 | 0.522846604 | 0 | 24843 | 12114 | 0.521882576 | 0 |
| 24760 | 12031 | 0.525009259 | 0 | 24788 | 12059 | 0.524006269 | -0.465434354 | 24816 | 12087 | 0.522846604 | 0 | 24844 | 12115 | 0.521882576 | 0 |
| 24761 | 12032 | 0.525009259 | 0 | 24789 | 12060 | 0.524006269 | -0.289343095 | 24817 | 12088 | 0.522846604 | 0 | 24845 | 12116 | 0.521882576 | 0 |
| 24762 | 12033 | 0.525009259 | 0 | 24790 | 12061 | 0.523651598 | 0 | 24818 | 12089 | 0.522846604 | 0 | 24846 | 12117 | 0.521882576 | 0 |
| 24763 | 12034 | 0.524919612 | 0 | 24791 | 12062 | 0.523558312 | 0 | 24819 | 12090 | 0.522698152 | 0 | 24847 | 12118 | 0.521882576 | 0 |
| 24764 | 12035 | 0.524781104 | 0 | 24792 | 12063 | 0.523558312 | 0 | 24820 | 12091 | 0.522698152 | 0 | 24848 | 12119 | 0.521882576 | 0 |
| 24765 | 12036 | 0.524781104 | 0 | 24793 | 12064 | 0.523558312 | 0 | 24821 | 12092 | 0.522698152 | 0 | 24849 | 12120 | 0.521882576 | 0 |
| 24766 | 12037 | 0.524637511 | 0 | 24794 | 12065 | 0.523558312 | 0 | 24822 | 12093 | 0.522698152 | 0 | 24850 | 12121 | 0.521882576 | 0 |
| 24767 | 12038 | 0.524538819 | 0 | 24795 | 12066 | 0.523558312 | 0 | 24823 | 12094 | 0.522698152 | 0 | 24851 | 12122 | 0.521882576 | 0 |
| 24768 | 12039 | 0.524538819 | 0 | 24796 | 12067 | 0.523398439 | 0 | 24824 | 12095 | 0.522698152 | 0 | 24852 | 12123 | 0.521882576 | 0 |
| 24769 | 12040 | 0.524538819 | 0 | 24797 | 12068 | 0.523398439 | 0 | 24825 | 12096 | 0.522698152 | 0 | 24853 | 12124 | 0.521882576 | 0 |
| 24770 | 12041 | 0.524538819 | 0 | 24798 | 12069 | 0.523398439 | 0 | 24826 | 12097 | 0.522506114 | 0 | 24854 | 12125 | 0.521882576 | 0 |
| 24771 | 12042 | 0.524538819 | 0 | 24799 | 12070 | 0.523398439 | -0.105085742 | 24827 | 12098 | 0.522506114 | 0 | 24855 | 12126 | 0.521882576 | 0 |
| 24772 | 12043 | 0.524538819 | 0 | 24800 | 12071 | 0.523266415 | 0 | 24828 | 12099 | 0.522506114 | 0 | 24856 | 12127 | 0.521882576 | 0 |
| 24773 | 12044 | 0.524538819 | 0 | 24801 | 12072 | 0.523266415 | 0 | 24829 | 12100 | 0.522506114 | 0 | 24857 | 12128 | 0.521882576 | 0 |
| 24774 | 12045 | 0.524538819 | -0.639058564 | 24802 | 12073 | 0.523266415 | 0 | 24830 | 12101 | 0.522506114 | 0 | 24858 | 12129 | 0.521882576 | 0 |
| 24775 | 12046 | 0.524538819 | -1.338028568 | 24803 | 12074 | 0.523061123 | 0 | 24831 | 12102 | 0.522506114 | 0 | 24859 | 12130 | 0.521882576 | 0 |
| 24776 | 12047 | 0.524006269 | 0 | 24804 | 12075 | 0.523061123 | 0 | 24832 | 12103 | 0.522506114 | -1.366390212 | 24860 | 12131 | 0.521882576 | 0 |
| 24777 | 12048 | 0.524006269 | 0 | 24805 | 12076 | 0.523061123 | 0 | 24833 | 12104 | 0.522387276 | 0 | 24861 | 12132 | 0.521882576 | 0 |
| 24778 | 12049 | 0.524006269 | 0 | 24806 | 12077 | 0.523061123 | 0 | 24834 | 12105 | 0.522306484 | 0 | 24862 | 12133 | 0.521882576 | 0 |
| 24779 | 12050 | 0.524006269 | 0 | 24807 | 12078 | 0.523061123 | 0 | 24835 | 12106 | 0.522306484 | 0 | 24863 | 12134 | 0.521882576 | -0.562533561 |
| 24780 | 12051 | 0.524006269 | 0 | 24808 | 12079 | 0.523061123 | 0 | 24836 | 12107 | 0.521882576 | 0 | 24864 | 12135 | 0.521882576 | -0.914716079 |
| 24781 | 12052 | 0.524006269 | 0 | 24809 | 12080 | 0.523061123 | 0 | 24837 | 12108 | 0.521882576 | 0 | 24865 | 12136 | 0.521882576 | -1.215746075 |
| 24782 | 12053 | 0.524006269 | 0 | 24810 | 12081 | 0.523061123 | 0 | 24838 | 12109 | 0.521882576 | 0 | 24866 | 12137 | 0.521882576 | -1.437594825 |
| 24783 | 12054 | 0.524006269 | 0 | 24811 | 12082 | 0.523061123 | 0 | 24839 | 12110 | 0.521882576 | 0 | 24867 | 12138 | 0.521422274 | 0 |
| 24784 | 12055 | 0.524006269 | 0 | 24812 | 12083 | 0.523061123 | 0 | 24840 | 12111 | 0.521882576 | 0 | 24868 | 12139 | 0.521325431 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24869 | 12140 | 0.521325431 | 0 | 24897 | 12168 | 0.520613326 | 0 | 24925 | 12196 | 0.519769216 | 0 | 24953 | 12224 | 0.519103971 | 0 |
| 24870 | 12141 | 0.521325431 | 0 | 24898 | 12169 | 0.520613326 | -0.933714096 | 24926 | 12197 | 0.519769216 | 0 | 24954 | 12225 | 0.519103971 | 0 |
| 24871 | 12142 | 0.521325431 | 0 | 24899 | 12170 | 0.520371985 | 0 | 24927 | 12198 | 0.519769216 | -0.059496942 | 24955 | 12226 | 0.519103971 | 0 |
| 24872 | 12143 | 0.521325431 | 0 | 24900 | 12171 | 0.520371985 | 0 | 24928 | 12199 | 0.519769216 | -0.439708184 | 24956 | 12227 | 0.519103971 | -0.816037044 |
| 24873 | 12144 | 0.521325431 | -1.415875575 | 24901 | 12172 | 0.520371985 | 0 | 24929 | 12200 | 0.519769216 | -1.138678188 | 24957 | 12228 | 0.519003265 | 0 |
| 24874 | 12145 | 0.521176979 | 0 | 24902 | 12173 | 0.520371985 | 0 | 24930 | 12201 | 0.519585931 | 0 | 24958 | 12229 | 0.519003265 | 0 |
| 24875 | 12146 | 0.521176979 | 0 | 24903 | 12174 | 0.520371985 | 0 | 24931 | 12202 | 0.519585931 | 0 | 24959 | 12230 | 0.518926744 | 0 |
| 24876 | 12147 | 0.521176979 | 0 | 24904 | 12175 | 0.520371985 | 0 | 24932 | 12203 | 0.519585931 | 0 | 24960 | 12231 | 0.518926744 | 0 |
| 24877 | 12148 | 0.521176979 | 0 | 24905 | 12176 | 0.520371985 | 0 | 24933 | 12204 | 0.519585931 | 0 | 24961 | 12232 | 0.518818157 | -1.630990942 |
| 24878 | 12149 | 0.521176979 | 0 | 24906 | 12177 | 0.520371985 | 0 | 24934 | 12205 | 0.519444995 | 0 | 24962 | 12233 | 0.518366002 | 0 |
| 24879 | 12150 | 0.521176979 | 0 | 24907 | 12178 | 0.520177452 | 0 | 24935 | 12206 | 0.519444995 | 0 | 24963 | 12234 | 0.518366002 | 0 |
| 24880 | 12151 | 0.521176979 | 0 | 24908 | 12179 | 0.52012073 | 0 | 24936 | 12207 | 0.519444995 | 0 | 24964 | 12235 | 0.518366002 | 0 |
| 24881 | 12152 | 0.520920683 | 0 | 24909 | 12180 | 0.520017314 | 0 | 24937 | 12208 | 0.519444995 | 0 | 24965 | 12236 | 0.518366002 | 0 |
| 24882 | 12153 | 0.520920683 | 0 | 24910 | 12181 | 0.520017314 | 0 | 24938 | 12209 | 0.519444995 | 0 | 24966 | 12237 | 0.518366002 | 0 |
| 24883 | 12154 | 0.520920683 | 0 | 24911 | 12182 | 0.520017314 | 0 | 24939 | 12210 | 0.519444995 | 0 | 24967 | 12238 | 0.518366002 | 0 |
| 24884 | 12155 | 0.520920683 | 0 | 24912 | 12183 | 0.520017314 | 0 | 24940 | 12211 | 0.519444995 | 0 | 24968 | 12239 | 0.518366002 | 0 |
| 24885 | 12156 | 0.520920683 | 0 | 24913 | 12184 | 0.520017314 | 0 | 24941 | 12212 | 0.519444995 | 0 | 24969 | 12240 | 0.518366002 | 0 |
| 24886 | 12157 | 0.520920683 | 0 | 24914 | 12185 | 0.520017314 | 0 | 24942 | 12213 | 0.519444995 | 0 | 24970 | 12241 | 0.518366002 | 0 |
| 24887 | 12158 | 0.520920683 | 0 | 24915 | 12186 | 0.520017314 | 0 | 24943 | 12214 | 0.519444995 | 0 | 24971 | 12242 | 0.518366002 | 0 |
| 24888 | 12159 | 0.520920683 | 0 | 24916 | 12187 | 0.520017314 | 0 | 24944 | 12215 | 0.519444995 | 0 | 24972 | 12243 | 0.518366002 | 0 |
| 24889 | 12160 | 0.520707218 | 0 | 24917 | 12188 | 0.519925409 | 0 | 24945 | 12216 | 0.519444995 | -1.252945762 | 24973 | 12244 | 0.518366002 | 0 |
| 24890 | 12161 | 0.520707218 | 0 | 24918 | 12189 | 0.519925409 | 0 | 24946 | 12217 | 0.519333251 | 0 | 24974 | 12245 | 0.518366002 | 0 |
| 24891 | 12162 | 0.520707218 | 0 | 24919 | 12190 | 0.519925409 | 0 | 24947 | 12218 | 0.51924248 | 0 | 24975 | 12246 | 0.518366002 | 0 |
| 24892 | 12163 | 0.520707218 | 0 | 24920 | 12191 | 0.519769216 | 0 | 24948 | 12219 | 0.51924248 | 0 | 24976 | 12247 | 0.518366002 | 0 |
| 24893 | 12164 | 0.520707218 | 0 | 24921 | 12192 | 0.519769216 | 0 | 24949 | 12220 | 0.51924248 | 0 | 24977 | 12248 | 0.518366002 | 0 |
| 24894 | 12165 | 0.520707218 | 0 | 24922 | 12193 | 0.519769216 | 0 | 24950 | 12221 | 0.51924248 | 0 | 24978 | 12249 | 0.518366002 | 0 |
| 24895 | 12166 | 0.520707218 | 0 | 24923 | 12194 | 0.519769216 | 0 | 24951 | 12222 | 0.51924248 | 0 | 24979 | 12250 | 0.518366002 | 0 |
| 24896 | 12167 | 0.520613326 | 0 | 24924 | 12195 | 0.519769216 | 0 | 24952 | 12223 | 0.51924248 | 0 | 24980 | 12251 | 0.518366002 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 24981 | 12252 | 0.518366002 | 0 | 25009 | 12280 | 0.517366475 | 0 | 25037 | 12308 | 0.516618336 | 0 | 25065 | 12336 | 0.515573102 | 0 |
| 24982 | 12253 | 0.518366002 | 0 | 25010 | 12281 | 0.517366475 | 0 | 25038 | 12309 | 0.516618336 | 0 | 25066 | 12337 | 0.515573102 | 0 |
| 24983 | 12254 | 0.518366002 | 0 | 25011 | 12282 | 0.517366475 | 0 | 25039 | 12310 | 0.516618336 | 0 | 25067 | 12338 | 0.515573102 | 0 |
| 24984 | 12255 | 0.518366002 | 0 | 25012 | 12283 | 0.517366475 | -0.287208966 | 25040 | 12311 | 0.516618336 | 0 | 25068 | 12339 | 0.515573102 | 0 |
| 24985 | 12256 | 0.518366002 | 0 | 25013 | 12284 | 0.517246686 | 0 | 25041 | 12312 | 0.516618336 | -0.090676547 | 25069 | 12340 | 0.515573102 | 0 |
| 24986 | 12257 | 0.518366002 | 0 | 25014 | 12285 | 0.517094275 | 0 | 25042 | 12313 | 0.516369242 | 0 | 25070 | 12341 | 0.515573102 | 0 |
| 24987 | 12258 | 0.518366002 | 0 | 25015 | 12286 | 0.517094275 | 0 | 25043 | 12314 | 0.516369242 | 0 | 25071 | 12342 | 0.515573102 | 0 |
| 24988 | 12259 | 0.518366002 | 0 | 25016 | 12287 | 0.517094275 | 0 | 25044 | 12315 | 0.516369242 | 0 | 25072 | 12343 | 0.515573102 | 0 |
| 24989 | 12260 | 0.518366002 | 0 | 25017 | 12288 | 0.517094275 | 0 | 25045 | 12316 | 0.516369242 | 0 | 25073 | 12344 | 0.515573102 | 0 |
| 24990 | 12261 | 0.517965915 | 0 | 25018 | 12289 | 0.517094275 | 0 | 25046 | 12317 | 0.516216025 | 0 | 25074 | 12345 | 0.515573102 | 0 |
| 24991 | 12262 | 0.517827509 | 0 | 25019 | 12290 | 0.517094275 | 0 | 25047 | 12318 | 0.516216025 | 0 | 25075 | 12346 | 0.515573102 | 0 |
| 24992 | 12263 | 0.517666091 | 0 | 25020 | 12291 | 0.517094275 | 0 | 25048 | 12319 | 0.516216025 | 0 | 25076 | 12347 | 0.515573102 | 0 |
| 24993 | 12264 | 0.517666091 | 0 | 25021 | 12292 | 0.516893816 | 0 | 25049 | 12320 | 0.516216025 | 0 | 25077 | 12348 | 0.515573102 | 0 |
| 24994 | 12265 | 0.517666091 | 0 | 25022 | 12293 | 0.516893816 | 0 | 25050 | 12321 | 0.516216025 | 0 | 25078 | 12349 | 0.515573102 | 0 |
| 24995 | 12266 | 0.517542695 | 0 | 25023 | 12294 | 0.516893816 | 0 | 25051 | 12322 | 0.516216025 | 0 | 25079 | 12350 | 0.515573102 | 0 |
| 24996 | 12267 | 0.517542695 | 0 | 25024 | 12295 | 0.516893816 | -0.943185935 | 25052 | 12323 | 0.516216025 | 0 | 25080 | 12351 | 0.515263885 | 0 |
| 24997 | 12268 | 0.517542695 | 0 | 25025 | 12296 | 0.516893816 | -1.42030719 | 25053 | 12324 | 0.51603734 | 0 | 25081 | 12352 | 0.51519364 | 0 |
| 24998 | 12269 | 0.517542695 | 0 | 25026 | 12297 | 0.516812174 | 0 | 25054 | 12325 | 0.51603734 | 0 | 25082 | 12353 | 0.515082096 | 0 |
| 24999 | 12270 | 0.517542695 | 0 | 25027 | 12298 | 0.516618336 | 0 | 25055 | 12326 | 0.51603734 | 0 | 25083 | 12354 | 0.515082096 | 0 |
| 25000 | 12271 | 0.517542695 | 0 | 25028 | 12299 | 0.516618336 | 0 | 25056 | 12327 | 0.51603734 | 0 | 25084 | 12355 | 0.515082096 | 0 |
| 25001 | 12272 | 0.517542695 | 0 | 25029 | 12300 | 0.516618336 | 0 | 25057 | 12328 | 0.51603734 | 0 | 25085 | 12356 | 0.515082096 | 0 |
| 25002 | 12273 | 0.517542695 | 0 | 25030 | 12301 | 0.516618336 | 0 | 25058 | 12329 | 0.515936376 | 0 | 25086 | 12357 | 0.515082096 | 0 |
| 25003 | 12274 | 0.517366475 | 0 | 25031 | 12302 | 0.516618336 | 0 | 25059 | 12330 | 0.515936376 | 0 | 25087 | 12358 | 0.515082096 | 0 |
| 25004 | 12275 | 0.517366475 | 0 | 25032 | 12303 | 0.516618336 | 0 | 25060 | 12331 | 0.515573102 | 0 | 25088 | 12359 | 0.515082096 | 0 |
| 25005 | 12276 | 0.517366475 | 0 | 25033 | 12304 | 0.516618336 | 0 | 25061 | 12332 | 0.515573102 | 0 | 25089 | 12360 | 0.514877674 | 0 |
| 25006 | 12277 | 0.517366475 | 0 | 25034 | 12305 | 0.516618336 | 0 | 25062 | 12333 | 0.515573102 | 0 | 25090 | 12361 | 0.514877674 | 0 |
| 25007 | 12278 | 0.517366475 | 0 | 25035 | 12306 | 0.516618336 | 0 | 25063 | 12334 | 0.515573102 | 0 | 25091 | 12362 | 0.514877674 | 0 |
| 25008 | 12279 | 0.517366475 | 0 | 25036 | 12307 | 0.516618336 | 0 | 25064 | 12335 | 0.515573102 | 0 | 25092 | 12363 | 0.514877674 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 25093 | 12364 | 0.514877674 | 0 | 25121 | 12392 | 0.513721097 | 0 | 25149 | 12420 | 0.51263536 | 0 | 25177 | 12448 | 0.511417142 | 0 |
| 25094 | 12365 | 0.514877674 | 0 | 25122 | 12393 | 0.513721097 | -0.320817567 | 25150 | 12421 | 0.51263536 | 0 | 25178 | 12449 | 0.511417142 | 0 |
| 25095 | 12366 | 0.514877674 | 0 | 25123 | 12394 | 0.513490151 | 0 | 25151 | 12422 | 0.51263536 | 0 | 25179 | 12450 | 0.511417142 | 0 |
| 25096 | 12367 | 0.514877674 | -1.523780972 | 25124 | 12395 | 0.513490151 | 0 | 25152 | 12423 | 0.51263536 | 0 | 25180 | 12451 | 0.511417142 | 0 |
| 25097 | 12368 | 0.514765613 | 0 | 25125 | 12396 | 0.513490151 | 0 | 25153 | 12424 | 0.51263536 | 0 | 25181 | 12452 | 0.511417142 | 0 |
| 25098 | 12369 | 0.514694852 | 0 | 25126 | 12397 | 0.513490151 | 0 | 25154 | 12425 | 0.51263536 | 0 | 25182 | 12453 | 0.511417142 | 0 |
| 25099 | 12370 | 0.514694852 | 0 | 25127 | 12398 | 0.513490151 | 0 | 25155 | 12426 | 0.51263536 | 0 | 25183 | 12454 | 0.511417142 | 0 |
| 25100 | 12371 | 0.514694852 | 0 | 25128 | 12399 | 0.513301286 | 0 | 25156 | 12427 | 0.512506966 | 0 | 25184 | 12455 | 0.511417142 | 0 |
| 25101 | 12372 | 0.514694852 | -1.121476158 | 25129 | 12400 | 0.513301286 | 0 | 25157 | 12428 | 0.512506966 | 0 | 25185 | 12456 | 0.511417142 | 0 |
| 25102 | 12373 | 0.514610498 | 0 | 25130 | 12401 | 0.513301286 | 0 | 25158 | 12429 | 0.512506966 | 0 | 25186 | 12457 | 0.511417142 | 0 |
| 25103 | 12374 | 0.514381621 | 0 | 25131 | 12402 | 0.513301286 | 0 | 25159 | 12430 | 0.512506966 | 0 | 25187 | 12458 | 0.511417142 | 0 |
| 25104 | 12375 | 0.514381621 | 0 | 25132 | 12403 | 0.513301286 | 0 | 25160 | 12431 | 0.512506966 | 0 | 25188 | 12459 | 0.511417142 | 0 |
| 25105 | 12376 | 0.514381621 | 0 | 25133 | 12404 | 0.513301286 | 0 | 25161 | 12432 | 0.512403055 | 0 | 25189 | 12460 | 0.511417142 | 0 |
| 25106 | 12377 | 0.514381621 | 0 | 25134 | 12405 | 0.513301286 | 0 | 25162 | 12433 | 0.512403055 | 0 | 25190 | 12461 | 0.511417142 | 0 |
| 25107 | 12378 | 0.514381621 | 0 | 25135 | 12406 | 0.513143961 | 0 | 25163 | 12434 | 0.512317235 | 0 | 25191 | 12462 | 0.511417142 | 0 |
| 25108 | 12379 | 0.514381621 | 0 | 25136 | 12407 | 0.513010885 | 0 | 25164 | 12435 | 0.512245158 | 0 | 25192 | 12463 | 0.511417142 | 0 |
| 25109 | 12380 | 0.514381621 | -0.086073837 | 25137 | 12408 | 0.513010885 | 0 | 25165 | 12436 | 0.512245158 | 0 | 25193 | 12464 | 0.511417142 | 0 |
| 25110 | 12381 | 0.514381621 | -0.187531478 | 25138 | 12409 | 0.513010885 | 0 | 25166 | 12437 | 0.512245158 | 0 | 25194 | 12465 | 0.511417142 | 0 |
| 25111 | 12382 | 0.514123035 | -1.506052205 | 25139 | 12410 | 0.513010885 | 0 | 25167 | 12438 | 0.512245158 | 0 | 25195 | 12466 | 0.511417142 | 0 |
| 25112 | 12383 | 0.514009953 | 0 | 25140 | 12411 | 0.512798048 | 0 | 25168 | 12439 | 0.512130855 | 0 | 25196 | 12467 | 0.511417142 | 0 |
| 25113 | 12384 | 0.514009953 | 0 | 25141 | 12412 | 0.512798048 | 0 | 25169 | 12440 | 0.512044282 | -0.761827075 | 25197 | 12468 | 0.511417142 | 0 |
| 25114 | 12385 | 0.514009953 | 0 | 25142 | 12413 | 0.512798048 | 0 | 25170 | 12441 | 0.511417142 | 0 | 25198 | 12469 | 0.511417142 | 0 |
| 25115 | 12386 | 0.514009953 | 0 | 25143 | 12414 | 0.512798048 | 0 | 25171 | 12442 | 0.511417142 | 0 | 25199 | 12470 | 0.511417142 | 0 |
| 25116 | 12387 | 0.514009953 | 0 | 25144 | 12415 | 0.512798048 | 0 | 25172 | 12443 | 0.511417142 | 0 | 25200 | 12471 | 0.511417142 | 0 |
| 25117 | 12388 | 0.514009953 | 0 | 25145 | 12416 | 0.512798048 | 0 | 25173 | 12444 | 0.511417142 | 0 | 25201 | 12472 | 0.511417142 | 0 |
| 25118 | 12389 | 0.513721097 | 0 | 25146 | 12417 | 0.512798048 | -0.042987015 | 25174 | 12445 | 0.511417142 | 0 | 25202 | 12473 | 0.511417142 | 0 |
| 25119 | 12390 | 0.513721097 | 0 | 25147 | 12418 | 0.51263536 | 0 | 25175 | 12446 | 0.511417142 | 0 | 25203 | 12474 | 0.511417142 | 0 |
| 25120 | 12391 | 0.513721097 | 0 | 25148 | 12419 | 0.51263536 | 0 | 25176 | 12447 | 0.511417142 | 0 | 25204 | 12475 | 0.511417142 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 25205 | 12476 | 0.511417142 | 0 | 25233 | 12504 | 0.510040613 | 0 | 25261 | 12532 | 0.509125345 | 0 | 25289 | 12560 | 0.508472761 | 0 |
| 25206 | 12477 | 0.511417142 | 0 | 25234 | 12505 | 0.510040613 | -1.324498051 | 25262 | 12533 | 0.509125345 | 0 | 25290 | 12561 | 0.508472761 | 0 |
| 25207 | 12478 | 0.511417142 | 0 | 25235 | 12506 | 0.509942456 | 0 | 25263 | 12534 | 0.509125345 | 0 | 25291 | 12562 | 0.508472761 | 0 |
| 25208 | 12479 | 0.511417142 | 0 | 25236 | 12507 | 0.509829226 | 0 | 25264 | 12535 | 0.509125345 | 0 | 25292 | 12563 | 0.508472761 | 0 |
| 25209 | 12480 | 0.511417142 | 0 | 25237 | 12508 | 0.509829226 | 0 | 25265 | 12536 | 0.509125345 | 0 | 25293 | 12564 | 0.508472761 | 0 |
| 25210 | 12481 | 0.511417142 | 0 | 25238 | 12509 | 0.509829226 | 0 | 25266 | 12537 | 0.509125345 | 0 | 25294 | 12565 | 0.508472761 | 0 |
| 25211 | 12482 | 0.511417142 | 0 | 25239 | 12510 | 0.509829226 | 0 | 25267 | 12538 | 0.509125345 | 0 | 25295 | 12566 | 0.508472761 | 0 |
| 25212 | 12483 | 0.511417142 | -0.448060258 | 25240 | 12511 | 0.509829226 | 0 | 25268 | 12539 | 0.509125345 | 0 | 25296 | 12567 | 0.508163985 | 0 |
| 25213 | 12484 | 0.511417142 | -1.05012025 | 25241 | 12512 | 0.509829226 | 0 | 25269 | 12540 | 0.509125345 | 0 | 25297 | 12568 | 0.508163985 | 0 |
| 25214 | 12485 | 0.511417142 | -1.101272772 | 25242 | 12513 | 0.509829226 | 0 | 25270 | 12541 | 0.509125345 | 0 | 25298 | 12569 | 0.508163985 | 0 |
| 25215 | 12486 | 0.510590701 | -1.545796712 | 25243 | 12514 | 0.509829226 | 0 | 25271 | 12542 | 0.509125345 | 0 | 25299 | 12570 | 0.508163985 | 0 |
| 25216 | 12487 | 0.510433462 | 0 | 25244 | 12515 | 0.509829226 | 0 | 25272 | 12543 | 0.509125345 | 0 | 25300 | 12571 | 0.508163985 | 0 |
| 25217 | 12488 | 0.510330046 | 0 | 25245 | 12516 | 0.509829226 | 0 | 25273 | 12544 | 0.508942523 | 0 | 25301 | 12572 | 0.508163985 | 0 |
| 25218 | 12489 | 0.510330046 | 0 | 25246 | 12517 | 0.509829226 | 0 | 25274 | 12545 | 0.508942523 | 0 | 25302 | 12573 | 0.508163985 | 0 |
| 25219 | 12490 | 0.510330046 | 0 | 25247 | 12518 | 0.509829226 | 0 | 25275 | 12546 | 0.508942523 | 0 | 25303 | 12574 | 0.508163985 | 0 |
| 25220 | 12491 | 0.510202332 | 0 | 25248 | 12519 | 0.509829226 | -1.563591526 | 25276 | 12547 | 0.508839719 | 0 | 25304 | 12575 | 0.507983966 | 0 |
| 25221 | 12492 | 0.510202332 | 0 | 25249 | 12520 | 0.509697162 | 0 | 25277 | 12548 | 0.508839719 | 0 | 25305 | 12576 | 0.507983966 | 0 |
| 25222 | 12493 | 0.510202332 | 0 | 25250 | 12521 | 0.509697162 | 0 | 25278 | 12549 | 0.508839719 | 0 | 25306 | 12577 | 0.507983966 | 0 |
| 25223 | 12494 | 0.510202332 | 0 | 25251 | 12522 | 0.509541137 | 0 | 25279 | 12550 | 0.508839719 | 0 | 25307 | 12578 | 0.507983966 | 0 |
| 25224 | 12495 | 0.510202332 | -0.424451485 | 25252 | 12523 | 0.509541137 | 0 | 25280 | 12551 | 0.508839719 | 0 | 25308 | 12579 | 0.507983966 | 0 |
| 25225 | 12496 | 0.510040613 | 0 | 25253 | 12524 | 0.509541137 | 0 | 25281 | 12552 | 0.508839719 | 0 | 25309 | 12580 | 0.507983966 | 0 |
| 25226 | 12497 | 0.510040613 | 0 | 25254 | 12525 | 0.509541137 | 0 | 25282 | 12553 | 0.508839719 | 0 | 25310 | 12581 | 0.507983966 | 0 |
| 25227 | 12498 | 0.510040613 | 0 | 25255 | 12526 | 0.509541137 | 0 | 25283 | 12554 | 0.508839719 | 0 | 25311 | 12582 | 0.507983966 | 0 |
| 25228 | 12499 | 0.510040613 | 0 | 25256 | 12527 | 0.509353981 | 0 | 25284 | 12555 | 0.508839719 | 0 | 25312 | 12583 | 0.507866064 | 0 |
| 25229 | 12500 | 0.510040613 | 0 | 25257 | 12528 | 0.509353981 | 0 | 25285 | 12556 | 0.508839719 | 0 | 25313 | 12584 | 0.507866064 | -0.121617645 |
| 25230 | 12501 | 0.510040613 | 0 | 25258 | 12529 | 0.509353981 | 0 | 25286 | 12557 | 0.508839719 | 0 | 25314 | 12585 | 0.507782857 | 0 |
| 25231 | 12502 | 0.510040613 | 0 | 25259 | 12530 | 0.509125345 | 0 | 25287 | 12558 | 0.508839719 | -0.575576418 | 25315 | 12586 | 0.507782857 | 0 |
| 25232 | 12503 | 0.510040613 | 0 | 25260 | 12531 | 0.509125345 | 0 | 25288 | 12559 | 0.508728004 | -1.511447237 | 25316 | 12587 | 0.507782857 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 25317 | 12588 | 0.507782857 | 0 | 25345 | 12616 | 0.506845579 | 0 | 25373 | 12644 | 0.505548208 | 0 | 25401 | 12672 | 0.504577718 | 0 |
| 25318 | 12589 | 0.507782857 | 0 | 25346 | 12617 | 0.506845579 | 0 | 25374 | 12645 | 0.505548208 | 0 | 25402 | 12673 | 0.504577718 | 0 |
| 25319 | 12590 | 0.507782857 | 0 | 25347 | 12618 | 0.506845579 | -1.406874331 | 25375 | 12646 | 0.505548208 | 0 | 25403 | 12674 | 0.504577718 | 0 |
| 25320 | 12591 | 0.507782857 | 0 | 25348 | 12619 | 0.506670707 | 0 | 25376 | 12647 | 0.505548208 | 0 | 25404 | 12675 | 0.504577718 | 0 |
| 25321 | 12592 | 0.507782857 | 0 | 25349 | 12620 | 0.506670707 | 0 | 25377 | 12648 | 0.505548208 | 0 | 25405 | 12676 | 0.504577718 | 0 |
| 25322 | 12593 | 0.507300576 | 0 | 25350 | 12621 | 0.506670707 | 0 | 25378 | 12649 | 0.505548208 | 0 | 25406 | 12677 | 0.504577718 | 0 |
| 25323 | 12594 | 0.507300576 | 0 | 25351 | 12622 | 0.506670707 | 0 | 25379 | 12650 | 0.505548208 | 0 | 25407 | 12678 | 0.504577718 | 0 |
| 25324 | 12595 | 0.507300576 | 0 | 25352 | 12623 | 0.506670707 | 0 | 25380 | 12651 | 0.505548208 | 0 | 25408 | 12679 | 0.504577718 | 0 |
| 25325 | 12596 | 0.507300576 | 0 | 25353 | 12624 | 0.506670707 | 0 | 25381 | 12652 | 0.505548208 | 0 | 25409 | 12680 | 0.504577718 | 0 |
| 25326 | 12597 | 0.507300576 | 0 | 25354 | 12625 | 0.506670707 | 0 | 25382 | 12653 | 0.505548208 | 0 | 25410 | 12681 | 0.504577718 | 0 |
| 25327 | 12598 | 0.507300576 | 0 | 25355 | 12626 | 0.506670707 | -1.26572005 | 25383 | 12654 | 0.505548208 | -1.299027232 | 25411 | 12682 | 0.504577718 | 0 |
| 25328 | 12599 | 0.507300576 | 0 | 25356 | 12627 | 0.506520873 | 0 | 25384 | 12655 | 0.505376788 | 0 | 25412 | 12683 | 0.504577718 | 0 |
| 25329 | 12600 | 0.507300576 | 0 | 25357 | 12628 | 0.506520873 | 0 | 25385 | 12656 | 0.505376788 | 0 | 25413 | 12684 | 0.504577718 | 0 |
| 25330 | 12601 | 0.507300576 | 0 | 25358 | 12629 | 0.506520873 | -1.474145827 | 25386 | 12657 | 0.505376788 | 0 | 25414 | 12685 | 0.504577718 | 0 |
| 25331 | 12602 | 0.507300576 | 0 | 25359 | 12630 | 0.506453723 | -0.660149171 | 25387 | 12658 | 0.505376788 | 0 | 25415 | 12686 | 0.504577718 | 0 |
| 25332 | 12603 | 0.507300576 | 0 | 25360 | 12631 | 0.506277502 | 0 | 25388 | 12659 | 0.505256833 | 0 | 25416 | 12687 | 0.504577718 | 0 |
| 25333 | 12604 | 0.507300576 | 0 | 25361 | 12632 | 0.506277502 | 0 | 25389 | 12660 | 0.505256833 | 0 | 25417 | 12688 | 0.504577718 | -0.288568261 |
| 25334 | 12605 | 0.507300576 | 0 | 25362 | 12633 | 0.506277502 | 0 | 25390 | 12661 | 0.505168193 | 0 | 25418 | 12689 | 0.504577718 | -0.434696297 |
| 25335 | 12606 | 0.507300576 | 0 | 25363 | 12634 | 0.506277502 | 0 | 25391 | 12662 | 0.505168193 | 0 | 25419 | 12690 | 0.504577718 | -0.454899683 |
| 25336 | 12607 | 0.507300576 | 0 | 25364 | 12635 | 0.506088309 | 0 | 25392 | 12663 | 0.504965654 | 0 | 25420 | 12691 | 0.504577718 | -0.755929679 |
| 25337 | 12608 | 0.507300576 | 0 | 25365 | 12636 | 0.506008673 | 0 | 25393 | 12664 | 0.504577718 | 0 | 25421 | 12692 | 0.504577718 | -0.755929679 |
| 25338 | 12609 | 0.507300576 | 0 | 25366 | 12637 | 0.506008673 | 0 | 25394 | 12665 | 0.504577718 | 0 | 25422 | 12693 | 0.504577718 | -0.932020938 |
| 25339 | 12610 | 0.507300576 | -0.482140048 | 25367 | 12638 | 0.505813265 | 0 | 25395 | 12666 | 0.504577718 | 0 | 25423 | 12694 | 0.504577718 | -1.233050933 |
| 25340 | 12611 | 0.506944451 | 0 | 25368 | 12639 | 0.505813265 | 0 | 25396 | 12667 | 0.504577718 | 0 | 25424 | 12695 | 0.504577718 | -1.409142192 |
| 25341 | 12612 | 0.506845579 | 0 | 25369 | 12640 | 0.505813265 | 0 | 25397 | 12668 | 0.504577718 | 0 | 25425 | 12696 | 0.504140141 | 0 |
| 25342 | 12613 | 0.506845579 | 0 | 25370 | 12641 | 0.505813265 | -1.495056821 | 25398 | 12669 | 0.504577718 | 0 | 25426 | 12697 | 0.504093284 | 0 |
| 25343 | 12614 | 0.506845579 | 0 | 25371 | 12642 | 0.505664813 | 0 | 25399 | 12670 | 0.504577718 | 0 | 25427 | 12698 | 0.504035188 | 0 |
| 25344 | 12615 | 0.506845579 | 0 | 25372 | 12643 | 0.505664813 | 0 | 25400 | 12671 | 0.504577718 | 0 | 25428 | 12699 | 0.50396126 | 0 |

FIG. 3 (Cont.)

| DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver | DNA SEQ ID NO | AA SEQ ID NO | Log 10 enrichment in the brain | Log 10 enrichment in the liver |
|---|---|---|---|---|---|---|---|---|---|---|---|---|---|---|---|
| 25429 | 12700 | 0.50396126 | 0 | 25440 | 12711 | 0.503730313 | 0 | 25451 | 12722 | 0.503534993 | 0 | 25462 | 12733 | 0.503534993 | -0.56988576 |
| 25430 | 12701 | 0.50396126 | 0 | 25441 | 12712 | 0.503730313 | 0 | 25452 | 12723 | 0.503534993 | 0 | 25463 | 12734 | 0.50339917 | 0 |
| 25431 | 12702 | 0.503864004 | 0 | 25442 | 12713 | 0.503730313 | 0 | 25453 | 12724 | 0.503534993 | 0 | 25464 | 12735 | 0.50339917 | 0 |
| 25432 | 12703 | 0.503864004 | 0 | 25443 | 12714 | 0.503730313 | 0 | 25454 | 12725 | 0.503534993 | 0 | 25465 | 12736 | 0.503222663 | 0 |
| 25433 | 12704 | 0.503864004 | 0 | 25444 | 12715 | 0.503730313 | 0 | 25455 | 12726 | 0.503534993 | 0 | 25466 | 12737 | 0.503222663 | 0 |
| 25434 | 12705 | 0.503864004 | 0 | 25445 | 12716 | 0.503730313 | 0 | 25456 | 12727 | 0.503534993 | 0 | 25467 | 12738 | 0.503222663 | 0 |
| 25435 | 12706 | 0.503864004 | 0 | 25446 | 12717 | 0.503730313 | 0 | 25457 | 12728 | 0.503534993 | 0 | 25468 | 12739 | 0.503222663 | 0 |
| 25436 | 12707 | 0.503864004 | 0 | 25447 | 12718 | 0.503730313 | 0 | 25458 | 12729 | 0.503534993 | 0 | | | | |
| 25437 | 12708 | 0.503864004 | 0 | 25448 | 12719 | 0.503730313 | 0 | 25459 | 12730 | 0.503534993 | 0 | | | | |
| 25438 | 12709 | 0.503864004 | 0 | 25449 | 12720 | 0.503534993 | 0 | 25460 | 12731 | 0.503534993 | 0 | | | | |
| 25439 | 12710 | 0.503864004 | 0 | 25450 | 12721 | 0.503534993 | 0 | 25461 | 12732 | 0.503534993 | 0 | | | | |

FIG. 4

| DNA SEQ ID NO | AA SEQ ID NO | Heart 1 Enrichment Score | Heart 2 Enrichment Score |
|---|---|---|---|
| 35472 | 25469 | 30.1804878 | 17.14982578 |
| 35473 | 25470 | 29.7247619 | 21.78741497 |
| 35474 | 25471 | 27.76 | 57.42857143 |
| 35475 | 25472 | 10.8 | 14.9047619 |
| 35476 | 25473 | 10.672 | 3.285714286 |
| 35477 | 25474 | 9.483076923 | 8.593406593 |
| 35478 | 25475 | 6.111428571 | 3.87244898 |
| 35479 | 25476 | 5.141176471 | 7.634453782 |
| 35480 | 25477 | 4.876 | 4.6 |
| 35481 | 25478 | 4.822068966 | 11.66995074 |
| 35482 | 25479 | 4.6 | 12.73214286 |
| 35483 | 25480 | 4.545882353 | 2.899159664 |
| 35484 | 25481 | 4.416 | 3.395238095 |
| 35485 | 25482 | 3.956 | 3.121428571 |
| 35486 | 25483 | 3.956 | 6.078571429 |
| 35487 | 25484 | 3.873684211 | 22.04887218 |
| 35488 | 25485 | 3.793230769 | 1.718681319 |
| 35489 | 25486 | 3.7536 | 1.577142857 |
| 35490 | 25487 | 3.68 | 1.334821429 |
| 35491 | 25488 | 3.68 | 2.738095238 |
| 35492 | 25489 | 3.571764706 | 6.764705882 |
| 35493 | 25490 | 3.538461538 | 3.95970696 |
| 35494 | 25491 | 3.504761905 | 5.163265306 |
| 35495 | 25492 | 3.475555556 | 1.022222222 |
| 35496 | 25493 | 3.445818182 | 1.254545455 |
| 35497 | 25494 | 3.434666667 | 1.679365079 |
| 35498 | 25495 | 3.434666667 | 4.307936508 |
| 35499 | 25496 | 3.423255814 | 4.661129568 |
| 35500 | 25497 | 3.417142857 | 2.863265306 |
| 35501 | 25498 | 3.3856 | 1.84 |
| 35502 | 25499 | 3.351428571 | 1.877755102 |
| 35503 | 25500 | 3.345454545 | 1.891774892 |
| 35504 | 25501 | 3.30031746 | 1.408163265 |
| 35505 | 25502 | 3.285714286 | 4.459183673 |
| 35506 | 25503 | 3.131914894 | 2.446808511 |
| 35507 | 25504 | 3.094545455 | 3.061688312 |
| 35508 | 25505 | 3.084705882 | 4.783613445 |
| 35509 | 25506 | 3.084705882 | 1.546218487 |
| 35510 | 25507 | 3.066666667 | 5.202380952 |
| 35511 | 25508 | 3.066666667 | 4.459183673 |
| 35512 | 25509 | 3.05509434 | 3.161725067 |
| 35513 | 25510 | 3.05509434 | 3.037735849 |
| 35514 | 25511 | 3.050526316 | 2.939849624 |
| 35515 | 25512 | 3.043076923 | 4.233516484 |
| 35516 | 25513 | 3.041632653 | 1.206997085 |
| 35517 | 25514 | 3.04 | 8.428571429 |
| 35518 | 25515 | 3.014468085 | 3.844984802 |
| 35519 | 25516 | 2.967741935 | 6.253456221 |
| 35520 | 25517 | 2.96 | 1.571428571 |
| 35521 | 25518 | 2.944 | 3.285714286 |
| 35522 | 25519 | 2.944 | 3.203571429 |
| 35523 | 25520 | 2.944 | 2.065306122 |
| 35524 | 25521 | 2.935238095 | 1.017006803 |
| 35525 | 25522 | 2.922352941 | 3.865546218 |
| 35526 | 25523 | 2.891428571 | 4.693877551 |
| 35527 | 25524 | 2.875 | 2.19047619 |
| 35528 | 25525 | 2.869152542 | 1.169491525 |
| 35529 | 25526 | 2.866153846 | 3.159340659 |
| 35530 | 25527 | 2.855172414 | 1.869458128 |
| 35531 | 25528 | 2.849032258 | 3.444700461 |
| 35532 | 25529 | 2.843636364 | 25.38961039 |
| 35533 | 25530 | 2.830769231 | 2.274725275 |
| 35534 | 25531 | 2.824186047 | 1.681063123 |
| 35535 | 25532 | 2.785555556 | 1.916666667 |
| 35536 | 25533 | 2.76 | 3.584415584 |
| 35537 | 25534 | 2.76 | 7.392857143 |
| 35538 | 25535 | 2.739555556 | 1.168253968 |
| 35539 | 25536 | 2.721666667 | 1.505952381 |
| 35540 | 25537 | 2.72 | 3.357142857 |
| 35541 | 25538 | 2.711578947 | 1.729323308 |
| 35542 | 25539 | 2.705882353 | 1.030812325 |
| 35543 | 25540 | 2.694285714 | 3.403061224 |
| 35544 | 25541 | 2.689230769 | 1.326923077 |
| 35545 | 25542 | 2.679298246 | 3.862155388 |
| 35546 | 25543 | 2.678481013 | 3.660036166 |
| 35547 | 25544 | 2.669803922 | 5.025210084 |
| 35548 | 25545 | 2.690110989 | 4.224489796 |
| 35549 | 25546 | 2.668 | 3.367857143 |
| 35550 | 25547 | 2.664827586 | 5.778325123 |
| 35551 | 25548 | 2.657777778 | 1.277777778 |
| 35552 | 25549 | 2.64 | 4 |
| 35553 | 25550 | 2.635675676 | 3.996138996 |
| 35554 | 25551 | 2.622 | 5.503571429 |
| 35555 | 25552 | 2.597647059 | 11.69327731 |
| 35556 | 25553 | 2.597647059 | 2.899159664 |
| 35557 | 25554 | 2.576 | 5.421428571 |
| 35558 | 25555 | 2.576 | 6.9 |
| 35559 | 25556 | 2.576 | 2.19047619 |
| 35560 | 25557 | 2.576 | 2.19047619 |
| 35561 | 25558 | 2.562857143 | 1.408163265 |
| 35562 | 25559 | 2.560559441 | 1.309690031 |
| 35563 | 25560 | 2.540952381 | 3.129251701 |
| 35564 | 25561 | 2.536969697 | 3.285714286 |
| 35565 | 25562 | 2.526101695 | 1.336561743 |
| 35566 | 25563 | 2.512307692 | 1.516483516 |
| 35567 | 25564 | 2.494915254 | 1.113801453 |
| 35568 | 25565 | 2.491076923 | 3.032967033 |
| 35569 | 25566 | 2.453333333 | 2.875 |
| 35570 | 25567 | 2.453333333 | 3.285714286 |
| 35571 | 25568 | 2.453333333 | 3.13968254 |
| 35572 | 25569 | 2.453333333 | 2.19047619 |
| 35573 | 25570 | 2.445263158 | 1.340225564 |
| 35574 | 25571 | 2.440816327 | 3.55393586 |
| 35575 | 25572 | 2.427234043 | 2.376899696 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 35576 | 25573 | 2.427234043 | 2.446808511 | 35604 | 25601 | 2.24 | 4.952380952 | 35632 | 25629 | 2.102857143 | 3.207482993 | 35660 | 25657 | 2.009846154 | 1.162637363 |
| 35577 | 25574 | 2.421052632 | 1.210526316 | 35605 | 25602 | 2.231 | 4.928571429 | 35633 | 25630 | 2.102857143 | 4.506122449 | 35661 | 25658 | 2.003960396 | 1.659123055 |
| 35578 | 25575 | 2.406153846 | 3.159340659 | 35606 | 25603 | 2.229230769 | 3.791208791 | 35634 | 25631 | 2.102857143 | 8.448979592 | 35662 | 25659 | 1.988387097 | 3.656682028 |
| 35579 | 25576 | 2.392 | 4.107142857 | 35607 | 25604 | 2.227368421 | 3.977443609 | 35635 | 25632 | 2.102857143 | 3.473469388 | 35663 | 25660 | 1.967524752 | 1.106082037 |
| 35580 | 25577 | 2.381176471 | 2.06162465 | 35608 | 25605 | 2.227368421 | 1.210526316 | 35636 | 25633 | 2.098245614 | 5.015037594 | 35664 | 25661 | 1.955 | 6.058035714 |
| 35581 | 25578 | 2.377846154 | 4.650549451 | 35609 | 25606 | 2.223333333 | 1.642857143 | 35637 | 25634 | 2.096744186 | 1.833887043 | 35665 | 25662 | 1.951515152 | 1.360750361 |
| 35582 | 25579 | 2.376666667 | 3.285714286 | 35610 | 25607 | 2.208 | 3.942857143 | 35638 | 25635 | 2.096744186 | 1.400885936 | 35666 | 25663 | 1.948235294 | 3.18907563 |
| 35583 | 25580 | 2.374193548 | 3.126728111 | 35611 | 25608 | 2.208 | 4.130612245 | 35639 | 25636 | 2.093793103 | 1.302955665 | 35667 | 25664 | 1.945142857 | 5.444897959 |
| 35584 | 25581 | 2.372631579 | 2.421052632 | 35612 | 25609 | 2.197777778 | 3.468253968 | 35640 | 25637 | 2.089491525 | 2.840193705 | 35668 | 25665 | 1.942222222 | 1.533333333 |
| 35585 | 25582 | 2.372631579 | 2.161654135 | 35613 | 25610 | 2.194698795 | 1.108433735 | 35641 | 25638 | 2.080952381 | 1.603741497 | 35669 | 25666 | 1.936842105 | 2.507518797 |
| 35586 | 25583 | 2.365714286 | 5.444897959 | 35614 | 25611 | 2.180740741 | 3.042328042 | 35642 | 25639 | 2.074181818 | 4.898701299 | 35670 | 25667 | 1.934358974 | 1.347985348 |
| 35587 | 25584 | 2.365714286 | 5.867346939 | 35615 | 25612 | 2.180740741 | 1.46031746 | 35643 | 25640 | 2.072911392 | 1.788426763 | 35671 | 25668 | 1.930491803 | 1.238875878 |
| 35588 | 25585 | 2.3575 | 3.799107143 | 35616 | 25613 | 2.174545455 | 1.672727273 | 35644 | 25641 | 2.07 | 5.75 | 35672 | 25669 | 1.921777778 | 1.606349206 |
| 35589 | 25586 | 2.353488372 | 1.146179402 | 35617 | 25614 | 2.174545455 | 9.409090909 | 35645 | 25642 | 2.067809524 | 4.412244898 | 35673 | 25670 | 1.9136 | 1.927619048 |
| 35590 | 25587 | 2.345098039 | 1.095238095 | 35618 | 25615 | 2.169552239 | 1.275053305 | 35646 | 25643 | 2.065306122 | 3.956268222 | 35674 | 25671 | 1.912631579 | 3.328947368 |
| 35591 | 25588 | 2.335384615 | 1.432234432 | 35619 | 25616 | 2.162 | 1.560714286 | 35647 | 25644 | 2.062068966 | 3.115763547 | 35675 | 25672 | 1.910769231 | 2.337912088 |
| 35592 | 25589 | 2.330666667 | 2.19047619 | 35620 | 25617 | 2.16 | 2 | 35648 | 25645 | 2.059701493 | 1.275053305 | 35676 | 25673 | 1.908148148 | 2.85978836 |
| 35593 | 25590 | 2.306133333 | 2.891428571 | 35621 | 25618 | 2.151384615 | 7.683516484 | 35649 | 25646 | 2.056470588 | 2.512605042 | 35677 | 25674 | 1.904561404 | 3.343358396 |
| 35594 | 25591 | 2.3 | 1.93622449 | 35622 | 25619 | 2.146666667 | 1.861904762 | 35650 | 25647 | 2.056470588 | 1.546218487 | 35678 | 25675 | 1.898412698 | 1.98185941 |
| 35595 | 25592 | 2.2816 | 2.497142857 | 35623 | 25620 | 2.146666667 | 2.628571429 | 35651 | 25648 | 2.053052632 | 2.006015038 | 35679 | 25676 | 1.892571429 | 1.689795918 |
| 35596 | 25593 | 2.28056338 | 1.342052314 | 35624 | 25621 | 2.139534884 | 1.833887043 | 35652 | 25649 | 2.044444444 | 3.285714286 | 35680 | 25677 | 1.888421053 | 4.107142857 |
| 35597 | 25594 | 2.274909091 | 1.135064935 | 35625 | 25622 | 2.137647059 | 1.691176471 | 35653 | 25650 | 2.044444444 | 4.137566138 | 35681 | 25678 | 1.887179487 | 4.886446886 |
| 35598 | 25595 | 2.269333333 | 2.40952381 | 35626 | 25623 | 2.136774194 | 2.755760369 | 35654 | 25651 | 2.037142857 | 1.87755102 | 35682 | 25679 | 1.886 | 1.013095238 |
| 35599 | 25596 | 2.268737864 | 1.882108183 | 35627 | 25624 | 2.130526316 | 3.285714286 | 35655 | 25652 | 2.033684211 | 1.268170426 | 35683 | 25680 | 1.884878049 | 4.24738676 |
| 35600 | 25597 | 2.252413793 | 1.07635468 | 35628 | 25625 | 2.130526316 | 2.593984962 | 35656 | 25653 | 2.033684211 | 1.556390977 | 35684 | 25681 | 1.881818182 | 1.642857143 |
| 35601 | 25598 | 2.251940299 | 1.176972281 | 35629 | 25626 | 2.123076923 | 1.074175824 | 35657 | 25654 | 2.024 | 7.721428571 | 35685 | 25682 | 1.88 | 1.928571429 |
| 35602 | 25599 | 2.248888889 | 1.277777778 | 35630 | 25627 | 2.118787879 | 1.692640693 | 35658 | 25655 | 2.020983607 | 2.585480094 | 35686 | 25683 | 1.874716981 | 3.781671159 |
| 35603 | 25600 | 2.248888889 | 2.920634921 | 35631 | 25628 | 2.116 | 2.053571429 | 35659 | 25656 | 2.019512195 | 1.682926829 | 35687 | 25684 | 1.874074074 | 2.646825397 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 35688 | 25685 | 1.861647059 | 1.58487395 | 35716 | 25713 | 1.736338028 | 2.822937626 | 35744 | 25741 | 1.666415094 | 1.859838275 | 35772 | 25769 | 1.623529412 | 4.058823529 |
| 35689 | 25686 | 1.84 | 1.449579832 | 35717 | 25714 | 1.734857143 | 1.971428571 | 35745 | 25742 | 1.664761905 | 6.727891156 | 35773 | 25770 | 1.623529412 | 4.831932773 |
| 35690 | 25687 | 1.84 | 1.115902965 | 35718 | 25715 | 1.734857143 | 1.595918367 | 35746 | 25743 | 1.660487805 | 2.591173055 | 35774 | 25771 | 1.620952381 | 6.102040816 |
| 35691 | 25688 | 1.84 | 2.324041812 | 35719 | 25716 | 1.734857143 | 2.534693878 | 35747 | 25744 | 1.656 | 1.38 | 35775 | 25772 | 1.616969697 | 6.272727273 |
| 35692 | 25689 | 1.84 | 1.25170068 | 35720 | 25717 | 1.731764706 | 9.277310924 | 35748 | 25745 | 1.656 | 1.204761905 | 35776 | 25773 | 1.614693878 | 2.413994169 |
| 35693 | 25690 | 1.84 | 2.503401361 | 35721 | 25718 | 1.728484848 | 4.779220779 | 35749 | 25746 | 1.656 | 1.642857143 | 35777 | 25774 | 1.614693878 | 1.542274052 |
| 35694 | 25691 | 1.84 | 2.527472527 | 35722 | 25719 | 1.728484848 | 1.692640693 | 35750 | 25747 | 1.656 | 1.807142857 | 35778 | 25775 | 1.614693878 | 4.626822157 |
| 35695 | 25692 | 1.84 | 1.216931217 | 35723 | 25720 | 1.721290323 | 2.437788018 | 35751 | 25748 | 1.656 | 3.203571429 | 35779 | 25776 | 1.601882353 | 1.005042017 |
| 35696 | 25693 | 1.84 | 1.971428571 | 35724 | 25721 | 1.72 | 1.142857143 | 35752 | 25749 | 1.656 | 2.628571429 | 35780 | 25777 | 1.6 | 4.571428571 |
| 35697 | 25694 | 1.815789474 | 1.815789474 | 35725 | 25722 | 1.717333333 | 1.226666667 | 35753 | 25750 | 1.652244898 | 2.145772595 | 35781 | 25778 | 1.598688525 | 2.962529274 |
| 35698 | 25695 | 1.815466667 | 2.497142857 | 35726 | 25723 | 1.717333333 | 1.401904762 | 35754 | 25751 | 1.645384615 | 1.200549451 | 35782 | 25779 | 1.596144578 | 3.008605852 |
| 35699 | 25696 | 1.812121212 | 1.045454545 | 35727 | 25724 | 1.713103448 | 5.21182266 | 35755 | 25752 | 1.642857143 | 8.331632653 | 35783 | 25780 | 1.591351351 | 3.196911197 |
| 35700 | 25697 | 1.806545455 | 2.24025974 | 35728 | 25725 | 1.708571429 | 4.869897959 | 35756 | 25753 | 1.641846154 | 1.567032967 | 35784 | 25781 | 1.590508475 | 1.169491525 |
| 35701 | 25698 | 1.801666667 | 3.62797619 | 35729 | 25726 | 1.708571429 | 1.25170068 | 35757 | 25754 | 1.64 | 2 | 35785 | 25782 | 1.58976 | 1.182857143 |
| 35702 | 25699 | 1.792 | 1.142857143 | 35730 | 25727 | 1.708571429 | 2.229591837 | 35758 | 25755 | 1.635555556 | 2.418650794 | 35786 | 25783 | 1.587945205 | 2.56555773 |
| 35703 | 25700 | 1.788888889 | 2.236111111 | 35731 | 25728 | 1.708571429 | 3.051020408 | 35759 | 25756 | 1.635555556 | 2.068783069 | 35787 | 25784 | 1.58745098 | 4.509803922 |
| 35704 | 25701 | 1.785882353 | 5.991596639 | 35732 | 25729 | 1.703703704 | 4.867724868 | 35760 | 25757 | 1.635555556 | 4.244047619 | 35788 | 25785 | 1.5824 | 4.008571429 |
| 35705 | 25702 | 1.781587302 | 2.920634921 | 35733 | 25730 | 1.702 | 4.764285714 | 35761 | 25758 | 1.635555556 | 4.654761905 | 35789 | 25786 | 1.577142857 | 1.733124019 |
| 35706 | 25703 | 1.771851852 | 1.095238095 | 35734 | 25731 | 1.6928 | 1.095238095 | 35762 | 25759 | 1.635555556 | 2.19047619 | 35790 | 25787 | 1.577142857 | 1.329931973 |
| 35707 | 25704 | 1.771851852 | 2.068783069 | 35735 | 25732 | 1.690810811 | 2.752895753 | 35763 | 25760 | 1.63364486 | 3.285714286 | 35791 | 25788 | 1.577142857 | 1.25170068 |
| 35708 | 25705 | 1.767843137 | 6.635854342 | 35736 | 25733 | 1.689795918 | 1.139941691 | 35764 | 25761 | 1.632 | 2.942857143 | 35792 | 25789 | 1.577142857 | 1.267346939 |
| 35709 | 25706 | 1.7664 | 1.84 | 35737 | 25734 | 1.688470588 | 2.628571429 | 35765 | 25762 | 1.627692308 | 1.769230769 | 35793 | 25790 | 1.577142857 | 1.689795918 |
| 35710 | 25707 | 1.762253521 | 4.6277666 | 35738 | 25735 | 1.687819549 | 2.939849624 | 35766 | 25763 | 1.627692308 | 3.412087912 | 35794 | 25791 | 1.577142857 | 2.413994169 |
| 35711 | 25708 | 1.75375 | 2.310267857 | 35739 | 25736 | 1.686666667 | 2.327380952 | 35767 | 25764 | 1.627692308 | 4.549450549 | 35795 | 25792 | 1.567407407 | 2.494708995 |
| 35712 | 25709 | 1.745641026 | 4.844322344 | 35740 | 25737 | 1.684507042 | 2.915492958 | 35768 | 25765 | 1.626046512 | 1.910299003 | 35796 | 25793 | 1.562264151 | 1.425876011 |
| 35713 | 25710 | 1.745154639 | 1.82916053 | 35741 | 25738 | 1.683404255 | 4.474164134 | 35769 | 25766 | 1.626046512 | 2.139534884 | 35797 | 25794 | 1.561212121 | 3.484848485 |
| 35714 | 25711 | 1.743157895 | 6.398496241 | 35742 | 25739 | 1.670526316 | 4.323308271 | 35770 | 25767 | 1.626046512 | 3.132890365 | 35798 | 25795 | 1.560506329 | 1.164556962 |
| 35715 | 25712 | 1.740540541 | 6.837837838 | 35743 | 25740 | 1.668837209 | 1.299003322 | 35771 | 25768 | 1.623529412 | 3.672268908 | 35799 | 25796 | 1.553027523 | 2.712975098 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 35800 | 25797 | 1.5525 | 1.026785714 | 35828 | 25825 | 1.505454545 | 1.493506494 | 35856 | 25853 | 1.448510638 | 6.082066869 | 35884 | 25881 | 1.411506849 | 2.56555773 |
| 35801 | 25798 | 1.551372549 | 2.254901961 | 35829 | 25826 | 1.505454545 | 4.032467532 | 35857 | 25854 | 1.445714286 | 4.224489796 | 35885 | 25882 | 1.410666667 | 4.326190476 |
| 35802 | 25799 | 1.549473684 | 5.187969925 | 35830 | 25827 | 1.502040816 | 1.810495627 | 35858 | 25855 | 1.445714286 | 4.576530612 | 35886 | 25883 | 1.408395062 | 1.703703704 |
| 35803 | 25800 | 1.548514851 | 1.26874116 | 35831 | 25828 | 1.495 | 6.229166667 | 35859 | 25856 | 1.444301075 | 1.837173579 | 35887 | 25884 | 1.408163265 | 2.179300292 |
| 35804 | 25801 | 1.547272727 | 1.642857143 | 35832 | 25829 | 1.492444444 | 1.788888889 | 35860 | 25857 | 1.443137255 | 2.995798319 | 35888 | 25885 | 1.407058824 | 2.029411765 |
| 35805 | 25802 | 1.546382979 | 1.013677812 | 35833 | 25830 | 1.491891892 | 2.752895753 | 35861 | 25858 | 1.440963855 | 1.425129088 | 35889 | 25886 | 1.407058824 | 1.739495798 |
| 35806 | 25803 | 1.541621622 | 2.575289575 | 35834 | 25831 | 1.486153846 | 6.445054945 | 35862 | 25859 | 1.44 | 2.085714286 | 35890 | 25887 | 1.402772277 | 1.236209335 |
| 35807 | 25804 | 1.537534247 | 2.520547945 | 35835 | 25832 | 1.486153846 | 1.642857143 | 35863 | 25860 | 1.4375 | 3.901785714 | 35891 | 25888 | 1.401904762 | 3.755102041 |
| 35808 | 25805 | 1.533333333 | 1.711309524 | 35836 | 25833 | 1.486153846 | 4.549450549 | 35864 | 25861 | 1.436712329 | 1.350293542 | 35892 | 25889 | 1.3984 | 1.945142857 |
| 35809 | 25806 | 1.533333333 | 2.555555556 | 35837 | 25834 | 1.484912281 | 1.268170426 | 35865 | 25862 | 1.435757576 | 1.493506494 | 35893 | 25890 | 1.397037037 | 1.399470899 |
| 35810 | 25807 | 1.533333333 | 3.230952381 | 35838 | 25835 | 1.482222222 | 3.285714286 | 35866 | 25863 | 1.433766234 | 1.706864564 | 35894 | 25891 | 1.395862069 | 2.719211823 |
| 35811 | 25808 | 1.533333333 | 1.87755102 | 35839 | 25836 | 1.48097561 | 5.048780488 | 35867 | 25864 | 1.433488372 | 2.941860465 | 35895 | 25892 | 1.39483871 | 2.80875576 |
| 35812 | 25809 | 1.533333333 | 1.696619048 | 35840 | 25837 | 1.48097561 | 1.362369338 | 35868 | 25865 | 1.431111111 | 8.214285714 | 35896 | 25893 | 1.393939394 | 1.692640693 |
| 35813 | 25810 | 1.529638554 | 1.425129088 | 35841 | 25838 | 1.478571429 | 1.87755102 | 35869 | 25866 | 1.431111111 | 4.472222222 | 35897 | 25894 | 1.393398058 | 1.435506241 |
| 35814 | 25811 | 1.525853659 | 3.285714286 | 35842 | 25839 | 1.472 | 1.774285714 | 35870 | 25867 | 1.431111111 | 1.135802469 | 35898 | 25895 | 1.392432432 | 5.283783784 |
| 35815 | 25812 | 1.524571429 | 1.971428571 | 35843 | 25840 | 1.472 | 1.117142857 | 35871 | 25868 | 1.431111111 | 2.555555556 | 35899 | 25896 | 1.392432432 | 2.575289575 |
| 35816 | 25813 | 1.52344086 | 5.016897081 | 35844 | 25841 | 1.472 | 6.352380952 | 35872 | 25869 | 1.431111111 | 2.555555556 | 35900 | 25897 | 1.390222222 | 2.044444444 |
| 35817 | 25814 | 1.521975309 | 1.176366843 | 35845 | 25842 | 1.472 | 1.971428571 | 35873 | 25870 | 1.428059701 | 2.452025586 | 35901 | 25898 | 1.388070175 | 1.037593985 |
| 35818 | 25815 | 1.52 | 2.142857143 | 35846 | 25843 | 1.472 | 5.585714286 | 35874 | 25871 | 1.426516854 | 2.399678973 | 35902 | 25899 | 1.385974026 | 1.237476809 |
| 35819 | 25816 | 1.516756757 | 1.50965251 | 35847 | 25844 | 1.467341772 | 1.081374322 | 35875 | 25872 | 1.426 | 2.546428571 | 35903 | 25900 | 1.38 | 1.916666667 |
| 35820 | 25817 | 1.516483516 | 1.083202512 | 35848 | 25845 | 1.466666667 | 2.857142857 | 35876 | 25873 | 1.426 | 2.464285714 | 35904 | 25901 | 1.38 | 2.558163265 |
| 35821 | 25818 | 1.516483516 | 4.982731554 | 35849 | 25846 | 1.465762712 | 1.615012107 | 35877 | 25874 | 1.424516129 | 2.013824885 | 35905 | 25902 | 1.38 | 9.035714286 |
| 35822 | 25819 | 1.514166667 | 1.950892857 | 35850 | 25847 | 1.464736842 | 1.426691729 | 35878 | 25875 | 1.424516129 | 2.755760369 | 35906 | 25903 | 1.38 | 7.275510204 |
| 35823 | 25820 | 1.511428571 | 4.459183673 | 35851 | 25848 | 1.464489796 | 3.151603499 | 35879 | 25876 | 1.419428571 | 1.157823129 | 35907 | 25904 | 1.38 | 1.525510204 |
| 35824 | 25821 | 1.510736842 | 1.62556391 | 35852 | 25849 | 1.461917808 | 2.160469667 | 35880 | 25877 | 1.418333333 | 1.026785714 | 35908 | 25905 | 1.377177914 | 1.471516214 |
| 35825 | 25822 | 1.507047619 | 1.314285714 | 35853 | 25850 | 1.456666667 | 1.163690476 | 35881 | 25878 | 1.415384615 | 2.852433281 | 35909 | 25906 | 1.374945055 | 1.624803768 |
| 35826 | 25823 | 1.505454545 | 1.593073593 | 35854 | 25851 | 1.455824176 | 1.227629513 | 35882 | 25879 | 1.413658537 | 1.162020906 | 35910 | 25907 | 1.373521127 | 1.573440644 |
| 35827 | 25824 | 1.505454545 | 1.792207792 | 35855 | 25852 | 1.44969697 | 2.356421356 | 35883 | 25880 | 1.413333333 | 1.952380952 | 35911 | 25908 | 1.373134328 | 1.275053305 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 35912 | 25909 | 1.373134328 | 5.051172708 | 35940 | 25937 | 1.355789474 | 2.19047619 | 35968 | 25965 | 1.297266187 | 2.08016444 | 35996 | 25993 | 1.257333333 | 3.55952381 |
| 35913 | 25910 | 1.373134328 | 1.324093817 | 35941 | 25938 | 1.351836735 | 2.346938776 | 35969 | 25966 | 1.295510204 | 2.246355685 | 35997 | 25994 | 1.257333333 | 1.478571429 |
| 35914 | 25911 | 1.372698413 | 1.616780045 | 35942 | 25939 | 1.351836735 | 2.816326531 | 35970 | 25967 | 1.294814815 | 2.312169312 | 35998 | 25995 | 1.255193798 | 1.782945736 |
| 35915 | 25912 | 1.37220339 | 3.564164649 | 35943 | 25940 | 1.351504425 | 2.587863464 | 35971 | 25968 | 1.294065934 | 1.588697017 | 35999 | 25996 | 1.253333333 | 3 |
| 35916 | 25913 | 1.371153846 | 2.148351648 | 35944 | 25941 | 1.349333333 | 2.226984127 | 35972 | 25969 | 1.290746269 | 3.089552239 | 36000 | 25997 | 1.252765957 | 3.844984802 |
| 35917 | 25914 | 1.370612245 | 2.548104956 | 35945 | 25942 | 1.349333333 | 1.533333333 | 35973 | 25970 | 1.288 | 4.6 | 36001 | 25998 | 1.25025641 | 3.412087912 |
| 35918 | 25915 | 1.370212766 | 1.118541033 | 35946 | 25943 | 1.347605634 | 1.203219316 | 35974 | 25971 | 1.288 | 1.519642857 | 36002 | 25999 | 1.248571429 | 5.163265306 |
| 35919 | 25916 | 1.370212766 | 7.200607903 | 35947 | 25944 | 1.346341463 | 2.724738676 | 35975 | 25972 | 1.288 | 1.916666667 | 36003 | 26000 | 1.248571429 | 2.757653061 |
| 35920 | 25917 | 1.370212766 | 1.607902736 | 35948 | 25945 | 1.346341463 | 2.885017422 | 35976 | 25973 | 1.286504065 | 1.709639954 | 36004 | 26001 | 1.247457627 | 2.394673123 |
| 35921 | 25918 | 1.36962406 | 2.791621912 | 35949 | 25946 | 1.3432 | 1.544285714 | 35977 | 25974 | 1.284528302 | 1.425876011 | 36005 | 26002 | 1.246451613 | 2.119815668 |
| 35922 | 25919 | 1.369302326 | 1.260797342 | 35950 | 25947 | 1.342702703 | 4.706563707 | 35978 | 25975 | 1.28372093 | 2.139534884 | 36006 | 26003 | 1.245538462 | 2.527472527 |
| 35923 | 25920 | 1.369302326 | 2.139534884 | 35951 | 25948 | 1.33952 | 1.156571429 | 35979 | 25976 | 1.282424242 | 3.683982684 | 36007 | 26004 | 1.244705882 | 2.705882353 |
| 35924 | 25921 | 1.368205128 | 2.232600733 | 35952 | 25949 | 1.338181818 | 1.941558442 | 35980 | 25977 | 1.278644068 | 1.280871671 | 36008 | 26005 | 1.243943662 | 1.249496982 |
| 35925 | 25922 | 1.366857143 | 9.857142857 | 35953 | 25950 | 1.338181818 | 2.19047619 | 35981 | 25978 | 1.278315789 | 2.282706767 | 36009 | 26006 | 1.240930233 | 1.528239203 |
| 35926 | 25923 | 1.365773196 | 3.488954345 | 35954 | 25951 | 1.338181818 | 4.107142857 | 35982 | 25979 | 1.277777778 | 4.426587302 | 36010 | 26007 | 1.240449438 | 1.033707865 |
| 35927 | 25924 | 1.36516129 | 1.589861751 | 35955 | 25952 | 1.332413793 | 1.019704433 | 35983 | 25980 | 1.276396396 | 1.598455598 | 36011 | 26008 | 1.238461538 | 1.200549451 |
| 35928 | 25925 | 1.36516129 | 1.837173579 | 35956 | 25953 | 1.33106383 | 2.097264438 | 35984 | 25981 | 1.273846154 | 1.642857143 | 36012 | 26009 | 1.23625 | 1.283482143 |
| 35929 | 25926 | 1.363571429 | 1.584183673 | 35957 | 25954 | 1.3248 | 3.811428571 | 35985 | 25982 | 1.273846154 | 2.401098901 | 36013 | 26010 | 1.23625 | 2.207589286 |
| 35930 | 25927 | 1.362962963 | 3.529100529 | 35958 | 25955 | 1.32 | 1.142857143 | 35986 | 25983 | 1.272666667 | 1.095238095 | 36014 | 26011 | 1.235428571 | 3.285714286 |
| 35931 | 25928 | 1.362962963 | 1.886243386 | 35959 | 25956 | 1.32 | 3.571428571 | 35987 | 25984 | 1.271272727 | 1.015584416 | 36015 | 26012 | 1.234146341 | 1.722996516 |
| 35932 | 25929 | 1.3616 | 2.825714286 | 35960 | 25957 | 1.319245283 | 3.037735849 | 35988 | 25985 | 1.270927835 | 1.083946981 | 36016 | 26013 | 1.233882353 | 1.816806723 |
| 35933 | 25930 | 1.36 | 1.857142857 | 35961 | 25958 | 1.318666667 | 3.011904762 | 35989 | 25986 | 1.27047619 | 2.738095238 | 36017 | 26014 | 1.233636364 | 3.50974026 |
| 35934 | 25931 | 1.36 | 5 | 35962 | 25959 | 1.317837838 | 1.953667954 | 35990 | 25987 | 1.27047619 | 1.642857143 | 36018 | 26015 | 1.232621359 | 2.041608877 |
| 35935 | 25932 | 1.358095238 | 2.659863946 | 35963 | 25960 | 1.307951807 | 1.148020654 | 35991 | 25988 | 1.262745098 | 1.739495798 | 36019 | 26016 | 1.226666667 | 2.38961039 |
| 35936 | 25933 | 1.358095238 | 4.459183673 | 35964 | 25961 | 1.307368421 | 1.729323308 | 35992 | 25989 | 1.262745098 | 1.030812325 | 36020 | 26017 | 1.226666667 | 1.325814536 |
| 35937 | 25934 | 1.357669903 | 1.850208044 | 35965 | 25962 | 1.304303797 | 2.620253165 | 35993 | 25990 | 1.26214876 | 1.357733176 | 36021 | 26018 | 1.226666667 | 1.684981685 |
| 35938 | 25935 | 1.355789474 | 1.12406015 | 35966 | 25963 | 1.302153846 | 1.87032967 | 35994 | 25991 | 1.258947368 | 1.959899749 | 36022 | 26019 | 1.226666667 | 1.314285714 |
| 35939 | 25936 | 1.355789474 | 1.296992481 | 35967 | 25964 | 1.301463415 | 1.763066202 | 35995 | 25992 | 1.258947368 | 1.971428571 | 36023 | 26020 | 1.226666667 | 1.23655914 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 36024 | 26021 | 1.226666667 | 1.46031746 | 36052 | 26049 | 1.180377358 | 2.23180593 | 36080 | 26077 | 1.157113402 | 1.050073638 | 36108 | 26105 | 1.113684211 | 1.815789474 |
| 36025 | 26022 | 1.226666667 | 4.015873016 | 36053 | 26050 | 1.179487179 | 3.36996337 | 36081 | 26078 | 1.155348837 | 3.285714286 | 36109 | 26106 | 1.110630631 | 1.184041184 |
| 36026 | 26023 | 1.226666667 | 4.107142857 | 36054 | 26051 | 1.179487179 | 2.527472527 | 36082 | 26079 | 1.153898305 | 7.406779661 | 36110 | 26107 | 1.10984127 | 1.616780045 |
| 36027 | 26024 | 1.217647059 | 5.025210084 | 36055 | 26052 | 1.17875 | 2.720982143 | 36083 | 26080 | 1.15 | 1.48489011 | 36111 | 26108 | 1.107572816 | 1.531206657 |
| 36028 | 26025 | 1.2144 | 4.205714286 | 36056 | 26053 | 1.178426966 | 1.476725522 | 36084 | 26081 | 1.15 | 2.258928571 | 36112 | 26109 | 1.104 | 1.567032967 |
| 36029 | 26026 | 1.2144 | 1.314285714 | 36057 | 26054 | 1.1776 | 2.497142857 | 36085 | 26082 | 1.15 | 3.051020408 | 36113 | 26110 | 1.104 | 3.285714286 |
| 36030 | 26027 | 1.213617021 | 2.272036474 | 36058 | 26055 | 1.1776 | 3.417142857 | 36086 | 26083 | 1.15 | 2.738095238 | 36114 | 26111 | 1.098507463 | 1.373134328 |
| 36031 | 26028 | 1.209863014 | 1.485322896 | 36059 | 26056 | 1.174939759 | 1.385542169 | 36087 | 26084 | 1.15 | 1.962301587 | 36115 | 26112 | 1.096923077 | 3.222527473 |
| 36032 | 26029 | 1.2075 | 1.334821429 | 36060 | 26057 | 1.174468085 | 3.565349544 | 36088 | 26085 | 1.147012987 | 1.045454545 | 36116 | 26113 | 1.095238095 | 3.950680272 |
| 36033 | 26030 | 1.2075 | 1.129464286 | 36061 | 26058 | 1.173793103 | 2.379310345 | 36089 | 26086 | 1.143030303 | 2.588744589 | 36117 | 26114 | 1.093333333 | 2.142857143 |
| 36034 | 26031 | 1.206222222 | 2.847619048 | 36062 | 26059 | 1.170909091 | 1.374025974 | 36090 | 26087 | 1.142736842 | 1.279699248 | 36118 | 26115 | 1.093333333 | 1.142857143 |
| 36035 | 26032 | 1.204363636 | 3.464935065 | 36063 | 26060 | 1.170909091 | 4.838961039 | 36091 | 26088 | 1.141686747 | 1.385542169 | 36119 | 26116 | 1.093069307 | 1.301272984 |
| 36036 | 26033 | 1.203076923 | 2.527472527 | 36064 | 26061 | 1.170909091 | 1.493506494 | 36092 | 26089 | 1.139047619 | 4.068027211 | 36120 | 26117 | 1.087883212 | 1.726798749 |
| 36037 | 26034 | 1.203076923 | 1.769230769 | 36065 | 26062 | 1.170909091 | 4.405844156 | 36093 | 26090 | 1.137894737 | 1.556390977 | 36121 | 26118 | 1.087272727 | 5.924242424 |
| 36038 | 26035 | 1.200842105 | 1.798496241 | 36066 | 26063 | 1.170909091 | 1.792207792 | 36094 | 26091 | 1.136470588 | 1.449579832 | 36122 | 26119 | 1.080634921 | 4.328798186 |
| 36039 | 26036 | 1.2 | 3.714285714 | 36067 | 26064 | 1.170909091 | 2.875 | 36095 | 26092 | 1.132307692 | 1.010989011 | 36123 | 26120 | 1.079669421 | 2.145218418 |
| 36040 | 26037 | 1.2 | 2.514285714 | 36068 | 26065 | 1.170909091 | 1.493506494 | 36096 | 26093 | 1.132307692 | 2.527472527 | 36124 | 26121 | 1.07862069 | 2.15270936 |
| 36041 | 26038 | 1.196 | 7.392857143 | 36069 | 26066 | 1.170909091 | 2.150649351 | 36097 | 26094 | 1.132307692 | 2.611721612 | 36125 | 26122 | 1.07862069 | 2.804187192 |
| 36042 | 26039 | 1.196 | 1.04047619 | 36070 | 26067 | 1.168253968 | 1.616780045 | 36098 | 26095 | 1.13060241 | 1.068846816 | 36126 | 26123 | 1.077368421 | 1.988721805 |
| 36043 | 26040 | 1.194805195 | 1.194805195 | 36071 | 26068 | 1.167692308 | 6.192307692 | 36099 | 26096 | 1.124444444 | 5.293650794 | 36127 | 26124 | 1.076226415 | 1.797843666 |
| 36044 | 26041 | 1.194385965 | 2.305764411 | 36072 | 26069 | 1.166829268 | 2.484320557 | 36100 | 26097 | 1.1224 | 3.811428571 | 36128 | 26125 | 1.073333333 | 1.212585034 |
| 36045 | 26042 | 1.194385965 | 2.536340852 | 36073 | 26070 | 1.165333333 | 1.861904762 | 36101 | 26098 | 1.12195122 | 1.322299652 | 36129 | 26126 | 1.073333333 | 1.56462585 |
| 36046 | 26043 | 1.191949686 | 1.260557053 | 36074 | 26071 | 1.162105263 | 4.669172932 | 36102 | 26099 | 1.12 | 2.357142857 | 36130 | 26127 | 1.073333333 | 2.646825397 |
| 36047 | 26044 | 1.190588235 | 1.224089636 | 36075 | 26072 | 1.162105263 | 3.458646617 | 36103 | 26100 | 1.118153846 | 2.856043956 | 36131 | 26128 | 1.071392405 | 4.533453888 |
| 36048 | 26045 | 1.188923077 | 1.263736264 | 36076 | 26073 | 1.161165049 | 2.360610264 | 36104 | 26101 | 1.117142857 | 4.693877551 | 36132 | 26129 | 1.071044776 | 1.83901919 |
| 36049 | 26046 | 1.186542056 | 1.873164219 | 36077 | 26074 | 1.160615385 | 2.78021978 | 36105 | 26102 | 1.115151515 | 1.593073593 | 36133 | 26130 | 1.069767442 | 2.648947951 |
| 36050 | 26047 | 1.185777778 | 4.088888889 | 36078 | 26075 | 1.160615385 | 1.718681319 | 36106 | 26103 | 1.115151515 | 4.430735931 | 36134 | 26131 | 1.069401709 | 1.432234432 |
| 36051 | 26048 | 1.184367816 | 1.775041051 | 36079 | 26076 | 1.16 | 4.142857143 | 36107 | 26104 | 1.113684211 | 1.988721805 | 36135 | 26132 | 1.067857143 | 1.701530612 |

FIG. 4 (Cont.)

| DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score | DNA SEQ ID NO | AA SEQ ID NO | Heart 1 Enrichment Score | Heart 2 Enrichment Score |
|---|---|---|---|---|---|---|---|---|---|---|---|---|---|---|---|
| 36136 | 26133 | 1.0672 | 1.708571429 | 36155 | 26152 | 1.042666667 | 4.819047619 | 36174 | 26171 | 1.02557377 | 1.885245902 | 36193 | 26190 | 1.013033708 | 2.731942215 |
| 36137 | 26134 | 1.066666667 | 1.142857143 | 36156 | 26153 | 1.042666667 | 2.738095238 | 36175 | 26172 | 1.025142857 | 3.520408163 | 36194 | 26191 | 1.013033708 | 1.845906902 |
| 36138 | 26135 | 1.065263158 | 3.156015038 | 36157 | 26154 | 1.041509434 | 2.169811321 | 36176 | 26173 | 1.024 | 2.4 | 36195 | 26192 | 1.010196078 | 1.224089636 |
| 36139 | 26136 | 1.063111111 | 3.212698413 | 36158 | 26155 | 1.041052632 | 1.729323308 | 36177 | 26174 | 1.022222222 | 10.31349206 | 36196 | 26193 | 1.009756098 | 2.203832753 |
| 36140 | 26137 | 1.063111111 | 1.216931217 | 36159 | 26156 | 1.04 | 1.142857143 | 36178 | 26175 | 1.022222222 | 1.861904762 | 36197 | 26194 | 1.009032258 | 3.444700461 |
| 36141 | 26138 | 1.061538462 | 2.085164835 | 36160 | 26157 | 1.037948718 | 2.948717949 | 36179 | 26176 | 1.022222222 | 5.841269841 | 36198 | 26195 | 1.007619048 | 3.911564626 |
| 36142 | 26139 | 1.059393939 | 2.090909091 | 36161 | 26158 | 1.037446809 | 2.446808511 | 36180 | 26177 | 1.022222222 | 1.616780045 | 36199 | 26196 | 1.005866667 | 1.139047619 |
| 36143 | 26140 | 1.059393939 | 2.24025974 | 36162 | 26159 | 1.037446809 | 1.013677812 | 36181 | 26178 | 1.022222222 | 1.049603175 | 36200 | 26197 | 1.005581395 | 1.681063123 |
| 36144 | 26141 | 1.055294118 | 1.594537815 | 36163 | 26160 | 1.035 | 3.422619048 | 36182 | 26179 | 1.022222222 | 2.555555556 | 36201 | 26198 | 1.005185185 | 1.642857143 |
| 36145 | 26142 | 1.055294118 | 2.174369748 | 36164 | 26161 | 1.035 | 4.928571429 | 36183 | 26180 | 1.019759036 | 1.385542169 | 36202 | 26199 | 1.004540541 | 1.687258687 |
| 36146 | 26143 | 1.054166667 | 1.779761905 | 36165 | 26162 | 1.035 | 2.854464286 | 36184 | 26181 | 1.01787234 | 2.446808511 | 36203 | 26200 | 1.003636364 | 4.281385281 |
| 36147 | 26144 | 1.051428571 | 2.464285714 | 36166 | 26163 | 1.035 | 1.505952381 | 36185 | 26182 | 1.01787234 | 1.607902736 | 36204 | 26201 | 1.003636364 | 9.25974026 |
| 36148 | 26145 | 1.051428571 | 1.783673469 | 36167 | 26164 | 1.035 | 1.711309524 | 36186 | 26183 | 1.01787234 | 3.495440729 | 36205 | 26202 | 1.003636364 | 9.25974026 |
| 36149 | 26146 | 1.051428571 | 3.227040816 | 36168 | 26165 | 1.032195122 | 2.644599303 | 36187 | 26184 | 1.01787234 | 1.817629179 | 36206 | 26203 | 1.003636364 | 2.38961039 |
| 36150 | 26147 | 1.049122807 | 1.556390977 | 36169 | 26166 | 1.0304 | 7.885714286 | 36188 | 26185 | 1.016842105 | 2.593984962 | 36207 | 26204 | 1.000701754 | 1.786967419 |
| 36151 | 26148 | 1.045894737 | 2.593984962 | 36170 | 26167 | 1.0304 | 1.445714286 | 36189 | 26186 | 1.016842105 | 3.458646617 | 36208 | 26205 | 1.000701754 | 1.412280702 |
| 36152 | 26149 | 1.044324324 | 1.554054054 | 36171 | 26168 | 1.029724771 | 1.296199214 | 36190 | 26187 | 1.016842105 | 2.334586466 | | | | |
| 36153 | 26150 | 1.044324324 | 4.884169884 | 36172 | 26169 | 1.028661417 | 2.457817773 | 36191 | 26188 | 1.015172414 | 4.022167488 | | | | |
| 36154 | 26151 | 1.042666667 | 2.738095238 | 36173 | 26170 | 1.02557377 | 1.023419204 | 36192 | 26189 | 1.015172414 | 3.0591133 | | | | |

FIG. 5

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36209 | 26206 | 227.125 | 48.80128205 | 36235 | 26232 | 40.38218391 | 10.39846743 | 36261 | 26258 | 31.83955224 | 13.04477612 | 36287 | 26284 | 27.671875 | 1.677083333 |
| 36210 | 26207 | 146.05 | 245.3333333 | 36236 | 26233 | 40.1097561 | 17.57723577 | 36262 | 26259 | 31.39189189 | 21.96396396 | 36288 | 26285 | 27.65267176 | 17.32315522 |
| 36211 | 26208 | 105.2692308 | 60.15384615 | 36237 | 26234 | 40.1097561 | 31.41463415 | 36263 | 26260 | 30.94047619 | 16.79365079 | 36289 | 26286 | 27.55208333 | 38.97222222 |
| 36212 | 26209 | 95.69642857 | 43.80952381 | 36238 | 26235 | 40.05833333 | 27.08888889 | 36264 | 26261 | 30.77941176 | 11.7254902 | 36290 | 26287 | 27.5 | 55.33333333 |
| 36213 | 26210 | 82.14285714 | 48.19047619 | 36239 | 26236 | 39.80769231 | 17.98717949 | 36265 | 26262 | 30.68684211 | 4.357894737 | 36291 | 26288 | 27.1875 | 1.833333333 |
| 36214 | 26211 | 80.40725806 | 6.924731183 | 36240 | 26237 | 39.79605263 | 34.70175439 | 36266 | 26263 | 30.64805825 | 19.35275081 | 36292 | 26289 | 27.15957447 | 28.38297872 |
| 36215 | 26212 | 80.02083333 | 1.277777778 | 36241 | 26238 | 38.64534884 | 6.775193798 | 36267 | 26264 | 30.53888889 | 48.38518519 | 36293 | 26290 | 27.09469697 | 13.93939394 |
| 36216 | 26213 | 76.02777778 | 48.55555556 | 36242 | 26239 | 37 | 4.666666667 | 36268 | 26265 | 30.46276596 | 42.73758865 | 36294 | 26291 | 27.025 | 3.833333333 |
| 36217 | 26214 | 73.05882353 | 42.39215686 | 36243 | 26240 | 36.19117647 | 51.41176471 | 36269 | 26266 | 30.35465116 | 67.03875969 | 36295 | 26292 | 26.80384615 | 1.415384615 |
| 36218 | 26215 | 63.25 | 74.47619048 | 36244 | 26241 | 36.05932203 | 42.10169492 | 36270 | 26267 | 30.01838235 | 9.019607843 | 36296 | 26293 | 26.57432432 | 3.315315315 |
| 36219 | 26216 | 61.83461538 | 2.123076923 | 36245 | 26242 | 35.0175 | 8.893333333 | 36271 | 26268 | 30.01219512 | 46.56097561 | 36297 | 26294 | 26.30625 | 34.88333333 |
| 36220 | 26217 | 58.77777778 | 50.54320988 | 36246 | 26243 | 35.01111111 | 30.32592593 | 36272 | 26269 | 29.98214286 | 30.66666667 | 36298 | 26295 | 26 | 44 |
| 36221 | 26218 | 55.13611111 | 3.918518519 | 36247 | 26244 | 34.7875 | 25.04444444 | 36273 | 26270 | 29.55925926 | 10.79012346 | 36299 | 26296 | 25.99 | 13.49333333 |
| 36222 | 26219 | 52.42954545 | 12.96363636 | 36248 | 26245 | 34.7875 | 13.99166667 | 36274 | 26271 | 29.51102941 | 10.82352941 | 36300 | 26297 | 25.93617021 | 56.76595745 |
| 36223 | 26220 | 50.14247312 | 21.2688172 | 36249 | 26246 | 34.3597561 | 22.43902439 | 36275 | 26272 | 29.49193548 | 24.97849462 | 36301 | 26298 | 25.81111111 | 11.58518519 |
| 36224 | 26221 | 49.28571429 | 6.571428571 | 36250 | 26247 | 34.3525641 | 42.06837607 | 36276 | 26273 | 29.45987654 | 12.11522634 | 36302 | 26299 | 25.71527778 | 3.691358025 |
| 36225 | 26222 | 48.58163265 | 49.75510204 | 36251 | 26248 | 34.32575758 | 13.93939394 | 36277 | 26274 | 29.44 | 36.18666667 | 36303 | 26300 | 25.53 | 61.33333333 |
| 36226 | 26223 | 48.39583333 | 65.16666667 | 36252 | 26249 | 34.18636364 | 13.66060606 | 36278 | 26275 | 29.2242268 | 18.81099656 | 36304 | 26301 | 25.50403226 | 6.677419355 |
| 36227 | 26224 | 48.36388889 | 5.111111111 | 36253 | 26250 | 33.97727273 | 32.06060606 | 36279 | 26276 | 29.18125 | 15.33333333 | 36305 | 26302 | 25.49528302 | 27.19496855 |
| 36228 | 26225 | 46.359375 | 25.39583333 | 36254 | 26251 | 33.6375 | 41.01666667 | 36280 | 26277 | 28.75 | 37.56666667 | 36306 | 26303 | 25.375 | 26.66666667 |
| 36229 | 26226 | 44.72222222 | 50.54320988 | 36255 | 26252 | 33.31034483 | 43.88505747 | 36281 | 26278 | 28.75 | 49.13636364 | 36307 | 26304 | 25.14759036 | 8.682730924 |
| 36230 | 26227 | 43.484375 | 13.03333333 | 36256 | 26253 | 32.75757576 | 14.63636364 | 36282 | 26279 | 28.45258621 | 28.81609195 | 36308 | 26305 | 25.09090909 | 56.22222222 |
| 36231 | 26228 | 42.80555556 | 28.39506173 | 36257 | 26254 | 32.29292929 | 25.24579125 | 36283 | 26280 | 28.40671642 | 29.52238806 | 36309 | 26306 | 25.06132075 | 21.11949686 |
| 36232 | 26229 | 42.5 | 17.33333333 | 36258 | 26255 | 32.24509804 | 12.32679739 | 36284 | 26281 | 28.23888889 | 42.25185185 | 36310 | 26307 | 25.04032258 | 29.67741935 |
| 36233 | 26230 | 41.75 | 27 | 36259 | 26256 | 32.2 | 15.33333333 | 36285 | 26282 | 27.92857143 | 54.76190476 | 36311 | 26308 | 24.91666667 | 16.72727273 |
| 36234 | 26231 | 40.99193548 | 25.72043011 | 36260 | 26257 | 32.11153846 | 11.79487179 | 36286 | 26283 | 27.79166667 | 41.61904762 | 36312 | 26309 | 24.62916667 | 20.95555556 |

FIG. 5 (Cont.)

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36313 | 26310 | 24.57368421 | 37.44561404 | 36341 | 26338 | 21.17460317 | 21.66137566 | 36369 | 26366 | 19.50490196 | 16.53594771 | 36397 | 26394 | 17.81557377 | 31.92349727 |
| 36314 | 26311 | 24.5 | 52 | 36342 | 26339 | 21.14830508 | 34.56497175 | 36370 | 26367 | 19.43103448 | 37.01149425 | 36398 | 26395 | 17.70544554 | 8.349834983 |
| 36315 | 26312 | 24.08235294 | 7.396078431 | 36343 | 26340 | 21.00961538 | 51.8974359 | 36371 | 26368 | 19.43103448 | 16.12643678 | 36399 | 26396 | 17.70098039 | 61.03267974 |
| 36316 | 26313 | 23.94902913 | 10.12297735 | 36344 | 26341 | 20.90909091 | 39.03030303 | 36372 | 26369 | 19.30357143 | 7.392857143 | 36400 | 26397 | 17.67592593 | 9.086419753 |
| 36317 | 26314 | 23.88461538 | 69 | 36345 | 26342 | 20.83529412 | 14.07058824 | 36373 | 26370 | 19.2625 | 1.533333333 | 36401 | 26398 | 17.51538462 | 10.61538462 |
| 36318 | 26315 | 23.82142857 | 11.60952381 | 36346 | 26343 | 20.81896552 | 14.01149425 | 36374 | 26371 | 19.16666667 | 56.22222222 | 36402 | 26399 | 17.46296296 | 7.950617284 |
| 36319 | 26316 | 23.61607143 | 25.19047619 | 36347 | 26344 | 20.77840909 | 14.11363636 | 36375 | 26372 | 19.00882353 | 3.968627451 | 36403 | 26400 | 17.44827586 | 16.91954023 |
| 36320 | 26317 | 23.54761905 | 24.82539683 | 36348 | 26345 | 20.66891892 | 9.738738739 | 36376 | 26373 | 18.95703125 | 9.34375 | 36404 | 26401 | 17.40972222 | 13.2037037 |
| 36321 | 26318 | 23.28395062 | 9.843621399 | 36349 | 26346 | 20.65740741 | 11.92592593 | 36377 | 26374 | 18.85245902 | 56.05464481 | 36405 | 26402 | 17.37777778 | 17.71851852 |
| 36322 | 26319 | 23.22115385 | 36.56410256 | 36350 | 26347 | 20.64457831 | 10.89959839 | 36378 | 26375 | 18.82311321 | 13.01886792 | 36406 | 26403 | 17.36386139 | 8.198019802 |
| 36323 | 26320 | 23.0982906 | 18.08547009 | 36351 | 26348 | 20.60416667 | 27.08888889 | 36379 | 26376 | 18.80532787 | 9.928961749 | 36407 | 26404 | 17.35087719 | 20.1754386 |
| 36324 | 26321 | 22.91153846 | 79.96923077 | 36352 | 26349 | 20.42241379 | 1.057471264 | 36380 | 26377 | 18.66313559 | 8.966101695 | 36408 | 26405 | 17.32467532 | 29.07359307 |
| 36325 | 26322 | 22.84666667 | 21.05777778 | 36353 | 26350 | 20.38636364 | 16.12987013 | 36381 | 26378 | 18.48214286 | 13.14285714 | 36409 | 26406 | 17.25 | 44.42735043 |
| 36326 | 26323 | 22.81451613 | 21.76344086 | 36354 | 26351 | 20.31666667 | 16.86666667 | 36382 | 26379 | 18.46052632 | 6.456140351 | 36410 | 26407 | 17.25 | 44.24761905 |
| 36327 | 26324 | 22.75 | 42.66666667 | 36355 | 26352 | 20.22191011 | 3.445692884 | 36383 | 26380 | 18.44207317 | 13.08943089 | 36411 | 26408 | 17.25 | 72.04819277 |
| 36328 | 26325 | 22.70258621 | 27.75862069 | 36356 | 26353 | 20.17924528 | 16.20125786 | 36384 | 26381 | 18.41949153 | 29.62711864 | 36412 | 26409 | 17.09868421 | 16.54385965 |
| 36329 | 26326 | 22.39473684 | 21.78947368 | 36357 | 26354 | 20.125 | 14.56666667 | 36385 | 26382 | 18.38915094 | 11.28301887 | 36413 | 26410 | 17 | 10.66666667 |
| 36330 | 26327 | 22.38392857 | 25.73809524 | 36358 | 26355 | 20.125 | 12.62745098 | 36386 | 26383 | 18.328125 | 21.5625 | 36414 | 26411 | 16.98863636 | 16.72727273 |
| 36331 | 26328 | 22.31343284 | 27.23383085 | 36359 | 26356 | 20.00684932 | 7.141552511 | 36387 | 26384 | 18.14444444 | 18.74074074 | 36415 | 26412 | 16.83928571 | 69.73015873 |
| 36332 | 26329 | 21.95454545 | 12.08080808 | 36360 | 26357 | 20.00265957 | 10.92907801 | 36388 | 26385 | 18.13461538 | 26.18461538 | 36416 | 26413 | 16.82926829 | 6.544715447 |
| 36333 | 26330 | 21.80519481 | 31.66233766 | 36361 | 26358 | 20.00265957 | 10.27659574 | 36389 | 26386 | 18.08467742 | 12.86021505 | 36417 | 26414 | 16.74561404 | 14.25730994 |
| 36334 | 26331 | 21.63978495 | 19.12544803 | 36362 | 26359 | 20 | 13.04761905 | 36390 | 26387 | 18.04521277 | 6.524822695 | 36418 | 26415 | 16.69097222 | 52.17592593 |
| 36335 | 26332 | 21.48684211 | 38.46783626 | 36363 | 26360 | 19.84677419 | 36.60215054 | 36391 | 26388 | 17.99675325 | 10.95238095 | 36419 | 26416 | 16.675 | 18.4 |
| 36336 | 26333 | 21.44411765 | 18.76078431 | 36364 | 26361 | 19.7345679 | 3.028806584 | 36392 | 26389 | 17.95769231 | 16.51282051 | 36420 | 26417 | 16.53865979 | 8.219931271 |
| 36337 | 26334 | 21.42688679 | 8.679245283 | 36365 | 26362 | 19.68644068 | 17.93220339 | 36393 | 26390 | 17.94172932 | 7.263157895 | 36421 | 26418 | 16.375 | 17 |
| 36338 | 26335 | 21.37264151 | 27.48427673 | 36366 | 26363 | 19.66129032 | 94.96774194 | 36394 | 26391 | 17.85526316 | 24.21052632 | 36422 | 26419 | 16.33522727 | 44.95454545 |
| 36339 | 26336 | 21.35714286 | 16.06349206 | 36367 | 26364 | 19.6130137 | 1.050228311 | 36395 | 26392 | 17.83474576 | 9.875706215 | 36423 | 26420 | 16.1971831 | 21.81220657 |
| 36340 | 26337 | 21.346875 | 17.05833333 | 36368 | 26365 | 19.5859375 | 16.53125 | 36396 | 26393 | 17.825 | 33.73333333 | 36424 | 26421 | 16.16509434 | 6.075471698 |

FIG. 5 (Cont.)

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36425 | 26422 | 16.06349206 | 15.57671958 | 36453 | 26450 | 14.95 | 9.966666667 | 36481 | 26478 | 13.63953488 | 15.68992248 | 36509 | 26506 | 12.81140351 | 15.60233918 |
| 36426 | 26423 | 16.04651163 | 46 | 36454 | 26451 | 14.91891892 | 27.76576577 | 36482 | 26479 | 13.60365854 | 18.69918699 | 36510 | 26507 | 12.74698795 | 15.33333333 |
| 36427 | 26424 | 16.01785714 | 1.533333333 | 36455 | 26452 | 14.88235294 | 7.215686275 | 36483 | 26480 | 13.56640625 | 20.125 | 36511 | 26508 | 12.68382353 | 22.32352941 |
| 36428 | 26425 | 15.97222222 | 51.11111111 | 36456 | 26453 | 14.84438776 | 25.03401361 | 36484 | 26481 | 13.56132075 | 13.59748428 | 36512 | 26509 | 12.67346939 | 38.48979592 |
| 36429 | 26426 | 15.96651786 | 11.08928571 | 36457 | 26454 | 14.82042254 | 18.57276995 | 36485 | 26482 | 13.55357143 | 18.25396825 | 36513 | 26510 | 12.65 | 8.554385965 |
| 36430 | 26427 | 15.96470588 | 25.25490196 | 36458 | 26455 | 14.75328947 | 9.684210526 | 36486 | 26483 | 13.54444444 | 20.44444444 | 36514 | 26511 | 12.62195122 | 3.085365854 |
| 36431 | 26428 | 15.93987342 | 13.39240506 | 36459 | 26456 | 14.68085106 | 17.29078014 | 36487 | 26484 | 13.37209302 | 18.18604651 | 36515 | 26512 | 12.59772727 | 7.806060606 |
| 36432 | 26429 | 15.91666667 | 17.55555556 | 36460 | 26457 | 14.67763158 | 20.98245614 | 36488 | 26485 | 13.35057471 | 13.04214559 | 36516 | 26513 | 12.434375 | 16.86666667 |
| 36433 | 26430 | 15.88815789 | 6.657894737 | 36461 | 26458 | 14.6625 | 10.73333333 | 36489 | 26486 | 13.34 | 9.813333333 | 36517 | 26514 | 12.42216981 | 4.48427673 |
| 36434 | 26431 | 15.86206897 | 6.344827586 | 36462 | 26459 | 14.625 | 17.33333333 | 36490 | 26487 | 13.25195313 | 5.03125 | 36518 | 26515 | 12.41755319 | 12.39716312 |
| 36435 | 26432 | 15.84756098 | 19.07317073 | 36463 | 26460 | 14.54411765 | 10.37254902 | 36491 | 26488 | 13.1875 | 2.333333333 | 36519 | 26516 | 12.38988095 | 6.571428571 |
| 36436 | 26433 | 15.72151899 | 13.97468354 | 36464 | 26461 | 14.51875 | 14.56666667 | 36492 | 26489 | 13.12735849 | 5.20754717 | 36520 | 26517 | 12.35185185 | 23.70987654 |
| 36437 | 26434 | 15.71666667 | 17.63333333 | 36465 | 26462 | 14.5104712 | 16.61780105 | 36493 | 26490 | 13.07843137 | 15.63398693 | 36521 | 26518 | 12.33467742 | 18.5483871 |
| 36438 | 26435 | 15.69594595 | 20.72072072 | 36466 | 26463 | 14.49479167 | 9.263888889 | 36494 | 26491 | 13.06818182 | 64.12121212 | 36522 | 26519 | 12.32142857 | 8.761904762 |
| 36439 | 26436 | 15.66666667 | 13.77777778 | 36467 | 26464 | 14.48148148 | 1.135802469 | 36495 | 26492 | 13.05532787 | 2.010928962 | 36523 | 26520 | 12.32142857 | 31.64021164 |
| 36440 | 26437 | 15.56707317 | 81.90243902 | 36468 | 26465 | 14.47992701 | 4.812652068 | 36496 | 26493 | 13.04807692 | 16.21794872 | 36524 | 26521 | 12.30701754 | 34.70175439 |
| 36441 | 26438 | 15.53723404 | 12.07092199 | 36469 | 26466 | 14.42727273 | 52.96969697 | 36497 | 26494 | 13.04569892 | 6.594982079 | 36525 | 26522 | 12.27403846 | 5.307692308 |
| 36442 | 26439 | 15.44879518 | 10.16064257 | 36470 | 26467 | 14.41233766 | 3.683982684 | 36498 | 26495 | 13.02797203 | 10.07925408 | 36526 | 26523 | 12.23015873 | 15.57671958 |
| 36443 | 26440 | 15.42548077 | 15.62820513 | 36471 | 26468 | 14.375 | 14.79844961 | 36499 | 26496 | 13.01315789 | 25.42105263 | 36527 | 26524 | 12.17647059 | 15.03267974 |
| 36444 | 26441 | 15.375 | 38.33333333 | 36472 | 26469 | 14.21226415 | 49.47169811 | 36500 | 26497 | 13.01315789 | 11.78245614 | 36528 | 26525 | 12.16346154 | 16.21794872 |
| 36445 | 26442 | 15.33333333 | 21.2962963 | 36473 | 26470 | 14.17897727 | 14.28787879 | 36501 | 26498 | 12.98387097 | 16.56989247 | 36529 | 26526 | 12.13888889 | 26.57777778 |
| 36446 | 26443 | 15.33333333 | 2.271604938 | 36474 | 26471 | 14.125 | 29.5 | 36502 | 26499 | 12.95895522 | 11.67164179 | 36530 | 26527 | 12.075 | 9.813333333 |
| 36447 | 26444 | 15.30844156 | 15.93073593 | 36475 | 26472 | 14.07758621 | 9.781609195 | 36503 | 26500 | 12.95666667 | 10.42666667 | 36531 | 26528 | 11.99568966 | 1.586206897 |
| 36448 | 26445 | 15.27857143 | 5.403174603 | 36476 | 26473 | 13.9939759 | 2.586345382 | 36504 | 26501 | 12.91975309 | 9.275720165 | 36532 | 26529 | 11.97131148 | 4.273224044 |
| 36449 | 26446 | 15.26234568 | 32.18106996 | 36477 | 26474 | 13.96428571 | 36.14285714 | 36505 | 26502 | 12.90406977 | 8.914728682 | 36533 | 26530 | 11.88701923 | 6.929487179 |
| 36450 | 26447 | 15.25961538 | 9.730769231 | 36478 | 26475 | 13.77604167 | 23.47916667 | 36506 | 26503 | 12.88 | 12.26666667 | 36534 | 26531 | 11.75 | 9 |
| 36451 | 26448 | 15.22972973 | 30.25225225 | 36479 | 26476 | 13.76329787 | 15.65957447 | 36507 | 26504 | 12.85294118 | 53.66666667 | 36535 | 26532 | 11.7254902 | 16.53594771 |
| 36452 | 26449 | 15.09375 | 24.53333333 | 36480 | 26477 | 13.68103448 | 17.09578544 | 36508 | 26505 | 12.82300885 | 27.81710914 | 36536 | 26533 | 11.69827586 | 7.270114943 |

FIG. 5 (Cont.)

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36537 | 26534 | 11.68157895 | 19.69122807 | 36565 | 26562 | 10.86111111 | 1.277777778 | 36593 | 26590 | 9.814655172 | 14.54022989 | 36621 | 26618 | 9.324324324 | 23.20720721 |
| 36538 | 26535 | 11.6796875 | 8.305555556 | 36566 | 26563 | 10.83653846 | 2.358974359 | 36594 | 26591 | 9.807459677 | 10.75806452 | 36622 | 26619 | 9.31712963 | 4.117283951 |
| 36539 | 26536 | 11.6402439 | 10.47154472 | 36567 | 26564 | 10.74131944 | 9.583333333 | 36595 | 26592 | 9.787234043 | 63.29078014 | 36623 | 26620 | 9.285185185 | 11.24444444 |
| 36540 | 26537 | 11.6 | 32.8 | 36568 | 26565 | 10.71590909 | 5.343434343 | 36596 | 26593 | 9.775 | 20.08666667 | 36624 | 26621 | 9.228395062 | 11.92592593 |
| 36541 | 26538 | 11.56686047 | 18.00775194 | 36569 | 26566 | 10.71078431 | 15.63398693 | 36597 | 26594 | 9.775 | 23.21904762 | 36625 | 26622 | 9.2 | 21.16 |
| 36542 | 26539 | 11.56534091 | 9.931818182 | 36570 | 26567 | 10.67857143 | 29.43452381 | 36598 | 26595 | 9.75 | 8.666666667 | 36626 | 26623 | 9.076785714 | 9.857142857 |
| 36543 | 26540 | 11.55582524 | 4.614886731 | 36571 | 26568 | 10.565625 | 10.54166667 | 36599 | 26596 | 9.741176471 | 10.82352941 | 36627 | 26624 | 9.067307692 | 23.29487179 |
| 36544 | 26541 | 11.5 | 27.83589744 | 36572 | 26569 | 10.56009615 | 1.695512821 | 36600 | 26597 | 9.725308642 | 6.057613169 | 36628 | 26625 | 9.04233871 | 7.419354839 |
| 36545 | 26542 | 11.5 | 23.13939394 | 36573 | 26570 | 10.54166667 | 29.60185185 | 36601 | 26598 | 9.715517241 | 12.68965517 | 36629 | 26626 | 9.031413613 | 12.36300175 |
| 36546 | 26543 | 11.5 | 10.62706271 | 36574 | 26571 | 10.5225 | 6.9 | 36602 | 26599 | 9.703125 | 11.30833333 | 36630 | 26627 | 9 | 12.44444444 |
| 36547 | 26544 | 11.44132653 | 25.34693878 | 36575 | 26572 | 10.46311475 | 23 | 36603 | 26600 | 9.699494949 | 17.96632997 | 36631 | 26628 | 8.997685185 | 7.240740741 |
| 36548 | 26545 | 11.43611111 | 7.496296296 | 36576 | 26573 | 10.41509434 | 7.522012579 | 36604 | 26601 | 9.679166667 | 2.044444444 | 36632 | 26629 | 8.992021277 | 3.09929078 |
| 36549 | 26546 | 11.41015625 | 5.989583333 | 36577 | 26574 | 10.39893617 | 38.82269504 | 36605 | 26602 | 9.655660377 | 21.40880503 | 36633 | 26630 | 8.975609756 | 32.53658537 |
| 36550 | 26547 | 11.40254237 | 6.237288136 | 36578 | 26575 | 10.35 | 26.57777778 | 36606 | 26603 | 9.651785714 | 6.43452381 | 36634 | 26631 | 8.927631579 | 22.4619883 |
| 36551 | 26548 | 11.375 | 1.5 | 36579 | 26576 | 10.33445946 | 8.702702703 | 36607 | 26604 | 9.614754098 | 15.58469945 | 36635 | 26632 | 8.909340659 | 7.245421245 |
| 36552 | 26549 | 11.32920792 | 2.732673267 | 36580 | 26577 | 10.22222222 | 8.518518519 | 36608 | 26605 | 9.611940299 | 4.119402985 | 36636 | 26633 | 8.879746835 | 6.308016878 |
| 36553 | 26550 | 11.30172414 | 27.49425287 | 36581 | 26578 | 10.22222222 | 17.52380952 | 36609 | 26606 | 9.61013986 | 19.08624709 | 36637 | 26634 | 8.851973684 | 34.5 |
| 36554 | 26551 | 11.2125 | 3.066666667 | 36582 | 26579 | 10.20343137 | 8.117647059 | 36610 | 26607 | 9.583333333 | 25.8245614 | 36638 | 26635 | 8.825581395 | 11.23255814 |
| 36555 | 26552 | 11.20762712 | 31.44632768 | 36583 | 26580 | 10.18859649 | 23.67251462 | 36611 | 26608 | 9.5234375 | 12.33854167 | 36639 | 26636 | 8.819548872 | 11.06766917 |
| 36556 | 26553 | 11.18055556 | 28.96296296 | 36584 | 26581 | 10.17307692 | 12.08974359 | 36612 | 26609 | 9.4875 | 13.03333333 | 36640 | 26637 | 8.811688312 | 29.87012987 |
| 36557 | 26554 | 11.155 | 39.86666667 | 36585 | 26582 | 10.12323944 | 15.11737089 | 36613 | 26610 | 9.459677419 | 9.562724014 | 36641 | 26638 | 8.8046875 | 19.40625 |
| 36558 | 26555 | 11.12295082 | 28.15300546 | 36586 | 26583 | 10.09593023 | 28.52713178 | 36614 | 26611 | 9.43359375 | 29.46875 | 36642 | 26639 | 8.725877193 | 48.69005848 |
| 36559 | 26556 | 11.12226277 | 28.54014599 | 36587 | 26584 | 10.08333333 | 24.22222222 | 36615 | 26612 | 9.421686747 | 23.8313253 | 36643 | 26640 | 8.71484375 | 17.48958333 |
| 36560 | 26557 | 11.05769231 | 28.6025641 | 36588 | 26585 | 10.02022059 | 7.328431373 | 36616 | 26613 | 9.384 | 12.144 | 36644 | 26641 | 8.688888889 | 24.7037037 |
| 36561 | 26558 | 11.03629032 | 15.08602151 | 36589 | 26586 | 9.974489796 | 20.65306122 | 36617 | 26614 | 9.381578947 | 11.06766917 | 36645 | 26642 | 8.662828947 | 4.842105263 |
| 36562 | 26559 | 11.02083333 | 18.84722222 | 36590 | 26587 | 9.966666667 | 18.4 | 36618 | 26615 | 9.364285714 | 35.7047619 | 36646 | 26643 | 8.579365079 | 24.58201058 |
| 36563 | 26560 | 10.93442623 | 8.295081967 | 36591 | 26588 | 9.926886792 | 13.3081761 | 36619 | 26616 | 9.34375 | 2.601190476 | 36647 | 26644 | 8.579365079 | 22.87830688 |
| 36564 | 26561 | 10.93309859 | 28.07511737 | 36592 | 26589 | 9.91875 | 27.98333333 | 36620 | 26617 | 9.330188679 | 7.522012579 | 36648 | 26645 | 8.577083333 | 35.39444444 |

FIG. 5 (Cont.)

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36649 | 26646 | 8.573660714 | 19.98809524 | 36677 | 26674 | 7.7625 | 11.11666667 | 36705 | 26702 | 7.102941176 | 2.88627451 | 36733 | 26730 | 6.388888889 | 19.42222222 |
| 36650 | 26647 | 8.554878049 | 28.98373984 | 36678 | 26675 | 7.747368421 | 16.6245614 | 36706 | 26703 | 7.085858586 | 9.912457912 | 36734 | 26731 | 6.376237624 | 17.15511551 |
| 36651 | 26648 | 8.551282051 | 22.41025641 | 36679 | 26676 | 7.7265625 | 42.00694444 | 36707 | 26704 | 7.036713287 | 4.289044289 | 36735 | 26732 | 6.370098039 | 11.87581699 |
| 36652 | 26649 | 8.51 | 4.293333333 | 36680 | 26677 | 7.705 | 33.42666667 | 36708 | 26705 | 7.0078125 | 13.89583333 | 36736 | 26733 | 6.335648148 | 1.845679012 |
| 36653 | 26650 | 8.5 | 6.666666667 | 36681 | 26678 | 7.695488722 | 12.10526316 | 36709 | 26706 | 6.994845361 | 9.484536082 | 36737 | 26734 | 6.297619048 | 8.46984127 |
| 36654 | 26651 | 8.473684211 | 23.67251462 | 36682 | 26679 | 7.666666667 | 19.0994152 | 36710 | 26707 | 6.967647059 | 43.65490196 | 36738 | 26735 | 6.23364486 | 15.61993769 |
| 36655 | 26652 | 8.4453125 | 10.30208333 | 36683 | 26680 | 7.62755102 | 1.56462585 | 36711 | 26708 | 6.966346154 | 23.88461538 | 36739 | 26736 | 6.229166667 | 12.01111111 |
| 36656 | 26653 | 8.419642857 | 6.571428571 | 36684 | 26681 | 7.603618421 | 10.79385965 | 36712 | 26709 | 6.945544554 | 3.03630363 | 36740 | 26737 | 6.21 | 3.986666667 |
| 36657 | 26654 | 8.389344262 | 11.56284153 | 36685 | 26682 | 7.588435374 | 1.77324263 | 36713 | 26710 | 6.933823529 | 30.89215686 | 36741 | 26738 | 6.207386364 | 9.583333333 |
| 36658 | 26655 | 8.363636364 | 1.393939394 | 36686 | 26683 | 7.542207792 | 1.593073593 | 36714 | 26711 | 6.919491525 | 37.16384181 | 36742 | 26739 | 6.1875 | 35 |
| 36659 | 26656 | 8.327586207 | 7.402298851 | 36687 | 26684 | 7.542207792 | 12.34632035 | 36715 | 26712 | 6.916666667 | 14 | 36743 | 26740 | 6.123376623 | 20.11255411 |
| 36660 | 26657 | 8.305555556 | 10.22222222 | 36688 | 26685 | 7.519230769 | 4.717948718 | 36716 | 26713 | 6.866504854 | 6.401294498 | 36744 | 26741 | 6.119266055 | 25.18042813 |
| 36661 | 26658 | 8.25 | 21.11111111 | 36689 | 26686 | 7.475 | 28.11111111 | 36717 | 26714 | 6.864795918 | 29.57142857 | 36745 | 26742 | 6.109375 | 22.52083333 |
| 36662 | 26659 | 8.246710526 | 9.48245614 | 36690 | 26687 | 7.461309524 | 6.023809524 | 36718 | 26715 | 6.860795455 | 41.29545455 | 36746 | 26743 | 6.095 | 17.63333333 |
| 36663 | 26660 | 8.203333333 | 25.96444444 | 36691 | 26688 | 7.446721311 | 18.85245902 | 36719 | 26716 | 6.858433735 | 6.65060241 | 36747 | 26744 | 6.052631579 | 11.45964912 |
| 36664 | 26661 | 8.154545455 | 18.95757576 | 36692 | 26689 | 7.421182266 | 24.62397373 | 36720 | 26717 | 6.795454545 | 5.111111111 | 36748 | 26745 | 6.05 | 7.066666667 |
| 36665 | 26662 | 8.13961039 | 54.76190476 | 36693 | 26690 | 7.373529412 | 14.61176471 | 36721 | 26718 | 6.795454545 | 13.59090909 | 36749 | 26746 | 6.044871795 | 18.47863248 |
| 36666 | 26663 | 8.123015873 | 35.77777778 | 36694 | 26691 | 7.350515464 | 6.323024055 | 36722 | 26719 | 6.789156627 | 11.45381526 | 36750 | 26747 | 5.932539683 | 20.44444444 |
| 36667 | 26664 | 8.008928571 | 13.69047619 | 36695 | 26692 | 7.318181818 | 12.74458874 | 36723 | 26720 | 6.779850746 | 30.20895522 | 36751 | 26748 | 5.829861111 | 27.47222222 |
| 36668 | 26665 | 7.995238095 | 5.403174603 | 36696 | 26693 | 7.266483516 | 10.44688645 | 36724 | 26721 | 6.708333333 | 15.33333333 | 36752 | 26749 | 5.828767123 | 3.465753425 |
| 36669 | 26666 | 7.94047619 | 10.46560847 | 36697 | 26694 | 7.215686275 | 52.61437908 | 36725 | 26722 | 6.664772727 | 3.310606061 | 36753 | 26750 | 5.809895833 | 7.826388889 |
| 36670 | 26667 | 7.937116564 | 10.44171779 | 36698 | 26695 | 7.211864407 | 13.7740113 | 36726 | 26723 | 6.653571429 | 23.21904762 | 36754 | 26751 | 5.75 | 12.96031746 |
| 36671 | 26668 | 7.873076923 | 19.57948718 | 36699 | 26696 | 7.202020202 | 1.239057239 | 36727 | 26724 | 6.639175258 | 11.5395189 | 36755 | 26752 | 5.686813187 | 8.424908425 |
| 36672 | 26669 | 7.858333333 | 1.788888889 | 36700 | 26697 | 7.1875 | 18.14444444 | 36728 | 26725 | 6.603515625 | 5.270833333 | 36756 | 26753 | 5.673333333 | 21.67111111 |
| 36673 | 26670 | 7.840909091 | 13.01010101 | 36701 | 26698 | 7.168831169 | 8.761904762 | 36729 | 26726 | 6.563131313 | 8.518518519 | 36757 | 26754 | 5.588028169 | 21.16431925 |
| 36674 | 26671 | 7.834375 | 4.791666667 | 36702 | 26699 | 7.136160714 | 12.86904762 | 36730 | 26727 | 6.534090909 | 30.2020202 | 36758 | 26755 | 5.583333333 | 4.222222222 |
| 36675 | 26672 | 7.829787234 | 7.014184397 | 36703 | 26700 | 7.111842105 | 23.60526316 | 36731 | 26728 | 6.518895349 | 1.782945736 | 36759 | 26756 | 5.5625 | 15.83333333 |
| 36676 | 26673 | 7.803571429 | 12.86904762 | 36704 | 26701 | 7.107638889 | 10.64814815 | 36732 | 26729 | 6.415289256 | 4.435261708 | 36760 | 26757 | 5.553418803 | 7.601139601 |

FIG. 5 (Cont.)

| DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment | DNA SEQ ID NO | AA SEQ ID NO | Intestine 1 Enrichment | Intestine 2 Enrichment |
|---|---|---|---|---|---|---|---|---|---|---|---|---|---|---|---|
| 36761 | 26758 | 5.543413174 | 2.387225549 | 36789 | 26786 | 4.778169014 | 14.03755869 | 36817 | 26814 | 4.177350427 | 5.373219373 | 36845 | 26842 | 3.242021277 | 1.631205674 |
| 36762 | 26759 | 5.485632184 | 7.049808429 | 36790 | 26787 | 4.768292683 | 9.723577236 | 36818 | 26815 | 4.12007874 | 11.71128609 | 36846 | 26843 | 3.114583333 | 3.274305556 |
| 36763 | 26760 | 5.48255814 | 24.42635659 | 36791 | 26788 | 4.701257862 | 17.7442348 | 36819 | 26816 | 4.107142857 | 16.56547619 | 36847 | 26844 | 2.970833333 | 30.15555556 |
| 36764 | 26761 | 5.447368421 | 25.01754386 | 36792 | 26789 | 4.657024793 | 13.93939394 | 36820 | 26817 | 4.074503311 | 15.13024283 | 36848 | 26845 | 2.946517413 | 5.873963516 |
| 36765 | 26762 | 5.436363636 | 11.29090909 | 36793 | 26790 | 4.64893617 | 11.09219858 | 36821 | 26818 | 4.03358209 | 15.33333333 | 36849 | 26846 | 2.78343949 | 14.94267516 |
| 36766 | 26763 | 5.41954023 | 21.50191571 | 36794 | 26791 | 4.638655462 | 15.33333333 | 36822 | 26819 | 4.02919708 | 10.52068127 | 36850 | 26847 | 2.762987013 | 11.54978355 |
| 36767 | 26764 | 5.39380531 | 15.19764012 | 36795 | 26792 | 4.6 | 2.146666667 | 36823 | 26820 | 4.007575758 | 13.47474747 | 36851 | 26848 | 2.728813559 | 3.118644068 |
| 36768 | 26765 | 5.360169492 | 15.33333333 | 36796 | 26793 | 4.6 | 20.15238095 | 36824 | 26821 | 3.86882716 | 13.81893004 | 36852 | 26849 | 2.662751678 | 12.14317673 |
| 36769 | 26766 | 5.340504451 | 2.09297725 | 36797 | 26794 | 4.566176471 | 4.058823529 | 36825 | 26822 | 3.859589041 | 9.662100457 | 36853 | 26850 | 2.613636364 | 14.4969697 |
| 36770 | 26767 | 5.339285714 | 10.95238095 | 36798 | 26795 | 4.560344828 | 3.172413793 | 36826 | 26823 | 3.822972973 | 11.43783784 | 36854 | 26851 | 2.603773585 | 17.06918239 |
| 36771 | 26768 | 5.31512605 | 3.736694678 | 36799 | 26796 | 4.550359712 | 6.067146283 | 36827 | 26824 | 3.820205479 | 11.13242009 | 36855 | 26852 | 2.5875 | 5.466666667 |
| 36772 | 26769 | 5.313291139 | 21.73839662 | 36800 | 26797 | 4.533653846 | 1.474358974 | 36828 | 26825 | 3.73540146 | 4.476885645 | 36856 | 26853 | 2.570588235 | 11.99607843 |
| 36773 | 26770 | 5.307692308 | 5.111111111 | 36801 | 26798 | 4.526595745 | 11.9893617 | 36829 | 26826 | 3.72972973 | 3.522522523 | 36857 | 26854 | 2.520547945 | 2.310502283 |
| 36774 | 26771 | 5.302777778 | 10.73333333 | 36802 | 26799 | 4.512658228 | 5.434599156 | 36830 | 26827 | 3.706325301 | 8.036144578 | 36858 | 26855 | 2.430059524 | 3.924603175 |
| 36775 | 26772 | 5.29 | 23.92 | 36803 | 26800 | 4.486742424 | 18.58585859 | 36831 | 26828 | 3.62037037 | 21.86419753 | 36859 | 26856 | 2.421052632 | 1.614035088 |
| 36776 | 26773 | 5.278688525 | 41.72677596 | 36804 | 26801 | 4.477099237 | 8.661577608 | 36832 | 26829 | 3.581140351 | 14.52631579 | 36860 | 26857 | 2.395833333 | 1.916666667 |
| 36777 | 26774 | 5.239919355 | 1.360215054 | 36805 | 26802 | 4.405844156 | 8.463203463 | 36833 | 26830 | 3.574324324 | 16.16216216 | 36861 | 26858 | 2.392 | 7.728 |
| 36778 | 26775 | 5.163265306 | 26.59863946 | 36806 | 26803 | 4.38559322 | 7.536723164 | 36834 | 26831 | 3.538461538 | 28.30769231 | 36862 | 26859 | 2.388461538 | 21.23076923 |
| 36779 | 26776 | 5.116525424 | 12.47457627 | 36807 | 26804 | 4.371900826 | 12.67217631 | 36835 | 26832 | 3.529100529 | 16.14462081 | 36863 | 26860 | 2.140277778 | 6.388888889 |
| 36780 | 26777 | 5.111111111 | 26.77248677 | 36808 | 26805 | 4.3125 | 6.426470588 | 36836 | 26833 | 3.528409091 | 45.12878788 | 36864 | 26861 | 2.12962963 | 10.22222222 |
| 36781 | 26778 | 5.106 | 8.096 | 36809 | 26806 | 4.300420168 | 6.056022409 | 36837 | 26834 | 3.508027523 | 6.119266055 | 36865 | 26862 | 2.101724138 | 6.133333333 |
| 36782 | 26779 | 5.100806452 | 26.70967742 | 36810 | 26807 | 4.291666667 | 11.33333333 | 36838 | 26835 | 3.47754491 | 12.11976048 | 36866 | 26863 | 2.100961538 | 1.081196581 |
| 36783 | 26780 | 5.090163934 | 30.66666667 | 36811 | 26808 | 4.264583333 | 12.65 | 36839 | 26836 | 3.473958333 | 4.791666667 | 36867 | 26864 | 2.096354167 | 3.833333333 |
| 36784 | 26781 | 4.983333333 | 39.86666667 | 36812 | 26809 | 4.259259259 | 9.512345679 | 36840 | 26837 | 3.45 | 12.44705882 | 36868 | 26865 | 1.651282051 | 6.526495726 |
| 36785 | 26782 | 4.956896552 | 43.09195402 | 36813 | 26810 | 4.241803279 | 13.95081967 | 36841 | 26838 | 3.45 | 30.66666667 | 36869 | 26866 | 1.515909091 | 6.83030303 |
| 36786 | 26783 | 4.938235294 | 11.00392157 | 36814 | 26811 | 4.224489796 | 21.59183673 | 36842 | 26839 | 3.375621891 | 7.781094527 | 36870 | 26867 | 1.419753086 | 12.49382716 |
| 36787 | 26784 | 4.810096154 | 7.224358974 | 36815 | 26812 | 4.216666667 | 12.13888889 | 36843 | 26840 | 3.354166667 | 26.83333333 | 36871 | 26868 | 1.384259259 | 40.60493827 |
| 36788 | 26785 | 4.799586777 | 8.743801653 | 36816 | 26813 | 4.2046875 | 7.1875 | 36844 | 26841 | 3.25 | 13.46666667 | 36872 | 26869 | 1.339805825 | 13.69579288 |

FIG. 5 (Cont.)

| 36873 | 26870 | 1.337209302 | 4.724806202 | 36874 | 26871 | 1.326923077 | 20.05128205 | 36875 | 26872 | 1.173469388 | 1.87755102 | 36876 | 26873 | 1.10106383 | 11.25531915 |

FIG. 6

| DNA SEQ ID NO | AA SEQ ID NO | Kidney 1 Enrichment |
|---|---|---|
| 36877 | 26874 | 376.1089744 |
| 36878 | 26875 | 335.3333333 |
| 36879 | 26876 | 312.1770833 |
| 36880 | 26877 | 63.52380952 |
| 36881 | 26878 | 50.66666667 |
| 36882 | 26879 | 42.77192982 |
| 36883 | 26880 | 40.88888889 |
| 36884 | 26881 | 38.33333333 |
| 36885 | 26882 | 36.24242424 |
| 36886 | 26883 | 35.77777778 |
| 36887 | 26884 | 30.66666667 |
| 36888 | 26885 | 30.66666667 |
| 36889 | 26886 | 30.66666667 |
| 36890 | 26887 | 30.66666667 |
| 36891 | 26888 | 29.76470588 |
| 36892 | 26889 | 28.75 |
| 36893 | 26890 | 25.875 |
| 36894 | 26891 | 25.19047619 |
| 36895 | 26892 | 23 |
| 36896 | 26893 | 20.44444444 |
| 36897 | 26894 | 19.93333333 |
| 36898 | 26895 | 19.71428571 |
| 36899 | 26896 | 18.4 |
| 36900 | 26897 | 18.28205128 |
| 36901 | 26898 | 17.25 |
| 36902 | 26899 | 16.61111111 |
| 36903 | 26900 | 16.51282051 |
| 36904 | 26901 | 16.29166667 |
| 36905 | 26902 | 15.63398693 |
| 36906 | 26903 | 15.33333333 |
| 36907 | 26904 | 15.33333333 |
| 36908 | 26905 | 15.33333333 |
| 36909 | 26906 | 15.33333333 |
| 36910 | 26907 | 15.33333333 |
| 36911 | 26908 | 15.33333333 |
| 36912 | 26909 | 15.33333333 |
| 36913 | 26910 | 14.91891892 |
| 36914 | 26911 | 14.88235294 |
| 36915 | 26912 | 14.48148148 |
| 36916 | 26913 | 13.74712644 |
| 36917 | 26914 | 13.62962963 |
| 36918 | 26915 | 13.14285714 |
| 36919 | 26916 | 13.14285714 |
| 36920 | 26917 | 13.14285714 |
| 36921 | 26918 | 12.77777778 |
| 36922 | 26919 | 12.77777778 |
| 36923 | 26920 | 12.54545455 |
| 36924 | 26921 | 12.54545455 |
| 36925 | 26922 | 12.20987654 |
| 36926 | 26923 | 12 |
| 36927 | 26924 | 11.92592593 |
| 36928 | 26925 | 11.81944444 |
| 36929 | 26926 | 11.5 |
| 36930 | 26927 | 11.2745098 |
| 36931 | 26928 | 11.2195122 |
| 36932 | 26929 | 11.15151515 |
| 36933 | 26930 | 10.95238095 |
| 36934 | 26931 | 10.95238095 |
| 36935 | 26932 | 10.69767442 |
| 36936 | 26933 | 10.36036036 |
| 36937 | 26934 | 10.22222222 |
| 36938 | 26935 | 10.22222222 |
| 36939 | 26936 | 10.22222222 |
| 36940 | 26937 | 10.22222222 |
| 36941 | 26938 | 10.22222222 |
| 36942 | 26939 | 10.22222222 |
| 36943 | 26940 | 10.22222222 |
| 36944 | 26941 | 10.22222222 |
| 36945 | 26942 | 10.22222222 |
| 36946 | 26943 | 10.09756098 |
| 36947 | 26944 | 10.07619048 |
| 36948 | 26945 | 10.0625 |
| 36949 | 26946 | 10.04597701 |
| 36950 | 26947 | 10.02564103 |
| 36951 | 26948 | 9.757575758 |
| 36952 | 26949 | 9.711111111 |
| 36953 | 26950 | 9.684210526 |
| 36954 | 26951 | 9.583333333 |
| 36955 | 26952 | 9.583333333 |
| 36956 | 26953 | 9.583333333 |
| 36957 | 26954 | 9.583333333 |
| 36958 | 26955 | 9.583333333 |
| 36959 | 26956 | 9.517241379 |
| 36960 | 26957 | 9.326460481 |
| 36961 | 26958 | 9.2 |
| 36962 | 26959 | 9.2 |
| 36963 | 26960 | 9.2 |
| 36964 | 26961 | 9.2 |
| 36965 | 26962 | 9.2 |
| 36966 | 26963 | 9.2 |
| 36967 | 26964 | 9.042735043 |
| 36968 | 26965 | 9.019607843 |
| 36969 | 26966 | 8.903225806 |
| 36970 | 26967 | 8.784722222 |
| 36971 | 26968 | 8.761904762 |
| 36972 | 26969 | 8.761904762 |
| 36973 | 26970 | 8.761904762 |
| 36974 | 26971 | 8.761904762 |
| 36975 | 26972 | 8.761904762 |
| 36976 | 26973 | 8.724137931 |
| 36977 | 26974 | 8.699763593 |
| 36978 | 26975 | 8.679245283 |
| 36979 | 26976 | 8.666666667 |
| 36980 | 26977 | 8.666666667 |
| 36981 | 26978 | 8.625 |
| 36982 | 26979 | 8.586666667 |
| 36983 | 26980 | 8.518518519 |
| 36984 | 26981 | 8.408602151 |
| 36985 | 26982 | 8.363636364 |
| 36986 | 26983 | 8.343137255 |
| 36987 | 26984 | 8.305555556 |
| 36988 | 26985 | 8.227642276 |
| 36989 | 26986 | 8.214285714 |
| 36990 | 26987 | 8.177777778 |
| 36991 | 26988 | 8.177777778 |
| 36992 | 26989 | 8.177777778 |
| 36993 | 26990 | 8.161290323 |
| 36994 | 26991 | 8.161290323 |
| 36995 | 26992 | 8.117647059 |
| 36996 | 26993 | 8.070175439 |
| 36997 | 26994 | 8.031746032 |
| 36998 | 26995 | 8.009950249 |
| 36999 | 26996 | 8 |
| 37000 | 26997 | 8 |
| 37001 | 26998 | 7.973333333 |
| 37002 | 26999 | 7.973333333 |
| 37003 | 27000 | 7.931034483 |
| 37004 | 27001 | 7.865247863 |
| 37005 | 27002 | 7.853658537 |
| 37006 | 27003 | 7.811320755 |
| 37007 | 27004 | 7.777777778 |
| 37008 | 27005 | 7.666666667 |
| 37009 | 27006 | 7.666666667 |
| 37010 | 27007 | 7.666666667 |
| 37011 | 27008 | 7.666666667 |

FIG. 6 (Cont.)

| DNA SEQ ID NO | AA SEQ ID NO | Kidney 1 Enrichment |
|---|---|---|
| 37012 | 27009 | 7.666666667 |
| 37013 | 27010 | 7.666666667 |
| 37014 | 27011 | 7.666666667 |
| 37015 | 27012 | 7.666666667 |
| 37016 | 27013 | 7.666666667 |
| 37017 | 27014 | 7.666666667 |
| 37018 | 27015 | 7.666666667 |
| 37019 | 27016 | 7.666666667 |
| 37020 | 27017 | 7.666666667 |
| 37021 | 27018 | 7.666666667 |
| 37022 | 27019 | 7.666666667 |
| 37023 | 27020 | 7.666666667 |
| 37024 | 27021 | 7.666666667 |
| 37025 | 27022 | 7.666666667 |
| 37026 | 27023 | 7.666666667 |
| 37027 | 27024 | 7.666666667 |
| 37028 | 27025 | 7.666666667 |
| 37029 | 27026 | 7.666666667 |
| 37030 | 27027 | 7.666666667 |
| 37031 | 27028 | 7.666666667 |
| 37032 | 27029 | 7.544973545 |
| 37033 | 27030 | 7.484126984 |
| 37034 | 27031 | 7.479674797 |
| 37035 | 27032 | 7.36 |
| 37036 | 27033 | 7.333333333 |
| 37037 | 27034 | 7.333333333 |
| 37038 | 27035 | 7.301587302 |
| 37039 | 27036 | 7.283333333 |
| 37040 | 27037 | 7.263157895 |
| 37041 | 27038 | 7.263157895 |
| 37042 | 27039 | 7.240740741 |
| 37043 | 27040 | 7.215686275 |
| 37044 | 27041 | 7.215686275 |
| 37045 | 27042 | 7.155555556 |
| 37046 | 27043 | 7.119047619 |
| 37047 | 27044 | 7.098765432 |
| 37048 | 27045 | 7.094527363 |
| 37049 | 27046 | 7.076923077 |
| 37050 | 27047 | 7.076923077 |
| 37051 | 27048 | 7.059628543 |
| 37052 | 27049 | 7.045045045 |
| 37053 | 27050 | 7.021806854 |
| 37054 | 27051 | 7.016949153 |
| 37055 | 27052 | 6.96969697 |
| 37056 | 27053 | 6.96969697 |
| 37057 | 27054 | 6.96969697 |
| 37058 | 27055 | 6.9 |
| 37059 | 27056 | 6.9 |
| 37060 | 27057 | 6.884353741 |
| 37061 | 27058 | 6.859649123 |
| 37062 | 27059 | 6.814814815 |
| 37063 | 27060 | 6.814814815 |
| 37064 | 27061 | 6.814814815 |
| 37065 | 27062 | 6.814814815 |
| 37066 | 27063 | 6.814814815 |
| 37067 | 27064 | 6.79047619 |
| 37068 | 27065 | 6.764705882 |
| 37069 | 27066 | 6.731707317 |
| 37070 | 27067 | 6.731707317 |
| 37071 | 27068 | 6.721461187 |
| 37072 | 27069 | 6.708333333 |
| 37073 | 27070 | 6.683760684 |
| 37074 | 27071 | 6.666666667 |
| 37075 | 27072 | 6.666666667 |
| 37076 | 27073 | 6.644444444 |
| 37077 | 27074 | 6.630630631 |
| 37078 | 27075 | 6.571428571 |
| 37079 | 27076 | 6.571428571 |
| 37080 | 27077 | 6.571428571 |
| 37081 | 27078 | 6.571428571 |
| 37082 | 27079 | 6.571428571 |
| 37083 | 27080 | 6.552706553 |
| 37084 | 27081 | 6.516666667 |
| 37085 | 27082 | 6.487179487 |
| 37086 | 27083 | 6.487179487 |
| 37087 | 27084 | 6.481099656 |
| 37088 | 27085 | 6.474074074 |
| 37089 | 27086 | 6.46875 |
| 37090 | 27087 | 6.456140351 |
| 37091 | 27088 | 6.456140351 |
| 37092 | 27089 | 6.456140351 |
| 37093 | 27090 | 6.44 |
| 37094 | 27091 | 6.418604651 |
| 37095 | 27092 | 6.374531835 |
| 37096 | 27093 | 6.372294372 |
| 37097 | 27094 | 6.357723577 |
| 37098 | 27095 | 6.344827586 |
| 37099 | 27096 | 6.31372549 |
| 37100 | 27097 | 6.31372549 |
| 37101 | 27098 | 6.290598291 |
| 37102 | 27099 | 6.290598291 |
| 37103 | 27100 | 6.284153005 |
| 37104 | 27101 | 6.278215223 |
| 37105 | 27102 | 6.272727273 |
| 37106 | 27103 | 6.272727273 |
| 37107 | 27104 | 6.272727273 |
| 37108 | 27105 | 6.24691358 |
| 37109 | 27106 | 6.24691358 |
| 37110 | 27107 | 6.24691358 |
| 37111 | 27108 | 6.24691358 |
| 37112 | 27109 | 6.24691358 |
| 37113 | 27110 | 6.229166667 |
| 37114 | 27111 | 6.229166667 |
| 37115 | 27112 | 6.19858156 |
| 37116 | 27113 | 6.19858156 |
| 37117 | 27114 | 6.187134503 |
| 37118 | 27115 | 6.133333333 |
| 37119 | 27116 | 6.133333333 |
| 37120 | 27117 | 6.133333333 |
| 37121 | 27118 | 6.133333333 |
| 37122 | 27119 | 6.133333333 |
| 37123 | 27120 | 6.133333333 |
| 37124 | 27121 | 6.133333333 |
| 37125 | 27122 | 6.133333333 |
| 37126 | 27123 | 6.133333333 |
| 37127 | 27124 | 6.133333333 |
| 37128 | 27125 | 6.084656085 |
| 37129 | 27126 | 6.075471698 |
| 37130 | 27127 | 6.052631579 |
| 37131 | 27128 | 6.052631579 |
| 37132 | 27129 | 6.04040404 |
| 37133 | 27130 | 6.04040404 |
| 37134 | 27131 | 6 |
| 37135 | 27132 | 6 |
| 37136 | 27133 | 5.983739837 |
| 37137 | 27134 | 5.97740113 |
| 37138 | 27135 | 5.97740113 |
| 37139 | 27136 | 5.97740113 |
| 37140 | 27137 | 5.97740113 |
| 37141 | 27138 | 5.97740113 |
| 37142 | 27139 | 5.962962963 |
| 37143 | 27140 | 5.962962963 |
| 37144 | 27141 | 5.945578231 |
| 37145 | 27142 | 5.935483871 |
| 37146 | 27143 | 5.935483871 |
| 37147 | 27144 | 5.914285714 |
| 37148 | 27145 | 5.897435897 |
| 37149 | 27146 | 5.841269841 |
| 37150 | 27147 | 5.841269841 |
| 37151 | 27148 | 5.841269841 |
| 37152 | 27149 | 5.841269841 |
| 37153 | 27150 | 5.801801802 |
| 37154 | 27151 | 5.786163522 |
| 37155 | 27152 | 5.75 |
| 37156 | 27153 | 5.75 |

FIG. 6 (Cont.)

| DNA SEQ ID NO | AA SEQ ID NO | Kidney 1 Enrichment |
|---|---|---|
| 37157 | 27154 | 5.75 |
| 37158 | 27155 | 5.75 |
| 37159 | 27156 | 5.75 |
| 37160 | 27157 | 5.75 |
| 37161 | 27158 | 5.75 |
| 37162 | 27159 | 5.75 |
| 37163 | 27160 | 5.75 |
| 37164 | 27161 | 5.75 |
| 37165 | 27162 | 5.717514124 |
| 37166 | 27163 | 5.705426357 |
| 37167 | 27164 | 5.695238095 |
| 37168 | 27165 | 5.695238095 |
| 37169 | 27166 | 5.679012346 |
| 37170 | 27167 | 5.679012346 |
| 37171 | 27168 | 5.679012346 |
| 37172 | 27169 | 5.679012346 |
| 37173 | 27170 | 5.649122807 |
| 37174 | 27171 | 5.649122807 |
| 37175 | 27172 | 5.649122807 |
| 37176 | 27173 | 5.637254902 |
| 37177 | 27174 | 5.632653061 |
| 37178 | 27175 | 5.632653061 |
| 37179 | 27176 | 5.622222222 |
| 37180 | 27177 | 5.622222222 |
| 37181 | 27178 | 5.622222222 |
| 37182 | 27179 | 5.609756098 |
| 37183 | 27180 | 5.609756098 |
| 37184 | 27181 | 5.609756098 |
| 37185 | 27182 | 5.609756098 |

| DNA SEQ ID NO | AA SEQ ID NO | Kidney 1 Enrichment |
|---|---|---|
| 37186 | 27183 | 5.597883598 |
| 37187 | 27184 | 5.586563307 |
| 37188 | 27185 | 5.575757576 |
| 37189 | 27186 | 5.575757576 |
| 37190 | 27187 | 5.575757576 |
| 37191 | 27188 | 5.575757576 |
| 37192 | 27189 | 5.575757576 |
| 37193 | 27190 | 5.575757576 |
| 37194 | 27191 | 5.575757576 |
| 37195 | 27192 | 5.56043956 |
| 37196 | 27193 | 5.555555556 |
| 37197 | 27194 | 5.551724138 |
| 37198 | 27195 | 5.551724138 |
| 37199 | 27196 | 5.551724138 |
| 37200 | 27197 | 5.542168675 |
| 37201 | 27198 | 5.537037037 |
| 37202 | 27199 | 5.537037037 |
| 37203 | 27200 | 5.537037037 |
| 37204 | 27201 | 5.530054645 |
| 37205 | 27202 | 5.530054645 |
| 37206 | 27203 | 5.510416667 |
| 37207 | 27204 | 5.504273504 |
| 37208 | 27205 | 5.492537313 |
| 37209 | 27206 | 5.476190476 |
| 37210 | 27207 | 5.476190476 |
| 37211 | 27208 | 5.476190476 |
| 37212 | 27209 | 5.476190476 |
| 37213 | 27210 | 5.476190476 |
| 37214 | 27211 | 5.476190476 |

| DNA SEQ ID NO | AA SEQ ID NO | Kidney 1 Enrichment |
|---|---|---|
| 37215 | 27212 | 5.457627119 |
| 37216 | 27213 | 5.455128205 |
| 37217 | 27214 | 5.447368421 |
| 37218 | 27215 | 5.440860215 |
| 37219 | 27216 | 5.430555556 |
| 37220 | 27217 | 5.430555556 |
| 37221 | 27218 | 5.425641026 |
| 37222 | 27219 | 5.411764706 |
| 37223 | 27220 | 5.411764706 |
| 37224 | 27221 | 5.411764706 |
| 37225 | 27222 | 5.411764706 |
| 37226 | 27223 | 5.395061728 |
| 37227 | 27224 | 5.390625 |
| 37228 | 27225 | 5.366666667 |
| 37229 | 27226 | 5.366666667 |
| 37230 | 27227 | 5.366666667 |
| 37231 | 27228 | 5.348837209 |
| 37232 | 27229 | 5.333333333 |
| 37233 | 27230 | 5.333333333 |
| 37234 | 27231 | 5.319727891 |
| 37235 | 27232 | 5.307692308 |
| 37236 | 27233 | 5.304504505 |
| 37237 | 27234 | 5.287356322 |
| 37238 | 27235 | 5.287356322 |
| 37239 | 27236 | 5.278688525 |
| 37240 | 27237 | 5.278688525 |
| 37241 | 27238 | 5.251141553 |
| 37242 | 27239 | 5.245614035 |
| 37243 | 27240 | 5.245614035 |

| DNA SEQ ID NO | AA SEQ ID NO | Kidney 1 Enrichment |
|---|---|---|
| 37244 | 27241 | 5.245614035 |
| 37245 | 27242 | 5.238888889 |
| 37246 | 27243 | 5.235772358 |
| 37247 | 27244 | 5.235772358 |
| 37248 | 27245 | 5.235772358 |
| 37249 | 27246 | 5.235772358 |
| 37250 | 27247 | 5.231372549 |
| 37251 | 27248 | 5.219858156 |
| 37252 | 27249 | 5.219858156 |
| 37253 | 27250 | 5.219858156 |
| 37254 | 27251 | 5.219858156 |
| 37255 | 27252 | 5.202380952 |
| 37256 | 27253 | 5.18627451 |
| 37257 | 27254 | 5.183098592 |
| 37258 | 27255 | 5.175 |
| 37259 | 27256 | 5.170542636 |
| 37260 | 27257 | 5.164912281 |
| 37261 | 27258 | 5.164912281 |
| 37262 | 27259 | 5.142276423 |
| 37263 | 27260 | 5.111111111 |
| 37264 | 27261 | 5.111111111 |
| 37265 | 27262 | 5.111111111 |
| 37266 | 27263 | 5.111111111 |
| 37267 | 27264 | 5.111111111 |
| 37268 | 27265 | 5.111111111 |
| 37269 | 27266 | 5.111111111 |
| 37270 | 27267 | 5.111111111 |
| 37271 | 27268 | 5.111111111 |
| 37272 | 27269 | 5.111111111 |

| DNA SEQ ID NO | AA SEQ ID NO | Kidney 1 Enrichment |
|---|---|---|
| 37273 | 27270 | 5.111111111 |
| 37274 | 27271 | 5.111111111 |
| 37275 | 27272 | 5.111111111 |
| 37276 | 27273 | 5.111111111 |
| 37277 | 27274 | 5.111111111 |
| 37278 | 27275 | 5.111111111 |
| 37279 | 27276 | 5.111111111 |
| 37280 | 27277 | 5.111111111 |
| 37281 | 27278 | 5.111111111 |
| 37282 | 27279 | 5.111111111 |
| 37283 | 27280 | 5.111111111 |
| 37284 | 27281 | 5.111111111 |
| 37285 | 27282 | 5.111111111 |
| 37286 | 27283 | 5.111111111 |
| 37287 | 27284 | 5.111111111 |
| 37288 | 27285 | 5.111111111 |
| 37289 | 27286 | 5.111111111 |
| 37290 | 27287 | 5.111111111 |
| 37291 | 27288 | 5.111111111 |
| 37292 | 27289 | 5.111111111 |
| 37293 | 27290 | 5.048780488 |
| 37294 | 27291 | 5.038095238 |
| 37295 | 27292 | 5.027322404 |
| 37296 | 27293 | 5.022988506 |
| 37297 | 27294 | 5.022988506 |
| 37298 | 27295 | 5.022988506 |
| 37299 | 27296 | 5.018181818 |
| 37300 | 27297 | 5.012820513 |
| 37301 | 27298 | 5.00990099 |

FIG. 6 (Cont.)

| DNA SEQ ID NO | AA SEQ ID NO | Kidney 1 Enrichment |
|---|---|---|
| 37302 | 27299 | 5.006802721 |
| 37303 | 27300 | 5 |
| 37304 | 27301 | 5 |
| 37305 | 27302 | 4.992248062 |
| 37306 | 27303 | 4.992248062 |
| 37307 | 27304 | 4.987951807 |
| 37308 | 27305 | 4.983333333 |
| 37309 | 27306 | 4.983333333 |
| 37310 | 27307 | 4.983333333 |
| 37311 | 27308 | 4.972972973 |
| 37312 | 27309 | 4.972972973 |
| 37313 | 27310 | 4.972972973 |
| 37314 | 27311 | 4.972972973 |
| 37315 | 27312 | 4.972972973 |
| 37316 | 27313 | 4.96713615 |
| 37317 | 27314 | 4.960784314 |
| 37318 | 27315 | 4.960784314 |
| 37319 | 27316 | 4.956228956 |
| 37320 | 27317 | 4.953846154 |
| 37321 | 27318 | 4.946236559 |
| 37322 | 27319 | 4.940740741 |
| 37323 | 27320 | 4.928571429 |
| 37324 | 27321 | 4.918238994 |
| 37325 | 27322 | 4.906666667 |
| 37326 | 27323 | 4.906666667 |
| 37327 | 27324 | 4.906666667 |
| 37328 | 27325 | 4.906666667 |
| 37329 | 27326 | 4.906666667 |
| 37330 | 27327 | 4.900343643 |

| DNA SEQ ID NO | AA SEQ ID NO | Kidney 1 Enrichment |
|---|---|---|
| 37331 | 27328 | 4.893617021 |
| 37332 | 27329 | 4.878787879 |
| 37333 | 27330 | 4.878787879 |
| 37334 | 27331 | 4.878787879 |
| 37335 | 27332 | 4.878787879 |
| 37336 | 27333 | 4.878787879 |
| 37337 | 27334 | 4.878787879 |
| 37338 | 27335 | 4.869369369 |
| 37339 | 27336 | 4.861788618 |
| 37340 | 27337 | 4.861788618 |
| 37341 | 27338 | 4.855555556 |
| 37342 | 27339 | 4.842105263 |
| 37343 | 27340 | 4.842105263 |
| 37344 | 27341 | 4.842105263 |
| 37345 | 27342 | 4.842105263 |
| 37346 | 27343 | 4.827160494 |
| 37347 | 27344 | 4.827160494 |
| 37348 | 27345 | 4.827160494 |
| 37349 | 27346 | 4.827160494 |
| 37350 | 27347 | 4.823970037 |
| 37351 | 27348 | 4.819047619 |
| 37352 | 27349 | 4.810457516 |
| 37353 | 27350 | 4.810457516 |
| 37354 | 27351 | 4.810457516 |
| 37355 | 27352 | 4.791666667 |
| 37356 | 27353 | 4.791666667 |
| 37357 | 27354 | 4.791666667 |
| 37358 | 27355 | 4.791666667 |
| 37359 | 27356 | 4.791666667 |

| DNA SEQ ID NO | AA SEQ ID NO | Kidney 1 Enrichment |
|---|---|---|
| 37360 | 27357 | 4.791666667 |
| 37361 | 27358 | 4.791666667 |
| 37362 | 27359 | 4.791666667 |
| 37363 | 27360 | 4.791666667 |
| 37364 | 27361 | 4.791666667 |
| 37365 | 27362 | 4.791666667 |
| 37366 | 27363 | 4.781362007 |
| 37367 | 27364 | 4.775956284 |
| 37368 | 27365 | 4.77037037 |
| 37369 | 27366 | 4.77037037 |
| 37370 | 27367 | 4.77037037 |
| 37371 | 27368 | 4.75862069 |
| 37372 | 27369 | 4.75862069 |
| 37373 | 27370 | 4.75862069 |
| 37374 | 27371 | 4.751173709 |
| 37375 | 27372 | 4.751173709 |
| 37376 | 27373 | 4.746031746 |
| 37377 | 27374 | 4.739393939 |
| 37378 | 27375 | 4.717948718 |
| 37379 | 27376 | 4.717948718 |
| 37380 | 27377 | 4.717948718 |
| 37381 | 27378 | 4.717948718 |
| 37382 | 27379 | 4.717948718 |
| 37383 | 27380 | 4.717948718 |
| 37384 | 27381 | 4.717948718 |
| 37385 | 27382 | 4.702222222 |
| 37386 | 27383 | 4.693877551 |
| 37387 | 27384 | 4.693877551 |
| 37388 | 27385 | 4.693877551 |

| DNA SEQ ID NO | AA SEQ ID NO | Kidney 1 Enrichment |
|---|---|---|
| 37389 | 27386 | 4.685185185 |
| 37390 | 27387 | 4.685185185 |
| 37391 | 27388 | 4.680701754 |
| 37392 | 27389 | 4.677966102 |
| 37393 | 27390 | 4.677966102 |
| 37394 | 27391 | 4.666666667 |
| 37395 | 27392 | 4.666666667 |
| 37396 | 27393 | 4.654761905 |
| 37397 | 27394 | 4.646464646 |
| 37398 | 27395 | 4.635658915 |
| 37399 | 27396 | 4.635658915 |
| 37400 | 27397 | 4.628930818 |
| 37401 | 27398 | 4.624338624 |
| 37402 | 27399 | 4.624338624 |
| 37403 | 27400 | 4.621004566 |
| 37404 | 27401 | 4.6 |
| 37405 | 27402 | 4.6 |
| 37406 | 27403 | 4.6 |
| 37407 | 27404 | 4.6 |
| 37408 | 27405 | 4.6 |
| 37409 | 27406 | 4.6 |
| 37410 | 27407 | 4.6 |
| 37411 | 27408 | 4.6 |
| 37412 | 27409 | 4.6 |
| 37413 | 27410 | 4.6 |
| 37414 | 27411 | 4.6 |
| 37415 | 27412 | 4.6 |
| 37416 | 27413 | 4.6 |
| 37417 | 27414 | 4.6 |

| DNA SEQ ID NO | AA SEQ ID NO | Kidney 1 Enrichment |
|---|---|---|
| 37418 | 27415 | 4.6 |
| 37419 | 27416 | 4.6 |
| 37420 | 27417 | 4.58008658 |
| 37421 | 27418 | 4.58008658 |
| 37422 | 27419 | 4.577114428 |
| 37423 | 27420 | 4.567375887 |
| 37424 | 27421 | 4.567375887 |
| 37425 | 27422 | 4.567375887 |
| 37426 | 27423 | 4.567375887 |
| 37427 | 27424 | 4.558558559 |
| 37428 | 27425 | 4.549450549 |
| 37429 | 27426 | 4.543209877 |
| 37430 | 27427 | 4.543209877 |
| 37431 | 27428 | 4.543209877 |
| 37432 | 27429 | 4.535211268 |
| 37433 | 27430 | 4.53030303 |
| 37434 | 27431 | 4.524590164 |
| 37435 | 27432 | 4.524590164 |
| 37436 | 27433 | 4.519298246 |
| 37437 | 27434 | 4.509803922 |
| 37438 | 27435 | 4.509803922 |
| 37439 | 27436 | 4.509803922 |
| 37440 | 27437 | 4.509803922 |
| 37441 | 27438 | 4.509803922 |
| 37442 | 27439 | 4.509803922 |
| 37443 | 27440 | 4.509803922 |
| 37444 | 27441 | 4.494252874 |
| 37445 | 27442 | 4.487804878 |
| 37446 | 27443 | 4.487804878 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 37447 | 27444 | 4.487804878 | 37476 | 27473 | 4.380952381 | 37505 | 27502 | 4.293333333 | 37534 | 27531 | 4.209150327 | 37563 | 27560 | 4.121863799 |
| 37448 | 27445 | 4.482051282 | 37477 | 27474 | 4.380952381 | 37506 | 27503 | 4.293333333 | 37535 | 27532 | 4.206489676 | 37564 | 27561 | 4.119402985 |
| 37449 | 27446 | 4.479400749 | 37478 | 27475 | 4.380952381 | 37507 | 27504 | 4.293333333 | 37536 | 27533 | 4.204301075 | 37565 | 27562 | 4.113821138 |
| 37450 | 27447 | 4.479400749 | 37479 | 27476 | 4.380952381 | 37508 | 27505 | 4.293333333 | 37537 | 27534 | 4.204301075 | 37566 | 27563 | 4.113821138 |
| 37451 | 27448 | 4.472222222 | 37480 | 27477 | 4.380952381 | 37509 | 27506 | 4.293333333 | 37538 | 27535 | 4.204301075 | 37567 | 27564 | 4.113821138 |
| 37452 | 27449 | 4.472222222 | 37481 | 27478 | 4.380952381 | 37510 | 27507 | 4.282282282 | 37539 | 27536 | 4.204301075 | 37568 | 27565 | 4.088888889 |
| 37453 | 27450 | 4.472222222 | 37482 | 27479 | 4.380952381 | 37511 | 27508 | 4.279069767 | 37540 | 27537 | 4.204301075 | 37569 | 27566 | 4.088888889 |
| 37454 | 27451 | 4.472222222 | 37483 | 27480 | 4.380952381 | 37512 | 27509 | 4.279069767 | 37541 | 27538 | 4.198412698 | 37570 | 27567 | 4.088888889 |
| 37455 | 27452 | 4.460606061 | 37484 | 27481 | 4.380952381 | 37513 | 27510 | 4.279069767 | 37542 | 27539 | 4.193732194 | 37571 | 27568 | 4.088888889 |
| 37456 | 27453 | 4.457364341 | 37485 | 27482 | 4.380952381 | 37514 | 27511 | 4.279069767 | 37543 | 27540 | 4.192708333 | 37572 | 27569 | 4.088888889 |
| 37457 | 27454 | 4.451612903 | 37486 | 27483 | 4.380952381 | 37515 | 27512 | 4.279069767 | 37544 | 27541 | 4.181818182 | 37573 | 27570 | 4.088888889 |
| 37458 | 27455 | 4.451612903 | 37487 | 27484 | 4.380952381 | 37516 | 27513 | 4.279069767 | 37545 | 27542 | 4.181818182 | 37574 | 27571 | 4.088888889 |
| 37459 | 27456 | 4.451612903 | 37488 | 27485 | 4.380952381 | 37517 | 27514 | 4.279069767 | 37546 | 27543 | 4.181818182 | 37575 | 27572 | 4.088888889 |
| 37460 | 27457 | 4.451612903 | 37489 | 27486 | 4.348258706 | 37518 | 27515 | 4.273224044 | 37547 | 27544 | 4.171568627 | 37576 | 27573 | 4.088888889 |
| 37461 | 27458 | 4.438596491 | 37490 | 27487 | 4.348258706 | 37519 | 27516 | 4.273224044 | 37548 | 27545 | 4.164609053 | 37577 | 27574 | 4.088888889 |
| 37462 | 27459 | 4.438596491 | 37491 | 27488 | 4.344444444 | 37520 | 27517 | 4.266666667 | 37549 | 27546 | 4.164609053 | 37578 | 27575 | 4.088888889 |
| 37463 | 27460 | 4.438596491 | 37492 | 27489 | 4.344444444 | 37521 | 27518 | 4.259259259 | 37550 | 27547 | 4.161904762 | 37579 | 27576 | 4.088888889 |
| 37464 | 27461 | 4.42962963 | 37493 | 27490 | 4.344444444 | 37522 | 27519 | 4.259259259 | 37551 | 27548 | 4.15819209 | 37580 | 27577 | 4.072916667 |
| 37465 | 27462 | 4.42962963 | 37494 | 27491 | 4.339622642 | 37523 | 27520 | 4.259259259 | 37552 | 27549 | 4.152777778 | 37581 | 27578 | 4.072916667 |
| 37466 | 27463 | 4.423076923 | 37495 | 27492 | 4.339622642 | 37524 | 27521 | 4.259259259 | 37553 | 27550 | 4.152777778 | 37582 | 27579 | 4.072916667 |
| 37467 | 27464 | 4.414141414 | 37496 | 27493 | 4.333333333 | 37525 | 27522 | 4.246153846 | 37554 | 27551 | 4.152777778 | 37583 | 27580 | 4.072916667 |
| 37468 | 27465 | 4.414141414 | 37497 | 27494 | 4.333333333 | 37526 | 27523 | 4.236842105 | 37555 | 27552 | 4.152777778 | 37584 | 27581 | 4.072916667 |
| 37469 | 27466 | 4.410958904 | 37498 | 27495 | 4.319248826 | 37527 | 27524 | 4.229885057 | 37556 | 27553 | 4.152777778 | 37585 | 27582 | 4.068027211 |
| 37470 | 27467 | 4.408333333 | 37499 | 27496 | 4.3125 | 37528 | 27525 | 4.229885057 | 37557 | 27554 | 4.152777778 | 37586 | 27583 | 4.064257028 |
| 37471 | 27468 | 4.406130268 | 37500 | 27497 | 4.304093567 | 37529 | 27526 | 4.229885057 | 37558 | 27555 | 4.15037594 | 37587 | 27584 | 4.058823529 |
| 37472 | 27469 | 4.406130268 | 37501 | 27498 | 4.304093567 | 37530 | 27527 | 4.224489796 | 37559 | 27556 | 4.144144144 | 37588 | 27585 | 4.058823529 |
| 37473 | 27470 | 4.380952381 | 37502 | 27499 | 4.300813008 | 37531 | 27528 | 4.216666667 | 37560 | 27557 | 4.128205128 | 37589 | 27586 | 4.058823529 |
| 37474 | 27471 | 4.380952381 | 37503 | 27500 | 4.300813008 | 37532 | 27529 | 4.212454212 | 37561 | 27558 | 4.128205128 | 37590 | 27587 | 4.050314465 |
| 37475 | 27472 | 4.380952381 | 37504 | 27501 | 4.293333333 | 37533 | 27530 | 4.211267606 | 37562 | 27559 | 4.121863799 | 37591 | 27588 | 4.046296296 |

FIG. 6 (Cont.)

| DNA SEQ ID NO | AA SEQ ID NO | Kidney 1 Enrichment |
|---|---|---|
| 37592 | 27589 | 4.044989775 |
| 37593 | 27590 | 4.035087719 |
| 37594 | 27591 | 4.035087719 |
| 37595 | 27592 | 4.035087719 |
| 37596 | 27593 | 4.035087719 |
| 37597 | 27594 | 4.035087719 |
| 37598 | 27595 | 4.035087719 |
| 37599 | 27596 | 4.035087719 |
| 37600 | 27597 | 4.021857923 |
| 37601 | 27598 | 4.019417476 |
| 37602 | 27599 | 4.015873016 |
| 37603 | 27600 | 4.015873016 |
| 37604 | 27601 | 4.015873016 |
| 37605 | 27602 | 4.01025641 |
| 37606 | 27603 | 4.01025641 |
| 37607 | 27604 | 4.01025641 |
| 37608 | 27605 | 4 |
| 37609 | 27606 | 4 |
| 37610 | 27607 | 4 |
| 37611 | 27608 | 4 |
| 37612 | 27609 | 4 |
| 37613 | 27610 | 4 |
| 37614 | 27611 | 4 |
| 37615 | 27612 | 4 |
| 37616 | 27613 | 4 |
| 37617 | 27614 | 4 |
| 37618 | 27615 | 4 |
| 37619 | 27616 | 4 |
| 37620 | 27617 | 3.986666667 |

| DNA SEQ ID NO | AA SEQ ID NO | Kidney 1 Enrichment |
|---|---|---|
| 37621 | 27618 | 3.986666667 |
| 37622 | 27619 | 3.984251969 |
| 37623 | 27620 | 3.982683983 |
| 37624 | 27621 | 3.975308642 |
| 37625 | 27622 | 3.975308642 |
| 37626 | 27623 | 3.975308642 |
| 37627 | 27624 | 3.975308642 |
| 37628 | 27625 | 3.975308642 |
| 37629 | 27626 | 3.975308642 |
| 37630 | 27627 | 3.965517241 |
| 37631 | 27628 | 3.965517241 |
| 37632 | 27629 | 3.961111111 |
| 37633 | 27630 | 3.956989247 |
| 37634 | 27631 | 3.956989247 |
| 37635 | 27632 | 3.956989247 |
| 37636 | 27633 | 3.949494949 |
| 37637 | 27634 | 3.947194719 |
| 37638 | 27635 | 3.942857143 |
| 37639 | 27636 | 3.942857143 |
| 37640 | 27637 | 3.942857143 |
| 37641 | 27638 | 3.936936937 |
| 37642 | 27639 | 3.931623932 |
| 37643 | 27640 | 3.931623932 |
| 37644 | 27641 | 3.926829268 |
| 37645 | 27642 | 3.92248062 |
| 37646 | 27643 | 3.92248062 |
| 37647 | 27644 | 3.92248062 |
| 37648 | 27645 | 3.92248062 |
| 37649 | 27646 | 3.919799499 |

| DNA SEQ ID NO | AA SEQ ID NO | Kidney 1 Enrichment |
|---|---|---|
| 37650 | 27647 | 3.914893617 |
| 37651 | 27648 | 3.914893617 |
| 37652 | 27649 | 3.908496732 |
| 37653 | 27650 | 3.908496732 |
| 37654 | 27651 | 3.908496732 |
| 37655 | 27652 | 3.905660377 |
| 37656 | 27653 | 3.905660377 |
| 37657 | 27654 | 3.903030303 |
| 37658 | 27655 | 3.903030303 |
| 37659 | 27656 | 3.898305085 |
| 37660 | 27657 | 3.898305085 |
| 37661 | 27658 | 3.898305085 |
| 37662 | 27659 | 3.898305085 |
| 37663 | 27660 | 3.898305085 |
| 37664 | 27661 | 3.898305085 |
| 37665 | 27662 | 3.888888889 |
| 37666 | 27663 | 3.887323944 |
| 37667 | 27664 | 3.884444444 |
| 37668 | 27665 | 3.878431373 |
| 37669 | 27666 | 3.877394636 |
| 37670 | 27667 | 3.877394636 |
| 37671 | 27668 | 3.875457875 |
| 37672 | 27669 | 3.873684211 |
| 37673 | 27670 | 3.870550162 |
| 37674 | 27671 | 3.861728395 |
| 37675 | 27672 | 3.833333333 |
| 37676 | 27673 | 3.833333333 |
| 37677 | 27674 | 3.833333333 |
| 37678 | 27675 | 3.833333333 |

| DNA SEQ ID NO | AA SEQ ID NO | Kidney 1 Enrichment |
|---|---|---|
| 37679 | 27676 | 3.833333333 |
| 37680 | 27677 | 3.833333333 |
| 37681 | 27678 | 3.833333333 |
| 37682 | 27679 | 3.833333333 |
| 37683 | 27680 | 3.833333333 |
| 37684 | 27681 | 3.833333333 |
| 37685 | 27682 | 3.833333333 |
| 37686 | 27683 | 3.833333333 |
| 37687 | 27684 | 3.833333333 |
| 37688 | 27685 | 3.833333333 |
| 37689 | 27686 | 3.833333333 |
| 37690 | 27687 | 3.833333333 |
| 37691 | 27688 | 3.833333333 |
| 37692 | 27689 | 3.833333333 |
| 37693 | 27690 | 3.833333333 |
| 37694 | 27691 | 3.833333333 |
| 37695 | 27692 | 3.833333333 |
| 37696 | 27693 | 3.833333333 |
| 37697 | 27694 | 3.833333333 |
| 37698 | 27695 | 3.833333333 |
| 37699 | 27696 | 3.833333333 |
| 37700 | 27697 | 3.833333333 |
| 37701 | 27698 | 3.833333333 |
| 37702 | 27699 | 3.833333333 |
| 37703 | 27700 | 3.833333333 |
| 37704 | 27701 | 3.833333333 |
| 37705 | 27702 | 3.833333333 |
| 37706 | 27703 | 3.833333333 |
| 37707 | 27704 | 3.833333333 |

| DNA SEQ ID NO | AA SEQ ID NO | Kidney 1 Enrichment |
|---|---|---|
| 37708 | 27705 | 3.833333333 |
| 37709 | 27706 | 3.833333333 |
| 37710 | 27707 | 3.833333333 |
| 37711 | 27708 | 3.833333333 |
| 37712 | 27709 | 3.833333333 |
| 37713 | 27710 | 3.833333333 |
| 37714 | 27711 | 3.833333333 |
| 37715 | 27712 | 3.833333333 |
| 37716 | 27713 | 3.833333333 |
| 37717 | 27714 | 3.833333333 |
| 37718 | 27715 | 3.833333333 |
| 37719 | 27716 | 3.833333333 |
| 37720 | 27717 | 3.833333333 |
| 37721 | 27718 | 3.833333333 |
| 37722 | 27719 | 3.833333333 |
| 37723 | 27720 | 3.833333333 |
| 37724 | 27721 | 3.833333333 |
| 37725 | 27722 | 3.833333333 |
| 37726 | 27723 | 3.833333333 |
| 37727 | 27724 | 3.833333333 |
| 37728 | 27725 | 3.804511278 |
| 37729 | 27726 | 3.798165138 |
| 37730 | 27727 | 3.793814433 |
| 37731 | 27728 | 3.792114695 |
| 37732 | 27729 | 3.790262172 |
| 37733 | 27730 | 3.788235294 |
| 37734 | 27731 | 3.78600823 |
| 37735 | 27732 | 3.783549784 |
| 37736 | 27733 | 3.783549784 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 37737 | 27734 | 3.780821918 | 37766 | 27763 | 3.717171717 | 37795 | 27792 | 3.647849462 | 37824 | 27821 | 3.577777778 | 37853 | 27850 | 3.538461538 |
| 37738 | 27735 | 3.770491803 | 37767 | 27764 | 3.712280702 | 37796 | 27793 | 3.635738832 | 37825 | 27822 | 3.577777778 | 37854 | 27851 | 3.538461538 |
| 37739 | 27736 | 3.770491803 | 37768 | 27765 | 3.709677419 | 37797 | 27794 | 3.631578947 | 37826 | 27823 | 3.577777778 | 37855 | 27852 | 3.538461538 |
| 37740 | 27737 | 3.766081871 | 37769 | 27766 | 3.701149425 | 37798 | 27795 | 3.631578947 | 37827 | 27824 | 3.577777778 | 37856 | 27853 | 3.538461538 |
| 37741 | 27738 | 3.766081871 | 37770 | 27767 | 3.701149425 | 37799 | 27796 | 3.624242424 | 37828 | 27825 | 3.577777778 | 37857 | 27854 | 3.538461538 |
| 37742 | 27739 | 3.766081871 | 37771 | 27768 | 3.701149425 | 37800 | 27797 | 3.624242424 | 37829 | 27826 | 3.577777778 | 37858 | 27855 | 3.526666667 |
| 37743 | 27740 | 3.761006289 | 37772 | 27769 | 3.694779116 | 37801 | 27798 | 3.624242424 | 37830 | 27827 | 3.577777778 | 37859 | 27856 | 3.524904215 |
| 37744 | 27741 | 3.761006289 | 37773 | 27770 | 3.694779116 | 37802 | 27799 | 3.622047244 | 37831 | 27828 | 3.570776256 | 37860 | 27857 | 3.522522523 |
| 37745 | 27742 | 3.761006289 | 37774 | 27771 | 3.691358025 | 37803 | 27800 | 3.62037037 | 37832 | 27829 | 3.565891473 | 37861 | 27858 | 3.520987654 |
| 37746 | 27743 | 3.761006289 | 37775 | 27772 | 3.691358025 | 37804 | 27801 | 3.62037037 | 37833 | 27830 | 3.55952381 | 37862 | 27859 | 3.519125683 |
| 37747 | 27744 | 3.755102041 | 37776 | 27773 | 3.691358025 | 37805 | 27802 | 3.617977528 | 37834 | 27831 | 3.55952381 | 37863 | 27860 | 3.513888889 |
| 37748 | 27745 | 3.75177305 | 37777 | 27774 | 3.691358025 | 37806 | 27803 | 3.617977528 | 37835 | 27832 | 3.55952381 | 37864 | 27861 | 3.513888889 |
| 37749 | 27746 | 3.748148148 | 37778 | 27775 | 3.68 | 37807 | 27804 | 3.616352201 | 37836 | 27833 | 3.555555556 | 37865 | 27862 | 3.510040161 |
| 37750 | 27747 | 3.748148148 | 37779 | 27776 | 3.68 | 37808 | 27805 | 3.607843137 | 37837 | 27834 | 3.555555556 | 37866 | 27863 | 3.504761905 |
| 37751 | 27748 | 3.748148148 | 37780 | 27777 | 3.68 | 37809 | 27806 | 3.607843137 | 37838 | 27835 | 3.555555556 | 37867 | 27864 | 3.504761905 |
| 37752 | 27749 | 3.744186047 | 37781 | 27778 | 3.68 | 37810 | 27807 | 3.607843137 | 37839 | 27836 | 3.550877193 | 37868 | 27865 | 3.504761905 |
| 37753 | 27750 | 3.739837398 | 37782 | 27779 | 3.68 | 37811 | 27808 | 3.607843137 | 37840 | 27837 | 3.549382716 | 37869 | 27866 | 3.504761905 |
| 37754 | 27751 | 3.735042735 | 37783 | 27780 | 3.68 | 37812 | 27809 | 3.607843137 | 37841 | 27838 | 3.538461538 | 37870 | 27867 | 3.504761905 |
| 37755 | 27752 | 3.72972973 | 37784 | 27781 | 3.68 | 37813 | 27810 | 3.607843137 | 37842 | 27839 | 3.538461538 | 37871 | 27868 | 3.504761905 |
| 37756 | 27753 | 3.72972973 | 37785 | 27782 | 3.671361502 | 37814 | 27811 | 3.607843137 | 37843 | 27840 | 3.538461538 | 37872 | 27869 | 3.5 |
| 37757 | 27754 | 3.72972973 | 37786 | 27783 | 3.666666667 | 37815 | 27812 | 3.607843137 | 37844 | 27841 | 3.538461538 | 37873 | 27870 | 3.497076023 |
| 37758 | 27755 | 3.72972973 | 37787 | 27784 | 3.661691542 | 37816 | 27813 | 3.607843137 | 37845 | 27842 | 3.538461538 | 37874 | 27871 | 3.497076023 |
| 37759 | 27756 | 3.723809524 | 37788 | 27785 | 3.659090909 | 37817 | 27814 | 3.601010101 | 37846 | 27843 | 3.538461538 | 37875 | 27872 | 3.495098039 |
| 37760 | 27757 | 3.721682848 | 37789 | 27786 | 3.650793651 | 37818 | 27815 | 3.596707819 | 37847 | 27844 | 3.538461538 | 37876 | 27873 | 3.491749175 |
| 37761 | 27758 | 3.717171717 | 37790 | 27787 | 3.650793651 | 37819 | 27816 | 3.588652482 | 37848 | 27845 | 3.538461538 | 37877 | 27874 | 3.490514905 |
| 37762 | 27759 | 3.717171717 | 37791 | 27788 | 3.650793651 | 37820 | 27817 | 3.588652482 | 37849 | 27846 | 3.538461538 | 37878 | 27875 | 3.487581699 |
| 37763 | 27760 | 3.717171717 | 37792 | 27789 | 3.650793651 | 37821 | 27818 | 3.588652482 | 37850 | 27847 | 3.538461538 | 37879 | 27876 | 3.484848485 |
| 37764 | 27761 | 3.717171717 | 37793 | 27790 | 3.650793651 | 37822 | 27819 | 3.584415584 | 37851 | 27848 | 3.538461538 | 37880 | 27877 | 3.484848485 |
| 37765 | 27762 | 3.717171717 | 37794 | 27791 | 3.650793651 | 37823 | 27820 | 3.582554517 | 37852 | 27849 | 3.538461538 | 37881 | 27878 | 3.484848485 |

FIG. 6 (Cont.)

| DNA SEQ ID NO | AA SEQ ID NO | Kidney 1 Enrichment |
|---|---|---|
| 37882 | 27879 | 3.484848485 |
| 37883 | 27880 | 3.484848485 |
| 37884 | 27881 | 3.484848485 |
| 37885 | 27882 | 3.484848485 |
| 37886 | 27883 | 3.471698113 |
| 37887 | 27884 | 3.471698113 |
| 37888 | 27885 | 3.471698113 |
| 37889 | 27886 | 3.462365591 |
| 37890 | 27887 | 3.462365591 |
| 37891 | 27888 | 3.462365591 |
| 37892 | 27889 | 3.462365591 |
| 37893 | 27890 | 3.462365591 |
| 37894 | 27891 | 3.462365591 |
| 37895 | 27892 | 3.462365591 |
| 37896 | 27893 | 3.462365591 |
| 37897 | 27894 | 3.462365591 |
| 37898 | 27895 | 3.455399061 |
| 37899 | 27896 | 3.453453453 |
| 37900 | 27897 | 3.45 |
| 37901 | 27898 | 3.45 |
| 37902 | 27899 | 3.45 |
| 37903 | 27900 | 3.45 |
| 37904 | 27901 | 3.45 |
| 37905 | 27902 | 3.45 |
| 37906 | 27903 | 3.445692884 |
| 37907 | 27904 | 3.445692884 |
| 37908 | 27905 | 3.444444444 |
| 37909 | 27906 | 3.436781609 |
| 37910 | 27907 | 3.436781609 |

| DNA SEQ ID NO | AA SEQ ID NO | Kidney 1 Enrichment |
|---|---|---|
| 37911 | 27908 | 3.436781609 |
| 37912 | 27909 | 3.434666667 |
| 37913 | 27910 | 3.432835821 |
| 37914 | 27911 | 3.429824561 |
| 37915 | 27912 | 3.429824561 |
| 37916 | 27913 | 3.42745098 |
| 37917 | 27914 | 3.425531915 |
| 37918 | 27915 | 3.407407407 |
| 37919 | 27916 | 3.407407407 |
| 37920 | 27917 | 3.407407407 |
| 37921 | 27918 | 3.407407407 |
| 37922 | 27919 | 3.407407407 |
| 37923 | 27920 | 3.407407407 |
| 37924 | 27921 | 3.407407407 |
| 37925 | 27922 | 3.407407407 |
| 37926 | 27923 | 3.407407407 |
| 37927 | 27924 | 3.407407407 |
| 37928 | 27925 | 3.407407407 |
| 37929 | 27926 | 3.407407407 |
| 37930 | 27927 | 3.407407407 |
| 37931 | 27928 | 3.407407407 |
| 37932 | 27929 | 3.407407407 |
| 37933 | 27930 | 3.407407407 |
| 37934 | 27931 | 3.407407407 |
| 37935 | 27932 | 3.407407407 |
| 37936 | 27933 | 3.407407407 |
| 37937 | 27934 | 3.407407407 |
| 37938 | 27935 | 3.407407407 |
| 37939 | 27936 | 3.407407407 |

| DNA SEQ ID NO | AA SEQ ID NO | Kidney 1 Enrichment |
|---|---|---|
| 37940 | 27937 | 3.407407407 |
| 37941 | 27938 | 3.407407407 |
| 37942 | 27939 | 3.407407407 |
| 37943 | 27940 | 3.407407407 |
| 37944 | 27941 | 3.407407407 |
| 37945 | 27942 | 3.407407407 |
| 37946 | 27943 | 3.389473684 |
| 37947 | 27944 | 3.382352941 |
| 37948 | 27945 | 3.378531073 |
| 37949 | 27946 | 3.378531073 |
| 37950 | 27947 | 3.373333333 |
| 37951 | 27948 | 3.373333333 |
| 37952 | 27949 | 3.373333333 |
| 37953 | 27950 | 3.36996337 |
| 37954 | 27951 | 3.365853659 |
| 37955 | 27952 | 3.365853659 |
| 37956 | 27953 | 3.365853659 |
| 37957 | 27954 | 3.360730594 |
| 37958 | 27955 | 3.360730594 |
| 37959 | 27956 | 3.354166667 |
| 37960 | 27957 | 3.354166667 |
| 37961 | 27958 | 3.354166667 |
| 37962 | 27959 | 3.354166667 |
| 37963 | 27960 | 3.354166667 |
| 37964 | 27961 | 3.354166667 |
| 37965 | 27962 | 3.354166667 |
| 37966 | 27963 | 3.354166667 |
| 37967 | 27964 | 3.354166667 |
| 37968 | 27965 | 3.354166667 |

| DNA SEQ ID NO | AA SEQ ID NO | Kidney 1 Enrichment |
|---|---|---|
| 37969 | 27966 | 3.350140056 |
| 37970 | 27967 | 3.348659004 |
| 37971 | 27968 | 3.345454545 |
| 37972 | 27969 | 3.345454545 |
| 37973 | 27970 | 3.345454545 |
| 37974 | 27971 | 3.341880342 |
| 37975 | 27972 | 3.341880342 |
| 37976 | 27973 | 3.341880342 |
| 37977 | 27974 | 3.333333333 |
| 37978 | 27975 | 3.333333333 |
| 37979 | 27976 | 3.333333333 |
| 37980 | 27977 | 3.333333333 |
| 37981 | 27978 | 3.333333333 |
| 37982 | 27979 | 3.333333333 |
| 37983 | 27980 | 3.333333333 |
| 37984 | 27981 | 3.333333333 |
| 37985 | 27982 | 3.328947368 |
| 37986 | 27983 | 3.325301205 |
| 37987 | 27984 | 3.322222222 |
| 37988 | 27985 | 3.322222222 |
| 37989 | 27986 | 3.319587629 |
| 37990 | 27987 | 3.319587629 |
| 37991 | 27988 | 3.315315315 |
| 37992 | 27989 | 3.315315315 |
| 37993 | 27990 | 3.315315315 |
| 37994 | 27991 | 3.315315315 |
| 37995 | 27992 | 3.310606061 |
| 37996 | 27993 | 3.307189542 |
| 37997 | 27994 | 3.307189542 |

| DNA SEQ ID NO | AA SEQ ID NO | Kidney 1 Enrichment |
|---|---|---|
| 37998 | 27995 | 3.307189542 |
| 37999 | 27996 | 3.307189542 |
| 38000 | 27997 | 3.307189542 |
| 38001 | 27998 | 3.302564103 |
| 38002 | 27999 | 3.302564103 |
| 38003 | 28000 | 3.300925926 |
| 38004 | 28001 | 3.297491039 |
| 38005 | 28002 | 3.285714286 |
| 38006 | 28003 | 3.285714286 |
| 38007 | 28004 | 3.285714286 |
| 38008 | 28005 | 3.285714286 |
| 38009 | 28006 | 3.285714286 |
| 38010 | 28007 | 3.285714286 |
| 38011 | 28008 | 3.285714286 |
| 38012 | 28009 | 3.285714286 |
| 38013 | 28010 | 3.285714286 |
| 38014 | 28011 | 3.285714286 |
| 38015 | 28012 | 3.285714286 |
| 38016 | 28013 | 3.285714286 |
| 38017 | 28014 | 3.285714286 |
| 38018 | 28015 | 3.285714286 |
| 38019 | 28016 | 3.285714286 |
| 38020 | 28017 | 3.285714286 |
| 38021 | 28018 | 3.285714286 |
| 38022 | 28019 | 3.275080906 |
| 38023 | 28020 | 3.27340824 |
| 38024 | 28021 | 3.27340824 |
| 38025 | 28022 | 3.267759563 |
| 38026 | 28023 | 3.262411348 |

FIG. 6 (Cont.)

| DNA SEQ ID NO | AA SEQ ID NO | Kidney 1 Enrichment |
|---|---|---|
| 38027 | 28024 | 3.262411348 |
| 38028 | 28025 | 3.262411348 |
| 38029 | 28026 | 3.262411348 |
| 38030 | 28027 | 3.262411348 |
| 38031 | 28028 | 3.262411348 |
| 38032 | 28029 | 3.25984252 |
| 38033 | 28030 | 3.258333333 |
| 38034 | 28031 | 3.258333333 |
| 38035 | 28032 | 3.258333333 |
| 38036 | 28033 | 3.258333333 |
| 38037 | 28034 | 3.256637168 |
| 38038 | 28035 | 3.252525253 |
| 38039 | 28036 | 3.247058824 |
| 38040 | 28037 | 3.243589744 |
| 38041 | 28038 | 3.23943662 |
| 38042 | 28039 | 3.23943662 |
| 38043 | 28040 | 3.237037037 |
| 38044 | 28041 | 3.234375 |
| 38045 | 28042 | 3.234375 |
| 38046 | 28043 | 3.228070175 |
| 38047 | 28044 | 3.228070175 |
| 38048 | 28045 | 3.228070175 |
| 38049 | 28046 | 3.228070175 |
| 38050 | 28047 | 3.228070175 |
| 38051 | 28048 | 3.228070175 |
| 38052 | 28049 | 3.228070175 |
| 38053 | 28050 | 3.228070175 |
| 38054 | 28051 | 3.228070175 |
| 38055 | 28052 | 3.228070175 |

| DNA SEQ ID NO | AA SEQ ID NO | Kidney 1 Enrichment |
|---|---|---|
| 38056 | 28053 | 3.228070175 |
| 38057 | 28054 | 3.228070175 |
| 38058 | 28055 | 3.228070175 |
| 38059 | 28056 | 3.228070175 |
| 38060 | 28057 | 3.221288515 |
| 38061 | 28058 | 3.218106996 |
| 38062 | 28059 | 3.218106996 |
| 38063 | 28060 | 3.218106996 |
| 38064 | 28061 | 3.215053763 |
| 38065 | 28062 | 3.209302326 |
| 38066 | 28063 | 3.209302326 |
| 38067 | 28064 | 3.2039801 |
| 38068 | 28065 | 3.2039801 |
| 38069 | 28066 | 3.201465201 |
| 38070 | 28067 | 3.194444444 |
| 38071 | 28068 | 3.194444444 |
| 38072 | 28069 | 3.194444444 |
| 38073 | 28070 | 3.194444444 |
| 38074 | 28071 | 3.194444444 |
| 38075 | 28072 | 3.194444444 |
| 38076 | 28073 | 3.188118812 |
| 38077 | 28074 | 3.186147186 |
| 38078 | 28075 | 3.186147186 |
| 38079 | 28076 | 3.186147186 |
| 38080 | 28077 | 3.184615385 |
| 38081 | 28078 | 3.182389937 |
| 38082 | 28079 | 3.182389937 |
| 38083 | 28080 | 3.182389937 |
| 38084 | 28081 | 3.178861789 |

| DNA SEQ ID NO | AA SEQ ID NO | Kidney 1 Enrichment |
|---|---|---|
| 38085 | 28082 | 3.178861789 |
| 38086 | 28083 | 3.176190476 |
| 38087 | 28084 | 3.172413793 |
| 38088 | 28085 | 3.172413793 |
| 38089 | 28086 | 3.172413793 |
| 38090 | 28087 | 3.172413793 |
| 38091 | 28088 | 3.172413793 |
| 38092 | 28089 | 3.166666667 |
| 38093 | 28090 | 3.164021164 |
| 38094 | 28091 | 3.164021164 |
| 38095 | 28092 | 3.164021164 |
| 38096 | 28093 | 3.161512027 |
| 38097 | 28094 | 3.156862745 |
| 38098 | 28095 | 3.156862745 |
| 38099 | 28096 | 3.156862745 |
| 38100 | 28097 | 3.156862745 |
| 38101 | 28098 | 3.156862745 |
| 38102 | 28099 | 3.156862745 |
| 38103 | 28100 | 3.152647975 |
| 38104 | 28101 | 3.150684932 |
| 38105 | 28102 | 3.145299145 |
| 38106 | 28103 | 3.145299145 |
| 38107 | 28104 | 3.145299145 |
| 38108 | 28105 | 3.145299145 |
| 38109 | 28106 | 3.145299145 |
| 38110 | 28107 | 3.140562249 |
| 38111 | 28108 | 3.139107612 |
| 38112 | 28109 | 3.136363636 |
| 38113 | 28110 | 3.136363636 |

| DNA SEQ ID NO | AA SEQ ID NO | Kidney 1 Enrichment |
|---|---|---|
| 38114 | 28111 | 3.129251701 |
| 38115 | 28112 | 3.129251701 |
| 38116 | 28113 | 3.129251701 |
| 38117 | 28114 | 3.129251701 |
| 38118 | 28115 | 3.12345679 |
| 38119 | 28116 | 3.12345679 |
| 38120 | 28117 | 3.12345679 |
| 38121 | 28118 | 3.118644068 |
| 38122 | 28119 | 3.118644068 |
| 38123 | 28120 | 3.114583333 |
| 38124 | 28121 | 3.111111111 |
| 38125 | 28122 | 3.108108108 |
| 38126 | 28123 | 3.108108108 |
| 38127 | 28124 | 3.105485232 |
| 38128 | 28125 | 3.105485232 |
| 38129 | 28126 | 3.103174603 |
| 38130 | 28127 | 3.103174603 |
| 38131 | 28128 | 3.101123596 |
| 38132 | 28129 | 3.09929078 |
| 38133 | 28130 | 3.09929078 |
| 38134 | 28131 | 3.097643098 |
| 38135 | 28132 | 3.090439276 |
| 38136 | 28133 | 3.089552239 |
| 38137 | 28134 | 3.066666667 |
| 38138 | 28135 | 3.066666667 |
| 38139 | 28136 | 3.066666667 |
| 38140 | 28137 | 3.066666667 |
| 38141 | 28138 | 3.066666667 |
| 38142 | 28139 | 3.066666667 |

| DNA SEQ ID NO | AA SEQ ID NO | Kidney 1 Enrichment |
|---|---|---|
| 38143 | 28140 | 3.066666667 |
| 38144 | 28141 | 3.066666667 |
| 38145 | 28142 | 3.066666667 |
| 38146 | 28143 | 3.066666667 |
| 38147 | 28144 | 3.066666667 |
| 38148 | 28145 | 3.066666667 |
| 38149 | 28146 | 3.066666667 |
| 38150 | 28147 | 3.066666667 |
| 38151 | 28148 | 3.066666667 |
| 38152 | 28149 | 3.066666667 |
| 38153 | 28150 | 3.066666667 |
| 38154 | 28151 | 3.066666667 |
| 38155 | 28152 | 3.066666667 |
| 38156 | 28153 | 3.066666667 |
| 38157 | 28154 | 3.066666667 |
| 38158 | 28155 | 3.066666667 |
| 38159 | 28156 | 3.066666667 |
| 38160 | 28157 | 3.066666667 |
| 38161 | 28158 | 3.066666667 |
| 38162 | 28159 | 3.066666667 |
| 38163 | 28160 | 3.066666667 |
| 38164 | 28161 | 3.066666667 |
| 38165 | 28162 | 3.066666667 |
| 38166 | 28163 | 3.066666667 |
| 38167 | 28164 | 3.066666667 |
| 38168 | 28165 | 3.066666667 |
| 38169 | 28166 | 3.066666667 |
| 38170 | 28167 | 3.066666667 |
| 38171 | 28168 | 3.066666667 |

FIG. 6 (Cont.)

| DNA SEQ ID NO | AA SEQ ID NO | Kidney 1 Enrichment |
|---|---|---|
| 38172 | 28169 | 3.066666667 |
| 38173 | 28170 | 3.066666667 |
| 38174 | 28171 | 3.066666667 |
| 38175 | 28172 | 3.066666667 |
| 38176 | 28173 | 3.066666667 |
| 38177 | 28174 | 3.066666667 |
| 38178 | 28175 | 3.066666667 |
| 38179 | 28176 | 3.066666667 |
| 38180 | 28177 | 3.066666667 |
| 38181 | 28178 | 3.066666667 |
| 38182 | 28179 | 3.066666667 |
| 38183 | 28180 | 3.066666667 |
| 38184 | 28181 | 3.066666667 |
| 38185 | 28182 | 3.066666667 |
| 38186 | 28183 | 3.066666667 |
| 38187 | 28184 | 3.066666667 |
| 38188 | 28185 | 3.066666667 |
| 38189 | 28186 | 3.031007752 |
| 38190 | 28187 | 3.031007752 |
| 38191 | 28188 | 3.028806584 |
| 38192 | 28189 | 3.028806584 |
| 38193 | 28190 | 3.026315789 |
| 38194 | 28191 | 3.026315789 |
| 38195 | 28192 | 3.026315789 |
| 38196 | 28193 | 3.023474178 |
| 38197 | 28194 | 3.023474178 |
| 38198 | 28195 | 3.02020202 |
| 38199 | 28196 | 3.016393443 |
| 38200 | 28197 | 3.011904762 |

| DNA SEQ ID NO | AA SEQ ID NO | Kidney 1 Enrichment |
|---|---|---|
| 38201 | 28198 | 3.011904762 |
| 38202 | 28199 | 3.011904762 |
| 38203 | 28200 | 3.011904762 |
| 38204 | 28201 | 3.011904762 |
| 38205 | 28202 | 3.006535948 |
| 38206 | 28203 | 3.006535948 |
| 38207 | 28204 | 3.006535948 |
| 38208 | 28205 | 3.006535948 |
| 38209 | 28206 | 3 |
| 38210 | 28207 | 3 |
| 38211 | 28208 | 3 |
| 38212 | 28209 | 3 |
| 38213 | 28210 | 3 |
| 38214 | 28211 | 3 |
| 38215 | 28212 | 3 |
| 38216 | 28213 | 3 |
| 38217 | 28214 | 3 |
| 38218 | 28215 | 2.996168582 |
| 38219 | 28216 | 2.991869919 |
| 38220 | 28217 | 2.991869919 |
| 38221 | 28218 | 2.991869919 |
| 38222 | 28219 | 2.991869919 |
| 38223 | 28220 | 2.991869919 |
| 38224 | 28221 | 2.991869919 |
| 38225 | 28222 | 2.991869919 |
| 38226 | 28223 | 2.991869919 |
| 38227 | 28224 | 2.991869919 |
| 38228 | 28225 | 2.988700565 |
| 38229 | 28226 | 2.987012987 |

| DNA SEQ ID NO | AA SEQ ID NO | Kidney 1 Enrichment |
|---|---|---|
| 38230 | 28227 | 2.987012987 |
| 38231 | 28228 | 2.981481481 |
| 38232 | 28229 | 2.981481481 |
| 38233 | 28230 | 2.981481481 |
| 38234 | 28231 | 2.981481481 |
| 38235 | 28232 | 2.981481481 |
| 38236 | 28233 | 2.975124378 |
| 38237 | 28234 | 2.972789116 |
| 38238 | 28235 | 2.971576227 |
| 38239 | 28236 | 2.971576227 |
| 38240 | 28237 | 2.967741935 |
| 38241 | 28238 | 2.967741935 |
| 38242 | 28239 | 2.967741935 |
| 38243 | 28240 | 2.967741935 |
| 38244 | 28241 | 2.967741935 |
| 38245 | 28242 | 2.967741935 |
| 38246 | 28243 | 2.967741935 |
| 38247 | 28244 | 2.967741935 |
| 38248 | 28245 | 2.967741935 |
| 38249 | 28246 | 2.962121212 |
| 38250 | 28247 | 2.959064327 |
| 38251 | 28248 | 2.955823293 |
| 38252 | 28249 | 2.955823293 |
| 38253 | 28250 | 2.955823293 |
| 38254 | 28251 | 2.955823293 |
| 38255 | 28252 | 2.95412844 |
| 38256 | 28253 | 2.948717949 |
| 38257 | 28254 | 2.948717949 |
| 38258 | 28255 | 2.948717949 |

| DNA SEQ ID NO | AA SEQ ID NO | Kidney 1 Enrichment |
|---|---|---|
| 38259 | 28256 | 2.948717949 |
| 38260 | 28257 | 2.948717949 |
| 38261 | 28258 | 2.948717949 |
| 38262 | 28259 | 2.948717949 |
| 38263 | 28260 | 2.948717949 |
| 38264 | 28261 | 2.948717949 |
| 38265 | 28262 | 2.948717949 |
| 38266 | 28263 | 2.948717949 |
| 38267 | 28264 | 2.948717949 |
| 38268 | 28265 | 2.944 |
| 38269 | 28266 | 2.942760943 |
| 38270 | 28267 | 2.942760943 |
| 38271 | 28268 | 2.940639269 |
| 38272 | 28269 | 2.940639269 |
| 38273 | 28270 | 2.938888889 |
| 38274 | 28271 | 2.936170213 |
| 38275 | 28272 | 2.936170213 |
| 38276 | 28273 | 2.936170213 |
| 38277 | 28274 | 2.936170213 |
| 38278 | 28275 | 2.936170213 |
| 38279 | 28276 | 2.936170213 |
| 38280 | 28277 | 2.931372549 |
| 38281 | 28278 | 2.927272727 |
| 38282 | 28279 | 2.920634921 |
| 38283 | 28280 | 2.920634921 |
| 38284 | 28281 | 2.920634921 |
| 38285 | 28282 | 2.920634921 |
| 38286 | 28283 | 2.920634921 |
| 38287 | 28284 | 2.920634921 |

| DNA SEQ ID NO | AA SEQ ID NO | Kidney 1 Enrichment |
|---|---|---|
| 38288 | 28285 | 2.920634921 |
| 38289 | 28286 | 2.920634921 |
| 38290 | 28287 | 2.920634921 |
| 38291 | 28288 | 2.920634921 |
| 38292 | 28289 | 2.920634921 |
| 38293 | 28290 | 2.920634921 |
| 38294 | 28291 | 2.920634921 |
| 38295 | 28292 | 2.920634921 |
| 38296 | 28293 | 2.920634921 |
| 38297 | 28294 | 2.920634921 |
| 38298 | 28295 | 2.920634921 |
| 38299 | 28296 | 2.920634921 |
| 38300 | 28297 | 2.920634921 |
| 38301 | 28298 | 2.920634921 |
| 38302 | 28299 | 2.920634921 |
| 38303 | 28300 | 2.913333333 |
| 38304 | 28301 | 2.911392405 |
| 38305 | 28302 | 2.911392405 |
| 38306 | 28303 | 2.911392405 |
| 38307 | 28304 | 2.905263158 |
| 38308 | 28305 | 2.905263158 |
| 38309 | 28306 | 2.900900901 |
| 38310 | 28307 | 2.900900901 |
| 38311 | 28308 | 2.900900901 |
| 38312 | 28309 | 2.900900901 |
| 38313 | 28310 | 2.896296296 |
| 38314 | 28311 | 2.896296296 |
| 38315 | 28312 | 2.893081761 |
| 38316 | 28313 | 2.893081761 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 38317 | 28314 | 2.893081761 | 38346 | 28343 | 2.875 | 38375 | 28372 | 2.839506173 | 38404 | 28401 | 2.807511737 | 38433 | 28430 | 2.787878788 |
| 38318 | 28315 | 2.893081761 | 38347 | 28344 | 2.864468864 | 38376 | 28373 | 2.834733894 | 38405 | 28402 | 2.807511737 | 38434 | 28431 | 2.787878788 |
| 38319 | 28316 | 2.893081761 | 38348 | 28345 | 2.862222222 | 38377 | 28374 | 2.830769231 | 38406 | 28403 | 2.807511737 | 38435 | 28432 | 2.787878788 |
| 38320 | 28317 | 2.893081761 | 38349 | 28346 | 2.862222222 | 38378 | 28375 | 2.830769231 | 38407 | 28404 | 2.807511737 | 38436 | 28433 | 2.787878788 |
| 38321 | 28318 | 2.888888889 | 38350 | 28347 | 2.862222222 | 38379 | 28376 | 2.830769231 | 38408 | 28405 | 2.807511737 | 38437 | 28434 | 2.787878788 |
| 38322 | 28319 | 2.888888889 | 38351 | 28348 | 2.862222222 | 38380 | 28377 | 2.830769231 | 38409 | 28406 | 2.802867384 | 38438 | 28435 | 2.787878788 |
| 38323 | 28320 | 2.888888889 | 38352 | 28349 | 2.858757062 | 38381 | 28378 | 2.830769231 | 38410 | 28407 | 2.801282051 | 38439 | 28436 | 2.787878788 |
| 38324 | 28321 | 2.884488449 | 38353 | 28350 | 2.858757062 | 38382 | 28379 | 2.824561404 | 38411 | 28408 | 2.8 | 38440 | 28437 | 2.787878788 |
| 38325 | 28322 | 2.875 | 38354 | 28351 | 2.858757062 | 38383 | 28380 | 2.824561404 | 38412 | 28409 | 2.792668958 | 38441 | 28438 | 2.787878788 |
| 38326 | 28323 | 2.875 | 38355 | 28352 | 2.858757062 | 38384 | 28381 | 2.824561404 | 38413 | 28410 | 2.787878788 | 38442 | 28439 | 2.787878788 |
| 38327 | 28324 | 2.875 | 38356 | 28353 | 2.858757062 | 38385 | 28382 | 2.824561404 | 38414 | 28411 | 2.787878788 | 38443 | 28440 | 2.787878788 |
| 38328 | 28325 | 2.875 | 38357 | 28354 | 2.858757062 | 38386 | 28383 | 2.824561404 | 38415 | 28412 | 2.787878788 | 38444 | 28441 | 2.77212806 |
| 38329 | 28326 | 2.875 | 38358 | 28355 | 2.858757062 | 38387 | 28384 | 2.824561404 | 38416 | 28413 | 2.787878788 | 38445 | 28442 | 2.768518519 |
| 38330 | 28327 | 2.875 | 38359 | 28356 | 2.852713178 | 38388 | 28385 | 2.821333333 | 38417 | 28414 | 2.787878788 | 38446 | 28443 | 2.765027322 |
| 38331 | 28328 | 2.875 | 38360 | 28357 | 2.852713178 | 38389 | 28386 | 2.819923372 | 38418 | 28415 | 2.787878788 | 38447 | 28444 | 2.765027322 |
| 38332 | 28329 | 2.875 | 38361 | 28358 | 2.852713178 | 38390 | 28387 | 2.819923372 | 38419 | 28416 | 2.787878788 | 38448 | 28445 | 2.76 |
| 38333 | 28330 | 2.875 | 38362 | 28359 | 2.852713178 | 38391 | 28388 | 2.816326531 | 38420 | 28417 | 2.787878788 | 38449 | 28446 | 2.76 |
| 38334 | 28331 | 2.875 | 38363 | 28360 | 2.852713178 | 38392 | 28389 | 2.816326531 | 38421 | 28418 | 2.787878788 | 38450 | 28447 | 2.76 |
| 38335 | 28332 | 2.875 | 38364 | 28361 | 2.847619048 | 38393 | 28390 | 2.816326531 | 38422 | 28419 | 2.787878788 | 38451 | 28448 | 2.76 |
| 38336 | 28333 | 2.875 | 38365 | 28362 | 2.847619048 | 38394 | 28391 | 2.816326531 | 38423 | 28420 | 2.787878788 | 38452 | 28449 | 2.76 |
| 38337 | 28334 | 2.875 | 38366 | 28363 | 2.847619048 | 38395 | 28392 | 2.816326531 | 38424 | 28421 | 2.787878788 | 38453 | 28450 | 2.76 |
| 38338 | 28335 | 2.875 | 38367 | 28364 | 2.845360825 | 38396 | 28393 | 2.816326531 | 38425 | 28422 | 2.787878788 | 38454 | 28451 | 2.76 |
| 38339 | 28336 | 2.875 | 38368 | 28365 | 2.839506173 | 38397 | 28394 | 2.816326531 | 38426 | 28423 | 2.787878788 | 38455 | 28452 | 2.76 |
| 38340 | 28337 | 2.875 | 38369 | 28366 | 2.839506173 | 38398 | 28395 | 2.811111111 | 38427 | 28424 | 2.787878788 | 38456 | 28453 | 2.757793765 |
| 38341 | 28338 | 2.875 | 38370 | 28367 | 2.839506173 | 38399 | 28396 | 2.811111111 | 38428 | 28425 | 2.787878788 | 38457 | 28454 | 2.756554307 |
| 38342 | 28339 | 2.875 | 38371 | 28368 | 2.839506173 | 38400 | 28397 | 2.811111111 | 38429 | 28426 | 2.787878788 | 38458 | 28455 | 2.752136752 |
| 38343 | 28340 | 2.875 | 38372 | 28369 | 2.839506173 | 38401 | 28398 | 2.811111111 | 38430 | 28427 | 2.787878788 | 38459 | 28456 | 2.752136752 |
| 38344 | 28341 | 2.875 | 38373 | 28370 | 2.839506173 | 38402 | 28399 | 2.807511737 | 38431 | 28428 | 2.787878788 | 38460 | 28457 | 2.752136752 |
| 38345 | 28342 | 2.875 | 38374 | 28371 | 2.839506173 | 38403 | 28400 | 2.807511737 | 38432 | 28429 | 2.787878788 | 38461 | 28458 | 2.752136752 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 38462 | 28459 | 2.752136752 | 38491 | 28488 | 2.705882353 | 38520 | 28517 | 2.683333333 | 38549 | 28546 | 2.653846154 | 38578 | 28575 | 2.628571429 |
| 38463 | 28460 | 2.752136752 | 38492 | 28489 | 2.705882353 | 38521 | 28518 | 2.683333333 | 38550 | 28547 | 2.653846154 | 38579 | 28576 | 2.628571429 |
| 38464 | 28461 | 2.752136752 | 38493 | 28490 | 2.705882353 | 38522 | 28519 | 2.683333333 | 38551 | 28548 | 2.653846154 | 38580 | 28577 | 2.628571429 |
| 38465 | 28462 | 2.752136752 | 38494 | 28491 | 2.705882353 | 38523 | 28520 | 2.683333333 | 38552 | 28549 | 2.653846154 | 38581 | 28578 | 2.628571429 |
| 38466 | 28463 | 2.746268657 | 38495 | 28492 | 2.705882353 | 38524 | 28521 | 2.677248677 | 38553 | 28550 | 2.653846154 | 38582 | 28579 | 2.628571429 |
| 38467 | 28464 | 2.746268657 | 38496 | 28493 | 2.705882353 | 38525 | 28522 | 2.677248677 | 38554 | 28551 | 2.653846154 | 38583 | 28580 | 2.628571429 |
| 38468 | 28465 | 2.743859649 | 38497 | 28494 | 2.705882353 | 38526 | 28523 | 2.674418605 | 38555 | 28552 | 2.653846154 | 38584 | 28581 | 2.628571429 |
| 38469 | 28466 | 2.742547425 | 38498 | 28495 | 2.705882353 | 38527 | 28524 | 2.666666667 | 38556 | 28553 | 2.653846154 | 38585 | 28582 | 2.628571429 |
| 38470 | 28467 | 2.741154562 | 38499 | 28496 | 2.705882353 | 38528 | 28525 | 2.666666667 | 38557 | 28554 | 2.652252252 | 38586 | 28583 | 2.628571429 |
| 38471 | 28468 | 2.738095238 | 38500 | 28497 | 2.705882353 | 38529 | 28526 | 2.666666667 | 38558 | 28555 | 2.651629073 | 38587 | 28584 | 2.628571429 |
| 38472 | 28469 | 2.738095238 | 38501 | 28498 | 2.705882353 | 38530 | 28527 | 2.666666667 | 38559 | 28556 | 2.650205761 | 38588 | 28585 | 2.628571429 |
| 38473 | 28470 | 2.738095238 | 38502 | 28499 | 2.705882353 | 38531 | 28528 | 2.666666667 | 38560 | 28557 | 2.650205761 | 38589 | 28586 | 2.626151013 |
| 38474 | 28471 | 2.732673267 | 38503 | 28500 | 2.705882353 | 38532 | 28529 | 2.666666667 | 38561 | 28558 | 2.650205761 | 38590 | 28587 | 2.624624625 |
| 38475 | 28472 | 2.730593607 | 38504 | 28501 | 2.705882353 | 38533 | 28530 | 2.666666667 | 38562 | 28559 | 2.650205761 | 38591 | 28588 | 2.617886179 |
| 38476 | 28473 | 2.730593607 | 38505 | 28502 | 2.705882353 | 38534 | 28531 | 2.666666667 | 38563 | 28560 | 2.643678161 | 38592 | 28589 | 2.617886179 |
| 38477 | 28474 | 2.730593607 | 38506 | 28503 | 2.699530516 | 38535 | 28532 | 2.666666667 | 38564 | 28561 | 2.643678161 | 38593 | 28590 | 2.617886179 |
| 38478 | 28475 | 2.730593607 | 38507 | 28504 | 2.697530864 | 38536 | 28533 | 2.666666667 | 38565 | 28562 | 2.643678161 | 38594 | 28591 | 2.617886179 |
| 38479 | 28476 | 2.725925926 | 38508 | 28505 | 2.695970696 | 38537 | 28534 | 2.666666667 | 38566 | 28563 | 2.643678161 | 38595 | 28592 | 2.617886179 |
| 38480 | 28477 | 2.725925926 | 38509 | 28506 | 2.693693694 | 38538 | 28535 | 2.666666667 | 38567 | 28564 | 2.643678161 | 38596 | 28593 | 2.613636364 |
| 38481 | 28478 | 2.720430108 | 38510 | 28507 | 2.69005848 | 38539 | 28536 | 2.666666667 | 38568 | 28565 | 2.643678161 | 38597 | 28594 | 2.609929078 |
| 38482 | 28479 | 2.720430108 | 38511 | 28508 | 2.69005848 | 38540 | 28537 | 2.666666667 | 38569 | 28566 | 2.643678161 | 38598 | 28595 | 2.609929078 |
| 38483 | 28480 | 2.705882353 | 38512 | 28509 | 2.69005848 | 38541 | 28538 | 2.666666667 | 38570 | 28567 | 2.643678161 | 38599 | 28596 | 2.609929078 |
| 38484 | 28481 | 2.705882353 | 38513 | 28510 | 2.69005848 | 38542 | 28539 | 2.666666667 | 38571 | 28568 | 2.637992832 | 38600 | 28597 | 2.609929078 |
| 38485 | 28482 | 2.705882353 | 38514 | 28511 | 2.69005848 | 38543 | 28540 | 2.666666667 | 38572 | 28569 | 2.635416667 | 38601 | 28598 | 2.609929078 |
| 38486 | 28483 | 2.705882353 | 38515 | 28512 | 2.69005848 | 38544 | 28541 | 2.657777778 | 38573 | 28570 | 2.635416667 | 38602 | 28599 | 2.606666667 |
| 38487 | 28484 | 2.705882353 | 38516 | 28513 | 2.69005848 | 38545 | 28542 | 2.657777778 | 38574 | 28571 | 2.635416667 | 38603 | 28600 | 2.603773585 |
| 38488 | 28485 | 2.705882353 | 38517 | 28514 | 2.69005848 | 38546 | 28543 | 2.653846154 | 38575 | 28572 | 2.628571429 | 38604 | 28601 | 2.603773585 |
| 38489 | 28486 | 2.705882353 | 38518 | 28515 | 2.69005848 | 38547 | 28544 | 2.653846154 | 38576 | 28573 | 2.628571429 | 38605 | 28602 | 2.603773585 |
| 38490 | 28487 | 2.705882353 | 38519 | 28516 | 2.687285223 | 38548 | 28545 | 2.653846154 | 38577 | 28574 | 2.628571429 | 38606 | 28603 | 2.598870056 |

FIG. 6 (Cont.)

| DNA SEQ ID NO | AA SEQ ID NO | Kidney 1 Enrichment |
|---|---|---|
| 38607 | 28604 | 2.597449909 |
| 38608 | 28605 | 2.594871795 |
| 38609 | 28606 | 2.594871795 |
| 38610 | 28607 | 2.594871795 |
| 38611 | 28608 | 2.591549296 |
| 38612 | 28609 | 2.591549296 |
| 38613 | 28610 | 2.591549296 |
| 38614 | 28611 | 2.588744589 |
| 38615 | 28612 | 2.586345382 |
| 38616 | 28613 | 2.586345382 |
| 38617 | 28614 | 2.58245614 |
| 38618 | 28615 | 2.58245614 |
| 38619 | 28616 | 2.580858086 |
| 38620 | 28617 | 2.580858086 |
| 38621 | 28618 | 2.579439252 |
| 38622 | 28619 | 2.579439252 |
| 38623 | 28620 | 2.577030812 |
| 38624 | 28621 | 2.575063613 |
| 38625 | 28622 | 2.575063613 |
| 38626 | 28623 | 2.573426573 |
| 38627 | 28624 | 2.555555556 |
| 38628 | 28625 | 2.555555556 |
| 38629 | 28626 | 2.555555556 |
| 38630 | 28627 | 2.555555556 |
| 38631 | 28628 | 2.555555556 |
| 38632 | 28629 | 2.555555556 |
| 38633 | 28630 | 2.555555556 |
| 38634 | 28631 | 2.555555556 |
| 38635 | 28632 | 2.555555556 |

| DNA SEQ ID NO | AA SEQ ID NO | Kidney 1 Enrichment |
|---|---|---|
| 38636 | 28633 | 2.555555556 |
| 38637 | 28634 | 2.555555556 |
| 38638 | 28635 | 2.555555556 |
| 38639 | 28636 | 2.555555556 |
| 38640 | 28637 | 2.555555556 |
| 38641 | 28638 | 2.555555556 |
| 38642 | 28639 | 2.555555556 |
| 38643 | 28640 | 2.555555556 |
| 38644 | 28641 | 2.555555556 |
| 38645 | 28642 | 2.555555556 |
| 38646 | 28643 | 2.555555556 |
| 38647 | 28644 | 2.555555556 |
| 38648 | 28645 | 2.555555556 |
| 38649 | 28646 | 2.555555556 |
| 38650 | 28647 | 2.555555556 |
| 38651 | 28648 | 2.555555556 |
| 38652 | 28649 | 2.555555556 |
| 38653 | 28650 | 2.555555556 |
| 38654 | 28651 | 2.555555556 |
| 38655 | 28652 | 2.555555556 |
| 38656 | 28653 | 2.555555556 |
| 38657 | 28654 | 2.555555556 |
| 38658 | 28655 | 2.555555556 |
| 38659 | 28656 | 2.555555556 |
| 38660 | 28657 | 2.555555556 |
| 38661 | 28658 | 2.555555556 |
| 38662 | 28659 | 2.555555556 |
| 38663 | 28660 | 2.555555556 |
| 38664 | 28661 | 2.555555556 |

| DNA SEQ ID NO | AA SEQ ID NO | Kidney 1 Enrichment |
|---|---|---|
| 38665 | 28662 | 2.555555556 |
| 38666 | 28663 | 2.555555556 |
| 38667 | 28664 | 2.555555556 |
| 38668 | 28665 | 2.555555556 |
| 38669 | 28666 | 2.555555556 |
| 38670 | 28667 | 2.555555556 |
| 38671 | 28668 | 2.555555556 |
| 38672 | 28669 | 2.555555556 |
| 38673 | 28670 | 2.555555556 |
| 38674 | 28671 | 2.555555556 |
| 38675 | 28672 | 2.555555556 |
| 38676 | 28673 | 2.555555556 |
| 38677 | 28674 | 2.555555556 |
| 38678 | 28675 | 2.555555556 |
| 38679 | 28676 | 2.555555556 |
| 38680 | 28677 | 2.555555556 |
| 38681 | 28678 | 2.555555556 |
| 38682 | 28679 | 2.555555556 |
| 38683 | 28680 | 2.555555556 |
| 38684 | 28681 | 2.555555556 |
| 38685 | 28682 | 2.555555556 |
| 38686 | 28683 | 2.539278132 |
| 38687 | 28684 | 2.536340852 |
| 38688 | 28685 | 2.530744337 |
| 38689 | 28686 | 2.530744337 |
| 38690 | 28687 | 2.529209622 |
| 38691 | 28688 | 2.529209622 |
| 38692 | 28689 | 2.527472527 |
| 38693 | 28690 | 2.525490196 |

| DNA SEQ ID NO | AA SEQ ID NO | Kidney 1 Enrichment |
|---|---|---|
| 38694 | 28691 | 2.525490196 |
| 38695 | 28692 | 2.523206751 |
| 38696 | 28693 | 2.523206751 |
| 38697 | 28694 | 2.520547945 |
| 38698 | 28695 | 2.520547945 |
| 38699 | 28696 | 2.520547945 |
| 38700 | 28697 | 2.520547945 |
| 38701 | 28698 | 2.520547945 |
| 38702 | 28699 | 2.517412935 |
| 38703 | 28700 | 2.517412935 |
| 38704 | 28701 | 2.517412935 |
| 38705 | 28702 | 2.515625 |
| 38706 | 28703 | 2.513661202 |
| 38707 | 28704 | 2.513661202 |
| 38708 | 28705 | 2.513661202 |
| 38709 | 28706 | 2.509090909 |
| 38710 | 28707 | 2.509090909 |
| 38711 | 28708 | 2.509090909 |
| 38712 | 28709 | 2.509090909 |
| 38713 | 28710 | 2.509090909 |
| 38714 | 28711 | 2.506410256 |
| 38715 | 28712 | 2.496124031 |
| 38716 | 28713 | 2.496124031 |
| 38717 | 28714 | 2.496124031 |
| 38718 | 28715 | 2.496124031 |
| 38719 | 28716 | 2.496124031 |
| 38720 | 28717 | 2.496124031 |
| 38721 | 28718 | 2.496124031 |
| 38722 | 28719 | 2.496124031 |

| DNA SEQ ID NO | AA SEQ ID NO | Kidney 1 Enrichment |
|---|---|---|
| 38723 | 28720 | 2.496124031 |
| 38724 | 28721 | 2.493975904 |
| 38725 | 28722 | 2.491666667 |
| 38726 | 28723 | 2.491666667 |
| 38727 | 28724 | 2.491666667 |
| 38728 | 28725 | 2.486486486 |
| 38729 | 28726 | 2.486486486 |
| 38730 | 28727 | 2.486486486 |
| 38731 | 28728 | 2.486486486 |
| 38732 | 28729 | 2.486486486 |
| 38733 | 28730 | 2.486486486 |
| 38734 | 28731 | 2.486486486 |
| 38735 | 28732 | 2.486486486 |
| 38736 | 28733 | 2.480392157 |
| 38737 | 28734 | 2.480392157 |
| 38738 | 28735 | 2.480392157 |
| 38739 | 28736 | 2.478114478 |
| 38740 | 28737 | 2.478114478 |
| 38741 | 28738 | 2.478114478 |
| 38742 | 28739 | 2.478114478 |
| 38743 | 28740 | 2.476190476 |
| 38744 | 28741 | 2.47311828 |
| 38745 | 28742 | 2.46743295 |
| 38746 | 28743 | 2.46743295 |
| 38747 | 28744 | 2.464285714 |
| 38748 | 28745 | 2.464285714 |
| 38749 | 28746 | 2.464285714 |
| 38750 | 28747 | 2.464285714 |
| 38751 | 28748 | 2.464285714 |

FIG. 6 (Cont.)

| DNA SEQ ID NO | AA SEQ ID NO | Kidney 1 Enrichment |
|---|---|---|
| 38752 | 28749 | 2.464285714 |
| 38753 | 28750 | 2.463186078 |
| 38754 | 28751 | 2.46090535 |
| 38755 | 28752 | 2.46090535 |
| 38756 | 28753 | 2.46090535 |
| 38757 | 28754 | 2.46090535 |
| 38758 | 28755 | 2.453333333 |
| 38759 | 28756 | 2.453333333 |
| 38760 | 28757 | 2.453333333 |
| 38761 | 28758 | 2.453333333 |
| 38762 | 28759 | 2.453333333 |
| 38763 | 28760 | 2.453333333 |
| 38764 | 28761 | 2.453333333 |
| 38765 | 28762 | 2.453333333 |
| 38766 | 28763 | 2.453333333 |
| 38767 | 28764 | 2.453333333 |
| 38768 | 28765 | 2.453333333 |
| 38769 | 28766 | 2.453333333 |
| 38770 | 28767 | 2.453333333 |
| 38771 | 28768 | 2.449704142 |
| 38772 | 28769 | 2.449074074 |
| 38773 | 28770 | 2.449074074 |
| 38774 | 28771 | 2.446808511 |
| 38775 | 28772 | 2.444444444 |
| 38776 | 28773 | 2.444444444 |
| 38777 | 28774 | 2.444444444 |
| 38778 | 28775 | 2.444444444 |
| 38779 | 28776 | 2.439393939 |
| 38780 | 28777 | 2.439393939 |
| 38781 | 28778 | 2.439393939 |
| 38782 | 28779 | 2.439393939 |
| 38783 | 28780 | 2.439393939 |
| 38784 | 28781 | 2.433862434 |
| 38785 | 28782 | 2.433862434 |
| 38786 | 28783 | 2.433862434 |
| 38787 | 28784 | 2.430894309 |
| 38788 | 28785 | 2.430894309 |
| 38789 | 28786 | 2.430894309 |
| 38790 | 28787 | 2.430894309 |
| 38791 | 28788 | 2.429042904 |
| 38792 | 28789 | 2.427777778 |
| 38793 | 28790 | 2.426160338 |
| 38794 | 28791 | 2.421052632 |
| 38795 | 28792 | 2.421052632 |
| 38796 | 28793 | 2.421052632 |
| 38797 | 28794 | 2.421052632 |
| 38798 | 28795 | 2.421052632 |
| 38799 | 28796 | 2.421052632 |
| 38800 | 28797 | 2.421052632 |
| 38801 | 28798 | 2.421052632 |
| 38802 | 28799 | 2.421052632 |
| 38803 | 28800 | 2.40952381 |
| 38804 | 28801 | 2.405228758 |
| 38805 | 28802 | 2.405228758 |
| 38806 | 28803 | 2.405228758 |
| 38807 | 28804 | 2.405228758 |
| 38808 | 28805 | 2.405228758 |
| 38809 | 28806 | 2.401606426 |
| 38810 | 28807 | 2.401606426 |
| 38811 | 28808 | 2.4 |
| 38812 | 28809 | 2.395833333 |
| 38813 | 28810 | 2.395833333 |
| 38814 | 28811 | 2.395833333 |
| 38815 | 28812 | 2.395833333 |
| 38816 | 28813 | 2.395833333 |
| 38817 | 28814 | 2.395833333 |
| 38818 | 28815 | 2.395833333 |
| 38819 | 28816 | 2.391437309 |
| 38820 | 28817 | 2.38961039 |
| 38821 | 28818 | 2.38961039 |
| 38822 | 28819 | 2.38961039 |
| 38823 | 28820 | 2.387978142 |
| 38824 | 28821 | 2.387978142 |
| 38825 | 28822 | 2.385185185 |
| 38826 | 28823 | 2.385185185 |
| 38827 | 28824 | 2.385185185 |
| 38828 | 28825 | 2.385185185 |
| 38829 | 28826 | 2.385185185 |
| 38830 | 28827 | 2.385185185 |
| 38831 | 28828 | 2.385185185 |
| 38832 | 28829 | 2.381877023 |
| 38833 | 28830 | 2.379310345 |
| 38834 | 28831 | 2.379310345 |
| 38835 | 28832 | 2.379310345 |
| 38836 | 28833 | 2.379310345 |
| 38837 | 28834 | 2.379310345 |
| 38838 | 28835 | 2.379310345 |
| 38839 | 28836 | 2.379310345 |
| 38840 | 28837 | 2.379310345 |
| 38841 | 28838 | 2.379310345 |
| 38842 | 28839 | 2.375586854 |
| 38843 | 28840 | 2.375586854 |
| 38844 | 28841 | 2.373015873 |
| 38845 | 28842 | 2.373015873 |
| 38846 | 28843 | 2.36969697 |
| 38847 | 28844 | 2.368563686 |
| 38848 | 28845 | 2.368563686 |
| 38849 | 28846 | 2.358974359 |
| 38850 | 28847 | 2.358974359 |
| 38851 | 28848 | 2.358974359 |
| 38852 | 28849 | 2.358974359 |
| 38853 | 28850 | 2.358974359 |
| 38854 | 28851 | 2.358974359 |
| 38855 | 28852 | 2.358974359 |
| 38856 | 28853 | 2.358974359 |
| 38857 | 28854 | 2.358974359 |
| 38858 | 28855 | 2.358974359 |
| 38859 | 28856 | 2.358974359 |
| 38860 | 28857 | 2.358974359 |
| 38861 | 28858 | 2.358974359 |
| 38862 | 28859 | 2.358974359 |
| 38863 | 28860 | 2.358974359 |
| 38864 | 28861 | 2.358974359 |
| 38865 | 28862 | 2.358974359 |
| 38866 | 28863 | 2.358974359 |
| 38867 | 28864 | 2.358974359 |
| 38868 | 28865 | 2.358974359 |
| 38869 | 28866 | 2.358974359 |
| 38870 | 28867 | 2.358974359 |
| 38871 | 28868 | 2.358974359 |
| 38872 | 28869 | 2.358974359 |
| 38873 | 28870 | 2.358974359 |
| 38874 | 28871 | 2.358974359 |
| 38875 | 28872 | 2.358974359 |
| 38876 | 28873 | 2.358974359 |
| 38877 | 28874 | 2.358974359 |
| 38878 | 28875 | 2.358974359 |
| 38879 | 28876 | 2.358974359 |
| 38880 | 28877 | 2.358974359 |
| 38881 | 28878 | 2.358974359 |
| 38882 | 28879 | 2.358974359 |
| 38883 | 28880 | 2.350364964 |
| 38884 | 28881 | 2.348348348 |
| 38885 | 28882 | 2.346938776 |
| 38886 | 28883 | 2.345098039 |
| 38887 | 28884 | 2.342592593 |
| 38888 | 28885 | 2.342592593 |
| 38889 | 28886 | 2.342592593 |
| 38890 | 28887 | 2.340350877 |
| 38891 | 28888 | 2.338983051 |
| 38892 | 28889 | 2.338983051 |
| 38893 | 28890 | 2.338983051 |
| 38894 | 28891 | 2.338983051 |
| 38895 | 28892 | 2.338983051 |
| 38896 | 28893 | 2.338983051 |

FIG. 6 (Cont.)

| DNA SEQ ID NO | AA SEQ ID NO | Kidney 1 Enrichment |
|---|---|---|
| 38897 | 28894 | 2.336507937 |
| 38898 | 28895 | 2.333333333 |
| 38899 | 28896 | 2.333333333 |
| 38900 | 28897 | 2.333333333 |
| 38901 | 28898 | 2.333333333 |
| 38902 | 28899 | 2.333333333 |
| 38903 | 28900 | 2.333333333 |
| 38904 | 28901 | 2.333333333 |
| 38905 | 28902 | 2.333333333 |
| 38906 | 28903 | 2.329113924 |
| 38907 | 28904 | 2.327380952 |
| 38908 | 28905 | 2.327380952 |
| 38909 | 28906 | 2.326436782 |
| 38910 | 28907 | 2.323232323 |
| 38911 | 28908 | 2.323232323 |
| 38912 | 28909 | 2.323232323 |
| 38913 | 28910 | 2.323232323 |
| 38914 | 28911 | 2.323232323 |
| 38915 | 28912 | 2.323232323 |
| 38916 | 28913 | 2.323232323 |
| 38917 | 28914 | 2.323232323 |
| 38918 | 28915 | 2.323232323 |
| 38919 | 28916 | 2.320175439 |
| 38920 | 28917 | 2.317829457 |
| 38921 | 28918 | 2.317829457 |
| 38922 | 28919 | 2.317829457 |
| 38923 | 28920 | 2.315972222 |
| 38924 | 28921 | 2.314465409 |
| 38925 | 28922 | 2.314465409 |
| 38926 | 28923 | 2.314465409 |
| 38927 | 28924 | 2.310502283 |
| 38928 | 28925 | 2.310502283 |
| 38929 | 28926 | 2.310502283 |
| 38930 | 28927 | 2.310502283 |
| 38931 | 28928 | 2.308243728 |
| 38932 | 28929 | 2.308243728 |
| 38933 | 28930 | 2.306784661 |
| 38934 | 28931 | 2.306784661 |
| 38935 | 28932 | 2.306784661 |
| 38936 | 28933 | 2.305010893 |
| 38937 | 28934 | 2.3 |
| 38938 | 28935 | 2.3 |
| 38939 | 28936 | 2.3 |
| 38940 | 28937 | 2.3 |
| 38941 | 28938 | 2.3 |
| 38942 | 28939 | 2.3 |
| 38943 | 28940 | 2.3 |
| 38944 | 28941 | 2.3 |
| 38945 | 28942 | 2.3 |
| 38946 | 28943 | 2.3 |
| 38947 | 28944 | 2.3 |
| 38948 | 28945 | 2.3 |
| 38949 | 28946 | 2.3 |
| 38950 | 28947 | 2.3 |
| 38951 | 28948 | 2.3 |
| 38952 | 28949 | 2.3 |
| 38953 | 28950 | 2.3 |
| 38954 | 28951 | 2.3 |
| 38955 | 28952 | 2.3 |
| 38956 | 28953 | 2.3 |
| 38957 | 28954 | 2.292834891 |
| 38958 | 28955 | 2.291187739 |
| 38959 | 28956 | 2.291187739 |
| 38960 | 28957 | 2.291187739 |
| 38961 | 28958 | 2.291187739 |
| 38962 | 28959 | 2.29004329 |
| 38963 | 28960 | 2.288557214 |
| 38964 | 28961 | 2.288557214 |
| 38965 | 28962 | 2.288557214 |
| 38966 | 28963 | 2.288557214 |
| 38967 | 28964 | 2.286549708 |
| 38968 | 28965 | 2.283687943 |
| 38969 | 28966 | 2.283687943 |
| 38970 | 28967 | 2.283687943 |
| 38971 | 28968 | 2.283687943 |
| 38972 | 28969 | 2.279279279 |
| 38973 | 28970 | 2.279279279 |
| 38974 | 28971 | 2.277227723 |
| 38975 | 28972 | 2.277227723 |
| 38976 | 28973 | 2.271604938 |
| 38977 | 28974 | 2.271604938 |
| 38978 | 28975 | 2.271604938 |
| 38979 | 28976 | 2.271604938 |
| 38980 | 28977 | 2.271604938 |
| 38981 | 28978 | 2.271604938 |
| 38982 | 28979 | 2.271604938 |
| 38983 | 28980 | 2.271604938 |
| 38984 | 28981 | 2.271604938 |
| 38985 | 28982 | 2.271604938 |
| 38986 | 28983 | 2.271604938 |
| 38987 | 28984 | 2.271604938 |
| 38988 | 28985 | 2.271604938 |
| 38989 | 28986 | 2.267605634 |
| 38990 | 28987 | 2.266666667 |
| 38991 | 28988 | 2.266009852 |
| 38992 | 28989 | 2.265151515 |
| 38993 | 28990 | 2.263982103 |
| 38994 | 28991 | 2.263982103 |
| 38995 | 28992 | 2.262295082 |
| 38996 | 28993 | 2.259649123 |
| 38997 | 28994 | 2.258397933 |
| 38998 | 28995 | 2.254901961 |
| 38999 | 28996 | 2.254901961 |
| 39000 | 28997 | 2.254901961 |
| 39001 | 28998 | 2.254901961 |
| 39002 | 28999 | 2.254901961 |
| 39003 | 29000 | 2.254901961 |
| 39004 | 29001 | 2.254901961 |
| 39005 | 29002 | 2.254901961 |
| 39006 | 29003 | 2.254901961 |
| 39007 | 29004 | 2.254901961 |
| 39008 | 29005 | 2.248888889 |
| 39009 | 29006 | 2.248888889 |
| 39010 | 29007 | 2.248888889 |
| 39011 | 29008 | 2.247126437 |
| 39012 | 29009 | 2.247126437 |
| 39013 | 29010 | 2.243902439 |
| 39014 | 29011 | 2.243902439 |
| 39015 | 29012 | 2.243902439 |
| 39016 | 29013 | 2.243902439 |
| 39017 | 29014 | 2.243902439 |
| 39018 | 29015 | 2.243902439 |
| 39019 | 29016 | 2.239700375 |
| 39020 | 29017 | 2.236111111 |
| 39021 | 29018 | 2.236111111 |
| 39022 | 29019 | 2.236111111 |
| 39023 | 29020 | 2.236111111 |
| 39024 | 29021 | 2.236111111 |
| 39025 | 29022 | 2.236111111 |
| 39026 | 29023 | 2.236111111 |
| 39027 | 29024 | 2.236111111 |
| 39028 | 29025 | 2.236111111 |
| 39029 | 29026 | 2.23030303 |
| 39030 | 29027 | 2.23030303 |
| 39031 | 29028 | 2.23030303 |
| 39032 | 29029 | 2.23030303 |
| 39033 | 29030 | 2.225806452 |
| 39034 | 29031 | 2.225806452 |
| 39035 | 29032 | 2.222222222 |
| 39036 | 29033 | 2.222222222 |
| 39037 | 29034 | 2.222222222 |
| 39038 | 29035 | 2.222222222 |
| 39039 | 29036 | 2.222222222 |
| 39040 | 29037 | 2.222222222 |
| 39041 | 29038 | 2.222222222 |

FIG. 6 (Cont.)

| DNA SEQ ID NO | AA SEQ ID NO | Kidney 1 Enrichment |
|---|---|---|
| 39042 | 29039 | 2.220689655 |
| 39043 | 29040 | 2.219298246 |
| 39044 | 29041 | 2.219298246 |
| 39045 | 29042 | 2.21686747 |
| 39046 | 29043 | 2.21686747 |
| 39047 | 29044 | 2.21686747 |
| 39048 | 29045 | 2.21686747 |
| 39049 | 29046 | 2.214814815 |
| 39050 | 29047 | 2.214814815 |
| 39051 | 29048 | 2.211538462 |
| 39052 | 29049 | 2.21021021 |
| 39053 | 29050 | 2.21021021 |
| 39054 | 29051 | 2.209039548 |
| 39055 | 29052 | 2.19047619 |
| 39056 | 29053 | 2.19047619 |
| 39057 | 29054 | 2.19047619 |
| 39058 | 29055 | 2.19047619 |
| 39059 | 29056 | 2.19047619 |
| 39060 | 29057 | 2.19047619 |
| 39061 | 29058 | 2.19047619 |
| 39062 | 29059 | 2.19047619 |
| 39063 | 29060 | 2.19047619 |
| 39064 | 29061 | 2.19047619 |
| 39065 | 29062 | 2.19047619 |
| 39066 | 29063 | 2.19047619 |
| 39067 | 29064 | 2.19047619 |
| 39068 | 29065 | 2.19047619 |
| 39069 | 29066 | 2.19047619 |
| 39070 | 29067 | 2.19047619 |

| DNA SEQ ID NO | AA SEQ ID NO | Kidney 1 Enrichment |
|---|---|---|
| 39071 | 29068 | 2.19047619 |
| 39072 | 29069 | 2.19047619 |
| 39073 | 29070 | 2.19047619 |
| 39074 | 29071 | 2.19047619 |
| 39075 | 29072 | 2.19047619 |
| 39076 | 29073 | 2.19047619 |
| 39077 | 29074 | 2.19047619 |
| 39078 | 29075 | 2.19047619 |
| 39079 | 29076 | 2.19047619 |
| 39080 | 29077 | 2.19047619 |
| 39081 | 29078 | 2.19047619 |
| 39082 | 29079 | 2.19047619 |
| 39083 | 29080 | 2.19047619 |
| 39084 | 29081 | 2.19047619 |
| 39085 | 29082 | 2.19047619 |
| 39086 | 29083 | 2.19047619 |
| 39087 | 29084 | 2.19047619 |
| 39088 | 29085 | 2.19047619 |
| 39089 | 29086 | 2.19047619 |
| 39090 | 29087 | 2.19047619 |
| 39091 | 29088 | 2.19047619 |
| 39092 | 29089 | 2.19047619 |
| 39093 | 29090 | 2.19047619 |
| 39094 | 29091 | 2.19047619 |
| 39095 | 29092 | 2.19047619 |
| 39096 | 29093 | 2.19047619 |
| 39097 | 29094 | 2.19047619 |
| 39098 | 29095 | 2.19047619 |
| 39099 | 29096 | 2.19047619 |

| DNA SEQ ID NO | AA SEQ ID NO | Kidney 1 Enrichment |
|---|---|---|
| 39100 | 29097 | 2.19047619 |
| 39101 | 29098 | 2.19047619 |
| 39102 | 29099 | 2.19047619 |
| 39103 | 29100 | 2.19047619 |
| 39104 | 29101 | 2.19047619 |
| 39105 | 29102 | 2.19047619 |
| 39106 | 29103 | 2.19047619 |
| 39107 | 29104 | 2.19047619 |
| 39108 | 29105 | 2.19047619 |
| 39109 | 29106 | 2.19047619 |
| 39110 | 29107 | 2.19047619 |
| 39111 | 29108 | 2.174940898 |
| 39112 | 29109 | 2.174940898 |
| 39113 | 29110 | 2.171091445 |
| 39114 | 29111 | 2.171091445 |
| 39115 | 29112 | 2.169811321 |
| 39116 | 29113 | 2.168350168 |
| 39117 | 29114 | 2.166666667 |
| 39118 | 29115 | 2.166666667 |
| 39119 | 29116 | 2.164705882 |
| 39120 | 29117 | 2.164705882 |
| 39121 | 29118 | 2.159624413 |
| 39122 | 29119 | 2.159624413 |
| 39123 | 29120 | 2.159624413 |
| 39124 | 29121 | 2.15625 |
| 39125 | 29122 | 2.152046784 |
| 39126 | 29123 | 2.152046784 |
| 39127 | 29124 | 2.152046784 |
| 39128 | 29125 | 2.152046784 |

| DNA SEQ ID NO | AA SEQ ID NO | Kidney 1 Enrichment |
|---|---|---|
| 39129 | 29126 | 2.146666667 |
| 39130 | 29127 | 2.146666667 |
| 39131 | 29128 | 2.146666667 |
| 39132 | 29129 | 2.146666667 |
| 39133 | 29130 | 2.146666667 |
| 39134 | 29131 | 2.146666667 |
| 39135 | 29132 | 2.146666667 |
| 39136 | 29133 | 2.144522145 |
| 39137 | 29134 | 2.143369176 |
| 39138 | 29135 | 2.139534884 |
| 39139 | 29136 | 2.139534884 |
| 39140 | 29137 | 2.139534884 |
| 39141 | 29138 | 2.139534884 |
| 39142 | 29139 | 2.139534884 |
| 39143 | 29140 | 2.139534884 |
| 39144 | 29141 | 2.139534884 |
| 39145 | 29142 | 2.139534884 |
| 39146 | 29143 | 2.139534884 |
| 39147 | 29144 | 2.139534884 |
| 39148 | 29145 | 2.137373737 |
| 39149 | 29146 | 2.135021097 |
| 39150 | 29147 | 2.135021097 |
| 39151 | 29148 | 2.132450331 |
| 39152 | 29149 | 2.12962963 |
| 39153 | 29150 | 2.12962963 |
| 39154 | 29151 | 2.12962963 |
| 39155 | 29152 | 2.12962963 |
| 39156 | 29153 | 2.12962963 |
| 39157 | 29154 | 2.12962963 |

| DNA SEQ ID NO | AA SEQ ID NO | Kidney 1 Enrichment |
|---|---|---|
| 39158 | 29155 | 2.12962963 |
| 39159 | 29156 | 2.12962963 |
| 39160 | 29157 | 2.12962963 |
| 39161 | 29158 | 2.12962963 |
| 39162 | 29159 | 2.12962963 |
| 39163 | 29160 | 2.125412541 |
| 39164 | 29161 | 2.123076923 |
| 39165 | 29162 | 2.123076923 |
| 39166 | 29163 | 2.123076923 |
| 39167 | 29164 | 2.123076923 |
| 39168 | 29165 | 2.120567376 |
| 39169 | 29166 | 2.120567376 |
| 39170 | 29167 | 2.120567376 |
| 39171 | 29168 | 2.119241192 |
| 39172 | 29169 | 2.114942529 |
| 39173 | 29170 | 2.114942529 |
| 39174 | 29171 | 2.114942529 |
| 39175 | 29172 | 2.114942529 |
| 39176 | 29173 | 2.114942529 |
| 39177 | 29174 | 2.114942529 |
| 39178 | 29175 | 2.114942529 |
| 39179 | 29176 | 2.114942529 |
| 39180 | 29177 | 2.114942529 |
| 39181 | 29178 | 2.114942529 |
| 39182 | 29179 | 2.114942529 |
| 39183 | 29180 | 2.114942529 |
| 39184 | 29181 | 2.114942529 |
| 39185 | 29182 | 2.114942529 |
| 39186 | 29183 | 2.114942529 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 39187 | 29184 | 2.114942529 | 39216 | 29213 | 2.090909091 | 39245 | 29242 | 2.072072072 | 39274 | 29271 | 2.044444444 | 39303 | 29300 | 2.01754386 |
| 39188 | 29185 | 2.108333333 | 39217 | 29214 | 2.090909091 | 39246 | 29243 | 2.072072072 | 39275 | 29272 | 2.044444444 | 39304 | 29301 | 2.01754386 |
| 39189 | 29186 | 2.108333333 | 39218 | 29215 | 2.090909091 | 39247 | 29244 | 2.068783069 | 39276 | 29273 | 2.044444444 | 39305 | 29302 | 2.01754386 |
| 39190 | 29187 | 2.104575163 | 39219 | 29216 | 2.090909091 | 39248 | 29245 | 2.06741573 | 39277 | 29274 | 2.044444444 | 39306 | 29303 | 2.01754386 |
| 39191 | 29188 | 2.104575163 | 39220 | 29217 | 2.090909091 | 39249 | 29246 | 2.06741573 | 39278 | 29275 | 2.044444444 | 39307 | 29304 | 2.01754386 |
| 39192 | 29189 | 2.104575163 | 39221 | 29218 | 2.090909091 | 39250 | 29247 | 2.064102564 | 39279 | 29276 | 2.044444444 | 39308 | 29305 | 2.01754386 |
| 39193 | 29190 | 2.104575163 | 39222 | 29219 | 2.090909091 | 39251 | 29248 | 2.064102564 | 39280 | 29277 | 2.044444444 | 39309 | 29306 | 2.01754386 |
| 39194 | 29191 | 2.102150538 | 39223 | 29220 | 2.090909091 | 39252 | 29249 | 2.064102564 | 39281 | 29278 | 2.044444444 | 39310 | 29307 | 2.01754386 |
| 39195 | 29192 | 2.100456621 | 39224 | 29221 | 2.090909091 | 39253 | 29250 | 2.064102564 | 39282 | 29279 | 2.044444444 | 39311 | 29308 | 2.01459854 |
| 39196 | 29193 | 2.098245614 | 39225 | 29222 | 2.085333333 | 39254 | 29251 | 2.064102564 | 39283 | 29280 | 2.044444444 | 39312 | 29309 | 2.013468013 |
| 39197 | 29194 | 2.096866097 | 39226 | 29223 | 2.084142395 | 39255 | 29252 | 2.064102564 | 39284 | 29281 | 2.044444444 | 39313 | 29310 | 2.013468013 |
| 39198 | 29195 | 2.096866097 | 39227 | 29224 | 2.084142395 | 39256 | 29253 | 2.064102564 | 39285 | 29282 | 2.044444444 | 39314 | 29311 | 2.013468013 |
| 39199 | 29196 | 2.096866097 | 39228 | 29225 | 2.082304527 | 39257 | 29254 | 2.064102564 | 39286 | 29283 | 2.044444444 | 39315 | 29312 | 2.010928962 |
| 39200 | 29197 | 2.090909091 | 39229 | 29226 | 2.079096045 | 39258 | 29255 | 2.064102564 | 39287 | 29284 | 2.044444444 | 39316 | 29313 | 2.010928962 |
| 39201 | 29198 | 2.090909091 | 39230 | 29227 | 2.079096045 | 39259 | 29256 | 2.064102564 | 39288 | 29285 | 2.044444444 | 39317 | 29314 | 2.010928962 |
| 39202 | 29199 | 2.090909091 | 39231 | 29228 | 2.079096045 | 39260 | 29257 | 2.064102564 | 39289 | 29286 | 2.044444444 | 39318 | 29315 | 2.010928962 |
| 39203 | 29200 | 2.090909091 | 39232 | 29229 | 2.079096045 | 39261 | 29258 | 2.059701493 | 39290 | 29287 | 2.044444444 | 39319 | 29316 | 2.010928962 |
| 39204 | 29201 | 2.090909091 | 39233 | 29230 | 2.079096045 | 39262 | 29259 | 2.059701493 | 39291 | 29288 | 2.044444444 | 39320 | 29317 | 2.010928962 |
| 39205 | 29202 | 2.090909091 | 39234 | 29231 | 2.079096045 | 39263 | 29260 | 2.059701493 | 39292 | 29289 | 2.038535645 | 39321 | 29318 | 2.010928962 |
| 39206 | 29203 | 2.090909091 | 39235 | 29232 | 2.079096045 | 39264 | 29261 | 2.059701493 | 39293 | 29290 | 2.036458333 | 39322 | 29319 | 2.007936508 |
| 39207 | 29204 | 2.090909091 | 39236 | 29233 | 2.079096045 | 39265 | 29262 | 2.056910569 | 39294 | 29291 | 2.033149171 | 39323 | 29320 | 2.00623053 |
| 39208 | 29205 | 2.090909091 | 39237 | 29234 | 2.079096045 | 39266 | 29263 | 2.054982818 | 39295 | 29292 | 2.032128514 | 39324 | 29321 | 2.005128205 |
| 39209 | 29206 | 2.090909091 | 39238 | 29235 | 2.076388889 | 39267 | 29264 | 2.052493438 | 39296 | 29293 | 2.029411765 | 39325 | 29322 | 2.005128205 |
| 39210 | 29207 | 2.090909091 | 39239 | 29236 | 2.07518797 | 39268 | 29265 | 2.050387597 | 39297 | 29294 | 2.029411765 | 39326 | 29323 | 2.003003003 |
| 39211 | 29208 | 2.090909091 | 39240 | 29237 | 2.072072072 | 39269 | 29266 | 2.047477745 | 39298 | 29295 | 2.027548209 | 39327 | 29324 | 2 |
| 39212 | 29209 | 2.090909091 | 39241 | 29238 | 2.072072072 | 39270 | 29267 | 2.044444444 | 39299 | 29296 | 2.025157233 | 39328 | 29325 | 2 |
| 39213 | 29210 | 2.090909091 | 39242 | 29239 | 2.072072072 | 39271 | 29268 | 2.044444444 | 39300 | 29297 | 2.025157233 | 39329 | 29326 | 2 |
| 39214 | 29211 | 2.090909091 | 39243 | 29240 | 2.072072072 | 39272 | 29269 | 2.044444444 | 39301 | 29298 | 2.025157233 | 39330 | 29327 | 2 |
| 39215 | 29212 | 2.090909091 | 39244 | 29241 | 2.072072072 | 39273 | 29270 | 2.044444444 | 39302 | 29299 | 2.021978022 | 39331 | 29328 | 2 |

FIG. 6 (Cont.)

| DNA SEQ ID NO | AA SEQ ID NO | Kidney 1 Enrichment |
|---|---|---|
| 39332 | 29329 | 2 |
| 39333 | 29330 | 2 |
| 39334 | 29331 | 2 |
| 39335 | 29332 | 2 |
| 39336 | 29333 | 2 |
| 39337 | 29334 | 2 |
| 39338 | 29335 | 2 |
| 39339 | 29336 | 1.994579946 |
| 39340 | 29337 | 1.994579946 |
| 39341 | 29338 | 1.993333333 |
| 39342 | 29339 | 1.991341991 |
| 39343 | 29340 | 1.991341991 |
| 39344 | 29341 | 1.991341991 |
| 39345 | 29342 | 1.991341991 |
| 39346 | 29343 | 1.991341991 |
| 39347 | 29344 | 1.987654321 |
| 39348 | 29345 | 1.987654321 |
| 39349 | 29346 | 1.987654321 |
| 39350 | 29347 | 1.987654321 |
| 39351 | 29348 | 1.987654321 |
| 39352 | 29349 | 1.987654321 |
| 39353 | 29350 | 1.987654321 |
| 39354 | 29351 | 1.987654321 |
| 39355 | 29352 | 1.987654321 |
| 39356 | 29353 | 1.987654321 |
| 39357 | 29354 | 1.984313725 |
| 39358 | 29355 | 1.978494624 |
| 39359 | 29356 | 1.978494624 |
| 39360 | 29357 | 1.978494624 |
| 39361 | 29358 | 1.978494624 |
| 39362 | 29359 | 1.978494624 |
| 39363 | 29360 | 1.971428571 |
| 39364 | 29361 | 1.971428571 |
| 39365 | 29362 | 1.971428571 |
| 39366 | 29363 | 1.96941896 |
| 39367 | 29364 | 1.968468468 |
| 39368 | 29365 | 1.965811966 |
| 39369 | 29366 | 1.965811966 |
| 39370 | 29367 | 1.965811966 |
| 39371 | 29368 | 1.965811966 |
| 39372 | 29369 | 1.965811966 |
| 39373 | 29370 | 1.965811966 |
| 39374 | 29371 | 1.965811966 |
| 39375 | 29372 | 1.965811966 |
| 39376 | 29373 | 1.965811966 |
| 39377 | 29374 | 1.965811966 |
| 39378 | 29375 | 1.96124031 |
| 39379 | 29376 | 1.959899749 |
| 39380 | 29377 | 1.957446809 |
| 39381 | 29378 | 1.957446809 |
| 39382 | 29379 | 1.957446809 |
| 39383 | 29380 | 1.957446809 |
| 39384 | 29381 | 1.954248366 |
| 39385 | 29382 | 1.954248366 |
| 39386 | 29383 | 1.95329087 |
| 39387 | 29384 | 1.951515152 |
| 39388 | 29385 | 1.951515152 |
| 39389 | 29386 | 1.951515152 |
| 39390 | 29387 | 1.947089947 |
| 39391 | 29388 | 1.943661972 |
| 39392 | 29389 | 1.943661972 |
| 39393 | 29390 | 1.943661972 |
| 39394 | 29391 | 1.943661972 |
| 39395 | 29392 | 1.94092827 |
| 39396 | 29393 | 1.94092827 |
| 39397 | 29394 | 1.94092827 |
| 39398 | 29395 | 1.938697318 |
| 39399 | 29396 | 1.938697318 |
| 39400 | 29397 | 1.936842105 |
| 39401 | 29398 | 1.935275081 |
| 39402 | 29399 | 1.933933934 |
| 39403 | 29400 | 1.932773109 |
| 39404 | 29401 | 1.930864198 |
| 39405 | 29402 | 1.93006993 |
| 39406 | 29403 | 1.916666667 |
| 39407 | 29404 | 1.916666667 |
| 39408 | 29405 | 1.916666667 |
| 39409 | 29406 | 1.916666667 |
| 39410 | 29407 | 1.916666667 |
| 39411 | 29408 | 1.916666667 |
| 39412 | 29409 | 1.916666667 |
| 39413 | 29410 | 1.916666667 |
| 39414 | 29411 | 1.916666667 |
| 39415 | 29412 | 1.916666667 |
| 39416 | 29413 | 1.916666667 |
| 39417 | 29414 | 1.916666667 |
| 39418 | 29415 | 1.916666667 |
| 39419 | 29416 | 1.916666667 |
| 39420 | 29417 | 1.916666667 |
| 39421 | 29418 | 1.916666667 |
| 39422 | 29419 | 1.916666667 |
| 39423 | 29420 | 1.916666667 |
| 39424 | 29421 | 1.916666667 |
| 39425 | 29422 | 1.916666667 |
| 39426 | 29423 | 1.916666667 |
| 39427 | 29424 | 1.916666667 |
| 39428 | 29425 | 1.916666667 |
| 39429 | 29426 | 1.916666667 |
| 39430 | 29427 | 1.916666667 |
| 39431 | 29428 | 1.916666667 |
| 39432 | 29429 | 1.916666667 |
| 39433 | 29430 | 1.916666667 |
| 39434 | 29431 | 1.916666667 |
| 39435 | 29432 | 1.916666667 |
| 39436 | 29433 | 1.916666667 |
| 39437 | 29434 | 1.916666667 |
| 39438 | 29435 | 1.916666667 |
| 39439 | 29436 | 1.916666667 |
| 39440 | 29437 | 1.916666667 |
| 39441 | 29438 | 1.916666667 |
| 39442 | 29439 | 1.916666667 |
| 39443 | 29440 | 1.916666667 |
| 39444 | 29441 | 1.916666667 |
| 39445 | 29442 | 1.916666667 |
| 39446 | 29443 | 1.916666667 |
| 39447 | 29444 | 1.916666667 |
| 39448 | 29445 | 1.916666667 |
| 39449 | 29446 | 1.916666667 |
| 39450 | 29447 | 1.916666667 |
| 39451 | 29448 | 1.916666667 |
| 39452 | 29449 | 1.916666667 |
| 39453 | 29450 | 1.900826446 |
| 39454 | 29451 | 1.899705015 |
| 39455 | 29452 | 1.899705015 |
| 39456 | 29453 | 1.898412698 |
| 39457 | 29454 | 1.896907216 |
| 39458 | 29455 | 1.895131086 |
| 39459 | 29456 | 1.894117647 |
| 39460 | 29457 | 1.893004115 |
| 39461 | 29458 | 1.893004115 |
| 39462 | 29459 | 1.893004115 |
| 39463 | 29460 | 1.887179487 |
| 39464 | 29461 | 1.887179487 |
| 39465 | 29462 | 1.887179487 |
| 39466 | 29463 | 1.887179487 |
| 39467 | 29464 | 1.887179487 |
| 39468 | 29465 | 1.887179487 |
| 39469 | 29466 | 1.887179487 |
| 39470 | 29467 | 1.885245902 |
| 39471 | 29468 | 1.885245902 |
| 39472 | 29469 | 1.883040936 |
| 39473 | 29470 | 1.883040936 |
| 39474 | 29471 | 1.883040936 |
| 39475 | 29472 | 1.87755102 |
| 39476 | 29473 | 1.87755102 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 39477 | 29474 | 1.87755102 | 39506 | 29503 | 1.858585859 | 39535 | 29532 | 1.833333333 | 39564 | 29561 | 1.803921569 | 39593 | 29590 | 1.782945736 |
| 39478 | 29475 | 1.874074074 | 39507 | 29504 | 1.850574713 | 39536 | 29533 | 1.830845771 | 39565 | 29562 | 1.803921569 | 39594 | 29591 | 1.782945736 |
| 39479 | 29476 | 1.874074074 | 39508 | 29505 | 1.850574713 | 39537 | 29534 | 1.828746177 | 39566 | 29563 | 1.803921569 | 39595 | 29592 | 1.782945736 |
| 39480 | 29477 | 1.874074074 | 39509 | 29506 | 1.850574713 | 39538 | 29535 | 1.825396825 | 39567 | 29564 | 1.803921569 | 39596 | 29593 | 1.782945736 |
| 39481 | 29478 | 1.869918699 | 39510 | 29507 | 1.848699764 | 39539 | 29536 | 1.825396825 | 39568 | 29565 | 1.803921569 | 39597 | 29594 | 1.782945736 |
| 39482 | 29479 | 1.869918699 | 39511 | 29508 | 1.847389558 | 39540 | 29537 | 1.825396825 | 39569 | 29566 | 1.803921569 | 39598 | 29595 | 1.782945736 |
| 39483 | 29480 | 1.869918699 | 39512 | 29509 | 1.847389558 | 39541 | 29538 | 1.825396825 | 39570 | 29567 | 1.803921569 | 39599 | 29596 | 1.782945736 |
| 39484 | 29481 | 1.869918699 | 39513 | 29510 | 1.847389558 | 39542 | 29539 | 1.825396825 | 39571 | 29568 | 1.803921569 | 39600 | 29597 | 1.782945736 |
| 39485 | 29482 | 1.869918699 | 39514 | 29511 | 1.847389558 | 39543 | 29540 | 1.825396825 | 39572 | 29569 | 1.803921569 | 39601 | 29598 | 1.782945736 |
| 39486 | 29483 | 1.869918699 | 39515 | 29512 | 1.845679012 | 39544 | 29541 | 1.825396825 | 39573 | 29570 | 1.803921569 | 39602 | 29599 | 1.782945736 |
| 39487 | 29484 | 1.869918699 | 39516 | 29513 | 1.844611529 | 39545 | 29542 | 1.825396825 | 39574 | 29571 | 1.803921569 | 39603 | 29600 | 1.782945736 |
| 39488 | 29485 | 1.869918699 | 39517 | 29514 | 1.84 | 39546 | 29543 | 1.821782178 | 39575 | 29572 | 1.803921569 | 39604 | 29601 | 1.782945736 |
| 39489 | 29486 | 1.869918699 | 39518 | 29515 | 1.84 | 39547 | 29544 | 1.821782178 | 39576 | 29573 | 1.803921569 | 39605 | 29602 | 1.777777778 |
| 39490 | 29487 | 1.864864865 | 39519 | 29516 | 1.84 | 39548 | 29545 | 1.81920904 | 39577 | 29574 | 1.803921569 | 39606 | 29603 | 1.777777778 |
| 39491 | 29488 | 1.864864865 | 39520 | 29517 | 1.84 | 39549 | 29546 | 1.81920904 | 39578 | 29575 | 1.803921569 | 39607 | 29604 | 1.777777778 |
| 39492 | 29489 | 1.864864865 | 39521 | 29518 | 1.84 | 39550 | 29547 | 1.81920904 | 39579 | 29576 | 1.803921569 | 39608 | 29605 | 1.777777778 |
| 39493 | 29490 | 1.861904762 | 39522 | 29519 | 1.84 | 39551 | 29548 | 1.81920904 | 39580 | 29577 | 1.792207792 | 39609 | 29606 | 1.775438596 |
| 39494 | 29491 | 1.858585859 | 39523 | 29520 | 1.84 | 39552 | 29549 | 1.81920904 | 39581 | 29578 | 1.792207792 | 39610 | 29607 | 1.774104683 |
| 39495 | 29492 | 1.858585859 | 39524 | 29521 | 1.84 | 39553 | 29550 | 1.813620072 | 39582 | 29579 | 1.792207792 | 39611 | 29608 | 1.774104683 |
| 39496 | 29493 | 1.858585859 | 39525 | 29522 | 1.84 | 39554 | 29551 | 1.811023622 | 39583 | 29580 | 1.790754258 | 39612 | 29609 | 1.774104683 |
| 39497 | 29494 | 1.858585859 | 39526 | 29523 | 1.84 | 39555 | 29552 | 1.803921569 | 39584 | 29581 | 1.788888889 | 39613 | 29610 | 1.774104683 |
| 39498 | 29495 | 1.858585859 | 39527 | 29524 | 1.84 | 39556 | 29553 | 1.803921569 | 39585 | 29582 | 1.788888889 | 39614 | 29611 | 1.769230769 |
| 39499 | 29496 | 1.858585859 | 39528 | 29525 | 1.84 | 39557 | 29554 | 1.803921569 | 39586 | 29583 | 1.788888889 | 39615 | 29612 | 1.769230769 |
| 39500 | 29497 | 1.858585859 | 39529 | 29526 | 1.84 | 39558 | 29555 | 1.803921569 | 39587 | 29584 | 1.788888889 | 39616 | 29613 | 1.769230769 |
| 39501 | 29498 | 1.858585859 | 39530 | 29527 | 1.84 | 39559 | 29556 | 1.803921569 | 39588 | 29585 | 1.788888889 | 39617 | 29614 | 1.769230769 |
| 39502 | 29499 | 1.858585859 | 39531 | 29528 | 1.84 | 39560 | 29557 | 1.803921569 | 39589 | 29586 | 1.787321063 | 39618 | 29615 | 1.769230769 |
| 39503 | 29500 | 1.858585859 | 39532 | 29529 | 1.834757835 | 39561 | 29558 | 1.803921569 | 39590 | 29587 | 1.782945736 | 39619 | 29616 | 1.769230769 |
| 39504 | 29501 | 1.858585859 | 39533 | 29530 | 1.834757835 | 39562 | 29559 | 1.803921569 | 39591 | 29588 | 1.782945736 | 39620 | 29617 | 1.769230769 |
| 39505 | 29502 | 1.858585859 | 39534 | 29531 | 1.833333333 | 39563 | 29560 | 1.803921569 | 39592 | 29589 | 1.782945736 | 39621 | 29618 | 1.769230769 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 39622 | 29619 | 1.769230769 | 39651 | 29648 | 1.752380952 | 39680 | 29677 | 1.735849057 | 39709 | 29706 | 1.703703704 | 39738 | 29735 | 1.703703704 |
| 39623 | 29620 | 1.769230769 | 39652 | 29649 | 1.752380952 | 39681 | 29678 | 1.735849057 | 39710 | 29707 | 1.703703704 | 39739 | 29736 | 1.703703704 |
| 39624 | 29621 | 1.769230769 | 39653 | 29650 | 1.752380952 | 39682 | 29679 | 1.735849057 | 39711 | 29708 | 1.703703704 | 39740 | 29737 | 1.703703704 |
| 39625 | 29622 | 1.769230769 | 39654 | 29651 | 1.752380952 | 39683 | 29680 | 1.735849057 | 39712 | 29709 | 1.703703704 | 39741 | 29738 | 1.703703704 |
| 39626 | 29623 | 1.769230769 | 39655 | 29652 | 1.752380952 | 39684 | 29681 | 1.731182796 | 39713 | 29710 | 1.703703704 | 39742 | 29739 | 1.703703704 |
| 39627 | 29624 | 1.769230769 | 39656 | 29653 | 1.752380952 | 39685 | 29682 | 1.731182796 | 39714 | 29711 | 1.703703704 | 39743 | 29740 | 1.703703704 |
| 39628 | 29625 | 1.769230769 | 39657 | 29654 | 1.752380952 | 39686 | 29683 | 1.731182796 | 39715 | 29712 | 1.703703704 | 39744 | 29741 | 1.703703704 |
| 39629 | 29626 | 1.769230769 | 39658 | 29655 | 1.752380952 | 39687 | 29684 | 1.731182796 | 39716 | 29713 | 1.703703704 | 39745 | 29742 | 1.703703704 |
| 39630 | 29627 | 1.769230769 | 39659 | 29656 | 1.752380952 | 39688 | 29685 | 1.731182796 | 39717 | 29714 | 1.703703704 | 39746 | 29743 | 1.703703704 |
| 39631 | 29628 | 1.769230769 | 39660 | 29657 | 1.752380952 | 39689 | 29686 | 1.731182796 | 39718 | 29715 | 1.703703704 | 39747 | 29744 | 1.703703704 |
| 39632 | 29629 | 1.76498801 | 39661 | 29658 | 1.752380952 | 39690 | 29687 | 1.731182796 | 39719 | 29716 | 1.703703704 | 39748 | 29745 | 1.703703704 |
| 39633 | 29630 | 1.764011799 | 39662 | 29659 | 1.748538012 | 39691 | 29688 | 1.731182796 | 39720 | 29717 | 1.703703704 | 39749 | 29746 | 1.703703704 |
| 39634 | 29631 | 1.764011799 | 39663 | 29660 | 1.746835443 | 39692 | 29689 | 1.731182796 | 39721 | 29718 | 1.703703704 | 39750 | 29747 | 1.703703704 |
| 39635 | 29632 | 1.764011799 | 39664 | 29661 | 1.745257453 | 39693 | 29690 | 1.727699531 | 39722 | 29719 | 1.703703704 | 39751 | 29748 | 1.703703704 |
| 39636 | 29633 | 1.762452107 | 39665 | 29662 | 1.742424242 | 39694 | 29691 | 1.727699531 | 39723 | 29720 | 1.703703704 | 39752 | 29749 | 1.703703704 |
| 39637 | 29634 | 1.762452107 | 39666 | 29663 | 1.742424242 | 39695 | 29692 | 1.727699531 | 39724 | 29721 | 1.703703704 | 39753 | 29750 | 1.703703704 |
| 39638 | 29635 | 1.762452107 | 39667 | 29664 | 1.742424242 | 39696 | 29693 | 1.727699531 | 39725 | 29722 | 1.703703704 | 39754 | 29751 | 1.703703704 |
| 39639 | 29636 | 1.759562842 | 39668 | 29665 | 1.742424242 | 39697 | 29694 | 1.725 | 39726 | 29723 | 1.703703704 | 39755 | 29752 | 1.691954023 |
| 39640 | 29637 | 1.759562842 | 39669 | 29666 | 1.742424242 | 39698 | 29695 | 1.725 | 39727 | 29724 | 1.703703704 | 39756 | 29753 | 1.689265537 |
| 39641 | 29638 | 1.759562842 | 39670 | 29667 | 1.742424242 | 39699 | 29696 | 1.725 | 39728 | 29725 | 1.703703704 | 39757 | 29754 | 1.688073394 |
| 39642 | 29639 | 1.759562842 | 39671 | 29668 | 1.738831615 | 39700 | 29697 | 1.725 | 39729 | 29726 | 1.703703704 | 39758 | 29755 | 1.688073394 |
| 39643 | 29640 | 1.759562842 | 39672 | 29669 | 1.738831615 | 39701 | 29698 | 1.721088435 | 39730 | 29727 | 1.703703704 | 39759 | 29756 | 1.688073394 |
| 39644 | 29641 | 1.759562842 | 39673 | 29670 | 1.738831615 | 39702 | 29699 | 1.721088435 | 39731 | 29728 | 1.703703704 | 39760 | 29757 | 1.686666667 |
| 39645 | 29642 | 1.752380952 | 39674 | 29671 | 1.735849057 | 39703 | 29700 | 1.719626168 | 39732 | 29729 | 1.703703704 | 39761 | 29758 | 1.686666667 |
| 39646 | 29643 | 1.752380952 | 39675 | 29672 | 1.735849057 | 39704 | 29701 | 1.719626168 | 39733 | 29730 | 1.703703704 | 39762 | 29759 | 1.684981685 |
| 39647 | 29644 | 1.752380952 | 39676 | 29673 | 1.735849057 | 39705 | 29702 | 1.717333333 | 39734 | 29731 | 1.703703704 | 39763 | 29760 | 1.684981685 |
| 39648 | 29645 | 1.752380952 | 39677 | 29674 | 1.735849057 | 39706 | 29703 | 1.71641791 | 39735 | 29732 | 1.703703704 | 39764 | 29761 | 1.682926829 |
| 39649 | 29646 | 1.752380952 | 39678 | 29675 | 1.735849057 | 39707 | 29704 | 1.703703704 | 39736 | 29733 | 1.703703704 | 39765 | 29762 | 1.682926829 |
| 39650 | 29647 | 1.752380952 | 39679 | 29676 | 1.735849057 | 39708 | 29705 | 1.703703704 | 39737 | 29734 | 1.703703704 | 39766 | 29763 | 1.680365297 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 39767 | 29764 | 1.680365297 | 39796 | 29793 | 1.666666667 | 39825 | 29822 | 1.638676845 | 39854 | 29851 | 1.614035088 | 39883 | 29880 | 1.604651163 |
| 39768 | 29765 | 1.680365297 | 39797 | 29794 | 1.662650602 | 39826 | 29823 | 1.637540453 | 39855 | 29852 | 1.614035088 | 39884 | 29881 | 1.604651163 |
| 39769 | 29766 | 1.677083333 | 39798 | 29795 | 1.662650602 | 39827 | 29824 | 1.635555556 | 39856 | 29853 | 1.614035088 | 39885 | 29882 | 1.604651163 |
| 39770 | 29767 | 1.674329502 | 39799 | 29796 | 1.661740558 | 39828 | 29825 | 1.635555556 | 39857 | 29854 | 1.614035088 | 39886 | 29883 | 1.60199005 |
| 39771 | 29768 | 1.672727273 | 39800 | 29797 | 1.657657658 | 39829 | 29826 | 1.633879781 | 39858 | 29855 | 1.614035088 | 39887 | 29884 | 1.60199005 |
| 39772 | 29769 | 1.672727273 | 39801 | 29798 | 1.657657658 | 39830 | 29827 | 1.631205674 | 39859 | 29856 | 1.614035088 | 39888 | 29885 | 1.60199005 |
| 39773 | 29770 | 1.672727273 | 39802 | 29799 | 1.657657658 | 39831 | 29828 | 1.631205674 | 39860 | 29857 | 1.614035088 | 39889 | 29886 | 1.60199005 |
| 39774 | 29771 | 1.672727273 | 39803 | 29800 | 1.657657658 | 39832 | 29829 | 1.631205674 | 39861 | 29858 | 1.614035088 | 39890 | 29887 | 1.6 |
| 39775 | 29772 | 1.672727273 | 39804 | 29801 | 1.657657658 | 39833 | 29830 | 1.631205674 | 39862 | 29859 | 1.614035088 | 39891 | 29888 | 1.597222222 |
| 39776 | 29773 | 1.672727273 | 39805 | 29802 | 1.657657658 | 39834 | 29831 | 1.631205674 | 39863 | 29860 | 1.614035088 | 39892 | 29889 | 1.597222222 |
| 39777 | 29774 | 1.672727273 | 39806 | 29803 | 1.657657658 | 39835 | 29832 | 1.631205674 | 39864 | 29861 | 1.614035088 | 39893 | 29890 | 1.597222222 |
| 39778 | 29775 | 1.672727273 | 39807 | 29804 | 1.657657658 | 39836 | 29833 | 1.628318584 | 39865 | 29862 | 1.614035088 | 39894 | 29891 | 1.597222222 |
| 39779 | 29776 | 1.672727273 | 39808 | 29805 | 1.657657658 | 39837 | 29834 | 1.628318584 | 39866 | 29863 | 1.614035088 | 39895 | 29892 | 1.597222222 |
| 39780 | 29777 | 1.672727273 | 39809 | 29806 | 1.653594771 | 39838 | 29835 | 1.626262626 | 39867 | 29864 | 1.614035088 | 39896 | 29893 | 1.597222222 |
| 39781 | 29778 | 1.672727273 | 39810 | 29807 | 1.653594771 | 39839 | 29836 | 1.626262626 | 39868 | 29865 | 1.614035088 | 39897 | 29894 | 1.597222222 |
| 39782 | 29779 | 1.672727273 | 39811 | 29808 | 1.651282051 | 39840 | 29837 | 1.626262626 | 39869 | 29866 | 1.614035088 | 39898 | 29895 | 1.594666667 |
| 39783 | 29780 | 1.669966997 | 39812 | 29809 | 1.651282051 | 39841 | 29838 | 1.626262626 | 39870 | 29867 | 1.614035088 | 39899 | 29896 | 1.593073593 |
| 39784 | 29781 | 1.669966997 | 39813 | 29810 | 1.64874552 | 39842 | 29839 | 1.626262626 | 39871 | 29868 | 1.614035088 | 39900 | 29897 | 1.593073593 |
| 39785 | 29782 | 1.666666667 | 39814 | 29811 | 1.642857143 | 39843 | 29840 | 1.626262626 | 39872 | 29869 | 1.614035088 | 39901 | 29898 | 1.590123457 |
| 39786 | 29783 | 1.666666667 | 39815 | 29812 | 1.642857143 | 39844 | 29841 | 1.626262626 | 39873 | 29870 | 1.614035088 | 39902 | 29899 | 1.586206897 |
| 39787 | 29784 | 1.666666667 | 39816 | 29813 | 1.642857143 | 39845 | 29842 | 1.626262626 | 39874 | 29871 | 1.614035088 | 39903 | 29900 | 1.586206897 |
| 39788 | 29785 | 1.666666667 | 39817 | 29814 | 1.642857143 | 39846 | 29843 | 1.626262626 | 39875 | 29872 | 1.614035088 | 39904 | 29901 | 1.586206897 |
| 39789 | 29786 | 1.666666667 | 39818 | 29815 | 1.642857143 | 39847 | 29844 | 1.626262626 | 39876 | 29873 | 1.614035088 | 39905 | 29902 | 1.586206897 |
| 39790 | 29787 | 1.666666667 | 39819 | 29816 | 1.642857143 | 39848 | 29845 | 1.623529412 | 39877 | 29874 | 1.614035088 | 39906 | 29903 | 1.586206897 |
| 39791 | 29788 | 1.666666667 | 39820 | 29817 | 1.642857143 | 39849 | 29846 | 1.623529412 | 39878 | 29875 | 1.614035088 | 39907 | 29904 | 1.586206897 |
| 39792 | 29789 | 1.666666667 | 39821 | 29818 | 1.642857143 | 39850 | 29847 | 1.621794872 | 39879 | 29876 | 1.614035088 | 39908 | 29905 | 1.586206897 |
| 39793 | 29790 | 1.666666667 | 39822 | 29819 | 1.642857143 | 39851 | 29848 | 1.621794872 | 39880 | 29877 | 1.614035088 | 39909 | 29906 | 1.586206897 |
| 39794 | 29791 | 1.666666667 | 39823 | 29820 | 1.642857143 | 39852 | 29849 | 1.620596206 | 39881 | 29878 | 1.614035088 | 39910 | 29907 | 1.586206897 |
| 39795 | 29792 | 1.666666667 | 39824 | 29821 | 1.638676845 | 39853 | 29850 | 1.614035088 | 39882 | 29879 | 1.614035088 | 39911 | 29908 | 1.586206897 |

FIG. 6 (Cont.)

| DNA SEQ ID NO | AA SEQ ID NO | Kidney 1 Enrichment |
|---|---|---|
| 39912 | 29909 | 1.586206897 |
| 39913 | 29910 | 1.586206897 |
| 39914 | 29911 | 1.586206897 |
| 39915 | 29912 | 1.582010582 |
| 39916 | 29913 | 1.582010582 |
| 39917 | 29914 | 1.582010582 |
| 39918 | 29915 | 1.578431373 |
| 39919 | 29916 | 1.578431373 |
| 39920 | 29917 | 1.578431373 |
| 39921 | 29918 | 1.578431373 |
| 39922 | 29919 | 1.576323988 |
| 39923 | 29920 | 1.576323988 |
| 39924 | 29921 | 1.576323988 |
| 39925 | 29922 | 1.575342466 |
| 39926 | 29923 | 1.572649573 |
| 39927 | 29924 | 1.572649573 |
| 39928 | 29925 | 1.572649573 |
| 39929 | 29926 | 1.572649573 |
| 39930 | 29927 | 1.572649573 |
| 39931 | 29928 | 1.572649573 |
| 39932 | 29929 | 1.572649573 |
| 39933 | 29930 | 1.572649573 |
| 39934 | 29931 | 1.572649573 |
| 39935 | 29932 | 1.572649573 |
| 39936 | 29933 | 1.572649573 |
| 39937 | 29934 | 1.572649573 |
| 39938 | 29935 | 1.566909976 |
| 39939 | 29936 | 1.56462585 |
| 39940 | 29937 | 1.56462585 |

| DNA SEQ ID NO | AA SEQ ID NO | Kidney 1 Enrichment |
|---|---|---|
| 39941 | 29938 | 1.56462585 |
| 39942 | 29939 | 1.56462585 |
| 39943 | 29940 | 1.56462585 |
| 39944 | 29941 | 1.561728395 |
| 39945 | 29942 | 1.561728395 |
| 39946 | 29943 | 1.561728395 |
| 39947 | 29944 | 1.559322034 |
| 39948 | 29945 | 1.559322034 |
| 39949 | 29946 | 1.559322034 |
| 39950 | 29947 | 1.559322034 |
| 39951 | 29948 | 1.559322034 |
| 39952 | 29949 | 1.555555556 |
| 39953 | 29950 | 1.555555556 |
| 39954 | 29951 | 1.555555556 |
| 39955 | 29952 | 1.552742616 |
| 39956 | 29953 | 1.550561798 |
| 39957 | 29954 | 1.550561798 |
| 39958 | 29955 | 1.550561798 |
| 39959 | 29956 | 1.550561798 |
| 39960 | 29957 | 1.548821549 |
| 39961 | 29958 | 1.548821549 |
| 39962 | 29959 | 1.548821549 |
| 39963 | 29960 | 1.546218487 |
| 39964 | 29961 | 1.546218487 |
| 39965 | 29962 | 1.546218487 |
| 39966 | 29963 | 1.544364508 |
| 39967 | 29964 | 1.533333333 |
| 39968 | 29965 | 1.533333333 |
| 39969 | 29966 | 1.533333333 |

| DNA SEQ ID NO | AA SEQ ID NO | Kidney 1 Enrichment |
|---|---|---|
| 39970 | 29967 | 1.533333333 |
| 39971 | 29968 | 1.533333333 |
| 39972 | 29969 | 1.533333333 |
| 39973 | 29970 | 1.533333333 |
| 39974 | 29971 | 1.533333333 |
| 39975 | 29972 | 1.533333333 |
| 39976 | 29973 | 1.533333333 |
| 39977 | 29974 | 1.533333333 |
| 39978 | 29975 | 1.533333333 |
| 39979 | 29976 | 1.533333333 |
| 39980 | 29977 | 1.533333333 |
| 39981 | 29978 | 1.533333333 |
| 39982 | 29979 | 1.533333333 |
| 39983 | 29980 | 1.533333333 |
| 39984 | 29981 | 1.533333333 |
| 39985 | 29982 | 1.533333333 |
| 39986 | 29983 | 1.533333333 |
| 39987 | 29984 | 1.533333333 |
| 39988 | 29985 | 1.533333333 |
| 39989 | 29986 | 1.533333333 |
| 39990 | 29987 | 1.533333333 |
| 39991 | 29988 | 1.533333333 |
| 39992 | 29989 | 1.533333333 |
| 39993 | 29990 | 1.533333333 |
| 39994 | 29991 | 1.533333333 |
| 39995 | 29992 | 1.533333333 |
| 39996 | 29993 | 1.533333333 |
| 39997 | 29994 | 1.533333333 |
| 39998 | 29995 | 1.533333333 |

| DNA SEQ ID NO | AA SEQ ID NO | Kidney 1 Enrichment |
|---|---|---|
| 39999 | 29996 | 1.533333333 |
| 40000 | 29997 | 1.533333333 |
| 40001 | 29998 | 1.533333333 |
| 40002 | 29999 | 1.533333333 |
| 40003 | 30000 | 1.533333333 |
| 40004 | 30001 | 1.533333333 |
| 40005 | 30002 | 1.533333333 |
| 40006 | 30003 | 1.533333333 |
| 40007 | 30004 | 1.533333333 |
| 40008 | 30005 | 1.533333333 |
| 40009 | 30006 | 1.533333333 |
| 40010 | 30007 | 1.533333333 |
| 40011 | 30008 | 1.533333333 |
| 40012 | 30009 | 1.533333333 |
| 40013 | 30010 | 1.533333333 |
| 40014 | 30011 | 1.533333333 |
| 40015 | 30012 | 1.533333333 |
| 40016 | 30013 | 1.533333333 |
| 40017 | 30014 | 1.524861878 |
| 40018 | 30015 | 1.518151815 |
| 40019 | 30016 | 1.516483516 |
| 40020 | 30017 | 1.516483516 |
| 40021 | 30018 | 1.514403292 |
| 40022 | 30019 | 1.514403292 |
| 40023 | 30020 | 1.514403292 |
| 40024 | 30021 | 1.514403292 |
| 40025 | 30022 | 1.511737089 |
| 40026 | 30023 | 1.511737089 |
| 40027 | 30024 | 1.51010101 |

| DNA SEQ ID NO | AA SEQ ID NO | Kidney 1 Enrichment |
|---|---|---|
| 40028 | 30025 | 1.508196721 |
| 40029 | 30026 | 1.508196721 |
| 40030 | 30027 | 1.508196721 |
| 40031 | 30028 | 1.508196721 |
| 40032 | 30029 | 1.508196721 |
| 40033 | 30030 | 1.508196721 |
| 40034 | 30031 | 1.505952381 |
| 40035 | 30032 | 1.503267974 |
| 40036 | 30033 | 1.503267974 |
| 40037 | 30034 | 1.5 |
| 40038 | 30035 | 1.5 |
| 40039 | 30036 | 1.5 |
| 40040 | 30037 | 1.498746867 |
| 40041 | 30038 | 1.495934959 |
| 40042 | 30039 | 1.495934959 |
| 40043 | 30040 | 1.495934959 |
| 40044 | 30041 | 1.495934959 |
| 40045 | 30042 | 1.495934959 |
| 40046 | 30043 | 1.495934959 |
| 40047 | 30044 | 1.495934959 |
| 40048 | 30045 | 1.495934959 |
| 40049 | 30046 | 1.495934959 |
| 40050 | 30047 | 1.492625369 |
| 40051 | 30048 | 1.490740741 |
| 40052 | 30049 | 1.490740741 |
| 40053 | 30050 | 1.490740741 |
| 40054 | 30051 | 1.487562189 |
| 40055 | 30052 | 1.483870968 |
| 40056 | 30053 | 1.483870968 |

FIG. 6 (Cont.)

| DNA SEQ ID NO | AA SEQ ID NO | Kidney 1 Enrichment |
|---|---|---|
| 40057 | 30054 | 1.483870968 |
| 40058 | 30055 | 1.483870968 |
| 40059 | 30056 | 1.483870968 |
| 40060 | 30057 | 1.483870968 |
| 40061 | 30058 | 1.483870968 |
| 40062 | 30059 | 1.483870968 |
| 40063 | 30060 | 1.483870968 |
| 40064 | 30061 | 1.483870968 |
| 40065 | 30062 | 1.483870968 |
| 40066 | 30063 | 1.483870968 |
| 40067 | 30064 | 1.481060606 |
| 40068 | 30065 | 1.477911647 |
| 40069 | 30066 | 1.477911647 |
| 40070 | 30067 | 1.477911647 |
| 40071 | 30068 | 1.477911647 |
| 40072 | 30069 | 1.474358974 |
| 40073 | 30070 | 1.474358974 |
| 40074 | 30071 | 1.474358974 |
| 40075 | 30072 | 1.474358974 |
| 40076 | 30073 | 1.474358974 |
| 40077 | 30074 | 1.474358974 |
| 40078 | 30075 | 1.474358974 |
| 40079 | 30076 | 1.470319635 |
| 40080 | 30077 | 1.470319635 |
| 40081 | 30078 | 1.470319635 |
| 40082 | 30079 | 1.468085106 |
| 40083 | 30080 | 1.468085106 |
| 40084 | 30081 | 1.468085106 |
| 40085 | 30082 | 1.466666667 |
| 40086 | 30083 | 1.465686275 |
| 40087 | 30084 | 1.46031746 |
| 40088 | 30085 | 1.46031746 |
| 40089 | 30086 | 1.46031746 |
| 40090 | 30087 | 1.46031746 |
| 40091 | 30088 | 1.46031746 |
| 40092 | 30089 | 1.46031746 |
| 40093 | 30090 | 1.46031746 |
| 40094 | 30091 | 1.46031746 |
| 40095 | 30092 | 1.46031746 |
| 40096 | 30093 | 1.46031746 |
| 40097 | 30094 | 1.46031746 |
| 40098 | 30095 | 1.46031746 |
| 40099 | 30096 | 1.46031746 |
| 40100 | 30097 | 1.46031746 |
| 40101 | 30098 | 1.46031746 |
| 40102 | 30099 | 1.46031746 |
| 40103 | 30100 | 1.46031746 |
| 40104 | 30101 | 1.46031746 |
| 40105 | 30102 | 1.46031746 |
| 40106 | 30103 | 1.46031746 |
| 40107 | 30104 | 1.46031746 |
| 40108 | 30105 | 1.454987835 |
| 40109 | 30106 | 1.454987835 |
| 40110 | 30107 | 1.454022989 |
| 40111 | 30108 | 1.45045045 |
| 40112 | 30109 | 1.45045045 |
| 40113 | 30110 | 1.45045045 |
| 40114 | 30111 | 1.45045045 |
| 40115 | 30112 | 1.446540881 |
| 40116 | 30113 | 1.446540881 |
| 40117 | 30114 | 1.446540881 |
| 40118 | 30115 | 1.446540881 |
| 40119 | 30116 | 1.446540881 |
| 40120 | 30117 | 1.446540881 |
| 40121 | 30118 | 1.446540881 |
| 40122 | 30119 | 1.446540881 |
| 40123 | 30120 | 1.443137255 |
| 40124 | 30121 | 1.441595442 |
| 40125 | 30122 | 1.441595442 |
| 40126 | 30123 | 1.4375 |
| 40127 | 30124 | 1.4375 |
| 40128 | 30125 | 1.4375 |
| 40129 | 30126 | 1.4375 |
| 40130 | 30127 | 1.4375 |
| 40131 | 30128 | 1.4375 |
| 40132 | 30129 | 1.4375 |
| 40133 | 30130 | 1.4375 |
| 40134 | 30131 | 1.4375 |
| 40135 | 30132 | 1.4375 |
| 40136 | 30133 | 1.4375 |
| 40137 | 30134 | 1.4375 |
| 40138 | 30135 | 1.4375 |
| 40139 | 30136 | 1.433021807 |
| 40140 | 30137 | 1.431111111 |
| 40141 | 30138 | 1.431111111 |
| 40142 | 30139 | 1.431111111 |
| 40143 | 30140 | 1.431111111 |
| 40144 | 30141 | 1.429378531 |
| 40145 | 30142 | 1.426356589 |
| 40146 | 30143 | 1.426356589 |
| 40147 | 30144 | 1.426356589 |
| 40148 | 30145 | 1.426356589 |
| 40149 | 30146 | 1.426356589 |
| 40150 | 30147 | 1.426356589 |
| 40151 | 30148 | 1.426356589 |
| 40152 | 30149 | 1.426356589 |
| 40153 | 30150 | 1.426356589 |
| 40154 | 30151 | 1.426356589 |
| 40155 | 30152 | 1.426356589 |
| 40156 | 30153 | 1.422680412 |
| 40157 | 30154 | 1.422680412 |
| 40158 | 30155 | 1.422680412 |
| 40159 | 30156 | 1.422680412 |
| 40160 | 30157 | 1.422680412 |
| 40161 | 30158 | 1.420849421 |
| 40162 | 30159 | 1.419753086 |
| 40163 | 30160 | 1.419753086 |
| 40164 | 30161 | 1.419753086 |
| 40165 | 30162 | 1.419753086 |
| 40166 | 30163 | 1.419753086 |
| 40167 | 30164 | 1.419753086 |
| 40168 | 30165 | 1.419753086 |
| 40169 | 30166 | 1.419753086 |
| 40170 | 30167 | 1.415384615 |
| 40171 | 30168 | 1.415384615 |
| 40172 | 30169 | 1.412280702 |
| 40173 | 30170 | 1.412280702 |
| 40174 | 30171 | 1.412280702 |
| 40175 | 30172 | 1.412280702 |
| 40176 | 30173 | 1.409961686 |
| 40177 | 30174 | 1.409961686 |
| 40178 | 30175 | 1.409961686 |
| 40179 | 30176 | 1.408163265 |
| 40180 | 30177 | 1.406727829 |
| 40181 | 30178 | 1.405555556 |
| 40182 | 30179 | 1.404580153 |
| 40183 | 30180 | 1.404580153 |
| 40184 | 30181 | 1.402439024 |
| 40185 | 30182 | 1.401904762 |
| 40186 | 30183 | 1.393939394 |
| 40187 | 30184 | 1.393939394 |
| 40188 | 30185 | 1.393939394 |
| 40189 | 30186 | 1.393939394 |
| 40190 | 30187 | 1.393939394 |
| 40191 | 30188 | 1.393939394 |
| 40192 | 30189 | 1.393939394 |
| 40193 | 30190 | 1.393939394 |
| 40194 | 30191 | 1.393939394 |
| 40195 | 30192 | 1.393939394 |
| 40196 | 30193 | 1.393939394 |
| 40197 | 30194 | 1.393939394 |
| 40198 | 30195 | 1.393939394 |
| 40199 | 30196 | 1.393939394 |
| 40200 | 30197 | 1.393939394 |
| 40201 | 30198 | 1.393939394 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 40202 | 30199 | 1.393939394 | 40231 | 30228 | 1.383458647 | 40260 | 30257 | 1.358649789 | 40289 | 30286 | 1.333333333 | 40318 | 30315 | 1.314285714 |
| 40203 | 30200 | 1.393939394 | 40232 | 30229 | 1.382513661 | 40261 | 30258 | 1.35600907 | 40290 | 30287 | 1.333333333 | 40319 | 30316 | 1.314285714 |
| 40204 | 30201 | 1.393939394 | 40233 | 30230 | 1.38 | 40262 | 30259 | 1.352941176 | 40291 | 30288 | 1.333333333 | 40320 | 30317 | 1.314285714 |
| 40205 | 30202 | 1.393939394 | 40234 | 30231 | 1.38 | 40263 | 30260 | 1.352941176 | 40292 | 30289 | 1.333333333 | 40321 | 30318 | 1.314285714 |
| 40206 | 30203 | 1.393939394 | 40235 | 30232 | 1.378277154 | 40264 | 30261 | 1.352941176 | 40293 | 30290 | 1.333333333 | 40322 | 30319 | 1.314285714 |
| 40207 | 30204 | 1.393939394 | 40236 | 30233 | 1.376068376 | 40265 | 30262 | 1.352941176 | 40294 | 30291 | 1.333333333 | 40323 | 30320 | 1.308943089 |
| 40208 | 30205 | 1.393939394 | 40237 | 30234 | 1.376068376 | 40266 | 30263 | 1.352941176 | 40295 | 30292 | 1.333333333 | 40324 | 30321 | 1.304964539 |
| 40209 | 30206 | 1.393939394 | 40238 | 30235 | 1.373134328 | 40267 | 30264 | 1.352941176 | 40296 | 30293 | 1.333333333 | 40325 | 30322 | 1.304964539 |
| 40210 | 30207 | 1.393939394 | 40239 | 30236 | 1.373134328 | 40268 | 30265 | 1.352941176 | 40297 | 30294 | 1.333333333 | 40326 | 30323 | 1.304964539 |
| 40211 | 30208 | 1.393939394 | 40240 | 30237 | 1.373134328 | 40269 | 30266 | 1.352941176 | 40298 | 30295 | 1.333333333 | 40327 | 30324 | 1.304964539 |
| 40212 | 30209 | 1.393939394 | 40241 | 30238 | 1.373134328 | 40270 | 30267 | 1.352941176 | 40299 | 30296 | 1.333333333 | 40328 | 30325 | 1.304964539 |
| 40213 | 30210 | 1.393939394 | 40242 | 30239 | 1.373134328 | 40271 | 30268 | 1.349333333 | 40300 | 30297 | 1.333333333 | 40329 | 30326 | 1.304964539 |
| 40214 | 30211 | 1.393939394 | 40243 | 30240 | 1.369047619 | 40272 | 30269 | 1.347985348 | 40301 | 30298 | 1.333333333 | 40330 | 30327 | 1.304964539 |
| 40215 | 30212 | 1.393939394 | 40244 | 30241 | 1.369047619 | 40273 | 30270 | 1.347985348 | 40302 | 30299 | 1.333333333 | 40331 | 30328 | 1.304964539 |
| 40216 | 30213 | 1.393939394 | 40245 | 30242 | 1.369047619 | 40274 | 30271 | 1.347985348 | 40303 | 30300 | 1.326923077 | 40332 | 30329 | 1.304964539 |
| 40217 | 30214 | 1.393939394 | 40246 | 30243 | 1.369047619 | 40275 | 30272 | 1.34502924 | 40304 | 30301 | 1.326923077 | 40333 | 30330 | 1.304964539 |
| 40218 | 30215 | 1.393939394 | 40247 | 30244 | 1.369047619 | 40276 | 30273 | 1.34502924 | 40305 | 30302 | 1.32183908 | 40334 | 30331 | 1.301886792 |
| 40219 | 30216 | 1.393939394 | 40248 | 30245 | 1.369047619 | 40277 | 30274 | 1.34502924 | 40306 | 30303 | 1.32183908 | 40335 | 30332 | 1.299435028 |
| 40220 | 30217 | 1.393939394 | 40249 | 30246 | 1.366336634 | 40278 | 30275 | 1.34502924 | 40307 | 30304 | 1.32183908 | 40336 | 30333 | 1.299435028 |
| 40221 | 30218 | 1.393939394 | 40250 | 30247 | 1.364746946 | 40279 | 30276 | 1.34502924 | 40308 | 30305 | 1.32183908 | 40337 | 30334 | 1.299435028 |
| 40222 | 30219 | 1.393939394 | 40251 | 30248 | 1.362962963 | 40280 | 30277 | 1.34502924 | 40309 | 30306 | 1.318996416 | 40338 | 30335 | 1.299435028 |
| 40223 | 30220 | 1.393939394 | 40252 | 30249 | 1.362962963 | 40281 | 30278 | 1.34502924 | 40310 | 30307 | 1.318996416 | 40339 | 30336 | 1.299435028 |
| 40224 | 30221 | 1.393939394 | 40253 | 30250 | 1.362962963 | 40282 | 30279 | 1.34502924 | 40311 | 30308 | 1.318996416 | 40340 | 30337 | 1.299435028 |
| 40225 | 30222 | 1.393939394 | 40254 | 30251 | 1.362962963 | 40283 | 30280 | 1.34502924 | 40312 | 30309 | 1.317708333 | 40341 | 30338 | 1.299435028 |
| 40226 | 30223 | 1.393939394 | 40255 | 30252 | 1.362962963 | 40284 | 30281 | 1.341666667 | 40313 | 30310 | 1.314285714 | 40342 | 30339 | 1.295774648 |
| 40227 | 30224 | 1.393939394 | 40256 | 30253 | 1.362962963 | 40285 | 30282 | 1.341666667 | 40314 | 30311 | 1.314285714 | 40343 | 30340 | 1.295774648 |
| 40228 | 30225 | 1.393939394 | 40257 | 30254 | 1.362962963 | 40286 | 30283 | 1.341666667 | 40315 | 30312 | 1.314285714 | 40344 | 30341 | 1.293172691 |
| 40229 | 30226 | 1.393939394 | 40258 | 30255 | 1.358649789 | 40287 | 30284 | 1.333333333 | 40316 | 30313 | 1.314285714 | 40345 | 30342 | 1.293172691 |
| 40230 | 30227 | 1.393939394 | 40259 | 30256 | 1.358649789 | 40288 | 30285 | 1.333333333 | 40317 | 30314 | 1.314285714 | 40346 | 30343 | 1.287531807 |

FIG. 6 (Cont.)

| DNA SEQ ID NO | AA SEQ ID NO | Kidney 1 Enrichment |
|---|---|---|
| 40347 | 30344 | 1.277777778 |
| 40348 | 30345 | 1.277777778 |
| 40349 | 30346 | 1.277777778 |
| 40350 | 30347 | 1.277777778 |
| 40351 | 30348 | 1.277777778 |
| 40352 | 30349 | 1.277777778 |
| 40353 | 30350 | 1.277777778 |
| 40354 | 30351 | 1.277777778 |
| 40355 | 30352 | 1.277777778 |
| 40356 | 30353 | 1.277777778 |
| 40357 | 30354 | 1.277777778 |
| 40358 | 30355 | 1.277777778 |
| 40359 | 30356 | 1.277777778 |
| 40360 | 30357 | 1.277777778 |
| 40361 | 30358 | 1.277777778 |
| 40362 | 30359 | 1.277777778 |
| 40363 | 30360 | 1.277777778 |
| 40364 | 30361 | 1.277777778 |
| 40365 | 30362 | 1.277777778 |
| 40366 | 30363 | 1.277777778 |
| 40367 | 30364 | 1.277777778 |
| 40368 | 30365 | 1.277777778 |
| 40369 | 30366 | 1.277777778 |
| 40370 | 30367 | 1.277777778 |
| 40371 | 30368 | 1.277777778 |
| 40372 | 30369 | 1.277777778 |
| 40373 | 30370 | 1.277777778 |
| 40374 | 30371 | 1.277777778 |
| 40375 | 30372 | 1.267217631 |
| 40376 | 30373 | 1.266055046 |
| 40377 | 30374 | 1.264604811 |
| 40378 | 30375 | 1.262745098 |
| 40379 | 30376 | 1.262745098 |
| 40380 | 30377 | 1.262745098 |
| 40381 | 30378 | 1.262745098 |
| 40382 | 30379 | 1.260273973 |
| 40383 | 30380 | 1.260273973 |
| 40384 | 30381 | 1.260273973 |
| 40385 | 30382 | 1.260273973 |
| 40386 | 30383 | 1.256830601 |
| 40387 | 30384 | 1.256830601 |
| 40388 | 30385 | 1.256830601 |
| 40389 | 30386 | 1.256830601 |
| 40390 | 30387 | 1.256830601 |
| 40391 | 30388 | 1.256830601 |
| 40392 | 30389 | 1.254545455 |
| 40393 | 30390 | 1.254545455 |
| 40394 | 30391 | 1.254545455 |
| 40395 | 30392 | 1.254545455 |
| 40396 | 30393 | 1.25170068 |
| 40397 | 30394 | 1.25170068 |
| 40398 | 30395 | 1.25170068 |
| 40399 | 30396 | 1.25170068 |
| 40400 | 30397 | 1.245833333 |
| 40401 | 30398 | 1.243243243 |
| 40402 | 30399 | 1.243243243 |
| 40403 | 30400 | 1.243243243 |
| 40404 | 30401 | 1.243243243 |
| 40405 | 30402 | 1.243243243 |
| 40406 | 30403 | 1.243243243 |
| 40407 | 30404 | 1.243243243 |
| 40408 | 30405 | 1.243243243 |
| 40409 | 30406 | 1.243243243 |
| 40410 | 30407 | 1.243243243 |
| 40411 | 30408 | 1.243243243 |
| 40412 | 30409 | 1.243243243 |
| 40413 | 30410 | 1.239057239 |
| 40414 | 30411 | 1.239057239 |
| 40415 | 30412 | 1.23655914 |
| 40416 | 30413 | 1.23655914 |
| 40417 | 30414 | 1.23655914 |
| 40418 | 30415 | 1.23655914 |
| 40419 | 30416 | 1.233716475 |
| 40420 | 30417 | 1.233716475 |
| 40421 | 30418 | 1.232142857 |
| 40422 | 30419 | 1.231143552 |
| 40423 | 30420 | 1.230452675 |
| 40424 | 30421 | 1.226666667 |
| 40425 | 30422 | 1.226666667 |
| 40426 | 30423 | 1.226666667 |
| 40427 | 30424 | 1.226666667 |
| 40428 | 30425 | 1.226666667 |
| 40429 | 30426 | 1.226666667 |
| 40430 | 30427 | 1.226666667 |
| 40431 | 30428 | 1.226666667 |
| 40432 | 30429 | 1.226666667 |
| 40433 | 30430 | 1.226666667 |
| 40434 | 30431 | 1.226666667 |
| 40435 | 30432 | 1.226666667 |
| 40436 | 30433 | 1.226666667 |
| 40437 | 30434 | 1.221238938 |
| 40438 | 30435 | 1.21969697 |
| 40439 | 30436 | 1.21969697 |
| 40440 | 30437 | 1.21969697 |
| 40441 | 30438 | 1.216931217 |
| 40442 | 30439 | 1.216931217 |
| 40443 | 30440 | 1.216931217 |
| 40444 | 30441 | 1.216931217 |
| 40445 | 30442 | 1.210526316 |
| 40446 | 30443 | 1.210526316 |
| 40447 | 30444 | 1.210526316 |
| 40448 | 30445 | 1.210526316 |
| 40449 | 30446 | 1.210526316 |
| 40450 | 30447 | 1.210526316 |
| 40451 | 30448 | 1.210526316 |
| 40452 | 30449 | 1.210526316 |
| 40453 | 30450 | 1.210526316 |
| 40454 | 30451 | 1.210526316 |
| 40455 | 30452 | 1.210526316 |
| 40456 | 30453 | 1.210526316 |
| 40457 | 30454 | 1.210526316 |
| 40458 | 30455 | 1.210526316 |
| 40459 | 30456 | 1.210526316 |
| 40460 | 30457 | 1.210526316 |
| 40461 | 30458 | 1.205992509 |
| 40462 | 30459 | 1.202614379 |
| 40463 | 30460 | 1.202614379 |
| 40464 | 30461 | 1.202614379 |
| 40465 | 30462 | 1.202614379 |
| 40466 | 30463 | 1.202614379 |
| 40467 | 30464 | 1.202614379 |
| 40468 | 30465 | 1.202614379 |
| 40469 | 30466 | 1.2 |
| 40470 | 30467 | 1.197916667 |
| 40471 | 30468 | 1.197916667 |
| 40472 | 30469 | 1.197916667 |
| 40473 | 30470 | 1.194805195 |
| 40474 | 30471 | 1.194805195 |
| 40475 | 30472 | 1.194805195 |
| 40476 | 30473 | 1.192592593 |
| 40477 | 30474 | 1.192592593 |
| 40478 | 30475 | 1.190938511 |
| 40479 | 30476 | 1.190938511 |
| 40480 | 30477 | 1.179487179 |
| 40481 | 30478 | 1.179487179 |
| 40482 | 30479 | 1.179487179 |
| 40483 | 30480 | 1.179487179 |
| 40484 | 30481 | 1.179487179 |
| 40485 | 30482 | 1.179487179 |
| 40486 | 30483 | 1.179487179 |
| 40487 | 30484 | 1.179487179 |
| 40488 | 30485 | 1.179487179 |
| 40489 | 30486 | 1.179487179 |
| 40490 | 30487 | 1.179487179 |
| 40491 | 30488 | 1.179487179 |

FIG. 6 (Cont.)

| DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment | DNA SEQ ID NO | AA SEQ ID NO | Kidney 1 Enrichment |
|---|---|---|---|---|---|---|---|---|---|---|---|---|---|---|
| 40492 | 30489 | 1.179487179 | 40521 | 30518 | 1.157232704 | 40550 | 30547 | 1.135802469 | 40579 | 30576 | 1.115151515 | 40608 | 30605 | 1.095238095 |
| 40493 | 30490 | 1.179487179 | 40522 | 30519 | 1.154121864 | 40551 | 30548 | 1.135802469 | 40580 | 30577 | 1.115151515 | 40609 | 30606 | 1.095238095 |
| 40494 | 30491 | 1.179487179 | 40523 | 30520 | 1.154121864 | 40552 | 30549 | 1.135802469 | 40581 | 30578 | 1.115151515 | 40610 | 30607 | 1.095238095 |
| 40495 | 30492 | 1.179487179 | 40524 | 30521 | 1.154121864 | 40553 | 30550 | 1.135802469 | 40582 | 30579 | 1.115151515 | 40611 | 30608 | 1.095238095 |
| 40496 | 30493 | 1.179487179 | 40525 | 30522 | 1.154121864 | 40554 | 30551 | 1.135802469 | 40583 | 30580 | 1.115151515 | 40612 | 30609 | 1.095238095 |
| 40497 | 30494 | 1.179487179 | 40526 | 30523 | 1.15 | 40555 | 30552 | 1.135802469 | 40584 | 30581 | 1.115151515 | 40613 | 30610 | 1.095238095 |
| 40498 | 30495 | 1.179487179 | 40527 | 30524 | 1.15 | 40556 | 30553 | 1.135802469 | 40585 | 30582 | 1.115151515 | 40614 | 30611 | 1.095238095 |
| 40499 | 30496 | 1.179487179 | 40528 | 30525 | 1.15 | 40557 | 30554 | 1.135802469 | 40586 | 30583 | 1.111111111 | 40615 | 30612 | 1.095238095 |
| 40500 | 30497 | 1.179487179 | 40529 | 30526 | 1.15 | 40558 | 30555 | 1.129824561 | 40587 | 30584 | 1.111111111 | 40616 | 30613 | 1.095238095 |
| 40501 | 30498 | 1.179487179 | 40530 | 30527 | 1.15 | 40559 | 30556 | 1.129824561 | 40588 | 30585 | 1.111111111 | 40617 | 30614 | 1.095238095 |
| 40502 | 30499 | 1.179487179 | 40531 | 30528 | 1.15 | 40560 | 30557 | 1.128834356 | 40589 | 30586 | 1.111111111 | 40618 | 30615 | 1.095238095 |
| 40503 | 30500 | 1.179487179 | 40532 | 30529 | 1.15 | 40561 | 30558 | 1.12745098 | 40590 | 30587 | 1.111111111 | 40619 | 30616 | 1.095238095 |
| 40504 | 30501 | 1.179487179 | 40533 | 30530 | 1.15 | 40562 | 30559 | 1.12745098 | 40591 | 30588 | 1.111111111 | 40620 | 30617 | 1.095238095 |
| 40505 | 30502 | 1.179487179 | 40534 | 30531 | 1.144278607 | 40563 | 30560 | 1.12745098 | 40592 | 30589 | 1.111111111 | 40621 | 30618 | 1.095238095 |
| 40506 | 30503 | 1.179487179 | 40535 | 30532 | 1.144278607 | 40564 | 30561 | 1.125382263 | 40593 | 30590 | 1.109649123 | 40622 | 30619 | 1.095238095 |
| 40507 | 30504 | 1.179487179 | 40536 | 30533 | 1.144278607 | 40565 | 30562 | 1.12195122 | 40594 | 30591 | 1.108433735 | 40623 | 30620 | 1.095238095 |
| 40508 | 30505 | 1.179487179 | 40537 | 30534 | 1.144278607 | 40566 | 30563 | 1.12195122 | 40595 | 30592 | 1.108433735 | 40624 | 30621 | 1.095238095 |
| 40509 | 30506 | 1.179487179 | 40538 | 30535 | 1.141843972 | 40567 | 30564 | 1.12195122 | 40596 | 30593 | 1.104 | 40625 | 30622 | 1.095238095 |
| 40510 | 30507 | 1.169491525 | 40539 | 30536 | 1.141843972 | 40568 | 30565 | 1.12195122 | 40597 | 30594 | 1.102396514 | 40626 | 30623 | 1.095238095 |
| 40511 | 30508 | 1.169491525 | 40540 | 30537 | 1.141843972 | 40569 | 30566 | 1.12195122 | 40598 | 30595 | 1.095238095 | 40627 | 30624 | 1.095238095 |
| 40512 | 30509 | 1.168253968 | 40541 | 30538 | 1.141843972 | 40570 | 30567 | 1.12195122 | 40599 | 30596 | 1.095238095 | 40628 | 30625 | 1.084175084 |
| 40513 | 30510 | 1.164556962 | 40542 | 30539 | 1.135802469 | 40571 | 30568 | 1.12195122 | 40600 | 30597 | 1.095238095 | 40629 | 30626 | 1.084175084 |
| 40514 | 30511 | 1.164556962 | 40543 | 30540 | 1.135802469 | 40572 | 30569 | 1.12195122 | 40601 | 30598 | 1.095238095 | 40630 | 30627 | 1.082352941 |
| 40515 | 30512 | 1.164556962 | 40544 | 30541 | 1.135802469 | 40573 | 30570 | 1.12195122 | 40602 | 30599 | 1.095238095 | 40631 | 30628 | 1.079812207 |
| 40516 | 30513 | 1.164556962 | 40545 | 30542 | 1.135802469 | 40574 | 30571 | 1.12195122 | 40603 | 30600 | 1.095238095 | 40632 | 30629 | 1.079812207 |
| 40517 | 30514 | 1.164556962 | 40546 | 30543 | 1.135802469 | 40575 | 30572 | 1.12195122 | 40604 | 30601 | 1.095238095 | 40633 | 30630 | 1.079812207 |
| 40518 | 30515 | 1.161616162 | 40547 | 30544 | 1.135802469 | 40576 | 30573 | 1.119221411 | 40605 | 30602 | 1.095238095 | 40634 | 30631 | 1.078125 |
| 40519 | 30516 | 1.161616162 | 40548 | 30545 | 1.135802469 | 40577 | 30574 | 1.118055556 | 40606 | 30603 | 1.095238095 | 40635 | 30632 | 1.076023392 |
| 40520 | 30517 | 1.157232704 | 40549 | 30546 | 1.135802469 | 40578 | 30575 | 1.115151515 | 40607 | 30604 | 1.095238095 | 40636 | 30633 | 1.076023392 |

FIG. 6 (Cont.)

| DNA SEQ ID NO | AA SEQ ID NO | Kidney 1 Enrichment |
|---|---|---|
| 40637 | 30634 | 1.076023392 |
| 40638 | 30635 | 1.069767442 |
| 40639 | 30636 | 1.069767442 |
| 40640 | 30637 | 1.069767442 |
| 40641 | 30638 | 1.069767442 |
| 40642 | 30639 | 1.069767442 |
| 40643 | 30640 | 1.069767442 |
| 40644 | 30641 | 1.069767442 |
| 40645 | 30642 | 1.069767442 |
| 40646 | 30643 | 1.069767442 |
| 40647 | 30644 | 1.064814815 |
| 40648 | 30645 | 1.062706271 |
| 40649 | 30646 | 1.057471264 |
| 40650 | 30647 | 1.057471264 |
| 40651 | 30648 | 1.057471264 |
| 40652 | 30649 | 1.057471264 |
| 40653 | 30650 | 1.057471264 |
| 40654 | 30651 | 1.057471264 |

| DNA SEQ ID NO | AA SEQ ID NO | Kidney 1 Enrichment |
|---|---|---|
| 40655 | 30652 | 1.057471264 |
| 40656 | 30653 | 1.057471264 |
| 40657 | 30654 | 1.057471264 |
| 40658 | 30655 | 1.057471264 |
| 40659 | 30656 | 1.057471264 |
| 40660 | 30657 | 1.057471264 |
| 40661 | 30658 | 1.057471264 |
| 40662 | 30659 | 1.057471264 |
| 40663 | 30660 | 1.057471264 |
| 40664 | 30661 | 1.050228311 |
| 40665 | 30662 | 1.050228311 |
| 40666 | 30663 | 1.050228311 |
| 40667 | 30664 | 1.050228311 |
| 40668 | 30665 | 1.050228311 |
| 40669 | 30666 | 1.050228311 |
| 40670 | 30667 | 1.048433048 |
| 40671 | 30668 | 1.045454545 |
| 40672 | 30669 | 1.045454545 |

| DNA SEQ ID NO | AA SEQ ID NO | Kidney 1 Enrichment |
|---|---|---|
| 40673 | 30670 | 1.045454545 |
| 40674 | 30671 | 1.045454545 |
| 40675 | 30672 | 1.045454545 |
| 40676 | 30673 | 1.045454545 |
| 40677 | 30674 | 1.045454545 |
| 40678 | 30675 | 1.045454545 |
| 40679 | 30676 | 1.045454545 |
| 40680 | 30677 | 1.042071197 |
| 40681 | 30678 | 1.039548023 |
| 40682 | 30679 | 1.039548023 |
| 40683 | 30680 | 1.039548023 |
| 40684 | 30681 | 1.039548023 |
| 40685 | 30682 | 1.036036036 |
| 40686 | 30683 | 1.032051282 |
| 40687 | 30684 | 1.030812325 |
| 40688 | 30685 | 1.029850746 |
| 40689 | 30686 | 1.022222222 |
| 40690 | 30687 | 1.022222222 |

| DNA SEQ ID NO | AA SEQ ID NO | Kidney 1 Enrichment |
|---|---|---|
| 40691 | 30688 | 1.022222222 |
| 40692 | 30689 | 1.022222222 |
| 40693 | 30690 | 1.022222222 |
| 40694 | 30691 | 1.022222222 |
| 40695 | 30692 | 1.022222222 |
| 40696 | 30693 | 1.022222222 |
| 40697 | 30694 | 1.022222222 |
| 40698 | 30695 | 1.022222222 |
| 40699 | 30696 | 1.022222222 |
| 40700 | 30697 | 1.022222222 |
| 40701 | 30698 | 1.022222222 |
| 40702 | 30699 | 1.022222222 |
| 40703 | 30700 | 1.022222222 |
| 40704 | 30701 | 1.022222222 |
| 40705 | 30702 | 1.022222222 |
| 40706 | 30703 | 1.022222222 |
| 40707 | 30704 | 1.022222222 |
| 40708 | 30705 | 1.022222222 |

| DNA SEQ ID NO | AA SEQ ID NO | Kidney 1 Enrichment |
|---|---|---|
| 40709 | 30706 | 1.022222222 |
| 40710 | 30707 | 1.022222222 |
| 40711 | 30708 | 1.022222222 |
| 40712 | 30709 | 1.022222222 |
| 40713 | 30710 | 1.022222222 |
| 40714 | 30711 | 1.012578616 |
| 40715 | 30712 | 1.010989011 |
| 40716 | 30713 | 1.010989011 |
| 40717 | 30714 | 1.00877193 |
| 40718 | 30715 | 1.00877193 |
| 40719 | 30716 | 1.00877193 |
| 40720 | 30717 | 1.00877193 |
| 40721 | 30718 | 1.005464481 |
| 40722 | 30719 | 1.005464481 |

FIG. 7

| DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment |
|---|---|---|---|---|---|---|---|---|---|---|---|---|---|---|---|
| 40723 | 30720 | 5.227272727 | 3.538461538 | 40749 | 30746 | 1.870813397 | 1.978744939 | 40775 | 30772 | 1.524621212 | 1.492788462 | 40801 | 30798 | 1.36489899 | 1.277777778 |
| 40724 | 30721 | 5.084710744 | 2.573426573 | 40750 | 30747 | 1.858585859 | 1.990384615 | 40776 | 30773 | 1.517595308 | 2.168734491 | 40802 | 30799 | 1.356265356 | 1.123700624 |
| 40725 | 30722 | 4.122077922 | 3.525824176 | 40751 | 30748 | 1.844919786 | 1.209841629 | 40777 | 30774 | 1.512572534 | 1.505728314 | 40803 | 30800 | 1.352941176 | 3.052790347 |
| 40726 | 30723 | 3.659090909 | 4.201923077 | 40752 | 30749 | 1.829545455 | 1.105769231 | 40778 | 30775 | 1.493506494 | 2.021978022 | 40804 | 30801 | 1.347474747 | 1.061538462 |
| 40727 | 30724 | 3.136363636 | 1.326923077 | 40753 | 30750 | 1.796875 | 1.520432692 | 40779 | 30776 | 1.493506494 | 1.453296703 | 40805 | 30802 | 1.347027972 | 1.122781065 |
| 40728 | 30725 | 3.090909091 | 2.807692308 | 40754 | 30751 | 1.792207792 | 1.39010989 | 40780 | 30777 | 1.493506494 | 2.021978022 | 40806 | 30803 | 1.34032634 | 1.088757396 |
| 40729 | 30726 | 3.055944056 | 2.517751479 | 40755 | 30752 | 1.787390029 | 1.598014888 | 40781 | 30778 | 1.478935698 | 7.141651032 | 40807 | 30804 | 1.339488636 | 1.592307692 |
| 40730 | 30727 | 3.013368984 | 4.475113122 | 40756 | 30753 | 1.777272727 | 1.857692308 | 40782 | 30779 | 1.475935829 | 1.509049774 | 40808 | 30805 | 1.327803583 | 1.478663672 |
| 40731 | 30728 | 2.955667789 | 2.178774929 | 40757 | 30754 | 1.777272727 | 1.238461538 | 40783 | 30780 | 1.473140496 | 1.145979021 | 40809 | 30806 | 1.326322931 | 1.161882893 |
| 40732 | 30729 | 2.923400673 | 1.015669516 | 40758 | 30755 | 1.756794752 | 1.942505948 | 40784 | 30781 | 1.473140496 | 1.005244755 | 40810 | 30807 | 1.324242424 | 1.518589744 |
| 40733 | 30730 | 2.882063882 | 1.47037422 | 40759 | 30756 | 1.742424242 | 1.503846154 | 40785 | 30782 | 1.470724191 | 1.859191656 | 40811 | 30808 | 1.322820037 | 1.335949765 |
| 40734 | 30731 | 2.852597403 | 1.074175824 | 40760 | 30757 | 1.669059011 | 1.458839406 | 40786 | 30783 | 1.463636364 | 1.194230769 | 40812 | 30809 | 1.318881119 | 1.047928994 |
| 40735 | 30732 | 2.851239669 | 2.573426573 | 40761 | 30758 | 1.666827853 | 1.373977087 | 40787 | 30784 | 1.444628099 | 1.238461538 | 40813 | 30810 | 1.314285714 | 1.023626374 |
| 40736 | 30733 | 2.800324675 | 1.216346154 | 40762 | 30759 | 1.638820639 | 1.004158004 | 40788 | 30785 | 1.443722944 | 1.221611722 | 40814 | 30811 | 1.306818182 | 1.232142857 |
| 40737 | 30734 | 2.566115702 | 3.833333333 | 40763 | 30760 | 1.636363636 | 1.211538462 | 40789 | 30786 | 1.442462601 | 1.466893866 | 40815 | 30812 | 1.302797203 | 1.279289941 |
| 40738 | 30735 | 2.538961039 | 1.769230769 | 40764 | 30761 | 1.631929047 | 1.100375235 | 40790 | 30787 | 1.439393939 | 1.192307692 | 40816 | 30813 | 1.300443459 | 1.672138837 |
| 40739 | 30736 | 2.352272727 | 1.105769231 | 40765 | 30762 | 1.628964059 | 1.398926655 | 40791 | 30788 | 1.436179982 | 1.331390831 | 40817 | 30814 | 1.296363636 | 1.096923077 |
| 40740 | 30737 | 2.352272727 | 1.769230769 | 40766 | 30763 | 1.585043988 | 1.255583127 | 40792 | 30789 | 1.425619835 | 1.548076923 | 40818 | 30815 | 1.296363636 | 5.118974359 |
| 40741 | 30738 | 2.3 | 1.326923077 | 40767 | 30764 | 1.575544174 | 1.270855905 | 40793 | 30790 | 1.421348315 | 1.500864304 | 40819 | 30816 | 1.294372294 | 1.053113553 |
| 40742 | 30739 | 2.3 | 1.592307692 | 40768 | 30765 | 1.568181818 | 1.326923077 | 40794 | 30791 | 1.418831169 | 1.105769231 | 40820 | 30817 | 1.281524927 | 1.612282878 |
| 40743 | 30740 | 2.233471074 | 2.452797203 | 40769 | 30766 | 1.568181818 | 1.326923077 | 40795 | 30792 | 1.418831169 | 1.358516484 | 40821 | 30818 | 1.277777778 | 1.4375 |
| 40744 | 30741 | 2.153636364 | 4.14 | 40770 | 30767 | 1.568181818 | 1.326923077 | 40796 | 30793 | 1.414438503 | 1.114479638 | 40822 | 30819 | 1.277777778 | 1.277777778 |
| 40745 | 30742 | 2.090909091 | 3.538461538 | 40771 | 30768 | 1.568181818 | 2.653846154 | 40797 | 30794 | 1.40684624 | 1.234093067 | 40823 | 30820 | 1.273310023 | 1.49704142 |
| 40746 | 30743 | 1.974747475 | 1.965811966 | 40772 | 30769 | 1.568181818 | 2.211538462 | 40798 | 30795 | 1.393939394 | 2.948717949 | 40824 | 30821 | 1.272727273 | 1.596153846 |
| 40747 | 30744 | 1.916666667 | 1.621794872 | 40773 | 30770 | 1.596125519 | 1.044136192 | 40799 | 30796 | 1.384520885 | 1.434511435 | 40825 | 30822 | 1.272727273 | 1.538461538 |
| 40748 | 30745 | 1.916666667 | 1.179487179 | 40774 | 30771 | 1.551846591 | 1.423677885 | 40800 | 30797 | 1.370707071 | 1.690598291 | 40826 | 30823 | 1.272727273 | 1.346153846 |

FIG. 7 (Cont.)

| DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment | DNA SEQ ID NO | AA SEQ ID NO | Liver 1 Enrichment | Liver 2 Enrichment |
|---|---|---|---|---|---|---|---|---|---|---|---|---|---|---|---|
| 40827 | 30824 | 1.272727273 | 1.192307692 | 40853 | 30850 | 1.194805195 | 1.990384615 | 40879 | 30876 | 1.085664336 | 1.156804734 | 40905 | 30902 | 1.045454545 | 1.575721154 |
| 40828 | 30825 | 1.258812616 | 1.173469388 | 40854 | 30851 | 1.187211094 | 1.274445893 | 40880 | 30877 | 1.082792208 | 1.57967033 | 40906 | 30903 | 1.045454545 | 3.538461538 |
| 40829 | 30826 | 1.254545455 | 1.454700855 | 40855 | 30852 | 1.184848485 | 1.415384615 | 40881 | 30878 | 1.080893683 | 1.304432855 | 40907 | 30904 | 1.045454545 | 1.474358974 |
| 40830 | 30827 | 1.254545455 | 1.216346154 | 40856 | 30853 | 1.180351906 | 1.227047146 | 40882 | 30879 | 1.08030303 | 1.110683761 | 40908 | 30905 | 1.045454545 | 1.326923077 |
| 40831 | 30828 | 1.25 | 1.115384615 | 40857 | 30854 | 1.176136364 | 1.216346154 | 40883 | 30880 | 1.077788191 | 1.285884219 | 40909 | 30906 | 1.045454545 | 1.326923077 |
| 40832 | 30829 | 1.249445676 | 1.03564728 | 40858 | 30855 | 1.173232323 | 1.15982906 | 40884 | 30881 | 1.077134986 | 1.045454545 | 40910 | 30907 | 1.030934343 | 1.105769231 |
| 40833 | 30830 | 1.248737374 | 1.326923077 | 40859 | 30856 | 1.169491525 | 1.244458931 | 40885 | 30882 | 1.077134986 | 1.501165501 | 40911 | 30908 | 1.030729834 | 1.196099675 |
| 40834 | 30831 | 1.247208931 | 1.25708502 | 40860 | 30857 | 1.168449198 | 1.990384615 | 40886 | 30883 | 1.075324675 | 1.061538462 | 40912 | 30909 | 1.028030303 | 1.091025641 |
| 40835 | 30832 | 1.243243243 | 1.123700624 | 40861 | 30858 | 1.161616162 | 1.818376068 | 40887 | 30884 | 1.075324675 | 1.112087912 | 40913 | 30910 | 1.026446281 | 1.576223776 |
| 40836 | 30833 | 1.239957717 | 1.913237925 | 40862 | 30859 | 1.157467532 | 1.263736264 | 40888 | 30885 | 1.074494949 | 1.056623932 | 40914 | 30911 | 1.026094276 | 1.261396011 |
| 40837 | 30834 | 1.2368758 | 1.171180932 | 40863 | 30860 | 1.156336088 | 1.179487179 | 40889 | 30886 | 1.074097136 | 1.514752371 | 40915 | 30912 | 1.02534965 | 1.394970414 |
| 40838 | 30835 | 1.233979136 | 1.392181589 | 40864 | 30861 | 1.142706131 | 1.54293381 | 40890 | 30887 | 1.071590909 | 1.371153846 | 40916 | 30913 | 1.02534965 | 1.105769231 |
| 40839 | 30836 | 1.233979136 | 1.116645649 | 40865 | 30862 | 1.140495868 | 1.769230769 | 40891 | 30888 | 1.070953437 | 1.197467167 | 40917 | 30914 | 1.023674242 | 2.432692308 |
| 40840 | 30837 | 1.233100233 | 1.633136095 | 40866 | 30863 | 1.140495868 | 1.206293706 | 40892 | 30889 | 1.069767442 | 1.080053667 | 40918 | 30915 | 1.021694215 | 1.02534965 |
| 40841 | 30838 | 1.233100233 | 1.088757396 | 40867 | 30864 | 1.137700535 | 1.378959276 | 40893 | 30890 | 1.069487983 | 1.230327144 | 40919 | 30916 | 1.020562771 | 1.010989011 |
| 40842 | 30839 | 1.233100233 | 1.247534517 | 40868 | 30865 | 1.132575758 | 1.007478632 | 40894 | 30891 | 1.061294766 | 1.005244755 | 40920 | 30917 | 1.014705882 | 1.040723982 |
| 40843 | 30840 | 1.228409091 | 1.205288462 | 40869 | 30866 | 1.124144673 | 1.20802316 | 40895 | 30892 | 1.045454545 | 1.114615385 | 40921 | 30918 | 1.013450835 | 1.426216641 |
| 40844 | 30841 | 1.224675325 | 1.516483516 | 40870 | 30867 | 1.12012987 | 1.137362637 | 40896 | 30893 | 1.045454545 | 1.061538462 | 40922 | 30919 | 1.010606061 | 1.091025641 |
| 40845 | 30842 | 1.21969697 | 1.474358974 | 40871 | 30868 | 1.117554859 | 1.113395225 | 40897 | 30894 | 1.045454545 | 1.184485007 | 40923 | 30920 | 1.006372133 | 1.339324227 |
| 40846 | 30843 | 1.21969697 | 1.032051282 | 40872 | 30869 | 1.110795455 | 1.202524038 | 40898 | 30895 | 1.045454545 | 1.608391608 | 40924 | 30921 | 1.006003431 | 1.185050798 |
| 40847 | 30844 | 1.21969697 | 2.211538462 | 40873 | 30870 | 1.103535354 | 1.081196581 | 40899 | 30896 | 1.045454545 | 1.032051282 | 40925 | 30922 | 1.004456328 | 1.16214178 |
| 40848 | 30845 | 1.217096336 | 1.399540758 | 40874 | 30871 | 1.100478469 | 2.188259109 | 40900 | 30897 | 1.045454545 | 2.653846154 | 40926 | 30923 | 1.000967118 | 1.138707038 |
| 40849 | 30846 | 1.210526316 | 1.489878543 | 40875 | 30872 | 1.099343955 | 1.422680412 | 40901 | 30898 | 1.045454545 | 1.061538462 | | | | |
| 40850 | 30847 | 1.206293706 | 1.147083686 | 40876 | 30873 | 1.096452328 | 1.488742964 | 40902 | 30899 | 1.045454545 | 3.685897436 | | | | |
| 40851 | 30848 | 1.203856749 | 1.594988345 | 40877 | 30874 | 1.095238095 | 1.558608059 | 40903 | 30900 | 1.045454545 | 1.274886878 | | | | |
| 40852 | 30849 | 1.194805195 | 1.137362637 | 40878 | 30875 | 1.088418431 | 1.163329821 | 40904 | 30901 | 1.045454545 | 1.326923077 | | | | |

FIG. 8

| DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment |
|---|---|---|---|---|---|---|---|---|---|---|---|---|---|---|---|
| 40927 | 30924 | 317.4 | 56.35 | 40953 | 30950 | 114.4102564 | 17.3974359 | 40979 | 30976 | 92 | 32.47058824 | 41005 | 31002 | 80.20512821 | 10.32051282 |
| 40928 | 30925 | 275.1481481 | 9.37037037 | 40954 | 30951 | 113.3170732 | 1.402439024 | 40980 | 30977 | 91.4025974 | 7.766233766 | 41006 | 31003 | 79.91919192 | 10.57070707 |
| 40929 | 30926 | 247.25 | 57.5 | 40955 | 30952 | 112.6206897 | 25.18103448 | 40981 | 30978 | 91.23333333 | 20.125 | 41007 | 31004 | 79.45454545 | 3.206060606 |
| 40930 | 30927 | 220.5909091 | 20.38636364 | 40956 | 30953 | 110.0392157 | 17.0245098 | 40982 | 30979 | 90.51612903 | 39.69354839 | 41008 | 31005 | 79.26153846 | 14.50769231 |
| 40931 | 30928 | 219.5454545 | 25.61363636 | 40957 | 30954 | 109.754386 | 8.877192982 | 40983 | 30980 | 90.06315789 | 5.205263158 | 41009 | 31006 | 79.14705882 | 16.91176471 |
| 40932 | 30929 | 200 | 54.5 | 40958 | 30955 | 109.6923077 | 7.961538462 | 40984 | 30981 | 89.25373134 | 11.84328358 | 41010 | 31007 | 78.64516129 | 36.72580645 |
| 40933 | 30930 | 163.915493 | 11.82394366 | 40959 | 30956 | 109.25 | 9.670454545 | 40985 | 30982 | 89.21212121 | 2.439393939 | 41011 | 31008 | 78.42622951 | 12.44262295 |
| 40934 | 30931 | 154.2352941 | 31.11764706 | 40960 | 30957 | 109.1641791 | 1.544776119 | 40986 | 30983 | 89.125 | 19.88541667 | 41012 | 31009 | 77.7027027 | 6.527027027 |
| 40935 | 30932 | 152.2058824 | 8.117647059 | 40961 | 30958 | 109.1162791 | 9.093023256 | 40987 | 30984 | 88.79069767 | 12.56976744 | 41013 | 31010 | 77.66233766 | 5.376623377 |
| 40936 | 30933 | 151.6296296 | 12.13888889 | 40962 | 30959 | 108.4285714 | 32.30952381 | 40988 | 30985 | 88.55 | 6.325 | 41014 | 31011 | 77 | 22.75 |
| 40937 | 30934 | 146.1176471 | 25.57058824 | 40963 | 30960 | 107.6818182 | 14.11363636 | 40989 | 30986 | 88.53763441 | 12.24193548 | 41015 | 31012 | 76.86075949 | 11.5 |
| 40938 | 30935 | 145.8113208 | 13.45283019 | 40964 | 30961 | 107.09375 | 15.09375 | 40990 | 30987 | 87.24137931 | 11.5 | 41016 | 31013 | 76.85365854 | 14.44512195 |
| 40939 | 30936 | 145.4022989 | 15.59770115 | 40965 | 30962 | 105.9393939 | 9.060606061 | 40991 | 30988 | 87.18095238 | 4.928571429 | 41017 | 31014 | 76.66666667 | 9.684210526 |
| 40940 | 30937 | 139.4375 | 15.2734375 | 40966 | 30963 | 103.7804878 | 7.152439024 | 40992 | 30989 | 86.88888889 | 23.76666667 | 41018 | 31015 | 75.44 | 40.71 |
| 40941 | 30938 | 135.8095238 | 59.14285714 | 40967 | 30964 | 101.7575758 | 17.42424242 | 40993 | 30990 | 86.65116279 | 14.70930233 | 41019 | 31016 | 75.3037037 | 1.874074074 |
| 40942 | 30939 | 135.7 | 73.025 | 40968 | 30965 | 101.7307692 | 16.03365385 | 40994 | 30991 | 85.03030303 | 24.39393939 | 41020 | 31017 | 75.27272727 | 3.833333333 |
| 40943 | 30940 | 134.7906977 | 22.73255814 | 40969 | 30966 | 101.627907 | 18.72093023 | 40995 | 30992 | 84.58064516 | 24.85483871 | 41021 | 31018 | 75.05263158 | 18.76315789 |
| 40944 | 30941 | 131.2352941 | 4.397058824 | 40970 | 30967 | 99.66666667 | 7.1875 | 40996 | 30993 | 84.5203252 | 5.329268293 | 41022 | 31019 | 74.47619048 | 6.936507937 |
| 40945 | 30942 | 130.9830508 | 9.161016949 | 40971 | 30968 | 97.52 | 15.41 | 40997 | 30994 | 84.23376623 | 6.870129987 | 41023 | 31020 | 73.47222222 | 12.9375 |
| 40946 | 30943 | 130.9230769 | 8.467032967 | 40972 | 30969 | 96.4 | 13 | 40998 | 30995 | 84.11428571 | 6.571428571 | 41024 | 31021 | 73.128205128 | 26.24358974 |
| 40947 | 30944 | 130 | 3.5 | 40973 | 30970 | 96.24615385 | 6.9 | 40999 | 30996 | 82.41666667 | 20.125 | 41025 | 31022 | 73.10714286 | 4.825892857 |
| 40948 | 30945 | 125.5254237 | 12.08474576 | 40974 | 30971 | 96.18181818 | 31.71212121 | 41000 | 30997 | 82.36190476 | 13.25238095 | 41026 | 31023 | 72.98666667 | 9.353333333 |
| 40949 | 30946 | 122.6666667 | 22.04166667 | 40975 | 30972 | 94.35897436 | 17.98717949 | 41001 | 30998 | 81.38461538 | 31.84615385 | 41027 | 31024 | 72.953125 | 13.56640625 |
| 40950 | 30947 | 119.4230769 | 24.99038462 | 40976 | 30973 | 94 | 23 | 41002 | 30999 | 81.17647059 | 12.40196078 | 41028 | 31025 | 72.92682927 | 14.30487805 |
| 40951 | 30948 | 116.0615385 | 11.67692308 | 40977 | 30974 | 92.68656716 | 12.52985075 | 41003 | 31000 | 81.10526316 | 30.86842105 | 41029 | 31026 | 72.66666667 | 8.5 |
| 40952 | 30949 | 115.3538462 | 1.061538462 | 40978 | 30975 | 92 | 19.32 | 41004 | 31001 | 80.39252336 | 14.61682243 | 41030 | 31027 | 72.48484848 | 7.492424242 |

FIG. 8 (Cont.)

| DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment |
|---|---|---|---|---|---|---|---|---|---|---|---|---|---|---|---|
| 41031 | 31028 | 71.90291262 | 6.475728155 | 41059 | 31056 | 61.75342466 | 11.34246575 | 41087 | 31084 | 55.3559322 | 8.771186441 | 41115 | 31112 | 48.70588235 | 12.62745098 |
| 41032 | 31029 | 71.72881356 | 9.745762712 | 41060 | 31057 | 61.33333333 | 4.259259259 | 41088 | 31085 | 55.2 | 35.9375 | 41116 | 31113 | 48.62857143 | 12.15714286 |
| 41033 | 31030 | 71.48648649 | 15.22972973 | 41061 | 31058 | 60.6031746 | 16.24603175 | 41089 | 31086 | 55.2 | 23 | 41117 | 31114 | 48.46428571 | 12.9375 |
| 41034 | 31031 | 70.27777778 | 11.5 | 41062 | 31059 | 60.52631579 | 16.79605263 | 41090 | 31087 | 54.68888889 | 18.52777778 | 41118 | 31115 | 48.3 | 7.475 |
| 41035 | 31032 | 70 | 9.5 | 41063 | 31060 | 60.52631579 | 8.070175439 | 41091 | 31088 | 54.36363636 | 11.5 | 41119 | 31116 | 47.97849462 | 16.56989247 |
| 41036 | 31033 | 69.97183099 | 21.38028169 | 41064 | 31061 | 60.34862385 | 5.591743119 | 41092 | 31089 | 54.19178082 | 5.51369863 | 41120 | 31117 | 47.84 | 10.12 |
| 41037 | 31034 | 69 | 48.875 | 41065 | 31062 | 60.2972973 | 10.41216216 | 41093 | 31090 | 53.85365854 | 28.32926829 | 41121 | 31118 | 47.76923077 | 36.04807692 |
| 41038 | 31035 | 69 | 9.2 | 41066 | 31063 | 60.27586207 | 11.5 | 41094 | 31091 | 53.51020408 | 1.173469388 | 41122 | 31119 | 47.73584906 | 5.316037736 |
| 41039 | 31036 | 69 | 9.234848485 | 41067 | 31064 | 60.05555556 | 4.046296296 | 41095 | 31092 | 53.34042553 | 5.260638298 | 41123 | 31120 | 47.73584906 | 22.3490566 |
| 41040 | 31037 | 69 | 22.09210526 | 41068 | 31065 | 59.90697674 | 14.1744186 | 41096 | 31093 | 53.15555556 | 13.03333333 | 41124 | 31121 | 47.5862069 | 7.336206897 |
| 41041 | 31038 | 68.53061224 | 11.57823129 | 41069 | 31066 | 59.84070796 | 13.94247788 | 41097 | 31094 | 52.73170732 | 14.02439024 | 41125 | 31122 | 47.31428571 | 8.542857143 |
| 41042 | 31039 | 67.02857143 | 17.41428571 | 41070 | 31067 | 59.225 | 7.7625 | 41098 | 31095 | 52.09638554 | 13.57831325 | 41126 | 31123 | 46.75409836 | 1.508196721 |
| 41043 | 31040 | 66.44444444 | 6.814814815 | 41071 | 31068 | 59.14285714 | 41.89285714 | 41099 | 31096 | 51.49253731 | 23.51492537 | 41127 | 31124 | 46.73015873 | 7.849206349 |
| 41044 | 31041 | 66.19512195 | 11.6402439 | 41072 | 31069 | 57.71974522 | 7.251592357 | 41100 | 31097 | 51.47619048 | 15.88095238 | 41128 | 31125 | 46.6969697 | 13.93939394 |
| 41045 | 31042 | 66.18705036 | 18.03597122 | 41073 | 31070 | 57.5 | 5.60625 | 41101 | 31098 | 51.16853933 | 7.494382022 | 41129 | 31126 | 46.60526316 | 7.868421053 |
| 41046 | 31043 | 65.91044776 | 9.268656716 | 41074 | 31071 | 57.23863636 | 4.508522727 | 41102 | 31099 | 51.11111111 | 13.92777778 | 41130 | 31127 | 46.52272727 | 6.272727273 |
| 41047 | 31044 | 65.52830189 | 5.099056604 | 41075 | 31072 | 57.21393035 | 8.467661692 | 41103 | 31100 | 51.04109589 | 11.34246575 | 41131 | 31128 | 46 | 3.653645833 |
| 41048 | 31045 | 65.40625 | 10.2421875 | 41076 | 31073 | 57.18918919 | 13.98648649 | 41104 | 31101 | 50.89361702 | 2.691489362 | 41132 | 31129 | 46 | 22.58928571 |
| 41049 | 31046 | 64.89285714 | 11.08928571 | 41077 | 31074 | 57.10344828 | 42.82758621 | 41105 | 31102 | 50.84210526 | 4.842105263 | 41133 | 31130 | 46 | 11.5 |
| 41050 | 31047 | 64.78873239 | 14.57746479 | 41078 | 31075 | 57.08433735 | 11.91566265 | 41106 | 31103 | 50.6 | 8.51 | 41134 | 31131 | 46 | 5.141176471 |
| 41051 | 31048 | 64.59574468 | 14.43617021 | 41079 | 31076 | 56.61538462 | 15.92307692 | 41107 | 31104 | 50.08888889 | 16.1 | 41135 | 31132 | 46 | 13.75 |
| 41052 | 31049 | 64.4 | 19.71428571 | 41080 | 31077 | 56.28235294 | 7.982352941 | 41108 | 31105 | 50.08888889 | 15.07777778 | 41136 | 31133 | 46 | 6.546153846 |
| 41053 | 31050 | 63.75438596 | 15.93859649 | 41081 | 31078 | 56.22222222 | 7.347222222 | 41109 | 31106 | 49.92682927 | 6.170731707 | 41137 | 31134 | 46 | 13.11 |
| 41054 | 31051 | 63.58823529 | 9.301470588 | 41082 | 31079 | 56.22222222 | 5.504273504 | 41110 | 31107 | 49.91489362 | 25.93617021 | 41138 | 31135 | 45.53535354 | 1.742424242 |
| 41055 | 31052 | 63.48 | 11.73 | 41083 | 31080 | 55.81333333 | 8.74 | 41111 | 31108 | 49.58865248 | 10.43971631 | 41139 | 31136 | 45.0212766 | 9.053191489 |
| 41056 | 31053 | 62.53932584 | 3.359550562 | 41084 | 31081 | 55.68421053 | 41.76315789 | 41112 | 31109 | 49.3253012 | 6.096385542 | 41140 | 31137 | 44.62686567 | 8.925373134 |
| 41057 | 31054 | 62.16216216 | 11.81081081 | 41085 | 31082 | 55.55844156 | 10.75324675 | 41113 | 31110 | 48.96774194 | 34.00537634 | 41141 | 31138 | 44.2962963 | 15.33333333 |
| 41058 | 31055 | 62 | 46.5 | 41086 | 31083 | 55.48453608 | 18.61340206 | 41114 | 31111 | 48.9009009 | 10.67117117 | 41142 | 31139 | 44.12244898 | 7.510204082 |

FIG. 8 (Cont.)

| DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment |
|---|---|---|---|---|---|---|---|---|---|---|---|---|---|---|---|
| 41143 | 31140 | 43.90909091 | 19.99431818 | 41171 | 31168 | 39.26829268 | 6.731707317 | 41199 | 31196 | 34.81081081 | 17.25 | 41227 | 31224 | 30.78195489 | 4.669172932 |
| 41144 | 31141 | 43.88990826 | 10.86697248 | 41172 | 31169 | 38.87323944 | 12.14788732 | 41200 | 31197 | 34.76744186 | 5.549418605 | 41228 | 31225 | 30.66666667 | 6.388888889 |
| 41145 | 31142 | 43.7 | 11.06875 | 41173 | 31170 | 38.33333333 | 5.083333333 | 41201 | 31198 | 34.73469388 | 15.95918367 | 41229 | 31226 | 30.66666667 | 5.649122807 |
| 41146 | 31143 | 43.7 | 12.075 | 41174 | 31171 | 38.21538462 | 13.26923077 | 41202 | 31199 | 34.2195122 | 2.243902439 | 41230 | 31227 | 30.66666667 | 2.555555556 |
| 41147 | 31144 | 43.29411765 | 20.51960784 | 41175 | 31172 | 38.14634146 | 2.617886179 | 41203 | 31200 | 34.07407407 | 15.58888889 | 41231 | 31228 | 30.66666667 | 7.027777778 |
| 41148 | 31145 | 43.07936508 | 37.78571429 | 41176 | 31173 | 38 | 8.833333333 | 41204 | 31201 | 34 | 4.125 | 41232 | 31229 | 30.2994012 | 6.473053892 |
| 41149 | 31146 | 42.89189189 | 8.081081081 | 41177 | 31174 | 37.88235294 | 4.735294118 | 41205 | 31202 | 33.73333333 | 10.05185185 | 41233 | 31230 | 30.29268293 | 8.274390244 |
| 41150 | 31147 | 42.79069767 | 14.97674419 | 41178 | 31175 | 37.84236453 | 2.60591133 | 41206 | 31203 | 33.62248996 | 5.149598394 | 41234 | 31231 | 30.10909091 | 10.24545455 |
| 41151 | 31148 | 42.71428571 | 16.92142857 | 41179 | 31176 | 37.69444444 | 8.784722222 | 41207 | 31204 | 33.52542373 | 15.98305085 | 41235 | 31232 | 30.07692308 | 7.224358974 |
| 41152 | 31149 | 42.27027027 | 11.81081081 | 41180 | 31177 | 37.57746479 | 3.077464789 | 41208 | 31205 | 33.49514563 | 13.39805825 | 41236 | 31233 | 29.9 | 3.59375 |
| 41153 | 31150 | 42.16666667 | 14.56666667 | 41181 | 31178 | 37.54022989 | 13.0862069 | 41209 | 31206 | 33.45454545 | 18.66883117 | 41237 | 31234 | 29.62711864 | 10.52542373 |
| 41154 | 31151 | 41.91111111 | 24.02222222 | 41182 | 31179 | 37.2972973 | 35.43243243 | 41210 | 31207 | 33.38709677 | 6.677419355 | 41238 | 31235 | 29.58918919 | 6.962162162 |
| 41155 | 31152 | 41.84337349 | 7.620481928 | 41183 | 31180 | 37.23809524 | 10.76984127 | 41211 | 31208 | 33.31034483 | 18.90229885 | 41239 | 31236 | 29.15492958 | 19.43661972 |
| 41156 | 31153 | 41.66037736 | 7.268867925 | 41184 | 31181 | 37.02439024 | 14.58536585 | 41212 | 31209 | 33.13978495 | 11.62365591 | 41240 | 31237 | 29.13333333 | 18.59166667 |
| 41157 | 31154 | 41.56626506 | 19.39759036 | 41185 | 31182 | 36.94488189 | 4.88976378 | 41213 | 31210 | 32.35862069 | 8.882758621 | 41241 | 31238 | 29.08045977 | 10.70689655 |
| 41158 | 31155 | 41.51219512 | 38.42682927 | 41186 | 31183 | 36.93939394 | 11.67424242 | 41214 | 31211 | 32.1369863 | 6.45890411 | 41242 | 31239 | 29.02912621 | 14.84951456 |
| 41159 | 31156 | 41.4 | 4.913636364 | 41187 | 31184 | 36.91358025 | 10.93209877 | 41215 | 31212 | 32.12698413 | 8.214285714 | 41243 | 31240 | 28.96296296 | 7.524691358 |
| 41160 | 31157 | 40.70503597 | 4.302158273 | 41188 | 31185 | 36.8 | 5.622222222 | 41216 | 31213 | 32.07894737 | 17.55263158 | 41244 | 31241 | 28.95104895 | 11.01748252 |
| 41161 | 31158 | 40.66666667 | 14.33333333 | 41189 | 31186 | 36.54794521 | 4.726027397 | 41217 | 31214 | 31.97560976 | 7.713414634 | 41245 | 31242 | 28.91428571 | 20.37142857 |
| 41162 | 31159 | 40.66666667 | 18.33333333 | 41190 | 31187 | 36.25423729 | 9.258474576 | 41218 | 31215 | 31.84615385 | 4.286982249 | 41246 | 31243 | 28.66666667 | 24.66666667 |
| 41163 | 31160 | 40.48 | 12.65 | 41191 | 31188 | 36 | 13.64285714 | 41219 | 31216 | 31.68888889 | 1.874074074 | 41247 | 31244 | 28.64912281 | 17.35087719 |
| 41164 | 31161 | 40.43956044 | 2.906593407 | 41192 | 31189 | 35.77777778 | 27.08888889 | 41220 | 31217 | 31.67213115 | 5.467213115 | 41248 | 31245 | 28.58252427 | 17.19417476 |
| 41165 | 31162 | 40.41428571 | 9.528571429 | 41193 | 31190 | 35.77777778 | 5.00462963 | 41221 | 31218 | 31.43333333 | 2.683333333 | 41249 | 31246 | 28.49253731 | 3.003731343 |
| 41166 | 31163 | 40.35849057 | 14.97169811 | 41194 | 31191 | 35.50877193 | 15.93859649 | 41222 | 31219 | 31.41463415 | 6.451219512 | 41250 | 31247 | 28.30769231 | 5.93956044 |
| 41167 | 31164 | 40.06451613 | 19.47580645 | 41195 | 31192 | 35.38461538 | 18.28205128 | 41223 | 31220 | 31.33333333 | 16.66666667 | 41251 | 31248 | 28.30769231 | 5.528846154 |
| 41168 | 31165 | 39.80769231 | 9.951923077 | 41196 | 31193 | 35.21875 | 10.421875 | 41224 | 31221 | 31.1496063 | 2.807086614 | 41252 | 31249 | 28.25714286 | 10.35 |
| 41169 | 31166 | 39.68627451 | 12.62745098 | 41197 | 31194 | 35.15447154 | 9.443089431 | 41225 | 31222 | 30.86842105 | 18.91447368 | 41253 | 31250 | 28.175 | 7.475 |
| 41170 | 31167 | 39.65517241 | 26.96551724 | 41198 | 31195 | 34.94230769 | 11.83173077 | 41226 | 31223 | 30.82978723 | 14.68085106 | 41254 | 31251 | 28.16326531 | 9.505102041 |

FIG. 8 (Cont.)

| DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment |
|---|---|---|---|---|---|---|---|---|---|---|---|---|---|---|---|
| 41255 | 31252 | 28.11111111 | 16.93055556 | 41283 | 31280 | 25.3 | 1.035 | 41311 | 31308 | 21.96129032 | 5.712903226 | 41339 | 31336 | 18.16806723 | 9.953781513 |
| 41256 | 31253 | 28.04878049 | 8.882113821 | 41284 | 31281 | 25.25490196 | 14.88235294 | 41312 | 31309 | 21.85 | 31.9125 | 41340 | 31337 | 18.13461538 | 10.61538462 |
| 41257 | 31254 | 28.02298851 | 30.53448276 | 41285 | 31282 | 24.98765432 | 7.666666667 | 41313 | 31310 | 21.26415094 | 6.726415094 | 41341 | 31338 | 17.95121951 | 8.040650407 |
| 41258 | 31255 | 27.97938144 | 16.83505155 | 41286 | 31283 | 24.5862069 | 8.922413793 | 41314 | 31311 | 21.12244898 | 15.60714286 | 41342 | 31339 | 17.94 | 6.9 |
| 41259 | 31256 | 27.6 | 12.65 | 41287 | 31284 | 24.53333333 | 2.453333333 | 41315 | 31312 | 21.10091743 | 26.79816514 | 41343 | 31340 | 17.90604027 | 20.53020134 |
| 41260 | 31257 | 27.6 | 16.24375 | 41288 | 31285 | 24.33057851 | 18.24793388 | 41316 | 31313 | 20.90909091 | 8.524475524 | 41344 | 31341 | 17.69230769 | 1.84965035 |
| 41261 | 31258 | 27.6 | 2.3 | 41289 | 31286 | 24.32183908 | 10.44252874 | 41317 | 31314 | 20.87037037 | 6.069444444 | 41345 | 31342 | 17.50442478 | 6.411504425 |
| 41262 | 31259 | 27.40425532 | 6.239361702 | 41290 | 31287 | 24.22900763 | 3.248091603 | 41318 | 31315 | 20.83018868 | 22.3490566 | 41346 | 31343 | 17.42424242 | 3.484848485 |
| 41263 | 31260 | 27.40425532 | 6.85106383 | 41291 | 31288 | 24.21052632 | 10.28947368 | 41319 | 31316 | 20.82432432 | 9.47972973 | 41347 | 31344 | 17.35087719 | 8.877192982 |
| 41264 | 31261 | 27.21666667 | 9.966666667 | 41292 | 31289 | 24.12195122 | 14.16463415 | 41320 | 31317 | 20.74509804 | 14.76960784 | 41348 | 31345 | 17.35087719 | 7.464912281 |
| 41265 | 31262 | 27.21126761 | 6.478873239 | 41293 | 31290 | 24.11290323 | 7.326612903 | 41321 | 31318 | 20.65306122 | 7.979591837 | 41349 | 31346 | 16.74871795 | 2.830769231 |
| 41266 | 31263 | 27.2 | 4.4 | 41294 | 31291 | 24.05504587 | 8.018348624 | 41322 | 31319 | 20 | 14.16666667 | 41350 | 31347 | 16.56 | 12.42 |
| 41267 | 31264 | 27.15662651 | 8.86746988 | 41295 | 31292 | 23.81176471 | 9.064705882 | 41323 | 31320 | 19.89189189 | 11.29279279 | 41351 | 31348 | 16.53125 | 1.4375 |
| 41268 | 31265 | 26.90566038 | 4.773584906 | 41296 | 31293 | 23.79310345 | 4.626436782 | 41324 | 31321 | 19.82113821 | 10.00406504 | 41352 | 31349 | 16.48333333 | 12.74583333 |
| 41269 | 31266 | 26.8 | 6.1 | 41297 | 31294 | 23.65714286 | 12.15714286 | 41325 | 31322 | 19.71428571 | 9.34375 | 41353 | 31350 | 16.34210526 | 3.404605263 |
| 41270 | 31267 | 26.7761194 | 9.611940299 | 41298 | 31295 | 23.58974359 | 8.256410256 | 41326 | 31323 | 19.66666667 | 5.75 | 41354 | 31351 | 16.32258065 | 3.338709677 |
| 41271 | 31268 | 26.70967742 | 4.266129032 | 41299 | 31296 | 23.42592593 | 3.833333333 | 41327 | 31324 | 19.55905512 | 2.625984252 | 41355 | 31352 | 16.171875 | 8.265625 |
| 41272 | 31269 | 26.59375 | 8.0859375 | 41300 | 31297 | 23.32857143 | 6.571428571 | 41328 | 31325 | 19.52830189 | 4.990566038 | 41356 | 31353 | 15.8125 | 6.109375 |
| 41273 | 31270 | 26.52252252 | 3.418918919 | 41301 | 31298 | 23.29113924 | 29.40506329 | 41329 | 31326 | 19.42222222 | 12.86296296 | 41357 | 31354 | 15.80152672 | 4.213740458 |
| 41274 | 31271 | 26.51764706 | 5.817647059 | 41302 | 31299 | 23.24210526 | 9.442105263 | 41330 | 31327 | 19.36842105 | 3.480263158 | 41358 | 31355 | 15.65277778 | 3.434027778 |
| 41275 | 31272 | 26.47169811 | 10.74056604 | 41303 | 31300 | 23 | 5 | 41331 | 31328 | 19.35172414 | 8.565517241 | 41359 | 31356 | 15.33333333 | 5.594594595 |
| 41276 | 31273 | 26.45 | 18.1125 | 41304 | 31301 | 22.8034188 | 10.41880342 | 41332 | 31329 | 19.16666667 | 6.882575758 | 41360 | 31357 | 15.33333333 | 6.683760684 |
| 41277 | 31274 | 26.28571429 | 23 | 41305 | 31302 | 22.8 | 4.6 | 41333 | 31330 | 19 | 4.5 | 41361 | 31358 | 15.11428571 | 21.68571429 |
| 41278 | 31275 | 25.65384615 | 8.735576923 | 41306 | 31303 | 22.77227723 | 8.198019802 | 41334 | 31331 | 18.99082569 | 6.119266055 | 41362 | 31359 | 14.93506494 | 4.555194805 |
| 41279 | 31276 | 25.55555556 | 6.708333333 | 41307 | 31304 | 22.38938053 | 5.902654867 | 41335 | 31332 | 18.95757576 | 7.527272727 | 41363 | 31360 | 14.22368421 | 7.036184211 |
| 41280 | 31277 | 25.55555556 | 18.74074074 | 41308 | 31305 | 22.34285714 | 7.721428571 | 41336 | 31333 | 18.31067961 | 10.7184466 | 41364 | 31361 | 13.88679245 | 10.8490566 |
| 41281 | 31278 | 25.42105263 | 11.80263158 | 41309 | 31306 | 22.16363636 | 12.44090909 | 41337 | 31334 | 18.21782178 | 9.336633663 | 41365 | 31362 | 13.66060606 | 5.715151515 |
| 41282 | 31279 | 25.3258427 | 7.235955056 | 41310 | 31307 | 22.1 | 1.75 | 41338 | 31335 | 18.21782178 | 2.448019802 | 41366 | 31363 | 12.71544715 | 4.674796748 |

FIG. 8 (Cont.)

| DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment | DNA SEQ ID NO | AA SEQ ID NO | Muscle 1 Enrichment | Muscle 2 Enrichment |
|---|---|---|---|---|---|---|---|---|---|---|---|---|---|---|---|
| 41367 | 31364 | 11.90049751 | 14.58955224 | 41390 | 31387 | 8.658823529 | 9.470588235 | 41413 | 31410 | 4.6 | 17.60384615 | 41436 | 31433 | 2.3 | 24.15 |
| 41368 | 31365 | 11.79487179 | 1.081196581 | 41391 | 31388 | 8.653465347 | 2.277227723 | 41414 | 31411 | 4.6 | 8.9125 | 41437 | 31434 | 2.3 | 12.3625 |
| 41369 | 31366 | 11.70909091 | 5.959090909 | 41392 | 31389 | 8.625 | 5.190972222 | 41415 | 31412 | 4.451612903 | 1.483870968 | 41438 | 31435 | 2.164705882 | 12.04117647 |
| 41370 | 31367 | 11.68548387 | 4.3125 | 41393 | 31390 | 8.363636364 | 3.397727273 | 41416 | 31413 | 4.404255319 | 6.239361702 | 41439 | 31436 | 2.123076923 | 15.39230769 |
| 41371 | 31368 | 11.67164179 | 16.30597015 | 41394 | 31391 | 8.214285714 | 10.0625 | 41417 | 31414 | 4.351351351 | 6.527027027 | 41440 | 31437 | 2.059701493 | 18.53731343 |
| 41372 | 31369 | 11.32835821 | 2.059701493 | 41395 | 31392 | 8.161290323 | 27.82258065 | 41418 | 31415 | 4.211267606 | 8.665492958 | 41441 | 31438 | 2.044444444 | 12.90555556 |
| 41373 | 31370 | 11.18232044 | 5.972375691 | 41396 | 31393 | 7.885714286 | 14.45714286 | 41419 | 31416 | 3.942857143 | 14.45714286 | 41442 | 31439 | 2 | 57.5 |
| 41374 | 31371 | 11.15151515 | 1.393939394 | 41397 | 31394 | 7.585106383 | 6.055851064 | 41420 | 31417 | 3.72972973 | 5.905405405 | 41443 | 31440 | 1.916666667 | 7.427083333 |
| 41375 | 31372 | 11.10344828 | 1.586206897 | 41398 | 31395 | 7.540983607 | 34.31147541 | 41421 | 31418 | 3.659090909 | 25.74431818 | 41444 | 31441 | 1.642857143 | 14.375 |
| 41376 | 31373 | 11.06329114 | 17.46835443 | 41399 | 31396 | 7.109090909 | 6.795454545 | 41422 | 31419 | 3.538461538 | 1.769230769 | 41445 | 31442 | 1.586206897 | 3.899425287 |
| 41377 | 31374 | 11.02083333 | 1.916666667 | 41400 | 31397 | 6.924731183 | 4.451612903 | 41423 | 31420 | 3.538461538 | 22.41025641 | 41446 | 31443 | 1.533333333 | 35.65 |
| 41378 | 31375 | 10.95238095 | 26.28571429 | 41401 | 31398 | 6.814814815 | 16.18518519 | 41424 | 31421 | 3.478991597 | 1.836134454 | 41447 | 31444 | 1.415384615 | 8.138461538 |
| 41379 | 31376 | 10.51038576 | 2.866468843 | 41402 | 31399 | 6.192307692 | 10.72596154 | 41425 | 31422 | 3.256637168 | 13.94247788 | 41448 | 31445 | 1.408163265 | 20.41836735 |
| 41380 | 31377 | 10.32653061 | 19.24489796 | 41403 | 31400 | 5.75 | 2.875 | 41426 | 31423 | 3.2 | 5.3 | 41449 | 31446 | 1.383458647 | 6.312030075 |
| 41381 | 31378 | 10.22222222 | 2.12962963 | 41404 | 31401 | 5.56043956 | 6.697802198 | 41427 | 31424 | 3.172413793 | 6.344827586 | 41450 | 31447 | 1.326923077 | 9.067307692 |
| 41382 | 31379 | 10.15584416 | 1.642857143 | 41405 | 31402 | 5.492537313 | 14.41791045 | 41428 | 31425 | 3.136363636 | 12.80681818 | 41451 | 31448 | 1.314285714 | 9.528571429 |
| 41383 | 31380 | 10.03636364 | 16.93636364 | 41406 | 31403 | 5.476190476 | 23.41071429 | 41429 | 31426 | 3.016393443 | 7.980874317 | 41452 | 31449 | 1.243243243 | 8.236486486 |
| 41384 | 31381 | 10.02564103 | 15.77564103 | 41407 | 31404 | 5.326315789 | 4.357894737 | 41430 | 31427 | 2.967741935 | 8.717741935 | 41453 | 31450 | 1.243243243 | 42.89189189 |
| 41385 | 31382 | 10 | 1.666666667 | 41408 | 31405 | 5.193548387 | 18.5483871 | 41431 | 31428 | 2.591549296 | 16.52112676 | 41454 | 31451 | 1.164556962 | 2.620253165 |
| 41386 | 31383 | 9.97044335 | 7.81773399 | 41409 | 31406 | 5.111111111 | 6.753968254 | 41432 | 31429 | 2.555555556 | 4.983333333 | | | | |
| 41387 | 31384 | 9.857142857 | 1.095238095 | 41410 | 31407 | 4.842105263 | 23.60526316 | 41433 | 31430 | 2.509090909 | 13.59090909 | | | | |
| 41388 | 31385 | 9.419795222 | 2.060580205 | 41411 | 31408 | 4.842105263 | 19.77192982 | 41434 | 31431 | 2.453333333 | 5.52 | | | | |
| 41389 | 31386 | 8.672131148 | 5.56147541 | 41412 | 31409 | 4.651685393 | 8.657303371 | 41435 | 31432 | 2.358974359 | 6.487179487 | | | | |

FIG. 9

| DNA SEQ ID NO | AA SEQ ID NO | Pancreas 1 Enrichment | Pancreas 2 Enrichment |
|---|---|---|---|
| 41455 | 31452 | 8198 | 14.18181818 |
| 41456 | 31453 | 3830.047619 | 27.48051948 |
| 41457 | 31454 | 3552.173077 | 33.91695804 |
| 41458 | 31455 | 371.0163934 | 6.478390462 |
| 41459 | 31456 | 356.8709677 | 3.271260997 |
| 41460 | 31457 | 301.2258065 | 8.431085044 |
| 41461 | 31458 | 221.3333333 | 3.696969697 |
| 41462 | 31459 | 51.27868852 | 2.947839046 |
| 41463 | 31460 | 11.5 | 23.83636364 |
| 41464 | 31461 | 3.833333333 | 52.27272727 |
| 41465 | 31462 | 2.520547945 | 3.207970112 |
| 41466 | 31463 | 1.703703704 | 6.698653199 |
| 41467 | 31464 | 1.533333333 | 29.27272727 |
| 41468 | 31465 | 1.277777778 | 11.79040404 |
| 41469 | 31466 | 1.121951220 | 3.39135255 |
| 41470 | 31467 | 1.045454545 | 9.219008264 |

FIG. 10

| DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment |
|---|---|---|---|---|---|---|---|---|---|---|---|
| 41471 | 31468 | 32.85714286 | 9.333333333 | 41497 | 31494 | 3.817687075 | 2.3 | 41549 | 31546 | 2.607709751 | 1.003968254 |
| 41472 | 31469 | 13.66941392 | 4.459935897 | 41498 | 31495 | 3.731922399 | 2.697530864 | 41550 | 31547 | 2.584761905 | 1.073333333 |
| 41473 | 31470 | 13.245553571 | 1.9765625 | 41499 | 31496 | 3.714285714 | 1.666666667 | 41551 | 31548 | 2.527472527 | 1.621794872 |
| 41474 | 31471 | 10.40476190 | 7.666666667 | 41500 | 31497 | 3.650793651 | 2.697530864 | 41552 | 31549 | 2.527472527 | 1.277777778 |
| 41475 | 31472 | 10.13095238 | 6.229166667 | 41501 | 31498 | 3.625615764 | 2.379310345 | 41553 | 31550 | 2.514991182 | 4.117283951 |
| 41476 | 31473 | 9.435897436 | 2.948717949 | 41502 | 31499 | 3.622710623 | 1.621794872 | 41554 | 31551 | 2.514991182 | 1.561728395 |
| 41477 | 31474 | 6.414965986 | 3.285714286 | 41503 | 31500 | 3.619047619 | 2 | 41555 | 31552 | 2.511033682 | 2.150406504 |
| 41478 | 31475 | 5.841269841 | 1.444444444 | 41504 | 31501 | 3.520408163 | 4.107142857 | 41556 | 31553 | 2.492610837 | 1.189655172 |
| 41479 | 31476 | 5.632653061 | 3.285714286 | 41505 | 31502 | 3.504761905 | 4.6 | 41557 | 31554 | 2.482539683 | 1.15 |
| 41480 | 31477 | 5.202380952 | 1.677083333 | 41506 | 31503 | 3.495440729 | 1.141843972 | 41558 | 31555 | 2.464285714 | 2.875 |
| 41481 | 31478 | 5.171957672 | 4.472222222 | 41507 | 31504 | 3.468253968 | 2.236111111 | 41559 | 31556 | 2.453333333 | 1.38 |
| 41482 | 31479 | 4.693877551 | 3.285714286 | 41508 | 31505 | 3.458646617 | 2.824561404 | 41560 | 31557 | 2.451247166 | 1.003968254 |
| 41483 | 31480 | 4.673015873 | 1.277777778 | 41509 | 31506 | 3.350140056 | 5.862745098 | 41561 | 31558 | 2.433862434 | 1.703703704 |
| 41484 | 31481 | 4.624338624 | 7.666666667 | 41510 | 31507 | 3.346560847 | 1.064814815 | 41562 | 31559 | 2.421052632 | 2.622807018 |
| 41485 | 31482 | 4.58008658 | 1.045454545 | 41511 | 31508 | 3.337868481 | 1.369047619 | 41563 | 31560 | 2.40952381 | 1.277777778 |
| 41486 | 31483 | 4.380952381 | 1.21969697 | 41512 | 31509 | 3.285714286 | 2.327380952 | 41564 | 31561 | 2.399092971 | 1.825396825 |
| 41487 | 31484 | 4.380952381 | 4.472222222 | 41513 | 31510 | 3.233560091 | 2.373015873 | 41565 | 31562 | 2.386638237 | 1.487562189 |
| 41488 | 31485 | 4.380952381 | 3.833333333 | 41514 | 31511 | 3.11417097 | 1.477911647 | 41566 | 31563 | 2.383753501 | 1.014705882 |
| 41489 | 31486 | 4.276643991 | 4.015873016 | 41515 | 31512 | 3.085177733 | 2.159624413 | 41567 | 31564 | 2.346938776 | 1.360047619 |
| 41490 | 31487 | 4.126245847 | 1.604651163 | 41516 | 31513 | 3.078507079 | 1.13963964 | 41568 | 31565 | 2.319327731 | 1.352941176 |
| 41491 | 31488 | 3.994397759 | 3.382352941 | 41517 | 31514 | 3.077097506 | 1.551587302 | 41569 | 31566 | 2.319327731 | 1.578431373 |
| 41492 | 31489 | 3.994397759 | 1.127450980 | 41518 | 31515 | 3.075987842 | 2.039007092 | 41570 | 31567 | 2.319327731 | 1.352941176 |
| 41493 | 31490 | 3.942857143 | 4.983333333 | 41519 | 31516 | 3.066666667 | 1.71025641 | 41571 | 31568 | 2.312169312 | 1.348765432 |
| 41494 | 31491 | 3.942857143 | 1.533333333 | 41520 | 31517 | 3.024943311 | 3.285714286 | 41572 | 31569 | 2.308243728 | 2.267025090 |
| 41495 | 31492 | 3.859410431 | 1.825396825 | 41521 | 31518 | 3.011904762 | 3.1625 | 41573 | 31570 | 2.302808303 | 1.081196581 |
| 41496 | 31493 | 3.844509232 | 1.564462585 | 41522 | 31519 | 3.011904762 | 1.4375 | 41574 | 31571 | 2.29004329 | 1.219969697 |

| DNA SEQ ID NO | AA SEQ ID NO | Spleen 1 Enrichment | Spleen 2 Enrichment |
|---|---|---|---|
| 41523 | 31520 | 2.976800977 | 3.047008547 |
| 41524 | 31521 | 2.972789116 | 4.517857143 |
| 41525 | 31522 | 2.972789116 | 1.916666667 |
| 41526 | 31523 | 2.967741935 | 1.483870968 |
| 41527 | 31524 | 2.952380952 | 4.5 |
| 41528 | 31525 | 2.920634921 | 1.277777778 |
| 41529 | 31526 | 2.920634921 | 1.916666667 |
| 41530 | 31527 | 2.864468864 | 1.769230769 |
| 41531 | 31528 | 2.857142857 | 1.333333333 |
| 41532 | 31529 | 2.816326531 | 1.752380952 |
| 41533 | 31530 | 2.80952381 | 1.833333333 |
| 41534 | 31531 | 2.787878788 | 2.29004329 |
| 41535 | 31532 | 2.758377425 | 1.419753086 |
| 41536 | 31533 | 2.738095238 | 1.194987179 |
| 41537 | 31534 | 2.738095238 | 1.277777778 |
| 41538 | 31535 | 2.724738676 | 1.869918699 |
| 41539 | 31536 | 2.723294723 | 2.279279279 |
| 41540 | 31537 | 2.716190476 | 2.913333333 |
| 41541 | 31538 | 2.708225108 | 2.578787879 |
| 41542 | 31539 | 2.705882353 | 1.803921569 |
| 41543 | 31540 | 2.700587084 | 1.99543379 |
| 41544 | 31541 | 2.688311688 | 2.090909091 |
| 41545 | 31542 | 2.665079365 | 1.086111111 |
| 41546 | 31543 | 2.659863946 | 3.833333333 |
| 41547 | 31544 | 2.635416667 | 2.455729167 |
| 41548 | 31545 | 2.634116938 | 1.116033755 |

FIG. 10 (Cont.)

| DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment |
|---|---|---|---|---|---|---|---|---|---|---|---|---|---|---|---|
| 41575 | 31572 | 2.268707483 | 1.916666667 | 41603 | 31600 | 2.021978022 | 1.769230769 | 41631 | 31628 | 1.84 | 1.226666667 | 41659 | 31656 | 1.642857143 | 1.022222222 |
| 41576 | 31573 | 2.238618524 | 2.358974359 | 41604 | 31601 | 2.01754386 | 1.614035088 | 41632 | 31629 | 1.825396825 | 1.742424242 | 41660 | 31657 | 1.642857143 | 1.829545455 |
| 41577 | 31574 | 2.238095238 | 1.916666667 | 41605 | 31602 | 2.016013485 | 1.017699115 | 41633 | 31630 | 1.80952381 | 1.166666667 | 41661 | 31658 | 1.637325637 | 1.084175084 |
| 41578 | 31575 | 2.228243021 | 1.057471264 | 41606 | 31603 | 2.01423098 | 1.409961686 | 41634 | 31631 | 1.806182122 | 1.00877193 | 41662 | 31659 | 1.633249791 | 1.176900585 |
| 41579 | 31576 | 2.19047619 | 1.032051282 | 41607 | 31604 | 2.005365526 | 3.023474178 | 41635 | 31632 | 1.803921569 | 1.014705882 | 41663 | 31660 | 1.632119514 | 3.006535948 |
| 41580 | 31577 | 2.19047619 | 6.098484848 | 41608 | 31605 | 2.001175779 | 1.609053498 | 41636 | 31633 | 1.797313797 | 2.555555556 | 41664 | 31661 | 1.628815629 | 1.769230769 |
| 41581 | 31578 | 2.19047619 | 1.533333333 | 41609 | 31606 | 1.991341991 | 2.265151515 | 41637 | 31634 | 1.784832451 | 2.768518519 | 41665 | 31662 | 1.627210884 | 1.478571429 |
| 41582 | 31579 | 2.19047619 | 1.15 | 41610 | 31607 | 1.991341991 | 2.003787879 | 41638 | 31635 | 1.777178796 | 2.386792453 | 41666 | 31663 | 1.614035088 | 1.210526316 |
| 41583 | 31580 | 2.19047619 | 3.120155039 | 41611 | 31608 | 1.991341991 | 1.568181818 | 41639 | 31636 | 1.77456299 | 1.164556962 | 41667 | 31664 | 1.614035088 | 1.361842105 |
| 41584 | 31581 | 2.19047619 | 2.896296296 | 41612 | 31609 | 1.991341991 | 1.045454545 | 41640 | 31637 | 1.752380952 | 1.672727273 | 41668 | 31665 | 1.614035088 | 1.614035088 |
| 41585 | 31582 | 2.19047619 | 2.175675676 | 41613 | 31610 | 1.985119048 | 1.557291667 | 41641 | 31638 | 1.73727422 | 1.80651341 | 41669 | 31666 | 1.611384784 | 1.498084291 |
| 41586 | 31583 | 2.19047619 | 1.317708333 | 41614 | 31611 | 1.971428571 | 2.683333333 | 41642 | 31639 | 1.73047619 | 1.878333333 | 41670 | 31667 | 1.604651163 | 2.228682171 |
| 41587 | 31584 | 2.139534884 | 1.515503876 | 41615 | 31612 | 1.955782313 | 2.875 | 41643 | 31640 | 1.721088435 | 1.779761905 | 41671 | 31668 | 1.600732601 | 1.621794872 |
| 41588 | 31585 | 2.138321995 | 1.003968254 | 41616 | 31613 | 1.943164363 | 1.731182796 | 41644 | 31641 | 1.716859717 | 1.087837838 | 41672 | 31669 | 1.598455598 | 1.346846847 |
| 41589 | 31586 | 2.131274131 | 1.761261261 | 41617 | 31614 | 1.937728938 | 2.358974359 | 41645 | 31642 | 1.714285714 | 1.111111111 | 41673 | 31670 | 1.593073593 | 1.161616162 |
| 41590 | 31587 | 2.124098124 | 1.626262626 | 41618 | 31615 | 1.935769657 | 3.298449612 | 41646 | 31643 | 1.712554113 | 1.184848485 | 41674 | 31671 | 1.593073593 | 2.787878788 |
| 41591 | 31588 | 2.112244898 | 2.053571429 | 41619 | 31616 | 1.932773109 | 1.578431373 | 41647 | 31644 | 1.703703704 | 1.064814815 | 41675 | 31672 | 1.593073593 | 1.443722944 |
| 41592 | 31589 | 2.102857143 | 1.226666667 | 41620 | 31617 | 1.927619048 | 1.38 | 41648 | 31645 | 1.693968254 | 1.635555556 | 41676 | 31673 | 1.589861751 | 2.287634409 |
| 41593 | 31590 | 2.099206349 | 1.118055556 | 41621 | 31618 | 1.898412698 | 1.022222222 | 41649 | 31646 | 1.690893901 | 1.68128655 | 41677 | 31674 | 1.589861751 | 2.040322581 |
| 41594 | 31591 | 2.097920858 | 1.187793427 | 41622 | 31619 | 1.898412698 | 1.277777778 | 41650 | 31647 | 1.688492063 | 2.315972222 | 41678 | 31675 | 1.589169001 | 1.954248366 |
| 41595 | 31592 | 2.089377289 | 1.120512821 | 41623 | 31620 | 1.898412698 | 1.788888889 | 41651 | 31648 | 1.67781155 | 1.875886525 | 41679 | 31676 | 1.584599797 | 1.141843972 |
| 41596 | 31593 | 2.082747853 | 2.136612022 | 41624 | 31621 | 1.895604396 | 1.032051282 | 41652 | 31649 | 1.656898657 | 1.326923077 | 41680 | 31677 | 1.584599797 | 1.712765957 |
| 41597 | 31594 | 2.068783069 | 2.768518519 | 41625 | 31622 | 1.890726817 | 1.533333333 | 41653 | 31650 | 1.650358774 | 1.155251142 | 41681 | 31678 | 1.579180509 | 1.515503876 |
| 41598 | 31595 | 2.06162465 | 1.12745098 | 41626 | 31623 | 1.87755102 | 1.095238095 | 41654 | 31651 | 1.649617872 | 1.325102881 | 41682 | 31679 | 1.577142857 | 1.993333333 |
| 41599 | 31596 | 2.06162465 | 2.198529412 | 41627 | 31624 | 1.87755102 | 2.3 | 41655 | 31652 | 1.642857143 | 1.384259259 | 41683 | 31680 | 1.574404762 | 1.677083333 |
| 41600 | 31597 | 2.050658561 | 1.060283688 | 41628 | 31625 | 1.865961199 | 2.413580247 | 41656 | 31653 | 1.642857143 | 1.105769231 | 41684 | 31681 | 1.56984127 | 1.15 |
| 41601 | 31598 | 2.044444444 | 1.277777778 | 41629 | 31626 | 1.853479853 | 1.769230769 | 41657 | 31654 | 1.642857143 | 1.109649123 | 41685 | 31682 | 1.569296375 | 1.258706468 |
| 41602 | 31599 | 2.034013605 | 1.505952381 | 41630 | 31627 | 1.846258503 | 1.423809524 | 41658 | 31655 | 1.642857143 | 1.677083333 | 41686 | 31683 | 1.551587302 | 4.152777778 |

FIG. 10 (Cont.)

| DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment |
|---|---|---|---|---|---|---|---|---|---|---|---|---|---|---|---|
| 41687 | 31684 | 1.546218487 | 2.029411765 | 41715 | 31712 | 1.432234432 | 1.032051282 | 41743 | 31740 | 1.335656214 | 1.495934959 | 41771 | 31768 | 1.25170068 | 3.833333333 |
| 41688 | 31685 | 1.544106167 | 1.256830601 | 41716 | 31713 | 1.430515063 | 1.603741497 | 41744 | 31741 | 1.335656214 | 2.056910569 | 41772 | 31769 | 1.24235963 | 1.315920398 |
| 41689 | 31686 | 1.541446208 | 2.910493827 | 41717 | 31714 | 1.427128427 | 1.103535354 | 41745 | 31742 | 1.333333333 | 1.666666667 | 41773 | 31770 | 1.241269841 | 1.277777778 |
| 41690 | 31687 | 1.535851122 | 1.718390805 | 41718 | 31715 | 1.423809524 | 1.15 | 41746 | 31743 | 1.331809524 | 1.165333333 | 41774 | 31771 | 1.235653236 | 1.376068376 |
| 41691 | 31688 | 1.533333333 | 1.4375 | 41719 | 31716 | 1.419753086 | 2.271604938 | 41747 | 31744 | 1.33146592 | 1.202614379 | 41775 | 31772 | 1.234632035 | 1.184848485 |
| 41692 | 31689 | 1.526695527 | 1.103535354 | 41720 | 31717 | 1.414104882 | 2.329113924 | 41748 | 31745 | 1.33146592 | 1.16503268 | 41776 | 31773 | 1.234071093 | 1.889671362 |
| 41693 | 31690 | 1.523809524 | 1.5 | 41721 | 31718 | 1.408163265 | 1.095238095 | 41749 | 31746 | 1.329931973 | 1.779761905 | 41777 | 31774 | 1.232142857 | 1.197916667 |
| 41694 | 31691 | 1.523809524 | 1.75 | 41722 | 31719 | 1.404151404 | 1.769230769 | 41750 | 31747 | 1.328649493 | 1.508196721 | 41778 | 31775 | 1.232142857 | 2.555555556 |
| 41695 | 31692 | 1.523809524 | 1.111111111 | 41723 | 31720 | 1.40327381 | 2.575520833 | 41751 | 31748 | 1.322551662 | 1.735849057 | 41779 | 31776 | 1.230839002 | 2.153968254 |
| 41696 | 31693 | 1.500326158 | 1.52283105 | 41724 | 31721 | 1.399470899 | 1.171296296 | 41752 | 31749 | 1.314285714 | 1.245833333 | 41780 | 31777 | 1.229741019 | 1.479532164 |
| 41697 | 31694 | 1.498746867 | 2.219298246 | 41725 | 31722 | 1.393939394 | 2.090909091 | 41753 | 31750 | 1.314285714 | 1.533333333 | 41781 | 31778 | 1.226666667 | 2.453333333 |
| 41698 | 31695 | 1.493506494 | 5.75 | 41726 | 31723 | 1.391865079 | 1.317708333 | 41754 | 31751 | 1.314285714 | 7.283333333 | 41782 | 31779 | 1.221611722 | 2.211538462 |
| 41699 | 31696 | 1.492063492 | 1.555555556 | 41727 | 31724 | 1.385811467 | 1.173469388 | 41755 | 31752 | 1.314285714 | 4.6 | 41783 | 31780 | 1.219440353 | 1.027491409 |
| 41700 | 31697 | 1.492063492 | 1.611111111 | 41728 | 31725 | 1.380300065 | 1.102739726 | 41756 | 31753 | 1.308943089 | 1.636178862 | 41784 | 31781 | 1.216931217 | 1.022222222 |
| 41701 | 31698 | 1.491388045 | 1.468085106 | 41729 | 31726 | 1.376870748 | 1.861904762 | 41757 | 31754 | 1.305860806 | 2.064102564 | 41785 | 31782 | 1.216931217 | 1.135802469 |
| 41702 | 31699 | 1.483870968 | 1.483870968 | 41730 | 31727 | 1.375415282 | 1.515503876 | 41758 | 31755 | 1.302445302 | 1.243243243 | 41786 | 31783 | 1.214285714 | 1.5 |
| 41703 | 31700 | 1.481792717 | 1.12745098 | 41731 | 31728 | 1.374416433 | 1.12745098 | 41759 | 31756 | 1.299435028 | 1.36440678 | 41787 | 31784 | 1.207570208 | 1.277777778 |
| 41704 | 31701 | 1.477297896 | 1.426356589 | 41732 | 31729 | 1.373688458 | 1.559322034 | 41760 | 31757 | 1.299003322 | 1.114341085 | 41788 | 31785 | 1.203558346 | 1.179487179 |
| 41705 | 31702 | 1.47172619 | 1.497395833 | 41733 | 31730 | 1.369047619 | 1.245833333 | 41761 | 31758 | 1.296404276 | 1.486394558 | 41789 | 31786 | 1.201228879 | 2.596774194 |
| 41706 | 31703 | 1.465686275 | 1.775735294 | 41734 | 31731 | 1.365491651 | 1.244588745 | 41762 | 31759 | 1.285714286 | 1.416666667 | 41790 | 31787 | 1.197460317 | 2.146666667 |
| 41707 | 31704 | 1.46031746 | 1.597222222 | 41735 | 31732 | 1.363881402 | 1.08490566 | 41763 | 31760 | 1.280586081 | 1.71025641 | 41791 | 31788 | 1.19047619 | 1.416666667 |
| 41708 | 31705 | 1.46031746 | 1.357638889 | 41736 | 31733 | 1.360401003 | 1.492982456 | 41764 | 31761 | 1.272844273 | 2.797297297 | 41792 | 31789 | 1.18501171 | 1.885245902 |
| 41709 | 31706 | 1.46031746 | 2.3 | 41737 | 31734 | 1.352941176 | 1.240196078 | 41765 | 31762 | 1.272562358 | 1.241269841 | 41793 | 31790 | 1.18501171 | 1.948087432 |
| 41710 | 31707 | 1.46031746 | 2.738095238 | 41738 | 31735 | 1.351570415 | 2.691489362 | 41766 | 31763 | 1.271889401 | 1.731182796 | 41794 | 31791 | 1.182161754 | 2.007936508 |
| 41711 | 31708 | 1.45211343 | 1.205992509 | 41739 | 31736 | 1.347985348 | 2.064102564 | 41767 | 31764 | 1.263736264 | 1.474358974 | 41795 | 31792 | 1.179487179 | 1.432234432 |
| 41712 | 31709 | 1.447941889 | 3.508474576 | 41740 | 31737 | 1.34595525 | 1.431726908 | 41768 | 31765 | 1.258358663 | 2.528368794 | 41796 | 31793 | 1.179487179 | 1.326923077 |
| 41713 | 31710 | 1.447941889 | 1.234463277 | 41741 | 31738 | 1.338624339 | 1.064814815 | 41769 | 31766 | 1.256830601 | 1.256830601 | 41797 | 31794 | 1.176972281 | 1.087064677 |
| 41714 | 31711 | 1.446540881 | 1.952830189 | 41742 | 31739 | 1.338624339 | 1.419753086 | 41770 | 31767 | 1.25170068 | 1.241269841 | 41798 | 31795 | 1.176972281 | 2.288557214 |

FIG. 10 (Cont.)

| DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment | DNA SEQ ID NO | AA SEQ ID NO | Spleen 1 Enrichment | Spleen 2 Enrichment |
|---|---|---|---|---|---|---|---|---|---|---|---|---|---|---|---|
| 41799 | 31796 | 1.17593985 | 1.492982456 | 41819 | 31816 | 1.131746032 | 1.118055556 | 41839 | 31836 | 1.095238095 | 1.13963964 | 41859 | 31856 | 1.035497835 | 1.324242424 |
| 41800 | 31797 | 1.174275896 | 1.067010309 | 41820 | 31817 | 1.129464286 | 1.4375 | 41840 | 31837 | 1.095238095 | 1.427304965 | 41860 | 31857 | 1.034870641 | 1.056430446 |
| 41801 | 31798 | 1.173469388 | 2.327380952 | 41821 | 31818 | 1.124839125 | 1.657657658 | 41841 | 31838 | 1.082932049 | 1.292134831 | 41861 | 31858 | 1.034391534 | 2.236111111 |
| 41802 | 31799 | 1.171650055 | 1.872093023 | 41822 | 31819 | 1.123321123 | 1.425213675 | 41842 | 31839 | 1.081014224 | 1.095238095 | 41862 | 31859 | 1.030812325 | 2.818627451 |
| 41803 | 31800 | 1.170771757 | 1.123563218 | 41823 | 31820 | 1.11957672 | 1.533333333 | 41843 | 31840 | 1.075324675 | 1.184848485 | 41863 | 31860 | 1.030812325 | 1.623529412 |
| 41804 | 31801 | 1.168253968 | 1.448148148 | 41824 | 31821 | 1.119047619 | 1.375 | 41844 | 31841 | 1.069767442 | 3.387596899 | 41864 | 31861 | 1.030812325 | 1.428104575 |
| 41805 | 31802 | 1.159663866 | 2.179738562 | 41825 | 31822 | 1.118541033 | 1.631205674 | 41845 | 31842 | 1.068524971 | 1.495934959 | 41865 | 31862 | 1.024577573 | 1.23655914 |
| 41806 | 31803 | 1.159663866 | 1.240196078 | 41826 | 31823 | 1.114795918 | 1.4375 | 41846 | 31843 | 1.067155067 | 1.376068376 | 41866 | 31863 | 1.022222222 | 1.405555556 |
| 41807 | 31804 | 1.159663866 | 1.202614379 | 41827 | 31824 | 1.112622827 | 1.582010582 | 41847 | 31844 | 1.065637066 | 1.657657658 | 41867 | 31864 | 1.022222222 | 1.788888889 |
| 41808 | 31805 | 1.152882206 | 1.210526316 | 41828 | 31825 | 1.112087912 | 1.887179487 | 41848 | 31845 | 1.063945578 | 4.380952381 | 41868 | 31865 | 1.018108652 | 2.051643192 |
| 41809 | 31806 | 1.152882206 | 2.824561404 | 41829 | 31826 | 1.112087912 | 1.651282051 | 41849 | 31846 | 1.062049062 | 1.742424242 | 41869 | 31866 | 1.017006803 | 1.848214286 |
| 41810 | 31807 | 1.152882206 | 1.815789474 | 41830 | 31827 | 1.111111111 | 2 | 41850 | 31847 | 1.058730159 | 1.597222222 | 41870 | 31867 | 1.016380952 | 1.349333333 |
| 41811 | 31808 | 1.152882206 | 1.311403509 | 41831 | 31828 | 1.110241357 | 1.52283105 | 41851 | 31848 | 1.057471264 | 1.32183908 | 41871 | 31868 | 1.013095238 | 1.102083333 |
| 41812 | 31809 | 1.151404151 | 1.228632479 | 41832 | 31829 | 1.109461967 | 1.244588745 | 41852 | 31849 | 1.056122449 | 1.505952381 | 41872 | 31869 | 1.010989011 | 2.137820513 |
| 41813 | 31810 | 1.14739229 | 2.099206349 | 41833 | 31830 | 1.095238095 | 1.823170732 | 41853 | 31850 | 1.051428571 | 4.063333333 | 41873 | 31870 | 1.006435006 | 1.346846847 |
| 41814 | 31811 | 1.14739229 | 1.216931217 | 41834 | 31831 | 1.095238095 | 1.742424242 | 41854 | 31851 | 1.051428571 | 1.226666667 | 41874 | 31871 | 1.001360544 | 1.095238095 |
| 41815 | 31812 | 1.142857143 | 1.333333333 | 41835 | 31832 | 1.095238095 | 2.555555556 | 41855 | 31852 | 1.047619048 | 4.666666667 | 41875 | 31872 | 1.000587889 | 1.514403292 |
| 41816 | 31813 | 1.134353741 | 1.095238095 | 41836 | 31833 | 1.095238095 | 2.058641975 | 41856 | 31853 | 1.041811847 | 1.12195122 | | | | |
| 41817 | 31814 | 1.133380715 | 1.029850746 | 41837 | 31834 | 1.095238095 | 1.277777778 | 41857 | 31854 | 1.04047619 | 1.29375 | | | | |
| 41818 | 31815 | 1.133004926 | 1.057471264 | 41838 | 31835 | 1.095238095 | 1.4375 | 41858 | 31855 | 1.039072039 | 3.391025641 | | | | |

FIG. 11

| DNA SEQ ID NO | AA SEQ ID NO | Stomach 1 Enrichment | Stomach 2 Enrichment |
|---|---|---|---|
| 41876 | 31873 | 2139.442308 | 239.7307692 |
| 41877 | 31874 | 2110 | 335.3333333 |
| 41878 | 31875 | 1502 | 36 |
| 41879 | 31876 | 1421.157895 | 36.31578947 |
| 41880 | 31877 | 1177.6 | 19.42222222 |
| 41881 | 31878 | 1048.690476 | 63.34126984 |
| 41882 | 31879 | 1023.189189 | 16.57657658 |
| 41883 | 31880 | 1000.676923 | 21.93846154 |
| 41884 | 31881 | 1000.074074 | 21.58024691 |
| 41885 | 31882 | 991.0444444 | 40.03703704 |
| 41886 | 31883 | 889.1232877 | 11.13242009 |
| 41887 | 31884 | 775.4285714 | 7.119047619 |
| 41888 | 31885 | 685.2083333 | 13.73611111 |
| 41889 | 31886 | 585.35 | 41.01666667 |
| 41890 | 31887 | 511.3488372 | 2.852713178 |
| 41891 | 31888 | 483.8846154 | 15.62820513 |
| 41892 | 31889 | 461.3939394 | 58.54545455 |
| 41893 | 31890 | 446.3703704 | 11.07407407 |
| 41894 | 31891 | 445.3191489 | 38.17021277 |
| 41895 | 31892 | 440.2150538 | 4.946236559 |
| 41896 | 31893 | 420.7153285 | 19.36253041 |
| 41897 | 31894 | 418.1071429 | 73.92857143 |
| 41898 | 31895 | 414.6478873 | 3.887323944 |
| 41899 | 31896 | 404 | 4.444444444 |
| 41900 | 31897 | 402.9259259 | 15.90123457 |
| 41901 | 31898 | 400.8571429 | 3.066666667 |

| DNA SEQ ID NO | AA SEQ ID NO | Stomach 1 Enrichment | Stomach 2 Enrichment |
|---|---|---|---|
| 41902 | 31899 | 381.8730159 | 24.33862434 |
| 41903 | 31900 | 381.5737705 | 12.31693989 |
| 41904 | 31901 | 378.5416667 | 8.944444444 |
| 41905 | 31902 | 373.52 | 6.378666667 |
| 41906 | 31903 | 370.2330097 | 28.13592233 |
| 41907 | 31904 | 365.8095238 | 15.33333333 |
| 41908 | 31905 | 365.4444444 | 8.802469136 |
| 41909 | 31906 | 363.4 | 5.914285714 |
| 41910 | 31907 | 359.4814815 | 24.04115226 |
| 41911 | 31908 | 358.9508197 | 38.20765027 |
| 41912 | 31909 | 351.7083333 | 14.21527778 |
| 41913 | 31910 | 350.7008547 | 14.28490028 |
| 41914 | 31911 | 337.3333333 | 5.366666667 |
| 41915 | 31912 | 337.3333333 | 13.62962963 |
| 41916 | 31913 | 327.1111111 | 14.19753086 |
| 41917 | 31914 | 319.9402985 | 1.144278607 |
| 41918 | 31915 | 309.58 | 14.72 |
| 41919 | 31916 | 300.4375 | 30.90625 |
| 41920 | 31917 | 297.4059406 | 1.214521452 |
| 41921 | 31918 | 291.7714286 | 7.885714286 |
| 41922 | 31919 | 285.0103093 | 12.64604811 |
| 41923 | 31920 | 276 | 5.484184915 |
| 41924 | 31921 | 270.3777778 | 17.54814815 |
| 41925 | 31922 | 269.6382979 | 14.5177305 |
| 41926 | 31923 | 265.8529412 | 14.09313725 |
| 41927 | 31924 | 264.2553191 | 16.96453901 |

| DNA SEQ ID NO | AA SEQ ID NO | Stomach 1 Enrichment | Stomach 2 Enrichment |
|---|---|---|---|
| 41928 | 31925 | 256.2857143 | 1.792207792 |
| 41929 | 31926 | 241.2653061 | 7.197278912 |
| 41930 | 31927 | 240.4545455 | 19.97979798 |
| 41931 | 31928 | 240.3870968 | 13.84946237 |
| 41932 | 31929 | 236.6506024 | 4.064257028 |
| 41933 | 31930 | 231.9166667 | 21.50925926 |
| 41934 | 31931 | 220.9896907 | 15.01718213 |
| 41935 | 31932 | 215.28 | 3.475555556 |
| 41936 | 31933 | 214.0533333 | 2.044444444 |
| 41937 | 31934 | 213.8241758 | 16.51282051 |
| 41938 | 31935 | 202.2891566 | 14.77911647 |
| 41939 | 31936 | 202.0166667 | 13.92777778 |
| 41940 | 31937 | 200.990991 | 15.47147147 |
| 41941 | 31938 | 198.7010309 | 7.745704467 |
| 41942 | 31939 | 198.1869159 | 3.439252336 |
| 41943 | 31940 | 192 | 16.83333333 |
| 41944 | 31941 | 187.3658537 | 23.74796748 |
| 41945 | 31942 | 176.3909774 | 13.25814536 |
| 41946 | 31943 | 176.0595238 | 1.642857143 |
| 41947 | 31944 | 174.8760331 | 15.96694215 |
| 41948 | 31945 | 170.5833333 | 21.08333333 |
| 41949 | 31946 | 158.4444444 | 7.666666667 |
| 41950 | 31947 | 156.852459 | 1.508196721 |
| 41951 | 31948 | 154.1343284 | 1.60199005 |
| 41952 | 31949 | 152.8135593 | 3.378531073 |
| 41953 | 31950 | 150.047619 | 10.03968254 |

| DNA SEQ ID NO | AA SEQ ID NO | Stomach 1 Enrichment | Stomach 2 Enrichment |
|---|---|---|---|
| 41954 | 31951 | 149.3982301 | 12.21238938 |
| 41955 | 31952 | 144.7083333 | 7.506944444 |
| 41956 | 31953 | 103.5966387 | 14.94677871 |
| 41957 | 31954 | 78.85714286 | 3.285714286 |
| 41958 | 31955 | 55.97202797 | 4.181818182 |
| 41959 | 31956 | 37.59437751 | 10.37617135 |
| 41960 | 31957 | 27.28813559 | 1.559322034 |
| 41961 | 31958 | 27.01587302 | 13.87301587 |
| 41962 | 31959 | 24.64285714 | 21.35714286 |
| 41963 | 31960 | 24.53333333 | 1.533333333 |
| 41964 | 31961 | 24.35294118 | 7.215686275 |
| 41965 | 31962 | 24 | 10 |
| 41966 | 31963 | 23 | 2.279279279 |
| 41967 | 31964 | 19.46153846 | 12.08974359 |
| 41968 | 31965 | 19.29032258 | 30.41935484 |
| 41969 | 31966 | 19.07317073 | 3.739837398 |
| 41970 | 31967 | 19.07317073 | 1.121951220 |
| 41971 | 31968 | 17.44827586 | 10.31034483 |
| 41972 | 31969 | 16.675 | 22.23333333 |
| 41973 | 31970 | 16.12987013 | 3.584415584 |
| 41974 | 31971 | 15.92307692 | 17.1025641 |
| 41975 | 31972 | 15.77142857 | 2.19047619 |
| 41976 | 31973 | 13.14285714 | 2.19047619 |
| 41977 | 31974 | 12.54545455 | 3.717171717 |
| 41978 | 31975 | 12.54545455 | 6.969696970 |
| 41979 | 31976 | 12.17647059 | 5.862745098 |

FIG. 11 (Cont.)

| DNA SEQ ID NO | AA SEQ ID NO | Stomach 1 Enrichment | Stomach 2 Enrichment | DNA SEQ ID NO | AA SEQ ID NO | Stomach 1 Enrichment | Stomach 2 Enrichment | DNA SEQ ID NO | AA SEQ ID NO | Stomach 1 Enrichment | Stomach 2 Enrichment | DNA SEQ ID NO | AA SEQ ID NO | Stomach 1 Enrichment | Stomach 2 Enrichment |
|---|---|---|---|---|---|---|---|---|---|---|---|---|---|---|---|
| 41980 | 31977 | 12.10526316 | 1.614035088 | 42002 | 31999 | 5.935483871 | 2.967741935 | 42024 | 32021 | 2.76 | 1.84 | 42046 | 32043 | 1.15 | 25.68333333 |
| 41981 | 31978 | 12 | 14.22222222 | 42003 | 32000 | 5.75 | 2.3 | 42025 | 32022 | 2.225806452 | 29.67741935 | 42047 | 32044 | 1.15 | 12.84166667 |
| 41982 | 31979 | 11.87096774 | 6.677419355 | 42004 | 32001 | 5.75 | 13.17708333 | 42026 | 32023 | 2.123076923 | 11.55897436 | 42048 | 32045 | 1.15 | 6.133333333 |
| 41983 | 31980 | 11.5 | 65.16666667 | 42005 | 32002 | 5.376623377 | 11.15151515 | 42027 | 32024 | 2 | 8.666666667 | 42049 | 32046 | 1.12195122 | 15.14634146 |
| 41984 | 31981 | 11.24444444 | 11.58518519 | 42006 | 32003 | 5.227272727 | 1.045454545 | 42028 | 32025 | 1.957446809 | 25.77304965 | 42050 | 32047 | 1.12195122 | 46 |
| 41985 | 31982 | 11.01408451 | 34.33802817 | 42007 | 32004 | 5.158878505 | 7.738317757 | 42029 | 32026 | 1.916666667 | 31.30555556 | 42051 | 32048 | 1.12195122 | 7.853658537 |
| 41986 | 31983 | 10.22222222 | 3.975308642 | 42008 | 32005 | 5.111111111 | 110.7407407 | 42030 | 32027 | 1.84 | 20.85333333 | 42052 | 32049 | 1.108433735 | 10.71485944 |
| 41987 | 31984 | 10.01980198 | 3.491749175 | 42009 | 32006 | 4.901639344 | 2.010928962 | 42031 | 32028 | 1.792207792 | 2.588744589 | 42053 | 32050 | 1.095238095 | 50.38095238 |
| 41988 | 31985 | 9.857142857 | 10.03968254 | 42010 | 32007 | 4.813953488 | 10.34108527 | 42032 | 32029 | 1.769230769 | 29.19230769 | 42054 | 32051 | 1.095238095 | 13.14285714 |
| 41989 | 31986 | 9.517241379 | 2.643678161 | 42011 | 32008 | 4.693877551 | 2.816326531 | 42033 | 32030 | 1.735849057 | 1.735849057 | 42055 | 32052 | 1.069767442 | 4.635658915 |
| 41990 | 31987 | 9.2 | 10.73333333 | 42012 | 32009 | 4.6 | 12.26666667 | 42034 | 32031 | 1.703703704 | 53.95061728 | 42056 | 32053 | 1.069767442 | 51.70542636 |
| 41991 | 31988 | 8 | 6.666666667 | 42013 | 32010 | 4.543209877 | 15.14403292 | 42035 | 32032 | 1.642857143 | 28.47619048 | 42057 | 32054 | 1.069767442 | 3.209302326 |
| 41992 | 31989 | 7.666666667 | 4.472222222 | 42014 | 32011 | 4.503496503 | 5.897435897 | 42036 | 32033 | 1.642857143 | 1.423809524 | 42058 | 32055 | 1.069767442 | 11.41085271 |
| 41993 | 31990 | 7.666666667 | 2.555555556 | 42015 | 32012 | 4.380952381 | 22.63492063 | 42037 | 32034 | 1.623529412 | 16.23529412 | 42059 | 32056 | 1.069767442 | 7.666666667 |
| 41994 | 31991 | 7.666666667 | 1.277777778 | 42016 | 32013 | 4.1 | 7.566666667 | 42038 | 32035 | 1.483870968 | 26.21505376 | 42060 | 32057 | 1.022222222 | 23.17037037 |
| 41995 | 31992 | 7.561643836 | 1.470319635 | 42017 | 32014 | 3.887323944 | 19.8685446 | 42039 | 32036 | 1.4375 | 16.77083333 | 42061 | 32058 | 1.022222222 | 13.11851852 |
| 41996 | 31993 | 7.527272727 | 8.642424242 | 42018 | 32015 | 3.59375 | 3.59375 | 42040 | 32037 | 1.393939394 | 56.22222222 | 42062 | 32059 | 1.022222222 | 36.11851852 |
| 41997 | 31994 | 7.276836158 | 8.316384181 | 42019 | 32016 | 3.538461538 | 1.651282051 | 42041 | 32038 | 1.277777778 | 48.55555556 | 42063 | 32060 | 1.010989011 | 2.695970696 |
| 41998 | 31995 | 7.1875 | 3.673611111 | 42020 | 32017 | 3.285714286 | 10.4829932 | 42042 | 32039 | 1.254545455 | 38.05454545 | | | | |
| 41999 | 31996 | 6.686046512 | 1.872093023 | 42021 | 32018 | 2.967741935 | 2.720430108 | 42043 | 32040 | 1.243243243 | 28.59459459 | | | | |
| 42000 | 31997 | 6.571428571 | 14.6031746 | 42022 | 32019 | 2.920634921 | 9.492063492 | 42044 | 32041 | 1.179487179 | 21.23076923 | | | | |
| 42001 | 31998 | 6.258503401 | 7.092970522 | 42023 | 32020 | 2.875 | 15.65277778 | 42045 | 32042 | 1.179487179 | 18.47863248 | | | | |

FIG. 12

| DNA SEQ ID NO | AA SEQ ID NO | Testicle 1 Enrichment |
|---|---|---|
| 42064 | 32061 | 26.45 |
| 42065 | 32062 | 10.15833333 |
| 42066 | 32063 | 8.625 |
| 42067 | 32064 | 8.05 |
| 42068 | 32065 | 7.59 |
| 42069 | 32066 | 7.283333333 |
| 42070 | 32067 | 7.1875 |
| 42071 | 32068 | 6.708333333 |
| 42072 | 32069 | 5.635 |
| 42073 | 32070 | 5.175 |
| 42074 | 32071 | 5.092857143 |
| 42075 | 32072 | 4.74375 |
| 42076 | 32073 | 4.6 |
| 42077 | 32074 | 4.45625 |
| 42078 | 32075 | 4.255 |
| 42079 | 32076 | 4.14 |
| 42080 | 32077 | 3.641666667 |
| 42081 | 32078 | 3.408928571 |
| 42082 | 32079 | 3.370689655 |
| 42083 | 32080 | 3.345454545 |
| 42084 | 32081 | 3.258333333 |
| 42085 | 32082 | 3.258333333 |
| 42086 | 32083 | 3.066666667 |
| 42087 | 32084 | 3.066666667 |
| 42088 | 32085 | 2.998214286 |
| 42089 | 32086 | 2.902380952 |
| 42090 | 32087 | 2.9 |

| DNA SEQ ID NO | AA SEQ ID NO | Testicle 1 Enrichment |
|---|---|---|
| 42091 | 32088 | 2.890540541 |
| 42092 | 32089 | 2.875 |
| 42093 | 32090 | 2.875 |
| 42094 | 32091 | 2.834883721 |
| 42095 | 32092 | 2.795138889 |
| 42096 | 32093 | 2.792857143 |
| 42097 | 32094 | 2.747222222 |
| 42098 | 32095 | 2.742307692 |
| 42099 | 32096 | 2.738095238 |
| 42100 | 32097 | 2.73125 |
| 42101 | 32098 | 2.653846154 |
| 42102 | 32099 | 2.60546875 |
| 42103 | 32100 | 2.5875 |
| 42104 | 32101 | 2.555555556 |
| 42105 | 32102 | 2.546428571 |
| 42106 | 32103 | 2.506410256 |
| 42107 | 32104 | 2.464285714 |
| 42108 | 32105 | 2.464285714 |
| 42109 | 32106 | 2.373404255 |
| 42110 | 32107 | 2.366666667 |
| 42111 | 32108 | 2.361333333 |
| 42112 | 32109 | 2.323469388 |
| 42113 | 32110 | 2.3 |
| 42114 | 32111 | 2.3 |
| 42115 | 32112 | 2.3 |
| 42116 | 32113 | 2.3 |
| 42117 | 32114 | 2.283088235 |

| DNA SEQ ID NO | AA SEQ ID NO | Testicle 1 Enrichment |
|---|---|---|
| 42118 | 32115 | 2.264615385 |
| 42119 | 32116 | 2.25 |
| 42120 | 32117 | 2.2425 |
| 42121 | 32118 | 2.223333333 |
| 42122 | 32119 | 2.211538462 |
| 42123 | 32120 | 2.167307692 |
| 42124 | 32121 | 2.15625 |
| 42125 | 32122 | 2.15 |
| 42126 | 32123 | 2.124576271 |
| 42127 | 32124 | 2.121111111 |
| 42128 | 32125 | 2.118421053 |
| 42129 | 32126 | 2.108333333 |
| 42130 | 32127 | 2.090909091 |
| 42131 | 32128 | 2.075609756 |
| 42132 | 32129 | 2.064772727 |
| 42133 | 32130 | 2.057894737 |
| 42134 | 32131 | 2.05 |
| 42135 | 32132 | 2.05 |
| 42136 | 32133 | 2.044444444 |
| 42137 | 32134 | 2.044444444 |
| 42138 | 32135 | 2.038636364 |
| 42139 | 32136 | 1.990384615 |
| 42140 | 32137 | 1.988235529 |
| 42141 | 32138 | 1.976056338 |
| 42142 | 32139 | 1.971428571 |
| 42143 | 32140 | 1.95 |
| 42144 | 32141 | 1.934090909 |

| DNA SEQ ID NO | AA SEQ ID NO | Testicle 1 Enrichment |
|---|---|---|
| 42145 | 32142 | 1.916666667 |
| 42146 | 32143 | 1.916666667 |
| 42147 | 32144 | 1.907317073 |
| 42148 | 32145 | 1.891111111 |
| 42149 | 32146 | 1.889285714 |
| 42150 | 32147 | 1.887735849 |
| 42151 | 32148 | 1.886 |
| 42152 | 32149 | 1.881818182 |
| 42153 | 32150 | 1.876315789 |
| 42154 | 32151 | 1.86875 |
| 42155 | 32152 | 1.865555556 |
| 42156 | 32153 | 1.861904762 |
| 42157 | 32154 | 1.861904762 |
| 42158 | 32155 | 1.84 |
| 42159 | 32156 | 1.826470588 |
| 42160 | 32157 | 1.807142857 |
| 42161 | 32158 | 1.807142857 |
| 42162 | 32159 | 1.786607143 |
| 42163 | 32160 | 1.785526316 |
| 42164 | 32161 | 1.777272727 |
| 42165 | 32162 | 1.775 |
| 42166 | 32163 | 1.758823529 |
| 42167 | 32164 | 1.756944444 |
| 42168 | 32165 | 1.753278689 |
| 42169 | 32166 | 1.752380952 |
| 42170 | 32167 | 1.750746269 |
| 42171 | 32168 | 1.744827586 |

| DNA SEQ ID NO | AA SEQ ID NO | Testicle 1 Enrichment |
|---|---|---|
| 42172 | 32169 | 1.742424242 |
| 42173 | 32170 | 1.737777778 |
| 42174 | 32171 | 1.735087719 |
| 42175 | 32172 | 1.725 |
| 42176 | 32173 | 1.725 |
| 42177 | 32174 | 1.725 |
| 42178 | 32175 | 1.71097561 |
| 42179 | 32176 | 1.709459459 |
| 42180 | 32177 | 1.707575758 |
| 42181 | 32178 | 1.707216495 |
| 42182 | 32179 | 1.703703704 |
| 42183 | 32180 | 1.702884615 |
| 42184 | 32181 | 1.684883721 |
| 42185 | 32182 | 1.680769231 |
| 42186 | 32183 | 1.680769231 |
| 42187 | 32184 | 1.677868852 |
| 42188 | 32185 | 1.675714286 |
| 42189 | 32186 | 1.671649485 |
| 42190 | 32187 | 1.669354839 |
| 42191 | 32188 | 1.6675 |
| 42192 | 32189 | 1.657352941 |
| 42193 | 32190 | 1.646315789 |
| 42194 | 32191 | 1.642857143 |
| 42195 | 32192 | 1.642857143 |
| 42196 | 32193 | 1.642857143 |
| 42197 | 32194 | 1.636538462 |
| 42198 | 32195 | 1.635555556 |

FIG. 12 (Cont.)

| DNA SEQ ID NO | AA SEQ ID NO | Testicle 1 Enrichment |
|---|---|---|
| 42199 | 32196 | 1.634210526 |
| 42200 | 32197 | 1.627922078 |
| 42201 | 32198 | 1.622321429 |
| 42202 | 32199 | 1.620454545 |
| 42203 | 32200 | 1.61 |
| 42204 | 32201 | 1.603947368 |
| 42205 | 32202 | 1.602459016 |
| 42206 | 32203 | 1.6 |
| 42207 | 32204 | 1.598780488 |
| 42208 | 32205 | 1.59516129 |
| 42209 | 32206 | 1.593373494 |
| 42210 | 32207 | 1.592307692 |
| 42211 | 32208 | 1.592307692 |
| 42212 | 32209 | 1.590833333 |
| 42213 | 32210 | 1.588815789 |
| 42214 | 32211 | 1.588095238 |
| 42215 | 32212 | 1.588095238 |
| 42216 | 32213 | 1.583333333 |
| 42217 | 32214 | 1.58125 |
| 42218 | 32215 | 1.580272109 |
| 42219 | 32216 | 1.575925926 |
| 42220 | 32217 | 1.568181818 |
| 42221 | 32218 | 1.564 |
| 42222 | 32219 | 1.560714286 |
| 42223 | 32220 | 1.560714286 |
| 42224 | 32221 | 1.553508772 |
| 42225 | 32222 | 1.546551724 |
| 42226 | 32223 | 1.544285714 |
| 42227 | 32224 | 1.543835616 |

| DNA SEQ ID NO | AA SEQ ID NO | Testicle 1 Enrichment |
|---|---|---|
| 42228 | 32225 | 1.541 |
| 42229 | 32226 | 1.539516129 |
| 42230 | 32227 | 1.533333333 |
| 42231 | 32228 | 1.533333333 |
| 42232 | 32229 | 1.519642857 |
| 42233 | 32230 | 1.519135802 |
| 42234 | 32231 | 1.518 |
| 42235 | 32232 | 1.517525773 |
| 42236 | 32233 | 1.515909091 |
| 42237 | 32234 | 1.511428571 |
| 42238 | 32235 | 1.506896552 |
| 42239 | 32236 | 1.503846154 |
| 42240 | 32237 | 1.500609756 |
| 42241 | 32238 | 1.5 |
| 42242 | 32239 | 1.5 |
| 42243 | 32240 | 1.495 |
| 42244 | 32241 | 1.495 |
| 42245 | 32242 | 1.487333333 |
| 42246 | 32243 | 1.482644628 |
| 42247 | 32244 | 1.478571429 |
| 42248 | 32245 | 1.478571429 |
| 42249 | 32246 | 1.474705882 |
| 42250 | 32247 | 1.465686275 |
| 42251 | 32248 | 1.458035714 |
| 42252 | 32249 | 1.458035714 |
| 42253 | 32250 | 1.456666667 |
| 42254 | 32251 | 1.456666667 |
| 42255 | 32252 | 1.450769231 |
| 42256 | 32253 | 1.448701299 |

| DNA SEQ ID NO | AA SEQ ID NO | Testicle 1 Enrichment |
|---|---|---|
| 42257 | 32254 | 1.447647059 |
| 42258 | 32255 | 1.445714286 |
| 42259 | 32256 | 1.444512195 |
| 42260 | 32257 | 1.444186047 |
| 42261 | 32258 | 1.442727273 |
| 42262 | 32259 | 1.4375 |
| 42263 | 32260 | 1.4375 |
| 42264 | 32261 | 1.4375 |
| 42265 | 32262 | 1.4375 |
| 42266 | 32263 | 1.4375 |
| 42267 | 32264 | 1.433950617 |
| 42268 | 32265 | 1.433561644 |
| 42269 | 32266 | 1.433561644 |
| 42270 | 32267 | 1.43245614 |
| 42271 | 32268 | 1.430916031 |
| 42272 | 32269 | 1.430813953 |
| 42273 | 32270 | 1.427007299 |
| 42274 | 32271 | 1.421818182 |
| 42275 | 32272 | 1.420588235 |
| 42276 | 32273 | 1.41744186 |
| 42277 | 32274 | 1.415384615 |
| 42278 | 32275 | 1.415384615 |
| 42279 | 32276 | 1.405555556 |
| 42280 | 32277 | 1.405555556 |
| 42281 | 32278 | 1.399166667 |
| 42282 | 32279 | 1.398648649 |
| 42283 | 32280 | 1.39845679 |
| 42284 | 32281 | 1.396428571 |
| 42285 | 32282 | 1.393939394 |

| DNA SEQ ID NO | AA SEQ ID NO | Testicle 1 Enrichment |
|---|---|---|
| 42286 | 32283 | 1.387931034 |
| 42287 | 32284 | 1.384259259 |
| 42288 | 32285 | 1.38 |
| 42289 | 32286 | 1.38 |
| 42290 | 32287 | 1.38 |
| 42291 | 32288 | 1.377325581 |
| 42292 | 32289 | 1.374390244 |
| 42293 | 32290 | 1.369852941 |
| 42294 | 32291 | 1.368103448 |
| 42295 | 32292 | 1.367567568 |
| 42296 | 32293 | 1.365625 |
| 42297 | 32294 | 1.362056738 |
| 42298 | 32295 | 1.36122449 |
| 42299 | 32296 | 1.359090909 |
| 42300 | 32297 | 1.359090909 |
| 42301 | 32298 | 1.355970149 |
| 42302 | 32299 | 1.355357143 |
| 42303 | 32300 | 1.354444444 |
| 42304 | 32301 | 1.354444444 |
| 42305 | 32302 | 1.351546392 |
| 42306 | 32303 | 1.348275862 |
| 42307 | 32304 | 1.348275862 |
| 42308 | 32305 | 1.345283019 |
| 42309 | 32306 | 1.341666667 |
| 42310 | 32307 | 1.341666667 |
| 42311 | 32308 | 1.341666667 |
| 42312 | 32309 | 1.341666667 |
| 42313 | 32310 | 1.34015748 |
| 42314 | 32311 | 1.3225 |

| DNA SEQ ID NO | AA SEQ ID NO | Testicle 1 Enrichment |
|---|---|---|
| 42315 | 32312 | 1.32037037 |
| 42316 | 32313 | 1.318292683 |
| 42317 | 32314 | 1.314285714 |
| 42318 | 32315 | 1.311 |
| 42319 | 32316 | 1.311 |
| 42320 | 32317 | 1.303333333 |
| 42321 | 32318 | 1.303333333 |
| 42322 | 32319 | 1.301315789 |
| 42323 | 32320 | 1.29375 |
| 42324 | 32321 | 1.29375 |
| 42325 | 32322 | 1.292380952 |
| 42326 | 32323 | 1.290243902 |
| 42327 | 32324 | 1.290243902 |
| 42328 | 32325 | 1.288 |
| 42329 | 32326 | 1.288 |
| 42330 | 32327 | 1.277777778 |
| 42331 | 32328 | 1.274698795 |
| 42332 | 32329 | 1.273214286 |
| 42333 | 32330 | 1.269480519 |
| 42334 | 32331 | 1.268556701 |
| 42335 | 32332 | 1.268382353 |
| 42336 | 32333 | 1.265 |
| 42337 | 32334 | 1.265 |
| 42338 | 32335 | 1.265 |
| 42339 | 32336 | 1.263114754 |
| 42340 | 32337 | 1.258235294 |
| 42341 | 32338 | 1.254545455 |
| 42342 | 32339 | 1.254545455 |
| 42343 | 32340 | 1.254545455 |

FIG. 12 (Cont.)

| DNA SEQ ID NO | AA SEQ ID NO | Testicle 1 Enrichment |
|---|---|---|
| 42344 | 32341 | 1.247457627 |
| 42345 | 32342 | 1.245833333 |
| 42346 | 32343 | 1.245833333 |
| 42347 | 32344 | 1.245833333 |
| 42348 | 32345 | 1.241089109 |
| 42349 | 32346 | 1.238461538 |
| 42350 | 32347 | 1.238461538 |
| 42351 | 32348 | 1.233333333 |
| 42352 | 32349 | 1.230232558 |
| 42353 | 32350 | 1.229310345 |
| 42354 | 32351 | 1.228767123 |
| 42355 | 32352 | 1.226666667 |
| 42356 | 32353 | 1.223404255 |
| 42357 | 32354 | 1.221875 |
| 42358 | 32355 | 1.220408163 |
| 42359 | 32356 | 1.219 |
| 42360 | 32357 | 1.217647059 |
| 42361 | 32358 | 1.217647059 |
| 42362 | 32359 | 1.217083333 |
| 42363 | 32360 | 1.216346154 |
| 42364 | 32361 | 1.214788732 |
| 42365 | 32362 | 1.213888889 |
| 42366 | 32363 | 1.212403101 |
| 42367 | 32364 | 1.211333333 |
| 42368 | 32365 | 1.210526316 |
| 42369 | 32366 | 1.208474576 |
| 42370 | 32367 | 1.2075 |
| 42371 | 32368 | 1.197916667 |
| 42372 | 32369 | 1.197916667 |

| DNA SEQ ID NO | AA SEQ ID NO | Testicle 1 Enrichment |
|---|---|---|
| 42373 | 32370 | 1.196938776 |
| 42374 | 32371 | 1.196 |
| 42375 | 32372 | 1.195098039 |
| 42376 | 32373 | 1.193396226 |
| 42377 | 32374 | 1.193396226 |
| 42378 | 32375 | 1.192073171 |
| 42379 | 32376 | 1.191071429 |
| 42380 | 32377 | 1.190350877 |
| 42381 | 32378 | 1.189655172 |
| 42382 | 32379 | 1.189655172 |
| 42383 | 32380 | 1.188333333 |
| 42384 | 32381 | 1.1845 |
| 42385 | 32382 | 1.182394366 |
| 42386 | 32383 | 1.181944444 |
| 42387 | 32384 | 1.179113924 |
| 42388 | 32385 | 1.17875 |
| 42389 | 32386 | 1.17804878 |
| 42390 | 32387 | 1.176744186 |
| 42391 | 32388 | 1.173 |
| 42392 | 32389 | 1.168253968 |
| 42393 | 32390 | 1.167424242 |
| 42394 | 32391 | 1.165131579 |
| 42395 | 32392 | 1.163855422 |
| 42396 | 32393 | 1.163690476 |
| 42397 | 32394 | 1.15 |
| 42398 | 32395 | 1.15 |
| 42399 | 32396 | 1.15 |
| 42400 | 32397 | 1.15 |
| 42401 | 32398 | 1.15 |

| DNA SEQ ID NO | AA SEQ ID NO | Testicle 1 Enrichment |
|---|---|---|
| 42402 | 32399 | 1.15 |
| 42403 | 32400 | 1.15 |
| 42404 | 32401 | 1.15 |
| 42405 | 32402 | 1.15 |
| 42406 | 32403 | 1.15 |
| 42407 | 32404 | 1.15 |
| 42408 | 32405 | 1.15 |
| 42409 | 32406 | 1.15 |
| 42410 | 32407 | 1.15 |
| 42411 | 32408 | 1.15 |
| 42412 | 32409 | 1.15 |
| 42413 | 32410 | 1.15 |
| 42414 | 32411 | 1.15 |
| 42415 | 32412 | 1.14222973 |
| 42416 | 32413 | 1.140944882 |
| 42417 | 32414 | 1.137894737 |
| 42418 | 32415 | 1.136470588 |
| 42419 | 32416 | 1.135802469 |
| 42420 | 32417 | 1.135064935 |
| 42421 | 32418 | 1.134459459 |
| 42422 | 32419 | 1.131451613 |
| 42423 | 32420 | 1.130833333 |
| 42424 | 32421 | 1.129464286 |
| 42425 | 32422 | 1.128504673 |
| 42426 | 32423 | 1.125789474 |
| 42427 | 32424 | 1.125531915 |
| 42428 | 32425 | 1.124157303 |
| 42429 | 32426 | 1.122177419 |
| 42430 | 32427 | 1.12125 |

| DNA SEQ ID NO | AA SEQ ID NO | Testicle 1 Enrichment |
|---|---|---|
| 42431 | 32428 | 1.119736842 |
| 42432 | 32429 | 1.119736842 |
| 42433 | 32430 | 1.117142857 |
| 42434 | 32431 | 1.115671642 |
| 42435 | 32432 | 1.115671642 |
| 42436 | 32433 | 1.1140625 |
| 42437 | 32434 | 1.1140625 |
| 42438 | 32435 | 1.112903226 |
| 42439 | 32436 | 1.111666667 |
| 42440 | 32437 | 1.111666667 |
| 42441 | 32438 | 1.111666667 |
| 42442 | 32439 | 1.111666667 |
| 42443 | 32440 | 1.111666667 |
| 42444 | 32441 | 1.108928571 |
| 42445 | 32442 | 1.108928571 |
| 42446 | 32443 | 1.106329114 |
| 42447 | 32444 | 1.106329114 |
| 42448 | 32445 | 1.105769231 |
| 42449 | 32446 | 1.105769231 |
| 42450 | 32447 | 1.104901961 |
| 42451 | 32448 | 1.102083333 |
| 42452 | 32449 | 1.102083333 |
| 42453 | 32450 | 1.1 |
| 42454 | 32451 | 1.1 |
| 42455 | 32452 | 1.1 |
| 42456 | 32453 | 1.098888889 |
| 42457 | 32454 | 1.097727273 |
| 42458 | 32455 | 1.097727273 |
| 42459 | 32456 | 1.096511628 |

| DNA SEQ ID NO | AA SEQ ID NO | Testicle 1 Enrichment |
|---|---|---|
| 42460 | 32457 | 1.095238095 |
| 42461 | 32458 | 1.095238095 |
| 42462 | 32459 | 1.094354839 |
| 42463 | 32460 | 1.0925 |
| 42464 | 32461 | 1.0925 |
| 42465 | 32462 | 1.090610329 |
| 42466 | 32463 | 1.089473684 |
| 42467 | 32464 | 1.088392857 |
| 42468 | 32465 | 1.088392857 |
| 42469 | 32466 | 1.086111111 |
| 42470 | 32467 | 1.086111111 |
| 42471 | 32468 | 1.085211268 |
| 42472 | 32469 | 1.084285714 |
| 42473 | 32470 | 1.08030303 |
| 42474 | 32471 | 1.078125 |
| 42475 | 32472 | 1.076595745 |
| 42476 | 32473 | 1.075 |
| 42477 | 32474 | 1.074590164 |
| 42478 | 32475 | 1.073333333 |
| 42479 | 32476 | 1.071590909 |
| 42480 | 32477 | 1.070689655 |
| 42481 | 32478 | 1.070689655 |
| 42482 | 32479 | 1.067857143 |
| 42483 | 32480 | 1.066363636 |
| 42484 | 32481 | 1.066145833 |
| 42485 | 32482 | 1.061538462 |
| 42486 | 32483 | 1.061538462 |
| 42487 | 32484 | 1.059803922 |
| 42488 | 32485 | 1.058730159 |

FIG. 12 (Cont.)

| DNA SEQ ID NO | AA SEQ ID NO | Testicle 1 Enrichment |
|---|---|---|
| 42489 | 32486 | 1.058730159 |
| 42490 | 32487 | 1.056122449 |
| 42491 | 32488 | 1.055294118 |
| 42492 | 32489 | 1.054166667 |
| 42493 | 32490 | 1.054166667 |
| 42494 | 32491 | 1.054166667 |
| 42495 | 32492 | 1.050393701 |
| 42496 | 32493 | 1.05 |
| 42497 | 32494 | 1.047321429 |
| 42498 | 32495 | 1.046794872 |
| 42499 | 32496 | 1.045454545 |

| DNA SEQ ID NO | AA SEQ ID NO | Testicle 1 Enrichment |
|---|---|---|
| 42500 | 32497 | 1.043846154 |
| 42501 | 32498 | 1.043518519 |
| 42502 | 32499 | 1.043023256 |
| 42503 | 32500 | 1.0421875 |
| 42504 | 32501 | 1.04047619 |
| 42505 | 32502 | 1.038709677 |
| 42506 | 32503 | 1.037804878 |
| 42507 | 32504 | 1.037254902 |
| 42508 | 32505 | 1.037254902 |
| 42509 | 32506 | 1.035 |
| 42510 | 32507 | 1.035 |

| DNA SEQ ID NO | AA SEQ ID NO | Testicle 1 Enrichment |
|---|---|---|
| 42511 | 32508 | 1.035 |
| 42512 | 32509 | 1.030208333 |
| 42513 | 32510 | 1.029651163 |
| 42514 | 32511 | 1.028947368 |
| 42515 | 32512 | 1.026344086 |
| 42516 | 32513 | 1.025 |
| 42517 | 32514 | 1.022222222 |
| 42518 | 32515 | 1.018571429 |
| 42519 | 32516 | 1.018032787 |
| 42520 | 32517 | 1.014705882 |
| 42521 | 32518 | 1.014705882 |

| DNA SEQ ID NO | AA SEQ ID NO | Testicle 1 Enrichment |
|---|---|---|
| 42522 | 32519 | 1.014705882 |
| 42523 | 32520 | 1.012393162 |
| 42524 | 32521 | 1.012 |
| 42525 | 32522 | 1.011445783 |
| 42526 | 32523 | 1.010606061 |
| 42527 | 32524 | 1.010606061 |
| 42528 | 32525 | 1.009183673 |
| 42529 | 32526 | 1.008461538 |
| 42530 | 32527 | 1.00625 |
| 42531 | 32528 | 1.00625 |
| 42532 | 32529 | 1.00625 |

| DNA SEQ ID NO | AA SEQ ID NO | Testicle 1 Enrichment |
|---|---|---|
| 42533 | 32530 | 1.00625 |
| 42534 | 32531 | 1.00625 |
| 42535 | 32532 | 1.003636364 |
| 42536 | 32533 | 1.003636364 |
| 42537 | 32534 | 1.003191489 |
| 42538 | 32535 | 1.002564103 |
| 42539 | 32536 | 1.002564103 |

FIG. 13

| DNA SEQ ID NO | AA SEQ ID NO | Lung 1 Enrichment |
|---|---|---|
| 42540 | 32537 | 34.5 |
| 42541 | 32538 | 29.30482456 |
| 42542 | 32539 | 11.5 |
| 42543 | 32540 | 8.116346154 |
| 42544 | 32541 | 7.1875 |
| 42545 | 32542 | 7.1875 |
| 42546 | 32543 | 7.027777778 |
| 42547 | 32544 | 6.160714286 |
| 42548 | 32545 | 5.869791667 |
| 42549 | 32546 | 5.75 |
| 42550 | 32547 | 5.75 |
| 42551 | 32548 | 5.75 |
| 42552 | 32549 | 5.75 |
| 42553 | 32550 | 5.175 |
| 42554 | 32551 | 5.105457227 |
| 42555 | 32552 | 5.03125 |
| 42556 | 32553 | 4.644230769 |
| 42557 | 32554 | 4.6 |
| 42558 | 32555 | 4.6 |
| 42559 | 32556 | 4.6 |
| 42560 | 32557 | 4.3125 |
| 42561 | 32558 | 4.3125 |
| 42562 | 32559 | 4.3125 |
| 42563 | 32560 | 4.3125 |
| 42564 | 32561 | 4.3125 |
| 42565 | 32562 | 4.3125 |
| 42566 | 32563 | 4.3125 |

| DNA SEQ ID NO | AA SEQ ID NO | Lung 1 Enrichment |
|---|---|---|
| 42567 | 32564 | 4.3125 |
| 42568 | 32565 | 4.216666667 |
| 42569 | 32566 | 4.212209302 |
| 42570 | 32567 | 4.201923077 |
| 42571 | 32568 | 4.181818182 |
| 42572 | 32569 | 4.107142857 |
| 42573 | 32570 | 4.046296296 |
| 42574 | 32571 | 4.004464286 |
| 42575 | 32572 | 3.953125 |
| 42576 | 32573 | 3.920454545 |
| 42577 | 32574 | 3.901785714 |
| 42578 | 32575 | 3.833333333 |
| 42579 | 32576 | 3.833333333 |
| 42580 | 32577 | 3.833333333 |
| 42581 | 32578 | 3.833333333 |
| 42582 | 32579 | 3.833333333 |
| 42583 | 32580 | 3.833333333 |
| 42584 | 32581 | 3.833333333 |
| 42585 | 32582 | 3.77734375 |
| 42586 | 32583 | 3.75 |
| 42587 | 32584 | 3.696428571 |
| 42588 | 32585 | 3.690909091 |
| 42589 | 32586 | 3.59375 |
| 42590 | 32587 | 3.59375 |
| 42591 | 32588 | 3.463068182 |
| 42592 | 32589 | 3.45 |
| 42593 | 32590 | 3.45 |

| DNA SEQ ID NO | AA SEQ ID NO | Lung 1 Enrichment |
|---|---|---|
| 42594 | 32591 | 3.397727273 |
| 42595 | 32592 | 3.367857143 |
| 42596 | 32593 | 3.285714286 |
| 42597 | 32594 | 3.285714286 |
| 42598 | 32595 | 3.234375 |
| 42599 | 32596 | 3.234375 |
| 42600 | 32597 | 3.234375 |
| 42601 | 32598 | 3.213235294 |
| 42602 | 32599 | 3.148809524 |
| 42603 | 32600 | 3.128676471 |
| 42604 | 32601 | 3.121428571 |
| 42605 | 32602 | 3.114583333 |
| 42606 | 32603 | 3.114583333 |
| 42607 | 32604 | 3.114583333 |
| 42608 | 32605 | 3.096153846 |
| 42609 | 32606 | 3.080357143 |
| 42610 | 32607 | 3.034722222 |
| 42611 | 32608 | 3.01875 |
| 42612 | 32609 | 2.981481481 |
| 42613 | 32610 | 2.9325 |
| 42614 | 32611 | 2.924568966 |
| 42615 | 32612 | 2.875 |
| 42616 | 32613 | 2.875 |
| 42617 | 32614 | 2.875 |
| 42618 | 32615 | 2.875 |
| 42619 | 32616 | 2.875 |
| 42620 | 32617 | 2.875 |

| DNA SEQ ID NO | AA SEQ ID NO | Lung 1 Enrichment |
|---|---|---|
| 42621 | 32618 | 2.875 |
| 42622 | 32619 | 2.875 |
| 42623 | 32620 | 2.875 |
| 42624 | 32621 | 2.875 |
| 42625 | 32622 | 2.875 |
| 42626 | 32623 | 2.875 |
| 42627 | 32624 | 2.875 |
| 42628 | 32625 | 2.875 |
| 42629 | 32626 | 2.875 |
| 42630 | 32627 | 2.875 |
| 42631 | 32628 | 2.826271186 |
| 42632 | 32629 | 2.815721649 |
| 42633 | 32630 | 2.78515625 |
| 42634 | 32631 | 2.764423077 |
| 42635 | 32632 | 2.75 |
| 42636 | 32633 | 2.75 |
| 42637 | 32634 | 2.75 |
| 42638 | 32635 | 2.738095238 |
| 42639 | 32636 | 2.738095238 |
| 42640 | 32637 | 2.738095238 |
| 42641 | 32638 | 2.738095238 |
| 42642 | 32639 | 2.731125 |
| 42643 | 32640 | 2.719594595 |
| 42644 | 32641 | 2.715277778 |
| 42645 | 32642 | 2.6875 |
| 42646 | 32643 | 2.683333333 |
| 42647 | 32644 | 2.683333333 |

| DNA SEQ ID NO | AA SEQ ID NO | Lung 1 Enrichment |
|---|---|---|
| 42648 | 32645 | 2.678977273 |
| 42649 | 32646 | 2.674418605 |
| 42650 | 32647 | 2.669642857 |
| 42651 | 32648 | 2.669642857 |
| 42652 | 32649 | 2.653846154 |
| 42653 | 32650 | 2.653846154 |
| 42654 | 32651 | 2.645 |
| 42655 | 32652 | 2.625 |
| 42656 | 32653 | 2.625 |
| 42657 | 32654 | 2.613636364 |
| 42658 | 32655 | 2.613636364 |
| 42659 | 32656 | 2.613636364 |
| 42660 | 32657 | 2.60755814 |
| 42661 | 32658 | 2.5875 |
| 42662 | 32659 | 2.577586207 |
| 42663 | 32660 | 2.577586207 |
| 42664 | 32661 | 2.569148936 |
| 42665 | 32662 | 2.566964286 |
| 42666 | 32663 | 2.55875 |
| 42667 | 32664 | 2.555555556 |
| 42668 | 32665 | 2.555555556 |
| 42669 | 32666 | 2.555555556 |
| 42670 | 32667 | 2.536764706 |
| 42671 | 32668 | 2.53 |
| 42672 | 32669 | 2.515625 |
| 42673 | 32670 | 2.507978723 |
| 42674 | 32671 | 2.5 |

FIG. 13 (Cont.)

| DNA SEQ ID NO | AA SEQ ID NO | Lung 1 Enrichment |
|---|---|---|
| 42675 | 32672 | 2.491666667 |
| 42676 | 32673 | 2.491666667 |
| 42677 | 32674 | 2.464285714 |
| 42678 | 32675 | 2.456818182 |
| 42679 | 32676 | 2.452205882 |
| 42680 | 32677 | 2.432692308 |
| 42681 | 32678 | 2.418650794 |
| 42682 | 32679 | 2.413580247 |
| 42683 | 32680 | 2.395833333 |
| 42684 | 32681 | 2.395833333 |
| 42685 | 32682 | 2.395833333 |
| 42686 | 32683 | 2.395833333 |
| 42687 | 32684 | 2.395833333 |
| 42688 | 32685 | 2.395833333 |
| 42689 | 32686 | 2.395833333 |
| 42690 | 32687 | 2.395833333 |
| 42691 | 32688 | 2.381313131 |
| 42692 | 32689 | 2.367647059 |
| 42693 | 32690 | 2.367647059 |
| 42694 | 32691 | 2.367647059 |
| 42695 | 32692 | 2.367647059 |
| 42696 | 32693 | 2.358974359 |
| 42697 | 32694 | 2.3359375 |
| 42698 | 32695 | 2.3359375 |
| 42699 | 32696 | 2.322115385 |
| 42700 | 32697 | 2.3 |
| 42701 | 32698 | 2.3 |
| 42702 | 32699 | 2.3 |
| 42703 | 32700 | 2.3 |
| 42704 | 32701 | 2.3 |
| 42705 | 32702 | 2.3 |
| 42706 | 32703 | 2.3 |
| 42707 | 32704 | 2.3 |
| 42708 | 32705 | 2.3 |
| 42709 | 32706 | 2.290254237 |
| 42710 | 32707 | 2.28525641 |
| 42711 | 32708 | 2.280172414 |
| 42712 | 32709 | 2.280172414 |
| 42713 | 32710 | 2.280172414 |
| 42714 | 32711 | 2.269736842 |
| 42715 | 32712 | 2.265151515 |
| 42716 | 32713 | 2.261666667 |
| 42717 | 32714 | 2.258928571 |
| 42718 | 32715 | 2.258928571 |
| 42719 | 32716 | 2.258928571 |
| 42720 | 32717 | 2.24609375 |
| 42721 | 32718 | 2.239182692 |
| 42722 | 32719 | 2.236111111 |
| 42723 | 32720 | 2.236111111 |
| 42724 | 32721 | 2.231343284 |
| 42725 | 32722 | 2.229591837 |
| 42726 | 32723 | 2.228125 |
| 42727 | 32724 | 2.225806452 |
| 42728 | 32725 | 2.224056604 |
| 42729 | 32726 | 2.211538462 |
| 42730 | 32727 | 2.211538462 |
| 42731 | 32728 | 2.20212766 |
| 42732 | 32729 | 2.200617284 |
| 42733 | 32730 | 2.198529412 |
| 42734 | 32731 | 2.198529412 |
| 42735 | 32732 | 2.19047619 |
| 42736 | 32733 | 2.185 |
| 42737 | 32734 | 2.185 |
| 42738 | 32735 | 2.181034483 |
| 42739 | 32736 | 2.178030303 |
| 42740 | 32737 | 2.170918367 |
| 42741 | 32738 | 2.15625 |
| 42742 | 32739 | 2.15625 |
| 42743 | 32740 | 2.15625 |
| 42744 | 32741 | 2.15625 |
| 42745 | 32742 | 2.15625 |
| 42746 | 32743 | 2.15625 |
| 42747 | 32744 | 2.15625 |
| 42748 | 32745 | 2.15625 |
| 42749 | 32746 | 2.15625 |
| 42750 | 32747 | 2.15625 |
| 42751 | 32748 | 2.15625 |
| 42752 | 32749 | 2.15625 |
| 42753 | 32750 | 2.15625 |
| 42754 | 32751 | 2.15625 |
| 42755 | 32752 | 2.143181818 |
| 42756 | 32753 | 2.140957447 |
| 42757 | 32754 | 2.140957447 |
| 42758 | 32755 | 2.140510949 |
| 42759 | 32756 | 2.137820513 |
| 42760 | 32757 | 2.135714286 |
| 42761 | 32758 | 2.12962963 |
| 42762 | 32759 | 2.125 |
| 42763 | 32760 | 2.125 |
| 42764 | 32761 | 2.118421053 |
| 42765 | 32762 | 2.118421053 |
| 42766 | 32763 | 2.118421053 |
| 42767 | 32764 | 2.113970588 |
| 42768 | 32765 | 2.112244898 |
| 42769 | 32766 | 2.108333333 |
| 42770 | 32767 | 2.100961538 |
| 42771 | 32768 | 2.097972973 |
| 42772 | 32769 | 2.090909091 |
| 42773 | 32770 | 2.090909091 |
| 42774 | 32771 | 2.090909091 |
| 42775 | 32772 | 2.090909091 |
| 42776 | 32773 | 2.079787234 |
| 42777 | 32774 | 2.061320755 |
| 42778 | 32775 | 2.060416667 |
| 42779 | 32776 | 2.053571429 |
| 42780 | 32777 | 2.053571429 |
| 42781 | 32778 | 2.053571429 |
| 42782 | 32779 | 2.053571429 |
| 42783 | 32780 | 2.053571429 |
| 42784 | 32781 | 2.053571429 |
| 42785 | 32782 | 2.053571429 |
| 42786 | 32783 | 2.053571429 |
| 42787 | 32784 | 2.053571429 |
| 42788 | 32785 | 2.0484375 |
| 42789 | 32786 | 2.029411765 |
| 42790 | 32787 | 2.029411765 |
| 42791 | 32788 | 2.029411765 |
| 42792 | 32789 | 2.026639344 |
| 42793 | 32790 | 2.019345238 |
| 42794 | 32791 | 2.018617021 |
| 42795 | 32792 | 2.016791045 |
| 42796 | 32793 | 2.0125 |
| 42797 | 32794 | 2.0125 |
| 42798 | 32795 | 2.0125 |
| 42799 | 32796 | 2.007936508 |
| 42800 | 32797 | 2.003787879 |
| 42801 | 32798 | 2.001 |
| 42802 | 32799 | 2 |
| 42803 | 32800 | 2 |
| 42804 | 32801 | 1.986363636 |
| 42805 | 32802 | 1.982758621 |
| 42806 | 32803 | 1.982758621 |
| 42807 | 32804 | 1.981418919 |
| 42808 | 32805 | 1.980555556 |
| 42809 | 32806 | 1.971428571 |
| 42810 | 32807 | 1.967105263 |
| 42811 | 32808 | 1.960227273 |
| 42812 | 32809 | 1.957446809 |
| 42813 | 32810 | 1.956932773 |
| 42814 | 32811 | 1.955 |
| 42815 | 32812 | 1.953525641 |
| 42816 | 32813 | 1.950892857 |
| 42817 | 32814 | 1.950892857 |
| 42818 | 32815 | 1.947580645 |
| 42819 | 32816 | 1.947580645 |

FIG. 13 (Cont.)

| DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment |
|---|---|---|---|---|---|---|---|---|---|---|---|---|---|---|
| 42820 | 32817 | 1.947580645 | 42849 | 32846 | 1.88671875 | 42878 | 32875 | 1.826822917 | 42907 | 32904 | 1.779761905 | 42936 | 32933 | 1.742424242 |
| 42821 | 32818 | 1.944852941 | 42850 | 32847 | 1.879807692 | 42879 | 32876 | 1.819620253 | 42908 | 32905 | 1.779761905 | 42937 | 32934 | 1.742424242 |
| 42822 | 32819 | 1.940625 | 42851 | 32848 | 1.879807692 | 42880 | 32877 | 1.819335938 | 42909 | 32906 | 1.779761905 | 42938 | 32935 | 1.740131579 |
| 42823 | 32820 | 1.940625 | 42852 | 32849 | 1.879807692 | 42881 | 32878 | 1.817528736 | 42910 | 32907 | 1.777960526 | 42939 | 32936 | 1.740131579 |
| 42824 | 32821 | 1.929276316 | 42853 | 32850 | 1.879807692 | 42882 | 32879 | 1.815789474 | 42911 | 32908 | 1.77393617 | 42940 | 32937 | 1.740131579 |
| 42825 | 32822 | 1.916666667 | 42854 | 32851 | 1.875 | 42883 | 32880 | 1.815789474 | 42912 | 32909 | 1.77393617 | 42941 | 32938 | 1.735849057 |
| 42826 | 32823 | 1.916666667 | 42855 | 32852 | 1.872093023 | 42884 | 32881 | 1.813461538 | 42913 | 32910 | 1.772260274 | 42942 | 32939 | 1.732876712 |
| 42827 | 32824 | 1.916666667 | 42856 | 32853 | 1.871031746 | 42885 | 32882 | 1.81125 | 42914 | 32911 | 1.769230769 | 42943 | 32940 | 1.725 |
| 42828 | 32825 | 1.916666667 | 42857 | 32854 | 1.86875 | 42886 | 32883 | 1.810185185 | 42915 | 32912 | 1.769230769 | 42944 | 32941 | 1.725 |
| 42829 | 32826 | 1.916666667 | 42858 | 32855 | 1.86875 | 42887 | 32884 | 1.810185185 | 42916 | 32913 | 1.769230769 | 42945 | 32942 | 1.725 |
| 42830 | 32827 | 1.916666667 | 42859 | 32856 | 1.86622807 | 42888 | 32885 | 1.810185185 | 42917 | 32914 | 1.769230769 | 42946 | 32943 | 1.725 |
| 42831 | 32828 | 1.916666667 | 42860 | 32857 | 1.863425926 | 42889 | 32886 | 1.810185185 | 42918 | 32915 | 1.769230769 | 42947 | 32944 | 1.725 |
| 42832 | 32829 | 1.916666667 | 42861 | 32858 | 1.860294118 | 42890 | 32887 | 1.810185185 | 42919 | 32916 | 1.766071429 | 42948 | 32945 | 1.725 |
| 42833 | 32830 | 1.916666667 | 42862 | 32859 | 1.860294118 | 42891 | 32888 | 1.807142857 | 42920 | 32917 | 1.766071429 | 42949 | 32946 | 1.725 |
| 42834 | 32831 | 1.916666667 | 42863 | 32860 | 1.860294118 | 42892 | 32889 | 1.805232558 | 42921 | 32918 | 1.762096774 | 42950 | 32947 | 1.725 |
| 42835 | 32832 | 1.916666667 | 42864 | 32861 | 1.85483871 | 42893 | 32890 | 1.805232558 | 42922 | 32919 | 1.760204082 | 42951 | 32948 | 1.725 |
| 42836 | 32833 | 1.916666667 | 42865 | 32862 | 1.852777778 | 42894 | 32891 | 1.796875 | 42923 | 32920 | 1.756944444 | 42952 | 32949 | 1.725 |
| 42837 | 32834 | 1.916666667 | 42866 | 32863 | 1.848214286 | 42895 | 32892 | 1.796875 | 42924 | 32921 | 1.756944444 | 42953 | 32950 | 1.725 |
| 42838 | 32835 | 1.916666667 | 42867 | 32864 | 1.848214286 | 42896 | 32893 | 1.796875 | 42925 | 32922 | 1.75304878 | 42954 | 32951 | 1.713942308 |
| 42839 | 32836 | 1.916666667 | 42868 | 32865 | 1.844339623 | 42897 | 32894 | 1.796875 | 42926 | 32923 | 1.75304878 | 42955 | 32952 | 1.712765957 |
| 42840 | 32837 | 1.916666667 | 42869 | 32866 | 1.844339623 | 42898 | 32895 | 1.796875 | 42927 | 32924 | 1.75304878 | 42956 | 32953 | 1.711309524 |
| 42841 | 32838 | 1.916666667 | 42870 | 32867 | 1.842429577 | 42899 | 32896 | 1.792207792 | 42928 | 32925 | 1.751953125 | 42957 | 32954 | 1.711309524 |
| 42842 | 32839 | 1.916666667 | 42871 | 32868 | 1.84 | 42900 | 32897 | 1.791666667 | 42929 | 32926 | 1.751953125 | 42958 | 32955 | 1.709459459 |
| 42843 | 32840 | 1.916666667 | 42872 | 32869 | 1.832107843 | 42901 | 32898 | 1.790983607 | 42930 | 32927 | 1.75 | 42959 | 32956 | 1.709459459 |
| 42844 | 32841 | 1.903716216 | 42873 | 32870 | 1.829545455 | 42902 | 32899 | 1.79009434 | 42931 | 32928 | 1.75 | 42960 | 32957 | 1.703703704 |
| 42845 | 32842 | 1.899553571 | 42874 | 32871 | 1.829545455 | 42903 | 32900 | 1.788888889 | 42932 | 32929 | 1.748958333 | 42961 | 32958 | 1.703703704 |
| 42846 | 32843 | 1.893292683 | 42875 | 32872 | 1.829545455 | 42904 | 32901 | 1.788888889 | 42933 | 32930 | 1.745535714 | 42962 | 32959 | 1.703703704 |
| 42847 | 32844 | 1.893292683 | 42876 | 32873 | 1.829545455 | 42905 | 32902 | 1.7825 | 42934 | 32931 | 1.743852459 | 42963 | 32960 | 1.701530612 |
| 42848 | 32845 | 1.891447368 | 42877 | 32874 | 1.829545455 | 42906 | 32903 | 1.7825 | 42935 | 32932 | 1.743852459 | 42964 | 32961 | 1.700704225 |

FIG. 13 (Cont.)

| DNA SEQ ID NO | AA SEQ ID NO | Lung1 Enrichment |
|---|---|---|
| 42965 | 32962 | 1.698863636 |
| 42966 | 32963 | 1.698863636 |
| 42967 | 32964 | 1.695512821 |
| 42968 | 32965 | 1.695512821 |
| 42969 | 32966 | 1.695512821 |
| 42970 | 32967 | 1.694736842 |
| 42971 | 32968 | 1.694736842 |
| 42972 | 32969 | 1.694196429 |
| 42973 | 32970 | 1.691176471 |
| 42974 | 32971 | 1.6875 |
| 42975 | 32972 | 1.68595679 |
| 42976 | 32973 | 1.685344828 |
| 42977 | 32974 | 1.682926829 |
| 42978 | 32975 | 1.681603774 |
| 42979 | 32976 | 1.681603774 |
| 42980 | 32977 | 1.680769231 |
| 42981 | 32978 | 1.680769231 |
| 42982 | 32979 | 1.677083333 |
| 42983 | 32980 | 1.677083333 |
| 42984 | 32981 | 1.677083333 |
| 42985 | 32982 | 1.672727273 |
| 42986 | 32983 | 1.671511628 |
| 42987 | 32984 | 1.671511628 |
| 42988 | 32985 | 1.671511628 |
| 42989 | 32986 | 1.669354839 |
| 42990 | 32987 | 1.669354839 |
| 42991 | 32988 | 1.669354839 |
| 42992 | 32989 | 1.664473684 |
| 42993 | 32990 | 1.664473684 |

| DNA SEQ ID NO | AA SEQ ID NO | Lung1 Enrichment |
|---|---|---|
| 42994 | 32991 | 1.660211268 |
| 42995 | 32992 | 1.658653846 |
| 42996 | 32993 | 1.658653846 |
| 42997 | 32994 | 1.657657658 |
| 42998 | 32995 | 1.65530303 |
| 42999 | 32996 | 1.650462963 |
| 43000 | 32997 | 1.650462963 |
| 43001 | 32998 | 1.648333333 |
| 43002 | 32999 | 1.642857143 |
| 43003 | 33000 | 1.642857143 |
| 43004 | 33001 | 1.642857143 |
| 43005 | 33002 | 1.642857143 |
| 43006 | 33003 | 1.642857143 |
| 43007 | 33004 | 1.642857143 |
| 43008 | 33005 | 1.642857143 |
| 43009 | 33006 | 1.642857143 |
| 43010 | 33007 | 1.642857143 |
| 43011 | 33008 | 1.642857143 |
| 43012 | 33009 | 1.642857143 |
| 43013 | 33010 | 1.642857143 |
| 43014 | 33011 | 1.642857143 |
| 43015 | 33012 | 1.635775862 |
| 43016 | 33013 | 1.634803922 |
| 43017 | 33014 | 1.633522727 |
| 43018 | 33015 | 1.626644737 |
| 43019 | 33016 | 1.625 |
| 43020 | 33017 | 1.625 |
| 43021 | 33018 | 1.625 |
| 43022 | 33019 | 1.625 |

| DNA SEQ ID NO | AA SEQ ID NO | Lung1 Enrichment |
|---|---|---|
| 43023 | 33020 | 1.622983871 |
| 43024 | 33021 | 1.622983871 |
| 43025 | 33022 | 1.621794872 |
| 43026 | 33023 | 1.620454545 |
| 43027 | 33024 | 1.6171875 |
| 43028 | 33025 | 1.6171875 |
| 43029 | 33026 | 1.6171875 |
| 43030 | 33027 | 1.6171875 |
| 43031 | 33028 | 1.6171875 |
| 43032 | 33029 | 1.6171875 |
| 43033 | 33030 | 1.612804878 |
| 43034 | 33031 | 1.612804878 |
| 43035 | 33032 | 1.612804878 |
| 43036 | 33033 | 1.61 |
| 43037 | 33034 | 1.608944954 |
| 43038 | 33035 | 1.608050847 |
| 43039 | 33036 | 1.608050847 |
| 43040 | 33037 | 1.606617647 |
| 43041 | 33038 | 1.606617647 |
| 43042 | 33039 | 1.606617647 |
| 43043 | 33040 | 1.606617647 |
| 43044 | 33041 | 1.606617647 |
| 43045 | 33042 | 1.604651163 |
| 43046 | 33043 | 1.604651163 |
| 43047 | 33044 | 1.604651163 |
| 43048 | 33045 | 1.600235849 |
| 43049 | 33046 | 1.597222222 |
| 43050 | 33047 | 1.597222222 |
| 43051 | 33048 | 1.597222222 |

| DNA SEQ ID NO | AA SEQ ID NO | Lung1 Enrichment |
|---|---|---|
| 43052 | 33049 | 1.597222222 |
| 43053 | 33050 | 1.597222222 |
| 43054 | 33051 | 1.597222222 |
| 43055 | 33052 | 1.597222222 |
| 43056 | 33053 | 1.597222222 |
| 43057 | 33054 | 1.597222222 |
| 43058 | 33055 | 1.597222222 |
| 43059 | 33056 | 1.591517857 |
| 43060 | 33057 | 1.590425532 |
| 43061 | 33058 | 1.588815789 |
| 43062 | 33059 | 1.587686567 |
| 43063 | 33060 | 1.586206897 |
| 43064 | 33061 | 1.586206897 |
| 43065 | 33062 | 1.586206897 |
| 43066 | 33063 | 1.584183673 |
| 43067 | 33064 | 1.584183673 |
| 43068 | 33065 | 1.582865169 |
| 43069 | 33066 | 1.58125 |
| 43070 | 33067 | 1.58125 |
| 43071 | 33068 | 1.58125 |
| 43072 | 33069 | 1.58125 |
| 43073 | 33070 | 1.58125 |
| 43074 | 33071 | 1.58125 |
| 43075 | 33072 | 1.578431373 |
| 43076 | 33073 | 1.576612903 |
| 43077 | 33074 | 1.574404762 |
| 43078 | 33075 | 1.574404762 |
| 43079 | 33076 | 1.573113208 |
| 43080 | 33077 | 1.568181818 |

| DNA SEQ ID NO | AA SEQ ID NO | Lung1 Enrichment |
|---|---|---|
| 43081 | 33078 | 1.568181818 |
| 43082 | 33079 | 1.568181818 |
| 43083 | 33080 | 1.568181818 |
| 43084 | 33081 | 1.568181818 |
| 43085 | 33082 | 1.568181818 |
| 43086 | 33083 | 1.568181818 |
| 43087 | 33084 | 1.568181818 |
| 43088 | 33085 | 1.568181818 |
| 43089 | 33086 | 1.568181818 |
| 43090 | 33087 | 1.564338235 |
| 43091 | 33088 | 1.564338235 |
| 43092 | 33089 | 1.563596491 |
| 43093 | 33090 | 1.560714286 |
| 43094 | 33091 | 1.55873494 |
| 43095 | 33092 | 1.557291667 |
| 43096 | 33093 | 1.557291667 |
| 43097 | 33094 | 1.555327869 |
| 43098 | 33095 | 1.554054054 |
| 43099 | 33096 | 1.5525 |
| 43100 | 33097 | 1.5525 |
| 43101 | 33098 | 1.550986842 |
| 43102 | 33099 | 1.548076923 |
| 43103 | 33100 | 1.548076923 |
| 43104 | 33101 | 1.548076923 |
| 43105 | 33102 | 1.548076923 |
| 43106 | 33103 | 1.548076923 |
| 43107 | 33104 | 1.548076923 |
| 43108 | 33105 | 1.548076923 |
| 43109 | 33106 | 1.548076923 |

FIG. 13 (Cont.)

| DNA SEQ ID NO | AA SEQ ID NO | Lung 1 Enrichment |
|---|---|---|
| 43110 | 33107 | 1.548076923 |
| 43111 | 33108 | 1.548076923 |
| 43112 | 33109 | 1.5453125 |
| 43113 | 33110 | 1.543981481 |
| 43114 | 33111 | 1.542682927 |
| 43115 | 33112 | 1.542682927 |
| 43116 | 33113 | 1.542682927 |
| 43117 | 33114 | 1.542682927 |
| 43118 | 33115 | 1.541666667 |
| 43119 | 33116 | 1.541666667 |
| 43120 | 33117 | 1.540178571 |
| 43121 | 33118 | 1.540178571 |
| 43122 | 33119 | 1.540178571 |
| 43123 | 33120 | 1.540178571 |
| 43124 | 33121 | 1.538732394 |
| 43125 | 33122 | 1.537790698 |
| 43126 | 33123 | 1.537790698 |
| 43127 | 33124 | 1.536637931 |
| 43128 | 33125 | 1.536637931 |
| 43129 | 33126 | 1.533333333 |
| 43130 | 33127 | 1.533333333 |
| 43131 | 33128 | 1.533333333 |
| 43132 | 33129 | 1.533333333 |
| 43133 | 33130 | 1.529255319 |
| 43134 | 33131 | 1.52734375 |
| 43135 | 33132 | 1.526548673 |
| 43136 | 33133 | 1.526548673 |
| 43137 | 33134 | 1.523065476 |
| 43138 | 33135 | 1.522058824 |

| DNA SEQ ID NO | AA SEQ ID NO | Lung 1 Enrichment |
|---|---|---|
| 43139 | 33136 | 1.522058824 |
| 43140 | 33137 | 1.522058824 |
| 43141 | 33138 | 1.522058824 |
| 43142 | 33139 | 1.519642857 |
| 43143 | 33140 | 1.518867925 |
| 43144 | 33141 | 1.518867925 |
| 43145 | 33142 | 1.518867925 |
| 43146 | 33143 | 1.517361111 |
| 43147 | 33144 | 1.517361111 |
| 43148 | 33145 | 1.515909091 |
| 43149 | 33146 | 1.513157895 |
| 43150 | 33147 | 1.513157895 |
| 43151 | 33148 | 1.513157895 |
| 43152 | 33149 | 1.513157895 |
| 43153 | 33150 | 1.513157895 |
| 43154 | 33151 | 1.513157895 |
| 43155 | 33152 | 1.51059322 |
| 43156 | 33153 | 1.509375 |
| 43157 | 33154 | 1.509375 |
| 43158 | 33155 | 1.508196721 |
| 43159 | 33156 | 1.505952381 |
| 43160 | 33157 | 1.505952381 |
| 43161 | 33158 | 1.505952381 |
| 43162 | 33159 | 1.502840909 |
| 43163 | 33160 | 1.501865672 |
| 43164 | 33161 | 1.501865672 |
| 43165 | 33162 | 1.5 |
| 43166 | 33163 | 1.5 |
| 43167 | 33164 | 1.5 |

| DNA SEQ ID NO | AA SEQ ID NO | Lung 1 Enrichment |
|---|---|---|
| 43168 | 33165 | 1.5 |
| 43169 | 33166 | 1.5 |
| 43170 | 33167 | 1.496173469 |
| 43171 | 33168 | 1.495 |
| 43172 | 33169 | 1.495 |
| 43173 | 33170 | 1.493506494 |
| 43174 | 33171 | 1.490740741 |
| 43175 | 33172 | 1.490740741 |
| 43176 | 33173 | 1.490740741 |
| 43177 | 33174 | 1.490740741 |
| 43178 | 33175 | 1.490740741 |
| 43179 | 33176 | 1.487068966 |
| 43180 | 33177 | 1.487068966 |
| 43181 | 33178 | 1.485416667 |
| 43182 | 33179 | 1.485416667 |
| 43183 | 33180 | 1.483870968 |
| 43184 | 33181 | 1.483870968 |
| 43185 | 33182 | 1.483870968 |
| 43186 | 33183 | 1.483870968 |
| 43187 | 33184 | 1.483870968 |
| 43188 | 33185 | 1.482421875 |
| 43189 | 33186 | 1.481060606 |
| 43190 | 33187 | 1.481060606 |
| 43191 | 33188 | 1.478571429 |
| 43192 | 33189 | 1.478571429 |
| 43193 | 33190 | 1.478571429 |
| 43194 | 33191 | 1.476351351 |
| 43195 | 33192 | 1.476351351 |
| 43196 | 33193 | 1.474358974 |

| DNA SEQ ID NO | AA SEQ ID NO | Lung 1 Enrichment |
|---|---|---|
| 43197 | 33194 | 1.472560976 |
| 43198 | 33195 | 1.472560976 |
| 43199 | 33196 | 1.470930233 |
| 43200 | 33197 | 1.470930233 |
| 43201 | 33198 | 1.466836735 |
| 43202 | 33199 | 1.466836735 |
| 43203 | 33200 | 1.464622642 |
| 43204 | 33201 | 1.464622642 |
| 43205 | 33202 | 1.464622642 |
| 43206 | 33203 | 1.462719298 |
| 43207 | 33204 | 1.461864407 |
| 43208 | 33205 | 1.459615385 |
| 43209 | 33206 | 1.459615385 |
| 43210 | 33207 | 1.458955224 |
| 43211 | 33208 | 1.458333333 |
| 43212 | 33209 | 1.458333333 |
| 43213 | 33210 | 1.458333333 |
| 43214 | 33211 | 1.458333333 |
| 43215 | 33212 | 1.457746479 |
| 43216 | 33213 | 1.457746479 |
| 43217 | 33214 | 1.457191781 |
| 43218 | 33215 | 1.456168831 |
| 43219 | 33216 | 1.44527027 |
| 43220 | 33217 | 1.4375 |
| 43221 | 33218 | 1.4375 |
| 43222 | 33219 | 1.4375 |
| 43223 | 33220 | 1.4375 |
| 43224 | 33221 | 1.4375 |
| 43225 | 33222 | 1.4375 |

| DNA SEQ ID NO | AA SEQ ID NO | Lung 1 Enrichment |
|---|---|---|
| 43226 | 33223 | 1.4375 |
| 43227 | 33224 | 1.4375 |
| 43228 | 33225 | 1.4375 |
| 43229 | 33226 | 1.4375 |
| 43230 | 33227 | 1.4375 |
| 43231 | 33228 | 1.4375 |
| 43232 | 33229 | 1.4375 |
| 43233 | 33230 | 1.4375 |
| 43234 | 33231 | 1.4375 |
| 43235 | 33232 | 1.4375 |
| 43236 | 33233 | 1.4375 |
| 43237 | 33234 | 1.4375 |
| 43238 | 33235 | 1.4375 |
| 43239 | 33236 | 1.4375 |
| 43240 | 33237 | 1.4375 |
| 43241 | 33238 | 1.4375 |
| 43242 | 33239 | 1.4375 |
| 43243 | 33240 | 1.4375 |
| 43244 | 33241 | 1.4375 |
| 43245 | 33242 | 1.4375 |
| 43246 | 33243 | 1.4375 |
| 43247 | 33244 | 1.4375 |
| 43248 | 33245 | 1.4375 |
| 43249 | 33246 | 1.4375 |
| 43250 | 33247 | 1.4375 |
| 43251 | 33248 | 1.4375 |
| 43252 | 33249 | 1.4375 |
| 43253 | 33250 | 1.4375 |
| 43254 | 33251 | 1.4375 |

FIG. 13 (Cont.)

| DNA SEQ ID NO | AA SEQ ID NO | Lung 1 Enrichment |
|---|---|---|
| 43255 | 33252 | 1.4375 |
| 43256 | 33253 | 1.4375 |
| 43257 | 33254 | 1.4375 |
| 43258 | 33255 | 1.4375 |
| 43259 | 33256 | 1.4375 |
| 43260 | 33257 | 1.4375 |
| 43261 | 33258 | 1.4375 |
| 43262 | 33259 | 1.4375 |
| 43263 | 33260 | 1.4375 |
| 43264 | 33261 | 1.4375 |
| 43265 | 33262 | 1.4375 |
| 43266 | 33263 | 1.4375 |
| 43267 | 33264 | 1.4375 |
| 43268 | 33265 | 1.4375 |
| 43269 | 33266 | 1.4375 |
| 43270 | 33267 | 1.4375 |
| 43271 | 33268 | 1.4375 |
| 43272 | 33269 | 1.4375 |
| 43273 | 33270 | 1.4375 |
| 43274 | 33271 | 1.4375 |
| 43275 | 33272 | 1.4375 |
| 43276 | 33273 | 1.4375 |
| 43277 | 33274 | 1.4375 |
| 43278 | 33275 | 1.425 |
| 43279 | 33276 | 1.423809524 |
| 43280 | 33277 | 1.422043011 |
| 43281 | 33278 | 1.422043011 |
| 43282 | 33279 | 1.421348315 |
| 43283 | 33280 | 1.420977011 |

| DNA SEQ ID NO | AA SEQ ID NO | Lung 1 Enrichment |
|---|---|---|
| 43284 | 33281 | 1.420180723 |
| 43285 | 33282 | 1.418831169 |
| 43286 | 33283 | 1.416044776 |
| 43287 | 33284 | 1.415384615 |
| 43288 | 33285 | 1.413934426 |
| 43289 | 33286 | 1.413541667 |
| 43290 | 33287 | 1.413135593 |
| 43291 | 33288 | 1.411363636 |
| 43292 | 33289 | 1.410377358 |
| 43293 | 33290 | 1.410377358 |
| 43294 | 33291 | 1.408163265 |
| 43295 | 33292 | 1.408163265 |
| 43296 | 33293 | 1.408163265 |
| 43297 | 33294 | 1.406914894 |
| 43298 | 33295 | 1.404829545 |
| 43299 | 33296 | 1.404069767 |
| 43300 | 33297 | 1.404069767 |
| 43301 | 33298 | 1.404069767 |
| 43302 | 33299 | 1.404069767 |
| 43303 | 33300 | 1.402439024 |
| 43304 | 33301 | 1.4015625 |
| 43305 | 33302 | 1.401260504 |
| 43306 | 33303 | 1.400641026 |
| 43307 | 33304 | 1.400641026 |
| 43308 | 33305 | 1.399671053 |
| 43309 | 33306 | 1.398648649 |
| 43310 | 33307 | 1.398648649 |
| 43311 | 33308 | 1.398648649 |
| 43312 | 33309 | 1.396428571 |

| DNA SEQ ID NO | AA SEQ ID NO | Lung 1 Enrichment |
|---|---|---|
| 43313 | 33310 | 1.396428571 |
| 43314 | 33311 | 1.396428571 |
| 43315 | 33312 | 1.396428571 |
| 43316 | 33313 | 1.396428571 |
| 43317 | 33314 | 1.39480198 |
| 43318 | 33315 | 1.394589552 |
| 43319 | 33316 | 1.393041237 |
| 43320 | 33317 | 1.391129032 |
| 43321 | 33318 | 1.389583333 |
| 43322 | 33319 | 1.389583333 |
| 43323 | 33320 | 1.387931034 |
| 43324 | 33321 | 1.387931034 |
| 43325 | 33322 | 1.387931034 |
| 43326 | 33323 | 1.387931034 |
| 43327 | 33324 | 1.387931034 |
| 43328 | 33325 | 1.386764706 |
| 43329 | 33326 | 1.386764706 |
| 43330 | 33327 | 1.384259259 |
| 43331 | 33328 | 1.382211538 |
| 43332 | 33329 | 1.381127451 |
| 43333 | 33330 | 1.38 |
| 43334 | 33331 | 1.38 |
| 43335 | 33332 | 1.38 |
| 43336 | 33333 | 1.377604167 |
| 43337 | 33334 | 1.377604167 |
| 43338 | 33335 | 1.377604167 |
| 43339 | 33336 | 1.376760563 |
| 43340 | 33337 | 1.375 |
| 43341 | 33338 | 1.375 |

| DNA SEQ ID NO | AA SEQ ID NO | Lung 1 Enrichment |
|---|---|---|
| 43342 | 33339 | 1.375 |
| 43343 | 33340 | 1.373134328 |
| 43344 | 33341 | 1.372747748 |
| 43345 | 33342 | 1.372159091 |
| 43346 | 33343 | 1.372159091 |
| 43347 | 33344 | 1.372159091 |
| 43348 | 33345 | 1.371153846 |
| 43349 | 33346 | 1.371153846 |
| 43350 | 33347 | 1.369047619 |
| 43351 | 33348 | 1.369047619 |
| 43352 | 33349 | 1.369047619 |
| 43353 | 33350 | 1.369047619 |
| 43354 | 33351 | 1.369047619 |
| 43355 | 33352 | 1.369047619 |
| 43356 | 33353 | 1.369047619 |
| 43357 | 33354 | 1.369047619 |
| 43358 | 33355 | 1.369047619 |
| 43359 | 33356 | 1.366803279 |
| 43360 | 33357 | 1.36489899 |
| 43361 | 33358 | 1.36440678 |
| 43362 | 33359 | 1.363782051 |
| 43363 | 33360 | 1.363782051 |
| 43364 | 33361 | 1.362962963 |
| 43365 | 33362 | 1.361842105 |
| 43366 | 33363 | 1.361842105 |
| 43367 | 33364 | 1.361842105 |
| 43368 | 33365 | 1.361842105 |
| 43369 | 33366 | 1.359496124 |
| 43370 | 33367 | 1.359090909 |

| DNA SEQ ID NO | AA SEQ ID NO | Lung 1 Enrichment |
|---|---|---|
| 43371 | 33368 | 1.358516484 |
| 43372 | 33369 | 1.357638889 |
| 43373 | 33370 | 1.357638889 |
| 43374 | 33371 | 1.357638889 |
| 43375 | 33372 | 1.357638889 |
| 43376 | 33373 | 1.357638889 |
| 43377 | 33374 | 1.356741573 |
| 43378 | 33375 | 1.356132075 |
| 43379 | 33376 | 1.356132075 |
| 43380 | 33377 | 1.352941176 |
| 43381 | 33378 | 1.352941176 |
| 43382 | 33379 | 1.352941176 |
| 43383 | 33380 | 1.352941176 |
| 43384 | 33381 | 1.352941176 |
| 43385 | 33382 | 1.352941176 |
| 43386 | 33383 | 1.352941176 |
| 43387 | 33384 | 1.352941176 |
| 43388 | 33385 | 1.352941176 |
| 43389 | 33386 | 1.352941176 |
| 43390 | 33387 | 1.352941176 |
| 43391 | 33388 | 1.352941176 |
| 43392 | 33389 | 1.352941176 |
| 43393 | 33390 | 1.352941176 |
| 43394 | 33391 | 1.351092896 |
| 43395 | 33392 | 1.349489796 |
| 43396 | 33393 | 1.348765432 |
| 43397 | 33394 | 1.34765625 |
| 43398 | 33395 | 1.34765625 |
| 43399 | 33396 | 1.34765625 |

FIG. 13 (Cont.)

| DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment |
|---|---|---|---|---|---|---|---|---|---|---|---|---|---|---|
| 43400 | 33397 | 1.345744681 | 43429 | 33426 | 1.328781513 | 43458 | 33455 | 1.317708333 | 43487 | 33484 | 1.29375 | 43516 | 33513 | 1.277777778 |
| 43401 | 33398 | 1.344758065 | 43430 | 33427 | 1.326923077 | 43459 | 33456 | 1.317708333 | 43488 | 33485 | 1.29375 | 43517 | 33514 | 1.277777778 |
| 43402 | 33399 | 1.344758065 | 43431 | 33428 | 1.326923077 | 43460 | 33457 | 1.317708333 | 43489 | 33486 | 1.29375 | 43518 | 33515 | 1.277777778 |
| 43403 | 33400 | 1.344758065 | 43432 | 33429 | 1.326923077 | 43461 | 33458 | 1.317708333 | 43490 | 33487 | 1.29375 | 43519 | 33516 | 1.277777778 |
| 43404 | 33401 | 1.344758065 | 43433 | 33430 | 1.326923077 | 43462 | 33459 | 1.316021127 | 43491 | 33488 | 1.29375 | 43520 | 33517 | 1.274764151 |
| 43405 | 33402 | 1.344758065 | 43434 | 33431 | 1.326923077 | 43463 | 33460 | 1.315677966 | 43492 | 33489 | 1.29375 | 43521 | 33518 | 1.273734177 |
| 43406 | 33403 | 1.344155844 | 43435 | 33432 | 1.326923077 | 43464 | 33461 | 1.313271605 | 43493 | 33490 | 1.29375 | 43522 | 33519 | 1.273734177 |
| 43407 | 33404 | 1.344155844 | 43436 | 33433 | 1.326923077 | 43465 | 33462 | 1.313271605 | 43494 | 33491 | 1.29375 | 43523 | 33520 | 1.273214286 |
| 43408 | 33405 | 1.344155844 | 43437 | 33434 | 1.326923077 | 43466 | 33463 | 1.3125 | 43495 | 33492 | 1.292635659 | 43524 | 33521 | 1.272540984 |
| 43409 | 33406 | 1.344155844 | 43438 | 33435 | 1.326923077 | 43467 | 33464 | 1.310661765 | 43496 | 33493 | 1.292134831 | 43525 | 33522 | 1.272540984 |
| 43410 | 33407 | 1.341666667 | 43439 | 33436 | 1.326923077 | 43468 | 33465 | 1.306818182 | 43497 | 33494 | 1.290816327 | 43526 | 33523 | 1.271634615 |
| 43411 | 33408 | 1.341666667 | 43440 | 33437 | 1.326923077 | 43469 | 33466 | 1.306818182 | 43498 | 33495 | 1.290816327 | 43527 | 33524 | 1.271634615 |
| 43412 | 33409 | 1.341666667 | 43441 | 33438 | 1.326923077 | 43470 | 33467 | 1.306818182 | 43499 | 33496 | 1.290816327 | 43528 | 33525 | 1.271634615 |
| 43413 | 33410 | 1.338362069 | 43442 | 33439 | 1.326923077 | 43471 | 33468 | 1.306818182 | 43500 | 33497 | 1.288793103 | 43529 | 33526 | 1.270833333 |
| 43414 | 33411 | 1.337209302 | 43443 | 33440 | 1.326923077 | 43472 | 33469 | 1.306818182 | 43501 | 33498 | 1.288793103 | 43530 | 33527 | 1.270348837 |
| 43415 | 33412 | 1.337209302 | 43444 | 33441 | 1.326923077 | 43473 | 33470 | 1.306818182 | 43502 | 33499 | 1.286184211 | 43531 | 33528 | 1.270348837 |
| 43416 | 33413 | 1.337209302 | 43445 | 33442 | 1.326923077 | 43474 | 33471 | 1.306818182 | 43503 | 33500 | 1.286184211 | 43532 | 33529 | 1.269480519 |
| 43417 | 33414 | 1.336267606 | 43446 | 33443 | 1.326923077 | 43475 | 33472 | 1.306818182 | 43504 | 33501 | 1.284574468 | 43533 | 33530 | 1.269480519 |
| 43418 | 33415 | 1.335629921 | 43447 | 33444 | 1.326923077 | 43476 | 33473 | 1.30377907 | 43505 | 33502 | 1.284574468 | 43534 | 33531 | 1.269480519 |
| 43419 | 33416 | 1.334821429 | 43448 | 33445 | 1.326923077 | 43477 | 33474 | 1.301886792 | 43506 | 33503 | 1.283482143 | 43535 | 33532 | 1.265 |
| 43420 | 33417 | 1.334821429 | 43449 | 33446 | 1.326923077 | 43478 | 33475 | 1.300595238 | 43507 | 33504 | 1.277777778 | 43536 | 33533 | 1.265 |
| 43421 | 33418 | 1.333762887 | 43450 | 33447 | 1.326923077 | 43479 | 33476 | 1.300595238 | 43508 | 33505 | 1.277777778 | 43537 | 33534 | 1.265 |
| 43422 | 33419 | 1.333333333 | 43451 | 33448 | 1.323412698 | 43480 | 33477 | 1.299657534 | 43509 | 33506 | 1.277777778 | 43538 | 33535 | 1.265 |
| 43423 | 33420 | 1.333333333 | 43452 | 33449 | 1.3225 | 43481 | 33478 | 1.298387097 | 43510 | 33507 | 1.277777778 | 43539 | 33536 | 1.265 |
| 43424 | 33421 | 1.332317073 | 43453 | 33450 | 1.320153061 | 43482 | 33479 | 1.296568627 | 43511 | 33508 | 1.277777778 | 43540 | 33537 | 1.263257576 |
| 43425 | 33422 | 1.331578947 | 43454 | 33451 | 1.319672131 | 43483 | 33480 | 1.296568627 | 43512 | 33509 | 1.277777778 | 43541 | 33538 | 1.262195122 |
| 43426 | 33423 | 1.331018519 | 43455 | 33452 | 1.319672131 | 43484 | 33481 | 1.296568627 | 43513 | 33510 | 1.277777778 | 43542 | 33539 | 1.262195122 |
| 43427 | 33424 | 1.331018519 | 43456 | 33453 | 1.319672131 | 43485 | 33482 | 1.296568627 | 43514 | 33511 | 1.277777778 | 43543 | 33540 | 1.262195122 |
| 43428 | 33425 | 1.331018519 | 43457 | 33454 | 1.317708333 | 43486 | 33483 | 1.294701987 | 43515 | 33512 | 1.277777778 | 43544 | 33541 | 1.260964912 |

FIG. 13 (Cont.)

| DNA SEQ ID NO | AA SEQ ID NO | Lung 1 Enrichment |
|---|---|---|
| 43545 | 33542 | 1.259831461 |
| 43546 | 33543 | 1.25952381 |
| 43547 | 33544 | 1.2578125 |
| 43548 | 33545 | 1.2578125 |
| 43549 | 33546 | 1.2578125 |
| 43550 | 33547 | 1.2578125 |
| 43551 | 33548 | 1.2578125 |
| 43552 | 33549 | 1.2578125 |
| 43553 | 33550 | 1.2578125 |
| 43554 | 33551 | 1.2578125 |
| 43555 | 33552 | 1.2578125 |
| 43556 | 33553 | 1.2578125 |
| 43557 | 33554 | 1.2578125 |
| 43558 | 33555 | 1.254545455 |
| 43559 | 33556 | 1.253989362 |
| 43560 | 33557 | 1.253759398 |
| 43561 | 33558 | 1.253205128 |
| 43562 | 33559 | 1.253205128 |
| 43563 | 33560 | 1.253205128 |
| 43564 | 33561 | 1.252016129 |
| 43565 | 33562 | 1.252016129 |
| 43566 | 33563 | 1.250954198 |
| 43567 | 33564 | 1.25 |
| 43568 | 33565 | 1.25 |
| 43569 | 33566 | 1.25 |
| 43570 | 33567 | 1.24897541 |
| 43571 | 33568 | 1.248737374 |
| 43572 | 33569 | 1.248737374 |
| 43573 | 33570 | 1.248737374 |

| DNA SEQ ID NO | AA SEQ ID NO | Lung 1 Enrichment |
|---|---|---|
| 43574 | 33571 | 1.247641509 |
| 43575 | 33572 | 1.246987952 |
| 43576 | 33573 | 1.245833333 |
| 43577 | 33574 | 1.245833333 |
| 43578 | 33575 | 1.245833333 |
| 43579 | 33576 | 1.245833333 |
| 43580 | 33577 | 1.245833333 |
| 43581 | 33578 | 1.245833333 |
| 43582 | 33579 | 1.245833333 |
| 43583 | 33580 | 1.245833333 |
| 43584 | 33581 | 1.244845361 |
| 43585 | 33582 | 1.244402985 |
| 43586 | 33583 | 1.243243243 |
| 43587 | 33584 | 1.243243243 |
| 43588 | 33585 | 1.243243243 |
| 43589 | 33586 | 1.243243243 |
| 43590 | 33587 | 1.243243243 |
| 43591 | 33588 | 1.240196078 |
| 43592 | 33589 | 1.240196078 |
| 43593 | 33590 | 1.240196078 |
| 43594 | 33591 | 1.239224138 |
| 43595 | 33592 | 1.238461538 |
| 43596 | 33593 | 1.237847222 |
| 43597 | 33594 | 1.237341772 |
| 43598 | 33595 | 1.237341772 |
| 43599 | 33596 | 1.237341772 |
| 43600 | 33597 | 1.235981308 |
| 43601 | 33598 | 1.23553719 |
| 43602 | 33599 | 1.235351563 |

| DNA SEQ ID NO | AA SEQ ID NO | Lung 1 Enrichment |
|---|---|---|
| 43603 | 33600 | 1.235351563 |
| 43604 | 33601 | 1.232142857 |
| 43605 | 33602 | 1.232142857 |
| 43606 | 33603 | 1.232142857 |
| 43607 | 33604 | 1.232142857 |
| 43608 | 33605 | 1.232142857 |
| 43609 | 33606 | 1.232142857 |
| 43610 | 33607 | 1.232142857 |
| 43611 | 33608 | 1.232142857 |
| 43612 | 33609 | 1.232142857 |
| 43613 | 33610 | 1.232142857 |
| 43614 | 33611 | 1.232142857 |
| 43615 | 33612 | 1.232142857 |
| 43616 | 33613 | 1.232142857 |
| 43617 | 33614 | 1.232142857 |
| 43618 | 33615 | 1.232142857 |
| 43619 | 33616 | 1.232142857 |
| 43620 | 33617 | 1.232142857 |
| 43621 | 33618 | 1.22752809 |
| 43622 | 33619 | 1.226666667 |
| 43623 | 33620 | 1.226102941 |
| 43624 | 33621 | 1.225409836 |
| 43625 | 33622 | 1.223404255 |
| 43626 | 33623 | 1.223404255 |
| 43627 | 33624 | 1.21969697 |
| 43628 | 33625 | 1.21969697 |
| 43629 | 33626 | 1.21969697 |
| 43630 | 33627 | 1.21969697 |
| 43631 | 33628 | 1.21969697 |

| DNA SEQ ID NO | AA SEQ ID NO | Lung 1 Enrichment |
|---|---|---|
| 43632 | 33629 | 1.218220339 |
| 43633 | 33630 | 1.216346154 |
| 43634 | 33631 | 1.216346154 |
| 43635 | 33632 | 1.216346154 |
| 43636 | 33633 | 1.213888889 |
| 43637 | 33634 | 1.213888889 |
| 43638 | 33635 | 1.213888889 |
| 43639 | 33636 | 1.212009804 |
| 43640 | 33637 | 1.21177686 |
| 43641 | 33638 | 1.210526316 |
| 43642 | 33639 | 1.210526316 |
| 43643 | 33640 | 1.210526316 |
| 43644 | 33641 | 1.210526316 |
| 43645 | 33642 | 1.210526316 |
| 43646 | 33643 | 1.210526316 |
| 43647 | 33644 | 1.210526316 |
| 43648 | 33645 | 1.210526316 |
| 43649 | 33646 | 1.210526316 |
| 43650 | 33647 | 1.210526316 |
| 43651 | 33648 | 1.208333333 |
| 43652 | 33649 | 1.208333333 |
| 43653 | 33650 | 1.207983193 |
| 43654 | 33651 | 1.205645161 |
| 43655 | 33652 | 1.205645161 |
| 43656 | 33653 | 1.205645161 |
| 43657 | 33654 | 1.204391892 |
| 43658 | 33655 | 1.204391892 |
| 43659 | 33656 | 1.203488372 |
| 43660 | 33657 | 1.203488372 |

| DNA SEQ ID NO | AA SEQ ID NO | Lung 1 Enrichment |
|---|---|---|
| 43661 | 33658 | 1.203488372 |
| 43662 | 33659 | 1.202806122 |
| 43663 | 33660 | 1.202272727 |
| 43664 | 33661 | 1.202272727 |
| 43665 | 33662 | 1.200549451 |
| 43666 | 33663 | 1.197916667 |
| 43667 | 33664 | 1.197916667 |
| 43668 | 33665 | 1.197916667 |
| 43669 | 33666 | 1.197916667 |
| 43670 | 33667 | 1.197916667 |
| 43671 | 33668 | 1.197916667 |
| 43672 | 33669 | 1.197916667 |
| 43673 | 33670 | 1.197916667 |
| 43674 | 33671 | 1.197916667 |
| 43675 | 33672 | 1.197916667 |
| 43676 | 33673 | 1.194805195 |
| 43677 | 33674 | 1.194230769 |
| 43678 | 33675 | 1.193396226 |
| 43679 | 33676 | 1.192819149 |
| 43680 | 33677 | 1.192073171 |
| 43681 | 33678 | 1.192073171 |
| 43682 | 33679 | 1.192073171 |
| 43683 | 33680 | 1.192073171 |
| 43684 | 33681 | 1.191071429 |
| 43685 | 33682 | 1.191071429 |
| 43686 | 33683 | 1.189655172 |
| 43687 | 33684 | 1.189655172 |
| 43688 | 33685 | 1.189655172 |
| 43689 | 33686 | 1.189655172 |

FIG. 13 (Cont.)

| DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment |
|---|---|---|---|---|---|---|---|---|---|---|---|---|---|---|
| 43690 | 33687 | 1.1875 | 43719 | 33716 | 1.175492611 | 43748 | 33745 | 1.15858209 | 43777 | 33774 | 1.15 | 43806 | 33803 | 1.134868421 |
| 43691 | 33688 | 1.1875 | 43720 | 33717 | 1.174295775 | 43749 | 33746 | 1.157986111 | 43778 | 33775 | 1.15 | 43807 | 33804 | 1.134868421 |
| 43692 | 33689 | 1.186926606 | 43721 | 33718 | 1.173469388 | 43750 | 33747 | 1.157986111 | 43779 | 33776 | 1.15 | 43808 | 33805 | 1.134868421 |
| 43693 | 33690 | 1.1859375 | 43722 | 33719 | 1.173469388 | 43751 | 33748 | 1.157012195 | 43780 | 33777 | 1.15 | 43809 | 33806 | 1.134868421 |
| 43694 | 33691 | 1.183823529 | 43723 | 33720 | 1.173469388 | 43752 | 33749 | 1.156609195 | 43781 | 33778 | 1.15 | 43810 | 33807 | 1.134174312 |
| 43695 | 33692 | 1.183823529 | 43724 | 33721 | 1.172697368 | 43753 | 33750 | 1.15625 | 43782 | 33779 | 1.15 | 43811 | 33808 | 1.133413462 |
| 43696 | 33693 | 1.183823529 | 43725 | 33722 | 1.172330097 | 43754 | 33751 | 1.15 | 43783 | 33780 | 1.15 | 43812 | 33809 | 1.132575758 |
| 43697 | 33694 | 1.183823529 | 43726 | 33723 | 1.171296296 | 43755 | 33752 | 1.15 | 43784 | 33781 | 1.15 | 43813 | 33810 | 1.132575758 |
| 43698 | 33695 | 1.183823529 | 43727 | 33724 | 1.170353982 | 43756 | 33753 | 1.15 | 43785 | 33782 | 1.15 | 43814 | 33811 | 1.132575758 |
| 43699 | 33696 | 1.183823529 | 43728 | 33725 | 1.17005814 | 43757 | 33754 | 1.15 | 43786 | 33783 | 1.15 | 43815 | 33812 | 1.132575758 |
| 43700 | 33697 | 1.183823529 | 43729 | 33726 | 1.169491525 | 43758 | 33755 | 1.15 | 43787 | 33784 | 1.15 | 43816 | 33813 | 1.131648936 |
| 43701 | 33698 | 1.182242991 | 43730 | 33727 | 1.169491525 | 43759 | 33756 | 1.15 | 43788 | 33785 | 1.15 | 43817 | 33814 | 1.131147541 |
| 43702 | 33699 | 1.180263158 | 43731 | 33728 | 1.168956044 | 43760 | 33757 | 1.15 | 43789 | 33786 | 1.144675926 | 43818 | 33815 | 1.131147541 |
| 43703 | 33700 | 1.180263158 | 43732 | 33729 | 1.167293233 | 43761 | 33758 | 1.15 | 43790 | 33787 | 1.142628205 | 43819 | 33816 | 1.131147541 |
| 43704 | 33701 | 1.180263158 | 43733 | 33730 | 1.165540541 | 43762 | 33759 | 1.15 | 43791 | 33788 | 1.142123288 | 43820 | 33817 | 1.131147541 |
| 43705 | 33702 | 1.179487179 | 43734 | 33731 | 1.165540541 | 43763 | 33760 | 1.15 | 43792 | 33789 | 1.141221374 | 43821 | 33818 | 1.13034188 |
| 43706 | 33703 | 1.179487179 | 43735 | 33732 | 1.165540541 | 43764 | 33761 | 1.15 | 43793 | 33790 | 1.140873016 | 43822 | 33819 | 1.129464286 |
| 43707 | 33704 | 1.179487179 | 43736 | 33733 | 1.165540541 | 43765 | 33762 | 1.15 | 43794 | 33791 | 1.140086207 | 43823 | 33820 | 1.129464286 |
| 43708 | 33705 | 1.179487179 | 43737 | 33734 | 1.165540541 | 43766 | 33763 | 1.15 | 43795 | 33792 | 1.139150943 | 43824 | 33821 | 1.129464286 |
| 43709 | 33706 | 1.179487179 | 43738 | 33735 | 1.164556962 | 43767 | 33764 | 1.15 | 43796 | 33793 | 1.139150943 | 43825 | 33822 | 1.129464286 |
| 43710 | 33707 | 1.179487179 | 43739 | 33736 | 1.163690476 | 43768 | 33765 | 1.15 | 43797 | 33794 | 1.139150943 | 43826 | 33823 | 1.128164557 |
| 43711 | 33708 | 1.179487179 | 43740 | 33737 | 1.163690476 | 43769 | 33766 | 1.15 | 43798 | 33795 | 1.139150943 | 43827 | 33824 | 1.12745098 |
| 43712 | 33709 | 1.179487179 | 43741 | 33738 | 1.163690476 | 43770 | 33767 | 1.15 | 43799 | 33796 | 1.138020833 | 43828 | 33825 | 1.12745098 |
| 43713 | 33710 | 1.177951389 | 43742 | 33739 | 1.162234043 | 43771 | 33768 | 1.15 | 43800 | 33797 | 1.138020833 | 43829 | 33826 | 1.127 |
| 43714 | 33711 | 1.177710843 | 43743 | 33740 | 1.162234043 | 43772 | 33769 | 1.15 | 43801 | 33798 | 1.138020833 | 43830 | 33827 | 1.126689189 |
| 43715 | 33712 | 1.176136364 | 43744 | 33741 | 1.162234043 | 43773 | 33770 | 1.15 | 43802 | 33799 | 1.137362637 | 43831 | 33828 | 1.12628866 |
| 43716 | 33713 | 1.176136364 | 43745 | 33742 | 1.160087719 | 43774 | 33771 | 1.15 | 43803 | 33800 | 1.136627907 | 43832 | 33829 | 1.12628866 |
| 43717 | 33714 | 1.176136364 | 43746 | 33743 | 1.159274194 | 43775 | 33772 | 1.15 | 43804 | 33801 | 1.136627907 | 43833 | 33830 | 1.125 |
| 43718 | 33715 | 1.176136364 | 43747 | 33744 | 1.159274194 | 43776 | 33773 | 1.15 | 43805 | 33802 | 1.135802469 | 43834 | 33831 | 1.125 |

FIG. 13 (Cont.)

| DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment | DNA SEQ ID NO | AA SEQ ID NO | Lung 1 Enrichment |
|---|---|---|---|---|---|---|---|---|---|---|---|---|---|---|
| 43835 | 33832 | 1.125 | 43864 | 33861 | 1.114795918 | 43893 | 33890 | 1.104304636 | 43922 | 33919 | 1.095238095 | 43951 | 33948 | 1.086111111 |
| 43836 | 33833 | 1.125 | 43865 | 33862 | 1.114795918 | 43894 | 33891 | 1.103535354 | 43923 | 33920 | 1.095238095 | 43952 | 33949 | 1.086111111 |
| 43837 | 33834 | 1.125 | 43866 | 33863 | 1.1140625 | 43895 | 33892 | 1.103197674 | 43924 | 33921 | 1.09375 | 43953 | 33950 | 1.086111111 |
| 43838 | 33835 | 1.123046875 | 43867 | 33864 | 1.1140625 | 43896 | 33893 | 1.102739726 | 43925 | 33922 | 1.093309859 | 43954 | 33951 | 1.086111111 |
| 43839 | 33836 | 1.12195122 | 43868 | 33865 | 1.113738739 | 43897 | 33894 | 1.102083333 | 43926 | 33923 | 1.093309859 | 43955 | 33952 | 1.086111111 |
| 43840 | 33837 | 1.12195122 | 43869 | 33866 | 1.112903226 | 43898 | 33895 | 1.102083333 | 43927 | 33924 | 1.0925 | 43956 | 33953 | 1.08490566 |
| 43841 | 33838 | 1.12195122 | 43870 | 33867 | 1.112903226 | 43899 | 33896 | 1.102083333 | 43928 | 33925 | 1.092054264 | 43957 | 33954 | 1.08490566 |
| 43842 | 33839 | 1.120762712 | 43871 | 33868 | 1.112903226 | 43900 | 33897 | 1.102083333 | 43929 | 33926 | 1.091772152 | 43958 | 33955 | 1.084016393 |
| 43843 | 33840 | 1.120762712 | 43872 | 33869 | 1.110344828 | 43901 | 33898 | 1.102083333 | 43930 | 33927 | 1.090517241 | 43959 | 33956 | 1.084016393 |
| 43844 | 33841 | 1.120762712 | 43873 | 33870 | 1.109649123 | 43902 | 33899 | 1.10106383 | 43931 | 33928 | 1.090517241 | 43960 | 33957 | 1.083653846 |
| 43845 | 33842 | 1.120762712 | 43874 | 33871 | 1.108928571 | 43903 | 33900 | 1.10106383 | 43932 | 33929 | 1.090517241 | 43961 | 33958 | 1.083333333 |
| 43846 | 33843 | 1.12012987 | 43875 | 33872 | 1.105769231 | 43904 | 33901 | 1.10106383 | 43933 | 33930 | 1.090517241 | 43962 | 33959 | 1.083333333 |
| 43847 | 33844 | 1.119736842 | 43876 | 33873 | 1.105769231 | 43905 | 33902 | 1.10106383 | 43934 | 33931 | 1.090517241 | 43963 | 33960 | 1.083333333 |
| 43848 | 33845 | 1.118055556 | 43877 | 33874 | 1.105769231 | 43906 | 33903 | 1.10106383 | 43935 | 33932 | 1.089473684 | 43964 | 33961 | 1.082792208 |
| 43849 | 33846 | 1.118055556 | 43878 | 33875 | 1.105769231 | 43907 | 33904 | 1.100308642 | 43936 | 33933 | 1.089015152 | 43965 | 33962 | 1.082352941 |
| 43850 | 33847 | 1.118055556 | 43879 | 33876 | 1.105769231 | 43908 | 33905 | 1.099264706 | 43937 | 33934 | 1.089015152 | 43966 | 33963 | 1.081422018 |
| 43851 | 33848 | 1.118055556 | 43880 | 33877 | 1.105769231 | 43909 | 33906 | 1.099264706 | 43938 | 33935 | 1.089015152 | 43967 | 33964 | 1.081422018 |
| 43852 | 33849 | 1.118055556 | 43881 | 33878 | 1.105769231 | 43910 | 33907 | 1.099264706 | 43939 | 33936 | 1.089015152 | 43968 | 33965 | 1.081422018 |
| 43853 | 33850 | 1.118055556 | 43882 | 33879 | 1.105769231 | 43911 | 33908 | 1.099264706 | 43940 | 33937 | 1.089015152 | 43969 | 33966 | 1.078125 |
| 43854 | 33851 | 1.118055556 | 43883 | 33880 | 1.105769231 | 43912 | 33909 | 1.098314607 | 43941 | 33938 | 1.088592233 | 43970 | 33967 | 1.078125 |
| 43855 | 33852 | 1.118055556 | 43884 | 33881 | 1.105769231 | 43913 | 33910 | 1.098090278 | 43942 | 33939 | 1.087837838 | 43971 | 33968 | 1.078125 |
| 43856 | 33853 | 1.118055556 | 43885 | 33882 | 1.105769231 | 43914 | 33911 | 1.097727273 | 43943 | 33940 | 1.087837838 | 43972 | 33969 | 1.078125 |
| 43857 | 33854 | 1.118055556 | 43886 | 33883 | 1.105769231 | 43915 | 33912 | 1.097727273 | 43944 | 33941 | 1.087837838 | 43973 | 33970 | 1.078125 |
| 43858 | 33855 | 1.118055556 | 43887 | 33884 | 1.105769231 | 43916 | 33913 | 1.097039474 | 43945 | 33942 | 1.087837838 | 43974 | 33971 | 1.078125 |
| 43859 | 33856 | 1.118055556 | 43888 | 33885 | 1.105769231 | 43917 | 33914 | 1.096649485 | 43946 | 33943 | 1.087837838 | 43975 | 33972 | 1.078125 |
| 43860 | 33857 | 1.118055556 | 43889 | 33886 | 1.105769231 | 43918 | 33915 | 1.095238095 | 43947 | 33944 | 1.087837838 | 43976 | 33973 | 1.078125 |
| 43861 | 33858 | 1.116735537 | 43890 | 33887 | 1.105769231 | 43919 | 33916 | 1.095238095 | 43948 | 33945 | 1.087837838 | 43977 | 33974 | 1.078125 |
| 43862 | 33859 | 1.114795918 | 43891 | 33888 | 1.105769231 | 43920 | 33917 | 1.095238095 | 43949 | 33946 | 1.086890244 | 43978 | 33975 | 1.078125 |
| 43863 | 33860 | 1.114795918 | 43892 | 33889 | 1.105769231 | 43921 | 33918 | 1.095238095 | 43950 | 33947 | 1.086614173 | 43979 | 33976 | 1.078125 |

FIG. 13 (Cont.)

| DNA SEQ ID NO | AA SEQ ID NO | Lung 1 Enrichment |
|---|---|---|
| 43980 | 33977 | 1.078125 |
| 43981 | 33978 | 1.078125 |
| 43982 | 33979 | 1.078125 |
| 43983 | 33980 | 1.078125 |
| 43984 | 33981 | 1.078125 |
| 43985 | 33982 | 1.078125 |
| 43986 | 33983 | 1.078125 |
| 43987 | 33984 | 1.078125 |
| 43988 | 33985 | 1.073795181 |
| 43989 | 33986 | 1.073795181 |
| 43990 | 33987 | 1.072033898 |
| 43991 | 33988 | 1.072033898 |
| 43992 | 33989 | 1.072033898 |
| 43993 | 33990 | 1.071078431 |
| 43994 | 33991 | 1.071078431 |
| 43995 | 33992 | 1.070478723 |
| 43996 | 33993 | 1.069767442 |
| 43997 | 33994 | 1.069767442 |
| 43998 | 33995 | 1.069767442 |
| 43999 | 33996 | 1.069767442 |
| 44000 | 33997 | 1.068910256 |
| 44001 | 33998 | 1.068584071 |
| 44002 | 33999 | 1.067857143 |
| 44003 | 34000 | 1.067857143 |
| 44004 | 34001 | 1.067857143 |
| 44005 | 34002 | 1.067857143 |
| 44006 | 34003 | 1.067857143 |
| 44007 | 34004 | 1.067857143 |
| 44008 | 34005 | 1.067857143 |

| DNA SEQ ID NO | AA SEQ ID NO | Lung 1 Enrichment |
|---|---|---|
| 44009 | 34006 | 1.067857143 |
| 44010 | 34007 | 1.066532258 |
| 44011 | 34008 | 1.066532258 |
| 44012 | 34009 | 1.066532258 |
| 44013 | 34010 | 1.066532258 |
| 44014 | 34011 | 1.066011236 |
| 44015 | 34012 | 1.065732759 |
| 44016 | 34013 | 1.064814815 |
| 44017 | 34014 | 1.064814815 |
| 44018 | 34015 | 1.064814815 |
| 44019 | 34016 | 1.064814815 |
| 44020 | 34017 | 1.064814815 |
| 44021 | 34018 | 1.064814815 |
| 44022 | 34019 | 1.063356164 |
| 44023 | 34020 | 1.0625 |
| 44024 | 34021 | 1.0625 |
| 44025 | 34022 | 1.0625 |
| 44026 | 34023 | 1.061538462 |
| 44027 | 34024 | 1.06045082 |
| 44028 | 34025 | 1.059210526 |
| 44029 | 34026 | 1.059210526 |
| 44030 | 34027 | 1.059210526 |
| 44031 | 34028 | 1.059210526 |
| 44032 | 34029 | 1.059210526 |
| 44033 | 34030 | 1.059210526 |
| 44034 | 34031 | 1.059210526 |
| 44035 | 34032 | 1.059210526 |
| 44036 | 34033 | 1.059210526 |
| 44037 | 34034 | 1.059210526 |

| DNA SEQ ID NO | AA SEQ ID NO | Lung 1 Enrichment |
|---|---|---|
| 44038 | 34035 | 1.059210526 |
| 44039 | 34036 | 1.059210526 |
| 44040 | 34037 | 1.056985294 |
| 44041 | 34038 | 1.056122449 |
| 44042 | 34039 | 1.056122449 |
| 44043 | 34040 | 1.056122449 |
| 44044 | 34041 | 1.055045872 |
| 44045 | 34042 | 1.054166667 |
| 44046 | 34043 | 1.054166667 |
| 44047 | 34044 | 1.054166667 |
| 44048 | 34045 | 1.054166667 |
| 44049 | 34046 | 1.054166667 |
| 44050 | 34047 | 1.054166667 |
| 44051 | 34048 | 1.054166667 |
| 44052 | 34049 | 1.054166667 |
| 44053 | 34050 | 1.052455357 |
| 44054 | 34051 | 1.051829268 |
| 44055 | 34052 | 1.051829268 |
| 44056 | 34053 | 1.051829268 |
| 44057 | 34054 | 1.051829268 |
| 44058 | 34055 | 1.051829268 |
| 44059 | 34056 | 1.051829268 |
| 44060 | 34057 | 1.050480769 |
| 44061 | 34058 | 1.050480769 |
| 44062 | 34059 | 1.050480769 |
| 44063 | 34060 | 1.050480769 |
| 44064 | 34061 | 1.050480769 |
| 44065 | 34062 | 1.049603175 |
| 44066 | 34063 | 1.048529412 |

| DNA SEQ ID NO | AA SEQ ID NO | Lung 1 Enrichment |
|---|---|---|
| 44067 | 34064 | 1.045454545 |
| 44068 | 34065 | 1.045454545 |
| 44069 | 34066 | 1.045454545 |
| 44070 | 34067 | 1.045454545 |
| 44071 | 34068 | 1.045454545 |
| 44072 | 34069 | 1.045454545 |
| 44073 | 34070 | 1.045454545 |
| 44074 | 34071 | 1.045454545 |
| 44075 | 34072 | 1.045454545 |
| 44076 | 34073 | 1.045454545 |
| 44077 | 34074 | 1.045454545 |
| 44078 | 34075 | 1.045454545 |
| 44079 | 34076 | 1.045454545 |
| 44080 | 34077 | 1.0421875 |
| 44081 | 34078 | 1.0421875 |
| 44082 | 34079 | 1.0421875 |
| 44083 | 34080 | 1.041338583 |
| 44084 | 34081 | 1.040948276 |
| 44085 | 34082 | 1.040948276 |
| 44086 | 34083 | 1.040948276 |
| 44087 | 34084 | 1.039893617 |
| 44088 | 34085 | 1.039893617 |
| 44089 | 34086 | 1.038194444 |
| 44090 | 34087 | 1.037371134 |
| 44091 | 34088 | 1.036337209 |
| 44092 | 34089 | 1.036337209 |
| 44093 | 34090 | 1.036337209 |
| 44094 | 34091 | 1.036337209 |
| 44095 | 34092 | 1.036036036 |

| DNA SEQ ID NO | AA SEQ ID NO | Lung 1 Enrichment |
|---|---|---|
| 44096 | 34093 | 1.035 |
| 44097 | 34094 | 1.035 |
| 44098 | 34095 | 1.035 |
| 44099 | 34096 | 1.035 |
| 44100 | 34097 | 1.035 |
| 44101 | 34098 | 1.035 |
| 44102 | 34099 | 1.033707865 |
| 44103 | 34100 | 1.032458564 |
| 44104 | 34101 | 1.032051282 |
| 44105 | 34102 | 1.032051282 |
| 44106 | 34103 | 1.032051282 |
| 44107 | 34104 | 1.032051282 |
| 44108 | 34105 | 1.03125 |
| 44109 | 34106 | 1.030660377 |
| 44110 | 34107 | 1.030660377 |
| 44111 | 34108 | 1.029850746 |
| 44112 | 34109 | 1.029850746 |
| 44113 | 34110 | 1.029320988 |
| 44114 | 34111 | 1.029320988 |
| 44115 | 34112 | 1.028947368 |
| 44116 | 34113 | 1.028669725 |
| 44117 | 34114 | 1.026785714 |
| 44118 | 34115 | 1.026785714 |
| 44119 | 34116 | 1.026785714 |
| 44120 | 34117 | 1.026785714 |
| 44121 | 34118 | 1.026785714 |
| 44122 | 34119 | 1.026785714 |
| 44123 | 34120 | 1.026785714 |
| 44124 | 34121 | 1.026785714 |

FIG. 13 (Cont.)

| DNA SEQ ID NO | AA SEQ ID NO | Lung 1 Enrichment |
|---|---|---|
| 44125 | 34122 | 1.026785714 |
| 44126 | 34123 | 1.026785714 |
| 44127 | 34124 | 1.026785714 |
| 44128 | 34125 | 1.026785714 |
| 44129 | 34126 | 1.026785714 |
| 44130 | 34127 | 1.026785714 |
| 44131 | 34128 | 1.026785714 |
| 44132 | 34129 | 1.026785714 |
| 44133 | 34130 | 1.02534965 |
| 44134 | 34131 | 1.023972603 |
| 44135 | 34132 | 1.023972603 |
| 44136 | 34133 | 1.023972603 |
| 44137 | 34134 | 1.023305085 |
| 44138 | 34135 | 1.023305085 |
| 44139 | 34136 | 1.023305085 |
| 44140 | 34137 | 1.022222222 |

| DNA SEQ ID NO | AA SEQ ID NO | Lung 1 Enrichment |
|---|---|---|
| 44141 | 34138 | 1.022222222 |
| 44142 | 34139 | 1.022222222 |
| 44143 | 34140 | 1.02016129 |
| 44144 | 34141 | 1.02016129 |
| 44145 | 34142 | 1.02016129 |
| 44146 | 34143 | 1.02016129 |
| 44147 | 34144 | 1.02016129 |
| 44148 | 34145 | 1.02016129 |
| 44149 | 34146 | 1.02016129 |
| 44150 | 34147 | 1.02016129 |
| 44151 | 34148 | 1.018987342 |
| 44152 | 34149 | 1.017307692 |
| 44153 | 34150 | 1.016768293 |
| 44154 | 34151 | 1.016768293 |
| 44155 | 34152 | 1.016768293 |
| 44156 | 34153 | 1.016414141 |

| DNA SEQ ID NO | AA SEQ ID NO | Lung 1 Enrichment |
|---|---|---|
| 44157 | 34154 | 1.014705882 |
| 44158 | 34155 | 1.014705882 |
| 44159 | 34156 | 1.014705882 |
| 44160 | 34157 | 1.014705882 |
| 44161 | 34158 | 1.014705882 |
| 44162 | 34159 | 1.014705882 |
| 44163 | 34160 | 1.014705882 |
| 44164 | 34161 | 1.014705882 |
| 44165 | 34162 | 1.014705882 |
| 44166 | 34163 | 1.014705882 |
| 44167 | 34164 | 1.014705882 |
| 44168 | 34165 | 1.014705882 |
| 44169 | 34166 | 1.012323944 |
| 44170 | 34167 | 1.012323944 |
| 44171 | 34168 | 1.010989011 |
| 44172 | 34169 | 1.010135135 |

| DNA SEQ ID NO | AA SEQ ID NO | Lung 1 Enrichment |
|---|---|---|
| 44173 | 34170 | 1.010135135 |
| 44174 | 34171 | 1.010135135 |
| 44175 | 34172 | 1.009308511 |
| 44176 | 34173 | 1.00877193 |
| 44177 | 34174 | 1.00877193 |
| 44178 | 34175 | 1.008116883 |
| 44179 | 34176 | 1.00729927 |
| 44180 | 34177 | 1.00625 |
| 44181 | 34178 | 1.00625 |
| 44182 | 34179 | 1.00625 |
| 44183 | 34180 | 1.00625 |
| 44184 | 34181 | 1.00625 |
| 44185 | 34182 | 1.00625 |
| 44186 | 34183 | 1.00625 |
| 44187 | 34184 | 1.00625 |
| 44188 | 34185 | 1.00625 |

| DNA SEQ ID NO | AA SEQ ID NO | Lung 1 Enrichment |
|---|---|---|
| 44189 | 34186 | 1.004518072 |
| 44190 | 34187 | 1.004518072 |
| 44191 | 34188 | 1.003968254 |
| 44192 | 34189 | 1.002906977 |
| 44193 | 34190 | 1.002906977 |
| 44194 | 34191 | 1.002906977 |
| 44195 | 34192 | 1.002906977 |
| 44196 | 34193 | 1.002906977 |
| 44197 | 34194 | 1.002293578 |
| 44198 | 34195 | 1.001893939 |
| 44199 | 34196 | 1.001893939 |
| 44200 | 34197 | 1.001893939 |
| 44201 | 34198 | 1.001893939 |

FIG. 14

| DNA SEQ ID NO | AA SEQ ID NO | Adipose 1 Enrichment |
|---|---|---|
| 44202 | 34199 | 1909 |
| 44203 | 34200 | 616.4 |
| 44204 | 34201 | 608.2222222 |
| 44205 | 34202 | 477.25 |
| 44206 | 34203 | 425.5 |
| 44207 | 34204 | 375.2631579 |
| 44208 | 34205 | 346.3529412 |
| 44209 | 34206 | 331.2 |
| 44210 | 34207 | 326 |
| 44211 | 34208 | 324.0909091 |
| 44212 | 34209 | 322 |
| 44213 | 34210 | 316.8888889 |
| 44214 | 34211 | 295.7142857 |
| 44215 | 34212 | 289.2888889 |
| 44216 | 34213 | 282.969697 |
| 44217 | 34214 | 279.9428571 |
| 44218 | 34215 | 276 |
| 44219 | 34216 | 271.6190476 |
| 44220 | 34217 | 266.8 |
| 44221 | 34218 | 261.4736842 |
| 44222 | 34219 | 250.7 |
| 44223 | 34220 | 250.125 |
| 44224 | 34221 | 248.7407407 |
| 44225 | 34222 | 243.3157895 |
| 44226 | 34223 | 239.7575758 |
| 44227 | 34224 | 239.2 |
| 44228 | 34225 | 236.5714286 |

| DNA SEQ ID NO | AA SEQ ID NO | Adipose 1 Enrichment |
|---|---|---|
| 44229 | 34226 | 235.9354839 |
| 44230 | 34227 | 230 |
| 44231 | 34228 | 225.6190476 |
| 44232 | 34229 | 224.4242424 |
| 44233 | 34230 | 224 |
| 44234 | 34231 | 216.5833333 |
| 44235 | 34232 | 215.5185185 |
| 44236 | 34233 | 213.7647059 |
| 44237 | 34234 | 213.5714286 |
| 44238 | 34235 | 212.75 |
| 44239 | 34236 | 211.2592593 |
| 44240 | 34237 | 209.0909091 |
| 44241 | 34238 | 207.92 |
| 44242 | 34239 | 207.5348837 |
| 44243 | 34240 | 203.7142857 |
| 44244 | 34241 | 199.3333333 |
| 44245 | 34242 | 192.3636364 |
| 44246 | 34243 | 191.9615385 |
| 44247 | 34244 | 185.6428571 |
| 44248 | 34245 | 178.8888889 |
| 44249 | 34246 | 178.6923077 |
| 44250 | 34247 | 177.2682927 |
| 44251 | 34248 | 174.8 |
| 44252 | 34249 | 173.902439 |
| 44253 | 34250 | 171.5675676 |
| 44254 | 34251 | 168.6666667 |
| 44255 | 34252 | 164.59375 |

| DNA SEQ ID NO | AA SEQ ID NO | Adipose 1 Enrichment |
|---|---|---|
| 44256 | 34253 | 162 |
| 44257 | 34254 | 160.28125 |
| 44258 | 34255 | 159.9047619 |
| 44259 | 34256 | 159.6470588 |
| 44260 | 34257 | 159.5625 |
| 44261 | 34258 | 159.2307692 |
| 44262 | 34259 | 157.4615385 |
| 44263 | 34260 | 156.6875 |
| 44264 | 34261 | 146.9444444 |
| 44265 | 34262 | 146.9032258 |
| 44266 | 34263 | 146 |
| 44267 | 34264 | 145.8113208 |
| 44268 | 34265 | 142.6 |
| 44269 | 34266 | 141.4074074 |
| 44270 | 34267 | 138.7301587 |
| 44271 | 34268 | 138 |
| 44272 | 34269 | 135.9090909 |
| 44273 | 34270 | 135.6410256 |
| 44274 | 34271 | 135.5135135 |
| 44275 | 34272 | 135.1692308 |
| 44276 | 34273 | 134 |
| 44277 | 34274 | 132.5882353 |
| 44278 | 34275 | 132.48 |
| 44279 | 34276 | 131.8666667 |
| 44280 | 34277 | 131.4285714 |
| 44281 | 34278 | 130.8125 |
| 44282 | 34279 | 130.6818182 |

| DNA SEQ ID NO | AA SEQ ID NO | Adipose 1 Enrichment |
|---|---|---|
| 44283 | 34280 | 130.3333333 |
| 44284 | 34281 | 129.1376147 |
| 44285 | 34282 | 128.5641026 |
| 44286 | 34283 | 128.2424242 |
| 44287 | 34284 | 127.65 |
| 44288 | 34285 | 127.1764706 |
| 44289 | 34286 | 126.5 |
| 44290 | 34287 | 126.2051282 |
| 44291 | 34288 | 126 |
| 44292 | 34289 | 125.7333333 |
| 44293 | 34290 | 124.7111111 |
| 44294 | 34291 | 124.5365854 |
| 44295 | 34292 | 124.5365854 |
| 44296 | 34293 | 123.6721311 |
| 44297 | 34294 | 123.625 |
| 44298 | 34295 | 123.4736842 |
| 44299 | 34296 | 122.6666667 |
| 44300 | 34297 | 122.4594595 |
| 44301 | 34298 | 122.137931 |
| 44302 | 34299 | 122 |
| 44303 | 34300 | 121.9 |
| 44304 | 34301 | 121.7083333 |
| 44305 | 34302 | 121.3888889 |
| 44306 | 34303 | 121.2727273 |
| 44307 | 34304 | 121.1020408 |
| 44308 | 34305 | 121.0526316 |
| 44309 | 34306 | 119.9016393 |

| DNA SEQ ID NO | AA SEQ ID NO | Adipose 1 Enrichment |
|---|---|---|
| 44310 | 34307 | 119.7352941 |
| 44311 | 34308 | 119.6 |
| 44312 | 34309 | 119.6 |
| 44313 | 34310 | 119.2881356 |
| 44314 | 34311 | 118.8333333 |
| 44315 | 34312 | 118.2857143 |
| 44316 | 34313 | 118 |
| 44317 | 34314 | 117.875 |
| 44318 | 34315 | 117.875 |
| 44319 | 34316 | 116.9166667 |
| 44320 | 34317 | 116.8852459 |
| 44321 | 34318 | 116.4081633 |
| 44322 | 34319 | 116.15 |
| 44323 | 34320 | 115 |
| 44324 | 34321 | 115 |
| 44325 | 34322 | 114.5490196 |
| 44326 | 34323 | 114.3428571 |
| 44327 | 34324 | 113.6470588 |
| 44328 | 34325 | 112.8301887 |
| 44329 | 34326 | 112.7 |
| 44330 | 34327 | 112.4444444 |
| 44331 | 34328 | 112.24 |
| 44332 | 34329 | 111.8918919 |
| 44333 | 34330 | 111.5342466 |
| 44334 | 34331 | 111.2363636 |
| 44335 | 34332 | 110.9411765 |
| 44336 | 34333 | 110.7209302 |

FIG. 14 (Cont.)

| DNA SEQ ID NO | AA SEQ ID NO | Adipose 1 Enrichment |
|---|---|---|
| 44337 | 34334 | 110.5483871 |
| 44338 | 34335 | 110.4 |
| 44339 | 34336 | 109.8888889 |
| 44340 | 34337 | 108.8076923 |
| 44341 | 34338 | 108.56 |
| 44342 | 34339 | 108.3555556 |
| 44343 | 34340 | 108.1 |
| 44344 | 34341 | 107.9591837 |
| 44345 | 34342 | 107.8360656 |
| 44346 | 34343 | 106.8135593 |
| 44347 | 34344 | 106.7857143 |
| 44348 | 34345 | 106.72 |
| 44349 | 34346 | 106.6808511 |
| 44350 | 34347 | 106.5263158 |
| 44351 | 34348 | 105.4827586 |
| 44352 | 34349 | 105.0617284 |
| 44353 | 34350 | 104.7777778 |
| 44354 | 34351 | 104.7234043 |
| 44355 | 34352 | 104.6896552 |
| 44356 | 34353 | 104.65 |
| 44357 | 34354 | 104.3214286 |
| 44358 | 34355 | 103.2745098 |
| 44359 | 34356 | 102.8235294 |
| 44360 | 34357 | 102.8235294 |
| 44361 | 34358 | 101.9215686 |
| 44362 | 34359 | 101.787234 |
| 44363 | 34360 | 101.7575758 |
| 44364 | 34361 | 101.34375 |
| 44365 | 34362 | 101.2 |

| DNA SEQ ID NO | AA SEQ ID NO | Adipose 1 Enrichment |
|---|---|---|
| 44366 | 34363 | 101.2 |
| 44367 | 34364 | 100.7027027 |
| 44368 | 34365 | 100.3636364 |
| 44369 | 34366 | 100.031746 |
| 44370 | 34367 | 99.93103448 |
| 44371 | 34368 | 99.93103448 |
| 44372 | 34369 | 99.81132075 |
| 44373 | 34370 | 99.81132075 |
| 44374 | 34371 | 99.55223881 |
| 44375 | 34372 | 99.36 |
| 44376 | 34373 | 99.21568627 |
| 44377 | 34374 | 98.9 |
| 44378 | 34375 | 97.96296296 |
| 44379 | 34376 | 97.84126984 |
| 44380 | 34377 | 97.63265306 |
| 44381 | 34378 | 96.38095238 |
| 44382 | 34379 | 96.24615385 |
| 44383 | 34380 | 96.18181818 |
| 44384 | 34381 | 95.89830508 |
| 44385 | 34382 | 95.83333333 |
| 44386 | 34383 | 95.28571429 |
| 44387 | 34384 | 95.11864407 |
| 44388 | 34385 | 95.06666667 |
| 44389 | 34386 | 95 |
| 44390 | 34387 | 94.875 |
| 44391 | 34388 | 93.80392157 |
| 44392 | 34389 | 93.7037037 |
| 44393 | 34390 | 93.12195122 |
| 44394 | 34391 | 92.8440367 |

| DNA SEQ ID NO | AA SEQ ID NO | Adipose 1 Enrichment |
|---|---|---|
| 44395 | 34392 | 92 |
| 44396 | 34393 | 92 |
| 44397 | 34394 | 92 |
| 44398 | 34395 | 92 |
| 44399 | 34396 | 91.11538462 |
| 44400 | 34397 | 91.08 |
| 44401 | 34398 | 90.93023256 |
| 44402 | 34399 | 90.75675676 |
| 44403 | 34400 | 90.4137931 |
| 44404 | 34401 | 90.35714286 |
| 44405 | 34402 | 90.2962963 |
| 44406 | 34403 | 90.10958904 |
| 44407 | 34404 | 89.78313253 |
| 44408 | 34405 | 89.73770492 |
| 44409 | 34406 | 89.49090909 |
| 44410 | 34407 | 89.25373134 |
| 44411 | 34408 | 89.19512195 |
| 44412 | 34409 | 89 |
| 44413 | 34410 | 88.76056338 |
| 44414 | 34411 | 88.75294118 |
| 44415 | 34412 | 88.46153846 |
| 44416 | 34413 | 88.32 |
| 44417 | 34414 | 88.16666667 |
| 44418 | 34415 | 88.11267606 |
| 44419 | 34416 | 87.89285714 |
| 44420 | 34417 | 87.88059701 |
| 44421 | 34418 | 87.66037736 |
| 44422 | 34419 | 87.28205128 |
| 44423 | 34420 | 86.88888889 |

| DNA SEQ ID NO | AA SEQ ID NO | Adipose 1 Enrichment |
|---|---|---|
| 44424 | 34421 | 86.03703704 |
| 44425 | 34422 | 85.42857143 |
| 44426 | 34423 | 85.06849315 |
| 44427 | 34424 | 85 |
| 44428 | 34425 | 84.92307692 |
| 44429 | 34426 | 84.73684211 |
| 44430 | 34427 | 84.51162791 |
| 44431 | 34428 | 84.33333333 |
| 44432 | 34429 | 83.88235294 |
| 44433 | 34430 | 83.54022989 |
| 44434 | 34431 | 83.375 |
| 44435 | 34432 | 83.20588235 |
| 44436 | 34433 | 83.17808219 |
| 44437 | 34434 | 82.6122449 |
| 44438 | 34435 | 82.26923077 |
| 44439 | 34436 | 82.14285714 |
| 44440 | 34437 | 82.05405405 |
| 44441 | 34438 | 82.03333333 |
| 44442 | 34439 | 81.46987952 |
| 44443 | 34440 | 81.30232558 |
| 44444 | 34441 | 81.17647059 |
| 44445 | 34442 | 81.08474576 |
| 44446 | 34443 | 80.92592593 |
| 44447 | 34444 | 80.84848485 |
| 44448 | 34445 | 80.07407407 |
| 44449 | 34446 | 79.73333333 |
| 44450 | 34447 | 79.54166667 |
| 44451 | 34448 | 78.76712329 |
| 44452 | 34449 | 78.58333333 |

| DNA SEQ ID NO | AA SEQ ID NO | Adipose 1 Enrichment |
|---|---|---|
| 44453 | 34450 | 78.47058824 |
| 44454 | 34451 | 78.47058824 |
| 44455 | 34452 | 78.32432432 |
| 44456 | 34453 | 78.06060606 |
| 44457 | 34454 | 77.79411765 |
| 44458 | 34455 | 77.68888889 |
| 44459 | 34456 | 77.42574257 |
| 44460 | 34457 | 77.33333333 |
| 44461 | 34458 | 77.28 |
| 44462 | 34459 | 77.05 |
| 44463 | 34460 | 76.66666667 |
| 44464 | 34461 | 76.43076923 |
| 44465 | 34462 | 76.37735849 |
| 44466 | 34463 | 76.31818182 |
| 44467 | 34464 | 76.16393443 |
| 44468 | 34465 | 75.30973451 |
| 44469 | 34466 | 75.27272727 |
| 44470 | 34467 | 75.17073171 |
| 44471 | 34468 | 75.13333333 |
| 44472 | 34469 | 75.10204082 |
| 44473 | 34470 | 75.08045977 |
| 44474 | 34471 | 74.91428571 |
| 44475 | 34472 | 74.67532468 |
| 44476 | 34473 | 74.6557377 |
| 44477 | 34474 | 74.5 |
| 44478 | 34475 | 74.30769231 |
| 44479 | 34476 | 74.30769231 |
| 44480 | 34477 | 74.19354839 |
| 44481 | 34478 | 74.16326531 |

FIG. 14 (Cont.)

| DNA SEQ ID NO | AA SEQ ID NO | Adipose 1 Enrichment |
|---|---|---|
| 44482 | 34479 | 74.14925373 |
| 44483 | 34480 | 74.04878049 |
| 44484 | 34481 | 74.02298851 |
| 44485 | 34482 | 74 |
| 44486 | 34483 | 74 |
| 44487 | 34484 | 73.94936709 |
| 44488 | 34485 | 73.28813559 |
| 44489 | 34486 | 73.23684211 |
| 44490 | 34487 | 73.18181818 |
| 44491 | 34488 | 73.12820513 |
| 44492 | 34489 | 73.05882353 |
| 44493 | 34490 | 72.20930233 |
| 44494 | 34491 | 72.10810811 |
| 44495 | 34492 | 72 |
| 44496 | 34493 | 71.93617021 |
| 44497 | 34494 | 71.91549296 |
| 44498 | 34495 | 71.50909091 |
| 44499 | 34496 | 71.37931034 |
| 44500 | 34497 | 71.34693878 |
| 44501 | 34498 | 71.3 |
| 44502 | 34499 | 71.26760563 |
| 44503 | 34500 | 71.22580645 |
| 44504 | 34501 | 71.03797468 |
| 44505 | 34502 | 70.64285714 |
| 44506 | 34503 | 70.57534247 |
| 44507 | 34504 | 70.48387097 |
| 44508 | 34505 | 69.95833333 |
| 44509 | 34506 | 69.8961039 |
| 44510 | 34507 | 69.85185185 |

| DNA SEQ ID NO | AA SEQ ID NO | Adipose 1 Enrichment |
|---|---|---|
| 44511 | 34508 | 69.56097561 |
| 44512 | 34509 | 69 |
| 44513 | 34510 | 69 |
| 44514 | 34511 | 69 |
| 44515 | 34512 | 68.69333333 |
| 44516 | 34513 | 68.66666667 |
| 44517 | 34514 | 68.46511628 |
| 44518 | 34515 | 68.46511628 |
| 44519 | 34516 | 68.425 |
| 44520 | 34517 | 68.38938053 |
| 44521 | 34518 | 68.32352941 |
| 44522 | 34519 | 68.32352941 |
| 44523 | 34520 | 68.26984127 |
| 44524 | 34521 | 68.04166667 |
| 44525 | 34522 | 68 |
| 44526 | 34523 | 67.74545455 |
| 44527 | 34524 | 67.50649351 |
| 44528 | 34525 | 67.39534884 |
| 44529 | 34526 | 67.35714286 |
| 44530 | 34527 | 67.23076923 |
| 44531 | 34528 | 67.19101124 |
| 44532 | 34529 | 67.01234568 |
| 44533 | 34530 | 66.73239437 |
| 44534 | 34531 | 66.62068966 |
| 44535 | 34532 | 66.60416667 |
| 44536 | 34533 | 66.125 |
| 44537 | 34534 | 65.93333333 |
| 44538 | 34535 | 65.42222222 |
| 44539 | 34536 | 65.33333333 |

| DNA SEQ ID NO | AA SEQ ID NO | Adipose 1 Enrichment |
|---|---|---|
| 44540 | 34537 | 65.29032258 |
| 44541 | 34538 | 65.29032258 |
| 44542 | 34539 | 65.23636364 |
| 44543 | 34540 | 65.10769231 |
| 44544 | 34541 | 65.07317073 |
| 44545 | 34542 | 64.975 |
| 44546 | 34543 | 64.91111111 |
| 44547 | 34544 | 64.87179487 |
| 44548 | 34545 | 64.71186441 |
| 44549 | 34546 | 64.59574468 |
| 44550 | 34547 | 64.50574713 |
| 44551 | 34548 | 64.50574713 |
| 44552 | 34549 | 64.4 |
| 44553 | 34550 | 64.29545455 |
| 44554 | 34551 | 64.20833333 |
| 44555 | 34552 | 64.03921569 |
| 44556 | 34553 | 63.95121951 |
| 44557 | 34554 | 63.88888889 |
| 44558 | 34555 | 63.825 |
| 44559 | 34556 | 63.63333333 |
| 44560 | 34557 | 63.56363636 |
| 44561 | 34558 | 63.46296296 |
| 44562 | 34559 | 63.42424242 |
| 44563 | 34560 | 63.1372549 |
| 44564 | 34561 | 63.12765957 |
| 44565 | 34562 | 63.11627907 |
| 44566 | 34563 | 63.08571429 |
| 44567 | 34564 | 63 |
| 44568 | 34565 | 62.82926829 |

| DNA SEQ ID NO | AA SEQ ID NO | Adipose 1 Enrichment |
|---|---|---|
| 44569 | 34566 | 62.8 |
| 44570 | 34567 | 62.72727273 |
| 44571 | 34568 | 62.675 |
| 44572 | 34569 | 62.51282051 |
| 44573 | 34570 | 62.47761194 |
| 44574 | 34571 | 62.45528455 |
| 44575 | 34572 | 62.3364486 |
| 44576 | 34573 | 62.32258065 |
| 44577 | 34574 | 62.07228916 |
| 44578 | 34575 | 61.94059406 |
| 44579 | 34576 | 61.72151899 |
| 44580 | 34577 | 61.65957447 |
| 44581 | 34578 | 61.63106796 |
| 44582 | 34579 | 61.525 |
| 44583 | 34580 | 61.51807229 |
| 44584 | 34581 | 61.453125 |
| 44585 | 34582 | 61.33333333 |
| 44586 | 34583 | 61.20967742 |
| 44587 | 34584 | 60.97674419 |
| 44588 | 34585 | 60.97674419 |
| 44589 | 34586 | 60.74358974 |
| 44590 | 34587 | 60.56666667 |
| 44591 | 34588 | 60.52631579 |
| 44592 | 34589 | 60.52631579 |
| 44593 | 34590 | 60.52631579 |
| 44594 | 34591 | 60.52631579 |
| 44595 | 34592 | 60.5 |
| 44596 | 34593 | 60 |
| 44597 | 34594 | 59.84466019 |

| DNA SEQ ID NO | AA SEQ ID NO | Adipose 1 Enrichment |
|---|---|---|
| 44598 | 34595 | 59.70212766 |
| 44599 | 34596 | 59.65625 |
| 44600 | 34597 | 59.64835165 |
| 44601 | 34598 | 59.52941176 |
| 44602 | 34599 | 59.52941176 |
| 44603 | 34600 | 59.5 |
| 44604 | 34601 | 59.5 |
| 44605 | 34602 | 59.34 |
| 44606 | 34603 | 59.31578947 |
| 44607 | 34604 | 59 |
| 44608 | 34605 | 58.9375 |
| 44609 | 34606 | 58.88 |
| 44610 | 34607 | 58.64122137 |
| 44611 | 34608 | 58.54545455 |
| 44612 | 34609 | 58.17647059 |
| 44613 | 34610 | 58.04761905 |
| 44614 | 34611 | 57.96 |
| 44615 | 34612 | 57.96 |
| 44616 | 34613 | 57.94805195 |
| 44617 | 34614 | 57.84848485 |
| 44618 | 34615 | 57.84158416 |
| 44619 | 34616 | 57.82857143 |
| 44620 | 34617 | 57.80530973 |
| 44621 | 34618 | 57.74468085 |
| 44622 | 34619 | 57.5 |
| 44623 | 34620 | 57.5 |
| 44624 | 34621 | 57.5 |
| 44625 | 34622 | 57.36470588 |
| 44626 | 34623 | 57.07407407 |

FIG. 14 (Cont.)

| DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment |
|---|---|---|---|---|---|---|---|---|---|---|---|---|---|---|
| 44627 | 34624 | 56.96923077 | 44656 | 34653 | 54.21428571 | 44685 | 34682 | 51.64912281 | 44714 | 34711 | 48.83076923 | 44743 | 34740 | 46.68148148 |
| 44628 | 34625 | 56.95238095 | 44657 | 34654 | 54.11764706 | 44686 | 34683 | 51.6097561 | 44715 | 34712 | 48.73513514 | 44744 | 34741 | 46.42990654 |
| 44629 | 34626 | 56.73333333 | 44658 | 34655 | 54.11764706 | 44687 | 34684 | 51.52 | 44716 | 34713 | 48.72592593 | 44745 | 34742 | 46.42201835 |
| 44630 | 34627 | 56.66666667 | 44659 | 34656 | 54.08108108 | 44688 | 34685 | 51.41176471 | 44717 | 34714 | 48.62857143 | 44746 | 34743 | 46.34074074 |
| 44631 | 34628 | 56.61538462 | 44660 | 34657 | 54 | 44689 | 34686 | 51.41176471 | 44718 | 34715 | 48.57943925 | 44747 | 34744 | 46 |
| 44632 | 34629 | 56.54166667 | 44661 | 34658 | 53.82 | 44690 | 34687 | 51.32631579 | 44719 | 34716 | 48.50909091 | 44748 | 34745 | 46 |
| 44633 | 34630 | 56.09756098 | 44662 | 34659 | 53.81132075 | 44691 | 34688 | 51.25714286 | 44720 | 34717 | 48.48648649 | 44749 | 34746 | 46 |
| 44634 | 34631 | 56.03636364 | 44663 | 34660 | 53.66666667 | 44692 | 34689 | 51.00990099 | 44721 | 34718 | 48.46428571 | 44750 | 34747 | 46 |
| 44635 | 34632 | 55.92156863 | 44664 | 34661 | 53.56164384 | 44693 | 34690 | 50.97297297 | 44722 | 34719 | 48.42105263 | 44751 | 34748 | 46 |
| 44636 | 34633 | 55.7962963 | 44665 | 34662 | 53.56164384 | 44694 | 34691 | 50.87058824 | 44723 | 34720 | 48.42105263 | 44752 | 34749 | 46 |
| 44637 | 34634 | 55.68421053 | 44666 | 34663 | 53.31818182 | 44695 | 34692 | 50.84210526 | 44724 | 34721 | 48.38961039 | 44753 | 34750 | 46 |
| 44638 | 34635 | 55.58333333 | 44667 | 34664 | 53.07692308 | 44696 | 34693 | 50.80597015 | 44725 | 34722 | 48.38961039 | 44754 | 34751 | 46 |
| 44639 | 34636 | 55.56435644 | 44668 | 34665 | 53.07692308 | 44697 | 34694 | 50.80597015 | 44726 | 34723 | 48.33898305 | 44755 | 34752 | 46 |
| 44640 | 34637 | 55.51724138 | 44669 | 34666 | 52.73170732 | 44698 | 34695 | 50.75862069 | 44727 | 34724 | 48.3 | 44756 | 34753 | 46 |
| 44641 | 34638 | 55.2 | 44670 | 34667 | 52.70833333 | 44699 | 34696 | 50.6 | 44728 | 34725 | 48.27722772 | 44757 | 34754 | 45.64885496 |
| 44642 | 34639 | 55.2 | 44671 | 34668 | 52.65060241 | 44700 | 34697 | 50.6 | 44729 | 34726 | 48.19047619 | 44758 | 34755 | 45.43902439 |
| 44643 | 34640 | 55.04918033 | 44672 | 34669 | 52.63461538 | 44701 | 34698 | 50.50980392 | 44730 | 34727 | 48.04444444 | 44759 | 34756 | 45.41025641 |
| 44644 | 34641 | 55.03571429 | 44673 | 34670 | 52.48717949 | 44702 | 34699 | 50.47222222 | 44731 | 34728 | 48 | 44760 | 34757 | 45.38666667 |
| 44645 | 34642 | 54.90322581 | 44674 | 34671 | 52.34482759 | 44703 | 34700 | 50.38095238 | 44732 | 34729 | 47.89041096 | 44761 | 34758 | 45.09803922 |
| 44646 | 34643 | 54.87719298 | 44675 | 34672 | 52.27272727 | 44704 | 34701 | 50.08064516 | 44733 | 34730 | 47.76923077 | 44762 | 34759 | 45.09803922 |
| 44647 | 34644 | 54.77456647 | 44676 | 34673 | 52.22916667 | 44705 | 34702 | 49.96551724 | 44734 | 34731 | 47.7037037 | 44763 | 34760 | 44.93023256 |
| 44648 | 34645 | 54.44897959 | 44677 | 34674 | 52.19230769 | 44706 | 34703 | 49.94285714 | 44735 | 34732 | 47.64285714 | 44764 | 34761 | 44.82051282 |
| 44649 | 34646 | 54.30555556 | 44678 | 34675 | 52.13333333 | 44707 | 34704 | 49.61797753 | 44736 | 34733 | 47.55932203 | 44765 | 34762 | 44.82051282 |
| 44650 | 34647 | 54.30555556 | 44679 | 34676 | 51.91428571 | 44708 | 34705 | 49.61797753 | 44737 | 34734 | 47.37313433 | 44766 | 34763 | 44.58461538 |
| 44651 | 34648 | 54.29508197 | 44680 | 34677 | 51.87234043 | 44709 | 34706 | 49.48484848 | 44738 | 34735 | 47.29577465 | 44767 | 34764 | 44.49180328 |
| 44652 | 34649 | 54.28828829 | 44681 | 34678 | 51.75 | 44710 | 34707 | 49.17241379 | 44739 | 34736 | 47.04545455 | 44768 | 34765 | 44.2962963 |
| 44653 | 34650 | 54.25641026 | 44682 | 34679 | 51.75 | 44711 | 34708 | 48.92727273 | 44740 | 34737 | 46.83636364 | 44769 | 34766 | 44.26415094 |
| 44654 | 34651 | 54.23880597 | 44683 | 34680 | 51.75 | 44712 | 34709 | 48.875 | 44741 | 34738 | 46.82142857 | 44770 | 34767 | 44.23076923 |
| 44655 | 34652 | 54.21428571 | 44684 | 34681 | 51.68539326 | 44713 | 34710 | 48.83076923 | 44742 | 34739 | 46.68148148 | 44771 | 34768 | 44.19607843 |

FIG. 14 (Cont.)

| DNA SEQ ID NO | AA SEQ ID NO | Adipose 1 Enrichment |
|---|---|---|
| 44772 | 34769 | 43.80952381 |
| 44773 | 34770 | 43.73770492 |
| 44774 | 34771 | 43.7 |
| 44775 | 34772 | 43.61038961 |
| 44776 | 34773 | 43.57894737 |
| 44777 | 34774 | 43.51351351 |
| 44778 | 34775 | 43.47945205 |
| 44779 | 34776 | 43.37142857 |
| 44780 | 34777 | 43.34615385 |
| 44781 | 34778 | 43.33884298 |
| 44782 | 34779 | 43.18367347 |
| 44783 | 34780 | 43.16923077 |
| 44784 | 34781 | 43.08860759 |
| 44785 | 34782 | 43.06382979 |
| 44786 | 34783 | 42.98360656 |
| 44787 | 34784 | 42.93333333 |
| 44788 | 34785 | 42.93333333 |
| 44789 | 34786 | 42.71428571 |
| 44790 | 34787 | 42.61764706 |
| 44791 | 34788 | 42.51515152 |
| 44792 | 34789 | 42.5 |
| 44793 | 34790 | 42.46153846 |
| 44794 | 34791 | 42.38202247 |
| 44795 | 34792 | 42.32 |
| 44796 | 34793 | 42.32 |
| 44797 | 34794 | 42.29032258 |
| 44798 | 34795 | 42.24489796 |
| 44799 | 34796 | 42.20618557 |
| 44800 | 34797 | 42.05714286 |
| 44801 | 34798 | 42 |
| 44802 | 34799 | 41.952 |
| 44803 | 34800 | 41.88617886 |
| 44804 | 34801 | 41.88059701 |
| 44805 | 34802 | 41.81818182 |
| 44806 | 34803 | 41.74074074 |
| 44807 | 34804 | 41.57692308 |
| 44808 | 34805 | 41.57692308 |
| 44809 | 34806 | 41.47540984 |
| 44810 | 34807 | 41.4 |
| 44811 | 34808 | 41.4 |
| 44812 | 34809 | 41.34831461 |
| 44813 | 34810 | 41.33333333 |
| 44814 | 34811 | 41.19402985 |
| 44815 | 34812 | 41.05376344 |
| 44816 | 34813 | 41.04615385 |
| 44817 | 34814 | 40.98181818 |
| 44818 | 34815 | 40.79245283 |
| 44819 | 34816 | 40.66666667 |
| 44820 | 34817 | 40.65116279 |
| 44821 | 34818 | 40.58823529 |
| 44822 | 34819 | 40.50746269 |
| 44823 | 34820 | 40.46616541 |
| 44824 | 34821 | 40.37777778 |
| 44825 | 34822 | 40.36734694 |
| 44826 | 34823 | 40.33497537 |
| 44827 | 34824 | 40.25 |
| 44828 | 34825 | 40.1025641 |
| 44829 | 34826 | 40.08571429 |
| 44830 | 34827 | 39.97619048 |
| 44831 | 34828 | 39.86666667 |
| 44832 | 34829 | 39.72727273 |
| 44833 | 34830 | 39.66666667 |
| 44834 | 34831 | 39.63076923 |
| 44835 | 34832 | 39.58787879 |
| 44836 | 34833 | 39.53125 |
| 44837 | 34834 | 39.51282051 |
| 44838 | 34835 | 39.4751773 |
| 44839 | 34836 | 39.42857143 |
| 44840 | 34837 | 39.42857143 |
| 44841 | 34838 | 39.42857143 |
| 44842 | 34839 | 39.32258065 |
| 44843 | 34840 | 39.31623932 |
| 44844 | 34841 | 39.30909091 |
| 44845 | 34842 | 39.29166667 |
| 44846 | 34843 | 39.28648649 |
| 44847 | 34844 | 39.2 |
| 44848 | 34845 | 39.16831683 |
| 44849 | 34846 | 39.06849315 |
| 44850 | 34847 | 38.86206897 |
| 44851 | 34848 | 38.83116883 |
| 44852 | 34849 | 38.83116883 |
| 44853 | 34850 | 38.78431373 |
| 44854 | 34851 | 38.77142857 |
| 44855 | 34852 | 38.6984127 |
| 44856 | 34853 | 38.66666667 |
| 44857 | 34854 | 38.60714286 |
| 44858 | 34855 | 38.58064516 |
| 44859 | 34856 | 38.58064516 |
| 44860 | 34857 | 38.33333333 |
| 44861 | 34858 | 38.33333333 |
| 44862 | 34859 | 38.24719101 |
| 44863 | 34860 | 38.21538462 |
| 44864 | 34861 | 38.17021277 |
| 44865 | 34862 | 38.01652893 |
| 44866 | 34863 | 37.96825397 |
| 44867 | 34864 | 37.78571429 |
| 44868 | 34865 | 37.76842105 |
| 44869 | 34866 | 37.75722543 |
| 44870 | 34867 | 37.74358974 |
| 44871 | 34868 | 37.63636364 |
| 44872 | 34869 | 37.55102041 |
| 44873 | 34870 | 37.45714286 |
| 44874 | 34871 | 37.44871795 |
| 44875 | 34872 | 37.375 |
| 44876 | 34873 | 37.20588235 |
| 44877 | 34874 | 37.13541667 |
| 44878 | 34875 | 37.09677419 |
| 44879 | 34876 | 37.03896104 |
| 44880 | 34877 | 37.02439024 |
| 44881 | 34878 | 36.90697674 |
| 44882 | 34879 | 36.56410256 |
| 44883 | 34880 | 36.55357143 |
| 44884 | 34881 | 36.52941176 |
| 44885 | 34882 | 36.44155844 |
| 44886 | 34883 | 36.3880597 |
| 44887 | 34884 | 36.37209302 |
| 44888 | 34885 | 36.26923077 |
| 44889 | 34886 | 36.17094017 |
| 44890 | 34887 | 35.9375 |
| 44891 | 34888 | 35.77777778 |
| 44892 | 34889 | 35.77777778 |
| 44893 | 34890 | 35.77777778 |
| 44894 | 34891 | 35.71052632 |
| 44895 | 34892 | 35.66292135 |
| 44896 | 34893 | 35.65 |
| 44897 | 34894 | 35.58490566 |
| 44898 | 34895 | 35.58490566 |
| 44899 | 34896 | 35.54545455 |
| 44900 | 34897 | 35.48571429 |
| 44901 | 34898 | 35.30232558 |
| 44902 | 34899 | 35.21875 |
| 44903 | 34900 | 35.21875 |
| 44904 | 34901 | 35.02752294 |
| 44905 | 34902 | 35.01492537 |
| 44906 | 34903 | 34.96 |
| 44907 | 34904 | 34.96 |
| 44908 | 34905 | 34.92592593 |
| 44909 | 34906 | 34.7804878 |
| 44910 | 34907 | 34.7804878 |
| 44911 | 34908 | 34.7804878 |
| 44912 | 34909 | 34.7804878 |
| 44913 | 34910 | 34.66666667 |
| 44914 | 34911 | 34.66666667 |
| 44915 | 34912 | 34.6185567 |
| 44916 | 34913 | 34.61386139 |

FIG. 14 (Cont.)

| DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment |
|---|---|---|---|---|---|---|---|---|---|---|---|---|---|---|
| 44917 | 34914 | 34.5 | 44946 | 34943 | 32.63513514 | 44975 | 34972 | 30.66666667 | 45004 | 35001 | 28.75 | 45033 | 35030 | 26.63157895 |
| 44918 | 34915 | 34.32307692 | 44947 | 34944 | 32.60194175 | 44976 | 34973 | 30.66666667 | 45005 | 35002 | 28.64150943 | 45034 | 35031 | 26.63157895 |
| 44919 | 34916 | 34.25531915 | 44948 | 34945 | 32.5 | 44977 | 34974 | 30.66666667 | 45006 | 35003 | 28.62222222 | 45035 | 35032 | 26.60240964 |
| 44920 | 34917 | 34.23255814 | 44949 | 34946 | 32.47058824 | 44978 | 34975 | 30.66666667 | 45007 | 35004 | 28.57575758 | 45036 | 35033 | 26.53846154 |
| 44921 | 34918 | 34.2195122 | 44950 | 34947 | 32.37037037 | 44979 | 34976 | 30.53448276 | 45008 | 35005 | 28.54216867 | 45037 | 35034 | 26.48484848 |
| 44922 | 34919 | 34.04 | 44951 | 34948 | 32.33142857 | 44980 | 34977 | 30.43076923 | 45009 | 35006 | 28.5 | 45038 | 35035 | 26.41584158 |
| 44923 | 34920 | 33.925 | 44952 | 34949 | 32.32432432 | 44981 | 34978 | 30.24657534 | 45010 | 35007 | 28.5 | 45039 | 35036 | 26.28571429 |
| 44924 | 34921 | 33.925 | 44953 | 34950 | 32.28070175 | 44982 | 34979 | 30.1875 | 45011 | 35008 | 28.42696629 | 45040 | 35037 | 26.28571429 |
| 44925 | 34922 | 33.78761062 | 44954 | 34951 | 32.26865672 | 44983 | 34980 | 30.13793103 | 45012 | 35009 | 28.24561404 | 45041 | 35038 | 26.28571429 |
| 44926 | 34923 | 33.73333333 | 44955 | 34952 | 32.2 | 44984 | 34981 | 30.13793103 | 45013 | 35010 | 28.21333333 | 45042 | 35039 | 26.13636364 |
| 44927 | 34924 | 33.67010309 | 44956 | 34953 | 31.88636364 | 44985 | 34982 | 30.11904762 | 45014 | 35011 | 28.19354839 | 45043 | 35040 | 25.8245614 |
| 44928 | 34925 | 33.65853659 | 44957 | 34954 | 31.88118812 | 44986 | 34983 | 30.10909091 | 45015 | 35012 | 28.06779661 | 45044 | 35041 | 25.80487805 |
| 44929 | 34926 | 33.65853659 | 44958 | 34955 | 31.68888889 | 44987 | 34984 | 30.0483871 | 45016 | 35013 | 28.04878049 | 45045 | 35042 | 25.78021978 |
| 44930 | 34927 | 33.56756757 | 44959 | 34956 | 31.58208955 | 44988 | 34985 | 29.8028169 | 45017 | 35014 | 28.04878049 | 45046 | 35043 | 25.74626866 |
| 44931 | 34928 | 33.56756757 | 44960 | 34957 | 31.43333333 | 44989 | 34986 | 29.79545455 | 45018 | 35015 | 27.94936709 | 45047 | 35044 | 25.55555556 |
| 44932 | 34929 | 33.55294118 | 44961 | 34958 | 31.3968254 | 44990 | 34987 | 29.67741935 | 45019 | 35016 | 27.6 | 45048 | 35045 | 25.55555556 |
| 44933 | 34930 | 33.488 | 44962 | 34959 | 31.13846154 | 44991 | 34988 | 29.65789474 | 45020 | 35017 | 27.51401869 | 45049 | 35046 | 25.37931034 |
| 44934 | 34931 | 33.45454545 | 44963 | 34960 | 31.06493506 | 44992 | 34989 | 29.65789474 | 45021 | 35018 | 27.48780488 | 45050 | 35047 | 25.33333333 |
| 44935 | 34932 | 33.45454545 | 44964 | 34961 | 30.98947368 | 44993 | 34990 | 29.62121212 | 45022 | 35019 | 27.40425532 | 45051 | 35048 | 25.3258427 |
| 44936 | 34933 | 33.39726027 | 44965 | 34962 | 30.96732026 | 44994 | 34991 | 29.54966887 | 45023 | 35020 | 27.39325843 | 45052 | 35049 | 25.24390244 |
| 44937 | 34934 | 33.38709677 | 44966 | 34963 | 30.96153846 | 44995 | 34992 | 29.5308642 | 45024 | 35021 | 27.33333333 | 45053 | 35050 | 25.22580645 |
| 44938 | 34935 | 33.36263736 | 44967 | 34964 | 30.94545455 | 44996 | 34993 | 29.50943396 | 45025 | 35022 | 27.3125 | 45054 | 35051 | 25.20547945 |
| 44939 | 34936 | 33.22222222 | 44968 | 34965 | 30.88571429 | 44997 | 34994 | 29.39849624 | 45026 | 35023 | 27.23684211 | 45055 | 35052 | 25.2 |
| 44940 | 34937 | 33.22222222 | 44969 | 34966 | 30.87671233 | 44998 | 34995 | 29.23364486 | 45027 | 35024 | 27.2244898 | 45056 | 35053 | 24.97142857 |
| 44941 | 34938 | 33.1627907 | 44970 | 34967 | 30.86842105 | 44999 | 34996 | 29.22352941 | 45028 | 35025 | 27.20430108 | 45057 | 35054 | 24.86486486 |
| 44942 | 34939 | 33.09756098 | 44971 | 34968 | 30.86075949 | 45000 | 34997 | 29.03278689 | 45029 | 35026 | 27.14754098 | 45058 | 35055 | 24.76923077 |
| 44943 | 34940 | 32.85714286 | 44972 | 34969 | 30.81553398 | 45001 | 34998 | 29.00900901 | 45030 | 35027 | 27.08888889 | 45059 | 35056 | 24.61971831 |
| 44944 | 34941 | 32.85714286 | 44973 | 34970 | 30.80357143 | 45002 | 34999 | 28.88372093 | 45031 | 35028 | 27.03092784 | 45060 | 35057 | 24.55932203 |
| 44945 | 34942 | 32.85714286 | 44974 | 34971 | 30.66666667 | 45003 | 35000 | 28.8627451 | 45032 | 35029 | 26.78481013 | 45061 | 35058 | 24.35294118 |

FIG. 14 (Cont.)

| DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment |
|---|---|---|---|---|---|---|---|---|---|---|---|---|---|---|
| 45062 | 35059 | 24.35294118 | 45091 | 35088 | 22.83916084 | 45120 | 35117 | 20.39175258 | 45149 | 35146 | 18.28915663 | 45178 | 35175 | 16.01785714 |
| 45063 | 35060 | 24.35294118 | 45092 | 35089 | 22.81889764 | 45121 | 35118 | 20.39175258 | 45150 | 35147 | 18.26950355 | 45179 | 35176 | 16 |
| 45064 | 35061 | 24.35294118 | 45093 | 35090 | 22.73563218 | 45122 | 35119 | 20.31168831 | 45151 | 35148 | 18.20833333 | 45180 | 35177 | 15.65957447 |
| 45065 | 35062 | 24.32692308 | 45094 | 35091 | 22.67605634 | 45123 | 35120 | 20.19512195 | 45152 | 35149 | 18.18604651 | 45181 | 35178 | 15.64948454 |
| 45066 | 35063 | 24.31428571 | 45095 | 35092 | 22.61016949 | 45124 | 35121 | 20.18367347 | 45153 | 35150 | 18.07142857 | 45182 | 35179 | 15.53246753 |
| 45067 | 35064 | 24.31428571 | 45096 | 35093 | 22.42016807 | 45125 | 35122 | 20.16438356 | 45154 | 35151 | 18.03921569 | 45183 | 35180 | 15.53246753 |
| 45068 | 35065 | 24.23655914 | 45097 | 35094 | 22.4 | 45126 | 35123 | 20.125 | 45155 | 35152 | 17.64383562 | 45184 | 35181 | 15.525 |
| 45069 | 35066 | 24.21052632 | 45098 | 35095 | 22.37837838 | 45127 | 35124 | 20.10084034 | 45156 | 35153 | 17.63333333 | 45185 | 35182 | 15.51162791 |
| 45070 | 35067 | 24.21052632 | 45099 | 35096 | 22.3030303 | 45128 | 35125 | 19.89189189 | 45157 | 35154 | 17.46296296 | 45186 | 35183 | 15.453125 |
| 45071 | 35068 | 24.16161616 | 45100 | 35097 | 22.25806452 | 45129 | 35126 | 19.71428571 | 45158 | 35155 | 17.44827586 | 45187 | 35184 | 15.33333333 |
| 45072 | 35069 | 24.15 | 45101 | 35098 | 22.16363636 | 45130 | 35127 | 19.71428571 | 45159 | 35156 | 17.44827586 | 45188 | 35185 | 15.33333333 |
| 45073 | 35070 | 24.12195122 | 45102 | 35099 | 22.02816901 | 45131 | 35128 | 19.66896552 | 45160 | 35157 | 17.42424242 | 45189 | 35186 | 15.33333333 |
| 45074 | 35071 | 24.0952381 | 45103 | 35100 | 22.0212766 | 45132 | 35129 | 19.51515152 | 45161 | 35158 | 17.37234043 | 45190 | 35187 | 15.33333333 |
| 45075 | 35072 | 24 | 45104 | 35101 | 21.78947368 | 45133 | 35130 | 19.51515152 | 45162 | 35159 | 17.33333333 | 45191 | 35188 | 15.16483516 |
| 45076 | 35073 | 23.95833333 | 45105 | 35102 | 21.74545455 | 45134 | 35131 | 19.49668874 | 45163 | 35160 | 17.25 | 45192 | 35189 | 15.088 |
| 45077 | 35074 | 23.88461538 | 45106 | 35103 | 21.64705882 | 45135 | 35132 | 19.44329897 | 45164 | 35161 | 17.01369863 | 45193 | 35190 | 15.05454545 |
| 45078 | 35075 | 23.85185185 | 45107 | 35104 | 21.32727273 | 45136 | 35133 | 19.33333333 | 45165 | 35162 | 16.94736842 | 45194 | 35191 | 15.01388889 |
| 45079 | 35076 | 23.82142857 | 45108 | 35105 | 21.26415094 | 45137 | 35134 | 19.32 | 45166 | 35163 | 16.9245283 | 45195 | 35192 | 14.91034483 |
| 45080 | 35077 | 23.74193548 | 45109 | 35106 | 20.90909091 | 45138 | 35135 | 19.13868613 | 45167 | 35164 | 16.86666667 | 45196 | 35193 | 14.86153846 |
| 45081 | 35078 | 23.74193548 | 45110 | 35107 | 20.90909091 | 45139 | 35136 | 19.05714286 | 45168 | 35165 | 16.78378378 | 45197 | 35194 | 14.8045977 |
| 45082 | 35079 | 23.39655172 | 45111 | 35108 | 20.84375 | 45140 | 35137 | 19.01333333 | 45169 | 35166 | 16.69354839 | 45198 | 35195 | 14.58536585 |
| 45083 | 35080 | 23.26436782 | 45112 | 35109 | 20.77419355 | 45141 | 35138 | 19 | 45170 | 35167 | 16.56 | 45199 | 35196 | 14.58536585 |
| 45084 | 35081 | 23.26436782 | 45113 | 35110 | 20.73239437 | 45142 | 35139 | 18.975 | 45171 | 35168 | 16.42857143 | 45200 | 35197 | 14.52631579 |
| 45085 | 35082 | 23.26436782 | 45114 | 35111 | 20.71755725 | 45143 | 35140 | 18.84337349 | 45172 | 35169 | 16.29166667 | 45201 | 35198 | 14.52631579 |
| 45086 | 35083 | 23.20720721 | 45115 | 35112 | 20.71755725 | 45144 | 35141 | 18.81818182 | 45173 | 35170 | 16.26262626 | 45202 | 35199 | 14.5045045 |
| 45087 | 35084 | 23.20353982 | 45116 | 35113 | 20.65306122 | 45145 | 35142 | 18.59574468 | 45174 | 35171 | 16.18518519 | 45203 | 35200 | 14.45714286 |
| 45088 | 35085 | 23.1965812 | 45117 | 35114 | 20.56060606 | 45146 | 35143 | 18.5483871 | 45175 | 35172 | 16.1 | 45204 | 35201 | 14.375 |
| 45089 | 35086 | 23 | 45118 | 35115 | 20.55319149 | 45147 | 35144 | 18.4 | 45176 | 35173 | 16.06349206 | 45205 | 35202 | 14.352 |
| 45090 | 35087 | 23 | 45119 | 35116 | 20.4 | 45148 | 35145 | 18.4 | 45177 | 35174 | 16.04651163 | 45206 | 35203 | 14.34117647 |

FIG. 14 (Cont.)

| DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment |
|---|---|---|---|---|---|---|---|---|---|---|---|---|---|---|
| 45207 | 35204 | 14.31111111 | 45236 | 35233 | 11.3034188 | 45265 | 35262 | 9.397849462 | 45294 | 35291 | 7.419354839 | 45323 | 35320 | 5.111111111 |
| 45208 | 35205 | 14.23809524 | 45237 | 35234 | 11.23255814 | 45266 | 35263 | 9.2 | 45295 | 35292 | 7.263157895 | 45324 | 35321 | 5.04109589 |
| 45209 | 35206 | 14.13253012 | 45238 | 35235 | 11.02083333 | 45267 | 35264 | 9.2 | 45296 | 35293 | 7.263157895 | 45325 | 35322 | 5 |
| 45210 | 35207 | 14.11881188 | 45239 | 35236 | 11 | 45268 | 35265 | 9.2 | 45297 | 35294 | 7.040816327 | 45326 | 35323 | 4.928571429 |
| 45211 | 35208 | 14 | 45240 | 35237 | 10.98507463 | 45269 | 35266 | 9.139072848 | 45298 | 35295 | 6.85106383 | 45327 | 35324 | 4.912621359 |
| 45212 | 35209 | 13.85897436 | 45241 | 35238 | 10.97727273 | 45270 | 35267 | 9.117117117 | 45299 | 35296 | 6.731707317 | 45328 | 35325 | 4.791666667 |
| 45213 | 35210 | 13.66336634 | 45242 | 35239 | 10.79591837 | 45271 | 35268 | 8.877192982 | 45300 | 35297 | 6.571428571 | 45329 | 35326 | 4.75862069 |
| 45214 | 35211 | 13.5 | 45243 | 35240 | 10.51428571 | 45272 | 35269 | 8.761904762 | 45301 | 35298 | 6.571428571 | 45330 | 35327 | 4.75862069 |
| 45215 | 35212 | 13.4015748 | 45244 | 35241 | 10.47524752 | 45273 | 35270 | 8.715789474 | 45302 | 35299 | 6.478873239 | 45331 | 35328 | 4.75 |
| 45216 | 35213 | 13.34 | 45245 | 35242 | 10.45454545 | 45274 | 35271 | 8.576271186 | 45303 | 35300 | 6.405063291 | 45332 | 35329 | 4.735294118 |
| 45217 | 35214 | 13.25423729 | 45246 | 35243 | 10.38709677 | 45275 | 35272 | 8.363636364 | 45304 | 35301 | 6.388888889 | 45333 | 35330 | 4.717948718 |
| 45218 | 35215 | 13.14285714 | 45247 | 35244 | 10.35 | 45276 | 35273 | 8.363636364 | 45305 | 35302 | 6.325 | 45334 | 35331 | 4.677966102 |
| 45219 | 35216 | 13.04477612 | 45248 | 35245 | 10.22222222 | 45277 | 35274 | 8.363636364 | 45306 | 35303 | 6.301369863 | 45335 | 35332 | 4.666666667 |
| 45220 | 35217 | 13.01010101 | 45249 | 35246 | 10.15172414 | 45278 | 35275 | 8.30075188 | 45307 | 35304 | 6.272727273 | 45336 | 35333 | 4.658227848 |
| 45221 | 35218 | 12.85294118 | 45250 | 35247 | 10.12 | 45279 | 35276 | 8.117647059 | 45308 | 35305 | 6.272727273 | 45337 | 35334 | 4.624338624 |
| 45222 | 35219 | 12.77777778 | 45251 | 35248 | 10.03636364 | 45280 | 35277 | 8.05 | 45309 | 35306 | 6.2 | 45338 | 35335 | 4.487804878 |
| 45223 | 35220 | 12.65 | 45252 | 35249 | 10.01612903 | 45281 | 35278 | 8 | 45310 | 35307 | 6.075471698 | 45339 | 35336 | 4.380952381 |
| 45224 | 35221 | 12.26666667 | 45253 | 35250 | 9.966666667 | 45282 | 35279 | 8 | 45311 | 35308 | 6.069444444 | 45340 | 35337 | 4.380952381 |
| 45225 | 35222 | 12.21875 | 45254 | 35251 | 9.966666667 | 45283 | 35280 | 8 | 45312 | 35309 | 6.023809524 | 45341 | 35338 | 4.339622642 |
| 45226 | 35223 | 12.03076923 | 45255 | 35252 | 9.931818182 | 45284 | 35281 | 7.931034483 | 45313 | 35310 | 5.75 | 45342 | 35339 | 4.181818182 |
| 45227 | 35224 | 12.01801802 | 45256 | 35253 | 9.796296296 | 45285 | 35282 | 7.90625 | 45314 | 35311 | 5.75 | 45343 | 35340 | 4.181818182 |
| 45228 | 35225 | 11.94230769 | 45257 | 35254 | 9.779527559 | 45286 | 35283 | 7.853658537 | 45315 | 35312 | 5.75 | 45344 | 35341 | 3.956989247 |
| 45229 | 35226 | 11.9389313 | 45258 | 35255 | 9.757575758 | 45287 | 35284 | 7.790322581 | 45316 | 35313 | 5.609756098 | 45345 | 35342 | 3.942857143 |
| 45230 | 35227 | 11.92592593 | 45259 | 35256 | 9.706422018 | 45288 | 35285 | 7.666666667 | 45317 | 35314 | 5.411764706 | 45346 | 35343 | 3.898305085 |
| 45231 | 35228 | 11.9020979 | 45260 | 35257 | 9.654320988 | 45289 | 35286 | 7.666666667 | 45318 | 35315 | 5.411764706 | 45347 | 35344 | 3.833333333 |
| 45232 | 35229 | 11.87096774 | 45261 | 35258 | 9.583333333 | 45290 | 35287 | 7.666666667 | 45319 | 35316 | 5.348837209 | 45348 | 35345 | 3.833333333 |
| 45233 | 35230 | 11.69491525 | 45262 | 35259 | 9.558441558 | 45291 | 35288 | 7.666666667 | 45320 | 35317 | 5.111111111 | 45349 | 35346 | 3.833333333 |
| 45234 | 35231 | 11.61616162 | 45263 | 35260 | 9.492063492 | 45292 | 35289 | 7.666666667 | 45321 | 35318 | 5.111111111 | 45350 | 35347 | 3.833333333 |
| 45235 | 35232 | 11.5 | 45264 | 35261 | 9.470588235 | 45293 | 35290 | 7.419354839 | 45322 | 35319 | 5.111111111 | 45351 | 35348 | 3.793814433 |

FIG. 14 (Cont.)

| DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment | DNA SEQ ID NO | AA SEQ ID NO | Adipose 1 Enrichment |
|---|---|---|---|---|---|---|---|---|---|---|---|---|---|---|
| 45352 | 35349 | 3.744186047 | 45377 | 35374 | 2.76 | 45402 | 35399 | 2.059701493 | 45427 | 35424 | 1.550561798 | 45452 | 35449 | 1.210526316 |
| 45353 | 35350 | 3.72972973 | 45378 | 35375 | 2.705882353 | 45403 | 35400 | 2.059701493 | 45428 | 35425 | 1.550561798 | 45453 | 35450 | 1.210526316 |
| 45354 | 35351 | 3.72972973 | 45379 | 35376 | 2.639344262 | 45404 | 35401 | 2 | 45429 | 35426 | 1.533333333 | 45454 | 35451 | 1.194805195 |
| 45355 | 35352 | 3.68 | 45380 | 35377 | 2.628571429 | 45405 | 35402 | 2 | 45430 | 35427 | 1.533333333 | 45455 | 35452 | 1.179487179 |
| 45356 | 35353 | 3.631578947 | 45381 | 35378 | 2.555555556 | 45406 | 35403 | 2 | 45431 | 35428 | 1.533333333 | 45456 | 35453 | 1.179487179 |
| 45357 | 35354 | 3.607843137 | 45382 | 35379 | 2.555555556 | 45407 | 35404 | 1.971428571 | 45432 | 35429 | 1.46031746 | 45457 | 35454 | 1.164556962 |
| 45358 | 35355 | 3.59375 | 45383 | 35380 | 2.555555556 | 45408 | 35405 | 1.890410959 | 45433 | 35430 | 1.452631579 | 45458 | 35455 | 1.15 |
| 45359 | 35356 | 3.577777778 | 45384 | 35381 | 2.555555556 | 45409 | 35406 | 1.87755102 | 45434 | 35431 | 1.4375 | 45459 | 35456 | 1.15 |
| 45360 | 35357 | 3.538461538 | 45385 | 35382 | 2.509090909 | 45410 | 35407 | 1.87755102 | 45435 | 35432 | 1.4375 | 45460 | 35457 | 1.15 |
| 45361 | 35358 | 3.538461538 | 45386 | 35383 | 2.509090909 | 45411 | 35408 | 1.858585859 | 45436 | 35433 | 1.4375 | 45461 | 35458 | 1.135802469 |
| 45362 | 35359 | 3.484848485 | 45387 | 35384 | 2.486486486 | 45412 | 35409 | 1.84 | 45437 | 35434 | 1.4375 | 45462 | 35459 | 1.12195122 |
| 45363 | 35360 | 3.45 | 45388 | 35385 | 2.464285714 | 45413 | 35410 | 1.803921569 | 45438 | 35435 | 1.415384615 | 45463 | 35460 | 1.108433735 |
| 45364 | 35361 | 3.421487603 | 45389 | 35386 | 2.442477876 | 45414 | 35411 | 1.769230769 | 45439 | 35436 | 1.38 | 45464 | 35461 | 1.095238095 |
| 45365 | 35362 | 3.345454545 | 45390 | 35387 | 2.421052632 | 45415 | 35412 | 1.769230769 | 45440 | 35437 | 1.352941176 | 45465 | 35462 | 1.095238095 |
| 45366 | 35363 | 3.285714286 | 45391 | 35388 | 2.38961039 | 45416 | 35413 | 1.769230769 | 45441 | 35438 | 1.333333333 | 45466 | 35463 | 1.095238095 |
| 45367 | 35364 | 3.228070175 | 45392 | 35389 | 2.262295082 | 45417 | 35414 | 1.703703704 | 45442 | 35439 | 1.314285714 | 45467 | 35464 | 1.078125 |
| 45368 | 35365 | 3.136363636 | 45393 | 35390 | 2.243902439 | 45418 | 35415 | 1.703703704 | 45443 | 35440 | 1.314285714 | 45468 | 35465 | 1.069767442 |
| 45369 | 35366 | 3.066666667 | 45394 | 35391 | 2.225806452 | 45419 | 35416 | 1.703703704 | 45444 | 35441 | 1.295774648 | 45469 | 35466 | 1.069767442 |
| 45370 | 35367 | 3.066666667 | 45395 | 35392 | 2.19047619 | 45420 | 35417 | 1.703703704 | 45445 | 35442 | 1.277777778 | 45470 | 35467 | 1.069767442 |
| 45371 | 35368 | 3.066666667 | 45396 | 35393 | 2.15625 | 45421 | 35418 | 1.703703704 | 45446 | 35443 | 1.277777778 | 45471 | 35468 | 1.069767442 |
| 45372 | 35369 | 3.016393443 | 45397 | 35394 | 2.123076923 | 45422 | 35419 | 1.642857143 | 45447 | 35444 | 1.243243243 | 45472 | 35469 | 1.057471264 |
| 45373 | 35370 | 2.967741935 | 45398 | 35395 | 2.090909091 | 45423 | 35420 | 1.642857143 | 45448 | 35445 | 1.210526316 | 45473 | 35470 | 1.045454545 |
| 45374 | 35371 | 2.875 | 45399 | 35396 | 2.090909091 | 45424 | 35421 | 1.586206897 | 45449 | 35446 | 1.210526316 | 45474 | 35471 | 1.022222222 |
| 45375 | 35372 | 2.816326531 | 45400 | 35397 | 2.090909091 | 45425 | 35422 | 1.559322034 | 45450 | 35447 | 1.210526316 | | | |
| 45376 | 35373 | 2.787878788 | 45401 | 35398 | 2.07518797 | 45426 | 35423 | 1.550561798 | 45451 | 35448 | 1.210526316 | | | |

FIG. 17A

Presence in viral library

| AA | # | A | C | D | E | F | G | H | I | K | L | M | N | P | Q | R | S | T | V | W | Y |
|---|---|---|---|---|---|---|---|---|---|---|---|---|---|---|---|---|---|---|---|---|---|
| 452 | - | + | o | + | + | - | + | + | - | o | o | o | + | - | + | o | + | + | o | - | - |
| 453 | - | + | - | o | o | - | ++ | + | o | + | o | o | + | + | + | o | + | + | o | - | - |
| 454 | - | + | - | + | + | - | + | + | o | + | - | o | + | + | + | o | + | + | o | - | - |
| 455 | - | + | - | + | + | - | ++ | + | - | ++ | - | - | + | + | + | o | + | + | o | - | - |
| 456 | - | + | - | + | o | - | + | + | - | ++ | - | - | o | + | + | o | + | + | o | - | - |
| 457 | - | + | - | + | o | - | + | + | o | + | o | + | + | + | o | o | + | + | o | - | - |
| 458 | - | + | o | o | + | - | ++ | o | - | + | o | + | o | o | + | + | + | + | + | - | - |

Prevalence: ++ + o - -- (high to low)

FIG. 17B

| SEQ ID NO | Variant | 450-451 | 452-458 7AA Sub | 459-560 |
|---|---|---|---|---|
| 1 | AAV9 | TI | NGSGQNQ | QT |
| 5 | PHP.eB | TI | NGSGQNQ | QT |
| 2933 | AAV.CAP-B1 | TI | LQTSPG | QT |
| 79 | AAV.CAP-B2 | TI | QQGKQSV | QT |
| 45475 | AAV.CAP-B4 | TI | SINTKTN | QT |
| 442 | AAV.CAP-B7 | TI | SNGTKQT | QT |
| 88 | AAV.CAP-B8 | TI | GSGKTAA | QT |
| 2466 | AAV.CAP-B9 | TI | MGDKPTR | QT |
| 3943 | AAV.CAP-B10 | TI | DGAATKN | QT |
| 2672 | AAV.CAP-B11 | TI | QPSGGNT | QT |
| 5192 | AAV.CAP-B14 | TI | ERGANTK | QT |
| 2743 | AAV.CAP-B16 | TI | TTGGHSS | QT |
| 3064 | AAV.CAP-B17 | TI | GTTKTSE | QT |
| 11958 | AAV.CAP-B18 | TI | GTGTSVL | QT |
| 780 | AAV.CAP-B19 | TI | NQSGTKG | QT |
| 2764 | AAV.CAP-B22 | TI | DGQSSKS | QT |
| 45476 | AAV.CAP-B23 | TI | KGPGQMG | QT |
| 2741 | AAV.CAP-B25 | TI | GTPSKAG | QT |

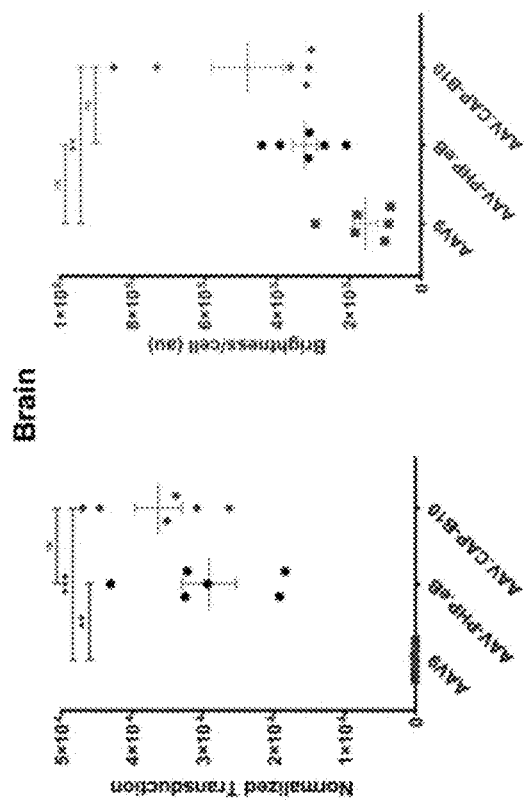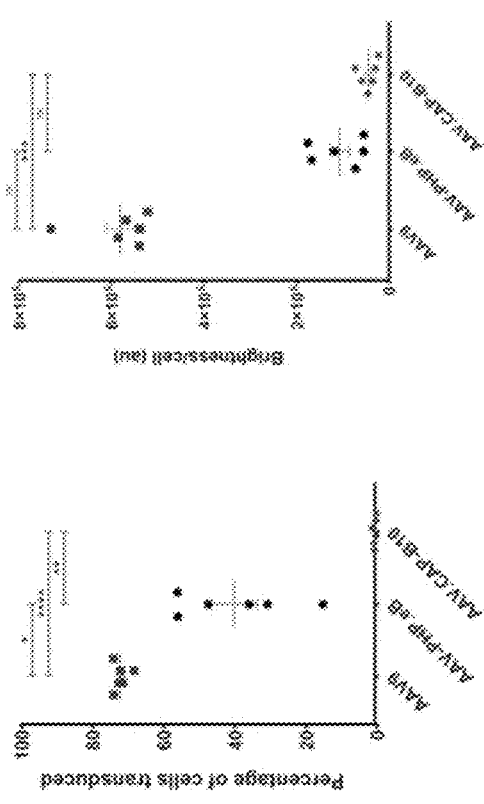
FIG. 18C Brain
FIG. 18D Liver

FIG. 20A

Enriched in brain

| AA | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 452 | o | - | +++ | +++ | - | + | o | - | - | - | o | ++ | - | ++ | - | o | o | o | - | - |
| 453 | o | o | o | o | - | + | o | o | o | - | o | ++ | - | ++ | - | o | o | o | - | - |
| 454 | o | - | + | + | - | + | o | o | o | - | - | + | - | + | - | o | o | o | - | - |
| 455 | o | - | + | + | - | o | o | - | +++ | - | - | + | - | ++ | - | o | o | - | - | - |
| 456 | o | - | + | + | - | o | o | - | +++ | - | - | + | - | + | - | o | o | - | - | - |
| 457 | + | - | + | o | - | o | - | o | o | - | o | +++ | + | + | - | o | o | - | - | - |
| 458 | o | - | + | ++ | - | + | + | + | ++ | - | o | + | - | + | - | - | + | o | - | - | z-score

| +++ | 3 |
| ++ | 2 |
| + | 1 |
| o | 0 |
| - | -1 |
| -- | -2 |

De-targeted from liver

| AA | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 452 | 0 | 0 | +++ | + | - | 0 | ++ | - | 0 | - | + | + | - | + | - | - | + | 0 | - | - |
| 453 | 0 | -- | + | 0 | - | - | + | + | 0 | - | + | +++ | 0 | +++ | - | - | + | 0 | - | - |
| 454 | 0 | -- | + | 0 | -- | - | + | + | + | - | 0 | + | - | + | - | - | + | - | -- | -- |
| 455 | 0 | -- | + | + | -- | - | + | + | + | - | 0 | + | 0 | + | - | - | + | - | -- | -- |
| 456 | 0 | -- | + | 0 | -- | - | + | - | + | - | -- | + | + | + | - | - | 0 | - | -- | -- |
| 457 | 0 | -- | 0 | - | - | - | ++ | + | 0 | - | 0 | + | + | + | - | - | + | + | -- | - |
| 458 | 0 | 0 | + | - | - | - | ++ | + | + | - | + | + | - | ++ | - | - | + | + | -- | - | z-score

Enriched in brain and de-targeted from liver

| AA  | A | C | D  | E  | F | G | H | I | K  | L | M | N  | P | Q | R | S | T | V | W | Y |
|-----|---|---|----|----|---|---|---|---|----|---|---|----|---|---|---|---|---|---|---|---|
| 452 | 0 | - | ++ | ++ | 0 | 0 | + | + | +  | - | + | +  | - | - | - | - | 0 | - | - | - |
| 453 | 0 | - | ++ | +  | - | 0 | + | + | +  | - | + | +  | - | + | - | - | 0 | - | - | - |
| 454 | 0 | - | ++ | ++ | - | 0 | + | + | +  | - | 0 | +  | - | + | - | - | 0 | - | - | - |
| 455 | 0 | - | ++ | ++ | - | 0 | 0 | - | +  | - | - | +  | - | + | - | - | 0 | - | - | - |
| 456 | 0 | - | +  | +  | - | 0 | + | + | +  | - | - | +  | - | + | - | - | 0 | - | - | - |
| 457 | 0 | - | +  | +  | - | 0 | + | + | +  | - | + | ++ | 0 | 0 | - | - | 0 | - | - | - |
| 458 | 0 | - | +  | +  | 0 | 0 | + | + | ++ | - | + | +  | - | + | - | - | 0 | 0 | - | - | z-score

| +++ | ++ | + | 0 | - | -- |
|-----|----|----|---|---|----|
| 3   | 2  | 1  | 0 | -1| -2 |

FIG. 23A
FIG. 23B
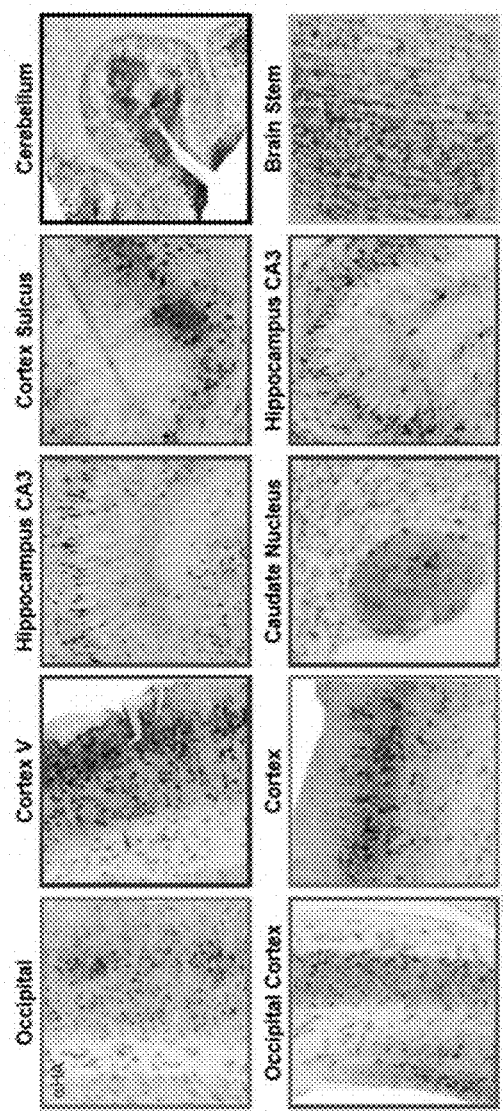
FIG. 23C
FIG. 23D

ADENO-ASSOCIATED VIRUS COMPOSITIONS FOR TARGETED GENE THERAPY

CROSS-REFERENCE

This application claims the benefit of U.S. Provisional Application Ser. No. 62/736,904, filed Sep. 26, 2018, and U.S. Provisional Application Ser. No. 62/832,812, filed Apr. 11, 2019, both of which are incorporate herein by reference in their entirety.

STATEMENT REGARDING FEDERALLY SPONSORED RESEARCH OR DEVELOPMENT

This invention was made with government support under Grant No. NS087949 awarded by the National Institutes of Health and under grant No. W911NF-17-2-0036 awarded by DARPA. The government has certain rights in the invention.

SEQUENCE LISTING

The instant application contains a Sequence Listing which has been submitted electronically in ASCII format and is hereby incorporated by reference in its entirety. Said ASCII copy, created on Sep. 20, 2019, is named 38075-733_201_SL.txt and is 10,656,833 bytes in size.

BACKGROUND

Recombinant adeno-associated viruses (rAAVs) are increasingly used for gene delivery in basic scientific research and therapeutic applications because of their ability to transduce both dividing and non-dividing cells, their long-term persistence as episomal DNA in infected cells, and their low immunogenicity. These characteristics make them appealing for applications in both basic science and in clinics, such as gene therapy. Current gene therapy approaches for many disorders have focused on direct delivery to increase transduction efficiency and restrict expression only to the cell types affected. However, this administrative route has led to limited success across many clinical trials and diseases due to the limited coverage of localized delivery.

Intravenous administration addresses these limitations and allows for broad and efficient access to tissues and organs throughout the body in a non-invasive manner. Unfortunately, the naturally occurring serotypes have limited transduction of certain cell types and organs, and non-specific, overlapping tropisms in others. This leads to several complications in gene therapy applications, including but not limited to off-target effects due to transduction of unimpacted organs and cell types (in particular, the liver), and the necessity for a larger viral load to achieve sufficient therapeutic levels in the tissue or organ of interest. In addition, even with systemic delivery, current rAAV-mediated gene therapies lack the specificity to cross the blood brain barrier (BBB) or the epithelium, limiting their reach as therapeutic interventions for disease and conditions of the brain or organs (e.g., the lung).

Thus, there is a need for rAAVs capable of achieving high specificity to target specific cell types or organs and low specificity for unimpacted (off-target) organs and cell types in a subject when delivered to the subject systemically (e.g., intravenously, intranasally).

SUMMARY

Disclosed herein are recombinant AAVs (rAAVs) comprising capsids with specificity engineered into the capsid structure through iterative rounds of positive and negative selection. This engineering yields rAAV variants with altered specificity for certain tissues or organs relative to the unmodified parental capsid from which they were derived. In some embodiments, the rAAV variant comprises an AAV capsid protein having a 7-mer peptide substitution at the residues corresponding to amino acids 452-458 of the AAV9 capsid protein VP1. In certain embodiments, the substitution is of amino acids 452-458 of AAV9 VP1. In certain other embodiments, the substitution is of amino acids 452-458 of AAV-PHP.B VP1. In yet other embodiments, the substitution is of amino acids 452-458 of AAV-PHP.eB VP1. In some embodiments, the substitution reduces the tropism of the rAAV capsid for a cell or tissue, enabling the rAAV variant to reduce the off-target effects of therapeutic viral transduction, thereby obviating a need for larger viral dosage amounts. In some embodiments, the substitution increases the tropism of the rAAV capsid for a cell or tissue, enabling the rAAV variant to achieve widespread transduction to a target environment (e.g., target cell types or tissues) in a subject upon systemic delivery (e.g., intravenous injection). Typically, the 7-mer peptide substitution is not ILGTGTS (SEQ ID NO: 45479), QSSQTPR (SEQ ID NO: 45480), or TLAVPFK (SEQ ID NO: 45477). The rAAVs described herein are identified using a modified version of the Cre recombination-based AAV targeted evolution (CREATE) method. The Multiplexed-CREATE (M-CREATE) method generates enhanced transduction efficiency and/or specificity by introducing variations in the capsid protein sequence, unbiased in vivo selection and recovery of only those variants that travel to defined cell populations, cross the cell membrane, travel to the nucleus, and unpackage and express their genetic payload. Variant capsids exhibiting the most desirable tropism (e.g., enhanced efficiency and specificity for a particular in vivo environment) are recovered and identified by deep sequencing. Strategies for unbiased selection and analysis include determining variants' enrichment score (by normalizing the target tissue library to starting virus library) and unbiased propagation between rounds of selections through a synthetic library construction (where each variant is represented equally). The detailed characterizations of the resultant libraries from sequencing data is also described herein, which provide useful insights on the selection of variants towards a target.

Also disclosed herein are AAV capsid libraries comprising AAV capsid proteins having 7-mer peptide substitutions at the residues corresponding to amino acids 452-458 of AAV9 VP1. In some embodiments, the library is a library of capsids comprising 7-mer peptide substitutions at amino acids 452-458 of the AAV9 variant AAV-PHP.eB or AAV-PHP.B. Such libraries find particular use in in vivo positive selections across different brain cell types (e.g., endothelial cells, neurons, and astrocytes) and negative selections across the liver, such libraries having been shown herein to yield a large pool of AAV9 variants with enhanced ability to cross the BBB, broadly transduce the central nervous system (CNS), and de-target off-target in vivo environments, e.g., the liver. In other embodiments, the library is an AAV capsid library comprising AAV capsid proteins having 7-mer peptide substitutions at amino acids 452-458 of AAV9. Such libraries find particular use in in vivo selections across different organs, such as the spinal cord, brain, a liver, a stomach, an intestine, a lung, a heart, teste, spleen, adipose (fat), and muscle.

Also disclosed herein are methods and kits for producing therapeutic recombinant AAV (rAAV) particles, as well as methods and pharmaceutical compositions or formulations comprising the rAAV particles for the treatment of a disease or condition affecting, for e.g., the CNS, PNS, or target in vivo environment in a subject in need thereof (e.g., lung).

Aspects disclosed herein provide recombinant AAV (rAAVs), the rAAV comprising: (a) a variant AAV capsid comprising a variant AAV capsid protein comprising an amino acid substitution of three or more amino acids within a 7-mer peptide sequence at a 3-fold axis of symmetry of a corresponding parental AAV capsid protein, wherein the 7-mer peptide sequence is at an amino acid position that corresponds to amino acid residues 452-458 of AAV9 VP1 (SEQ ID NO:1), and wherein the amino acid substitution is not ILGTGTS (SEQ ID NO: 45479), QSSQTPR (SEQ ID NO: 45480), or TLAVPFK (SEQ ID NO: 45477); and (b) a heterologous polynucleotide comprising a nucleotide sequence encoding a gene product. In some embodiments, the variant AAV capsid has an increased tropism for a target tissue or a target cell, when measured in a subject, relative to a tropism of the corresponding parental AAV capsid. In some embodiments, the target tissue or the target cell comprises a tissue or a cell of a central nervous system (CNS) or a peripheral nervous system (PNS), or a combination thereof. In some embodiments, the variant AAV capsid has a decreased tropism for an off-target tissue comprising liver tissue or an off-target cell comprising a liver cell, when measured in a subject, relative to the tropism of the corresponding parental AAV capsid. In some embodiments, the three or more amino acids comprise three contiguous amino acids, each amino acid independently selected from the group consisting of A, D, E, G, K, H, M, N, P, L Q, S, T, and V at amino acid positions in the parental AAV capsid protein corresponding to amino acid residues 452-454, 453-455, 454-456, 455-457, or 456-458 of AAV9 VP1 (SEQ ID NO: 1). In some embodiments, the three or more amino acids comprise four contiguous amino acids, each amino acid independently selected from the group consisting of A, D, E, G, K, H, M, N, P, L Q, S, T, and V at amino acid positions in the parental AAV capsid protein corresponding to amino acid residues 452-455, 453-456, 454-457, or 455-458 of AAV9 VP1 (SEQ ID NO: 1). In some embodiments, three or more amino acids comprise at least five contiguous amino acids, each amino acid independently selected from the group consisting of A, D, E, G, K, H, M, N, P, L Q, S, T, and V at amino acid positions in the parental AAV capsid protein corresponding to amino acid residues 452-456, 453-457, or 454-458 of AAV9 VP1 (SEQ ID NO: 1). In some embodiments, the three or more amino acids comprise three or more of: (a) A, D, E, G, H, M, N, Q, S, T, or V substituted at an amino acid position corresponding to amino acid residue 452 of AAV9 VP1 (SEQ ID NO: 1); (b) A, D, E, G, K, N, Q, S, T, or V substituted at an amino acid position corresponding to amino acid residue 453 of AAV9 VP1 (SEQ ID NO: 1); (c) A, D, E, G, K, N, Q, S, T, or V substituted at amino acid position corresponding to amino acid residue 454 of AAV9 VP1 (SEQ ID NO: 1); (d) A, D, E, G, K, N, P, Q, S, or T substituted at an amino acid position corresponding to amino acid residue 455 of AAV9 VP1 (SEQ ID NO: 1); (e) A, D, E, G, H, K, N, P, Q, S, or T substituted at an amino acid position corresponding to amino acid residue 456 of AAV9 VP1 (SEQ ID NO: 1); (f) A, D, E, G, K, N, P, S, T, or V substituted at an amino acid position corresponding to amino acid residue 457 of AAV9 VP1 (SEQ ID NO: 1); and (g) A, E, G, H, K, L, N, Q, S, T, or V substituted at amino acid position corresponding to amino acid residue 458 of AAV9 VP1 (SEQ ID NO: 1). In some embodiments, the three or more amino acids comprise three or more of: (a) A, D, E, G, H, K, L, M, N, Q, S, T, or V substituted at an amino acid position corresponding to amino acid residue 452 of AAV9 VP1 (SEQ ID NO: 1); (b) A, D, G, H, M, N, P, Q, S, T, or V substituted at an amino acid position corresponding to amino acid residue 453 of AAV9 VP1 (SEQ ID NO: 1); (c) A, D, E, G, K, N, Q, S, T, or V substituted at amino acid position corresponding to amino acid residue 454 of AAV9 VP1 (SEQ ID NO: 1); (d) A, D, E, G, K, N, P, Q, S, or T substituted at an amino acid position corresponding to amino acid residue 455 of AAV9 VP1 (SEQ ID NO: 1); (e) A, D, G, K, N, P, Q, S, or T substituted at an amino acid position corresponding to amino acid residue 456 of AAV9 VP1 (SEQ ID NO: 1); (f) A, G, H, L, M, N, P, Q, S, T, or V substituted at an amino acid position corresponding to amino acid residue 457 of AAV9 VP1 (SEQ ID NO: 1); and (g) A, D, E, G, H, I, K, L, N, Q, R, S, T, or V substituted at amino acid position corresponding to amino acid residue 458 of AAV9 VP1 (SEQ ID NO: 1). In some embodiments, the amino acid substitution comprises an amino acid sequence selected from DGAATKN (SEQ ID NO: 3943), and DGQSSKS (SEQ ID NO: 2764). In some embodiments, the three or more amino acids comprises three or more of: (a) A, D, G, L, N, Q, S, or T substituted at an amino acid at a position corresponding to amino acid residue 452 of AAV9 VP1 (SEQ ID NO: 1); (b) A, G, N, P, Q, R, S, or substituted at an amino acid at a position corresponding to amino acid residue 453 of AAV9 VP1 (SEQ ID NO: 1); (c) A, D, G, N, S, or T substituted at an amino acid at a position corresponding to amino acid residue 454 of AAV9 VP1 (SEQ ID NO: 1); (d) A, D, G, K, N, P, Q, S, or T substituted at an amino acid at a position corresponding to amino acid residue 455 of AAV9 VP1 (SEQ ID NO: 1); (e) A, G, K, N, P, R, S, or T substituted at an amino acid at a position corresponding to amino acid residue 456 of AAV9 VP (SEQ ID NO: 1); (f) A, G, K, N, P, R, S, T, or V substituted at an amino acid at a position corresponding to amino acid residue 457 of AAV9 VP1 (SEQ ID NO: 1); and (g) A, G, K, L, R, S, T, or V substituted at an amino acid at a position corresponding to amino acid residue 458 of AAV9 VP1 (SEQ ID NO: 1). In some embodiments, the amino acid substitution comprises an amino acid sequence selected from the group consisting of LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), KGPGQMG (SEQ ID NO: 45476), and GTPSKAG (SEQ ID NO: 2741). In some embodiments, the target tissue or the target cell in the tissue is selected from the group consisting of lung, intestine, kidney, heart, and stomach. In some embodiments, the three or more amino acids comprise three contiguous amino acids at an amino acid position corresponding to amino acid residues 452-454, 453-455, 454-456, 455-457, or 456-458 of AAV9 VP1, wherein: (a) 452 is selected from the group consisting of N, K, R, and T; (b) 453 is selected from the group consisting of L, N, P, and S; (c) 454 is selected from the group consisting of A, D, G, N, S, and T; (d) 455 is selected from the group consisting of L, P, S, and T; (e) 456 is selected from the group consisting of P, R, and S; (f) 457 is selected from the group consisting of G, N, S, and T; and (g) 458 is selected from the group consisting of I, L, and R. In some embodiments, the three or more amino acids comprise: (a) four contiguous amino acids at an amino acid position corresponding to amino acid residues 452-455, 453-456, 454-457, or 455-458 of AAV9 VP1 (SEQ ID NO:

1); (b) five contiguous amino acids at an amino acid position corresponding to amino acid residues 452-456, 453-457, or 453-458 of AAV9 VP1 (SEQ ID NO: 1); (c) six contiguous amino acids at an amino acid position corresponding to amino acid residues 452-457 or 453-458 of AAV9 VP1 (SEQ ID NO: 1); and (d) seven contiguous amino acids at an amino acid position corresponding to amino acid residues 452-458 of AAV9 VP1 (SEQ ID NO: 1). In some embodiments, the target tissue is lung, and the three or more amino acids are provided in an amino acid sequence comprising KDNTPGR (SEQ ID NO: 32538), NNLPRNL (SEQ ID NO: 32867), or any amino acid sequence provided in FIG. 13. In some embodiments, the target tissue is intestine, and the three or more amino acids are provided in an amino acid sequence comprising RESSPSL (SEQ ID NO: 26474), KDNTPGR (SEQ ID NO: 26584), or any amino acid sequence provided in FIG. 5. In some embodiments, the tissue is kidney, and the three or more amino acids are provided in an amino acid sequence comprising RVPLSTI (SEQ ID NO: 26933), NNLPRNL (SEQ ID NO: 27530), KDNTPGR (SEQ ID NO: 28509), or any amino acid sequence provided in FIG. 6. In some embodiments, the tissue is heart, and the three or more amino acids are provided in an amino acid sequence comprising KDNTPGR (SEQ ID NO: 25633), or any amino acid sequence provided in FIG. 4. In some embodiments, the tissue is stomach, and the three or more amino acids are provided in an amino acid sequence comprising RESSPSL (SEQ ID NO: 31904) or any amino acid sequence of FIG. 12. In some embodiments, the corresponding parental AAV capsid protein is AAV9 VP1 or a variant thereof. In some embodiments, the AAV9 VP1 variant has a sequences identity of 90% or more to SEQ ID NO:1. In some embodiments, the AAV9 VP1 variant has a sequences identity of 95% or more to SEQ ID NO:1. In some embodiments, the corresponding parental AAV capsid protein further comprises an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), at an amino acid position corresponding to 588_589 of the AAV9 VP1 (SEQ ID NO: 1), wherein X is any amino acid other than V. In some embodiments, the parental AAV capsid protein is from AAV-PHP.B or AAV-PHP.eB. In some embodiments, the rAAV is isolated and purified.

Aspects disclosed herein provide pharmaceutical formulations comprising the rAAV of the present disclosure and a pharmaceutical excipient. In some embodiments, the pharmaceutical formulation is formulated for intravenous, intraarterial, intranasal, intrathecal, intracisternae magna, or subcutaneous injection.

Aspects disclosed herein provide methods of treating a disease or condition in a subject, the method comprising administering to the subject a therapeutically effective amount the rAAV of the present disclosure, or the pharmaceutical formulation of the present disclosure, wherein the gene product is a therapeutic gene product. In some embodiments, the administering is by intravenous, intraarterial, intranasal, intrathecal, intracisternae magna, or subcutaneous injection. In some embodiments, the disease or the condition is selected from the group consisting of pulmonary fibrosis, surfactant protein disorders, peroxisome biogenesis disorders, or COPD. In some embodiments, the disease of the condition is a central nervous system (CNS) peripheral nervous system (PNS) disorder.

A method of manufacturing an rAAV of the present disclosure, the method comprising: (a) introducing into a cell a nucleic acid comprising: (i) a first nucleic acid sequence encoding a therapeutic gene expression product enclosed by a 5' and a 3' inverted terminal repeat (ITR) sequence; (ii) a second nucleic acid sequence encoding a viral genome comprising a 5' ITR sequence, a Replication (Rep) gene, Capsid (Cap) gene, and a 3' ITR, wherein the Cap gene encodes a rAAV capsid protein; and (iii) a third nucleic acid sequence encoding a first helper virus protein selected from the group consisting of E4orf6, E2a, and VA RNA, and optionally, a second helper virus protein comprising E1a or E1b55k; (b) expressing in the cell the AAV capsid protein; (c) assembling the rAAV of the present disclosure; and (d) packaging the first nucleic acid sequence in the rAAV. Aspects disclosed herein provide variant adeno-associated virus (AAV) capsids comprising: (a) at least one of a decreased specificity and a decreased transduction efficiency, as measured in a liver of a primate subject when delivered to the primate subject intravenously, relative to a corresponding parental AAV capsid with an AAV capsid protein of SEQ ID NO: 1; and (b) at least one of an increased specificity and an increased transduction efficiency, as measured in a central nervous system (CNS) of the primate subject when delivered to the primate subject intravenously, relative to the corresponding parental AAV capsid. In some embodiments, the variant AAV capsids further comprising a variant AAV capsid protein comprising an amino acid substitution of three or more amino acids within a 7-mer peptide sequence at an amino acid position that corresponds to amino acid residues 452-458 of AAV9 VP1 (SEQ ID NO:1). In some embodiments, the three or more amino acids comprise three contiguous amino acids, each amino acid independently selected from the group consisting of A, D, E, G, K, H, M, N, P, L Q, S, T, and V at amino acid positions in the parental AAV capsid protein corresponding to amino acid residues 452-454, 453-455, 454-456, 455-457, or 456-458 of AAV9 VP1 (SEQ ID NO: 1). In some embodiments, the 7-mer peptide sequence is DGAATKN (SEQ ID NO: 3943). In some embodiments, the variant AAV capsid protein further comprises an amino acid sequence that is at least 96% identical to an amino acid sequence between amino acid 217 to amino acid 736 of SEQ ID NO: 1. In some embodiments, the amino acid substitution is not ILGTGTS (SEQ ID NO: 45479), QSSQTPR (SEQ ID NO: 45480), or TLAVPFK (SEQ ID NO: 45477). In some embodiments, the variant AAV capsid protein further comprises an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), at an amino acid position corresponding to 588_589 of the AAV9 VP1 (SEQ ID NO: 1), wherein X is any amino acid other than V. Aspects disclosed herein provide variant adeno-associated virus (AAV) capsids comprising: (a) a variant AAV capsid protein comprising an amino acid sequence with an amino acid substitution of three or more amino acids within a 7-mer peptide sequence at an amino acid position that corresponds to amino acid residues 452-458 of AAV9 VP1 (SEQ ID NO: 1); and (b) at least one of an increased specificity and increased transduction efficiency in a target tissue as measured in the target tissue of a subject when delivered to the subject intranasally or intravenously, relative to a corresponding parental AAV capsid protein of SEQ ID NO: 1 or SEQ ID NO: 2, wherein the target tissue is selected from the group consisting of lung, intestine, kidney, heart, and stomach. In some embodiments, the three or more amino acids comprise three contiguous amino acids at an amino acid position corresponding to amino acid residues 452-454, 453-455, 454-456, 455-457, or 456-458 of AAV9 VP1, wherein: (a) 452 is selected from the group consisting of N, K, R, and T; (b) 453 is selected from the group consisting of L, N, P, and S; (c) 454 is selected from the group consisting of A, D, G, N, S, and T; (d) 455 is selected from the group consisting of L, P, S, and T; (e) 456 is selected from the group consisting of P, R, and S; (f) 457 is selected from the group consisting of G, N, S, and T; and (g) 458 is selected from the group consisting of I, L, and R. In some embodiments, the target tissue is the lung, and the three or more amino acids are provided in an amino acid sequence comprising KDNTPGR (SEQ ID NO: 32538), NNLPRNL (SEQ ID NO: 32867), or any amino acid sequence provided in FIG. 13. In some embodiments, the target tissue is the intestine, and the three or more amino acids are provided in an amino acid sequence comprising RESSPSL (SEQ ID NO: 26474), KDNTPGR (SEQ ID NO: 26584), or any amino acid sequence provided in FIG. 5. In some embodiments, the tissue is the kidney, and the three or more amino acids are provided in an amino acid sequence comprising RVPLSTI (SEQ ID NO: 26933), NNLPRNL (SEQ ID NO: 27530), KDNTPGR (SEQ ID NO: 28509), or any amino acid sequence provided in FIG. 6. In some embodiments, the tissue is the heart, and the three or more amino acids are provided in an amino acid sequence comprising KDNTPGR (SEQ ID NO: 25633), or any amino acid sequence provided in FIG. 4. In some embodiments, the tissue is the stomach, and the three or more amino acids are provided in an amino acid sequence comprising RESSPSL (SEQ ID NO: 31904) or any amino acid sequence of FIG. 12. In some embodiments, the variant AAV capsid protein further comprises an amino acid sequence that is at least 96% identical to an amino acid sequence between amino acid 217 to amino acid 736 of SEQ ID NO: 1. In some embodiments, the variant AAV capsid of the present disclosure is isolated and purified. In some embodiments, the variant AAV capsid of the present disclosure is formulated as a pharmaceutical formulation further comprising a pharmaceutically acceptable carrier. In some embodiments, the pharmaceutical formulation is formulated for intranasal or intravenous administration.

Aspects disclosed provide methods of treating a disease or condition in a subject, the method comprising administering to the subject a therapeutically effective amount the rAAV of the present disclosure or the pharmaceutical formulation of the present disclosure. In some embodiments, the disease or the condition is selected from the group consisting of pulmonary fibrosis, surfactant protein disorders, peroxisome biogenesis disorders, chronic obstructive pulmonary disease (COPD), a CNS disease or condition, and a PNS disease or condition.

Aspects disclosed herein provide recombinant adeno-associated virus (rAAV) capsids comprising variant AAV capsid proteins, the rAAV capsids having at least one of an increased specificity and an increased transduction efficiency when measured in a target tissue in a primate subject relative to the corresponding parental AAV capsid, and at least one of a decreased specificity and a decreased transduction efficiency when measured in an off-target tissue in the primate subject relative to the corresponding parental AAV capsid. In some instances, the specificity or the transduction efficiency is measured following administration of the rAAV capsid to the subject intravenously, intraarterially, intrathecally, or subcutaneously. In some instances, the rAAV capsid is chimeric. In some instances, the rAAV, or variant AAV protein comprises therein, confer an increase in a localization of the rAAV within the target tissue, as compared to the parental AAV capsid or capsid protein.

In some instances, the variant AAV capsid protein (and rAAV capsid) comprises an amino acid substitution to an amino acid selected from the group consisting of A, D, E, G, K, H, M, N, P, L Q, S, T, and V at one or more amino acid positions corresponding to one or more of residues 452-458 in an amino acid sequence of the AAV9 VP1 capsid protein provided in SEQ ID NO: 1. In some instances, the amino acid sequence of the AAV9 capsid protein is provided in amino acid 217-736 within SEQ ID NO: 1. In some instances, the target tissue is the central nervous system (CNS). In some instances, the CNS comprises a region selected from the neocortex, the basal ganglia, the hippocampus, the thalamus, the cerebellum, the brain stem, and the spinal cord. In some embodiments, the target tissue is the peripheral nervous system (PNS). In some instances, the PNS comprises a ganglion. In some instances, the ganglion comprises a trigeminal or dorsal root ganglion. In some instances, the target tissue is a non-dividing cell. In some instances, the non-dividing cell is selected from the group consisting of a neuron, an astrocyte, a microglial cell, an oligodendrocyte, and a Schwann cell. In some instances, the off-target tissue is a liver. In some instances, VP1, VP2, and VP3 of the AAV capsid comprise the amino acid substitution. In some instances, the amino acid substitution is at a three (3)-fold axis of symmetry of a corresponding parental AAV capsid protein. In some instances, the amino acid substitution comprises at least three contiguous amino acids, each amino acid independently selected from the group consisting of A, D, E, G, K, H, M, N, P, L Q, S, T, and V at amino acid positions corresponding to residues 452-454, 453-455, 454-456, 455-457, or 456-458 of the amino acid sequence of the AAV9 VP1 capsid protein. In some instances, the amino acid substitution comprises at least four contiguous amino acids, each amino acid independently selected from the group consisting of A, D, E, G, K, H, M, N, P, L Q, S, T, and V at amino acid positions corresponding to residues 452-455, 453-456, 454-457, or 455-458 of the amino acid sequence of the AAV9 VP1 capsid protein. In some instances, the amino acid substitution comprises at least five contiguous amino acids, each amino acid independently selected from the group consisting of A, D, E, G, K, H, M, N, P, L Q, S, T, and V at amino acid positions corresponding to residues 452-456, 453-457, or 454-458 of the amino acid sequence the AAV9 VP1 capsid protein. In some instances, the corresponding parental AAV capsid (or AAV capsid protein) is a native AAV9 capsid. In some instances, the corresponding parental AAV capsid is a variant of AAV9 comprising an amino acid sequence provided in any one of SEQ ID NOS: 3-6.

In some instances, the amino acid substitution at the amino acid position corresponding to residue 452 in AAV9 VP1 is selected from the group consisting of N452A, N452D, N452E, N452G, N452H, N452M, N452N, N452Q, N452S, N452T, and N452V. In some instances, the amino acid substitution at the amino acid position corresponding to residue 453 in AAV9 VP1 is selected from the group consisting of G453A, G453D, G453E, G453G, G453K, G453N, G453Q, G453S, G453T, and G453V. In some instances, the amino acid substitution at the amino acid position corresponding to residue 454 in AAV9 VP1 is selected from the group consisting of S454A, S454D, S454E, S454G, S454K, S454N, S454Q, S454S, S454T, and S454V. In some instances, the amino acid substitution at the amino acid position corresponding to residue 455 in AAV9 VP1 is selected from the group consisting of G455A, G455D, G455E, G455G, G455K, G455N, G455P, G455Q, G455S, and G455T. In some instances, the amino acid substitution at the amino acid position corresponding to residue 456 in AAV9 VP1 is selected from the group consisting Q456A, Q456D, Q456E, Q456G, Q456H, Q456K, Q456N, Q456P, Q456Q, Q456S, and Q456T. In some instances, the amino acid substitution at the amino acid position corresponding to residue 457 in AAV9 VP1 is selected from the group consisting N457A, N457D, N457E, N457G, N457K, N457N, N457P, N457S, N457T, and N457V. In some instances, the amino acid substitution at the amino acid position corresponding to residue 458 in AAV9 VP1 is selected from the group consisting Q458A, Q458E, Q458G, Q458H, Q458K, Q458L, Q458N, Q458Q, Q458S, Q458T, and Q458V. In some instances, the amino acid substitution at amino acid positions corresponding to residues 452-458 in AAV9 VP1 is DGAATKN (SEQ ID NO: 3943). In some instances, the amino acid substitution comprises an amino acid sequence selected from FIG. 3 or Table 1, or a combination thereof.

In some instances, the variant AAV capsid protein further comprises an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), following the amino acid at the position corresponding to residue 588 in the amino acid sequence of the AAV9 VP1, wherein X is any amino acid other than V. In some instances, the substitution comprises an amino acid sequence provided in FIG. 3.

In some instances, the target tissue is a brain, and the rAAV capsids, or variant AAV capsid proteins comprised therein, have the increased specificity for the brain, as compared to the parental AAV capsid or capsid protein (e.g., AAV9). In some instances, the off-target tissue is a liver, and the rAAV capsids, or variant AVV capsid proteins, have a decreased specificity for the liver, as compared to the parental AAV capsid or capsid protein (e.g., AAV9). In some instances, the target tissue is a central nervous system (CNS), and the rAAV capsid s, or variant AVV capsid proteins, have an increased efficiency of viral transduction of at least 12-fold in the central nervous system (CNS), as compared to the corresponding parental AAV capsid or capsid protein (e.g., AAV9). In some instances, the target tissue is a spinal cord, and the rAAV capsid s, or variant AVV capsid proteins, have an increased efficiency of viral transduction of at least 20-fold in the spinal cord, as compared to the corresponding parental AAV capsid or capsid protein. In some instances, the target tissue is a neuron, and the rAAV capsid s, or variant AVV capsid proteins, have an increased specificity for the neuron, as compared to the corresponding parental AAV capsid or capsid protein. In some instances, the off-target tissue is a liver, and the rAAV capsid s, or variant AVV capsid proteins, have a decreased efficiency of viral transduction of at least 50-fold in the liver, as compared to the corresponding parental AAV capsid or capsid protein. In some instances, the off-target tissue is a Purkinje cell, and the rAAV capsid s, or variant AVV capsid proteins, have a decreased efficiency of viral transduction of at least 4-fold in the Purkinje cell, as compared to the corresponding parental AAV capsid or capsid protein. In some instances, the off-target tissue is a liver, and the rAAV capsid s, or variant AVV capsid proteins, have a decreased efficiency of viral transduction of at least 100-fold in the liver, as compared to the corresponding parental AAV capsid or capsid protein. In some instances, the AAV further comprises a heterologous nucleic acid encoding a therapeutic gene expression product. In some instances, the AAV capsid is isolated and purified. In some instances, the AAV capsids described herein are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient. In some instances, the pharmaceutical formulation is formulated for intravenous, intraarterial, intrathecal, or subcutaneous administration to treat a disease or a condition of the CNS or PNS.

Aspects disclosed herein provide rAAV capsids comprising variant AAV capsid proteins with an amino acid substitution to an amino acid selected from the group consisting of A, D, E, G, K, H, M, N, P, L Q, S, T, and V, at an amino acid position corresponding to residues selected from 452-458 within an amino acid sequence of the AAV9 VP1, the rAAV capsids, and variant AAV capsids proteins, having at least one of a decreased specificity and a decreased transduction efficiency for an off-target tissue in a subject, relative to a corresponding parental AAV capsid or capsid protein, and at least one of an increased specificity and an increased transduction efficiency for a target tissue in a subject, relative to the corresponding parental AAV capsid or capsid protein. In some instances, the rAAV capsid is chimeric. In some instances, the amino acid substitution is at a three (3)-fold axis of symmetry of the rAAV capsid. In some instances, the rAAV, or variant AAV protein comprises therein, confer an increase in a localization of the rAAV within the target tissue, as compared to the corresponding parental AAV capsid or capsid protein.

In some instances, the target tissue is the central nervous system (CNS) or the peripheral nervous system (PNS). In some instances, the CNS comprises a region selected from the neocortex, the basal ganglia, the hippocampus, the thalamus, the cerebellum, the brain stem, and the spinal cord. In some instances, the PNS comprises a ganglion. In some instances, the ganglion comprises a trigeminal or dorsal root ganglion. In some instances, the target tissue is a non-dividing cell. In some instances, the CNS comprises a cell selected from the group consisting of a neuron, a spinal cord, an astrocyte, an oligodendrocyte, and Schwann cell. In some instances, the off-target tissue is a liver.

In some instances, the amino acid substitution comprises at least three contiguous amino acids, each amino acid independently selected from the group consisting of A, D, E, G, K, H, M, N, P, L Q, S, T, and V at amino acid positions corresponding to residues 452-454, 453-455, 454-456, 455-457, or 456-458, in the amino acid sequence of the AAV9 capsid protein. In some instances, the amino acid substitution comprises at least four contiguous amino acids, each amino acid independently selected from the group consisting of A, D, E, G, K, H, M, N, P, L Q, S, T, and V at amino acid positions corresponding to residues 452-455, 453-456, 454-457, or 455-458, in the amino acid sequence of the AAV9 capsid protein. In some instances, the amino acid substitution comprises at least five contiguous amino acids, each amino acid independently selected from the group consisting of A, D, E, G, K, H, M, N, P, L Q, S, T, and V at amino acid positions corresponding to residues 452-456, 453-457, or 454-458, in the amino acid sequence of the AAV9 capsid protein. In some instances, the AAV capsid protein is an AAV9 capsid protein.

In some instances, the amino acid substitution at the amino acid position corresponding to residue 452 in AAV9 VP1 is selected from the group consisting of N452A, N452D, N452E, N452G, N452H, N452M, N452N, N452Q, N452S, N452T, and N452V. In some instances, the amino acid substitution at the amino acid position corresponding to residue 453 in AAV9 VP1 is selected from the group consisting of G453A, G453D, G453E, G453G, G453K, G453N, G453Q, G453S, G453T, and G453V. In some instances, the amino acid substitution at the amino acid position corresponding to residue 454 in AAV9 VP1 is selected from the group consisting of S454A, S454D, S454E, S454G, S454K, S454N, S454Q, S454S, S454T, and S454V. In some instances, the amino acid substitution at the amino acid position corresponding to residue 455 in AAV9 VP1 is selected from the group consisting of G455A, G455D, G455E, G455G, G455K, G455N, G455P, G455Q, G455S, and G455T. In some instances, the amino acid substitution at the amino acid position corresponding to residue 456 in AAV9 VP1 is selected from the group consisting Q456A, Q456D, Q456E, Q456H, Q456H, Q456K, Q456N, Q456P, Q456Q, Q456S, and Q456T. In some instances, the amino acid substitution at the amino acid position corresponding to residue 457 in AAV9 VP1 is selected from the group consisting N457A, N457D, N457E, N457G, N457K, N457N, N457P, N457S, N457T, and N457V. In some instances, the amino acid substitution at the amino acid position corresponding to residue 458 in AAV9 VP1 is selected from the group consisting Q458A, Q458E, Q458G, Q458H, Q458K, Q458L, Q458N, Q458Q, Q458S, Q458T, and Q458V. In some instances, the amino acid substitution comprises at least three contiguous amino acids in an amino acid sequence selected from the group consisting of DGAATKN (SEQ ID NO: 3943), DGQSSKS (SEQ ID NO: 2764), and an amino acid sequence provided in Table 1. In some instances, an amino acid sequence of the AAV9 VP1 is provided in SEQ ID NO: 1. In some instances, the amino acid sequence of the AAV9 VP1 is provided in amino acid 217-736 within SEQ ID NO: 1. In some instances, VP1, VP2, and VP3 of the AAV capsid protein comprise the amino acid substitution. In some instances, the corresponding parental AAV capsid or capsid protein is a native AAV9 VP1 capsid. In some instances, the native AAV capsid protein comprises an amino acid sequence provided in SEQ ID NO: 1. In some instances, the corresponding parental AAV capsid or capsid protein is a variant of AAV9 comprising an amino acid sequence provided in any one of SEQ ID NOS: 3-6.

In some instances, the rAAV capsids, or variant AAV capsid proteins, further comprise an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), at an amino acid position 588_589 within an amino acid sequence of the AAV capsid protein, wherein X is any amino acid other than V.

In some instances, the target tissue is a brain, and the rAAV capsids, or variant AVV capsid proteins, have the increased specificity for the brain, as compared to the corresponding parental AAV capsid or capsid protein. In some instances, the off-target tissue is a liver, and the rAAV capsid s, or variant AVV capsid proteins, have a decreased specificity for the liver, as compared to the corresponding parental AAV capsid or capsid protein. In some instances, the target tissue is a central nervous system (CNS), and the rAAV capsid s, or variant AVV capsid proteins, have an increased efficiency of viral transduction of at least 12-fold in the CNS, as compared to the corresponding parental AAV capsid or capsid protein. In some instances, the target tissue is a spinal cord, and the rAAV capsid s, or variant AVV capsid proteins, have an increased efficiency of viral transduction of at least 20-fold in the spinal cord, as compared to the corresponding parental AAV capsid or capsid protein. In some instances, the target tissue is a neuron, and the rAAV capsid s, or variant AVV capsid proteins, have an increased specificity for the neuron, as compared to the corresponding parental AAV capsid or capsid protein. In some instances, the off-target tissue is a liver, and the rAAV capsid s, or variant AVV capsid proteins, have a decreased efficiency of viral transduction of at least 50-fold in the liver, as compared to the corresponding parental AAV capsid or capsid protein. In some instances, the off-target tissue is a Purkinje cell, and the rAAV capsid s, or variant AVV capsid proteins, have a decreased efficiency of viral transduction of at least 4-fold in the Purkinje cell, as compared to the r corresponding parental AAV capsid or capsid protein. In some instances, the off-target tissue is a liver, and the rAAV capsid s, or variant AVV capsid proteins, have a decreased efficiency of viral transduction of at least 100-fold in the liver, as compared to the corresponding parental AAV capsid or capsid protein. In some instances, the rAAV capsids, or variant AVV capsid proteins, have described herein are isolated and purified. In some instances, the rAAV capsids or variant capsid proteins described herein are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient. In some instances, the pharmaceutical formulation is formulated for intravenous, intraarterial, intrathecal, or subcutaneous administration to treat a disease or a condition of the CNS or PNS.

Aspects disclosed herein provide recombinant AAV (rAAV) capsids comprising an variant AAV capsid proteins comprising at least four contiguous amino acids at amino acid positions corresponding to residues selected from the group consisting of 452-455, 453-456, 454-457, and 455-458 of an amino acid sequence of the AAV9 capsid protein according to VP1 numbering, conferring at least one of an increased specificity and an increased transduction efficiency for a target tissue in a subject, wherein: (a) an amino acid at amino acid position corresponding to residue 452 is selected from the group consisting of A, D, G, L, N, Q, S, and T; (b) an amino acid at amino acid position corresponding to residue 453 is selected from the group consisting of A, G, N, P, Q, R, S, and T; (c) an amino acid at amino acid position corresponding to residue 454 is selected from the group consisting of A, D, G, N, S, and T; (d) an amino acid at amino acid position corresponding to residue 455 is selected from the group consisting of A, D, G, K, N, P, Q, S, and T; (e) an amino acid at amino acid position corresponding to residue 456 is selected from the group consisting of A, G, K, N, P, R, S, and T; (f) an amino acid at amino acid position corresponding to residue 457 is selected from the group consisting of A, G, K, N, P, R, S, T, and V; and (g) an amino acid at amino acid position corresponding to residue 458 is selected from the group consisting of A, G, K, L, R, S, T, and V. In some instances, the AAV capsid protein does not contain at amino acid positions corresponding to residues selected from the group consisting of 452-455, 453-456, 454-457, and 455-458 of AAV9 VP1 an amino acid sequence ILGTGTS (SEQ ID NO: 45479), QSSQTPR (SEQ ID NO: 45480), or TLAVPFK (SEQ ID NO: 45477). In some instances, the amino acid substitution is at a three (3)-fold axis of symmetry of the rAAV capsid. In some instances, the specificity or the transduction efficiency is measured following systemically administration of the rAAV capsid to the subject. In some instances, systemic administration comprises intraarterial, intravenous, or subcutaneous, administration. In some instances, the rAAV capsid, or variant AAV capsid protein therein, is from AAV9. In some instances, the rAAV, or variant AAV protein comprises therein, confer an increase in a localization of the rAAV within the target tissue, as compared to the corresponding parental AAV capsid or capsid protein.

In some instances, the substitution comprises an amino acid sequence provided in FIG. 3. In some such instances, the at least four contiguous amino acids are provided in an amino acid sequence selected from the group consisting of LQTSSPG (SEQ ID NO: 2933), SINTKTN (SEQ ID NO: 45475), ERGANTK (SEQ ID NO: 5192), TTGGHSS (SEQ ID NO: 2743), GTTKTSE (SEQ ID NO: 3064), GTGTSVL (SEQ ID NO: 11958), and GTPSKAG (SEQ ID NO: 2741). In some instances, the substitution comprises an amino acid sequence provided in FIG. 2. In some such instances the at least four contiguous amino acids are provided in an amino acid sequence selected from the group consisting of QQGKQSV (SEQ ID NO: 79), SNGTKQT (SEQ ID NO: 442), GSGKTAA (SEQ ID NO: 88), MGDKPTR (SEQ ID NO: 2466), QPSGGNT (SEQ ID NO: 2672), and NQSGTKG (SEQ ID NO: 780). In some instances, the at least four contiguous amino acids are provided in an amino acid sequence selected from the group consisting of LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), and GTPSKAG (SEQ ID NO: 2741). In some instances, the at least four contiguous amino acids are provided in an amino acid sequence provided in Table 2. In some instances, the target tissue is a central nervous system (CNS). In some instances, the CNS comprises a region selected from the neocortex, the basal ganglia, the hippocampus, the thalamus, the cerebellum, the brain stem, and the spinal cord. In some embodiments, the target tissue is the peripheral nervous system (PNS). In some instances, the PNS comprises a ganglion. In some instances, the ganglion is a trigeminal or dorsal root ganglion. In some instances, the target tissue is a non-dividing cell. In some instances, the CNS comprises a cell selected from the group consisting of a neuron, an astrocyte, a microglial cell, an oligodendrocyte, and a Schwann cell. In some instances, the target tissue is a CNS, and the AAV capsid has an increased efficiency of viral transduction of at least 12-fold in the CNS, as compared to the parental AAV capsid or AAV capsid protein. In some instances, the target tissue is a brain, and the AAV capsid has the increased specificity for the brain, as compared to the parental AAV capsid or AAV capsid protein. In some instances, the target tissue is a spinal cord, and the AAV capsid has an increased efficiency of viral transduction of at least 20-fold in the spinal cord, as compared to the parental AAV capsid or AAV capsid protein. In some instances, the target tissue is a neuron, and the AAV capsid has an increased specificity for the neuron, as compared to the parental AAV capsid or AAV capsid protein. In some instances, the rAAV capsids, or variant AAV capsid proteins, described herein are isolated and purified. In some instances, the rAAV capsids, or variant AAV proteins, described herein are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient. In some instances, the pharmaceutical formulation is formulated for intravenous, intraarterial, intrathecal, or subcutaneous administration to treat a disease or a condition of the CNS or PNS.

Aspects disclosed herein provide rAAV capsids comprising AAV capsid proteins comprising at least four contiguous amino acids from an amino acid sequence provided in FIG. 2 or Table 2 at an amino acid position corresponding to residues selected from the group consisting of 452-455, 453-456, 454-457, and 455-458 of AAV9 VP1 conferring at least one of an increased specificity and an increased transduction efficiency when measured in a target tissue in a subject, as compared to a parental AAV capsid or capsid protein. In some instances, the at least four contiguous amino acids are at a three (3)-fold axis of symmetry of the rAAV capsid. In some instances, the AAV capsid protein does not contain at amino acid positions corresponding to residues selected from the group consisting of 452-455, 453-456, 454-457, and 455-458 of AAV9 VP1 an amino acid sequence ILGTGTS (SEQ ID NO: 45479), QSSQTPR (SEQ ID NO: 45480), or TLAVPFK (SEQ ID NO: 45477). In some instances, the specificity or the transduction efficiency is measured following systemically administration of the AAV capsid to the subject. In some instances, the rAAV capsid is chimeric. In some instances, the rAAV, or variant AAV protein comprises therein, confer an increase in a localization of the rAAV within the target tissue, as compared to the parental AAV capsid or capsid protein.

In some instances, the at least four contiguous amino acids comprise at least four, five, six, or seven contiguous amino acids in an amino acid sequence selected from the group consisting of LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), and GTPSKAG (SEQ ID NO: 2741)

In some instances, the target tissue is a central nervous system (CNS). In some instances, the CNS comprises a region selected from the neocortex, the basal ganglia, the hippocampus, the thalamus, the cerebellum, the brain stem, and the spinal cord. In some embodiments, the target tissue is the peripheral nervous system (PNS). In some instances, the PNS comprises a ganglion. In some instances, the ganglion is a trigeminal or dorsal root ganglion. In some instances, the target tissue is a non-dividing cell. In some instances, the CNS comprises a cell selected from the group consisting of a neuron, an astrocyte, a microglial cell, an oligodendrocyte, and a Schwann cell.

In some instances, the rAAV capsid, or variant AAV capsid protein comprised therein, further comprises an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), at an amino acid position corresponding to residues 588_589 in the amino acid sequence of AAV9 VP1, wherein X is any amino acid other than V. In some instances, the parental AAV capsid or capsid protein is AAV9. In some instances, the amino acid sequence of a AAV9 capsid protein is provided in SEQ ID NO: 1. In some instances, the amino acid sequence of the AAV9 capsid protein is provided in amino acid 217-736 within SEQ ID NO: 1

In some instances, the target tissue is a brain, and the rAAV capsid, or variant AAV capsid protein, has the increased specificity for the brain, as compared to the parental AAV capsid or capsid protein. In some instances, the target tissue is the CNS, and the rAAV capsid, or variant AAV capsid protein, has an increased efficiency of viral transduction of at least 12-fold in the CNS, as compared to the parental AAV capsid or capsid protein. In some instances, the target tissue is a spinal cord, and the rAAV capsid, or variant AAV capsid protein, has an increased efficiency of viral transduction of at least 20-fold in the spinal cord, as compared to the parental AAV capsid or capsid protein. In some instances, the target tissue is a neuron, and the rAAV capsid, or variant AAV capsid protein, has an increased specificity for the neuron, as compared to the parental AAV capsid or capsid protein. In some instances, the rAAV capsids, or variant AAV capsid proteins, described herein are isolated and purified. In some instances, the rAAV capsids, or variant AAV capsid proteins, described herein are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient.

Aspects provided herein provide rAAV capsids comprising variant AAV capsid proteins, the rAAV capsids having at least one of an increased specificity and increased transduction efficiency when measured in a target tissue of a subject relative to a corresponding parental AAV capsid or capsid protein, the AAV capsid protein comprising three amino acids (X1-X2-X3) at an amino acid position corresponding to residues selected from the group consisting of 452-454, 453-455, 454-456, 455-457, and 456-458 in AAV9 VP1, wherein: (a) X1 is selected from the group consisting of N, K, R, L, and T; (b) X2 is selected from the group consisting of N, S, L, E, D, and P; and (c) X3 is selected from the group consisting of N, S, A, D, G, L, and T. In some instances, the target tissue is selected from the group consisting of a lung, a heart, an intestine, a kidney, and a stomach. In some instances, the target tissue is a non-dividing cell. In some instances, the tissue is the lung and the amino acid sequence is KDNTPGR (SEQ ID NO: 32538), or any amino acid sequence provided in FIG. 13. In some instances, the tissue is the lung and the amino acid sequence is NNLPRNL (SEQ ID NO: 32867), or any amino acid sequence provided in FIG. 13. In some instances, the tissue is an intestine and the amino acid sequence is RESSPSL (SEQ ID NO: 29065), or any amino acid sequence provided in FIG. 5. In some instances, the tissue is the kidney and the amino acid sequence is RVPLSTI (SEQ ID NO: 26933), or any amino acid sequence provided in FIG. 6. In some instances, the AAV capsid protein is an AAV9 capsid protein. In some instances, the AAV9 capsid protein is provided in SEQ ID NO: 1. In some instances, the AAV capsid protein further comprises four amino acids at an amino acid position selected from the group consisting of 452-455, 453-456, 454-457, and 455-458, wherein X4 is selected from the group consisting of T, S, P, and L. In some instances, the AAV capsid protein further comprises five amino acids at an amino acid position selected from the group consisting of 452-456, 453-457, and 453-458, wherein X5 is selected from the group consisting of P, R, and S. In some instances, the AAV capsid protein further comprises six amino acids at an amino acid position 452-457 or 453-458, wherein X6 is selected from the group consisting of N, G, S, and T. In some instances, the AAV capsid protein further comprises seven amino acids at an amino acid position 452-458, wherein X7 is selected from the group consisting of R, L, and I. In some instances, VP1, VP2, and VP3 of the AAV capsid protein comprise the amino acid sequence. In some instances, the corresponding parental AAV capsid is a native AAV9 capsid. In some instances, an amino acid sequence of the VP1 protein of the native AAV9 capsid is provided in SEQ ID NO: 1. In some instances, the corresponding parental AAV is a native AAV5 capsid. In some instances, an amino acid sequence of the VP1 protein of the native AAV5 capsid is provided in SEQ ID NO: 2.

In some instances, the rAAV, or variant AAV capsid proteins described herein, have at least one of the increased specificity and increased transduction efficiency for a target tissue when measured in a subject as compared to the corresponding parental AAV capsid or capsid protein. In some instances, the target tissue is a lung cell-type that is an alveolar type II epithelial (ATII) cell, and the rAAV capsid, or variant AAV capsid, has an increased efficiency of viral transduction of at least 60-fold in the ATII cell, as compared to a parental AAV capsid or capsid protein. In some instances, the target tissue is a lung cell-type that is an ATII cell, and the rAAV capsid, or variant AAV capsid, has an increased efficiency of viral transduction of at least 60-fold in the ATII cell, as compared to the parental AAV capsid or capsid protein. In some instances, the rAAV capsid, or variant AAV capsid, has an increased efficiency of viral transduction of at least 15-fold in the lung, as compared to the parental AAV capsid or capsid protein. In some instances, the rAAV capsid, or variant AAV capsid, has an increased efficiency of viral transduction of at least 30-fold in the lung, as compared to the parental AAV capsid or capsid protein. Also envisioned are AAV capsids comprising these AAV capsid proteins. In some instances, the rAAV capsids, or variant AAV capsids, described herein are isolated and purified. In some instances, the rAAV capsids, or variant AAV capsids, described herein are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient. In some instances, the pharmaceutical formulation is formulated for intravenous, intraarterial, subcutaneous, or intranasal administration to treat a disease or a condition of the target tissue.

Aspects disclosed herein provide rAAV capsids comprising variant AAV capsid proteins comprising three amino acids at an amino acid position corresponding to residues selected from the group consisting of 452-454, 453-455, 454-456, 455-457, and 456-458 in AAV9 VP1, wherein the three amino acids are provided in an amino acid sequence is provided in one or more of FIG. 4-FIG. 14. In some instances, the rAAV capsid or variant AAV capsid proteins, have at least one of an increased specificity and increased transduction efficiency when measured in a target tissue in a subject. In some instances, the target tissue is selected from the group consisting of a lung, an intestine, a liver, a stomach, a heart, a muscle, an adipose tissue, a spleen, a kidney, or reproductive organs (e.g., testis, ovaries). In some instances, the target tissue is a non-dividing cell. In some instances, the amino acid sequence is provided in FIG. 4. In some instances, the amino acid sequence is provided in FIG. 5. In some instances, the amino acid sequence is provided in FIG. 6. In some instances, the amino acid sequence is provided in FIG. 7. In some instances, the amino acid sequence is provided in FIG. 8. In some instances, the amino acid sequence is provided in FIG. 9. In some instances, the amino acid sequence is provided in FIG. 10. In some instances, the amino acid sequence is provided in FIG. 11. In some instances, the amino acid sequence is provided in FIG. 12. In some instances, the amino acid sequence is provided in FIG. 13. In some instances, the amino acid sequence is provided in FIG. 14. In some instances, the rAAV, or variant AAV protein comprises therein, confer an increase in a localization of the rAAV within the target tissue, as compared to the parental AAV capsid or capsid protein.

In some instances, the parental AAV capsid a native AAV9. In some instances, an amino acid sequence of a VP1 protein of the native AAV9 capsid protein is provided in SEQ ID NO: 1.

In some instances, the three amino acids further comprises four amino acids at an amino acid position corresponding to residues selected from the group consisting of 452-455, 453-456, 454-457, and 455-458 of AAV9 VP1, wherein the amino acid sequence is provided in one or more of FIG. 4-FIG. 14. In some instances, the three amino acids comprises five amino acids at an amino acid position corresponding to residues selected from the group consisting of 452-456, 453-457, and 453-458 of AAV9 VP1, wherein the amino acid sequence is provided in one or more of FIG. 4-FIG. 14. In some instances, the three amino acids further comprises six amino acids at an amino acid position corresponding to residues 452-457 or 453-458, wherein the amino acid sequence is provided in one or more of FIG. 4-FIG. 14. In some instances, the three amino acids further comprises seven amino acids at an amino acid position corresponding to residues 452-458, wherein the amino acid sequence is provided in one or more of FIG. 4-FIG. 14. In some instances, VP1, VP2, and VP3 of the rAAV capsid comprise the amino acid sequence. In some instances, the rAAV capsid, or variant AAV capsid proteins, described herein are isolated and purified. In some instances, the AAV capsids, or variant AAV capsid proteins described herein, are formulated as a pharmaceutical formulation further comprising a pharmaceutically acceptable carrier. In some instances, the pharmaceutical formulation further comprises a heterologous nucleic acid encoding a therapeutic gene expression product. In some instances, the pharmaceutical formulation further comprises a pharmaceutical excipient. In some instances, the pharmaceutical formulation is formulated for intravenous, intraarterial, subcutaneous, or intranasal administration to treat a disease or a condition of the target tissue.

Aspects disclosed herein provide methods of treating a disease or condition in a subject comprising administering to the subject a therapeutically effective amount of a composition comprising the rAAV capsids disclosed herein, the rAAV capsid encapsidating a nucleic acid sequence encoding a therapeutic gene expression product. In some instances, the mammalian subject is a primate. In some instances, the mammalian subject is a non-human primate. In some instances, the mammalian subject is a human. In some instances, the therapeutic gene expression product is a protein. In other instances, the therapeutic gene expression product is an RNA, e.g. a small interfering RNA (siRNA), a short hairpin RNA (shRNA), or a microRNA (miRNA). In some instances, the administering comprises intravenous or intranasal administration. In some instances, the disease or condition is a disease or condition of the central nervous system or peripheral nervous system. In some instances, the disease or condition is a disease or condition of the CNS or PNS. In some instances, the disease or condition is selected from the group consisting of Adrenoleukodystrophy, Alzheimer's disease, Amyotrophic lateral sclerosis, Angelman syndrome, Ataxia telangiectasia, Charcot-Marie-Tooth syndrome, classical rhizomelic chondrodysplasia punctata (RCDP), Cockayne syndrome, Deafness, Dravet Syndrome, Duchenne muscular dystrophy, Epilepsy, Essential tremor, Fragile X syndrome, Friedreich's ataxia, Frontotemporal dementia (FTD), Gaucher disease, glioblastoma, Huntington disease, infantile Refsum disease (IRD), Lesch-Nyhan syndrome, Maple syrup urine disease, Menkes syndrome, Myotonic dystrophy, Narcolepsy, Neurofibromatosis, Niemann-Pick disease, Parkinson disease, Phenylketonuria, Prader-Willi syndrome, Refsum disease, Rett syndrome, Spinal muscular atrophy, Spinocerebellar ataxia, Tangier disease, Tay-Sachs disease, Tuberous sclerosis, Von Hippel-Lindau syndrome, Williams syndrome, Wilson's disease, and Zellweger syndrome. In some instances, the therapeutic gene expression product is effective to modulate an activity or an expression of a target gene or gene expression product selected from the group consisting of Sarcoglycan Alpha (SGCA), glutamic acid decarboxylase 65 (GAD65), glutamic acid decarboxylase 67 (GAD67), CLN2, Nerve Growth Factor (NGF), Survival Of Motor Neuron 1, Telomeric (SMN1), Factor X (FIX), Retinoid Isomerohydrolase (RPE65), sarco/endoplasmic reticulum Ca2+-ATPase (SERCA2a), β-Glucocerebrosidase (GCase), Frataxin (FXN), Huntingtin (HTN), methyl-CpG binding protein 2 (MECP2), a peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and a NLRP3 inflammasome. In some instances, the therapeutic gene expression product comprises gene editing components. In some instances, the gene editing components are selected from the group consisting of, an artificial site-specific RNA endonuclease (ASRE), a zinc finger endonuclease (ZFN), a transcription factor like effector nuclease (TALEN), a clustered regularly interspaced short palindromic repeats (CRISPR)/Cas enzyme, and a CRISPR)/Cas guide RNA.

Aspects disclosed herein comprise plasmid vectors comprising a nucleic acid sequence encoding the AAV capsids described herein. In some instances, the plasmid vector is bacterial. In some instances, the plasmid vector is derived from *Escherichia coli*. In some instances, the nucleic acid sequence comprises, in a 5' to 3' direction: (1) a 5' inverted terminal repeat (ITR) sequence, (2) a Replication (Rep) gene, (3) a Capsid (Cap) gene, and (4) a 3' ITR, wherein the Cap gene encodes the AAV capsid protein described herein. In some instances, the plasmid vector encodes a pseudotyped AAV capsid protein. In some instances, the Cap gene is derived from the deoxyribose nucleic acid (DNA) provided in any one of SEQ ID NOs: 6-10. In some instances, the nucleic acid sequence comprising the Cap gene is at least 90%, 91%, 92%, 93%, 94%, 95%, 96%, 97%, 98%, 99%, or 100% identical to any one of the DNA sequences provided in SEQ ID NOS: 46364-46383. In some instances, the 5' ITR and the 3' ITR are derived from an AAV2 serotype. In some instances, the 5' ITR and the 3' ITR are derived from an AAV5 serotype. In some instances, the 5' ITR and the 3' ITR are derived from an AAV9 serotype.

Aspects disclosed herein provide methods of manufacturing comprising: (a) introducing into a cell a nucleic acid comprising: (i) a first nucleic acid sequence encoding a therapeutic gene expression product, flanked by at its 5' and 3' ends by inverted terminal repeat (ITR) sequences; (ii) a second nucleic acid sequence encoding a viral genome comprising a 5' ITR sequence, a Replication (Rep) gene, Capsid (Cap) gene, and a 3' ITR, wherein the Cap gene encodes the AAV capsid protein described herein; and (iii) a third nucleic acid sequence encoding a first helper virus protein selected from the group consisting of E4orf6, E2a, and VA RNA, and optionally, a second helper virus protein comprising E1a or E1b55k; (b) expressing in the cell the AAV capsid protein described herein; (c) assembling an AAV particle comprising the AAV capsid proteins disclosed herein; and (d) packaging the first nucleic acid sequence in the AAV particle. In some instances, the nucleic acid is comprised by a plasmid and the cell is mammalian. In some instances, the cell is immortalized. In some instances, the immortalized cell is an embryonic stem cell. In some instances, the embryonic stem cell is a human embryonic stem cell. In certain instances, the human embryonic stem cell is a human embryonic kidney 293 (HEK-293) cell. In other instances, the nucleic acid is comprised by a virus, e.g. a baculovirus. In some such instances, the cell is an insect cell. In certain such instances, the cell is an SF9 cell. In some instances, the Cap gene is derived from the deoxyribose nucleic acid (DNA) provided in any one of SEQ ID NOs: 6-10. In some instances, the nucleic acid sequence comprising the Cap gene is at least 90%, 91%, 92%, 93%, 94%, 95%, 96%, 97%, 98%, 99%, or 100% identical to any one of the DNA sequences provided in SEQ ID NOS: 46364-46383. In some instances, the 5' ITR and the 3' ITR are derived from an AAV2 serotype. In some instances, the 5' ITR and the 3' ITR are derived from an AAV5 serotype. In some instances, the 5' ITR and the 3' ITR are derived from an AAV9 serotype. In some instances, the first nucleic acid sequence (encoding a therapeutic gene expression product) and the second nucleic acid sequence (encoding the cap gene) are in trans. In some instances, the first nucleic acid sequence and the second nucleic acid sequence are in cis. In some instances, the first nucleic acid sequence, the second nucleic acid sequence and the third nucleic acid sequence (encoding the helper virus), are in trans.

Aspects disclosed herein provide kits comprising: (a) a first vector comprising a first nucleic acid sequence encoding a viral genome comprising in a 5' to 3' direction: (i) a 5' inverted terminal repeat (ITR) sequence; (ii) a Replication (Rep) gene; (iii) a Capsid (Cap) gene encoding the AAV capsid proteins described herein, and (iv) a 3' ITR; and (b) optionally, a second vector comprising a second nucleic acid sequence encoding a helper virus protein comprising at least one of E4orf6, E2a, VA RNA, E1a and E1b55k. In some instances, the kit further comprises a cell. In some instances, the cell is mammalian. In some instances, the cell is immortalized. In some instances, the immortalized cell is an embryonic stem cell. In some instances, the embryonic stem cell is a human embryonic stem cell. In some instances, the human embryonic stem cell is a human embryonic kidney 293 (HEK-293) cell. In some instances, the kit further comprises a vector comprising a heterologous nucleic acid encoding a therapeutic gene expression product. In some instances, the vector is an episome.

INCORPORATE BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The embodiments are set forth with particularity in the appended claims. A better understanding of the features and advantages of the present invention will be obtained by reference to the following detailed description that sets forth illustrative embodiments, in which the principles of the invention are utilized, and the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1A shows a surface model of three monomers comprising the 3-fold symmetry of AAV9 (circled), illustrating the location of the 7 amino acid substitution introduced in this library at amino acids 452-458, and the 2 amino acid substitution and 7 amino acid insertion introduced by AAV-PHP.eB previously at amino acids 588-589. FIG. 1B shows the position of the two loops within a single AAV9 monomer, indicating the proximity of the loops and their relation to the capsid surface (AAV interior is down, exterior is up). FIG. 1C shows the spike created by the 588 (left) and 455 (right) loops of one AAV9 monomer interacting with the 495 (middle) loop of a second monomer. FIG. 1D shows a schematic of the engineering process ("TATT NNKNNK . . . NNKNNK CAAC" disclosed as SEQ ID NOS 45492-45493 and "TATT AACGGT . . . AATCAA CAAC" disclosed as SEQ ID NOS 45494-45495). Using PCR, diversity is introduced in the form of a 9-amino acid substitution/insertion (AAV-PHP.eB) and/or substitution (AA 452-458) in the rAAV9 genome, which harbors a Cre inducible switch surrounding the polyadenylation sequence. The DNA capsid library is transfected into HEK-293T cells, and diverse viral capsid libraries are harvested 60 hours later. The viral library is systemically injected into a panel of Cre-transgenic animals Following three weeks of expression, tissue is harvested, and DNA extracted from all organs. Using PCR, sequences are selectively recovered from only those capsids which transduced Cre+ cells, flipping their polyadenylation sequence. The recovered sequences are subsequently prepared for next generation sequencing (NGS) by PCR, adding dual-index barcodes unique to each specific Cre− tissue combination. Following NGS, the data is mined using positive and negative selection for enrichment (increased prevalence within a specific tissue compared to other sequences, normalized to their presence in the injected viral library) and specificity (increased prevalence within a specific tissue or cell type compared to other tissues or cell types). After one to two rounds of selection, individual variants are tested based on their enrichment and specificity scores. Sequence in italics represents AAV9, which is highly enriched in liver (right) but not in brain (left).

FIG. 2 shows 7-mer variant AAV capsid amino acid sequences and DNA sequences encoding the 7-mer variant AAV capsid amino acid sequences positively enriched in the central nervous system (CNS) after two rounds of in vivo selection.

FIG. 3 shows 7-mer variant AAV capsid amino acid sequences and DNA sequences encoding the 7-mer variant AAV capsid amino acid sequences with a tropism specific to the CNS, and that detarget the liver, after two rounds of in vivo selection. "Enrichment" is the prevalence of a given variant in the tissue compared to its prevalence in the viral library that was administered to the transgenic animal. An enrichment score of above 1 indicates a positive enrichment; and an enrichment score below 0 indicates negative enrichment. An enrichment score of 0 indicates that the variant could not be detected in the tissue.

FIG. 4 shows 7-mer variant AAV capsid amino acid sequences and DNA sequences encoding the 7-mer variant AAV capsid amino acid sequences with a tropism specific to the heart after two rounds of in vivo selection.

FIG. 5 shows 7-mer variant AAV capsid amino acid sequences and DNA sequences encoding the 7-mer variant AAV capsid amino acid sequences with a tropism specific to the intestine after two rounds of in vivo selection.

FIG. 6 shows 7-mer variant AAV capsid amino acid sequences and DNA sequences encoding the 7-mer variant AAV capsid amino acid sequences with a tropism specific to the kidney after two rounds of in vivo selection.

FIG. 7 shows 7-mer variant AAV capsid amino acid sequences and DNA sequences encoding the 7-mer variant AAV capsid amino acid sequences with a tropism specific to the liver after two rounds of in vivo selection.

FIG. 8 shows 7-mer variant AAV capsid amino acid sequences and DNA sequences encoding the 7-mer variant AAV capsid amino acid sequences with a tropism specific to muscle after two rounds of in vivo selection.

FIG. 9 shows 7-mer variant AAV capsid amino acid sequences and DNA sequences encoding the 7-mer variant AAV capsid amino acid sequences with a tropism specific to the pancreas after two rounds of in vivo selection.

FIG. 10 shows 7-mer variant AAV capsid amino acid sequences and DNA sequences encoding the 7-mer variant AAV capsid amino acid sequences with a tropism specific to the spleen after two rounds of in vivo selection.

FIG. 11 shows 7-mer variant AAV capsid amino acid sequences and DNA sequences encoding the 7-mer variant AAV capsid amino acid sequences with a tropism specific to the stomach after two rounds of in vivo selection.

FIG. 12 shows 7-mer variant AAV capsid amino acid sequences and DNA sequences encoding the 7-mer variant AAV capsid amino acid sequences with a tropism specific to the testicle after two rounds of in vivo selection.

FIG. 13 shows 7-mer variant AAV capsid amino acid sequences and DNA sequences encoding the 7-mer variant AAV capsid amino acid sequences with a tropism specific to lung after two rounds of in vivo selection.

FIG. 14 shows 7-mer variant AAV capsid amino acid sequences and DNA sequences encoding the 7-mer variant AAV capsid amino acid sequences with a tropism specific to adipose tissue after two rounds of in vivo selection.

FIG. 15A shows the relative abundance in log enrichment of two candidate variants, AAV.CAP-A4 and AAV.CAP-A14, and a randomly chosen variant. The NGS data shows significant enrichment of AAV.CAP-A4 in the lung, with negative enrichment in several peripheral organs. Conversely, AAV.CAP-A14 is enriched in neurons within the stomach and intestine, and negatively enriched in other organs like the lung. FIG. 15B shows In vivo transduction 2 weeks after systemic administration of $5\times10^{11}$ vg of rAAV: CAG-mNeonGreen confirms the NGS data from in 2A, with AAV.CAP-A4 strongly transducing the lung when compared to AAV9, and AAV.CAP-A14 more strongly transducing neurons in the stomach and intestine. For the avoidance of doubt, AAV.CAP-A4 is KDNTPGR, which is provided in SEQ ID NO: 32538 (enrichment in the lung), SEQ ID NO: 25633 (enrichment in the heart), SEQ ID NO: 26584 (enrichment in the intestine), and SEQ ID NO: 28509 (enrichment in the kidney). AAV.CAP-A14 is RESSPSL, which is provided in SEQ ID NO: 26474 (enrichment in the intestine), SEQ ID NO: 29065 (enrichment in the kidney), and SEQ ID NO: 31904 (enrichment in the stomach).

FIG. 16A provides a comparison of the total number of cells transduced by AAV.CAP-A4, compared to its parents capsid AAV9. FIG. 16B shows overall transduction, as assessed by EGFP expression, is increased 15-30 fold compared to AAV5 and AAV9. FIG. 16C provides a cell-type specific quantification, as assessed by colocalization of EGFP signal with antibody staining and shows that AAV.CAP-A4 transduction of ATII cells is increased 30-60 fold compared to AAV5 and AAV9 (respectively). A significant number of the cells transduced by AAV.CAP-A4 are alveolar type II pneumocytes. FIG. 16D shows quantification of cell-type specificity with 60% of cells transduced in the lung identified as ATII cells. For quantification: n=3 mice per group for AAV9, AAV5 and AAV.CAP-A4, mean±SE, one-way ANOVA (*P≤0.05; n.s., P≥0.05). Scale bars are 50 µm.

FIG. 17A-17E show the characterization of the 7 amino acid (AA) substitution library in AAV-PHP.eB. FIG. 17A shows the distribution across the 7 amino acid substitution in AAV-PHP.eB, showing a relatively uniform distribution (with a few notable exceptions) a low prevalence of stop codons, and no bias towards the wildtype (WT) AAV9 sequence (NGSGQNQ (SEQ ID NO: 545)) following PCR generation of the DNA library and packaging of the viral capsid library. FIG. 17B shows a subset of the top performing variants (SEQ ID NOS: 45496-45513), respectively, in order of appearance) obtained from two rounds of positive and negative selection, showing a strong divergence from the WT AAV9 sequence. TI: threonine and isoleucine residues present at positions 450-451; QT: glutamine and threonine residues present at positions 459-460. FIG. 17C shows a heat map plotting the log-enrichment scores of a subset of the top performers, demonstrating specificity for, and enrichment in, neuronal populations, a target for which AAV-PHP.eB is already biased towards. FIG. 17D shows ssAAV9:CAG-mNeonGreen, ssAAV-PHP.eB:CAG-mNeonGreen, ssAAV.CAP-B1:CAG-mNeonGreen (LQTSSPG; SEQ ID NO: 2933), ssAAV.CAP-B2:CAG-mNeonGreen (QQGKQSV; SEQ ID NO: 79), ssAAV.CAP-B4:CAG-mNeonGreen (SINTKTN; SEQ ID NO: 45475), and ssAAV.CAP-B7:CAG-mNeonGreen (SNGTKQT; SEQ ID NO: 442) was intravenously injected into male adult mice at $5\times10^{11}$ vg/mouse and mNeonGreen fluorescence assessed after two weeks. FIG. 17E shows ssAAV.CAP-B8: CAG-mNeonGreen (GSGKTAA; SEQ ID NO: 88), ssAAV.CAP-B9:CAG-mNeonGreen (MGDKPTR; SEQ ID NO: 2466), ssAAV.CAP-B10:CAG-mNeonGreen (DGAATKN; SEQ ID NO: 3943), ssAAV.CAP-B11:CAG-mNeonGreen (QPSGGNT; SEQ ID NO: 2672), ssAAV.CAP-B14:CAG-mNeonGreen (ERGANTK; SEQ ID NO: 5192), ssAAV.CAP-B16:CAG-mNeonGreen (TTGGHSS; SEQ ID NO: 2743), ssAAV.CAP-B17:CAG-mNeonGreen (GTTKTSE; SEQ ID NO: 3064), ssAAV.CAP-B18:CAG-mNeonGreen (GTGTSVL; SEQ ID NO: 11958), ssAAV.CAP-B19:CAG-mNeonGreen (NQSGTKG; SEQ ID NO: 780), ssAAV.CAP-B22:CAG-mNeonGreen (DGQSSKS; SEQ ID NO: 2764), ssAAV.CAP-B23:CAG-mNeonGreen (KGPGQMG; SEQ ID NO: 45476), or ssAAV.CAP-B25:CAG-mNeonGreen (GTPSKAG; SEQ ID NO: 2741) was intravenously injected into male adult mice at $5 \times 10^{11}$ vg/mouse and mNeonGreen fluorescence assessed after two weeks. In FIG. 17D and FIG. 17E, direct comparison of the transduction profiles of the top performing variants shows a strong correlation between validated tropisms, and those predicted by the NGS data. Scale bars are 2 mm.

FIG. 18A-18D shows the tropism of AAV.CAP-B10 is strongly biased towards the brain, with significant liver detargeting. ssAAV9:CAG-NLSx2-EGFP, ssAAV-PHP.eB:CAG-NLSx2-EGFP or ssAAV.CAP-B10:CAG-NLSx2-EGFP was intravenously injected into male adult mice at $1 \times 10^{11}$ vg/mouse. GFP fluorescence was assessed after three weeks of expression. FIG. 18A shows a comparison of BBB crossing and brain transduction in AAV9, AAV-PHP.eB, and AAV.CAP-B10, showing a progressive increase in transduction efficiency in the brain following iterative engineering of the WT capsid. FIG. 18B shows the same comparison in the livers, showing a progressive decrease in transduction efficiency. FIG. 18C provides quantification of the total number of cells transduced in the brain, and shows a non-significant increase in total transduction for AAV.CAP-B10 compared to AAV-PHP.eB, both of which are significantly increased compared to AAV9. Comparison of the average brightness per cell shows a significant increase of AAV.CAP-B10 over AAV9 but not over AAV-PHP.eB. FIG. 18D provides quantification of the total number of cells transduced in the liver, and shows a significant decrease comparing AAV.CAP-B10 to both AAV9 and AAV-PHP.eB. Brightness per cell is also significant decreased when comparing AAV.CAP-B10 and AAV9, with no significant difference observed with AAV-PHP.eB. For quantification: n=6 mice per group, mean±SE, Brown-Forsythe and Welch ANOVA tests for transduction and Kruskal-Wallis test for brightness (*$P \leq 0.05$; n.s., $P \geq 0.05$). Scale bars are 1 mm.

FIG. 19A-19B shows that across multiple brain regions, AAV.CAP-B10 showed non-significant increases in the total number of neurons transduced compared to AAV-PHP.eB. FIG. 19C-19D shows that AAV.CAP-B10 shows significantly reduced transduction of astrocytes across all brain regions quantified compared to AAV-PHP.eB. FIG. 19E-19F shows that AAV.CAP-B10 shows significantly reduced transduction of oligodendrocytes across all brain regions quantified compared to AAV-PHP.eB. For quantification: n=6 mice per group, mean±SE, Mann-Whitney test (*$P \leq 0.05$; n.s., $P \geq 0.05$). Scale bars are 200 μm.

FIG. 20A-20C shows the amino-acid contribution across the 7-mer substitution to variants enriched in the brain and detargeted from the liver. FIG. 20A shows the amino acid contribution across the 7-mer substitution to variants enriched in the brain. FIG. 20B shows the amino acid contribution across the 7-mer substitution to variants negatively enriched (de-targeted) from the liver. FIG. 20C shows the amino acid contribution across the 7-mer substitution to variants enriched in the brain and negatively enriched (de-targeted) from the liver. The 1000 variants with highest enrichment in the brain of hSyn-Cre animals, the 1000 variants with lowest enrichment in the liver of Tek-Cre animals, and all variants with positive enrichment in the brain and negative enrichment in the liver were analyzed. Plotted is the z-score of all amino acids at each position.

FIG. 22A shows immunofluorescence in cerebellum sections. FIG. 22B shows quantification of purkinje cell transduction in the cerebellum, and shows significantly fewer purkinje cells transduced by AAV.CAP-B10 when compared to AAV-PHP.eB. For quantification: n=6 mice per group, mean±SE, Mann-Whitney test (*$P \leq 0.05$; n.s., $P \geq 0.05$). Scale bar is 200 μm.

FIG. 23A-23F shows the characterization of pooled expression in non-human primates. FIG. 23A shows the experimental paradigm for pooled injection of the novel variants AAV.CAP-B1, AAV.CAP-B2, AAV.CAP-B8, AAV.CAP-B10, AAV.CAP-B18 and AAV.CAP-B22 and controls AAV9 and AAV-PHP.eB. Human FXN fused to an HA tag is packaged in each variant under control of the ubiquitous CAG promoter, with a unique 12 bp RNA barcode in the 5' UTR differentiating each variant. Two marmosets were injected at a dose of 1.2×10^14 vg/kg, of which ⅛ was contributed by each variant in the pool. FIG. 23B shows six sections distributed through the anterior-posterior axis and cerebellum of the marmoset brain. Counter-staining for the HA tag on the FXN transgene show robust expression distributed throughout the brain following IV administration of the pool of variants. FIG. 23C shows NGS quantification of RNA barcode expression from two marmosets for each of the 8 variants in the pool, showing a dramatic increase for several variants, including >12-fold increase in RNA levels of AAV.CAP-B22 and >5-fold increase for AAV.CAP-B10 compared to AAV9. FIG. 23D shows zoomed-in frames from a variety of cortical and sub-cortical regions shows significant and broad transduction across most brain regions, including cortex, hippocampus, and cerebellum. FIG. 23E shows counter-staining for the HA tag in the liver, revealing low overall transduction from the viral pool. NGS quantification shows relative detargeting from the liver, with AAV.CAP-B22 contributing similar RNA levels to AAV9, and AAV.CAP-B10 contributing >5-fold less. FIG. 23F shows that transduction of the heart is increased from AAV9 for several of the variants with AAV.CAP-B22 contributing almost 5-fold more RNA in comparison. Transduction of the adrenal cortex by the variants was varied in comparison with AAV9. RNA was collected from two animals for analysis of liver transduction, and one animal for heart and adrenal transduction.

DETAILED DESCRIPTION OF THE DISCLOSURE

Figure 1B:
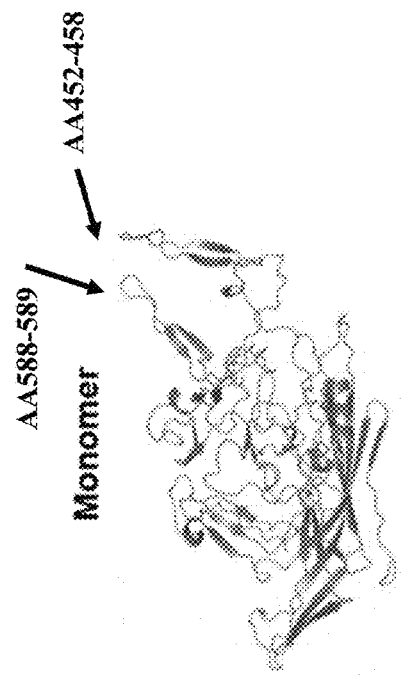
FIG. 1A-1D show a viral engineering overview according to the present embodiments.
Figure 1A:
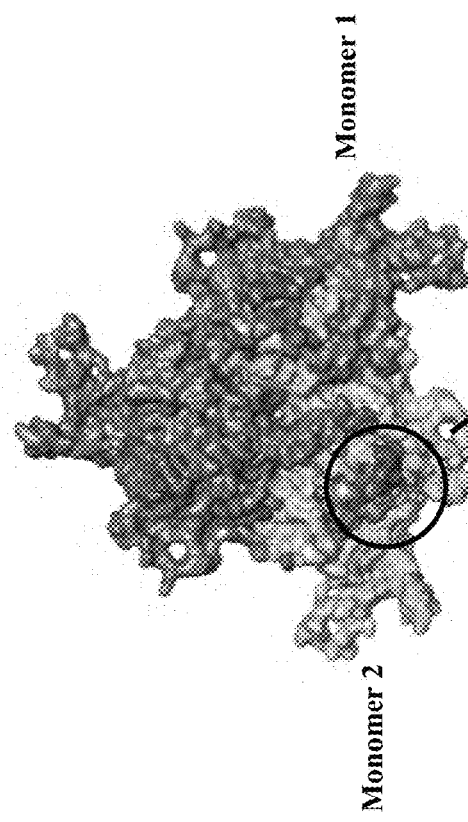
Figure 1C:
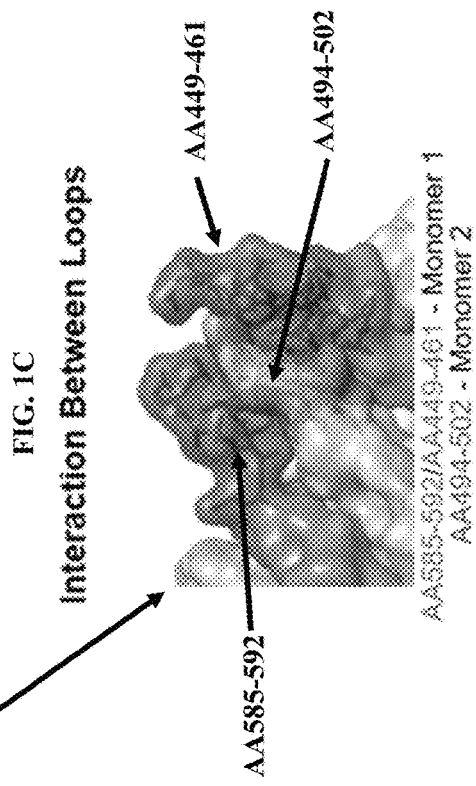
Figure 1D:
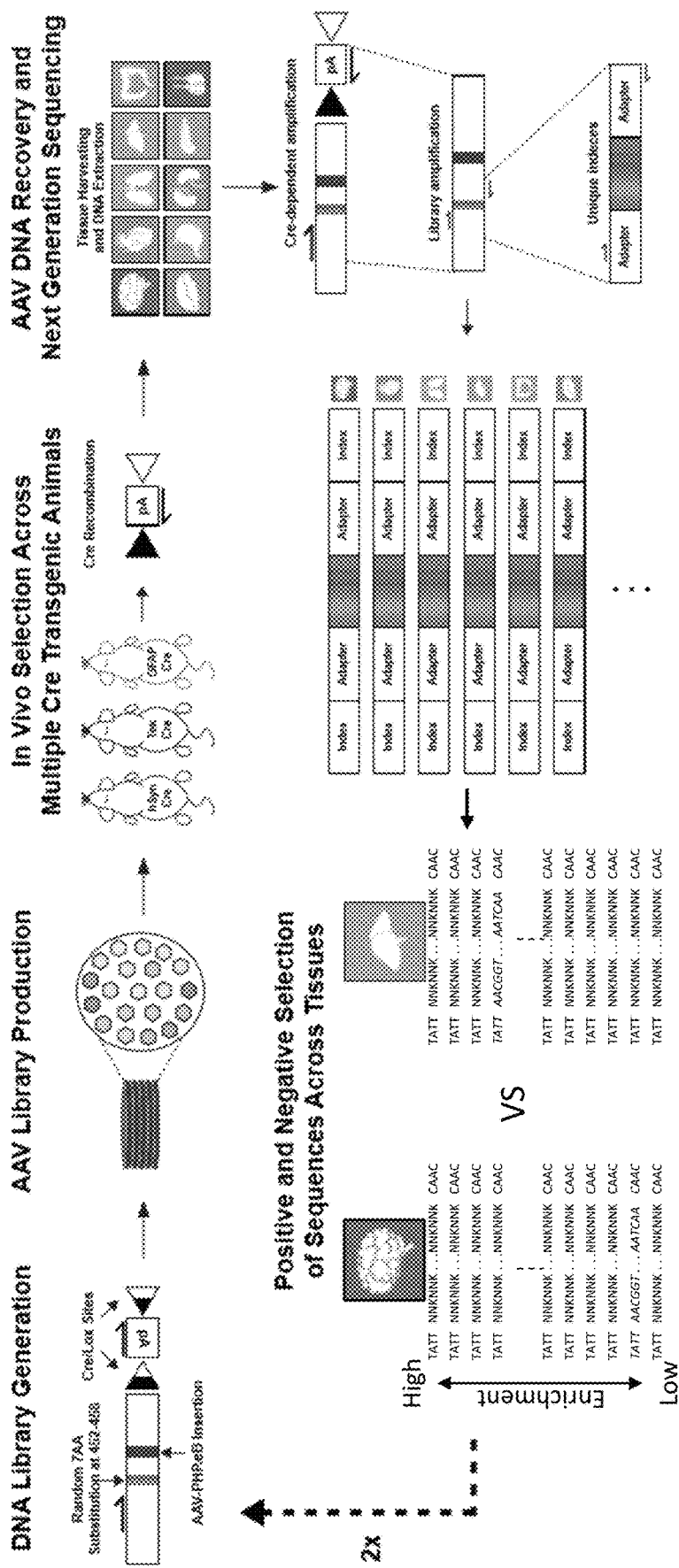

Provided herein are modified adeno-associated (AAV) virus capsid protein compositions useful for integrating a transgene into a target cell or environment (e.g., a cell-type or tissue) in a subject when they are administered to the subject. The modified AAV capsid proteins of the present disclosure comprise at least one insertion or substitution of an amino acid in a corresponding parental AAV capsid protein that confers a desired tropism such as an increased or decreased specificity as compared to a reference AAV capsid protein, e.g. the corresponding unmodified parental capsid protein, or increased or decreased transgene transduction efficiency as compared to a reference AAV capsid protein, e.g. the corresponding unmodified parental capsid protein.

The most commonly manipulated loop in AAVs is the 588 loop, due to it being the site of heparan sulfate binding of AAV2 and amenable to peptide display. The only known receptor for AAV9 is N-linked terminal galactose, but many indications point toward there being others. Although modifications to AAV9 588 loop have been shown to confer an increased specificity and transgene transduction efficiency in target in vivo environments as compared to a correspond parental AAV capsid protein in rodent models, these desired tropisms do not translate in non-human primate models, rendering them of limited value to treat human disease. Non-limiting examples of modified AAV capsid proteins include AAV-PHP.B, AAV-PHP.eB, AAV-PHP.S, and AAV-PHP.

Disclosed herein are modified AAV capsid proteins with desired tropisms observed in both rodent and non-human primate models of human disease that comprise an insertion or a substitution of at least one amino acid relative to the corresponding parental AAV capsid protein, that insertion or substitution residing in the loop corresponding to the amino acid 455 loop (AA455 loop) of AAV9. The AA455 loop is the furthest protruding from the surface of the capsid and has been implicated in neutralizing antibody binding. The AA455 loop is believed to play a significant role in cell-surface receptor binding, either on its own or by interaction with the 588 loop. In some cases, the parental AAV capsid protein is AAV5, AAV9, or a previously modified AAV5 or AAV9 (e.g., AAV-PHP.eB, AAV-PHP.B, and the like).

The most common method of AAV-mediated transgene delivery is by direct injection to the target in vivo environment, which is disadvantageous for many reasons, including risk of injury or death, pain, and higher cost, as compared to less invasive methods. Previous AAV-mediated delivery by intravenous administration avoids a need for a direct injection, but suffers from reduced specificity and transduction efficiency for the target in vivo environment resulting in off-target transduction events and necessitating a larger viral load to achieve sufficient therapeutic levels in the target in vivo environment. This is especially evident when the AAV must cross the blood brain barrier (BBB) or the epithelial lining to reach the target in vivo environment, such as to treat a disease or condition of the central nervous system (CNS) and the lung.

Disclosed herein are methods comprising systemically administering a modified AAV capsid of the present disclosure encapsidating a viral vector comprising a transgene (e.g., therapeutic nucleic acid) with an increased specificity and an increased transduction efficiency, as compared to a reference AAV capsid protein, e.g. the corresponding parental capsid protein. The modified AAV capsid proteins of the present disclosure are capable of crossing the BBB, and transducing a transgene in a particular target cell-type (e.g., neuron) in both rodent and non-human primate models. In addition, the modified AAV capsid proteins of the present disclosure are capable of targeting a cell-type of the lung (e.g., a type II epithelial (ATII) cell) with in some cases a 60-fold increase in transgene transduction efficiency as compared to a reference AAV capsid protein, e.g. the corresponding parental capsid protein. The modified AAV capsid proteins of the present disclosure are capable of detargeting off-target in vivo environments, such as the liver by, in some cases, a 100-fold decrease in transgene transduction efficiency relative to a reference AAV capsid protein, e.g. the corresponding parental capsid protein. Accordingly, the modified AAV capsid proteins of the present disclosure are suitable for transgene therapy to treat human disease.

Disclosed herein are transgenes contained in a recombinant AAV (rAAV) vector and encapsidated by the modified AAV capsid proteins of the present disclosure. The transgenes disclosed herein are delivered to a subject for a variety of purposes, e.g., to treat a disease or condition in the subject. The transgene can be gene editing components that modulate the activity or expression of a target gene or gene expression product. Alternatively, the transgene is a gene encoding a therapeutic gene expression product that is effective to modulate the activity or expression of itself, of another target gene or gene expression product.

Methods of producing recombinant AAV (rAAV) virions, or rAAV particles, comprising AAV capsids comprising the modified AAV capsid proteins and heterologous polynucleotide encoding a therapeutic nucleic acid are also provided. The modified capsid proteins are produced by introducing to a cell (e.g., immortalized stem cell) a heterologous polynucleotide encoding the transgene (e.g., containing the therapeutic nucleic acid), a first plasmid vector encoding the AAV genome with a modified AAV capsid protein, and a second plasmid vector encoding helper virus proteins, required for assembly of the modified capsid structure and packaging of the transgene in the modified capsid. The assembled rAAV particle can be isolated and purified from the cell using suitable methods known in the art.

The vectors comprising a nucleic acid sequence encoding the modified AAV capsid proteins of the present disclosure are also provided herein. For example, the vectors of the present disclosure comprise a nucleic acid sequence encoding the two AAV viral genes, Rep (Replication), Cap (Capsid), wherein the Cap gene, encoding viral capsid proteins VP1, VP2, and VP3 is modified to produce the modified AAV capsid proteins of the present disclosure. The vector can comprise the viral genome from one or more AAV serotype (e.g., AAV5, AAV9), or a variant AAV serotype (e.g., AAV-PHP.eB, AAV-PHP.B, and the like).

Overview

Recombinant AAV (rAAV) mediated gene delivery leverages the AAV mechanism of viral transduction for nuclear expression of an episomal heterologous nucleic acid (e.g., a transgene, therapeutic nucleic acid). Upon delivery to a host in vivo environment, a rAAV will (1) bind or attach to cellular surface receptors on the target cell, (2) endocytose, (3) traffic to the nucleus, (4) uncoat the virus to release the encapsidated heterologous nucleic acid, (5) convert of the heterologous nucleic acid from single-stranded to double-stranded DNA as a template for transcription in the nucleus, and (6) transcribe of the episomal heterologous nucleic acid in the nucleus of the host cell ("transduction"). rAAVs engineered to have an increased specificity (binding to cellular surface receptors on the target cell) and transduction efficiency (transcription of the episomal heterologous nucleic acid in the host cell) are desirable for gene therapy applications.

The AAV capsid is made up of three capsid protein monomers, VP1, VP2, and VP3. Sixty copies of these three VP proteins interact in a 1:1:10 ratio to form the viral capsid. VP1 covers the whole of VP2 protein in addition to a ~137 amino acid N-terminal region (VP1u), VP2 covers the whole of VP3 in addition to ~65 amino acid N-terminal region (VP1/2 common region). The three capsid proteins share a conserved amino acid sequence of VP3, which in some cases is the region beginning at amino acid position 217 (e.g., AA 217-736).

The AAV VP3 structure contains highly conserved regions that are common to all serotypes, a core eight-stranded β-barrel motif (βB-βI) and a small α-helix (αA). The loop regions inserted between the β-strands consist of the distinctive HI loop between β-strands H and I, the DE loop between β-strands D and E, and nine variable regions (VRs), which form the top of the loops. These VRs are found on the capsid surface and can be associated with specific functional roles in the AAV life cycle including receptor binding, transduction and antigenic specificity. For example, the AA455 loop is the furthest protruding from the surface of the capsid, has been implicated in neutralizing antibody binding, and is believed to play a significant role in cell-surface receptor binding, either on its own or by interaction with the 588 loop.

Disclosed herein are recombinant adeno-associated viruses (rAAVs) with AAV capsids comprising modified AAV capsid proteins at the AA455 loop that confer a desired tropism characterized by a higher efficiency and specificity for transduction in specific cell-types, e.g., brain cell types. In particular, the modified AAV capsids disclosed herein enable rAAV-mediated transduction of a heterologous gene (e.g., transgene), while de-targeting others, thereby preventing off-target transduction events in peripheral organs, such as the liver. Also Disclosed herein are rAAVs with AAV capsids comprising modified AAV capsid proteins that confer a tropism characterized by a higher efficiency and specificity for transduction in particular organs or environments, e.g., the lungs, intestine, stomach, heart, muscle, adipose tissue, spleen, kidney, or reproductive organs (e.g., testis, ovaries). The rAAVs described herein are useful for a wide range of applications, including but not limited to the treatment of disease.

Compositions rAAV Capsids and Variant AAV Capsid Proteins

Disclosed herein are recombinant AAV (rAAV) with variant capsid proteins (e.g., rAAV capsid proteins) that are engineered with a modified capsid protein (e.g., VP1, VP2, VP3). In some embodiments, the rAAV capsid proteins of the present disclosure are generated using the methods disclosed herein (e.g., M-CREATE). In some embodiments, the AAV capsid proteins are used in the methods of delivering a therapeutic nucleic acid (e.g., a transgene) to a subject. In some instances, the rAAV capsid proteins have desired AAV tropisms rendering them particularly suitable for certain therapeutic applications, e.g., the treatment of a disease or disorder in a subject such as those disclosed herein.

The rAAV capsid proteins are engineered for optimized entry into and through the blood brain barrier (BBB) of a subject upon systemic administration of the rAAV to the subject, such as those provided in Tables 3-4. Prior methods of AAV-mediated delivery of a therapeutic transgene to the brain required intracranial injection. Intracranial injection is an invasive procedure that causes a subject discomfort, and in some cases, pain. For example, intracranial injection can cause hemorrhaging of the brain. Additionally, intracranial delivery has limited spread and is highly heterogeneous. The rAAV capsid proteins provided in Tables 3-4 are engineered to have tropisms that eliminate the need for intracranial injection, while also achieving widespread and efficient transduction of an encapsidated transgene. In particular, the tropisms comprise at least one of an increased specificity and efficiency (e.g., of viral transduction) in the central nervous system (CNS) of a subject, and/or peripheral nervous system (PNS) of a subject, as compared to a corresponding parental AAV or a reference AAV. The rAAVs disclosed herein may also de-target certain peripheral organs (e.g., the liver), thereby avoiding off-target viral transduction, such as those provided in Table 1.

Also disclosed herein are rAAVs with engineered capsid proteins that are optimized for targeting specific organ or tissue within a subject. In some embodiments, the organ is the heart. In some embodiments, the organ is the lung. In some embodiments, the organ is the liver. In some embodiments, the organ is the intestine. In some embodiments, the organ is the stomach. In some embodiments, the organ is the spleen. In some embodiments, the organ is the kidney. In some embodiments, the tissue is the fat (adipose). In some embodiments, the tissue is the muscle. The muscle may be cardiac muscle. The muscle may be skeletal muscle. In some embodiments, the organ is the pancreas. In some embodiments, the organ is the reproductive organ, such as a testicle or ovary. In further embodiments, the rAAVs disclosed herein may also de-target certain peripheral organs, thereby reducing or avoiding off-target viral transduction. In a non-limiting example, the rAAVs of the present embodiment, Table 1 have increased specificity and transduction in the brain (e.g., target environment), and very low transduction efficiency and no specificity in the liver (e.g., off-target environment), as compared to a reference AAV (e.g., AAV9).

The engineered AAV capsid proteins described herein have, in some cases, an insertion or substitution of an amino acid that is heterologous to the parental AAV capsid protein at the amino acid position of the insertion or substitution. In some embodiments, the amino acid is not endogenous to the parental AAV capsid protein at the amino acid position of the insertion or substitution. The amino acid may be a naturally occurring amino acid in the same or equivalent amino acid position as the insertion of the substitution in a different AAV capsid protein.

Generally, the insertion or substitution comprises a five-, six-, or seven-amino acid polymer (5-mer, 6-mer, or 7-mer, respectively) that is inserted or substituted at the 455 loop in a parental AAV capsid protein. The 7-mers described herein were advantageously generated using polymerase chain reaction (PCR) with degenerate primers, where each of the seven amino acids is encoded by a deoxyribose nucleic acid (DNA) sequence N-N-K. "N" is any of the four DNA nucleotides and K is guanine (G) or thymine (T). This method of generating random 7-mer amino acid sequences enables 1.28 billion possible combinations at the protein level. Since the 7-mers developed are random, some amino acids in the 7-mer may be naturally occurring in the AAC capsid protein at that amino acid position, while other amino acids may differ.

Recombinant AAVs (rAAVs) were generated, each with a unique 7-mer at the 455 loop and each encapsidating a reporter gene that, when administered systemically in multiple transgenic animals, enabled the selective amplification and recovery of sequences that effectively transduced the reporter gene in a target in vivo environment of the transgenic animal. 7-mers that were found to be positively enriched in the target in vivo environment (e.g., central nervous system, lung), and negatively enriched in off-target in vivo environments (e.g., the liver), are provided herein. "Enrichment" is the prevalence of a given 7-mer in the tissue of the in vivo environment compared to its prevalence in the viral library that was administered to the transgenic animal. An enrichment score above 0 indicates a positive enrichment. An enrichment score below 0 indicates a negative enrichment. An enrichment score of 0 indicates that the variant is not present in the tissue. A subset of the rAAVs with desired enrichment profiles were tested individually in vivo to determine exact systemic expression (e.g., specificity and transduction efficiency). rAAVs from this subset exhibiting a desired tropism comprising increased specificity, and in some cases, transduction efficiency are considered to be uniquely suited for targeted rAAV-mediated transgene delivery useful for a wide variety of purposes (e.g., therapeutic, diagnostic, scientific discovery).

The rAAV particles with the 7-mer insertion or substitutions described herein have an increased transduction efficiency in a target in vivo environment (e.g., tissue or cell type). In some instances, the increased transduction efficiency comprises a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold increase, or more, relative to a reference AAV, e.g. the corresponding parental capsid protein. In some instances, the increased transduction efficiency is at least 30-fold. In some instances, the increased transduction efficiency is at least 40-fold. In some instances, the increased transduction efficiency is at least 50-fold. In some instances, the increased transduction efficiency is at least 60-fold. In some instances, the increased transduction efficiency is at least 80-fold. In some instances, the increased transduction efficiency is at least 90-fold. In some instances, the increased transduction efficiency is at least 100-fold.

The rAAV particles with the 7-mer insertion or substitutions described herein have decreased transduction efficiency in an off-target in vivo environment (e.g., tissue or cell type). In some instances, the off-target gene transfer is reduced by 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold, or more, relative to a reference AAV, e.g. the corresponding parental capsid protein. In some instances, the off-target gene transfer is reduced by at least 20-fold. In some instances, the off-target gene transfer is reduced by at least 30-fold. In some instances, the off-target gene transfer is reduced by at least 40-fold. In some instances, the off-target gene transfer is reduced by at least 50-fold. In some instances, the off-target gene transfer is reduced by at least 60-fold. In some instances, the off-target gene transfer is reduced by at least 80-fold. In some instances, the off-target gene transfer is reduced by at least 90-fold. In some instances, the off-target gene transfer is reduced by at least 100-fold.

The rAAV particles with the 7-mer insertion or substitutions described herein have an increased or decreased specificity in a target in vivo environment (e.g., tissue or cell type), as compared to a reference AAV, e.g. the corresponding parental capsid protein. Detecting whether a rAAV possesses more or less specificity for a target in vivo environment than a reference AAV, includes measuring a level of gene expression product (e.g., RNA or protein) expressed from the heterologous nucleic acid encapsidated by the rAAV in a tissue sample obtained from the target in vivo environment in a subject; and comparing the measured level to a control level (e.g., the gene expression product expressed from a heterologous nucleic acid encapsidated by a reference AAV (e.g., AAV9). Suitable methods for measuring expression of a gene expression product luciferase reporter assay and quantitative polymerase chain reaction (qPCR).

The increased specificity is correlated with an increased enrichment in the target in vivo environment, which in some cases is represented with an enrichment score provided herein in FIGS. 2-14. As a non-limiting example, AAV.CAP-B10 (SEQ ID NO: 3943; DGAATKN), which is shown herein to be positively enriched in the brain (enrichment score of approximately 0.950) and not enriched in the liver (enrichment score of ~0), as compared to a reference AAV9, also exhibited an increase in reporter gene expression (e.g., measured by luciferase reporter assay) in the brain and not in the liver as compared to a reference AAV9. Without being bound by a particular theory, the inventors of the present disclosure would expect to see this correlation for all rAAVs disclosed herein, and further, would expect that a more significant the enrichment score (whether negative or positive) would correlate with a more significant specificity to the in vivo environment(s) as indicated by a measured level of the gene expression product in the in vivo environment(s).

Transduction efficiency, as disclosed herein, may be measured by at least one of (1) a number of cells in a target in vivo or off-target in vivo environment expressing the heterologous nucleic acid encapsidated by the modified AAV capsid proteins disclosed herein, and (2) a quantity of expression of the heterologous nucleic acid in a single cell. Specificity for a target in vivo environment may be inferred when a presence, or an increase in a level, of rAAV-mediated transduction in a target in vivo environment is observed, as compared to a reference AAV. A lack of, or reduced, specificity to an off-target in vivo environment may be inferred when an absence, or a decrease in a level, of rAAV-mediated transduction in the off-target in vivo environment is observed, as compared to a reference AAV.

Native AAV serotypes have been shown to exhibit distinct tropism for various tissues and organs. The rAAV particles of the present disclosure include modified (e.g., chimeric) AAV9 capsids. AAV9 has been shown to exhibit a strong tropism for the central nervous system (CNS), lung, heart, liver, muscle, and testes as compared to AAV serotypes 1-8. In a direct comparison of AAV serotypes 1-9 administered intravenously via a tail vein injection in mice, AAV9 exhibits an increased specificity for viral transduction for the liver, lung, muscle, brain, testes, and heart as compared to AAV serotypes 1-8. In addition, AAV9 exhibits a high level of transduction efficiency in the liver, muscle, brain, and heart, as compared to AAV serotypes 1-8. However, the 7-mers disclosed herein may be engineered into a capsid protein from an AAV serotype other than AAV9, such as AAV2 or AAV8.

AAV capsid proteins from native AAV serotypes, such as AAV9, with tropisms specific to the liver activate the innate immune response, which is come cases causes a severe inflammatory response in a subject, which can lead to multi-organ failure. By improving transduction efficiency of a native AAV serotype for a target in vivo tissue (e.g., brain) and decreasing the specificity of the AAV capsid protein to the liver, the rAAV particles of the present disclosure reduce the immunogenic properties of AAV-mediated transgene delivery and prevent activation of the innate immune response.

The rAAV may comprise a chimeric AAV capsid. A "chimeric" AAV capsid refers to a capsid that has an exogenous amino acid or amino acid sequence (e.g., 7-mer substitution). The rAAV may comprise a mosaic AAV capsid. A "mosaic" AAV capsid refers to a capsid that made up of two or more capsid proteins or polypeptides, each derived from a different AAV serotype. The rAAV may be a result of transcapsidation, which, in some cases, refers to the packaging of an inverted terminal repeat (ITR) from a first serotype into a capsid of a second serotype, wherein the first and second serotypes are not the same. In some cases, the capsid genes of the parental AAV serotype is pseudotyped, which means that the \ITRs from a first AAV serotype (e.g., AAV2) are used in a capsid from a second AAV serotype (e.g., AAV9), wherein the first and second AAV serotypes are not the same. As a non-limiting example, a pseudotyped AAV serotype comprising the AAV2 ITRs and AAV9 capsid protein may be indicated AAV2/9. The rAAV may additionally, or alternatively, comprise a capsid that has been engineered to express an exogenous ligand binding moiety (e.g., receptor), or a native receptor that is modified. For example, the 7-mer substitutions described herein may alter the ligand-binding function of the parental AAV to provide an increased specificity for a particular cell-surface antigen.

The reference AAV disclosed herein, in some cases, is AAV9, because it provides the best comparison of a native AAV with strong tropisms for the CNS, lung, heart, liver, muscle, and testes. However, the reference AAV may be any serotype, e.g. a serotype selected from the group consisting of AAV1, AAV2, AAV3, AAV4, AAV5, AAV6, AAV7, AAV8, AAV9, AAV10, AAV11, AAV12, or variant thereof. For example, the reference AAV can have a serotype selected from the group consisting of AAV-PHP.B, AAV-PHP.eB, and AAV-PHP.S. In many instances, the reference AAV is the parental AAV, e.g., the corresponding unmodified AAV from which the variant AAV was engineered.

The rAAV capsid proteins of the present disclosure comprise a substitution of one or more amino acids in an amino acid sequence of an AAV capsid protein. The AAV capsid protein from which the engineered AAV capsid protein of the present disclosure is produced is referred to as a "parental" AAV capsid protein, or a "corresponding unmodified capsid protein". In some cases, the parental AAV capsid protein has a serotype selected from the group consisting of AAV1, AAV2, rAAV3, AAV4, AAV5, AAV6, AAV7, AAV8, AAV9, AAV10, AAV11, and AAV12. The complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in *Mol. Ther.*, 13(1): 67-76 (2006); the AAV-11 genome is provided in *Virology*, 330(2): 375-383 (2004); portions of the AAV-12 genome are provided in Genbank Accession No. DQ813647; portions of the AAV-13 genome are provided in Genbank Accession No. EU285562.

In some cases, the parental AAV is derived from an AAV with a serotype selected from the group consisting of AAV1, AAV2, AAV3, AAV4, AAV5, AAV6, AAV7, AAV8, AAV9, AAV10, AAV11, and AAV12. Put another way, the parental AAV is a variant of AAV1, AAV2, AAV3, AAV4, AAV5, AAV6, AAV7, AAV8, AAV9, AAV10, AAV11, or AAV12. By an AAV variant, it is meant an AAV having a sequence identity of 70% or more to AAV1, AAV2, AAV3, AAV4, AAV5, AAV6, AAV7, AAV8, AAV9, AAV10, AAV11, or AAV12, for example, a sequence identity of 80%, 85%, or 90% or more; of 91%, 92%, 93%, 94%, 95% or more, in some instances of 96%, 97%, 98%, or 99% to AAV1, AAV2, AAV3, AAV4, AAV5, AAV6, AAV7, AAV8, AAV9, AAV10, AAV11, and AAV12, A variant may include, for example, an AAV comprising a heterologous amino acid or heterologous amino acid sequence within an amino acid sequence of the AAV capsid protein. The heterologous amino acid may be naturally occurring in a different AAV capsid protein. In some instances, the parental AAV capsid is described in US2019/0055578, US2018/0230489, US2017/0067908, US2019/0048041, U.S. Pat. No. 9,585,971, or US2017/0166926, all of which are incorporated herein in their entirety.

In some instances, the parental AAV is AAV9. In some instances, the amino acid sequence of the AAV9 capsid protein comprises SEQ ID NO: 1. In some instances, the parental AAV capsid protein sequence is 70%, 75%, 80%, 85%, 90%, 91%, 92%, 93%, 94%, 95%, 96%, 97%, 98%, 99%, or 100% homologous to SEQ ID NO: 1, or part of SEQ ID NO: 1. In some instances, the parental AAV capsid protein comprises the entire VP1 region provided in SEQ ID NO: 1 (e.g., amino acids 1-736). In some instances, the parental AAV capsid protein comprises amino acids 217-736 in SEQ ID NO: 1, which is the common region found in VP1, VP2 and VP3 AAV9 capsid proteins. In some instances, the AAV capsid protein comprises amino acids 64-736 in SEQ ID NO: 1, which is the common region found in VP1 and VP2. The parental AAV capsid protein sequence may comprise amino acids selected from the group consisting of 1-736, 10-736, 20-736, 30-736, 40-736, 50-736, 60-736, 70-736, 80-736, 90-736, 100-736, 110-736, 120-736, 130-736, 140-736, 150-736, 160-736, 170-736, 180-736, 190-736, 200-736, 210-736, 220-736, 230-736, 240-736, 250-736, 260-736, 270-736, 280-736, 290-736, 300-

736, 310-736, 320-736, 330-736, 340-736, 350-736, 360-736, 370-736, 380-736, 390-736, 400-736, 410-736, 420-736, 430-736, 440-736, and 450-736, from SEQ ID NO: 1.

In some instances, the parental AAV is AAV5. In some instances, the amino acid sequence of the AAV5 capsid protein comprises SEQ ID NO: 2. In some instances, the parental AAV capsid protein sequence is 70%, 75%, 80%, 85%, 90%, 91%, 92%, 93%, 94%, 95%, 96%, 97%, 98%, 99%, or 100% homologous to SEQ ID NO: 2, or part of SEQ ID NO: 2. The parental AAV capsid protein sequence may comprise amino acids selected from the group consisting of 1-724, 10-724, 20-724, 30-724, 40-724, 50-724, 60-724, 70-724, 80-724, 90-724, 100-724, 110-724, 120-724, 130-724, 140-724, 150-724, 160-724, 170-724, 180-724, 190-724, 200-724, 210-724, 220-724, 230-724, 240-724, 250-724, 260-724, 270-724, 280-724, 290-724, 300-724, 310-724, 320-724, 330-724, 340-724, 350-724, 360-724, 370-724, 380-724, 390-724, 400-724, 410-724, 420-724, 430-724, 440-724, and 450-724, of SEQ ID NO: 2.

In some instances, the parental AAV is AAV-PHP.B. In some instances, the amino acid sequence of the AAV-PHP.B capsid protein comprises SEQ ID NO: 3. In some instances, the parental AAV capsid protein is 70%, 75%, 80%, 85%, 90%, 91%, 92%, 93%, 94%, 95%, 96%, 97%, 98%, 99%, or 100% homologous to SEQ ID NO: 3, or part of SEQ ID NO: 3. The parental AAV capsid protein sequence may comprise amino acids selected from the group consisting of 1-743, 10-743, 20-743, 30-743, 40-743, 50-743, 60-743, 70-743, 80-743, 90-743, 100-743, 110-743, 120-743, 130-743, 140-743, 150-743, 160-743, 170-743, 180-743, 190-743, 200-743, 210-743, 220-743, 230-743, 240-743, 250-743, 260-743, 270-743, 280-743, 290-743, 300-743, 310-743, 320-743, 330-743, 340-743, 350-743, 360-743, 370-743, 380-743, 390-743, 400-743, 410-743, 420-743, 430-743, 440-743, and 450-743, of SEQ ID NO: 3.

In some instances, the parental AAV is AAV.PHP.S. In some instances, the amino acid sequence of the AAV-PHP.S capsid protein comprises SEQ ID NO: 4. In some instances, the parental capsid protein is 70%, 75%, 80%, 85%, 90%, 91%, 92%, 93%, 94%, 95%, 96%, 97%, 98%, 99%, or 100% homologous to SEQ ID NO: 4, or part of SEQ ID NO: 4. The parental AAV capsid protein sequence may comprise amino acids selected from the group consisting of 1-743, 10-743, 20-743, 30-743, 40-743, 50-743, 60-743, 70-743, 80-743, 90-743, 100-743, 110-743, 120-743, 130-743, 140-743, 150-743, 160-743, 170-743, 180-743, 190-743, 200-743, 210-743, 220-743, 230-743, 240-743, 250-743, 260-743, 270-743, 280-743, 290-743, 300-743, 310-743, 320-743, 330-743, 340-743, 350-743, 360-743, 370-743, 380-743, 390-743, 400-743, 410-743, 420-743, 430-743, 440-743, and 450-743, of SEQ ID NO: 4.

In some instances, the parental AAV is AAV-PHP.eB. In some instances, the amino acid sequence of the AAV-PHP.eB capsid protein comprises SEQ ID NO: 5. In some instances, the AAV parental capsid protein is 70%, 75%, 80%, 85%, 90%, 91%, 92%, 93%, 94%, 95%, 96%, 97%, 98%, 99%, or 100% homologous to SEQ ID NO: 5, or part of SEQ ID NO: 5. The parental AAV capsid protein sequence may comprise amino acids selected from the group consisting of 1-743, 10-743, 20-743, 30-743, 40-743, 50-743, 60-743, 70-743, 80-743, 90-743, 100-743, 110-743, 120-743, 130-743, 140-743, 150-743, 160-743, 170-743, 180-743, 190-743, 200-743, 210-743, 220-743, 230-743, 240-743, 250-743, 260-743, 270-743, 280-743, 290-743, 300-743, 310-743, 320-743, 330-743, 340-743, 350-743, 360-743, 370-743, 380-743, 390-743, 400-743, 410-743, 420-743, 430-743, 440-743, and 450-743, of SEQ ID NO: 5.

In some instances, the insertion is introduced after any one amino acid position selected from 452-458 within an AAV9 (VP1 numbering), or equivalent amino acid position in a variant thereof. The amino acid sequence of AAV9 (VP1) is provided in SEQ ID NO: 1. In some instances, the substitution is a substitution of an amino acid at any one amino acid position selected from 452-458 within an AAV9 (VP1 numbering), or equivalent amino acid position in a variant thereof. In the some instances, the substitution is a substitution of the amino acid at amino acid position 452. In the some instances, the substitution is a substitution of the amino acid at amino acid position 453. In the some instances, the substitution is a substitution of the amino acid at amino acid position 454. In the some instances, the substitution is a substitution of the amino acid at amino acid position 455. In the some instances, the substitution is a substitution of the amino acid at amino acid position 456. In the some instances, the substitution is a substitution of the amino acid at amino acid position 457. In the some instances, the substitution is a substitution of the amino acid at amino acid position 458. In some instances, the substitution comprises a substitution of one amino acid. In some instances, the substitution comprises a substitution of two amino acids. In some instances, the substitution comprises a substitution of three amino acids. In some instances, the substitution comprises a substitution of four amino acids. In some instances, the substitution comprises a substitution of five amino acids. In some instances, the substitution comprises a substitution of six amino acids. In some instances, the substitution comprises a substitution of seven amino acids. The substitution or the insertion of two or more amino acids may be contiguous. The substitution or the insertion of two or more amino acids may not be contiguous.

Amino acids at position 452-458 according to VP1 numbering within SEQ ID NO: 1 (AAV9), SEQ ID NO: 3 (AAV-PHP.B), SEQ ID NO: 4 (AAV-PHP.S), and SEQ ID NO: 5 (AAV-PHP.eB) are indicated as "NGSGQNQ" (SEQ ID NO: 545). In some instances, amino acids at positions 452-458 within SEQ ID NO: 2 (AAV5) is indicated by a "NLAGRYA" (SEQ ID NO: 45478). In some instances, the substitution is at an amino acid position N452, G453, S454, G455, Q456, N457, or Q458, or a combination thereof, of an AAV9 capsid protein or variant thereof. In some instances, the substitution is an amino acid position N452, L453, A454, G455, G455, R456, Y457, or A458, or a combination thereof, of an AAV5 capsid protein or variant thereof. In some instances, the amino acid(s) substituted are located at amino acids 452-453, which may include a substituted amino acid at position 452 and 453. In some instances, two amino acids are substituted at an amino acid position selected from the group consisting of 452-453, 453-455, 455-456, 456-457, and 457-458. In some instances, three amino acids are substituted at an amino acid position selected from the group consisting of 452-454, 453-455, 454-456, 455-457, and 456-458. In some instances, four amino acids are substituted at an amino acid position selected from the group consisting of 452-455, 452-456, 453-457, 454-458. In some instances, five amino acids are substituted at an amino acid position selected from the group consisting of 452-456, 453-457, and 454-458. In some instances, six amino acids are substituted at an amino acid position 452-457 or 453-458. In some instances, seven amino acids are substituted at an amino acid position 452-458.

The rAAV capsid proteins described herein may be isolated and purified. The AAV may be isolated and purified by methods standard in the art such as by column chromatography or cesium chloride gradients. Methods for purifying AAV from helper virus are known in the art and may include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118 and WO 98/09657.

The rAAV capsid protein can be conjugated to a nanoparticle, a second molecule, or a viral capsid protein. In some cases, the nanoparticle or viral capsid protein would encapsidate the therapeutic nucleic acid described herein. In some instances, the second molecule is a therapeutic agent, e.g., a small molecule, antibody, antigen-binding fragment, peptide, or protein, such as those described herein. In some instances, the second molecule is a detectable moiety. For example, the modified AAV capsid protein conjugated to a detectable moiety may be used for in vitro, ex vivo, or in vivo biomedical research applications, the detectable moiety used to visualize the modified capsid protein. The modified AAV capsid protein conjugated to a detectable moiety may also be used for diagnostic purposes.

rAAV Capsid Proteins Targeting the Central Nervous System

Disclosed herein are recombinant AAVs (rAAV) with variant capsid proteins comprising a desired tropism characterized by a substitution or an insertion of at least one amino acid at an amino acid position described above in a corresponding parental AAV capsid protein. In some instances, the rAAV capsid protein has a desired a tropism comprising increased specificity for a target in vivo environment in a subject. In some instances, the target in vivo environment comprises the central nervous system (CNS), or peripheral nervous system (PNS). One of the many advantages of the tropism of the rAAV capsid proteins described herein is their ability to target the CNS and penetrate the blood brain barrier (BBB). In some instances, the desired tropism further comprises a decreased specificity for an off-target in vivo environment, relative to a tropism of a corresponding parental AAV capsid protein. In some instances, the off-target in vivo environment comprises a peripheral organ, such as a liver. Another advantage of the rAAV capsid proteins described herein, is their ability to avoid expression of the heterologous nucleic acid in the liver, thereby reducing liver toxicity and the viral dosage amount required for therapeutic effectiveness.

The in vivo environment can be a cell. The cell can be a cell-type selected from the group consisting of a central nervous system (CNS) cell and a peripheral nervous system (PNS) cell. Non-limiting examples of CNS cells include a neuron and a glial cell. Glial cells can be selected from the group consisting of an oligodendrocyte, an ependymal cell, and an astrocytes. Non-limiting examples of a PNS cell includes a neuron or a glial cell. The glial cell can be selected from the group consisting of a Schwann cell a satellite cell, and an enteric glial cell.

The in vivo environment can be a tissue, such as from an organ or organ system. The organ can be the brain, or the spinal cord. The tissue can be a region of an organ, such as for example, the cerebrum, the cerebellum, the brainstem, the cortex, the striatum, the thalamus, the lateral ventricles, the putamen, the hypothalamus, the medulla, the pons, the hippocampus, the amygdala, the motor cortex, or a combination thereof.

Disclosed herein are rAAV capsid proteins comprising an amino acid sequence that confers an increased specificity and/or increased transduction efficiency for the CNS or PNS of a subject, as compared to a reference AAV. In some cases, the amino acid sequence also confers a decreased specificity or decreased transduction efficiency for a peripheral organ (e.g., liver), as compared to the reference AAV. The amino acid sequence, in some cases, comprises a substitution of at least one amino acid at an amino acid position selected from the group consisting of 452, 453, 454, 455, 456, 457, and 458 in an amino acid sequence of the AAV capsid protein (e.g., parental AAV). In some embodiments, the parental AAV is AAV9 or variant thereof.

Provided herein are rAAV capsid proteins with an increased specificity and/or increased transduction efficiency for the CNS or PNS as compared to a reference AAV, the rAAV capsid proteins comprising an amino acid (X1), wherein X1 is A, D, G, L, N, Q, S, or T. The rAAV capsid protein can comprise at least two amino acids, wherein X1 is A, D, G, L, N, Q, S, or T; and X2 is A, G, N, P, Q, R, S, or T. The rAAV can comprise at least three amino, wherein X1 is A, D, G, L, N, Q, S, or T; and X2 is A, G, N, P, Q, R, S, or T; and X3 is A, D, G, N, S, or T. The rAAV can comprise at least four amino acids, wherein X1 is A, D, G, L, N, Q, S, or T; X2 is A, G, N, P, Q, R, S, or T; X3 is A, D, G, N, S, or T; and X4 is A, D, G, K, N, P Q, S, or T. The rAAV can comprise at least five amino acids, wherein X1 is A, D, G, L, N, Q, S, or T; X2 is A, G, N, P, Q, R, S, or T; X3 is A, D, G, N, S, or T; X4 is A, D, G, K, N, P Q, S, or T; and X5 is A, G, K, N, P, R, S, or T. The rAAV can comprise at least six amino acids, wherein X1 is A, D, G, L, N, Q, S, or T; X2 is A, G, N, P, Q, R, S, or T; X3 is A, D, G, N, S, or T; X4 is A, D, G, K, N, P Q, S, or T; X5 is A, G, K, N, P, R, S, or T; and X6 is A, G, K, N, P, R, S, T, or V. The rAAV can comprise at least seven amino acids, wherein X1 is A, D, G, L, N, Q, S, or T; X2 is A, G, N, P, Q, R, S, or T; X3 is A, D, G, N, S, or T; X4 is A, D, G, K, N, P Q, S, or T; X5 is A, G, K, N, P, R, S, or T; X6 is A, G, K, N, P, R, S, T, or V; and X7 is A, G, K, L, R, S, T, or V.

Provided herein are rAAV capsid proteins with an increased specificity and/or increased transduction efficiency for the CNS or PNS as compared to a reference AAV and a decreased specificity and/or a decreased transduction efficiency for a peripheral organ (e.g., liver) as compared to a reference AAV. The rAAV, in some cases, comprises an amino acid (X1), wherein X1 is G, A, V, N, S, H, L, E or Q. The rAAV capsid protein can comprise at least two amino acids, wherein X1 is G, A, V, N, S, H, L, E or Q; and X2 is A, I, T, P, N, R, T, G, S, K, H, or Q. The rAAV can comprise at least three amino, wherein X1 is G, A, V, N, S, H, L, E or Q; and X2 is A, I, T, P, N, R, T, G, S, K, H, or Q; and X3 is S, N, D, A, T, H, K, Q. The rAAV can comprise at least four amino acids. In some embodiments X1 is G, A, V, N, S, H, L, E or Q; X2 is A, I, T, P, N, R, T, G, S, K, H, or Q; X3 is, N, D, A, T, H, K, Q; and X4 is N, G, T, S, D, P, R, T, or Q. The rAAV can comprise at least five amino acids, wherein X1 is G, A, V, N, S, H, L, E or Q; X2 is A, I, T, P, N, R, T, G, S, K, H, or Q; X3 is, N, D, A, T, H, K, Q; X4 is N, G, T, S, D, P, R, T, or Q; and X5 is S, K, P, T, G, D, P, N, or V. The rAAV can comprise at least six amino acids, wherein X1 is G, A, V, N, S, H, L, E or Q; X2 is A, I, T, P, N, R, T, G, S, K, H, or Q; X3 is, N, D, A, T, H, K, Q; X4 is N, G, T, S, D, P, R, T, or Q; X5 is S, K, P, T, G, D, P, N, or V; and X6 is T, A, R, S, N, G, D, P, or V. The rAAV can comprise at least seven amino acids, wherein X1 is G, A, V, N, S, H, L, E or Q; X2 is A, I, T, P, N, R, T, G, S, K, H, or Q; X3 is, N, D, A, T, H, K, Q; X4 is N, G, T, S, D, P, R, T, or Q; X5 is S, K, P, T, G, D, P, N, or V; X6 is T, A, R, S, N, G, D, P, or V; and X7 is G, N, S, L, A, E, K, or Q.

In some cases, the rAAV, in some cases, comprises an amino acid (X1), wherein X1 is A, D, E, G, H, M, N, Q, S, T, or V. The rAAV can comprise at least two amino acids, wherein X1 is A, D, E, G, H, M, N, Q, S, T, or V; and X2 is A, D, E, G, K, N, Q, S, T, or V. The rAAV can comprise at least three amino acids, wherein X1 is A, D, E, G, H, M, N, Q, S, T, or V; X2 is A, D, E, G, K, N, Q, S, T, or V; and X3 is A, D, E, G, K, N, Q, S, T, or V. The rAAV can comprise at least four amino acids, wherein X1 is A, D, E, G, H, M, N, Q, S, T, or V; X2 is A, D, E, G, K, N, Q, S, T, or V; X3 is A, D, E, G, K, N, Q, S, T, or V; and X4 is A, D, E, G, K, N, P, Q, S, or T. The rAAV can comprise at least five amino acids, wherein X1 is A, D, E, G, H, M, N, Q, S, T, or V; X2 is A, D, E, G, K, N, Q, S, T, or V; X3 is A, D, E, G, K, N, Q, S, T, or V; X4 is A, D, E, G, K, N, P, Q, S, or T; and X5 is A, D, E, G, H, K, N, P, Q, S, or T. The rAAV can comprise at least six amino acids, wherein X1 is A, D, E, G, H, M, N, Q, S, T, or V; X2 is A, D, E, G, K, N, Q, S, T, or V; X3 is A, D, E, G, K, N, Q, S, T, or V; X4 is A, D, E, G, K, N, P, Q, S, or T; X5 is A, D, E, G, H, K, N, P, Q, S, or T; and X6 is A, D, E, G, K, N, P, S, T, or V. The rAAV can comprise at least seven amino acids, wherein X1 is A, D, E, G, H, M, N, Q, S, T, or V; X2 is A, D, E, G, K, N, Q, S, T, or V; X3 is A, D, E, G, K, N, Q, S, T, or V; X4 is A, D, E, G, K, N, P, Q, S, or T; X5 is A, D, E, G, H, K, N, P, Q, S, or T; X6 is A, D, E, G, K, N, P, S, T, or V; and X7 is A, E, G, H, K, L, N, Q, S, T, or V.

In some cases, X1, X2, X3, X4, X5, X6, and X7 are contiguous (X1-X2-X3-X4-X5-X6-X7). Alternatively, X1, X2, X3, X4, X5, X6, and X7 are not contiguous. In some embodiments, any two of X1, X2, X3, X4, X5, X6 and X7 are contiguous. In some embodiments, any three of X1, X2, X3, X4, X5, X6, and X7 are contiguous. In some embodiments, any four of X1, X2, X3, X4, X5, X6, and X7 are contiguous. In some embodiments, any five of X1, X2, X3, X4, X5, X6, and X7 are contiguous. In some embodiments, any six of X1, X2, X3, X4, X5, X6, and X7 are contiguous. In some embodiments, any seven of X1, X2, X3, X4, X5, X6, and X7 are contiguous. In some embodiments, X1 is at an amino acid position 452 within an AAV9 capsid protein, or variant thereof. In some embodiments X2 is at an amino acid position 453 within an AAV9 capsid protein, or variant thereof. In some embodiments X3 is at an amino acid position 454 within an AAV9 capsid protein, or variant thereof. In some embodiments X4 is at an amino acid position 455 within an AAV9 capsid protein, or variant thereof. In some embodiments X5 is at an amino acid position 456 within an AAV9 capsid protein, or variant thereof. In some embodiments X6 is at an amino acid position 457 within an AAV9 capsid protein, or variant thereof. In some embodiments X7 is at an amino acid position 458 within an AAV9 capsid protein, or variant thereof. In some embodiments, the amino acid sequence of the rAAV does not comprise of an amino acid sequence ILGTGTS (SEQ ID NO: 45479) or QSSQTPR (SEQ ID NO: 45480) at amino acids 452-458 in a parental AAV9 capsid protein, or variant thereof.

Disclosed herein are rAAV capsid proteins comprising a substitution of one, two, three, four, five, six, or seven amino acids in an amino acid sequence provided any one of SEQ ID NOS: 11-12739. In some embodiments, the rAAV capsid proteins comprise a substitution of two amino acids in an amino acid sequence provided in any one of SEQ ID NOS: 11-12739. In some embodiments, the rAAV capsid proteins comprise a substitution of three amino acids in an amino acid sequence provided in any one of SEQ ID NOS: 11-12739. In some embodiments, the rAAV capsid proteins comprise a substitution of four amino acids in an amino acid sequence provided in any one of SEQ ID NOS: 11-12739. In some embodiments, the rAAV capsid proteins comprise a substitution of five amino acids in an amino acid sequence provided in any one of SEQ ID NOS: 11-12739. In some embodiments, the rAAV capsid proteins comprise a substitution of six amino acids in an amino acid sequence provided in any one of SEQ ID NOS: 11-12739.

Disclosed herein are rAAV capsid proteins that have an increased specificity and/or increased transduction efficiency for the central nervous system (CNS) or the peripheral nervous system (PNS). Exemplary substitutions include N452D, N452A, N452G, N452L, N452Q, N452S, N452T, G453I, G453N, G453S, G453P, G453R, G453T, S454A, S454Q, S454D, S454G, S454N, S454T, G455A, G455S, G455D, G455K, G455N, G455P, G455Q, G455T, Q456T, Q456S, Q456A, Q456G, Q456K, Q456N, Q456R, Q456P, N457K, N457A, N457G, N457P, N457R, N457S, N457T, N457V, Q458N, Q458A, Q458G, Q458K, Q458L, Q458R, Q458S, Q458T, or Q458V, in an amino acid sequence of the AAV9 capsid protein, or a variant thereof. In some embodiments, the substitution is of at least or about one two, three, four, five, six, or seven amino acids of an amino acid sequence LQTSSPG (SEQ ID NO: 2933). In some embodiments, the amino acid sequence is QQGKQSV (SEQ ID NO: 79). In some embodiments, the amino acid sequence is SINTKTN (SEQ ID NO: 45475). In some embodiments, the amino acid sequence is SNGTKQT (SEQ ID NO: 442). In some embodiments, the amino acid sequence is GSGKTAA (SEQ ID NO: 88). In some embodiments, the amino acid sequence is MGDKPTR (SEQ ID NO: 2466). In some embodiments, the amino acid sequence is DGAATKN (SEQ ID NO: 3943). In some embodiments, the amino acid sequence is QPSGGNT (SEQ ID NO: 2672). In some embodiments, the amino acid sequence is ERGANTK (SEQ ID NO: 5192). In some embodiments, the amino acid sequence is TTGGHSS (SEQ ID NO: 2743). In some embodiments, the amino acid sequence is GTTKTSE (SEQ ID NO: 3064). In some embodiments, the amino acid sequence is GTGTSVL (SEQ ID NO: 11958). In some embodiments, the amino acid sequence is NQSGTKG (SEQ ID NO: 780). In some embodiments, the amino acid sequence is DGQSSKS (SEQ ID NO: 2764). In some embodiments, the amino acid sequence is KGPGQMG (SEQ ID NO: 45476). In some embodiments, the amino acid sequence is GTPSKAG (SEQ ID NO: 2741).

Also provided herein are rAAV capsid proteins that have an increased specificity and/or increased transduction efficiency for the CNS and PNS, and a decrease in specificity and/or a decrease in transduction efficiency for an off-target in vivo environment, such as the liver. Exemplary substitutions include N452D, N452G, N452A, N452V, N452S, N452H, N452L, N452E, N452Q, G452A, G452I, G452T, G452P, G452R, G452T, G452S, G452K, G452H, S454A, S454N, S454D, S454G, S454T, S454H, S454K, S454Q, G455A, G455N, G455T, G455S, G455D, G455P, G455R, G455Q, Q456T, Q456S, Q456K, Q456P, Q456G, Q456D, Q456V, Q456A, Q456N, N457K, N457T, N457A, N457R, N457S, N457G, N457D, N457P, N457V, Q458N, Q458G, Q458S, Q458L, Q458A, Q458E, and Q458K, in an amino acid sequence of the AAV9 capsid protein, or a variant thereof. Additional exemplary substitutions include N452A, N452D, N452E, N452G, N452H, N452M, N452N, N452Q, N452S, N452T, N452V, G453A, G453D, G453E, G453G, G453K, G453N, G453Q, G453S, G453T, G453V, S454A, S454D, S454E, S454G, S454K, S454N, S454Q, S454S, S454T, S454V, G455A, G455D, G455E, G455G, G455K, G455N, G455P, G455Q, G455S, G455T, Q456A, Q456D, Q456E, Q456H, Q456H, Q456K, Q456N, Q456P, Q456Q, Q456S, Q456T, N457A, N457D, N457E, N457G, N457K, N457N, N457P, N457S, N457T, N457V, Q458A, Q458E, Q458G, Q458H, Q458K, Q458L, Q458N, Q458Q, Q458S, Q458T, and Q458V. Additional exemplary substitutions include N452A, N452D, N452E, N452G, N452H, N452K, N452L, N452M, N452N, N452Q, N452S, N452T, N452V, G453A, G453D, G453G, G453H, G453M, G453N, G453P, G453Q, G453S, G453T, G453V, S454A, S454D, S454E, S454G, S454K, S454N, S454Q, S454S, S454T, S454V, G455A, G455D, G455E, G455G, G455K, G455N, G455P, G455Q, G455S, G455T, Q456A, Q456D, Q456G, Q456K, Q456N, Q456P, Q456Q, Q456S, Q456T, N457A, N457G, N457H, N457L, N457M, N457N, N457P, N457Q, N457S, N457T, N457V, Q458A, Q458D, Q458E, Q458G, Q458H, Q458I, Q458K, Q458L, Q458N, Q458Q, Q458R, Q458S, Q458T, and Q458V. In some embodiments, the substitution is of at least or about one two, three, four, five, six, or seven amino acids of an amino acid sequence DGAATKN (SEQ ID NO: 3943). In some embodiments, the substitution is of at least or about one two, three, four, five, six, or seven amino acids of an amino acid sequence DGQSSKS (SEQ ID NO: 2764).

In some instances, the substitution of an amino acid is at an amino acid position selected from 452-458 in a capsid amino acid sequence of AAV9 or a variant thereof. In some instances, the substitution of the amino acid is at amino acid position selected from 452-458 in a capsid amino acid sequence provided in SEQ ID NO: 1. In some instances, the substitution of the amino acid is at amino acid position selected from 452-458 in a capsid amino acid sequence of AAV5 or variant thereof. In some instances, the substitution of the amino acid is at amino acid position selected from 452-458 in a capsid amino acid sequence of provided in SEQ ID NO: 2. In some instances, the substitution of the amino acid is at amino acid position selected from 452-458 in the AAVV-PHP.B capsid protein sequence (SEQ ID NO: 3). In some instances, the substitution of the amino acid is at amino acid position selected from 452-458 in the AAV-PHP.S capsid protein sequence (SEQ ID NO: 4). In some instances, the substitution of the amino acid is at amino acid position selected from 452-458 in the AAV-PHP.eB capsid protein sequence (SEQ ID NO: 5). In some embodiments, the rAAV of the present disclosure comprises the substitution of the amino acid at an amino acid position selected from 452-458 in a parental AAV capsid protein, and an insertion of an amino acid or amino acid sequence at an amino acid position 588-589 in the parental AAV capsid protein.

The rAAV capsid proteins of the present disclosure may also have an insertion of an amino acid sequence at amino acid position 588-589 in a parental AAV9 capsid protein, or variant thereof. In some embodiments, the insertion of the amino acid sequence comprises X1LAVPFK (SEQ ID NO: 45481) at amino acid position 588-589 in the parental AAV9 capsid protein, wherein X1 is any amino acid other than T, S, or N. In some embodiments, the insertion of the amino acid sequence comprises X1X2AVPFK (SEQ ID NO: 45482) at amino acid position 588-589 in the parental AAV9 capsid protein, wherein X2 is any amino acid other than L or V. In some embodiments, the insertion of the amino acid sequence comprises X1X2X3VPFK (SEQ ID NO: 45483) at amino acid position 588-589 in the parental AAV9 capsid protein, wherein X3 is any amino acid other than A, S, Q, P, and T. In some embodiments, the insertion of the amino acid sequence comprises X1X2X3X4PFK (SEQ ID NO: 45484) at amino acid position 588-589 in the parental AAV9 capsid protein, wherein X4 is any amino acid other than V, T, Q, N, L, and M. In some embodiments, the insertion of the amino acid sequence comprises TLAX4PFK (SEQ ID NO: 45485) at amino acid position 588-589 in the parental AAV9 capsid protein, wherein X is any amino acid other than V, T, Q, N, L, and M. In some embodiments, the rAAV further comprises a substitution of an amino acid at an amino acid position 587 in the parental AAV9 capsid protein, or variant thereof. In some embodiments, the substitution is A587D. In some embodiments, the substitution is a substitution with amino acid other than D. In some embodiments, the rAAV further comprises a substitution of an amino acid at an amino acid position 588 in the parental AAV9 capsid protein or variant thereof. In, some embodiments, the substitution is Q588G. In some embodiments, the substitution is a substitution with amino acid other than G.

In some embodiments, the rAAV capsid has a variant AAV capsid protein (e.g., an rAAV capsid protein) comprises a substitution of at least or about three, four, five, six, or seven amino acids of an amino acid sequence LQTSSPG (SEQ ID NO: 2933) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence LQTSSPG (SEQ ID NO: 2933) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence LQTSSPG (SEQ ID NO: 2933) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46386.

In some embodiments, the rAAV capsid protein comprises a substitution of at least or about three, four, five, six, or seven amino acids of an amino acid sequence QQGKQSV (SEQ ID NO: 79) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence QQGKQSV (SEQ ID NO: 79) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence QQGKQSV (SEQ ID NO: 79) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46387.

In some embodiments, the rAAV capsid protein comprises a substitution of at least or about three, four, five, six, or seven amino acids of an amino acid sequence SINTKTN (SEQ ID NO: 45475) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence SINTKTN (SEQ ID NO: 45475) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence SINTKTN (SEQ ID NO: 45475) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46368.

In some embodiments, the rAAV capsid protein comprises a substitution of at least or about three, four, five, six, or seven amino acids of an amino acid sequence SNGTKQT (SEQ ID NO: 442) at an amino acid position 452-458 in a parental AAV9 capsid protein represented by SEQ ID NO: 1. In some embodiments, the rAAV capsid protein comprises a substitution of at least or about three, four, five, six, or seven amino acids of an amino acid sequence SNGTKQT (SEQ ID NO: 442) at an amino acid position 452-458 in a parental AAV9 variant capsid protein represented by SEQ ID NO: 3 or SEQ ID NO: 5. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46389.

In some embodiments, the rAAV capsid protein comprises a substitution of at least or about three, four, five, six, or seven amino acids of an amino acid sequence GSGKTAA (SEQ ID NO: 88) at an amino acid position 452-458 in a parental AAV9 capsid protein represented by SEQ ID NO: 1. In some embodiments, the rAAV capsid protein comprises a substitution of at least or about three, four, five, six, or seven amino acids of an amino acid sequence GSGKTAA (SEQ ID NO: 88) at an amino acid position 452-458 in a parental AAV9 variant capsid protein represented by SEQ ID NO: 3 or SEQ ID NO:5. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46390.

In some embodiments, the rAAV capsid protein comprises a substitution of at least or about three, four, five, six, or seven amino acids of an amino acid sequence MGDKPTR (SEQ ID NO: 2466) at an amino acid position 452-458 in a parental AAV9 capsid protein represented by SEQ ID NO: 1. In some embodiments, the rAAV capsid protein comprises a substitution of at least or about three, four, five, six, or seven amino acids of an amino acid sequence MGDKPTR (SEQ ID NO: 2466) at an amino acid position 452-458 in a parental AAV9 variant capsid protein represented by SEQ ID NO: 3 or SEQ ID NO: 5. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46391.

In some embodiments, the rAAV capsid protein comprises a substitution of at least or about three, four, five, six, or seven amino acids of an amino acid sequence DGAATKN (SEQ ID NO: 3943) at an amino acid position 452-458 in a parental AAV9 capsid protein represented by SEQ ID NO: 1. In some embodiments, the rAAV capsid protein comprises a substitution of at least or about three, four, five, six, or seven amino acids of an amino acid sequence DGAATKN (SEQ ID NO: 3943) at an amino acid position 452-458 in a parental AAV9 variant capsid protein represented by SEQ ID NO: 3 or SEQ ID NO:5. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46384.

In some embodiments, the rAAV capsid protein comprises a substitution of at least or about three, four, five, six, or seven amino acids of an amino acid sequence QPSGGNT (SEQ ID NO: 2672) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence QPSGGNT (SEQ ID NO: 2672) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence QPSGGNT (SEQ ID NO: 2672) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46392.

In some embodiments, the rAAV capsid protein comprises a substitution of at least or about three, four, five, six, or seven amino acids of an amino acid sequence ERGANTK (SEQ ID NO: 5192) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence ERGANTK (SEQ ID NO: 5192) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence ERGANTK (SEQ ID NO: 5192) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46393.

In some embodiments, the rAAV capsid protein comprises a substitution of at least or about three, four, five, six, or seven amino acids of an amino acid sequence TTGGHSS (SEQ ID NO: 2743) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence TTGGHSS (SEQ ID NO: 2743) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence TTGGHSS (SEQ ID NO: 2743) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46394.

In some embodiments, the rAAV capsid protein comprises a substitution of at least or about three, four, five, six, or seven amino acids of an amino acid sequence GTTKTSE (SEQ ID NO: 3064) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence GTTKTSE (SEQ ID NO: 3064) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence GTTKTSE (SEQ ID NO: 3064) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46395.

In some embodiments, the rAAV capsid protein comprises a substitution of at least or about three, four, five, six, or seven amino acids of an amino acid sequence GTGTSVL (SEQ ID NO: 11958) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence GTGTSVL (SEQ ID NO: 11958) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence GTGTSVL (SEQ ID NO: 11958) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46396.

In some embodiments, the rAAV capsid protein comprises a substitution of at least or about three, four, five, six, or seven amino acids of an amino acid sequence NQSGTKG (SEQ ID NO: 780) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence NQSGTKG (SEQ ID NO: 780) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence NQSGTKG (SEQ ID NO: 780) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of an amino acid sequence comprising at least or about three, four, five, six, seven, eight, nine, ten, or eleven amino acids. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46397.

In some embodiments, the rAAV capsid protein comprises a substitution of at least or about three, four, five, six, or seven amino acids of an amino acid sequence DGQSSKS (SEQ ID NO: 2764) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence DGQSSKS (SEQ ID NO: 2764) at an amino acid position 452-458 in a parental AAV9 variant capsid protein (SEQ ID NO: 5). In some embodiments, the rAAV capsid protein comprises a substitution of at least or about three, four, five, six, or seven amino acids of an amino acid sequence DGQSSKS (SEQ ID NO: 2764) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46385.

In some embodiments, the rAAV capsid protein comprises a substitution of at least or about three, four, five, six, or seven amino acids of an amino acid sequence KGPGQMG (SEQ ID NO: 45476) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence KGPGQMG (SEQ ID NO: 45476) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence KGPGQMG (SEQ ID NO: 45476) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46398.

In some embodiments, the rAAV capsid protein comprises a substitution of at least or about three, four, five, six, or seven amino acids of an amino acid sequence GTPSKAG (SEQ ID NO: 2741) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence GTPSKAG (SEQ ID NO: 2741) at an amino acid position 452-458 in a parental AAV9 capsid protein (SEQ ID NO: 5). In some embodiments, the rAAV capsid protein comprises a substitution of at least or about three, four, five, six, or seven amino acids of an amino acid sequence GTPSKAG (SEQ ID NO: 2741) at an amino acid position 452-458 in a parental AAV9 variant capsid protein (SEQ ID NO: 5). In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the insertion of an amino acid sequence comprising at least or about three, four, five, six, seven, eight, nine, ten, or eleven amino acids. In some embodiments, the insertion of the amino acid sequence comprises TLAVPFK (SEQ ID NO: 45477) at amino acid position 588-589 in the parental AAV9 capsid protein. In some embodiments, the rAAV capsid protein comprises an amino acid sequence provided in SEQ ID NO: 46399.

Table 1 provides amino acid sequences of top performing rAAV capsid proteins, ranked based on a positive enrichment in the brain and negative enriched in the liver after two rounds of in vivo selection, as well as the DNA sequences encoding them. Table 2 provides amino acid sequences of top performing rAAV capsid proteins ranked based on an enrichment in the brain alone after two rounds of in vivo selection, and corresponding DNA sequences. Example 3 provides details on how the enrichment score was calculated. An AAV variant was determined to de-target a tissue if its enrichment score in that tissue was less than or equal to 0.

TABLE 1

List of 7 amino acid targeting peptides of rAAVs that target the CNS and detarget the liver

| SEQ ID NO | DNA Sequence | SEQ ID NO | Amino Acid Sequence | Log 10 enrichment in the brain | Log 10 enrichment in the liver |
|---|---|---|---|---|---|
| 15469 | AGCAGCACCAGCGGCGCCGGC | 2740 | SSTSGAG | 1.805607713 | 0 |
| 15470 | GGCACCCCCAGCAAAGCCGGC | 2741 | GTPSKAG | 1.782483914 | 0 |
| 15471 | GACAAAACCACCGCCGGCCAA | 2742 | DKTTAGQ | 1.756796407 | 0 |
| 15472 | ACCACCGGCGGCCACAGCAGC | 2743 | TTGGHSS | 1.7086977 | 0 |
| 15473 | GGCGCCAGCAACAGCACCGGC | 2744 | GASNSTG | 1.6215475 | 0 |
| 15474 | GCCATCAACGGCAAAGCCGGC | 2745 | AINGKAG | 1.611787687 | 0 |
| 15475 | GTCATCGACACCAAAGCCGGC | 2746 | VIDTKAG | 1.611787687 | 0 |
| 15476 | AACGCCAGCAGCAGCACCGGC | 2747 | NASSSTG | 1.599553231 | 0 |
| 15477 | GGTACGAGTAGTCCGGCTAAT | 2748 | GTSSPAN | 1.593175811 | 0 |
| 15478 | GGCCCCGGCGACACCAGAAGC | 2749 | GPGDTRS | 1.559758687 | 0 |
| 15479 | GGGAATGGGTCGTCGGCGCTG | 2750 | GNGSSAL | 1.534699431 | -1.140781313 |
| 15480 | GGCAGAAGCGGCGGCACCGGC | 2751 | GRSGGTG | 1.532606441 | 0 |

TABLE 1-continued

List of 7 amino acid targeting peptides of rAAVs that target the CNS and detarget the liver

| SEQ ID NO | DNA Sequence | SEQ ID NO | Amino Acid S

TABLE 1-continued

List of 7 amino acid targeting peptides of rAAVs that target the CNS and detarget the liver

| SEQ ID NO | DNA Sequence | SEQ ID NO | Amino Acid Sequence | Log 10 enrichment in the brain | Log 10 enrichment in the liver |
|---|---|---|---|---|---|
| 15517 | GAGTCTGGGAAGGGTAGTTTG | 2788 | ESGKGSL | 1.345977191 | 0 |
| 15518 | GAAAACAGCAGCGGCCACGCC | 2789 | ENSSGHA | 1.3451798 | 0 |

TABLE 2

List of 7 amino acid targeting peptides of rAAVs that target the CNS

| SEQ ID NO | DNA Sequence | SEQ ID NO | Amino Acid Sequence | Log 10 enrichment in the brain |
|---|---|---|---|---|
| 12740 | AGCGGCCTCAAAGGCACCGGC | 11 | SGLKGTG | 1.912817683 |
| 15469 | AGCAGCACCAGCGGCGCCGGC | 2740 | SSTSGAG | 1.805607713 |
| 15470 | GGCACCCCCAGCAAAGCCGGC | 2741 | GTPSKAG | 1.782483914 |
| 15471 | GACAAAACCACCGCCGGCCAA | 2742 | DKTTAGQ | 1.756796407 |
| 15472 | ACCACCGGCGGCCACAGCAGC | 2743 | TTGGHSS | 1.7086977 |
| 12741 | GTGGGTGGGACTCAGGGTAAG | 12 | VGGTQGK | 1.683542214 |
| 12742 | AGCATGGACAGCAGACCCGGC | 13 | SMDSRPG | 1.646549793 |
| 12743 | GGTAGTAGTCCTAGTAAGGCT | 14 | GSSPSKA | 1.624376814 |
| 15473 | GGCGCCAGCAACAGCACCGGC | 2744 | GASNSTG | 1.6215475 |
| 15474 | GCCATCAACGGCAAAGCCGGC | 2745 | AINGKAG | 1.611787687 |
| 15475 | GTCATCGACACCAAAGCCGGC | 2746 | VIDTKAG | 1.611787687 |
| 12744 | ACTGGTACGGCGAATCCGTTG | 15 | TGTANPL | 1.609487799 |
| 15476 | AACGCCAGCAGCAGCACCGGC | 2747 | NASSSTG | 1.599553231 |
| 15477 | GGTACGAGTAGTCCGGCTAAT | 2748 | GTSSPAN | 1.593175811 |
| 12745 | AGCCAAGGCGCCAAACCCGTC | 16 | SQGAKPV | 1.581298365 |
| 12746 | CAGGGGGAGAAGAATACTATG | 17 | QGEKNTM | 1.560127515 |
| 15478 | GGCCCCGGCGACACCAGAAGC | 2749 | GPGDTRS | 1.559758687 |
| 15479 | GGGAATGGGTCGTCGGCGCTG | 2750 | GNGSSAL | 1.534699431 |
| 15480 | GGCAGAAGCGGCGGCACCGGC | 2751 | GRSGGTG | 1.532606441 |
| 15481 | AGCACCGGCCCCACCCCCGCC | 2752 | STGPTPA | 1.532606441 |
| 12747 | ACCAGCGGCAACAGCAGCAAA | 18 | TSGNSSK | 1.532606441 |
| 15482 | CATGGGGGAGGGATTCTAGT | 2753 | HGGRDSS | 1.514877674 |
| 15483 | GGTTCTGGTACGCCTAATGGG | 2754 | GSGTPNG | 1.511287094 |
| 12748 | ACGACGTCTAAGCCTGGTACT | 19 | TTSKPGT | 1.510809312 |
| 15484 | GGCAAAGCCGGCAGCACCGGC | 2755 | GKAGSTG | 1.497844335 |
| 12749 | AGCCAAGGCAAAGGCGGCAGC | 20 | SQGKGGS | 1.497374065 |
| 15485 | CTTAGTGCGGGTAAGGGTGAG | 2756 | LSAGKGE | 1.496394268 |
| 12750 | GGGTCGATTAAGGGGGAGGCT | 21 | GSIKGEA | 1.495179943 |
| 12751 | AACAGCGGCACCACCGGCAAC | 22 | NSGTTGN | 1.492959081 |

TABLE 2-continued

List of 7 amino acid targeting peptides of rAAVs that target the CNS

| SEQ ID NO | DNA Sequence | SEQ ID NO | Amino Acid Sequence | Log 10 enrichment in the brain |
|---|---|---|---|---|
| 15486 | GTCGGCATCCCCAGCGCCGGC | 2757 | VGIPSAG | 1.486848951 |
| 15487 | AGTGGTGGGCAGAAGGATAAT | 2758 | SGGQKDN | 1.480843526 |
| 12752 | GAAAGAACCAAAGAAACCCTC | 23 | ERTKETL | 1.465659651 |
| 12753 | GATCATGGTAAGGGGAATCAG | 24 | DHGKGNQ | 1.464822053 |
| 12754 | GATGGGCAGCAGCGGAGTAGT | 25 | DGQQRSS | 1.464030027 |
| 12755 | TCGGGTAATAGTACTAATAAG | 26 | SGNSTNK | 1.458626389 |
| 15488 | GAAACCGGCGGCAGCCCCAAA | 2759 | ETGGSPK | 1.45728072 |
| 12756 | GGTGTTGAGCAGCGTTCGGGG | 27 | GVEQRSG | 1.456753138 |
| 15489 | CAAGGCCACACCAACGTCGCC | 2760 | QGHTNVA | 1.455309339 |
| 12757 | AATGGTGGTAAGTCGAGTTCG | 28 | NGGKSSS | 1.451684533 |
| 12758 | TCGACTAATAAGAGTAATCTG | 29 | STNKSNL | 1.44624661 |
| 15490 | TCGCATGGGAGTCCGGCTAGT | 2761 | SHGSPAS | 1.445456265 |
| 15491 | AGCCAAAAAGCGTCGCCGGC | 2762 | SQKSVAG | 1.445456265 |
| 15492 | GTTGGTCAGTCTGCTGCTCAG | 2763 | VGQSAAQ | 1.444470352 |
| 15493 | GACGGCCAAAGCAGCAAAAGC | 2764 | DGQSSKS | 1.444085169 |
| 15494 | GCCCAAGCCAAACCCGCCGGC | 2765 | AQAKPAG | 1.442429811 |
| 15495 | ACCGGCCACAACAGCAGCATG | 2766 | TGHNSSM | 1.435696428 |
| 15496 | GGCCAAAGCACCAGCAGCGGC | 2767 | GQSTSSG | 1.432491288 |
| 15497 | ACCGGCATCAGCGGCGCCGGC | 2768 | TGISGAG | 1.429944099 |
| 12759 | GACGGCCAAGGCAACGGCAAA | 30 | DGQGNGK | 1.424823398 |
| 15498 | GTCAGAGACACCAGCAGCAGC | 2769 | VRDTSSS | 1.417512639 |

Modified AAV Capsid Proteins Targeting Organs or Tissues

Disclosed herein are recombinant AAV (rAAV) capsid proteins comprising a desired tropism characterized by a substitution or an insertion of at least one amino acid at an amino acid position described above in a parental AAV capsid protein (e.g., AAV5 or AAV9). The AAV capsid protein of the present disclosure is engineered to have a desired tropism comprising increased specificity for a target in vivo environment in a subject, such as an organ or organ system. One of the many advantages of the tropism of the rAAV capsid proteins described herein is their ability to express the heterologous nucleic acid in the organ, or organ system selectively and efficiently, while avoiding expression of the heterologous nucleic acid in an off-target organ, thereby reducing toxicity and the viral dosage amount required for therapeutic effectiveness.

The in vivo environment can be a tissue or a cell. The in vivo environment can be a tissue, such as from an organ or organ system. Non-limiting examples of an organ or organ system include a liver, intestine, heart, lung, reproductive organ, muscle, adipose, pancreas, a brain, and spleen. Non-limiting examples of a reproductive organ include an ovary and a testicle. The in vivo environment can be a cell. The cell can be a cell-type selected from the group consisting of a central nervous system (CNS) cell, a peripheral nervous system (PNS) cell, a liver cell, an intestine cell, a lung cell, a heart cell, an adipose cell, a muscle cell, a kidney cell, a muscle cell, a pancreas cell, a spleen cell, a reproductive organ cell, and a stomach cell. The CNS cell can be a neuron or a glial cell. The glial cell can be selected from the group consisting of an oligodendrocyte, an ependymal cell, and an astrocyte. The PNS cell can be a neuron or a glial cell. The glial cell can be selected from the group consisting of a Schwann cell a satellite cell, and an enteric glial cell. The liver cell can be a hepatocyte. The intestine cell can be selected from the group consisting of an enterocyte, a goblet cell, an enteroendocrine cell, a cup cell, a tuft cell, and a Paneth cell. The lung cell can be selected from the group consisting of an alveolar type I epithelial cell, an alveolar type II epithelial cell, an alveolar type I pneumocyte, an alveolar type II pneumocyte, a capillary endothelial cell, and an alveolar macrophage. The heart cell can be a cardiomyocyte. The stomach cell can be selected from the group consisting of a mucous cell, a parietal cell, a chief cell, and a G cell. The muscle cell can be a myocyte.

rAAVs of the present disclosure that are optimized for targeting specific organ or tissue within a subject have amino acid sequences comprising an amino acid sequence provided in SEQ ID NOS: 25469-35471. In some embodiments, rAAVs optimized for targeting the heart have amino acid sequence comprising an amino acid sequence provided in SEQ ID NOS: 25469-26205. In some embodiments, rAAVs optimized for targeting the lung have amino acid sequences comprising an amino acid sequence provided in SEQ ID NOS: 32537-34198. In some embodiments, rAAVs optimized for targeting the liver have amino acid sequences that comprise an amino acid sequence provided in SEQ ID NOS: 30720-30923. In some embodiments, rAAVs optimized for targeting the intestine have amino acid sequences comprising an amino acid sequence provided in SEQ ID NOS: 26206-26873. In some embodiments, rAAVs optimized for targeting the stomach have amino acid sequences comprising amino acid sequence provided in SEQ ID NOS: 31873-32060. In some embodiments, rAAVs optimized for targeting the spleen have amino acid sequences comprising an amino acid sequence provided in SEQ ID NOS: 31468-31872. In some embodiments, rAAVs optimized for targeting the kidney have amino acid sequences comprising an amino acid sequence provided in SEQ ID NOS: 26874-30719. In some embodiments, rAAVs optimized for targeting the fat (adipose) have amino acid sequences comprising an amino acid sequence provided in SEQ ID NOS: 34199-35471. In some embodiments, rAAVs optimized for targeting the muscle have amino acid sequences comprising an amino acid sequence provided in SEQ ID NO: 30924-31451. The muscle may be cardiac muscle. The muscle may be skeletal muscle. In some embodiments, rAAVs optimized for targeting the pancreas have amino acid sequences comprising an amino acid sequence provided in SEQ ID NOS: 31452-31467. In some embodiments, rAAVs optimized for targeting a reproductive organ, such as a testicle, comprise amino acid sequences comprising an amino acid sequence provided in SEQ ID NOS: 32061-32536. In some instances, the reproductive organ is an ovary.

Disclosed herein are rAAV capsid proteins comprising a desired tropism characterized by a substitution of at least one amino acid at an amino acid position selected from 452-458 in an amino acid sequence of a parental AAV9 capsid protein, or a variant thereof. The rAAV capsid protein can comprise a substitution of at least one amino acid in a parental AAV capsid protein. In some instances, X1 is K, R, N, or T. The rAAV capsid protein can comprise a substitution or an insertion of at least two amino acids in a parental AAV capsid protein, wherein X1 is K, R, N, or T; and X2 is D, E, N, or V. The rAAV capsid protein can comprise a substitution or an insertion of at least three amino acids in a parental AAV capsid protein, wherein X1 is K, R, N, or T; X2 is D, E, N, or V; and X3 is N, S, L, or P. The rAAV capsid protein can comprise a substitution or an insertion of at least four amino acids in a parental AAV capsid protein, wherein X1 is K, R, N, or T; X2 is D, E, N, or V; X3 is N, S, L, or P; and X4 is T, S, P, or L. The rAAV capsid protein can comprise a substitution or an insertion of at least five amino acids in a parental AAV capsid protein, wherein X1 is K, R, N, or T; X2 is D, E, N, or V; X3 is N, S, L, or P; X4 is T, S, P, or L; and X5 is P, R, or S. The rAAV capsid protein can comprise a substitution or an insertion of at least six amino acids in a parental AAV capsid protein, wherein X1 is K, R, N, or T; X2 is D, E, N, or V; X3 is N, S, L, or P; X4 is T, S, P, or L; X5 is P, R, or S; and X6 is G, S, N, or T. The rAAV capsid protein can comprise a substitution or an insertion of at least seven amino acids in a parental AAV capsid protein, wherein, X1 is K, R, N, or T; X2 is D, E, N, or V; X3 is N, S, L, or P; IX4 is T, S, P, or L; X5 is P, R, or S; X6 is G, S, N, or T; and X7 is R, L or I.

In some embodiments, X1, X2, X3, X4, X5, X6, and X7 are contiguous (X1-X2-X3-X4-X5-X6-X7). In some embodiments, any two of X1, X2, X3, X4, X5, X6, and X7 are contiguous. In some embodiments, any three of X1, X2, X3, X4, X5, X6, and X7 are contiguous. In some embodiments, any four of X1, X2, X3, X4, X5, X6, and X7 are contiguous. In some embodiments, any five of X1, X2, X3, X4, X5, X6, and X7 are contiguous. In some embodiments, any six of X1, X2, X3, X4, X5, X6, and X7 are contiguous. In some embodiments, any seven of X1, X2, X3, X4, X5, X6, and X7 are contiguous. In some embodiments, X1, X2, X3, X4, X5, X6, and X7 are not contiguous. In some embodiments, X1 is at an amino acid position 452 within an AAV9 capsid protein, or variant thereof. In some embodiments X2 is at an amino acid position 453 within an AAV9 capsid protein, or variant thereof. In some embodiments X3 is at an amino acid position 454 within an AAV9 capsid protein, or variant thereof. In some embodiments X4 is at an amino acid position 455 within an AAV9 capsid protein, or variant thereof. In some embodiments X5 is at an amino acid position 456 within an AAV9 capsid protein, or variant thereof. In some embodiments X6 is at an amino acid position 457 within an AAV9 capsid protein, or variant thereof. In some embodiments X7 is at an amino acid position 458 within an AAV9 capsid protein, or variant thereof.

Disclosed herein are rAAV capsid proteins that comprise a substitution of at least one, two, three, four, five, six, or seven amino acids provided any one of SEQ ID NOS: 25469-35471. In some embodiments, the at least one, two, three, four, five, six, or seven amino acids are provided in an amino acid sequence selected from SEQ ID NOS: 25469-26205. In some embodiments, the at least one, two, three, four, five, six, or seven amino acids are provided in an amino acid sequence selected from SEQ ID NOS: 26206-26873. In some embodiments, the at least one, two, three, four, five, six, or seven amino acids are provided in an amino acid sequence selected from SEQ ID NOS: 26874-30719. In some embodiments, the at least one, two, three, four, five, six, or seven amino acids are provided in an amino acid sequence selected from SEQ ID NOS: 30720-30923. In some embodiments, the at least one, two, three, four, five, six, or seven amino acids are provided in an amino acid sequence selected from SEQ ID NO: 30924-31451. In some embodiments, the at least one, two, three, four, five, six, or seven amino acids are provided in an amino acid sequence selected from SEQ ID NOS: 31452-31467. In some embodiments, the at least one, two, three, four, five, six, or seven amino acids are provided in an amino acid sequence selected from SEQ ID NOS: 31468-31872. In some embodiments, the at least one, two, three, four, five, six, or seven amino acids are provided in an amino acid sequence selected from SEQ ID NOS: 31873-32060. In some embodiments, the at least one, two, three, four, five, six, or seven amino acids are provided in an amino acid sequence selected from SEQ ID NOS: 32061-32536. In some embodiments, the at least one, two, three, four, five, six, or seven amino acids are provided in an amino acid sequence selected from SEQ ID NOS: 32537-34198. In some embodiments, the at least one, two, three, four, five, six, or seven amino acids are provided in an amino acid sequence selected from SEQ ID NOS: 34199-35471. In some embodiments, the substitution comprises N452K, N452R, N452T, G453D, G453L, G453E, G453V, G453N, G453S, G453L, G453P, S454L, S454P, S454A, S454D, S454G, S454T, G455T, G455S, G455P, G455L, Q456P, Q456R, Q456S, N457G, N457S, N457T, Q458R, Q458L or Q458I, or a combination thereof.

Disclosed herein are rAAV capsid proteins that comprise a substitution of at least or about one, two, three, four, five, six, or seven amino acids of an amino acid sequence provided herein. In some embodiments, the amino acid sequence is KDNTPGR (SEQ ID NO: 32538). In some embodiments, the amino acid sequence is NNLPRNL (SEQ ID NO: 32867). In some embodiments, the amino acid sequence is RESSPSL (SEQ ID NO: 29065). In some embodiments, the amino acid sequence is RVPLSTI (SEQ ID NO: 26933).

In some instances, the substitution of an amino acid is at an amino acid position selected from 452-458 in a capsid amino acid sequence of AAV9 or a variant thereof. In some instances, the substitution of the amino acid is at amino acid position selected from 452-458 in a capsid amino acid sequence provided in SEQ ID NO: 1. In some instances, the substitution of the amino acid is at amino acid position selected from 452-458 in a capsid amino acid sequence of AAV5 or variant thereof. In some instances, the substitution of the amino acid is at amino acid position selected from 452-458 in a capsid amino acid sequence of provided in SEQ ID NO: 2. In some instances, the substitution of the amino acid is at amino acid position selected from 452-458 in the AAVV-PHP.B capsid protein sequence (SEQ ID NO: 3). In some instances, the substitution of the amino acid is at amino acid position selected from 452-458 in the AAV-PHP.S capsid protein sequence (SEQ ID NO: 4). In some instances, the substitution of the amino acid is at amino acid position selected from 452-458 in the AAV-PHP.eB capsid protein sequence (SEQ ID NO: 5). In some embodiments, the rAAV of the present disclosure comprises the substitution of the amino acid at an amino acid position selected from 452-458 in a parental AAV capsid protein, and an insertion of an amino acid or amino acid sequence at an amino acid position 588-589 in the parental AAV capsid protein.

The rAAV capsid proteins of the present disclosure may also have an insertion of an amino acid sequence at amino acid position 588 in a parental AAV9 or AAV5 capsid protein, or variant thereof. In some embodiments, the insertion of the amino acid sequence comprises X1LAVPFK (SEQ ID NO: 45481) at amino acid position 588-589 in the parental AAV9 AAV5 capsid protein, wherein X1 is any amino acid other than T, S, or N. In some embodiments, the insertion of the amino acid sequence comprises X1X2AVPFK (SEQ ID NO: 45482) at amino acid position 588-589 in the parental AAV9 or AAV5 capsid protein, wherein X2 is any amino acid other than L or V. In some embodiments, the insertion of the amino acid sequence comprises X1X2X3VPFK (SEQ ID NO: 45483) at amino acid position 588-589 in the parental AAV9 or AAV5 capsid protein, wherein X3 is any amino acid other than A, S, Q, P, and T. In some embodiments, the insertion of the amino acid sequence comprises X1X2X3X4PFK (SEQ ID NO: 45484) at amino acid position 588-589 in the parental AAV9 or AAV5 capsid protein, wherein X4 is any amino acid other than V, T, Q, N, L, and M. In some embodiments, the insertion of the amino acid sequence comprises TLAX4PFK (SEQ ID NO: 45485) at amino acid position 588-589 in the parental AAV9 or AAV5 capsid protein, wherein X is any amino acid other than V, T, Q, N, L, and M. In some embodiments, the rAAV further comprises a substitution of an amino acid at an amino acid position 587 in the parental AAV9 or AAV5 capsid protein, or variant thereof. In some embodiments, the substitution is A587D. In some embodiments, the substitution is a substitution with amino acid other than D. In some embodiments, the rAAV further comprises a substitution of an amino acid at an amino acid position 588 in the parental AAV9 or AAV5 capsid protein or variant thereof. In, some embodiments, the substitution is Q588G. In some embodiments, the substitution is a substitution with amino acid other than G.

In some embodiments, the rAAV capsid protein comprises a substitution of at least or about three, four, five, six, or seven amino acids of an amino acid sequence KDNTPGR (SEQ ID NO:32538) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence KDNTPGR (SEQ ID NO:32538) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence KDNTPGR (SEQ ID NO:32538) at an amino acid position 452-458 in a parental AAV9 variant capsid protein (SEQ ID NO: 5). In some embodiments, the rAAV capsid protein comprises a substitution of at least or about three, four, five, six, or seven amino acids of an amino acid sequence KDNTPGR (SEQ ID NO:32538) at an amino acid position 452-458 in a parental AAV5 capsid protein (SEQ ID NO: 2). In some embodiments, the rAAV capsid protein comprises a substitution of at least or about three, four, five, six, or seven amino acids of an amino acid sequence KDNTPGR (SEQ ID NO:32538) at an amino acid position 452-458 in a parental AAV5 variant capsid protein. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the rAAV capsid protein comprises an amino acid sequence provided in SEQ ID NO: 46400.

In some embodiments, the rAAV capsid protein comprises a substitution of at least or about three, four, five, six, or seven amino acids of an amino acid sequence NNLPRNL (SEQ ID NO: 32867) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence NNLPRNL (SEQ ID NO: 32867) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence NNLPRNL (SEQ ID NO: 32867) at an amino acid position 452-458 in a parental AAV9 variant capsid protein (SEQ ID NO: 5). In some embodiments, the rAAV capsid protein comprises a substitution of at least or about three, four, five, six, or seven amino acids of an amino acid sequence NNLPRNL (SEQ ID NO: 32867) at an amino acid position 452-458 in a parental AAV5 capsid protein (SEQ ID NO: 2). In some embodiments, the rAAV capsid protein comprises a substitution of at least or about three, four, five, six, or seven amino acids of an amino acid sequence NNLPRNL (SEQ ID NO: 32867) at an amino acid position 452-458 in a parental AAV5 variant capsid protein. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the rAAV capsid protein comprises an amino acid sequence provided in SEQ ID NO: 46401.

In some embodiments, the rAAV capsid protein comprises a substitution of at least or about three, four, five, six, or seven amino acids of an amino acid sequence RESSPSL (SEQ ID NO: 29065) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence RESSPSL (SEQ ID NO: 29065) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence RESSPSL (SEQ ID NO: 29065) at an amino acid position 452-458 in a parental AAV9 variant capsid protein (SEQ ID NO: 5). In some embodiments, the rAAV capsid protein comprises a substitution of at least or about three, four, five, six, or seven amino acids of an amino acid sequence RESSPSL (SEQ ID NO: 29065) at an amino acid position 452-458 in a parental AAV5 capsid protein (SEQ ID NO: 2). In some embodiments, the rAAV capsid protein comprises a substitution of at least or about three, four, five, six, or seven amino acids of an amino acid sequence RESSPSL (SEQ ID NO: 29065) at an amino acid position 452-458 in a parental AAV5 variant capsid protein. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the rAAV capsid protein comprises an amino acid sequence provided in SEQ ID NO: 46402.

In some embodiments, the rAAV capsid protein comprises a substitution of at least or about three, four, five, six, or seven amino acids of an amino acid sequence RVPLSTI (SEQ ID NO: 26933) at an amino acid position 452-458 in a parental AAV9 capsid protein (SEQ ID NO: 1). In some embodiments, the rAAV capsid protein comprises a substitution of at least or about three, four, five, six, or seven amino acids of an amino acid sequence RVPLSTI (SEQ ID NO: 26933) at an amino acid position 452-458 in a parental AAV9 variant capsid protein (SEQ ID NO: 3). In some embodiments, the rAAV capsid protein comprises a substitution of at least or about three, four, five, six, or seven amino acids of an amino acid sequence RVPLSTI (SEQ ID NO: 26933) at an amino acid position 452-458 in a parental AAV9 variant capsid protein (SEQ ID NO: 5). In some embodiments, the rAAV capsid protein comprises a substitution of at least or about three, four, five, six, or seven amino acids of an amino acid sequence RVPLSTI (SEQ ID NO: 26933) at an amino acid position 452-458 in a parental AAV5 capsid protein (SEQ ID NO: 2). In some embodiments, the rAAV capsid protein comprises a substitution of at least or about three, four, five, six, or seven amino acids of an amino acid sequence RVPLSTI (SEQ ID NO: 26933) at an amino acid position 452-458 in a parental AAV5 variant capsid protein. In some embodiments, the rAAV capsid protein comprises an insertion of at least or about three, four, five, six, seven, eight, nine, ten, or eleven amino acids at an amino acid position 588-589 in the parental AAV9 capsid protein, or variant thereof. In some embodiments, the rAAV capsid protein comprises an amino acid sequence provided in SEQ ID NO: 46403.

Heterologous Nucleic Acids

Disclosed herein are heterologous nucleic acids comprising therapeutic nucleic acids useful for the treatment or prevention of a disease or condition, or symptom of the disease or condition, disclosed herein. In some embodiments, the therapeutic nucleic acids encode a therapeutic gene expression product. Non-limiting examples of gene expression products include proteins, polypeptides, peptides, enzymes, antibodies, antigen binding fragments, nucleic acid (RNA, DNA, antisense oligonucleotide, siRNA, and the like), and gene editing components, for use in the treatment, prophylaxis, and/or amelioration of the disease or disorder, or symptoms of the disease or disorder. In some instances, the therapeutic nucleic acids are placed in an organism, cell, tissue or organ of a subject by way of a rAAV, such as those disclosed herein.

Disclosed herein are rAAVs, each comprising a viral genome (e.g., a single stranded DNA molecule (ssDNA)). In some instances, the viral vector comprises two inverted terminal repeat (ITR) sequences that are about 145 bases each, flanking the heterologous nucleic acid or transgene. In some embodiments, the transgene comprises a therapeutic nucleic acid, and in some cases, a promoter in cis with the therapeutic nucleic acid in an open reading frame (ORF). The promoter is capable of initiating transcription of therapeutic nucleic acid in the nucleus of the target cell. The ITR sequences can be from any AAV serotype. Non-limiting examples of AAV serotypes include AAV1, AAV2, AAV3, AAV4, AAV5, AAV6, AAV7, AAV8, AAV9, AAV10, AAV11, and AAV12. In some cases, an ITR is from AAV2. In some cases, an ITR is from AAV9.

Disclosed herein are transgenes that can comprise any number of nucleotides. In some cases, a transgene can comprise less than about 100 nucleotides. In some cases, a transgene can comprise at least about 100 nucleotides. In some cases, a transgene can comprise at least about 200 nucleotides. In some cases, a transgene can comprise at least about 300 nucleotides. In some cases, a transgene can comprise at least about 400 nucleotides. In some cases, a transgene can comprise at least about 500 nucleotides. In some cases, a transgene can comprise at least about 1000 nucleotides. In some cases, a transgene can comprise at least about 5000 nucleotides. In some cases, a transgene can comprise at least about 10,000 nucleotides. In some cases, a transgene can comprise at least about 20,000 nucleotides. In some cases, a transgene can comprise at least about 30,000 nucleotides. In some cases, a transgene can comprise at least about 40,000 nucleotides. In some cases, a transgene can comprise at least about 50,000 nucleotides. In some cases, a transgene can comprise between about 500 and about 5000 nucleotides. In some cases, a transgene can comprise between about 5000 and about 10,000 nucleotides. In any of the cases disclosed herein, the transgene can comprise DNA, RNA, or a hybrid of DNA and RNA. In some cases, the transgene can be single stranded. In some cases, the transgene can be double stranded.

Disclosed herein are transgenes useful for modulating the expression or activity of a target gene or gene expression product thereof. In some instances, the transgene is encapsidated by an rAAV capsid protein of an rAAV particle described herein. In some instances, the rAAV particle is delivered to a subject to treat a disease or condition disclosed herein in the subject. In some instances, the delivery is systemic (e.g., intravenous, intranasal).

The transgenes disclosed herein are useful for expressing an endogenous gene at a level similar to that of a healthy or normal individual. This is particularly useful in the treatment of a disease or condition related to the underexpression, or lack of expression, of a gene expression product. In some embodiments, the transgenes disclosed herein are useful for overexpressing an endogenous gene, such that an expression level of the endogenous gene is above the expression level of a healthy or normal individual. Additionally, transgenes can be used to express exogenous genes (e.g., active agent such as an antibody, peptide, nucleic acid, or gene editing components). In some embodiments, the therapeutic gene expression product is capable of altering, enhancing, increasing, or inducing the activity of one or more endogenous biological processes in the cell. In some embodiments, the transgenes disclosed herein are useful for reducing expressing an endogenous gene, such as for example, a dominant negative gene. In some embodiments, the therapeutic gene expression product is capable of altering, inhibiting, reducing, preventing, eliminating, or impairing the activity of one or more endogenous biological processes in the cell. In some aspects, the increase of gene expression refers to an increase by at least about 20%, 30%, 40%, 50%, 60%, 70%, 80%, 85%, 90%, 95% and 100%. In one aspect, the protein product of the targeted gene may be increased by at least about 20%, 30%, 40%, 50%, 60%, 70%, 80%, 85%, 90%, 95% and 100%. In some aspects, the decrease of gene expression refers to an increase by at least about 20%, 30%, 40%, 50%, 60%, 70%, 80%, 85%, 90%, 95% and 100%. In one aspect, the protein product of the targeted gene may be decreased by at least about 20%, 30%, 40%, 50%, 60%, 70%, 80%, 85%, 90%, 95% and 100%.

When endogenous sequences (endogenous or part of a transgene) are expressed with a transgene, the endogenous sequences can be full-length sequences (wild-type or mutant) or partial sequences. The endogenous sequences can be functional. Non-limiting examples of the function of these full length or partial sequences include increasing the serum half-life of the polypeptide expressed by a transgene (e.g., therapeutic gene) and/or acting as a carrier.

A transgene can be inserted into an endogenous gene such that all, some or none of the endogenous gene is expressed. For example, a transgene as described herein can be inserted into an endogenous locus such that some (N-terminal and/or C-terminal to a transgene) or none of the endogenous sequences are expressed, for example as a fusion with a transgene. In other cases, a transgene (e.g., with or without additional coding sequences such as for the endogenous gene) is integrated into any endogenous locus, for example a safe-harbor locus. For example, a Frataxin (FXN) transgene can be inserted into an endogenous FXN gene. A transgene can be inserted into any gene, e.g., the genes as described herein.

At least one advantage of the present disclosure is that virtually any therapeutic nucleic acid may be used to express any therapeutic gene expression product. In some instances, the therapeutic gene expression product is a therapeutic protein or a peptide (e.g., antibody, antigen-binding fragment, peptide, or protein). In one embodiment the protein encoded by the therapeutic nucleic acid is between 50-5000 amino acids in length. In some embodiments the protein encoded is between 50-2000 amino acids in length. In some embodiments the protein encoded is between 50-1000 amino acids in length. In some embodiments the protein encoded is between 50-1500 amino acids in length. In some embodiments the protein encoded is between 50-800 amino acids in length. In some embodiments the protein encoded is between 50-600 amino acids in length. In some embodiments the protein encoded is between 50-400 amino acids in length. In some embodiments the protein encoded is between 50-200 amino acids in length. In some embodiments the protein encoded is between 50-100 amino acids in length. In some embodiments the peptide encoded is between 4-50 amino acids in length. In some embodiments, the protein encoded is a tetrapeptide, a pentapeptide, a hexapeptide, a heptapeptide, an octapeptide, a nonapeptide, or a decapeptide. In some embodiments, the protein encoded comprises a peptide of 2-30 amino acids, such as 5-30, 10-30, 2-25, 5-25, 10-25, or 10-20 amino acids. In some embodiments, the protein encoded comprises a peptide of at least 11, 12, 13, 14, 15, 17, 20, 25 or 30 amino acids, or a peptide that is no longer than 50 amino acids, e.g. no longer than 35, 30, 25, 20, 17, 15, 14, 13, 12, 11 or 10 amino acids.

Non-limiting examples of therapeutic protein or peptides include an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphoring, a semaphorin receptor, a serotonin transport protein, a serotonin uptake inhibitor, a serotonin receptor, a serpin, a serpin receptor, and a tumor suppressor. In certain embodiments, the therapeutic protein or peptide is selected from the group consisting of brain-derived neurotrophic factor (BDNF), ciliary neurotrophic factor (CNTF), macrophage colony-stimulating factor (CSF), epidermal growth factor (EGF), fibroblast growth factor (FGF), gonadotropin, interferon-gamma (IFN), insulin-like growth factor 1 (IFG-1), nerve growth factor (NGF), platelet-derived growth factor (PDGF), pigment epithelium-derived factor (PEDF), transforming growth factor (TGF), transforming growth factor-beta (TGF-B), tumor necrosis factor (TNF), vascular endothelial growth factor (VEGF), prolactin, somatotropin, X-linked inhibitor of apoptosis protein 1 (XIAP1), interleukin 1 (IL-1), IL-2, IL-3, IL-4, IL-5, IL-6, IL-7, IL-8, IL-9, IL-10, IL-10, viral IL-10, IL-11, IL-12, IL-13, IL-14, IL-15, IL-16, IL-17, and IL-18.

A therapeutic gene expression product can comprise gene editing components. Non-limiting examples of gene editing components include those required for CRISPR/Cas, artificial site-specific RNA endonuclease (ASRE), zinc finger endonuclease (ZFN), and transcription factor like effector nuclease (TALEN). In a non-limiting example, a subject having Huntington's disease is identified. The subject is then systemically administered a first amount of a rAAV encapsidating a viral vector encoding ZFN engineered to represses the transcription of the Huntingtin (HTT) gene. In some instances, the route of administration is intravenous. The rAAV will include a modified AAV capsid protein that includes an amino acid sequence provided in any one of Tables 1-2, or SEQ ID NOS: 11-12739, so as to allow proper targeting of the ZFN to the nervous system, while retargeting off-target organs, such as the liver. If needed, the subject is administered a second or third dose of the rAAV, until a therapeutically effective amount of the ZFN is expressed the subject in the nervous system. In another non-limiting example, a subject with cystic fibrosis is identified. The subject is then systemically administered a first amount of a rAAV encapsidating a transgene encoding ZFN engineered to represses the transcription of the cystic fibrosis transmembrane conductance regulator (CFTR) gene. In some instances the route of administration is intranasal (e.g., intranasal spray). The rAAV will include a modified AAV capsid protein that includes an amino acid sequence provided in any one of SEQ ID NOS: 32537-34198, so as to allow proper targeting of the ZFN to the lung. If needed, the subject is administered a second or third dose of the rAAV, until a therapeutically effective amount of the ZFN is expressed the subject in the lung.

A therapeutic nucleic acid can comprise a non-protein coding gene e.g., sequences encoding antisense RNAs, RNAi, shRNAs and micro RNAs (miRNAs), miRNA sponges or decoys, recombinase delivery for conditional gene deletion, conditional (recombinase-dependent) expression, includes those required for the gene editing components described herein. The a non-protein coding gene may also encode a tRNA, rRNA, tmRNA, piRNA, double stranded RNA, snRNA, snoRNA, and/or long non-coding RNA (lncRNA). In some cases, the non-protein coding gene can modulate the expression or the activity of a target gene or gene expression product. a non-protein coding gene. For example, the RNAs described herein may be used to inhibit gene expression in a target cell, for example, a cell in the central nervous system (CNS) or peripheral organ (e.g., lung). In some cases, inhibition of gene expression refers to an inhibition by at least about 20%, 30%, 40%, 50%, 60%, 70%, 80%, 85%, 90%, 95% and 100%. In some cases, the protein product of the targeted gene may be inhibited by at least about 20%, 30%, 40%, 50%, 60%, 70%, 80%, 85%, 90%, 95% and 100%. The gene can be either a wild type gene or a gene with at least one mutation. The targeted protein may be either a wild type protein or a protein with at least one mutation.

A therapeutic nucleic acid can modulates the expression or activity of a gene or gene expression product expressed from the gene that is implicated in disease or disorder of the brain. For example, the therapeutic nucleic acid, in some cases is a gene or a modified version of the gene described herein. In another example, the therapeutic nucleic acid comprises an effector gene expression product such as a gene editing components specific to target a gene therein. Non-limited examples of genes include Sarcoglycan Alpha (SGCA), glutamic acid decarboxylase 65 (GAD65), glutamic acid decarboxylase 67 (GAD67), CLN2 gene, Nerve Growth Factor (NGF), glial cell derived neurotrophic factor (GDNF), Neurturin, Survival Of Motor Neuron 1, Telomeric (SMN1), β-Glucocerebrosidase (GCase), Frataxin (FXN), Huntingtin (HTN), methyl-CpG binding protein 2 (MECP2), peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and NPS3. In some embodiments, the peroxisomal biogenesis factor (PEX) is selected from the group consisting of PEX1, PEX2, PEX3, PEX4, PEX5, PEX6, PEX7, PEX10, PEX1113, PEX12, PEX13, PEX14, PEX16, PEX19, and PEX26. In some instances, the gene or gene expression product is inhibited. In some instances, the gene or gene expression product is enhanced.

A therapeutic nucleic acid modulates expression or activity of a gene or gene expression product expressed from the gene that is implicated in disease or disorder of a particular organ (e.g., lung, heart, liver, muscle, eye). Non-limited examples of genes include Cystic Fibrosis Transmembrane Conductance Regulator (CFTR), Factor X (FIX), RPE65, Retinoid Isomerohydrolase (RPE65), Sarcoglycan Alpha (SGCA), and sarco/endoplasmic reticulum Ca2+-ATPase (SERCA2a). In some embodiments, the therapeutic gene expression product is of human, murine, avian, porcine, bovine, ovine, feline, canine, equine, epine, caprine, lupine or primate origin. In some instances, the gene or gene expression product is inhibited. In some instances, the gene or gene expression product is enhanced.

Disclosed herein are modified viral genomes comprising genetic information (e.g., heterologous nucleic acid) that are assembled into a rAAV via viral packaging. In some instances, the viral genome is from an AAV serotypes selected from the group consisting of AAV1, AAV2, AAV3, AAV4, AAV5, AAV6, AAV7, AAV8, AAV9, AAV10, AAV11, and AAV12. In some instances, the viral genome is from a modified AAV serotype selected from the group consisting of AAV-PHP.B, AAV-PHP.eB, and AAV-PHP.S.

A viral genome, such as those described herein, can comprise a transgene, which in some cases encodes a heterologous gene expression product (e.g., therapeutic gene expression product, recombinant capsid protein, and the like). The transgene is in cis with two inverted terminal repeats (ITRs) flanking the transgene. The transgene may comprise a therapeutic nucleic acid encoding a therapeutic gene expression product. Due to the limited packaging capacity of the rAAV (~2.5 kB), in some cases, a longer transgene may be split between two AAV vectors, the first with 3' splice donor and the second with a 5' splice acceptor. Upon co-infection of a cell, concatemers form, which are spliced together to express a full-length transgene.

The viral genome, in some cases, is a single stranded viral DNA comprising the transgene. The AAV vector can be episomal. In some instances, the viral genome is a concatemer. An episomal viral genome can develop chromatin-like organization in the target cell that does not integrate into the genome of the target cell. When infected into non-dividing cells, the stability of the episomal viral genome in the target cell enable the long-term transgene expression. Alternatively, the AAV vector integrates the transgene into the genome of the target cell predominantly at a specific site (e.g., AAVS1 on human chromosome 19).

A transgene is generally inserted so that its expression is driven by the endogenous promoter at the integration site, namely the promoter that drives expression of the endogenous gene into which a transgene is inserted. In some instances, a transgene comprises a promoter and/or enhancer, for example a constitutive promoter or an inducible or tissue/cell specific promoter. As a non-limiting example, the promoter may be CMV promoter, a CMV-β-Actin-intron-β-Globin hybrid promoter (CAG), CBA promoter, FRDA or FXN promoter, UBC promoter, GUSB promoter, NSE promoter, Synapsin promoter, MeCP2 promoter, GFAP promoter, H1 promoter, U6 promoter, NFL promoter, NFH promoter, SCN8A promoter, or PGK promoter. As a non-limiting example, promoters can be tissue-specific expression elements include, but are not limited to, human elongation factor 1α-subunit (EF1α), immediate-early cytomegalovirus (CMV), chicken β-actin (CBA) and its derivative CAG, the β glucuronidase (GUSB), and ubiquitin C (UBC). The transgene may include a tissue-specific expression elements for neurons such as, but not limited to, neuron-specific enolase (NSE), platelet-derived growth factor (PDGF), platelet-derived growth factor B-chain (PDGF-β), the synapsin (Syn), the methyl-CpG binding protein 2 (MeCP2), Ca2+/calmodulin-dependent protein kinase II (CaMKII), metabotropic glutamate receptor 2 (mGluR2), NFL, NFH, np32, PPE, Enk and EAAT2 promoters. The transgene may comprise a tissue-specific expression elements for astrocytes such as, but not limited to, the glial fibrillary acidic protein (GFAP) and EAAT2 promoters. The transgene may comprise tissue-specific expression elements for oligodendrocytes such as, but not limited to, the myelin basic protein (MBP) promoter. In one embodiment, the transgene comprises a region located approximately ~5 kb upstream of the first exon of the encoded therapeutic nucleic acid, more specifically, there is a 17 bp region located approximately 4.9 kb upstream of the first exon of the encoded frataxin gene in order to allow for expression with the FRDA promoter (See e.g., Puspasari et al. Long Range Regulation of Human FXN Gene Expression, PLOS ONE, 2011; the contents of which is herein incorporated by reference in its entirety).

In some embodiments, the promoter is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. The promoter may provide expression of the therapeutic gene expression product for a period of time in targeted tissues such as, but not limited to, the central nervous system and peripheral organs (e.g., lung). Expression of the therapeutic gene expression product may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years. Expression of the payload may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years or 10-15 years, or 15-20 years, or 20-25 years, or 25-30 years, or 30-35 years, or 35-40 years, or 40-45 years, or 45-50 years, or 50-55 years, or 55-60 years, or 60-65 years.

Heterologous nucleic acids and transgenes of the present embodiment may also include plasmid vectors. Plasmid vectors are useful for the generation of the recombinant AAV (rAAV) particles described herein. An AAV vector can comprise a genome of a helper virus. Helper virus proteins are required for the assembly of a recombinant rAAV, and packaging of a transgene containing a heterologous nucleic acid into the rAAV. The helper virus genes are adenovirus genes E4, E2a and VA, that when expressed in the cell, assist with AAV replication. In some embodiments, an AAV vector comprises E2. In some embodiments, an AAV vector comprises E4. In some embodiments, an AAV vector comprises VA. In some instances, the AAV vector comprises one of helper virus proteins, or any combination thereof.

An plasmid vector can comprise a viral genome comprising a nucleic acid encoding the recombinant AAV (rAAV) capsid protein described herein. The viral genome can comprise a Replication (Rep) gene encoding a Rep protein, and Capsid (Cap) gene encoding an Aap protein in the first open reading frame (ORF1) or a Cap protein in the second open reading frame (ORF2). The Rep protein is selected from the group consisting of Rep78, Rep68, Rep52, and Rep40. In some instances, the Cap gene is modified encoding a modified AAV capsid protein described herein. A wild-type Cap gene encodes three proteins, VP1, VP2, and VP3. In some cases, VP1 is modified. In some cases, VP2 is modified. In some cases, VP3 is modified. In some cases, all three VP1-VP3 are modified. The AAV vector can comprise nucleic acids encoding wild-type Rep78, Rep68, Rep52, Rep40 and Aap proteins.

In some instances, the plasmid vector is bacterial. In some instances, the plasmid vector is derived from *Escherichia coli*. In some instances, the nucleic acid sequence comprises, in a 5' to 3' direction: (1) a 5' inverted terminal repeat (ITR) sequence, (2) a Replication (Rep) gene, (3) a Capsid (Cap) gene, and (4) a 3' ITR, wherein the Cap gene encodes the AAV capsid protein described herein. In some instances, the plasmid vector encodes a pseudotyped AAV capsid protein. In some instances, the Cap gene is derived from the deoxyribose nucleic acid (DNA) provided in any one of SEQ ID NOs: 6-10.

In some instances, the 5' ITR and the 3' ITR are derived from an AAV2 serotype. In some instances, the 5' ITR and the 3' ITR are derived from an AAV5 serotype. In some instances, the 5' ITR and the 3' ITR are derived from an AAV9 serotype.

Disclosed herein are plasmid vectors comprising any one of SEQ ID NOS: 12740-25468 and 35472-45474, which are the DNA sequences encoding the rAAV capsid proteins of the present disclosure. In some instances, plasmid vector comprises a Cap gene that is at least 90%, 91%, 92%, 93%, 94%, 95%, 96%, 97%, 98%, 99%, or 100% identical to any one of the DNA sequences provided in SEQ ID NOS: 46404-46423. The plasmid vector of the present disclosure can comprise the VP1 Cap gene comprises any one of SEQ ID NOS: 6-10. An AAV vector can comprise 70%, 75%, 80%, 85%, 90%, 91%, 92%, 93%, 94%, 95%, 96%, 97%, 98%, 99%, or 100% of any one of SEQ ID NOS: 6-10.

Also disclosed are nucleic acids encoding the rAAV capsids comprising variant AAV capsid proteins (e.g., rAAV capsid proteins) of the present disclosure. In some instances, the rAAV capsid proteins comprise a DNA sequence provided in any one of SEQ ID NOS: 46404-46423, which encode the full-length VP1 protein with the 7-mer substituted at amino acid position 452-458. In some cases, the 7-mer is encoded by DNA sequence provided in any one of SEQ ID NOS: 46364-46383.

Provided here are plasmid vectors encoding the rAAV capsid proteins of the present disclosure comprising: (a) a nucleic acid sequence encoding 7-mer amino acid sequence provided in any one of FIGS. 2-14; and (b) a nucleic acid sequence that is 70%, 75%, 80%, 85%, 90%, 91%, 92%, 93%, 94%, 95%, 96%, 97%, 98%, 99%, or 100% of any one of SEQ ID NOS: 6-10. In some instances, AAV9 (SEQ ID NO: 6) is modified to include any one of SEQ ID NOS:

12740-25468 and 35472-45474. In some instances, the AAV-PHP.eB (SEQ ID NO: 10) is modified to include any one of SEQ ID NOS: 12740-25468 and 35472-45474. In some instances, AAV5 (SEQ ID NO: 7) is modified to include any one of SEQ ID NOS: 35472-45474. In some instances, AAV-PHP.B (SEQ ID NO: 8) is modified to include any one of SEQ ID NOS: SEQ ID NOS: 12740-25468 and 35472-45474. In some instances, AAV-PHP.S VP1 (SEQ ID NO: 9) is modified to include any one of SEQ ID NOS: 12740-25468 and 35472-45474. The AAV vector described herein may be used to produce a variant AAV capsid by the methods described herein.

Methods

Methods of Producing rAAVs

Disclosed herein are methods of producing a recombinant AAV (rAAV). In some instances all elements that are required for AAV production in target cell (e.g., HEK293 cells) are transiently transfected into the target cell using suitable methods known in the art. For example, the rAAV of the present disclosure can be product by co-transfecting three plasmid vectors, a first vector with ITR-containing plasmid carrying the transgene (e.g., therapeutic nucleic acid), a second vector that carries the AAV Rep and Cap genes; and (3), a third vector that provides the helper genes isolated from adenovirus. The methods described herein generate high-titer AAV vectors that are free of adenovirus. The Cap gene disclosed here comprises any one of SEQ ID NOS: 12740-25468 and 35472-45474, which are the DNA sequences encoding the modified AAV capsid proteins of the present disclosure. In some cases, rAAVs of the present disclosure are generated using the methods described in Challis, R. C. et al. Systemic AAV vectors for widespread and targeted gene delivery in rodents. *Nat. Protoc.* 14, 379 (2019), which is hereby incorporated by reference in its entirety. Briefly, triple transfection of HEK293T cells (ATCC) using polyethylenimine (PEI) is performed, viruses are collected after 120 hours from both cell lysates and media and purified over iodixanol.

Disclosed herein, are methods of manufacturing comprising: (a) introducing into a cell a nucleic acid comprising: (i) a first nucleic acid sequence encoding a therapeutic gene expression product enclosed by a 5' and a 3' inverted terminal repeat (ITR) sequence; (ii) a second nucleic acid sequence encoding a viral genome comprising a 5' ITR sequence, a Replication (Rep) gene, Capsid (Cap) gene, and a 3' ITR, wherein the Cap gene encodes the AAV capsid protein described herein; and (iii) a third nucleic acid sequence encoding a first helper virus protein selected from the group consisting of E4orf6, E2a, and VA RNA, and optionally, a second helper virus protein comprising E1a or E1b55k; (b) expressing in the cell the AAV capsid protein described herein; (c) assembling an AAV particle comprising the AAV capsid proteins disclosed herein; and (d) packaging the first nucleic acid sequence in the AAV particle. In some instances, the AAV particle is a rAAV capsid with an increased specificity when measured in a target tissue (e.g., CNS, PNS, lung) in a subject and a decreased specificity when measured in an off-target tissue (e.g., liver), relative to a reference AAV capsid. In some instances, the methods further comprise packing the first nucleic acid sequence encoding the therapeutic gene expression product such that it becomes encapsidated by the rAAV capsid protein. In some embodiments, the rAAV particles are isolated, concentrated, and purified using suitable viral purification methods, such as those described herein.

In a non-limiting example, the rAAVs are generated by triple transfection of precursor cells (e.g., HEK293T) cells using a standard transfection protocol (e.g., with PEI). Viral particles are harvested from the media after a period of time (e.g., 72 h post transfection) and from the cells and media at a later point in time (e.g., 120 h post transfection). Virus present in the media is concentrated by precipitation with 8% poly(ethylene glycol) and 500 mM sodium chloride and the precipitated virus is added to the lysates prepared from the collected cells. The viruses are purified over iodixanol (Optiprep, Sigma) step gradients (15%, 25%, 40% and 60%). Viruses are concentrated and formulated in PBS. Virus titers are determined by measuring the number of DNaseI-resistant vector genome copies (VGs) using qPCR and the linearized genome plasmid as a control.

The Rep protein can be selected from the group consisting of Rep78, Rep68, Rep52, and Rep40. The genome of the AAV helper virus comprises an AAV helper gene selected from the group consisting of E2, E4, and VA. In some instances, the first nucleic acid sequence and the second nucleic acid sequence are in trans. In some instances, the first nucleic acid sequence and the second nucleic acid sequence are in cis. In some instances, the first nucleic acid sequence, the second nucleic acid sequence and the third nucleic acid sequence, are in trans.

The cell can be selected from a group consisting of a human, a primate, a murine, a feline, a canine, a porcine, an ovine, a bovine, an equine, an epine, a caprine and a lupine host cell. In some instances, the cell is a progenitor or precursor cell, such as a stem cell. In some instances, the stem cell is a mesenchymal cell, embryonic stem cell, induced pluripotent stem cell (iPSC), fibroblast or other tissue specific stem cell. The cell can be immortalized. In some instances, the embryonic stem cell is a human embryonic stem cell. In some instances, the human embryonic stem cell is a human embryonic kidney 293 (HEK-293) cell. In some instances, the cell is a differentiated cell. Base on the disclosure provided, it is expected that this system can be used in conjunction with any transgenic line expressing a recombinase in the target cell type of interest to develop AAV capsids that more efficiently transduce that target cell population.

Methods of rAAV-Mediated Delivering a Heterologous Nucleic Acid

Disclosed herein are methods of delivering a heterologous nucleic acid (e.g., therapeutic nucleic acid or transgene disclosed herein) to subject in need thereof. The transgene may be encapsidated by a recombinant AAV (rAAV) capsid protein or rAAV particle such as those described herein.

Methods may be ex vivo, e.g., scientific research purposes or for producing adoptive cellular therapies. The subject may be a human primary cell or a mature cell, or cell line. The subject may be a cell from a monkey, hamster, or mouse. In either case, delivery may include contacting the composition with the cell or cell line.

Methods may be in vivo, e.g., treating a disease or a condition in a subject in need thereof. In some instances, the subject may be mammal, such as a human or non-human primate, in which case delivery of the composition may comprise administering the composition to the subject. In some embodiments, delivery of the heterologous nucleic acid comprises administering to the subject the composition using any one of the routes of administration described herein. In a non-limiting example, the rAAV encapsidating an aromatic L-amino acid decarboxylase deficiency (AADC) gene may be administered to a subject intravenously to treat AADC deficiency.

In some embodiments, methods of increasing transduction of a heterologous nucleic acid in a target in vivo or ex vivo tissue comprise delivering a rAAV particle described herein, the rAAV engineered to have an increased transduction efficiency in a target in vivo environment (e.g., tissue or cell type). In some instances, the increased transduction efficiency comprises a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold increase, or more, relative to a reference AAV. In some instances, the increased transduction efficiency is at least 30-fold. In some instances, the increased transduction efficiency is at least 40-fold. In some instances, the increased transduction efficiency is at least 50-fold. In some instances, the increased transduction efficiency is at least 60-fold. In some instances, the increased transduction efficiency is at least 80-fold. In some instances, the increased transduction efficiency is at least 90-fold. In some instances, the increased transduction efficiency is at least 100-fold.

In some embodiments, methods of decreasing transduction of a heterologous nucleic acid in an off-target in vivo or ex vivo tissue comprise delivering a rAAV particle described herein, the rAAV engineered to have a reduced transduction efficiency by 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold, or more, relative to a reference AAV. In some instances, the off-target gene transfer is reduced by at least 20-fold. In some instances, the off-target gene transfer is reduced by at least 30-fold. In some instances, the off-target gene transfer is reduced by at least 40-fold. In some instances, the off-target gene transfer is reduced by at least 50-fold. In some instances, the off-target gene transfer is reduced by at least 60-fold. In some instances, the off-target gene transfer is reduced by at least 80-fold. In some instances, the off-target gene transfer is reduced by at least 90-fold. In some instances, the off-target gene transfer is reduced by at least 100-fold.

Methods of delivering a heterologous nucleic acid to a target in vivo environment are also provided comprising delivering the a rAAV particle described herein that has been engineered to have an increased specificity in a target in vivo or ex vivo tissue (e.g., organ or cell type), as compared to a reference AAV. In some embodiment, the rAAV particle has been engineered to have a decreased specificity for an off-target in vivo or ex vivo tissue. Methods, in some cases, comprise detecting whether a rAAV possesses more specificity for a target in vivo or ex vivo tissue than a reference AAV, includes measuring a level of gene expression product (e.g., RNA or protein) expressed from the heterologous nucleic acid encapsidated by the rAAV in a tissue sample obtained from the target in vivo environment in a subject; and comparing the measured level to a control level (such as, for e.g., the gene expression product expressed from a heterologous nucleic acid encapsidated by a reference AAV (e.g., AAV9)). Suitable methods for measuring expression of a gene expression product luciferase reporter assay and quantitative polymerase chain reaction (qPCR).

In some instances, the reference AAV has a serotype selected from the group consisting of AAV1, AAV2, AAV3, AAV4, AAV5, AAV6, AAV7, AAV8, AAV9, AAV10, AAV11, AAV12, or variant thereof. For example, the reference AAV can have a serotype selected from the group consisting of AAV-PHP.B, AAV-PHP.eB, and AAV-PHP.S.

Delivery to the Central or Peripheral Nervous System

Provided herein are methods of delivering a heterologous nucleic acid to a target in vivo environment comprising delivering a composition to the target in vivo environment selected from the group consisting of a central nervous system (CNS) and the peripheral nervous system (PNS) in a subject, the composition comprising a rAAV particle with a rAAV capsid protein, the rAAV capsid protein encapsidating a viral vector encoding a heterologous nucleic acid (e.g., therapeutic nucleic acid). In some embodiments, the rAAV particle encapsidating the heterologous nucleic acid comprises a rAAV capsid protein engineered with an increased specificity and, in some cases, transduction efficiency for the CNS or the PNS of the subject, even when administered to the subject systemically, as compared to a reference AAV.

Methods comprise delivering a rAAV particle comprising an rAAV capsid protein with increased specificity and/or transduction efficiency for the CNS or the PNS in the subject, as compared to a reference AAV (e.g., AAV9, AAV5). The rAAV capsid protein, in some cases, has a decreased specificity and/or transduction efficiency for a peripheral organ (e.g., liver). In some instances, the delivery is systemic. Alternatively, delivery is direct (e.g., into the affected area of the CNS or PNS). The rAAV capsid protein may comprise a substitution of at least one amino acid in an amino acid sequence in an amino acid sequence of a parental AAV, wherein X1 is A, D, G, L, N, Q, S, or T. The rAAV capsid protein can comprise a substitution of at least two amino acids in an amino acid sequence of a parental AAV, wherein X1 is A, D, G, L, N, Q, S, or T; and X2 is A, G, N, P, Q, R, S, or T. The rAAV can comprise a substitution of at least three amino in an amino acid sequence of a parental AAV, wherein X1 is A, D, G, L, N, Q, S, or T; and X2 is A, G, N, P, Q, R, S, or T; and X3 is A, D, G, N, S, or T. The rAAV can comprise a substitution of at least four amino acids in an amino acid sequence of a parental AAV, wherein X1 is A, D, G, L, N, Q, S, or T; X2 is A, G, N, P, Q, R, S, or T; X3 is A, D, G, N, S, or T; and X4 is A, D, G, K, N, P Q, S, or T. The rAAV can comprise a substitution of at least five amino acids in an amino acid sequence of a parental AAV, wherein X1 is A, D, G, L, N, Q, S, or T; X2 is A, G, N, P, Q, R, S, or T; X3 is A, D, G, N, S, or T; X4 is A, D, G, K, N, P Q, S, or T; and X5 is A, G, K, N, P, R, S, or T. The rAAV can comprise a substitution of at least six amino acids in an amino acid sequence of a parental AAV, wherein X1 is A, D, G, L, N, Q, S, or T; X2 is A, G, N, P, Q, R, S, or T; X3 is A, D, G, N, S, or T; X4 is A, D, G, K, N, P Q, S, or T; X5 is A, G, K, N, P, R, S, or T; and X6 is A, G, K, N, P, R, S, T, or V. The rAAV can comprise a substitution of at least seven amino acids in an amino acid sequence of a parental AAV, wherein X1 is A, D, G, L, N, Q, S, or T; X2 is A, G, N, P, Q, R, S, or T; X3 is A, D, G, N, S, or T; X4 is A, D, G, K, N, P Q, S, or T; X5 is A, G, K, N, P, R, S, or T; X6 is A, G, K, N, P, R, S, T, or V; and X7 is A, G, K, L, R, S, T, or V.

X1, X2, X3, X4, X5, X6, and X7 are, in some cases, contiguous (X1-X2-X3-X4-X5-X6-X7). Any two, three, four, five, six or seven of X1, X2, X3, X4, X5, X6, and X7 may be contiguous. In some embodiments, X1 is at an amino acid position 452 within an AAV9 capsid protein, or variant thereof. In some embodiments X2 is at an amino acid position 453 within an AAV9 capsid protein, or variant thereof. In some embodiments X3 is at an amino acid position 454 within an AAV9 capsid protein, or variant thereof. In some embodiments X4 is at an amino acid position 455 within an AAV9 capsid protein, or variant thereof. In some embodiments X5 is at an amino acid position 456 within an AAV9 capsid protein, or variant thereof. In some embodiments X6 is at an amino acid position 457 within an AAV9 capsid protein, or variant thereof. In some embodiments X7 is at an amino acid position 458 within an AAV9 capsid protein, or variant thereof.

Methods disclosed herein provide delivering a rAAV particle comprising an rAAV capsid protein with increased specificity and/or transduction efficiency for the CNS or the PNS in the subject, as compared to a reference AAV, wherein the substitution comprises N452D, N452A, N452G, N452L, N452Q, N452S, N452T, G453I, G453N, G453S, G453P, G453R, G453T, S454A, S454Q, S454D, S454G, S454N, S454T, G455A, G455S, G455D, G455K, G455N, G455P, G455Q, G455T, Q456T, Q456S, Q456A, Q456G, Q456K, Q456N, Q456R, Q456P, N457K, N457A, N457G, N457P, N457R, N457S, N457T, N457V, Q458N, Q458A, Q458G, Q458K, Q458L, Q458R, Q458S, Q458T, or Q458V in an amino acid sequence of the AAV9 capsid protein (VP1 numbering), variant thereof, or equivalent amino acid position in a different AAV serotype. In some embodiments, methods comprising delivering a rAAV particle comprising a rAAV capsid protein comprising a substitution of one, two, three, four, five, six, or seven amino acids in an amino acid sequence provided any one of SEQ ID NOS: 11-12739. The substitution can comprise at least one, two, three, four, five, six, or seven, amino acids from an amino acid sequence selected from the group consisting of LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), KGPGQMG (SEQ ID NO: 45476), GTPSKAG (SEQ ID NO: 2741), and any amino acid sequence provided in Table 1 or Table 2. In some embodiments, the rAAV capsid proteins suitable for delivery of a heterologous nucleic acid to the CNS or PNS of a subject may also have an insertion of an amino acid sequence at amino acid position 588 (AAV9 VP1 numbering). In some cases, the rAAV capsid protein has a decreased specificity and/or transduction efficiency for the liver. In some embodiments, the substitution does not consist of an amino acid sequence ILGTGTS (SEQ ID NO: 45479) or QSSQTPR (SEQ ID NO: 45480) at amino acids 452-458 in a parental AAV9 capsid protein, or variant thereof. In some embodiments, the rAAV capsid proteins suitable for delivery of a heterologous nucleic acid to the CNS or PNS of a subject may also have an insertion of an amino acid sequence at amino acid position 588 (AAV9 VP1 numbering).

Disclosed herein are methods comprising delivering a rAAV particle encapsidating a heterologous nucleic acid to a CNS or PNS in a subject, the rAAV particle comprising (i) an increased specificity and/or transduction efficiency of the heterologous nucleic acid for the CNS or PNS, and (ii) a decreased specificity and/or transduction efficiency for the heterologous nucleic acid for the liver, wherein the rAAV particle has an rAAV capsid protein comprising a substitution selected from the group consisting of N452D, N452A, N452V, N452S, N452H, N452L, N452E, N452Q, G452A, G452I, G452T, G452P, G452R, G452T, G452S, G452K, G452H, S454A, S454N, S454D, S454G, S454T, S454H, S454K, S454Q, G455A, G455N, G455T, G455S, G455D, G455P, G455R, G455G, G455Q, Q456T, Q456S, Q456K, Q456P, Q456G, Q456D, Q456V, Q456A, Q456N, N457K, N457T, N457A, N457R, N457S, N457G, N457D, N457P, N457V, Q458N, Q458G, Q458S, Q458L, Q458A, Q458E, and Q458K, in an amino acid sequence of the AAV9 capsid protein, or a variant thereof, or equivalent amino acid position in a different AAV serotype. In some cases, the substitution is of at least or about one two, three, four, five, six, or seven amino acids of an amino acid sequence DGAATKN (SEQ ID NO: 3943). In some cases, the substitution is of at least or about one two, three, four, five, six, or seven amino acids of an amino acid sequence DGQSSKS (SEQ ID NO: 2764). In some cases, the substitution is any amino acid sequence provided in Table 1 or Table 2. In some embodiments, the delivering is systemic. In some embodiments, the delivery is direct (e.g., injected into the in vivo environment). In some embodiments, the parental AAV capsid protein is AAV9 capsid protein (for e.g., provided in SEQ ID NO: 1). In some embodiments, the parental AAV capsid protein is an AAV9 variant capsid protein AAV-PHP.B (SEQ ID NO: 3). In some embodiments, the parental AAV capsid protein is AAV9 variant capsid protein AAV-PHP.eB (SEQ ID NO: 5). In some embodiments, the parental AAV capsid protein further comprises an insertion of at least or about three, four, five, six, seven, eight, nine, ten, or eleven amino acids of an amino acid in an amino acid position 588-589 of the amino acid sequence of the parental AAV (AAV9 VP1 numbering). In some embodiments, delivery is more specific than a delivery of the heterologous nucleic acid by a reference AAV, e.g., AAV9. In some embodiments, methods further comprise reducing or ablating delivery of the heterologous nucleic acid in an off-target in vivo environment, such as the liver. In some embodiments, delivery is characterized by an increase in efficiency of transduction (e.g., of the heterologous nucleic acid) in the CNS or PNS than a transduction efficiency in the CNS or PNS of the reference AAV. In some embodiments, the delivery is systemic (e.g., intravenous). In some embodiments, the subject is a human or a non-human primate.

Delivery to a Target Organs or Tissues

In some cases, the methods of delivering a heterologous nucleic acid comprise delivering to a target in vivo environment in a subject a composition, the composition comprising a rAAV particle with a rAAV capsid protein, the rAAV capsid protein encapsidating a viral vector encoding a heterologous nucleic acid (e.g., therapeutic nucleic acid). In some cases, the target in vivo environment is the liver, intestine, heart, lung, reproductive organ, muscle, adipose, pancreas, a brain, or spleen. In some embodiments, the rAAV particle encapsidating the heterologous nucleic acid comprises a rAAV capsid protein engineered with an increased specificity and, in some cases, transduction efficiency for the target in vivo environment of the subject, even when administered to the subject systemically.

Disclosed herein are methods that comprise delivering to a subject a rAAV particle encapsidating a heterologous nucleic acid, the rAAV comprising an rAAV capsid protein with increased specificity and/or transduction efficiency of the heterologous nucleic acid when measured in the heart of the subject, as compared to a reference AAV (e.g., AAV9, AAV5). In some embodiments, rAAVs optimized for targeting the heart have amino acid sequence comprising an amino acid sequence provided in SEQ ID NOS: 25469-26205. In some embodiments, methods comprise delivering a rAAV particle comprising an rAAV capsid protein with increased specificity and/or transduction efficiency of the heterologous nucleic acid when measured in the lung in the subject, as compared to a reference AAV (e.g., AAV9, AAV5). In some embodiments, rAAVs optimized for targeting the lung have amino acid sequences comprising an amino acid sequence provided in SEQ ID NOS: 32537-34198. In some embodiments, methods comprise delivering a rAAV particle comprising an rAAV capsid protein with increased specificity and/or transduction efficiency of the heterologous nucleic acid when measured in the liver in the subject, as compared to a reference AAV (e.g., AAV9, AAV5). In some embodiments, rAAVs optimized for targeting the liver have amino acid sequences that comprise an amino acid sequence provided in SEQ ID NOS: 30720-30923. In some embodiments, methods comprise delivering a rAAV particle comprising an rAAV capsid protein with increased specificity and/or transduction efficiency of the heterologous nucleic acid when measured in the intestine in the subject, as compared to a reference AAV (e.g., AAV9, AAV5). In some embodiments, rAAVs optimized for targeting the intestine have amino acid sequences comprising an amino acid sequence provided in SEQ ID NOS: 26206-26873. In some embodiments, methods comprise delivering a rAAV particle comprising a rAAV capsid protein with increased specificity and/or transduction efficiency of the heterologous nucleic acid when measured in the stomach in the subject, as compared to a reference AAV (e.g., AAV9, AAV5). In some embodiments, rAAVs optimized for targeting the stomach have amino acid sequences comprising amino acid sequence provided in SEQ ID NOS: 31873-32060. In some embodiments, methods comprise delivering a rAAV particle comprising an rAAV capsid protein with increased specificity and/or transduction efficiency of the heterologous nucleic acid when measured in the spleen in the subject, as compared to a reference AAV (e.g., AAV9, AAV5). In some embodiments, rAAVs optimized for targeting the spleen have amino acid sequences comprising an amino acid sequence provided in SEQ ID NOS: 31468-31872. In some embodiments, methods comprise delivering a rAAV particle comprising a rAAV capsid protein with increased specificity and/or transduction efficiency of the heterologous nucleic acid when measured in the kidney in the subject, as compared to a reference AAV (e.g., AAV9, AAV5). In some embodiments, rAAVs optimized for targeting the kidney have amino acid sequences comprising an amino acid sequence provided in SEQ ID NOS: 26874-30719. In some embodiments, methods comprise delivering a rAAV particle comprising an rAAV capsid protein with increased specificity and/or transduction efficiency of the heterologous nucleic acid when measured in the fat of the subject, as compared to a reference AAV (e.g., AAV9, AAV5). In some embodiments, rAAVs optimized for targeting the fat (adipose) have amino acid sequences comprising an amino acid sequence provided in SEQ ID NOS: 34199-35471.

Provided herein are methods that comprise delivering a rAAV particle to a subject, the rAAV comprising an rAAV capsid protein with increased specificity and/or transduction efficiency of the heterologous nucleic acid for the muscle in the subject, as compared to a reference AAV (e.g., AAV9, AAV5). In some embodiments, rAAVs optimized for targeting the muscle have amino acid sequences comprising an amino acid sequence provided in SEQ ID NO: 30924-31451. The muscle may be cardiac muscle. The muscle may be skeletal muscle. In some embodiments, methods comprise delivering a rAAV particle comprising an rAAV capsid protein with increased specificity and/or transduction efficiency of the heterologous nucleic acid for the pancreas in the subject, as compared to a reference AAV (e.g., AAV9, AAV5). In some embodiments, rAAVs optimized for targeting the pancreas have amino acid sequences comprising an amino acid sequence provided in SEQ ID NOS: 31452-31467. In some embodiments, methods comprise delivering a rAAV particle comprising an rAAV capsid protein with increased specificity and/or transduction efficiency of the heterologous nucleic acid for the reproductive organ(s) in the subject, as compared to a reference AAV (e.g., AAV9, AAV5). In some embodiments, rAAVs optimized for targeting a reproductive organ, such as a testicle, comprise amino acid sequences comprising an amino acid sequence provided in SEQ ID NOS: 32061-32536. In some instances, the reproductive organ is an ovary.

The rAAV capsid protein suitable for delivery of the heterologous nucleic acid to the liver, intestine, heart, lung, reproductive organ, muscle, adipose, pancreas, a brain, or spleen can comprise a substitution of at least one amino acid in a parental AAV capsid protein. In some embodiments, X1 is K, R, N, or T. The rAAV capsid protein can comprise a substitution or an insertion of at least two amino acids in a parental AAV capsid protein. In some embodiments, X1 is K, R, N, or T; and X2 is D, E, N, or V. The rAAV capsid protein can comprise a substitution or an insertion of at least three amino acids in a parental AAV capsid protein. In some embodiments, X1 is K, R, N, or T; X2 is D, E, N, or V; and X3 is N, S, L, or P. The rAAV capsid protein can comprise a substitution or an insertion of at least four amino acids in a parental AAV capsid protein. In some embodiments, X1 is K, R, N, or T; X2 is D, E, N, or V; X3 is N, S, L, or P; and X4 is T, S, P, or L. The rAAV capsid protein can comprise a substitution or an insertion of at least five amino acids in a parental AAV capsid protein. In some embodiments, X1 is K, R, N, or T; X2 is D, E, N, or V; X3 is N, S, L, or P; X4 is T, S, P, or L; and X5 is P, R, or S. The rAAV capsid protein can comprise a substitution or an insertion of at least six amino acids in a parental AAV capsid protein. In some embodiments, X1 is K, R, N, or T; X2 is D, E, N, or V; X3 is N, S, L, or P; X4 is T, S, P, or L; X5 is P, R, or S; and X6 is G, S, N, or T. The rAAV capsid protein can comprise a substitution or an insertion of at least seven amino acids in a parental AAV capsid protein. In some embodiments, X1 is K, R, N, or T; X2 is D, E, N, or V; X3 is N, S, L, or P; IX4 is T, S, P, or L; X5 is P, R, or S; X6 is G, S, N, or T; and X7 is R, L or I. In some embodiments, X1, X2, X3, X4, X5, X6, and X7 are contiguous (X1-X2-X3-X4-X5-X6-X7). In some embodiments, any two, three, four, five, six, or seven, of X1, X2, X3, X4, X5, X6, and X7 are contiguous. In some embodiments, X1, X2, X3, X4, X5, X6, and X7 are not contiguous. In some embodiments, X1 is at an amino acid position 452 within an AAV9 capsid protein, or variant thereof. In some embodiments X2 is at an amino acid position 453 within an AAV9 capsid protein, or variant thereof. In some embodiments X3 is at an amino acid position 454 within an AAV9 capsid protein, or variant thereof. In some embodiments X4 is at an amino acid position 455 within an AAV9 capsid protein, or variant thereof. In some embodiments X5 is at an amino acid position 456 within an AAV9 capsid protein, or variant thereof. In some embodiments X6 is at an amino acid position 457 within an AAV9 capsid protein, or variant thereof. In some embodiments X7 is at an amino acid position 458 within an AAV9 capsid protein, or variant thereof. In some embodiments, the substitution does not consist of an amino acid sequence ILGTGTS (SEQ ID NO: 45479) or QSSQTPR (SEQ ID NO: 45480) at amino acids 452-458 in a parental AAV9 capsid protein, or variant thereof. In some embodiments, the rAAV capsid proteins suitable for delivery of a heterologous nucleic acid to the target in vivo environment of a subject may also have an insertion of an amino acid sequence at amino acid position 588 (AAV9 VP1 numbering).

Disclosed herein are methods comprising delivering a rAAV particle encapsidating a heterologous nucleic acid to the target in vivo environment selected from the group consisting of the liver, intestine, heart, lung, reproductive organ, muscle, adipose, pancreas, a brain, and spleen, in a subject, the rAAV particle comprising an increased specificity and/or transduction efficiency of the heterologous nucleic acid for the target in vivo environment, wherein the rAAV particle has an rAAV capsid protein comprising a substitution of at least or about three, four, five, six, or seven amino acids of an amino acid sequence KDNTPGR (SEQ ID NO: 32538), NNLPRNL (SEQ ID NO: 32867), RESSPSL (SEQ ID NO: 29065), or RVPLSTI (SEQ ID NO: 26933) at an amino acid position 452-458 in a parental AAV capsid protein. In some embodiments, the parental AAV capsid protein is AAV9 capsid protein (for e.g., provided in SEQ ID NO: 1). In some embodiments, the parental AAV capsid protein is AAV5 capsid protein (for e.g., provided in SEQ ID NO: 2). In some embodiments, the parental AAV capsid protein is an AAV9 variant capsid protein AAV-PHP.B (SEQ ID NO: 3). In some embodiments, the parental AAV capsid protein is AAV9 variant capsid protein AAV-PHP.eB (SEQ ID NO: 5). In some embodiments, the parental AAV capsid protein further comprises an insertion of at least or about three, four, five, six, seven, eight, nine, ten, or eleven amino acids of an amino acid in an amino acid position 588-589 of the amino acid sequence of the parental AAV (AAV9 VP1 numbering). In some embodiments, delivery is more specific than a delivery of the heterologous nucleic acid by a reference AAV, e.g., AAV9. In some embodiments, methods further comprise reducing or ablating delivery of the heterologous nucleic acid in an off-target in vivo environment, such as the liver, compared to a reference AAV. In some embodiments, delivery is characterized by an increase in efficiency of transduction (e.g., of the heterologous nucleic acid) in the target in vivo environment than a transduction efficiency in the target in vivo environment of the reference AAV. In some embodiments, the delivery is systemic (e.g., intravenous). In some embodiments, the subject is a human or a non-human primate.

Methods of Treatment

Disclosed herein are methods of treating a disease or condition, or a symptom of the disease or condition, in a subject, comprising administrating of therapeutically effective amount of one or more compositions (e.g., rAAV particle, AAV vector, pharmaceutical formulations and composition) disclosed herein to the subject. In some embodiments, the composition is a rAAV capsid protein described herein. In some embodiments, the composition is an isolated and purified rAAV capsid protein described herein. In some embodiments, the rAAV particle encapsidates a heterologous nucleic acid comprising a transgene (e.g., therapeutic nucleic acid). In some embodiments, the composition is a rAAV capsid protein described herein conjugated with a therapeutic agent disclosed herein. In some embodiments, the composition is a pharmaceutical composition comprising the rAAV particle and a pharmaceutically acceptable carrier. In some embodiments, the one or more compositions are administered to the subject alone (e.g., standalone therapy). In some embodiments, the one or more compositions are administered in combination with an additional agent. In some embodiments, the composition is a first-line therapy for the disease or condition. In some embodiments, the composition is a second-line, third-line, or fourth-line therapy, for the disease or condition.

Provided herein are methods of treating a disease or a condition, or a symptom of the disease or condition, in a subject, comprising: (a) diagnosing a subject with a disease or a condition affecting a target in vivo environment; and (b) treating the disease or the condition by administering to the subject a therapeutically effective amount of a composition disclosed herein (e.g., rAAV particle, AAV vector, pharmaceutical composition), wherein the composition is engineered with an increased specificity for the target in vivo environment. In some cases, the composition is engineered with a decreased specificity for an off-target in vivo environment, e.g., the liver.

Disclosed herein are methods of treating a disease or a condition, or a symptom of the disease or the condition, afflicting a target in vivo environment in a subject comprising: (a) administering to the subject a composition (e.g., rAAV particle, AAV vector, pharmaceutical composition); and (b) expressing the therapeutic nucleic acid into a target in vivo environment in the subject with an increased specificity and/or transduction efficiency, as compared to a reference AAV. In some cases, the reference AAV is AAV9 or AAV5, or a variant thereof.

Methods of treating a disease or condition affecting the central nervous system (CNS) or peripheral nervous system (PNS) comprise administering a rAAV particle to a subject, the rAAV particle comprising an rAAV capsid protein comprising a substitution of at least or about three, four, five, six, or seven amino acids of an amino acid sequence DGAATKN (SEQ ID NO: 3943) or DGQSSKS (SEQ ID NO: 2764), LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), KGPGQMG (SEQ ID NO: 45476), GTPSKAG (SEQ ID NO: 2741), and any amino acid sequence provided in Table 1, Table 2, FIG. 2, or FIG. 3, at an amino acid position 452-458 in a parental AAV capsid protein. In some embodiments, the rAAV capsid protein comprises an amino acid sequence provided in any one of SEQ ID NOS: 46384-46399.

In some embodiments, the parental AAV capsid protein is AAV9 capsid protein (for e.g., provided in SEQ ID NO: 1). In some embodiments, the parental AAV capsid protein is an AAV9 variant capsid protein AAV-PHP.B (SEQ ID NO: 3). In some embodiments, the parental AAV capsid protein is AAV9 variant capsid protein AAV-PHP.eB (SEQ ID NO: 5). In some embodiments, the parental AAV capsid protein further comprises an insertion of at least or about three, four, five, six, seven, eight, nine, ten, or eleven amino acids of an amino acid in an amino acid position 588-589 of the amino acid sequence of the parental AAV (AAV9 VP1 numbering). In some embodiments, delivery is more specific than a delivery of the heterologous nucleic acid by a reference AAV, e.g., AAV9. In some embodiments, methods further comprise reducing or ablating delivery of the heterologous nucleic acid in an off-target in vivo environment, such as the liver. In some embodiments, delivery is characterized by an increase in efficiency of transduction (e.g., of the heterologous nucleic acid) in the CNS or PNS than a transduction efficiency in the CNS or PNS of the reference AAV. In some embodiments, the delivery is systemic (e.g., intravenous). In some embodiments, the subject is a human or a non-human primate.

Methods of treating a disease or a condition afflicting a target in vivo environment selected from the group consisting of the liver, intestine, heart, lung, reproductive organ, muscle, adipose, pancreas, a brain, or spleen, comprise administering to a subject a rAAV particle comprising an amino acid provided in any one of FIG. 4-14, the rAAV particle comprising an rAAV capsid protein comprising a substitution of at least or about three, four, five, six, or seven amino acids of an amino acid sequence provided in any one of SEQ ID NOS: 25469-26205. In some embodiments, methods comprise delivering a rAAV particle an amino acid sequence KDNTPGR (SEQ ID NO: 32538) or NNLPRNL (SEQ ID NO: 32867), at an amino acid position 452-458 in a parental AAV capsid protein, thereby targeting the lung. In some embodiments, methods comprise delivering a rAAV particle comprising an amino acid sequence RESSPSL (SEQ ID NO: 26474) at an amino acid position 452-458 in a parental AAV capsid protein, thereby targeting the intestine. In some embodiments, methods comprise delivering a rAAV particle an amino acid sequence RVPLSTI (SEQ ID NO: 26933) or RESSPSL (SEQ ID NO: 29065) at an amino acid position 452-458 in a parental AAV capsid protein, thereby targeting the kidney. In some embodiments, methods comprise delivering a rAAV particle comprising an amino acid sequence RESSPSL (SEQ ID NO: 31904) at an amino acid position 452-458 in a parental AAV capsid protein, thereby targeting the stomach. In some embodiments, the rAAV capsid protein comprises an amino acid sequence provided in any one of SEQ ID NOS: 46400-46403. In some embodiments, the parental AAV capsid protein is AAV9 capsid protein (for e.g., provided in SEQ ID NO: 1). In some embodiments, the parental AAV capsid protein is AAV5 capsid protein (for e.g., provided in SEQ ID NO: 2). In some embodiments, the parental AAV capsid protein is an AAV9 variant capsid protein AAV-PHP.B (SEQ ID NO: 3). In some embodiments, the parental AAV capsid protein is AAV9 variant capsid protein AAV-PHP.eB (SEQ ID NO: 5). In some embodiments, the parental AAV capsid protein further comprises an insertion of at least or about three, four, five, six, seven, eight, nine, ten, or eleven amino acids of an amino acid in an amino acid position 588-589 of the amino acid sequence of the parental AAV (AAV9 VP1 numbering). In some embodiments, delivery is more specific than a delivery of the heterologous nucleic acid by a reference AAV, e.g., AAV9. In some embodiments, methods further comprise reducing or ablating delivery of the heterologous nucleic acid in an off-target in vivo environment, such as the liver. In some embodiments, delivery is characterized by an increase in efficiency of transduction (e.g., of the heterologous nucleic acid) in the target in vivo environment than a transduction efficiency in the target in vivo environment of the reference AAV. In some embodiments, the delivery is systemic (e.g., intravenous or intranasal). In some embodiments, the subject is a human or a non-human primate.

Also provide are methods of modulating a target gene expression product, the methods comprising administering to a subject in need thereof a composition (e.g., rAAV particle, AAV vector, pharmaceutical composition) disclosed herein. For example, methods provided herein comprise administering to a subject a rAAV with a rAAV capsid protein encapsidating a viral vector comprising a heterologous nucleic acid that modulates the expression or the activity of the target gene expression product. In some embodiments, the disease or the condition is characterized by an increased or enhanced expression or activity of a gene or gene expression product thereof, as compared to a normal individual. In some cases, administering the therapeutically effective amount of the composition restores the expression or the activity of the gene or gene expression product thereof to a level that is typical in a normal individual. The term "normal individual" refers to an unaffected individual, i.e. an individual that is not afflicted with the disease or the condition characterized by the variation in expression or activity of the gene or gene expression product thereof.

Non-limiting examples of genes involved in central nervous system (CNS) diseases or disorders include Sarcoglycan Alpha (SGCA), glutamic acid decarboxylase 65 (GAD65), glutamic acid decarboxylase 67 (GAD67), CLN2 gene, Nerve Growth Factor (NGF), glial cell derived neurotrophic factor (GDNF), Neurturin, Survival Of Motor Neuron 1, Telomeric (SMN1), β-Glucocerebrosidase (GCase), Frataxin (FXN), Huntingtin (HTN), methyl-CpG binding protein 2 (MECP2), peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and NPS3. In some embodiments, the peroxisomal biogenesis factor (PEX) is selected from the group consisting of PEX1, PEX2, PEX3, PEX4, PEX5, PEX6, PEX7, PEX10, PEX1113, PEX12, PEX13, PEX14, PEX16, PEX19, and PEX26. Non-limiting examples of genes implicated in disease or disorder of a particular organ (e.g., lung, heart, liver, muscle, eye) include Cystic Fibrosis Transmembrane Conductance Regulator (CFTR), Factor X (FIX), RPE65, Retinoid Isomerohydrolase (RPE65), Sarcoglycan Alpha (SGCA), and sarco/endoplasmic reticulum Ca2+-ATPase (SERCA2a). In some instances, the expression of a gene or expression or activity of a gene expression product is inhibited by the administration of the composition to the subject. In some instances, the expression of a gene or the expression or the activity of a gene expression product is enhanced by the administration of the composition to the subject.

In some cases, the composition is administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some cases, the viral genome (vg) concentration of the composition that is administered is between $1.0 \times 10^{11}$ vg per kilogram (kg) and $1.0 \times 10^{16}$ vg/kg. In some cases, the concentration of infectious particles of at least or about $10^7$, $10^8$, $10^9$, $10^{10}$, $10^{11}$, $10^{12}$, $10^{13}$, $10^{14}$, $10^{15}$, $10^{16}$, or $10^{17}$. In some cases the concentration of infectious particles is $2 \times 10^7$, $2 \times 10^8$, $2 \times 10^9$, $2 \times 10^{10}$, $2 \times 10^{11}$, $2 \times 10^{12}$, $2 \times 10^{13}$, $2 \times 10^{14}$, $2 \times 10^{15}$, $2 \times 10^{16}$, or $2 \times 10^{17}$. In some cases the concentration of the infectious particles $3 \times 10^7$, $3 \times 10^8$, $3 \times 10^9$, $3 \times 10^{10}$, $3 \times 10^{11}$, $3 \times 10^{12}$, $3 \times 10^{13}$, $3 \times 10^{14}$, $3 \times 10^{15}$, $3 \times 10^{16}$, or $3 \times 10^{17}$. In some cases the concentration of the infectious particles $4 \times 10^7$, $4 \times 10^8$, $4 \times 10^9$, $4 \times 10^{10}$, $4 \times 10^{11}$, $4 \times 10^{12}$, $4 \times 10^{13}$, $4 \times 10^{14}$, $4 \times 10^{15}$, $4 \times 10^{16}$, or $4 \times 10^{17}$. In some cases the concentration of the infectious particles $5 \times 10^7$, $5 \times 10^8$, $5 \times 10^9$, $5 \times 10^{10}$, $5 \times 10^{11}$, $5 \times 10^{12}$, $5 \times 10^{13}$, $5 \times 10^{14}$, $5 \times 10^{15}$, $5 \times 10^{16}$, or $5 \times 10^{17}$. In some cases the concentration of the infectious particles $6 \times 10^7$, $6 \times 10^8$, $6 \times 10^9$, $6 \times 10^{10}$, $6 \times 10^{11}$, $6 \times 10^{12}$, $6 \times 10^{13}$, $6 \times 10^{14}$, $6 \times 10^{15}$, $6 \times 10^{16}$, or $6 \times 10^{17}$. In some cases the concentration of the infectious particles $7 \times 10^7$, $7\times10^8$, $7\times10^9$, $7\times10^{10}$, $7\times10^{11}$, $7\times10^{12}$, $7\times10^{13}$, $7\times10^{14}$, $7\times10^{15}$, $7\times10^{16}$, or $7\times10^{17}$. In some cases the concentration of the infectious particles $8\times10^7$, $8\times10^8$, $8\times10^9$, $8\times10^{10}$, $8\times10^{11}$, $8\times10^{12}$, $8\times10^{13}$, $8\times10^{14}$, $8\times10^{15}$, $8\times10^{16}$, or $8\times10^{17}$. In some cases the concentration of the infectious particles $9\times10^7$, $9\times10^8$, $9\times10^9$, $9\times10^{10}$, $9\times10^{11}$, $9\times10^{12}$, $9\times10^{13}$, $9\times10^{14}$, $9\times10^{15}$, $9\times10^{16}$, or $9\times10^{17}$.

In some embodiments, the administering of step is performed once. Alternatively, the administering of step is repeated at least twice. The administering of step may be performed once daily. In some cases, the administering of step comprises intravenous administration. In some cases, the administering comprises pulmonary administration. In some cases, the administering comprises intranasal administration (such as a spray). In some cases, the administering of step comprises injecting the composition into a target in vivo environment. In some cases, the administering of step does not comprise injecting the composition into the target in vivo environment.

Subject

Disclosed herein methods of delivering at least one of an AAV particle and viral vector to a subject, for example—to treat or prevent a disease or condition in a subject. The subject, in some cases, is a mammal. Non-limiting examples of a mammal include a mouse, rat, guinea pig, rabbit, chimpanzee, or farm animal. In some instances, the mammal is a non-human primate. In some instances, the subject is human. The subject of the present disclosure may not be diagnosed with a disease or condition. Alternatively, the subject may be a patient that is diagnosed with a disease or disorder, or suspected of having the disease or the disorder.

Disease or Condition

Disclosed herein are methods of treating a disease or condition in a subject by administering a composition comprising a rAAV such as those disclosed herein. At least one advantage of the rAAVs disclosed herein, is that the rAAV may be used to treat virtually any disease or condition that would benefit from a transgene therapy, including but not limited to spinal muscular atrophy (SMA), amyotrophic lateral sclerosis (ALS), Parkinson's disease, Pompe disease, Huntington's disease, Alzheimer's disease, Battens disease, lysosomal storage disorders, glioblastoma multiforme, Rett syndrome, Leber's congenital amaurosis, Late infantile neuronal ceroid lipofuscinosis (LINCL), chronic pain, stroke, spinal cord injury, traumatic brain injury and lysosomal storage disorders.

The disease or the condition may, in some embodiments, be characterized by a reduced or ablated expression or activity of a gene or gene expression product thereof, as compared to a normal individual. In some embodiments, be characterized by an increased or enhanced expression or activity of a gene or gene expression product thereof, as compared to a normal individual.

In some cases, the disease or condition is localized to a particular in vivo environment in the subject, e.g., the brain or the lung. The compositions of the present disclosure are particularly useful for the treatment of the diseases or conditions described herein because they specifically target the in vivo environment and deliver a therapeutic nucleic acid engineered to modulate the activity or the expression of a target gene expression product involved with the pathogenesis or pathology of the disease or condition.

In some instances, the disease or condition comprises a disease or condition of the central nervous system (CNS). Non-limiting examples of disease of the CNS include Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Cerebral Autosomal Dominant Arteriopathy with Subcortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavemous Malformation, Cerebral Gigantism, Cerebral Hypoxia, Cerebral Palsy, Cerebro-Oculo-Facio-Skeletal Syndrome (COFS), Charcot-Marie-Tooth Disease, Charcot-Marie-Tooth syndrome, classical rhizomelic chondrodysplasia punctata (RCDP), Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt—Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, Deafness, De Morsier's Syndrome, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Duchenne muscular dystrophy, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy (familial infantile), Encephalotrigeminal Angiomatosis, Epilepsy, Epileptic Hemiplegia, Erb's Palsy, Erb-Duchenne and Dejerine-Klumpke Palsies, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, glioblastoma, Globoid Cell Leukodystrophy, Glossopharyngeal Neuralgia, Glycogen Storage Disease, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliiver-Bucy Syndrome, Korsakoff s Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Moebius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy—Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, and X-Linked Spinal and Bulbar Muscular Atrophy.

In some instances, the disease or condition comprises a liver disease or disorder, or is associated with a liver disease or disorder. Non-limiting examples include disorders of bile acid synthesis (e.g., Wilson disease, Progressive familial intrahepatic cholestasis type 3), disorders of carbohydrate metabolism (e.g., Hereditary fructose intolerance, Glycogen storage disease type IV), disorders of amino acids metabolism (e.g., tyrosinemia type I), Urea cycle disorders (e.g., argininosuccinate lyase deficiency, citrin deficiency (CTLN2, NICCD)), disorders of lipid metabolism (e.g., cholesteryl ester storage disease), and others including but not limited to Alpha-1 antitrypsin deficiency, cystic fibrosis, hereditary hemochromatosis, Alström syndrome, and congenital hepatic fibrosis.

In some instances, the disease or condition is a disease or condition is a pulmonary disease or disorder (of the lung). In some instances, the pulmonary disease or disorder is selected form the group consisting of chronic obstructive pulmonary disease (COPD), pulmonary fibrosis (PF), and plasmalogen deficiency disorders.

Provided here, are methods of treating a disease or a condition associated with an aberrant expression or activity of a target gene or gene expression product thereof, the method comprising modulating the expression or the activity of a target gene or gene expression product in a subject by administering a rAAV encapsidating a heterologous nucleic acid of the present disclosure. In some instances, administration is systemic administration. In some instances, the expression or the activity of the target gene or gene expression product is decreased, relative to that in a normal (non-diseased) individual; and administering the rAAV to the subject is sufficient to increase the expression of the activity of the target gene or gene expression product to that of a normal individual. In some instances, the expression or the activity of the gene or gene expression product is increased, relative to that in a normal individual; and administering the rAAV to the subject is sufficient to decrease the expression or the activity of the target gene or gene expression product. In a non-limiting example, a subject diagnosed with Alzheimer's disease, which is caused, in some cases, by a gain-of-function of a Presenilin 1 and/or Presenilin 2 (encoded by the gene PSEN1 and PSEN2, respectively) is administered a rAAV disclosed herein encapsidating a therapeutic nucleic acid that is a silencing RNA (siRNA), or other RNAi with a loss-of-function effect on PSEN1 mRNA.

Formulations, Dosages, and Routes of Administration

In general, methods disclosed herein comprise administering a therapeutic rAAV composition by systemic administration. In some instances, methods comprise administering a therapeutic rAAV composition by oral administration. In some instances, methods comprise administering a therapeutic rAAV composition by intraperitoneal injection. In some instances, methods comprise administering a therapeutic rAAV composition in the form of an anal suppository. In some instances, methods comprise administering a therapeutic rAAV composition by intravenous ("i.v.") administration. It is conceivable that one may also administer therapeutic rAAV compositions disclosed herein by other routes, such as subcutaneous injection, intramuscular injection, intradermal injection, transdermal injection percutaneous administration, intranasal administration, intralymphatic injection, rectal administration intragastric administration, intraocular administration, intracerebro-ventricularly administration, intrathecally, or any other suitable parenteral administration. In some instances, methods comprise administering a therapeutic rAAV composition by topical administration, such as for example, by brushing or otherwise contacting the rAAV composition to a region of the subject (e.g., eardrum, bladder). In some embodiments, routes for local delivery closer to site of injury or inflammation are preferred over systemic routes. Routes, dosage, time points, and duration of administrating therapeutics may be adjusted. In some embodiments, administration of therapeutics is prior to, or after, onset of either, or both, acute and chronic symptoms of the disease or condition.

An effective dose and dosage of pharmaceutical compositions to prevent or treat the disease or condition disclosed herein is defined by an observed beneficial response related to the disease or condition, or symptom of the disease or condition. Beneficial response comprises preventing, alleviating, arresting, or curing the disease or condition, or symptom of the disease or condition. In some embodiments, the beneficial response may be measured by detecting a measurable improvement in the presence, level, or activity, of biomarkers, transcriptomic risk profile, or intestinal microbiome in the subject. An "improvement," as used herein refers to shift in the presence, level, or activity towards a presence, level, or activity, observed in normal individuals (e.g. individuals who do not suffer from the disease or condition). In instances wherein the therapeutic rAAV composition is not therapeutically effective or is not providing a sufficient alleviation of the disease or condition, or symptom of the disease or condition, then the dosage amount and/or route of administration may be changed, or an additional agent may be administered to the subject, along with the therapeutic rAAV composition. In some embodiments, as a patient is started on a regimen of a therapeutic rAAV composition, the patient is also weaned off (e.g., step-wise decrease in dose) a second treatment regimen.

In some embodiments, pharmaceutical compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect. It will be understood that the above dosing concentrations may be converted to vg or viral genomes per kg or into total viral genomes administered by one of skill in the art.

In some cases, a dose of the pharmaceutical composition may comprise a concentration of infectious particles of at least or about $10^7$, $10^8$, $10^9$, $10^{10}$, $10^{11}$, $10^{12}$, $10^{13}$, $10^{14}$, $10^{15}$, $10^{16}$, or $10^{17}$. In some cases the concentration of infectious particles is $2\times10^7$, $2\times10^8$, $2\times10^9$, $2\times10^{10}$, $2\times10^{11}$, $2\times10^{12}$, $2\times10^{13}$, $2\times10^{14}$, $2\times10^{15}$, $2\times10^{16}$, or $2\times10^{17}$. In some cases the concentration of the infectious particles is $3\times10^7$, $3\times10^8$, $3\times10^9$, $3\times10^{10}$, $3\times10^{11}$, $3\times10^{12}$, $3\times10^{13}$, $3\times10^{14}$, $3\times10^{15}$, $3\times10^{16}$, or $3\times10^{17}$. In some cases the concentration of the infectious particles is $4\times10^7$, $4\times10^8$, $4\times10^9$, $4\times10^{10}$, $4\times10^{11}$, $4\times10^{12}$, $4\times10^{13}$, $4\times10^{14}$, $4\times10^{15}$, $4\times10^{16}$, or $4\times10^{17}$. In some cases the concentration of the infectious particles is $5\times10^7$, $5\times10^8$, $5\times10^9$, $5\times10^{10}$, $5\times10^{11}$, $5\times10^{12}$, $5\times10^{13}$, $5\times10^{14}$, $5\times10^{15}$, $5\times10^{16}$, or $5\times10^{17}$. In some cases the concentration of the infectious particles is $6\times10^7$, $6\times10^8$, $6\times10^9$, $6\times10^{10}$, $6\times10^{11}$, $6\times10^{12}$, $6\times10^{13}$, $6\times10^{14}$, $6\times10^{15}$, $6\times10^{16}$, or $6\times10^{17}$. In some cases the concentration of the infectious particles is $7\times10^7$, $7\times10^8$, $7\times10^9$, $7\times10^{10}$, $7\times10^{11}$, $7\times10^{12}$, $7\times10^{13}$, $7\times10^{14}$, $7\times10^{15}$, $7\times10^{16}$, or $7\times10^{17}$. In some cases the concentration of the infectious particles is $8\times10^7$, $8\times10^8$, $8\times10^9$, $8\times10^{10}$, $8\times10^{11}$, $8\times10^{12}$, $8\times10^{13}$, $8\times10^{14}$, $8\times10^{15}$, $8\times10^{16}$, or $8\times10^{17}$. In some cases the concentration of the infectious particles is $9\times10^7$, $9\times10^8$, $9\times10^9$, $9\times10^{10}$, $9\times10^{11}$, $9\times10^{12}$, $9\times10^{13}$, $9\times10^{14}$, $9\times10^{15}$, $9\times10^{16}$, or $9\times10^{17}$.

Disclosed herein, in some embodiments are formulations of pharmaceutically-acceptable excipients and carrier solutions suitable for delivery of the rAAV compositions described herein, as well as suitable dosing and treatment regimens for using the particular compositions described herein in a variety of treatment regimens. In some embodiments, the amount of therapeutic gene expression product in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. In some instances, the rAAV compositions are suitably formulated pharmaceutical compositions disclosed herein, to be delivered either intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

In some embodiments, the pharmaceutical forms of the AAV-based viral compositions suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some cases, for administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Disclosed herein are sterile injectable solutions comprising the rAAV compositions disclosed herein, which are prepared by incorporating the rAAV compositions disclosed herein in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Injectable solutions may be advantageous for systemic administration, for example by intravenous administration.

Also provided herein are formulations in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

Pulmonary administration may be advantageously achieved via the buccal administration. In some embodiments, formulations may comprise dry particles comprising active ingredients. In such embodiments, dry particles may have a diameter in the range from about 0.5 nm to about 7 nm or from about 1 nm to about 6 nm. In some embodiments, formulations may be in the form of dry powders for administration using devices comprising dry powder reservoirs to which streams of propellant may be directed to disperse such powder. In some embodiments, self-propelling solvent/powder dispensing containers may be used. In such embodiments, active ingredients may be dissolved and/or suspended in low-boiling propellant in sealed containers. Such powders may comprise particles wherein at least 98% of the particles by weight have diameters greater than 0.5 nm and at least 95% of the particles by number have diameters less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form. Low boiling propellants generally include liquid propellants having a boiling point of below 65° F. at atmospheric pressure. Generally, propellants may constitute 50% to 99.9% (w/w) of the composition, and active ingredient may constitute 0.1% to 20% (w/w) of the composition. Propellants may further comprise additional ingredients such as liquid non-ionic and/or solid anionic surfactant and/or solid diluent (which may have particle sizes of the same order as particles comprising active ingredients).

Pharmaceutical compositions formulated for pulmonary delivery may provide active ingredients in the form of droplets of solution and/or suspension. Such formulations may be prepared, packaged, and/or sold as aqueous and/or dilute alcoholic solutions and/or suspensions, optionally sterile, comprising active ingredients, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm. Formulations described herein useful for pulmonary delivery may also be useful for intranasal delivery. In some embodiments, formulations for intranasal administration comprise a coarse powder comprising the active ingredient and having an average particle size from about 0.2 µm to 500 µm. Such formulations are administered in the manner in which snuff is taken, e.g. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, comprise 0.1% to 20% (w/w) active ingredient, the balance comprising an orally dissolvable and/or degradable composition and, optionally, one or more of the additional ingredients described herein. Alternately, formulations suitable for buccal administration may comprise powders and/or an aerosolized and/or atomized solutions and/or suspensions comprising active ingredients. Such powdered, aerosolized, and/or aerosolized formulations, when dispersed, may comprise average particle and/or droplet sizes in the range of from about 0.1 nm to about 200 nm, and may further comprise one or more of any additional ingredients described herein.

Suitable dose and dosage administrated to a subject is determined by factors including, but not limited to, the particular therapeutic rAAV composition, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject or host being treated.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. This is made possible, at least in part, by the fact that certain target cells (e.g., neurons) do not divide, obviating the need for multiple or chronic dosing.

Alternatively, in some circumstances, it may be desirable to provide multiple, or successive administrations of the AAV vector compositions, either over a relatively short, or a relatively prolonged period of time, as may be determined by the medical practitioner overseeing the administration of such compositions. For example, the number of infectious particles administered to a mammal may be on the order of about $10^7$, $10^8$, $10^9$, $10^{10}$, $10^{11}$, $10^{12}$, $10^{13}$, or even higher, infectious particles/ml given either as a single dose, or divided into two or more administrations as may be required to achieve therapy of the particular disease or disorder being treated. In fact, in certain embodiments, it may be desirable to administer two or more different AAV vector compositions, either alone, or in combination with one or more other therapeutic drugs to achieve the desired effects of a particular therapy regimen. In various embodiments, the daily and unit dosages are altered depending on a number of variables including, but not limited to, the activity of the therapeutic rAAV composition used, the disease or condition to be treated, the mode of administration, the requirements of the individual subject, the severity of the disease or condition being treated, and the judgment of the practitioner.

In some embodiments, the administration of the therapeutic rAAV composition is hourly, once every 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours 22 hours, 23 hours, 1 day, 2 days, 3 days, 4 days, 5 days, 6 days, 7 days, 8 days, 9 days, 10 days, 11 days, 12 days, 13 days, 14 days, 15 days, 1 month, 2 months, 3 months, 4 months, 5 months, 6 months, 7 months, 8 months, 9 months, 10 months, 11 months, 1 year, 2 years, 3 years, 4 years, 5 years, or 10 years. The effective dosage ranges may be adjusted based on subject's response to the treatment. Some routes of administration will require higher concentrations of effective amount of therapeutics than other routes.

Although not anticipated given the advantages of the present disclosure, in certain embodiments wherein the patient's condition does not improve, upon the doctor's discretion the administration of therapeutic rAAV composition is administered chronically, that is, for an extended period of time, including throughout the duration of the patient's life in order to ameliorate or otherwise control or limit the symptoms of the patient's disease or condition. In certain embodiments wherein a patient's status does improve, the dose of therapeutic rAAV composition being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In certain embodiments, the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the dosage amount of the therapeutic rAAV composition described herein lies within a range of circulating concentrations that include the ED50 with minimal toxicity. In certain embodiments, the daily dosage range and/or the unit dosage amount varies within this range depending upon the dosage form employed and the route of administration utilized.

Kits

Disclosed herein are kits comprising compositions disclosed herein. Also disclosed herein are kits for the treatment or prevention of a disease or conditions of the central nervous system (CNS), peripheral nervous system (PNS), or target organ or environment (e.g., lung, heart, liver). In some instances, the disease or condition is cancer, a pathogen infection, pulmonary disease or condition, neurological disease, muscular disease, or an immune disorder, such as those described herein. In one embodiment, a kit can include a therapeutic or prophylactic composition containing an effective amount of a composition of a rAAV particle encapsidating a heterologous nucleic acid comprising a therapeutic nucleic acid (e.g., therapeutic nucleic acid) and a recombinant AAV (rAAV) capsid protein of the present disclosure. In another embodiment, a kit can include a therapeutic or prophylactic composition containing an effective amount of cells modified by the rAAV described herein ("modified cell"), in unit dosage form that express therapeutic nucleic acid. In some embodiments, a kit comprises a sterile container which can contain a therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In some cases, rAAV are provided together with instructions for administering the rAAV to a subject having or at risk of developing the disease or condition (e.g., disease of the CNS, PNS, liver, and the like). Instructions can generally include information about the use of the composition for the treatment or prevention of the disease or condition.

In some cases, a kit can include allogenic cells. In some cases, a kit can include cells that can comprise a genomic modification. In some cases, a kit can comprise "off-the-shelf" cells. In some cases, a kit can include cells that can be expanded for clinical use. In some cases, a kit can contain contents for a research purpose.

In some cases, the instructions include at least one of the following: description of the therapeutic rAAV composition; dosage schedule and administration for treatment or prevention of the disease or condition disclosed herein; precautions; warnings; indications; counter-indications; overdosage information; adverse reactions; animal pharmacology; clinical studies; and/or references. The instructions can be printed directly on the container (when present), or as a label applied to the container, or as a separate sheet, pamphlet, card, or folder supplied in or with the container. In some cases, instructions provide procedures for administering the rAAV to the subject alone. In some cases, instructions provide procedures for administering the rAAV to the subject at least about 1 hour (hr), 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 25 hr, 26 hr, 27 hr, 28 hr, 29 hr, 30 hr, or up to 2 days, 3 days, 4 days, 5 days, 6 days, or 7 days after or before administering an additional therapeutic agent disclosed herein. In some instances, the instructions provide that the rAAV is formulated for intravenous injection. In some instances, the instructions provide that the rAAV is formulated for intranasal administration.

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

As used herein "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure, such as compositions for treating skin disorders like acne, eczema, psoriasis, and rosacea.

The terms "homologous," "homology," or "percent homology" are used herein to generally mean an amino acid sequence or a nucleic acid sequence having the same, or similar sequence to a reference sequence. Percent homology of sequences can be determined using the most recent version of BLAST, as of the filing date of this application.

The terms "increased," or "increase" are used herein to generally mean an increase by a statically significant amount. In some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The terms "subject" is any organism. In some instances, the organism is a mammal Non-limiting examples of mammal include, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In some instances, the subject is a patient, which as used herein, may refer to a subject diagnosed with a particular disease or disorder.

The term "gene," as used herein, refers to a segment of nucleic acid that encodes an individual protein or RNA (also referred to as a "coding sequence" or "coding region"), optionally together with associated regulatory region such as promoter, operator, terminator and the like, which may be located upstream or downstream of the coding sequence.

The term "adeno-associated virus," or "AAV" as used herein refers to the adeno-associated virus or derivatives thereof. Non-limited examples of AAV's include AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), AAV type 12 (AAV12), avian AAV, bovine AAV, canine AAV, equine AAV, primate AAV, non-primate AAV, and ovine AAV. In some instances, the AAV is described as a "Primate AAV," which refers to AAV that infect primates. Likewise an AAV may infect bovine animals (e.g., "bovine AAV", and the like). In some instances, the AAV is wildtype, or naturally occurring. In some instances the AAV is recombinant.

The term "AAV capsid" as used herein refers to a capsid protein or peptide of an adeno-associated virus. In some instances, the AAV capsid protein is configured to encapsidate genetic information (e.g., a transgene, therapeutic nucleic acid, viral genome). In some instances, the AAV capsid of the instant disclosure is a variant AAV capsid, which means in some instances that it is a parental AAV capsid that has been modified in an amino acid sequence of the parental AAV capsid protein.

The term "tropism" as used herein refers to a quality or characteristic of the AAV capsid that may include specificity for, and/or an increase or a decrease in efficiency of, expressing the encapsidated genetic information into one in in vivo environment, relative to a second in vivo environment. An in vivo environment, in some instances, is a cell-type. An in vivo environment, in some instances, is a tissue, organ, or organ system.

The term "AAV genome" as used herein refers to nucleic acid polynucleotide encoding genetic information related to the virus. The genome, in some instances, comprises a nucleic acid sequence flanked by AAV inverted terminal repeat (ITR) sequences. The AAV genome may be a recombinant AAV genome generated using recombinatorial genetics methods, and which can include a heterologous nucleic acid (e.g., transgene) that is flanked by the ITR sequences.

The term "AAV particle" or an "AAV vector" as used interchangeably herein refers to an AAV virus or virion comprising an AAV capsid within which is packaged a heterologous DNA polynucleotide, or "genome", comprising nucleic acid sequence flanked by AAV inverted terminal repeat (ITR) sequences. In some cases, the AAV particle is modified relative to a parental AAV particle.

The term "gene product" of "gene expression product" refers to an expression product of a polynucleotide sequence such as, for e.g., a polypeptide, peptide, protein or RNA, including but not limited to interfering RNA (e.g., siRNA, miRNA, shRNA) and messenger RNA (mRNA).

The terms "operatively linked" or "operably linked" refers to a location of two or more elements in cis with one another, and in some cases, next to one other (e.g., genetic elements such as a promoter, enhancer, termination signal sequence, polyadenylation sequence, and the like) that enables a functional relationship between the two or more elements. In one non-limiting example, a promoter that is operatively linked to a coding region enables the initiation of transcription of the coding sequence.

The term "heterologous" as used herein refers to a genetic element (e.g., coding region) or gene expression product (e.g., RNA, protein) that is derived from a genotypically distinct entity from that of the rest of the entity to which it is being compared.

The term "endogenous" as used herein refers to a genetic element (e.g., coding region) or gene expression product (e.g., RNA, protein) that is naturally occurring in or associated with an organism or a particular cell within the organism.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

The terms "treat," "treating," and "treatment" as used herein refers to alleviating or abrogating a disorder, disease, or condition; or one or more of the symptoms associated with the disorder, disease, or condition; or alleviating or eradicating a cause of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" refers to the amount of a compound or therapy that, when administered, is sufficient to prevent development of, or alleviate to some extent, one or more of the symptoms of a disorder, disease, or condition of the disease; or the amount of a compound that is sufficient to elicit biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration.

Non-limiting examples of "sample" include any material from which nucleic acids and/or proteins can be obtained. As non-limiting examples, this includes whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. In some embodiments, the sample is obtained directly from the patient. Alternatively, a sample can be obtained through primary patient derived cell lines, or archived patient samples in the form of preserved samples, or fresh frozen samples.

EXAMPLES

Example 1. Method of Producing an rAAV

A recombinant AAV (rAAV) is produced. Three plasmid vectors are triple-transfected into immortalized HEK293 cells using a standard transfection protocol (e.g., with PEI). The first vector contains a transgene cassette flanked by inverted terminal repeat (ITR) sequences from a parental AAV virus. The transgene cassette has a promoter sequence and that drives transcription of a heterologous nucleic acid in the nucleus of the target cell. The second vector contains nucleic acids encoding the AAV Rep gene, as well as a modified Cap gene e.g., AAV2/9 REP-AAP-ΔCap). The modified Cap gene comprises any one of SEQ ID NOS: 12740-25468, 35472-45474, and 46364-46383, which are the DNA sequences encoding the modified AAV capsid proteins of the present disclosure. The modified Cap gene, in some cases, comprises any one of SEQ ID NOS: 46404-46423, which are the DNA sequences encoding the full-length VP1 protein with the 7-mer substitute at amino acid positions 452-458. The third vector contains nucleic acids encoding helper virus proteins needed for viral assembly, and packaging of the heterologous nucleic acid into the modified capsid structure.

Viral particles are harvested from the media after 72 h post transfection and from the cells and media at 120 h post transfection. Virus present in the media is concentrated by precipitation with 8% poly(ethylene glycol) and 500 mM sodium chloride and the precipitated virus is added to the lysates prepared from the collected cells. The viruses are purified over iodixanol (Optiprep, Sigma) step gradients (15%, 25%, 40% and 60%). Viruses are concentrated and formulated in PBS. Virus titers are determined by measuring the number of DNaseI-resistant vector genome copies (VGs) using qPCR and the linearized genome plasmid as a control.

Example 2. Method of Identifying the Modified Capsid Proteins

Plasmids.

First round viral DNA library was generated by amplification of a section of the AAV9-PHP.eB capsid genome between amino acids 450-599 using NNK degenerate primers (Integrated DNA Technologies, Inc., IDT) to substitute amino acids 452-458 with all possible variations. The resulting library inserts were then introduced into the rAAV-ΔCap-in-cis-Lox plasmid via Gibson assembly as previously described. The resulting capsid DNA library, rAAV-Cap-in-cis-Lox, contained a diversity of ~1.28 billion variants at the amino acid level. Second round viral DNA library was generated similarly to the first round, but instead of NNK degenerate primers at the 452-458 location, a synthesized oligo pool (Twist Bioscience) was used to only generate selected variants. This second round DNA library contained a diversity of ~82,000 variants at the amino acid level.

The AAV2/9 REP-AAP-ΔCap plasmid transfected into HEK293T cells for library viral production was modified from the AAV2/9 REP-AAP plasmid previously used by deletion of the amino acids between 450-592. This modification prevents production of an AAV9 capsid during viral library production after a plausible recombination event between this plasmid co-transfected with rAAV-ΔCap-in-cis-Lox containing the library inserts.

Two rAAV genomes were used in this study. The first, pAAV-CAG-mNeonGreen, utilizes a single-stranded (ss) rAAV genome containing the fluorescent protein mNeonGreen under control of the ubiquitous CMV-β-Actin-intron-β-Globin hybrid promoter (CAG). The second, pAAV-CAG-NLS-GFP (Addgene #104061), utilizes a ssAAV genome containing the fluorescent protein EGFP flanked by two nuclear localization sites, PKKKRKV (SEQ ID NO: 45486), under control of the CAG promoter.

Viral Production

Recombinant AAVs were described in Challis, R. C. et al. Systemic AAV vectors for widespread and targeted gene delivery in rodents. Nat. Protoc. 14, 379 (2019). Briefly, triple transfection of HEK293T cells (ATCC) using polyethylenimine (PEI) was performed, virus was collected after 120 hours from both cell lysates and media and purified over iodixanol (Optiprep, Sigma).

A modified protocol was used for transfection and purification of viral libraries. First, to prevent mosaic capsid formation, only 10 ng of rAAV-Cap-in-cis-Lox library DNA was transfected (per 150 mm plate) to decrease the likelihood of multiple library DNAs entering the same cell. Second, virus was collected after 60 hours, instead of 120, to limit secondary transduction of producer cells. Finally, instead of PEG precipitation of the viral particles from the media, as performed in the standard protocol, media was concentrated >60-fold for loading onto iodixanol. This step was performed to prevent aggregation and loss of viral diversity, something that was noticed during PEG precipitation.

Animals

All rodent procedures were approved by the Institutional Animal Use and Care Committee (IACUC) of the California Institute of Technology. Transgenic animals, expressing Cre under control of various cell-type specific promoters, as well as C57Bl/6J WT mice (000664) were purchased from the Jackson Laboratory (JAX). Transgenic mice included Syn1-Cre (3966), GFAP-Cre (012886) and Tek-Cre (8863). For round 1 and round 2 selections of viral library, one male and one female mouse, 8-12 weeks of age, of each transgenic line were used, as well as a single male C57Bl/6J. For validation of individual viral variants, male C57Bl/6J mice were used, aged 6-8 weeks. Intravenous administration of rAAV vectors was performed via injection into the retro-orbital sinus.

Viral Library Recovery and Sequencing

Round 1 and round 2 viral libraries were injected into C57Bl/6J and Cre-transgenic animals at a dose of $8\times10^{10}$ vg/animal and rAAV genomes were recovered two weeks post injection. Mice were euthanized, and most major organs were recovered, snap frozen on dry ice and placed into long-term storage at −80° C. Tissues included: brain, spinal cord, DRGs, liver, lungs, heart, stomach, intestines, kidneys, spleen, pancreas, skeletal muscle and adipose tissue. 100 mg of each tissue (~250 mg for brain hemisphere, <100 mg for DRGs) was homogenized in Trizol (Life Technologies, 15596) using a BeadBug (Benchmark Scientific, D1036) and viral DNA isolated according to the manufacturer's recommended protocol. Recovered viral DNA was treated with RNase, underwent restriction digestion with SmaI (found within the ITRs) to improve later rAAV genome recovery by PCR, and purified with a Zymo DNA Clean and Concentrator kit (D4033). Viral genomes flipped by Cre-recombinase in select transgenic lines (or pre-flipped in WT animals) were selectively recovered using the following primers: 5'-CTTCCAGTTCAGCTACGAGTTTGAGAAC-3'(SEQ ID NO: 45487) and 5'-CAAGTAAAACCTCTA-CAAATGTGGTAAAATCG-3' (SEQ ID NO: 45488), after 25 cycles of 98° C. for 10s, 60° C. for 15s and 72° C. for 40s, using Q5 DNA polymerase in five 25 µl reactions with 50% of the total extracted viral DNA as a template.

After Zymo DNA purification, samples from the WT C57Bl/6J animals were serially diluted between 1:10-1:10,000 and each dilution further amplified around the library variable region. This amplification was done using primers: 5'-ACGCTCTTCCGATCTAATACTTGTAC-TATCTCTCTAGAACTATT-3' (SEQ ID NO: 45489) and 5'-TGTGCTCTTCCGATCTCACACTGAATTT-TAGCGTTTG-3' (SEQ ID NO: 45490) and 10 cycles of 98° C. for 10s, 61° C. for 15s and 72° C. for 20s, to recover 73 bp of viral genome around and including the 21 bp variable region and add adapters for Illumina next-generation sequencing. After PCR cleanup, these products were further amplified using NEBNext Dual Index Primers for Illumina sequencing (New England Biolabs, E7600), after 10 cycles of 98° C. for 10s, 60° C. for 15s and 72° C. for 20s. The amplification products were run on a 2% low-melting-point agarose gel (ThermoFisher Scientific, 162050) for better separation and recovery of the 210 bp band. The dilution series was analyzed for each WT tissue and the highest concentration dilution which resulted in no product was chosen for further amplification of the viral DNA from the transgenic animal tissues. This process was performed to differentiate between viral genomes flipped prior to packaging or due to Cre in the animal Pre-flipped viral genomes should be avoided to minimize false-positives in the NGS sequencing results.

Using the dilutions resulting in a product that doesn't contain pre-flipped viral genomes, all Cre-flipped viral genomes from transgenic animal tissues were similarly amplified to add Illumina sequencing adapters and subsequently for index labeling. The amplified products now containing unique indices for each tissue from each animal were run on a low-melting-point agarose gel and the correct bands extracted and purified with a Zymoclean Gel DNA Recovery kit.

Packaged viral library DNA was isolated from the injected viral library by digestion of the viral capsid and purification of the contained ssDNA. These viral genomes were amplified by two PCR amplification steps, like the viral DNA extracted from tissue, to add Illumina adapters and then indices and extracted and purified after gel electrophoresis. This viral library DNA, along with the viral DNA extracted from tissue was sent for deep sequencing using an Illumina HiSeq 2500 System (Millard and Muriel Jacobs Genetics and Genomics Laboratory, Caltech).

NGS Data Alignment and Processing

Raw fastq files from NGS runs were processed with custom built that align the data to an AAV9 template DNA fragment containing the 21 bp diversified region between AA 452-458. The pipeline to process these datasets involved filtering to remove low-quality reads, utilizing a quality score for each sequence and eliminating bias from PCR-induced mutations or high GC-content. The filtered dataset was then aligned by perfect string match algorithm and trimmed to improve the alignment quality. Read counts for each sequence were then pulled out and displayed along with their enrichment score, defined as the relative abundance of the sequence found within the specific tissue over the relative abundance of that sequence within the injected viral library.

Enrichment quantification. Enrichment for a specific variant in a target tissue was calculated in reference to the entire library within that tissue and was defined as the prevalence of the variant within the target tissue normalized to the prevalence in the variant within the injected viral library.

$$\text{Enrichment(Var1)} = \log\frac{\text{probability of Var1 in tissue}}{\text{probability of Var1 in injected library}}$$

A positive enrichment score is achieved if the AAV variant is found more prevalently in the tissue than in the injected viral library and a negative one is achieved if the AAV variant is found less prevalently. An enrichment score of 0 means that either the variant was found in exactly the same prevalence in tissue and injected viral library, or that there were no read counts of the specific variant in the target tissue, i.e. the variant could not be detected in the tissue. As the former is unlikely, an enrichment score of 0 is interpreted to meant that the variant is not present in the tissue. Thus, an AAV variant was determined to de-target a tissue if its enrichment score in that tissue was less than or equal to 0. In vivo characterization of liver transduction from a number of AAV variants having an enrichment score of 0 relative to their parental AAV vector AAV9 verified that this interpretation was accurate (see, e.g., FIG. 17D, E).

Tissue Preparation and Immunohistochemistry

Mice were euthanized with Euthasol and transcardially perfused with ice-cold 1×PBS and then freshly prepared, ice-cold 4% paraformaldehyde (PFA) in 1×PBS. All organs were excised and post-fixed in 4% PFA at 4° for 48 hours and then sectioned by vibratome. IHC was performed on floating sections with primary and secondary antibodies in PBS containing 10% donkey serum and 0.1% Triton X-100. Primary antibodies used were rabbit anti-NeuN (1:200, Abcam, 177487), rabbit anti-S100 (1:200, Abcam, 868), rabbit anti-Olig2 (1:200, Abcam, 109186) and rabbit anti-Calbindin (1:200, Abcam, 25085). Primary antibody incubations were performed for 16-20 hours at room temperature (RT). The sections were then washed and incubated with secondary Alexa-647 conjugated anti-rabbit FAB fragment antibody (1:200, Jackson ImmunoResearch Laboratories, Inc., 711-607-003) for 6-8 hours at RT. For nuclear staining, floating sections were incubated in PBS containing 0.2% Triton X-100 and DAPI (1:1000, Sigma Aldrich, 10236276001) for 6-8 hours and then washed. Stained sections were then mounted with ProLong Diamond Antifade Mountant (ThermoFisher Scientific, P36970).

Imaging and Quantification

All CAG-mNeonGreen expressing tissues were imaged on a Zeiss LSM 880 confocal microscope using a Fluar 5×0.25 M27 objective, with matched laser powers, gains and gamma across all samples of the same tissue. The acquired images were processed in Zen Black 2.3 SP1 (Zeiss).

All CAG-NLS-GFP expressing tissues were imaged on a Keyence BZ-X all-in-one fluorescence microscope at 48-bit resolution with the following objectives: PlanApo-λ 20×/0/75 (1 mm working distance) or PlanApo-λ 10×/0.45 (4 mm working distance). For colocalization of GFP expression to antibody staining, in some cases the exposure time for the green (GFP) channel was adjusted to facilitate imaging of high and low expressing cells while avoiding oversaturation. In all cases in which fluorescent intensity was compared between samples, exposure settings and changes to gamma or contrast were maintained across images. To minimize bias, multiple fields of view per brain region and peripheral organ were acquired for each sample. For brain regions, the fields of view were matched between samples and chosen based upon the antibody staining rather than GFP signal. For peripheral tissues, fields of view were chosen based upon the DAPI or antibody staining to preclude observer bias.

All image processing was performed with the Keyence BZ-X Analyzer. Data analysis was performed with Microsoft Excel 2018 and GraphPad Prism 7. Colocalization between GFP signal and antibody or DAPI staining was performed using the Keyence BZ-X Analyzer with the hybrid cell count automated plugin. Automated counts were validated and routinely monitored by comparison to manual hand-counts and found to be below the margin of error for manual counts.

To compare total cell counts and fluorescent intensity throughout the brain between samples, an entire sagittal section located 1200 μM from midline was imaged using matched exposure conditions with the Keyence BZ-X automated XY stitching module. Stitched images were then deconstructed in the Keyence BZ-X Analyzer suite and run through the hybrid cell count automated plugin to count the total number of cells in the entire sagittal section. Average fluorescent intensity was calculated by creating a mask of all GFP positive cells throughout the sagittal section and measuring the integrated pixel intensity of that mask. The total integrated pixel intensity was divided by the total cell count to obtain the fluorescent intensity per cell measure. In all cases where direct comparisons were made of fluorescent intensity, exposure settings and postprocessing contrast adjustments were matched between samples.

Statistics

Microsoft Excel 2018 and GraphPad Prism 7 were used for statistical analysis and data representation. Unless otherwise noted, all experimental groups were n=6 and determined using preliminary data and experimental power analysis. For the statistical analysis and their graphs, a single data point was defined as two tissue sections per animal with multiple technical replicates per section when possible. Technical replicates are defined as multiple fields of view per section, with the following numbers for each region or tissue of interest: cerebellum=3, cortex=4, hippocampus=3, midbrain=1, striatum=3, thalamus=4, liver=4, spleen=2, testi=2, kidney=2, lung=2, spine=1, DRG=1, whole sagittal=1.

Example 2. Overview of Cre-Dependent Positive and Negative Selection of Viral Libraries For the express purpose of engineering AAVs with high efficiency toward specific organs and away from others after systemic administration, an updated version of the CREATE screening method (M-CREATE) was used, which allowed for the selection of large libraries of viral variants in vivo. FIG. 1 shows a schematic of the M-CREATE methods used. With CREATE, a library of AAV capsids with mutations at a specific location was generated by PCR with degenerate primers, viruses packaging a replication-incompetent version of their own genome with a polyadenylation site flanked by Cre/Lox sites are produced in HEK293 cells, and the viral library is injected into transgenic animals expressing Cre in a specific population of cells. If variants of the library successfully transduce cells expressing Cre, their genome is flipped and the sequence of those variants can be recovered in a Cre-dependent manner.

Selection of variants in multiple transgenic mouse lines expressing Cre in different cell populations: Tek-Cre for endothelial cells throughout the body, hSynl-Cre for neurons of the CNS and PNS, and GFAP-Cre for astrocytes, was performed. By performing selections in parallel in multiple transgenic lines, both positive and negative selection can be applied thereby recovering target sequences from a specific tissue of interest, that were not recovered from others. Next, the recovered viral DNA from the tissues of interest were sequenced and indexed. The sequences were then ranked based on prevalence in target environment or cell-type of interest. A second-round library was synthesized containing only the top-performing sequences from round 1.

The AA455 loop of AAV9 is the furthest protruding from the surface of the capsid and has previously been implicated in neutralizing antibody binding. The most commonly manipulated loop in AAVs is the AA588 loop, due to it being the site of heparan sulfate binding of AAV2 and amenable to peptide display. The only known receptor for AAV9 is N-linked terminal galactose, but many indications point toward there being others.

Without wishing to be bound by any particular theory, the AA455 loop may also play a role in cell-surface receptor binding, either on its own or by interaction with the AA588 loop. To determine whether variant amino acid sequences at the AA455 loop contribute to desired AAV tropisms, rAAVs were engineered and rounds of selection were performed using the M-CREATE method of a 7 amino acid substitution library of the 455 loop, between AA452-458 (FIG. 1A-1B) in AAV-PHP.eB, a variant of AAV9 previously engineered at the AA588 loop for increased efficiency in crossing the BBB.

Figure 15A:
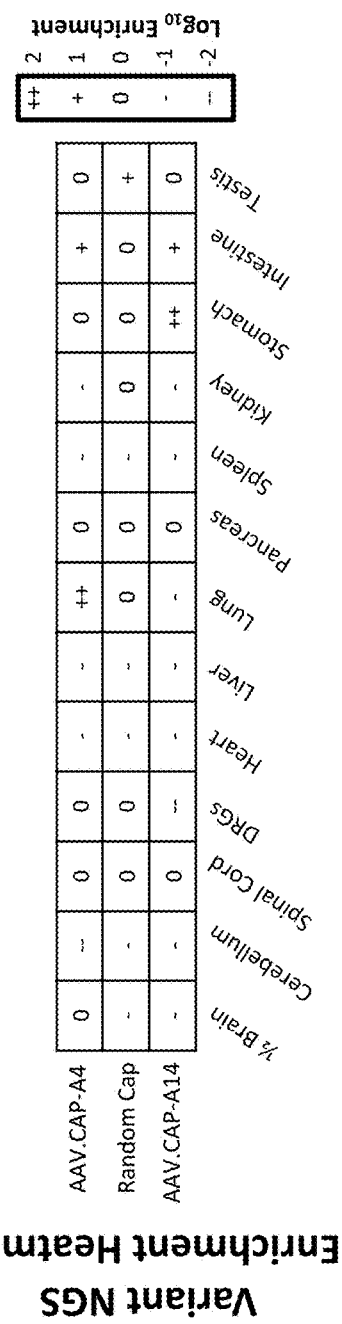
FIG. 15A-15B shows next generation sequencing data and in vivo transduction efficiency of candidate variants.
Figure 15B:
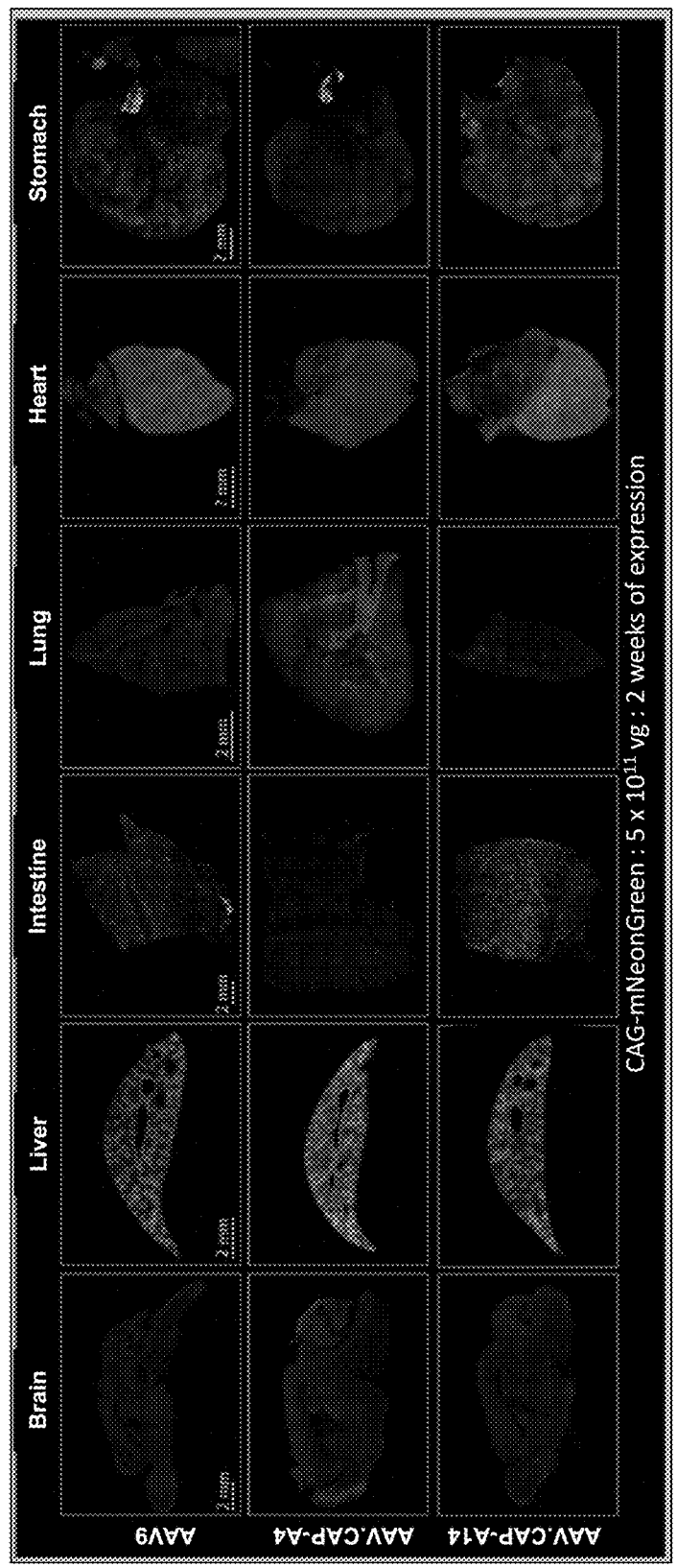

Example 3. AAV Capsid Variants with Tropisms Bias Toward the Lung and Against the Liver in Rodents AAV.CAP-A4 Exhibits Strong Lung-Specific Transduction Highly enriched variants for a number of targets were discovered after two rounds of in vivo selection. The results from the second round of selection for lung enrichment yielded several candidate variants, one of which showed significant enrichment in the lung, with detargeting of several peripheral organs A randomly chosen variant (FIG. 15A), as well as a second novel capsid that emerged from this screen that was found to be enriched specifically in gut neurons are provided as a comparison. To directly assess transduction efficiencies, the capsid sequences for the candidate variants were cloned into an AAV9 backbone, and virus was produced for each variant packaging mNeonGreen, a fluorescent reporter, driven by the ubiquitous synthetic promoter CAG. This construct will drive strong expression of the fluorescent promoter in all cell types transduced by the vector, thereby giving a visual readout of the transduction of each variant across cell and tissue types. Following purification, $5 \times 10^{11}$ vector genomes (vg) of each variant, including AAV9 as a control, were injected into 2 male c57bl/6 mice. Following two weeks of expression, animals were sacrificed, perfusion fixed, and a panel of organs were sectioned and imaged for fluorescence (FIG. 15B). The expression pattern confirms the next generation sequencing (NGS) results, with AAV.CAP-A4 (KDNTPGR (SEQ ID NO: 32538) encoded by AACAACCTCCCCAGAAACCTC (SEQ ID NO: 46429)) showing increased transduction throughout the lung. As a comparison, AAV.CAP-A14 shows increased expression in neurons within the intestine and stomach, which is in accordance with the NGS results.

Figure 16A:
FIG. 16A-16D shows the tropism of AAV.CAP-A4 is strongly enriched in submucosal cells within the lung. ssAAV9:CAG-NLSx2-EGFP, ssAAV5:CAG-NLSx2-EGFP or ssAAV.CAP-A4:CAG-NLSx2-EGFP was intravenously injected into male adult mice at $1\times10^{11}$ vg/mouse. GFP fluorescence was assessed after three weeks of expression.
Figure 16B:
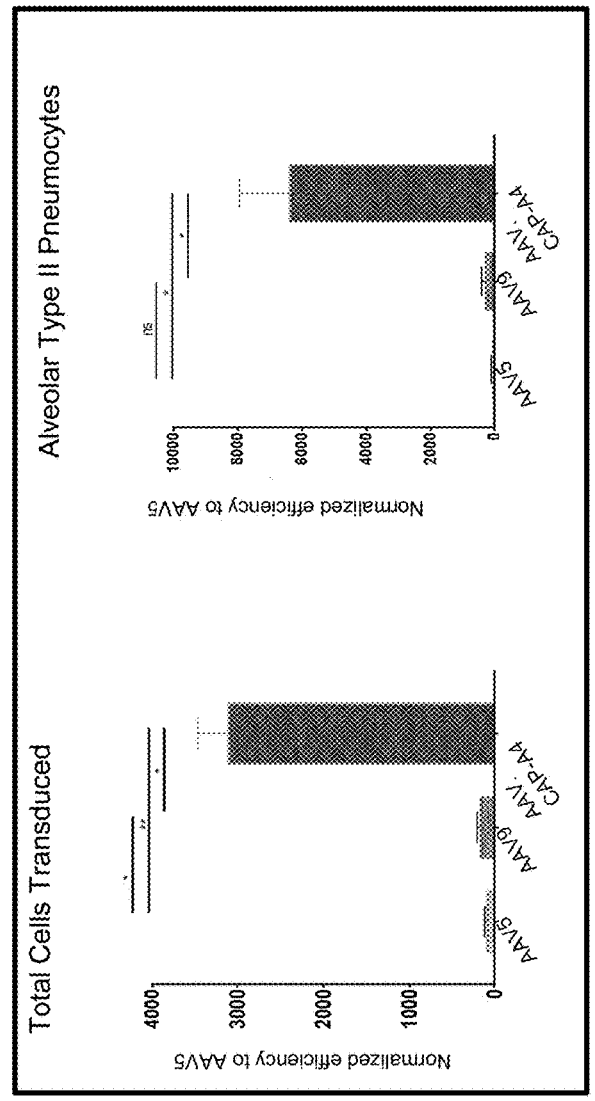
Figure 16C:
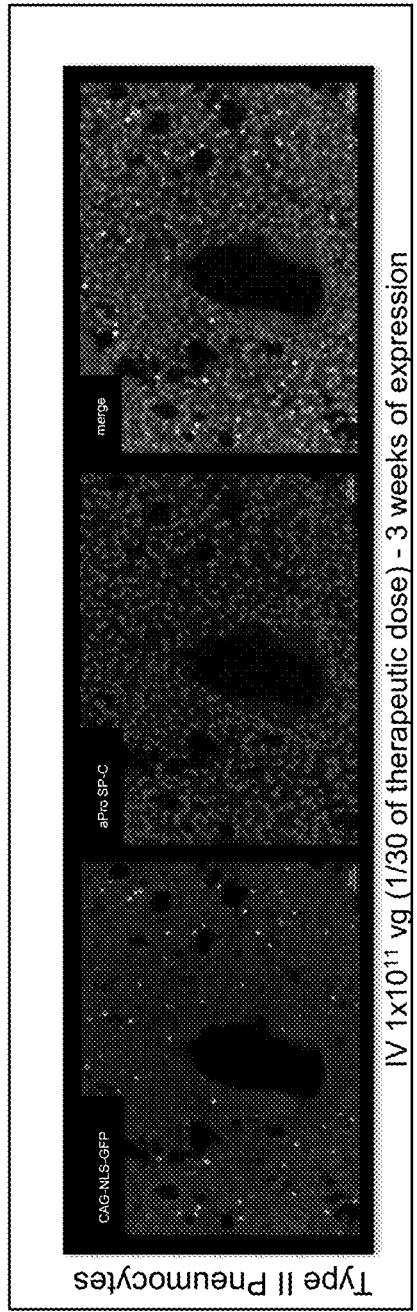
Figure 16D:
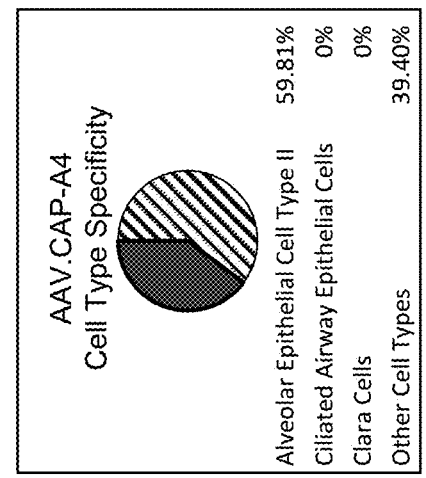

Following confirmation that AAV.CAP-A4 showed increased transduction of the lung, transduction efficiencies of AAV.CAP-A4, along with AAV9 and AAV5 as controls, were quantified across time in clinically relevant cell types following low-dose systemic injection. For these experiments, AAV.CAP-A4, AAV5, and AAV9 were injected into age-matched male mice and allowed to express for 3 weeks (n=3) or 6 months (n=3). In addition, a nuclear localization sequence (NLS) was cloned into a CAG-GFP expression cassette to restrict expression of the fluorescent reporter to the nucleus, aiding in co-localization with specific antibody staining. Following tissue preparation, serialized sections of the lungs from each of the variants were stained with antibodies for ciliated airway epithelial cells, clara cells, and alveolar epithelial type II (ATII) cells (FIG. 16A). Quantification shows that systemically injected AAV.CAP-A4 transduces submucosal cells at ~15 fold greater efficiency than AAV9, and ~30 fold greater than AAV5 (FIG. 16B). Similarly, transduction of ATII cells is ~30 fold greater than AAV9, and ~60 fold greater than AAV5 (FIG. 16C). Of the total number of cells transduced by AAV.CAP-A4, approximately 60% of them are ATII cells, with the other 40% being of an unknown, submucosal cell type (FIG. 3D). These results demonstrate that AAV.CAP-A4 provides unprecedented, non-invasive genetic access to submucosal cells in the lungs following systemic administration which, alone or in conjunction with delivery direct to the airways, may provide sufficient CFTR functionalization to reduce CF disease progression.

FIG. 4 shows 7-mer variant AAV capsid amino acid sequences and DNA sequences encoding the 7-mer variant AAV capsid amino acid sequences with a tropism specific to the heart. FIG. 5 shows 7-mer variant AAV capsid amino acid sequences and DNA sequences encoding the 7-mer variant AAV capsid amino acid sequences with a tropism specific to the intestine. FIG. 6 shows 7-mer variant AAV capsid amino acid sequences and DNA sequences encoding the 7-mer variant AAV capsid amino acid sequences with a tropism specific to the kidney. FIG. 7 shows 7-mer variant AAV capsid amino acid sequences and DNA sequences encoding the 7-mer variant AAV capsid amino acid sequences with a tropism specific to the liver. FIG. 8 shows 7-mer variant AAV capsid amino acid sequences and DNA sequences encoding the 7-mer variant AAV capsid amino acid sequences with a tropism specific to muscle. FIG. 9 shows 7-mer variant AAV capsid amino acid sequences and DNA sequences encoding the 7-mer variant AAV capsid amino acid sequences with a tropism specific to the pancreas. FIG. 10 shows 7-mer variant AAV capsid amino acid sequences and DNA sequences encoding the 7-mer variant AAV capsid amino acid sequences with a tropism specific to the spleen. FIG. 11 shows 7-mer variant AAV capsid amino acid sequences and DNA sequences encoding the 7-mer variant AAV capsid amino acid sequences with a tropism specific to the stomach. FIG. 12 shows 7-mer variant AAV capsid amino acid sequences and DNA sequences encoding the 7-mer variant AAV capsid amino acid sequences with a tropism specific to the testicle. FIG. 13 shows 7-mer variant AAV capsid amino acid sequences and DNA sequences encoding the 7-mer variant AAV capsid amino acid sequences with a tropism specific to lung. FIG. 14 shows 7-mer variant AAV capsid amino acid sequences and DNA sequences encoding the 7-mer variant AAV capsid amino acid sequences with a tropism specific to adipose tissue.

Figure 17C:
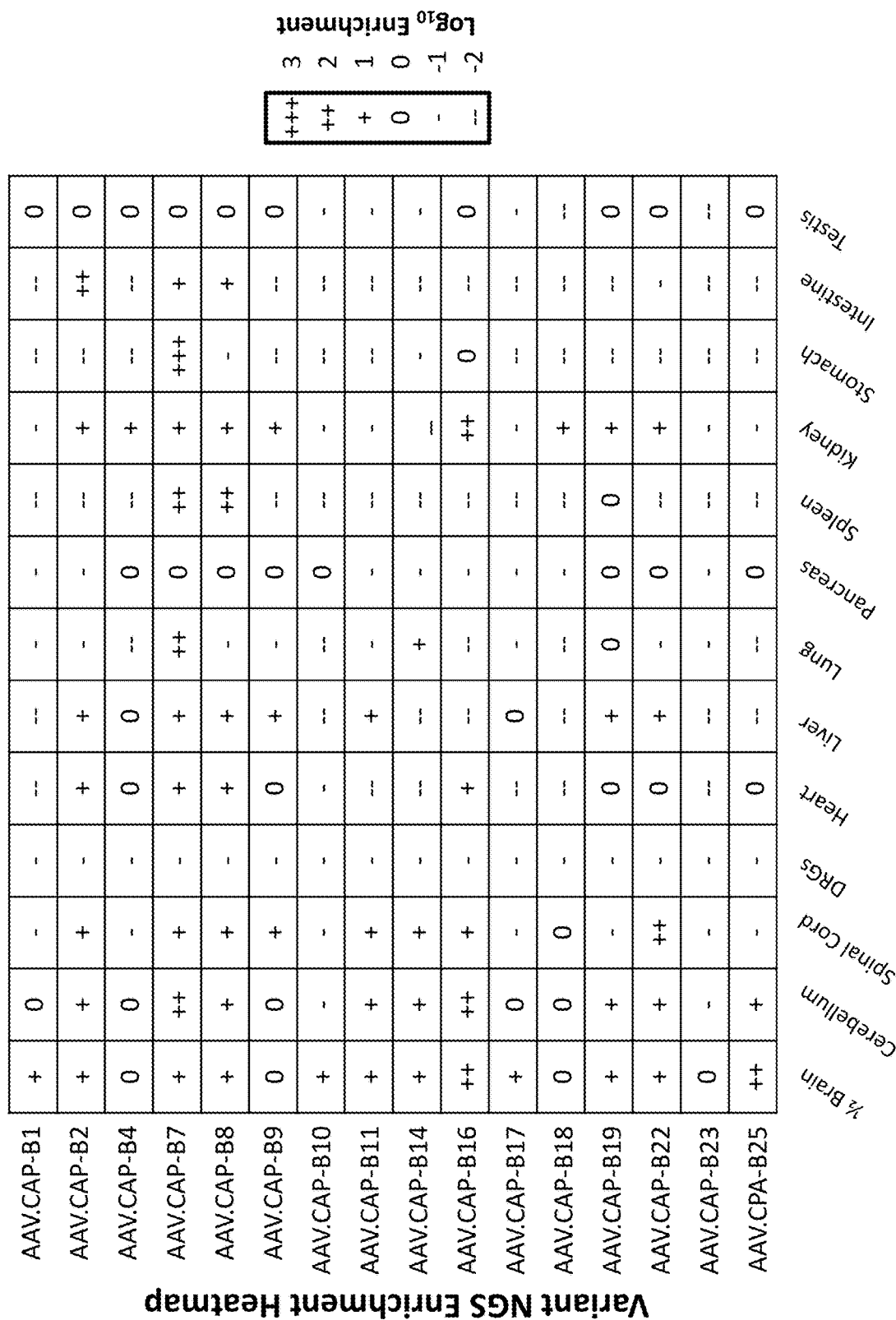
Figure 17D:
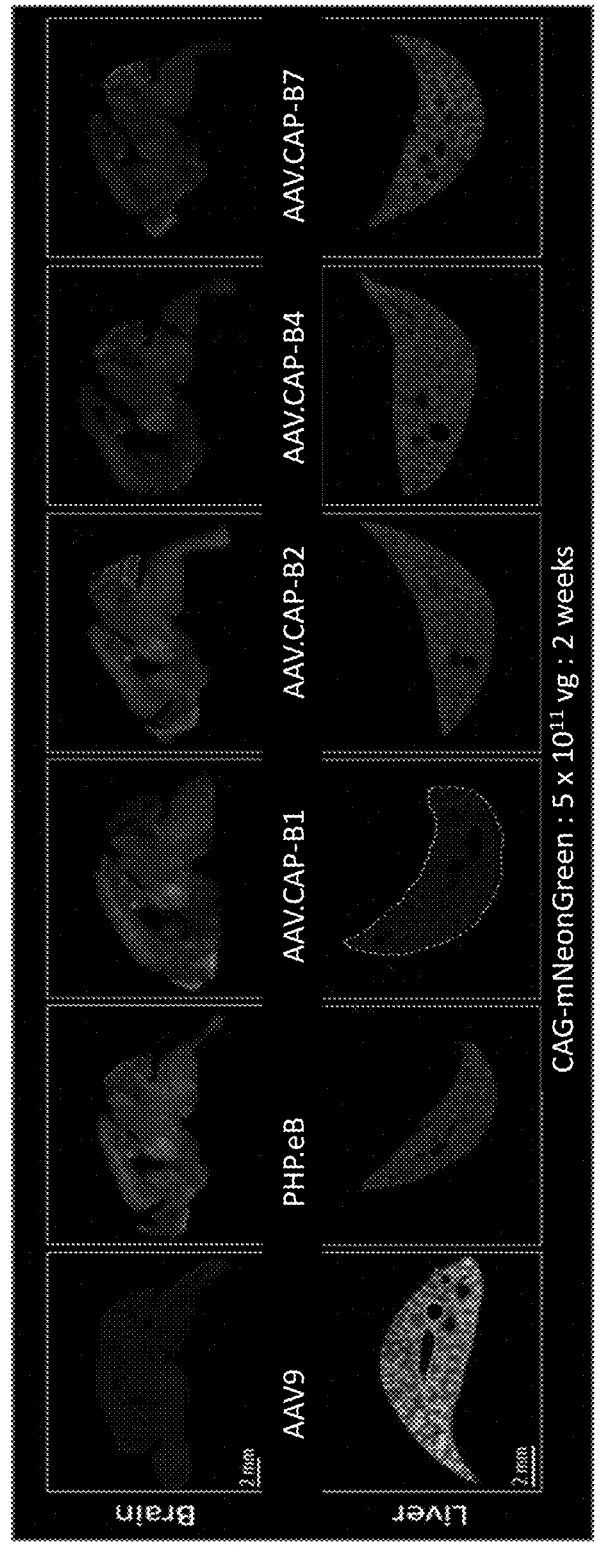
Figure 17E:
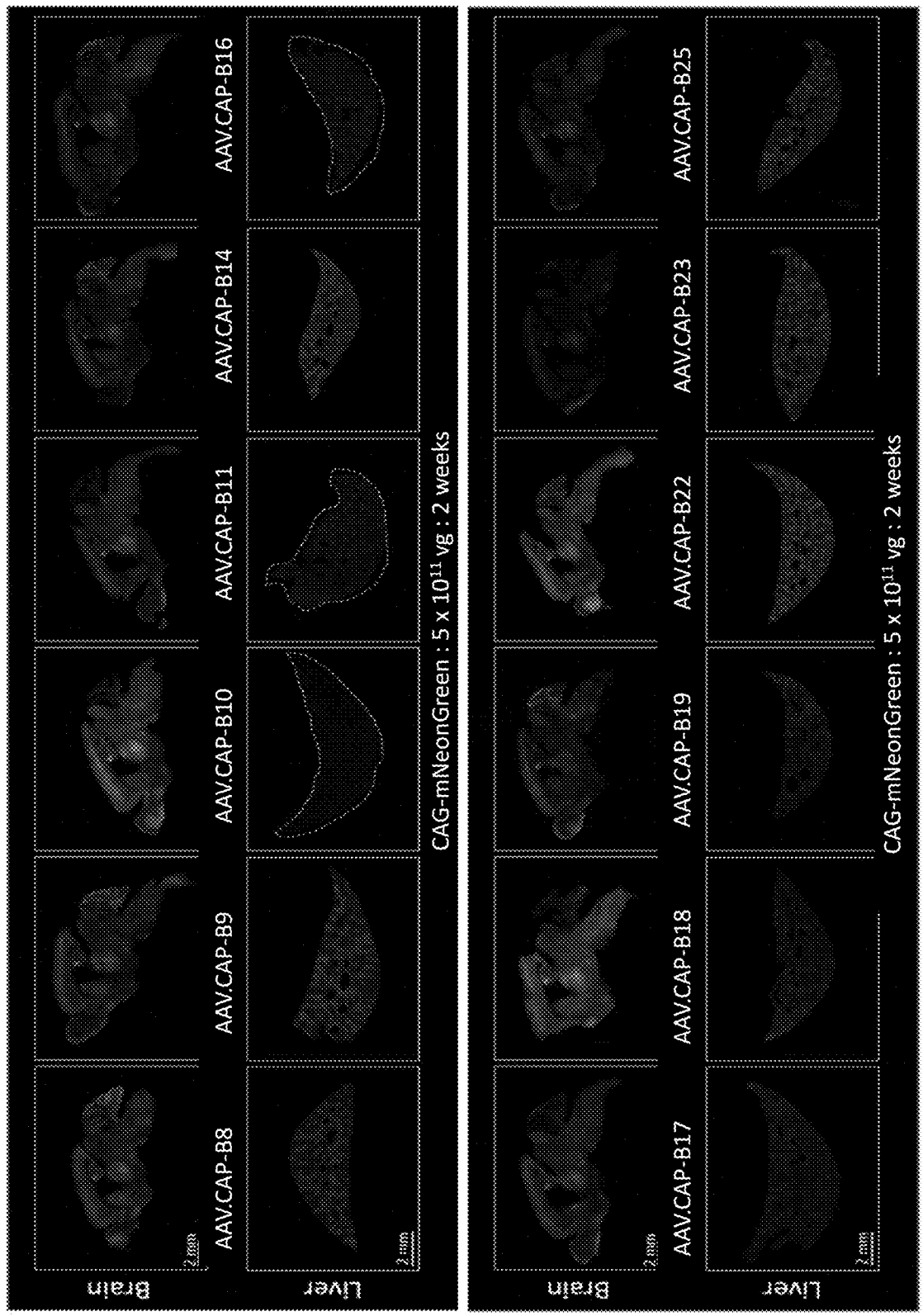

Example 4. AAV Capsid Variants with Tropism Bias Toward Central and Peripheral Nervous System and Against the Liver in Rodents Engineering AAV-PHP.eB Away from Peripheral Expression After the first round of selection, the recovered sequences were analyzed. A second round was synthesized, which contained approximately 82,000 unique variants enriched in the brain compared to peripheral organs. After a second round of selection which narrowed down the top performing variants by a couple orders of magnitude, a small subset of sequences to test were selected (FIG. 4b) that exhibited high levels of enrichment for the brain, and negative enrichment for the liver and other peripheral organs (FIG. 17C). This subset was tested individually in wild-type mice, injecting $5 \times 10^{11}$ viral genomes packaging CAG-mNeonGreen and allowing for two weeks of expression. The resulting expression in the brains and livers (FIG. 17D) correlated very closely with the next generation sequencing (NGS) enrichments, with variant AAV.CAP-B10 standing out as exhibiting higher fluorescence in the brain than PHP.eB and negligible liver transduction.

The above results match NGS enrichment findings for both brain and periphery. In this case, the insertion/substitution at the AA588 loop to make PHP.eB seems to confer a brain phenotype, while the substitutions at AA455 detarget that phenotype from the liver and other peripheral organs. Of the 82,000 variants that comprised the second round of selection, roughly 39,000 exhibited positive enrichment in the brain and negative enrichment in the liver. These results serve as a validation that the NGS results can be used as an accurate proxy of in vivo performance.

For the ~39,000 sequences that exhibited brain enrichment and liver de-targeting, the amino acid makeup was analyzed that resulted in this phenotype. The frequency at which amino acids were selected throughout the 7-mer substitution were analyzed and plotted their deviation from the mean as a heat map of enriched amino-acids at specific positions. These positively enriched amino acids de-target the capsid from the liver, while retaining CNS enrichment.

AAV.CAP-B10 Exhibits CNS-Specific Transduction

Figure 18A:
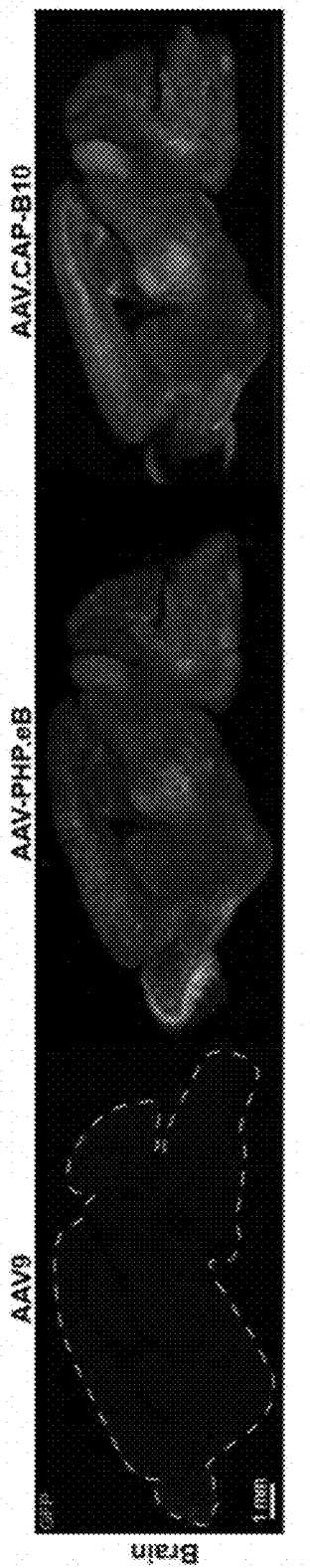
Figure 18B:
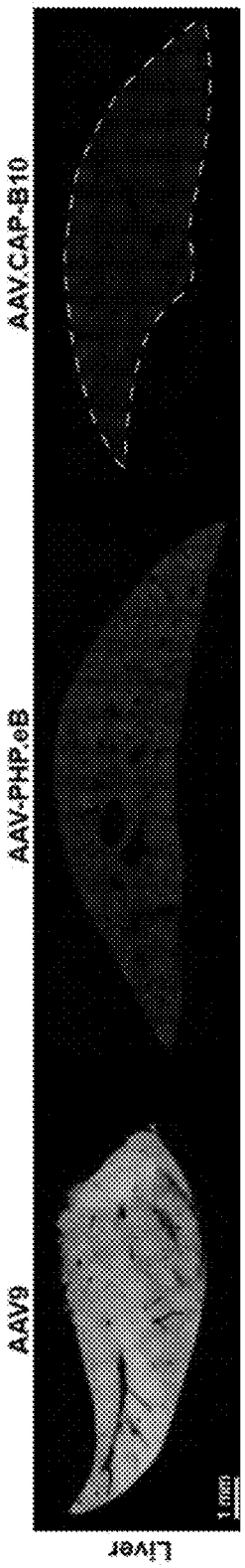

To fully characterize the performance of AAV.CAP-B10 in comparison with AAV9 and PHP.eB, nuclear localized CAG-EGFP were packaged and injected $1 \times 10^{11}$ viral genomes into animals Expression was measured after three weeks. This dose was chosen as an average dose for previous experiments utilizing systemic delivery to the brain. The results show an increase in the average number of cells transduced in the brain, as well as the average level of expression per cell, between AAV.CAP-B10 and PHP.eB, while both are very significantly higher than AAV9 (FIG. 18A-5C). In the spinal cord, AAV.CAP-B10 performs at roughly 60% of the efficiency of PHP.eB, yet still almost 20-fold higher than AAV9. Conversely, AAV.CAP-B10 is very significantly reduced in the liver compared to both PHP.eB (~50-fold) and AAV9 (>100-fold), and slightly, yet insignificantly, dimmer in brightness/cell compared to PHP.eB, while both are significantly dimmer than AAV9 (~10-fold) (FIG. 18B-18D). In the rest of the periphery, the results follow the same trend, with PHP.eB being lower than AAV9, and AAV.CAP-B10 being a fraction of PHP.eB (FIG. 18D).

AAV.CAP-B10 Exhibits Strong Neuronal Bias

Figure 19A:
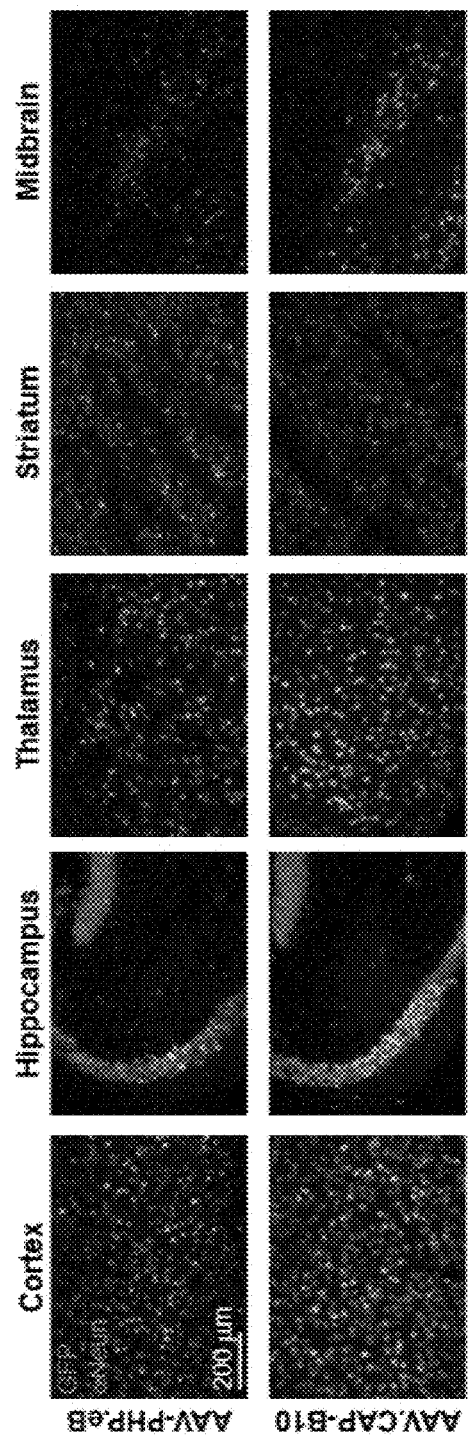
FIG. 19A-F shows that within the brain, AAV.CAP-B10 is strongly biased towards neurons. ssAAV-PHP.eB:CAG-NLSx2-EGFP or ssAAV.CAP-BB10:CAG-NLSx2-EGFP was intravenously injected into male adult mice at $1 \times 10^{11}$ vg/mouse. GFP fluorescence was assessed after three weeks of expression.
Figure 19B:
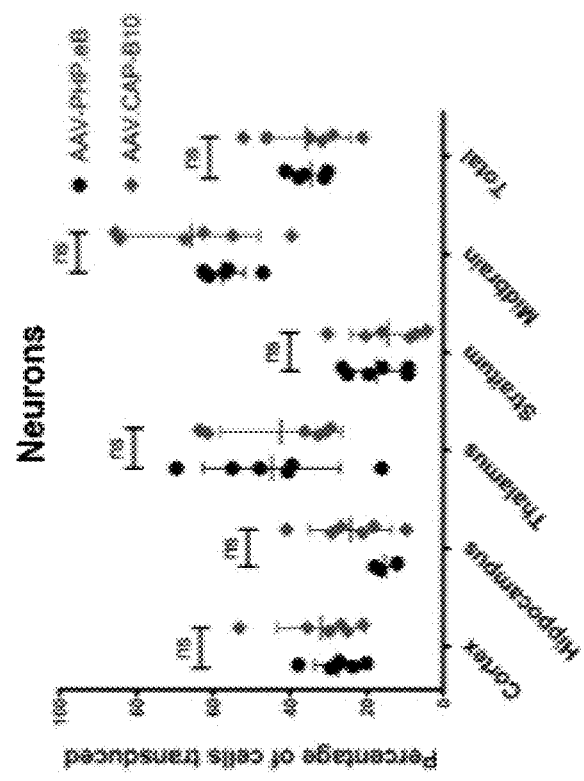
Figure 19C:
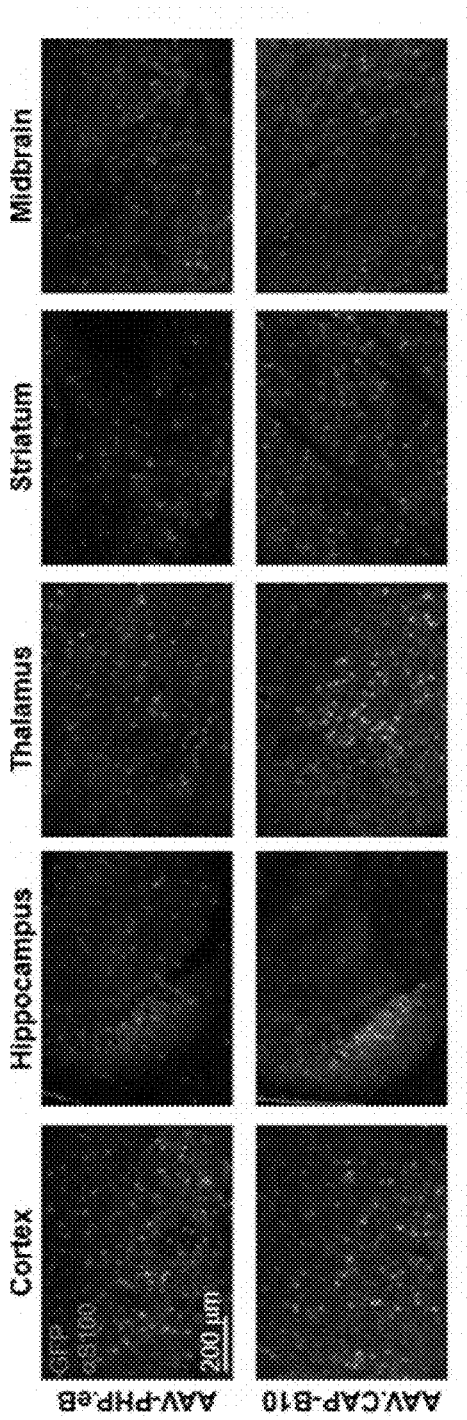
Figure 19D:
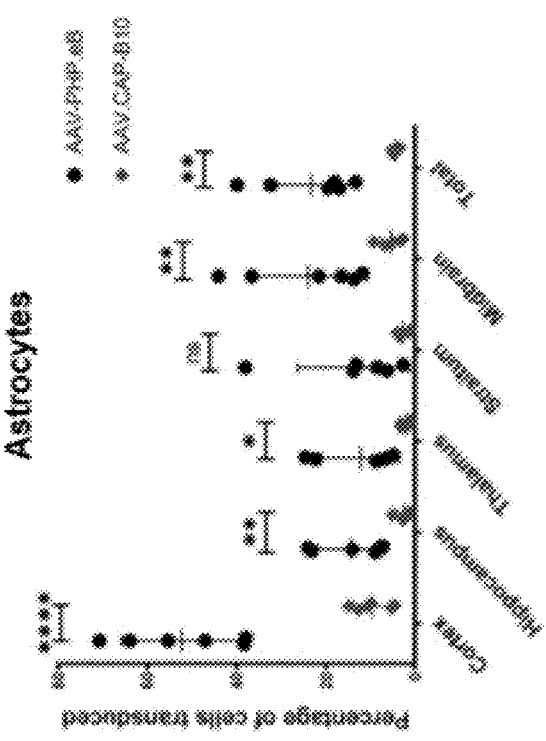
Figure 19E:
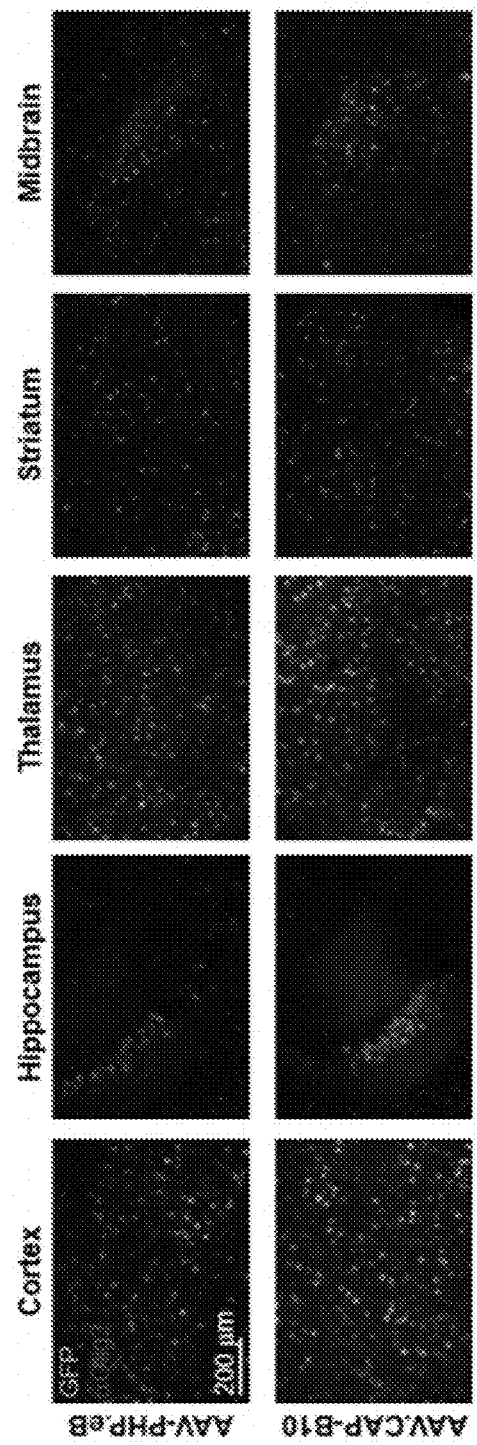
Figure 19F:
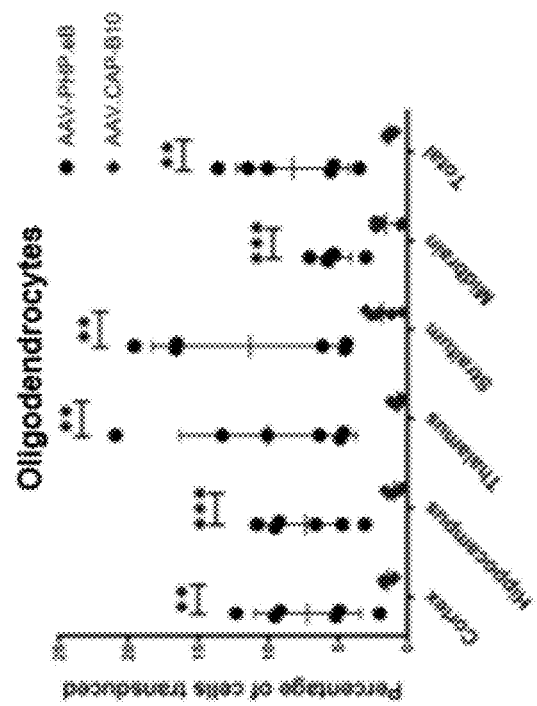
Figure 20B:
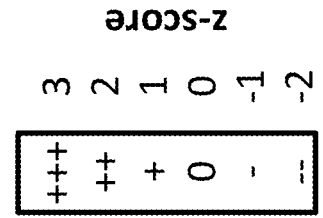
Figure 21:
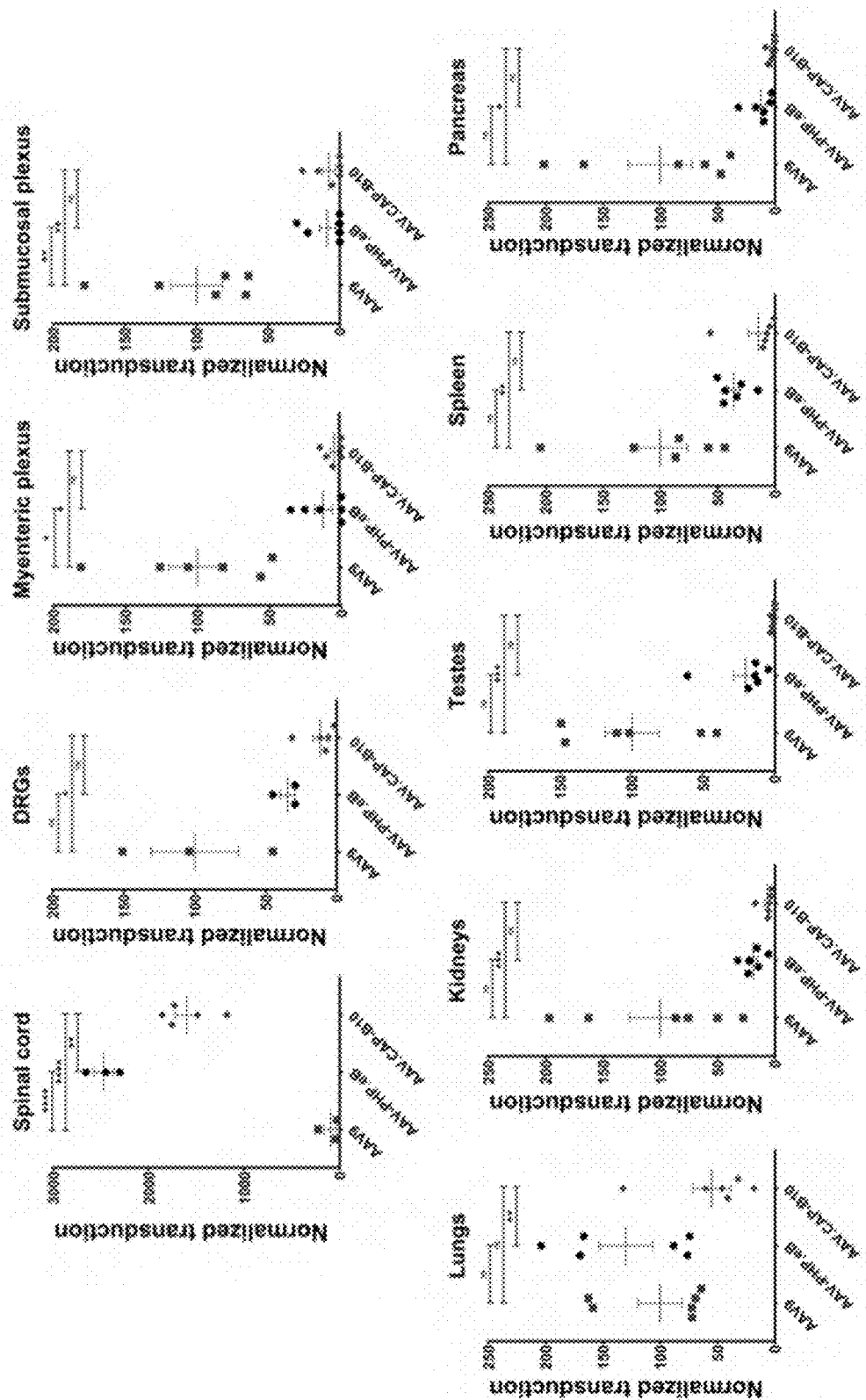
FIG. 21 shows that AAV.CAP-B10 is detargeted from peripheral organs. ssAAV9:CAG-NLSx2-EGFP, ssAAV-PHP.eB:CAG-NLSx2-EGFP or ssAAV.CAP-B10:CAG-NLSx2-EGFP was intravenously injected into male adult mice at 1×1011 vg/mouse. GFP fluorescence was assessed after three weeks of expression. Transduction efficiencies in peripheral tissues show a significant increase and decrease in spinal cord transduction for AAV.CAP-B10 when compared to AAV9 or AAV-PHP.eB, respectively. In the DRGs, AAV.CAP-B10 is significantly decreased when compared to AAV9 and non-significantly decreased when compared to AAV-PHP.eB. In the myenteric and submucosal plexi of the intestines, AAV.CAP-B10 is significantly decreased compared to AAV9 and non-significantly decreased compared to AAV-PHP.eB. In the lungs, AAV.CAP-B10 is significantly decreased when compared to AAV-PHP.eB and non-significantly decreased compared to AAV9. In the kidneys, spleen, pancreas and testes, AAV.CAP-B10 is significantly decreased when compared to AAV9 and non-significantly decreased compared to AAV-PHP.eB. For quantification: n=6 mice per group except for spinal cord and DRGs where n=3 mice for AAV9 and AAV-PHP.eB and n=5 mice for AAV.CAP-B10, mean±SE, ANOVA for spinal cord, Brown-Forsythe and Welch ANOVA tests for myenteric plexus and pancreas, Kruskal-Wallis test for DRGs, submucosal plexus, lungs, kidneys, spleen and testes (*$P \leq 0.05$; n.s., $P \geq 0.05$).
Figure 22B:
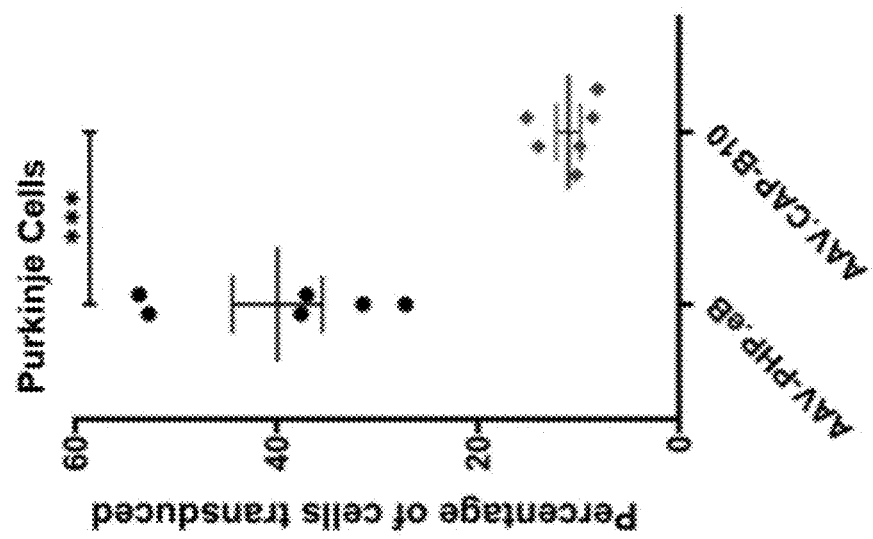
FIG. 22A-22B shows that AAV.CAP-B10 is significantly detargeted from purkinje cells in the cerebellum. ssAAV-PHP.eB:CAG-NLSx2-EGFP or ssAAVCAP-B10:CAG-NLSx2-EGFP was intravenously injected into male adult mice at $1 \times 10^{11}$ vg/mouse. GFP fluorescence was assessed after three weeks of expression.
Figure 22A:
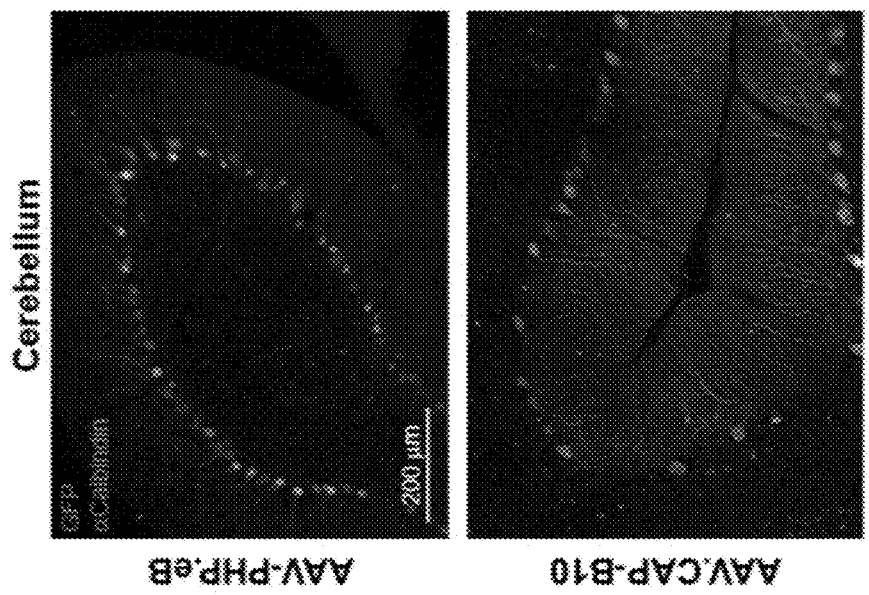
Figure 23E:
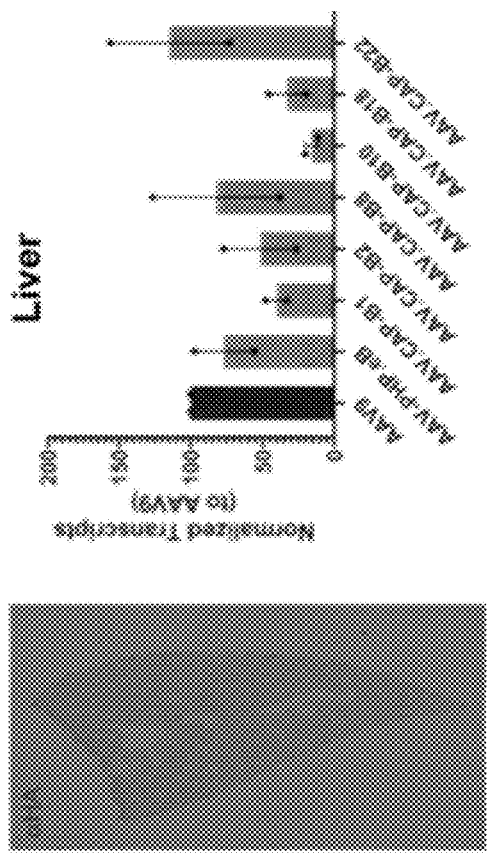
Figure 23F:
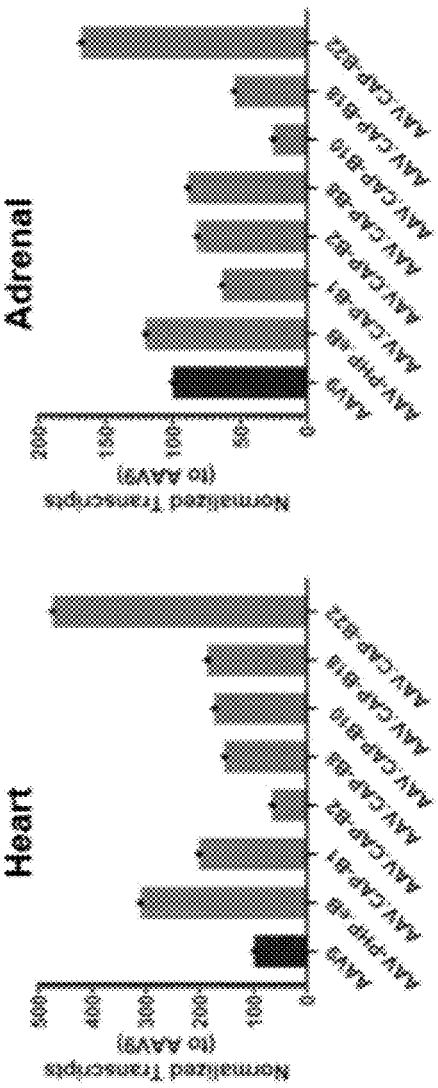

To further characterize what expression within the brain looked like for AAV.CAP-B10 compared to PHP.eB, neurons, astrocytes and oligodendrocytes, were stained and quantified for the efficiency of the viruses at targeting those cell-types in various regions of the brain. While AAV.CAP-B10 and PHP.eB transduced neurons at a similar efficiency across brain regions (FIG. 19A-19B), astrocytes and oligodendrocytes were targeted roughly 4-5-fold lower levels across the whole brain by AAV.CAP-B10 compared to PHP.eB (FIG. 19C, 19D, 19E, 19F). This result indicates a bias for neurons compared to other cell-types conferred by the AAV.CAP-B10 mutations, an interesting deviation from AAV9, which mostly targets astrocytes in the brain. An interesting indication from the NGS data for AAV.CAP-B10 (FIG. 15C) was the variant's negative enrichment in the cerebellum. When characterizing the expression of AAV.CAP-B10 compared to PHP.eB in the cerebellum, there was indeed a significant, roughly 4-fold, decrease in transduction of purkinje cells (FIG. 22).

FIG. 3 shows 7-mer variant AAV capsid amino acid sequences and DNA sequences encoding the 7-mer variant AAV capsid amino acid sequences with a tropism specific to the central nervous system (CNS), and detargeting the liver. FIG. 2 shows 7-mer variant AAV capsid amino acid sequences and DNA sequences encoding the 7-mer variant AAV capsid amino acid sequences with a tropism specific to the CNS.

Example 5. AAV Capsid Variants with Tropisms Bias Toward Central and Peripheral Nervous System and Against the Liver in Non-Human Primates Of primary concern for the therapeutic applicability of variants engineered in rodents is how well their transduction profiles translate to non-human primates (NHPs). As such, the NHP transduction profiles of a subset of the variants that had been validated in rodents were characterized, along with AAV9 and AAV-PHP.eB as controls. A pool of eight viruses, AAV9, AAV-PHP.eB, AAV.CAP-B1, AAV.CAP-B2, AAV.CAP-B8, AAV.CAP-B10, AAV.CAP-B18 and AAV.CAP-B22, were produced, each packaging an HA tagged frataxin under control of the ubiquitous CAG promoter. The use of frataxin was chosen as it is an endogenous protein expressed throughout the body and previous efforts to characterize NHP transduction of naturally occurring and engineered serotypes has found deleterious results potentially due to the packaging of an exogenous transgene like GFP. Each packaged FXN contained a separate 12-base RNA barcode to differentiate the contribution of one virus from the rest after sequencing. The eight viruses were pooled at equal ratios and injected into two adult marmosets at $1.2 \times 10^{14}$ vg/kg total. Following six weeks of expression, brains and livers were recovered, and coronal sections taken for RNA sequencing and immunohistochemistry.

AAV.CAP-B10 showed a greater than 6-fold increase in RNA levels in the brain and greater than 5-fold decrease in liver RNA levels compared to AAV9. Another selected variant, AAV.CAP-B22, showed a greater than 12-fold increase in brain RNA levels with no significant difference in liver RNA levels. Without being bound by any particular theory, these results show that AAV.CAP-B22 and AAV.CAP-B10 are promising variant capsids for the treatment of human disease of the brain. Although a select number of variants were tested in the present example, these finds also suggest that other modified AAV capsid proteins described herein with equal to, or greater, enrichment scores as AAV.CAP-B22 and AAV.CAP-B10 in any target in vivo environment, would also provide a promising therapeutic solution for human disease.

Example 6. Phase 1A Clinical Trial (Huntington's Disease)

A phase 1A clinical trial is performed to evaluate the safety, tolerability, pharmacokinetics, and pharmacodynamics of an one-time intravenous injection of test composition comprising viral vector including a modified AAV capsid protein with an amino acid sequence provided in any one of SEQ ID NOS: 2933, 88, 2466, 3943, 2672, 2743, 3064, 11958, 780, 2764, and 2741, or any of the amino acid sequences provided in Tables 3-4, or FIGS. 2-3, in subjects with late Huntington's Disease (HD). Eligible subjects are men and women between 21 and 65 years of age.

Inclusion Criteria: Eligible subjects are men and women between 21 and 65 years of age. Subjects that (1) sign and date International Classification of Functioning, Disability and Health (ICF); (2) male or female participant aged ≥21 and ≤65; (3) participants who submit medical report (PCR) attesting Huntington's disease with a number of CAG repeats on chromosome 4, greater than or equal to 40 and less than or equal to 50 (if the participant has not performed the examination and/or if he does not have the report available, a new exam should be done); (4) Score 5 points or more in motor assessment UHDRS scale (Unified Huntington's Disease Rating Scale) at the time of enrollment; (5) Score between 8 and 11 points in the functional capacity of the UHDRS scale at the time of enrollment.

Exclusion Criteria: (1) Any medical observation data (clinical and physical) that medical research judge as a risk for subject if enrollment at the study; (2) any laboratory exam data that medical research judge as a risk for subject if enrollment at the study; (3) history of epilepsy; (4)

diagnostic of major cognitive impairment; (5) active decompensated psychiatric disease; (6) current or prior history of neoplasia; (7) current history of gastrointestinal, hepatic, renal, endocrine, pulmonary, hematologic, immune, metabolic pathology or severe and uncontrolled cardiovascular disease; (8) diagnostic of any active infection, be it viral, bacterial, fungal, or caused by another pathogen; (9) participants who have contraindication to undergo any of the tests performed in this study, for example, have pacemakers or surgical clip; (10) history of alcohol or illegal drugs abusers; (11) history of 1 or more episodes of suicide in the two years before Visit V-4; (12) active smoker or have stopped smoking less than six months prior to enrollment; (13) test positive in at least one of the serological tests: HIV 1 and 2 (Anti-HIV-1,2), HTLV I and II, HBV (HBsAg, anti-HBc), HCV (anti-HCV-Ab) and VDRL (*Treponema pallidum*); (14) history of drug allergy, including contrasts for imaging, or bovine products; (15) in use or expected use of immunosuppressive drugs or prohibited medicines for the first three months after the first administration of the investigational product; (16) any clinical changes that is interpreted by the medical researcher as a risk to participant's enrollment.

Experimental:

Placebo. One-time injection of placebo at Week 0.

Test High Dose. One-time injection of test composition $2\times10^{10}$ vg at Week 0.

Test Middle Dose. One-time injection of test composition $6\times10^{9}$ vg at Week 0.

Test Low Dose. One-time injection of test composition $2\times10^{9}$ vg at Week 0.

Test Lowest Dose. One-time injection of test composition $2\times10^{8}$ vg at Week 0.

Primary Outcome Measures: Safety of the test composition by periodic monitoring changes at adverse events, vital signs, laboratory tests, ECG and incidence of benign and malignant neoplasms [Time Frame: five years]. The safety of the investigational product will be evaluated in detail from periodic evaluations contemplating monitoring changes of: (1) adverse events including type, frequency, intensity, seriousness, severity, and action taken related to the investigational product study; (2) vital signs (BP, HR, axillary temperature), physical and medical examination (BMI, weight, height, medical condition—cardiovascular, pulmonary, digestive, musculoskeletal and peripheral, with emphasis on the neurological assessment and others); (3) laboratory tests included hematologic, biochemical, urologic and serological analysis; (4) electrocardiogram (ECG) of 12 derivations; (5) and incidence and classification of benign and malignant neoplasms in the following organs/systems: CNS, lung, liver, spleen, pancreas, prostate, testicle, urinary, hematological and skeletal system through the laboratory tests, magnetic resonance imaging, computerized tomography and ultrasonography.

Secondary Outcome Measures: Preliminary efficacy of Cellavita HD by global clinical response (CIBIS) and UHDRS improvement [Time Frame: five years] will be evaluated by statistical comparison of the results of each UHDRS scale component: motor, cognitive and behavior. The global clinical response will be assessed by statistical comparison between baseline score observed by the Investigator before and after Cellavita HD treatment. Preliminary efficacy of Cellavita HD by comparison of the inflammatory markers [Time Frame: one year] will be evaluated by statistical comparison of the inflammatory markers included IL-4, IL-6, IL-10 (interleukin IL) and TNF-alpha (tumoral necrosis factor alpha). Immunological Response of Cellavita HD [Time Frame: one year]. The immunological response induced by Cellavita HD will be evaluated by statistical comparison between baseline results of CD4+ and CD8+ proliferation and the other evaluated times. Preliminary efficacy of Cellavita HD by comparison of the CNS assessment [Time Frame: one year]. Will be evaluated by statistical comparison of the CNS assessment through magnetic resonance image at cortical thickness measurements, volumes of different brain structures, especially the basal ganglia, with special attention to caudate and metabolic changes identified in proton spectroscopy. Risk of suicidal ideation by Hamilton Depression Rating Scale (HDRS) [Time Frame: five years] will be evaluated by suicidal domain. The classificatory punctuation may correspond to mild depression (score: 8 to 13), moderate depression (score: 19-22) and severe depression (score: >23).

While preferred embodiments of the present examples have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11149256B2). An electronic copy of the "Sequence Listing" will also be available from the USPTO upon request and payment of the fee set forth in 37 CFR 1.19(b)(3).

The invention claimed is:

1. A recombinant AAV (rAAV), the rAAV comprising:
a) a variant AAV capsid comprising a variant AAV capsid protein comprising an amino acid substitution of three or more amino acids within a 7-mer peptide sequence of a parental AAV capsid protein, wherein the 7-mer peptide sequence is from amino acid positions that correspond to amino acid residues 452-458 of AAV9 VP1 (SEQ ID NO:1), and wherein the amino acid substitution is not ILGTGTS (SEQ ID NO: 45479), not QSSQTPR (SEQ ID NO: 45480), and not TLAVPFK (SEQ ID NO: 45477); and b) a heterologous polynucleotide comprising a nucleotide sequence encoding a gene product.

2. The rAAV of claim 1, wherein the variant AAV capsid has an increased tropism for a target tissue or a target cell, when measured in a subject, relative to a tropism of the parental AAV capsid.

3. The rAAV of claim 2, wherein the target tissue or the target cell comprises a tissue or a cell of a central nervous system (CNS) or a peripheral nervous system (PNS), or a combination thereof.

4. The rAAV of claim 3, wherein the variant AAV capsid has a decreased tropism for an off-target tissue comprising liver tissue or an off-target cell comprising a liver cell, when measured in a subject, relative to the tropism of the parental AAV capsid.

5. The rAAV of claim 4, wherein the three or more amino acids comprise three contiguous amino acids, each amino acid independently selected from the group consisting of A, D, E, G, K, H, M, N, P, L Q, S, T, and V at amino acid positions in the parental AAV capsid protein corresponding to amino acid residues 452-454, 453-455, 454-456, 455-457, or 456-458 of AAV9 VP1 (SEQ ID NO: 1).

6. The rAAV of claim 4, wherein the three or more amino acids comprise four contiguous amino acids, each amino acid independently selected from the group consisting of A, D, E, G, K, H, M, N, P, L Q, S, T, and V at amino acid positions in the parental AAV capsid protein corresponding to amino acid residues 452-455, 453-456, 454-457, or 455-458 of AAV9 VP1 (SEQ ID NO: 1).

7. The rAAV of claim 4, wherein three or more amino acids comprise at least five contiguous amino acids, each amino acid independently selected from the group consisting of A, D, E, G, K, H, M, N, P, L Q, S, T, and V at amino acid positions in the parental AAV capsid protein corresponding to amino acid residues 452-456, 453-457, or 454-458 of AAV9 VP1 (SEQ ID NO: 1).

8. The rAAV of claim 4, wherein the three or more amino acids comprise three or more of:
   a) A, D, E, G, H, M, N, Q, S, T, or V substituted at an amino acid position corresponding to amino acid residue 452 of AAV9 VP1 (SEQ ID NO: 1);
   b) A, D, E, G, K, N, Q, S, T, or V substituted at an amino acid position corresponding to amino acid residue 453 of AAV9 VP1 (SEQ ID NO: 1);
   c) A, D, E, G, K, N, Q, S, T, or V substituted at amino acid position corresponding to amino acid residue 454 of AAV9 VP1 (SEQ ID NO: 1);
   d) A, D, E, G, K, N, P, Q, S, or T substituted at an amino acid position corresponding to amino acid residue 455 of AAV9 VP1 (SEQ ID NO: 1);
   e) A, D, E, G, H, K, N, P, Q, S, or T substituted at an amino acid position corresponding to amino acid residue 456 of AAV9 VP1 (SEQ ID NO: 1);
   f) A, D, E, G, K, N, P, S, T, or V substituted at an amino acid position corresponding to amino acid residue 457 of AAV9 VP1 (SEQ ID NO: 1); and
   g) A, E, G, H, K, L, N, Q, S, T, or V substituted at amino acid position corresponding to amino acid residue 458 of AAV9 VP1 (SEQ ID NO: 1).

9. The rAAV of claim 5, wherein the amino acid substitution comprises an amino acid sequence selected from DGAATKN (SEQ ID NO: 3943), and DGQSSKS (SEQ ID NO: 2764).

10. The rAAV of claim 4, wherein the three or more amino acids comprises three or more of:
   a) A, D, G, L, N, Q, S, or T substituted at an amino acid at a position corresponding to amino acid residue 452 of AAV9 VP1 (SEQ ID NO: 1);
   b) A, G, N, P, Q, R, S, or substituted at an amino acid at a position corresponding to amino acid residue 453 of AAV9 VP1 (SEQ ID NO: 1);
   c) A, D, G, N, S, or T substituted at an amino acid at a position corresponding to amino acid residue 454 of AAV9 VP1 (SEQ ID NO: 1);
   d) A, D, G, K, N, P, Q, S, or T substituted at an amino acid at a position corresponding to amino acid residue 455 of AAV9 VP1 (SEQ ID NO: 1);
   e) A, G, K, N, P, R, S, or T substituted at an amino acid at a position corresponding to amino acid residue 456 of AAV9 VP (SEQ ID NO: 1);
   f) A, G, K, N, P, R, S, T, or V substituted at an amino acid at a position corresponding to amino acid residue 457 of AAV9 VP1 (SEQ ID NO: 1); and
   g) A, G, K, L, R, S, T, or V substituted at an amino acid at a position corresponding to amino acid residue 458 of AAV9 VP1 (SEQ ID NO: 1).

11. The rAAV of claim 10, wherein the amino acid substitution comprises an amino acid sequence selected from the group consisting of LQTSSPG (SEQ ID NO: 2933), QQGKQSV (SEQ ID NO: 79), SINTKTN (SEQ ID NO: 45475), SNGTKQT (SEQ ID NO: 442), GSGKTAA (SEQ ID NO: 88), MGDKPTR (SEQ ID NO: 2466), QPSGGNT (SEQ ID NO: 2672), ERGANTK (SEQ ID NO: 5192), TTGGHSS (SEQ ID NO: 2743), GTTKTSE (SEQ ID NO: 3064), GTGTSVL (SEQ ID NO: 11958), NQSGTKG (SEQ ID NO: 780), KGPGQMG (SEQ ID NO: 45476), and GTPSKAG (SEQ ID NO: 2741).

12. The rAAV of claim 2, wherein the target tissue or the target cell in the tissue is selected from the group consisting of lung, intestine, kidney, heart, and stomach.

13. The rAAV of claim 12, wherein the three or more amino acids comprise three contiguous amino acids at amino acid positions corresponding to amino acid residues 452-454, 453-455, 454-456, 455-457, or 456-458 of AAV9 VP1, wherein:
   a) 452 is selected from the group consisting of N, K, R, and T;
   b) 453 is selected from the group consisting of L, N, P, and S;
   c) 454 is selected from the group consisting of A, D, G, N, S, and T;
   d) 455 is selected from the group consisting of L, P, S, and T;
   e) 456 is selected from the group consisting of P, R, and S;
   f) 457 is selected from the group consisting of G, N, S, and T; and
   g) 458 is selected from the group consisting of I, L, and R.

14. The rAAV of claim 13, wherein the three or more amino acids comprise:
   a) four contiguous amino acids at amino acid positions corresponding to amino acid residues 452-455, 453-456, 454-457, or 455-458 of AAV9 VP1 (SEQ ID NO: 1);
   b) five contiguous amino acids at amino acid positions corresponding to amino acid residues 452-456, 453-457, or 453-458 of AAV9 VP1 (SEQ ID NO: 1);
   c) six contiguous amino acids at amino acid positions corresponding to amino acid residues 452-457 or 453-458 of AAV9 VP1 (SEQ ID NO: 1); and d) seven contiguous amino acids at amino acid positions corresponding to amino acid residues 452-458 of AAV9 VP1 (SEQ ID NO: 1).

15. The rAAV of claim 13, wherein the target tissue is lung, and the three or more amino acids are provided in an amino acid sequence comprising KDNTPGR (SEQ ID NO: 32538), NNLPRNL (SEQ ID NO: 32867), or any amino acid sequence provided in FIG. 13.

16. The rAAV of claim 13, wherein the target tissue is intestine, and the three or more amino acids are provided in an amino acid sequence comprising RESSPSL (SEQ ID NO: 26474), KDNTPGR (SEQ ID NO: 26584), or any amino acid sequence provided in FIG. 5.

17. The rAAV of claim 13, wherein the tissue is kidney, and the three or more amino acids are provided in an amino acid sequence comprising RVPLSTI (SEQ ID NO: 26933), NNLPRNL (SEQ ID NO: 27530), KDNTPGR (SEQ ID NO: 28509), or any amino acid sequence provided in FIG. 6.

18. The rAAV of claim 13, wherein the tissue is heart, and the three or more amino acids are provided in an amino acid sequence comprising KDNTPGR (SEQ ID NO: 25633), or any amino acid sequence provided in FIG. 4.

19. The rAAV of claim 13, wherein the tissue is stomach, and the three or more amino acids are provided in an amino acid sequence comprising RESSPSL (SEQ ID NO: 31904) or any amino acid sequence of FIG. 12.

20. The rAAV of claim 1, wherein the parental AAV capsid protein is AAV9 VP1 or a variant thereof.

21. The rAAV of claim 20, wherein the AAV9 VP1 variant has a sequence identity of 90% or more to SEQ ID NO: 1.

22. The rAAV of claim 20, wherein the AAV9 VP1 variant has a sequence identity of 95% or more to SEQ ID NO: 1.

23. The rAAV of claim 1, wherein the parental AAV capsid protein further comprises an insertion of an amino acid sequence selected from the group consisting of TLAXPFK (SEQ ID NO: 46424), TLAX (SEQ ID NO: 46425), LAVX (SEQ ID NO: 46426), AVPX (SEQ ID NO: 46427), and VPFX (SEQ ID NO: 46428), between amino acids corresponding to positions 588-589 of AAV9 VP1 (SEQ ID NO: 1), wherein X is any amino acid other than V.

24. The rAAV of claim 23, wherein the parental AAV capsid protein is from AAV-PHP.B or AAVPHP.eB.

25. The rAAV of claim 1, wherein the rAAV is isolated and purified.

* * * * *

UNITED STATES PATENT AND TRADEMARK OFFICE
CERTIFICATE OF CORRECTION

| | | |
|---|---|---|
| PATENT NO. | : 11,149,256 B2 | Page 1 of 1 |
| APPLICATION NO. | : 16/582635 | |
| DATED | : October 19, 2021 | |
| INVENTOR(S) | : Viviana Gradinaru et al. | |

It is certified that error appears in the above-identified patent and that said Letters Patent is hereby corrected as shown below:

In the Specification

Column 1 Line 15 insert:
--This invention was made with government support under Grant No. NS087949 awarded by the National Institutes of Health and under grant No. W911NF-17-2-0036 awarded by ARO. The government has certain rights in the invention.--

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*